(12) United States Patent
McAuliffe et al.

(10) Patent No.: US 8,476,049 B2
(45) Date of Patent: Jul. 2, 2013

(54) CONVERSION OF PRENYL DERIVATIVES TO ISOPRENE

(75) Inventors: Joseph C. McAuliffe, Sunnyvale, CA (US); Samira Rathnayake, Danville, CA (US); Karl J. Sanford, Cupertino, CA (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 486 days.

(21) Appl. No.: 12/560,370

(22) Filed: Sep. 15, 2009

(65) Prior Publication Data
US 2010/0113846 A1    May 6, 2010

Related U.S. Application Data

(60) Provisional application No. 61/097,204, filed on Sep. 15, 2008.

(51) Int. Cl.
*C12P 5/02* (2006.01)
*C07C 11/10* (2006.01)

(52) U.S. Cl.
USPC ............................................. 435/167; 585/16

(58) Field of Classification Search
USPC ............................................. 435/167; 585/16
See application file for complete search history.

(56) References Cited

U.S. PATENT DOCUMENTS

| | | |
|---|---|---|
| 3,792,104 A | 2/1974 | Mueller et al. |
| 4,570,029 A | 2/1986 | Kulprathipanja et al. |
| 4,683,202 A | 7/1987 | Mullis |
| 4,703,007 A | 10/1987 | Mulholland et al. |
| 5,849,970 A | 12/1998 | Fall et al. |
| 5,874,276 A | 2/1999 | Fowler et al. |
| 6,022,725 A | 2/2000 | Fowler et al. |
| 6,106,888 A | 8/2000 | Dale et al. |
| 6,176,176 B1 | 1/2001 | Dale et al. |
| 6,268,328 B1 | 7/2001 | Mitchinson et al. |
| 6,689,593 B2 | 2/2004 | Millis et al. |
| 7,132,527 B2 | 11/2006 | Payne et al. |
| 7,241,587 B2 | 7/2007 | Dodge et al. |
| 7,262,041 B2 | 8/2007 | Baldwin et al. |
| 2004/0176570 A1* | 9/2004 | Bacher et al. ................. 530/350 |
| 2008/0092829 A1 | 4/2008 | Renninger et al. |

FOREIGN PATENT DOCUMENTS

| | | |
|---|---|---|
| DE | 19629568 C1 | 1/1998 |
| EP | 215 594 A2 | 3/1987 |
| EP | 215 594 A3 | 3/1987 |

(Continued)

OTHER PUBLICATIONS

Anderson, M.S. et al. (Nov. 15, 1989). "Isopentenyl Diphosphate: Dimethylallyl Diphosphate Isomerare. An Improved Purification of the Enzyme and Isolation of the Gene From *Saccharomyces cerevisia*." *J. Biol. Chem.* 264:19169-19175.

(Continued)

*Primary Examiner* — Rosanne Kosson
(74) *Attorney, Agent, or Firm* — Morrison & Foerster LLP

(57) ABSTRACT

The present invention provides methods for producing derivatives from cultured cells. In addition, the present invention provides methods for conversion of prenyl deerivatives, obtained from biological or petrochemical sources, to isoprene by employing chemical or biological catalysts. The present invention also provides compositions that include the cultured cells or isoprene or prenyl derivatives produced there from.

14 Claims, 241 Drawing Sheets

FOREIGN PATENT DOCUMENTS

| | | |
|---|---|---|
| EP | 215 594 B1 | 3/1987 |
| EP | 215 594 B2 | 3/1987 |
| EP | 238 023 A2 | 9/1987 |
| EP | 238 023 A3 | 9/1987 |
| EP | 238 023 B1 | 9/1987 |
| EP | 238 023 B2 | 9/1987 |
| EP | 244 234 A2 | 11/1987 |
| EP | 244 234 A3 | 11/1987 |
| EP | 244 234 B1 | 11/1987 |
| EP | 244 234 B2 | 11/1987 |
| EP | 137 280 B1 | 3/1992 |
| EP | 1 354 956 A1 | 10/2003 |
| JP | 47-014105 A | 1/1972 |
| WO | WO 95/04134 A1 | 2/1995 |
| WO | WO 96/35796 A1 | 11/1996 |
| WO | WO 98/02550 A2 | 1/1998 |
| WO | WO 98/02550 A3 | 1/1998 |
| WO | WO 00/01650 A1 | 1/2000 |
| WO | WO 2004/033646 A2 | 4/2004 |
| WO | WO 2004/033646 A3 | 4/2004 |
| WO | WO 2005/001036 A2 | 1/2005 |
| WO | WO 2005/001036 C1 | 1/2005 |
| WO | WO 2010/003007 A2 | 1/2010 |
| WO | WO 2010/003007 A3 | 1/2010 |

OTHER PUBLICATIONS

Boel, E. et al. (1984). "Two Different Types of Intervening Sequences in the Glucoamylase Gene From *Aspergillus niger.*" *EMBO J.* 3:1581-1585.

Bouvier, F. et al. (2005). "Biogenesis, <Molecular Regulation and Function of Plant Isoprenoids." *Progress in Lipid Research* 44:357-429.

Bunge, M. et al. (2008). "On-Line Monitoring of Microbial Volatile Metabolites by Proton Transfer Reaction-Mass Spectrometry." *Applied and Environmental Microbiology* 74(7):2179-2186.

Campbell, E. et al. (1989). "Improved Transformation Efficiency of *Aspergillus niger* Using the Homologous *nia*D Gene for Nitrate Reductase." *Curr Genet* 16:53-56.

Cao, Q. et al. (2000). "Penicillopepsin-JT2, a recombinant Enzyme From *Penicillium janthinellum* and the Contribution of a Hydrogen Bond in Subsite $S_3$ to $k_{cat}$." *Protein Science* 9:991-1001.

Dhe-Paganon, S. et al. (1994). "Mechanism of Mevalonate Pyrophosphate Decarboxyase: Evidence for a Carbocationic Transition State." *Biochemistry*, 33(45):13355-13362.

GenBank Accession No. AY341431, last updated Feb. 15, 2005, located at http://www.ncbi.nlm.nih.gov/nuccore/AY341431, last visited on Feb. 27, 2012, 2 pages.

Farzaneh F., et al. (2005). "Optimization of the Ammonia Fiber Explosion (AFEX) Treatment Parameters for Enzymatic Hydrolysis of Corn Stover." *Bioresource Technology*, 96 (18):2014-2018.

Goedegebuur, F. et al. (2002). "Cloning and Relational Analysis of 15 Novel Fungal Endoglucanases from Family 12 Glycosyl Hydrolase." *Curr Genet* 41:89-98.

Grawert, T. et al. (Sep. 21, 2004). "IspH Protein of *Escherichia coli*: Studies on Iron-Sulfur Cluster Implementation and Catalysis." *Journal American Chemistry Society*, 126(40):12847-12855.

Greenbert, J. et al. (1993). "Sub-Parts Per Billion Detection of Isoprene Using a Reduction Gas Detector with a Portable Gas Chromatograph." *Atmos. Environment* 27A: 2689-2692.

Groot, W.J. et al. (1992). "Technologies for Butanol Recovery Integreated With Fermentations." *Process Biochemistry*, 27:61-75 (1992).

Harkki, A., et al. (1991). "Genetic engineering of *Trichoderma* to Produce Strains With Novel Cellulas Profiles." *Enzyme Microb. Technol.* 13:227-233.

Harkki, A. et al. (1989). "Novel Fungal Expression System : Secretion of Acitve Calf Chymosin From theh Filamentous Fungus *Trichoderma reesei*." *Bio/Technol.* 7:596-603.

Hedl, M. et al. (2002). "*Enterococcus taecalis* Acetoacetyl-Coenzyme A Thiolase/3-Hydroxy-3-Methyglutaryl-Coenzyme A Reductase, A Dual-Function Protein of Isopentenyl Diphosphate Biosynthesis." *J. Bacteriol.* 184(8):2116-2122.

Hoefler, J-F. et al. (2002). "Isoprenoid Biosynthesis via the Methylerythritol Posphate Pathway. Mechanistic Investigations of the 1-Deox Y-D-Xylulose 5-Phosphate D Reductiosimerase." *Eur. J. Biochem.* 269:4446-4457.

Hunter, B. et. al. (1985). "Formaldehyde Meta bolism by *Escherichia coli*. Carbon and Solvent Deuterium Incorporation into Glycerol, 1,2-Propanediol, and 1,3-Propanediol." *Biochemistry* 24, 4148-4155.

Ilmen, M. et al. (1997). "Regulation of Cellulase Gene Expression in the Filamentous Fungus *Trichoderma reese*." *Appl. Environ. Microbiol.* 63:1298-1306.

Innis, M.A. et al. (1985). "Expression, Glycosylation, and Secretion of an *Aspergillus* Glucoamylase by *Saccharomyces cervisiae*." *Science* 228: 21-26.

Julsing, M. et al. (2007). "Functional Analysis of Genes Involved in the Biosynthesis of Isoprene in *Bacillus subtilis*." *Applied. Microbiol. Biotechnol.* 75: 1377-84.

Kelley, J.M. et al. (1985). "Transformation of *Aspergillus niger* by the amdS gene of *Aspergillus nidulans*." *EMBO Journal* 4:475-479.

Koga, Y. et al. (2007). "Biosynthesis of Ether-Type Polar Lipids in Archaea and Evolutionary Considerations." *Microbiology and Mol. Biology Reviews*, 71(1):97-120.

Luttgen, H. et al. (2000). "Biosynthesis of Terpenoids: YchB Protein *Escherichia coli* Phosphorylates the 2-Hydroy Group of 4-Diphosphocytiidyl-2C-Methyl-o-Erythritol." *PNAS*, 97(3):1062-1067.

Miller, B. et al. (2001). "First Isolation of an Isoprene Synthase Gene from Poplar and Successful Expression of the Gene in *Escherichia coli*." *Planta* 213:483-487.

Neidhardt, F. et al. (1974). "Culture Medium for Enterobacteria." *Journal of Bacteriology* 119:736-747.

Newman, JD et al. (2006). "High-Level Production of Amorpha-4,11-diene in a Two-Phase Partitioning Bioreactor of Metabolically Engineered *Escherichia coli*." *Biotech and Bioeng*, 95:684-691.

Nunberg, J.H. et al. (1984). "Molecular Cloning and Charactgerization of the Glycoiamylase Gene of *Aspergillus awamori*. "*Molecular and Cell Biology* 4:2306-2315.

Oulmouden, A. et al. (1991). "Nucleotide Sequence of the ERG 12 Gene of *Saccharomyces cerevisiae* Encoding Mevalonate Kinase." *Curr Genet* 19:9-14.

Penttila, M. et al. (1987). "A Versatile Transformation System for the Cellulolytic Filamentous Fungus *Trichoderma reesei*." *Gene* 61:155-164.

Rohdich, F. et al. (2000). "Biosynthesis of Terpenoids: 4-Diphosphocytidyl-2C-Methyl-o-Erythritol Synthase of *Arabidopis thaliana*." *PNAS*, 97: 6451-6456.

Rohdich, F. et al. (1999). "Cytidine 5'-Triphosphate-Dependent Biosynthesis of Isoprenoids: TgbP Protein of *Esherichia coli* Catalyzes the Formation of 4-Diphosphocytidyl-D-2-Methylerythritol." *PNAS*, 96:11758-11763.

Schnitzler, J-P. et al. (2005). "Biochemical Properties of Isoprene Synthase in Poplar (*Populus* x *Canescens*)." *Planta* 222:777-786.

Sharkey, T.D. et al. (2005). "Evolution of the Isoprene Biosynthetic Pathway in Kudzu." *Plant Physiology* 137:700-712.

Sheir-Neiss, G. et al. (1984). "Characterization of the Secreted Cellulases of *Trichoderma reesei* Wild Type and Mutants During Controlled Fermentations." *Appl. Microbiol. Biotechnol* 20:46-53.

Silver, G.M. et al. (1991). "Enzymatic Synthesis of Isoprene from Dimethylally Diphosphate in Aspen Leaf Extracts." *Plant Physiol.* 97:1588-1591.

Silver, G.M. et al. (1995). "Characterization of Aspen Isoprene Synthase, an Enzyme Responsible for Leaf Isoprene Emission to the Atmosphere." *J. Biol. Chem.* 270:13010-13016.

Sprenger, G.A. et al. (1997). "Identification of a Thiamin-Dependent Synthase in *Escherichia coli* Required for the Formation of the 1-Deox Y-o-Xylulose 5-Phosphate Precursor to Isoprenoids, Thiamin, and pyridoxol." *PNAS*, 94:12857-12862.

Sulter, G.J. et al. (1990). "Proliferation and Metabolic Significance of Peroxisomes Iin *Canduida boidinii* During Growth on D-alanine or Oleic Acid as the Sole Carbon Source." *Arch. Microbiol.* 153(5), 485-489.

Sutherlin, A. et al. (2002). "*Entrococcus taecalis* 3-Hydroxy-3-Methylglutaryl Coenzyme A Synthase, an Enzyme of Isopentenyl Diphosphate Biosynthesis." *J. Bacteriol.*, 184:4065-4070.

Tsay, Y.H. et al. (1991). "Cloning and Charaterization of *ERG8*, an Essential Gene of *Saccharomyces cerevisiae* That Encodes Phosphomevalonate Kinase." *Mol Cell Biol.*, 11:620-631.

Vane, L.M. (2005). "A Review of Pervaporation for Product Recovery from Biomass Fermentation Processes." *J Chem Technol Biotechnol*, 80:603-629 (2005).

Ward, M. et al. (1993). "Use of *Aspergillus* Ovrefproducing Mutants, Cured for Integrated Plasmid, to Overproduce Heterologous Proteins." *Appl. Microbiol. Biotechnol.* 39:7380743.

Withers, S. et al. (2007). "Identification of Isopentenol Biosynthetic Genes from *Bacillus subtilis* by a Screening Method Based on Isopenoid Precursor Toxicity." *Appl Environ Microbiol.* 73(19):6277-83.

Yamada, K. et al. (1989). "Production of Glycerol From Methanol by a Mutant Strain of *Candida boidinii*." *Agric. Biol. Chem.*, 53(2) 541-543.

Yelton, M. et al.(1984). "Transformation of *Aspergillus nidulans* by using a *trpC* Plasmid." *Proceedings. Natl. Acad. Sci. USA* 81:1470-1474.

Zepeck, F. et al. (2005). "Biosynthesis of Isoprenoids. Purification and Properties of IspG Protein from *Escherichia coli*." *J. Org. Chem.*, 70:9168-9174.

GenBank Accession No. AAQ84170.1, Isoprene Synthase (*Pueraria montana* Var. Lobata), Sharkey, T.D. et al., (2005). "Evolution of the Isoprene Biosynthetic Pathway in Kudzu," *Plant Physiol.* 137(2):700-712, last updated on Feb. 15, 2005, located at <http://www.ncbi.nlm.nih.gov/protein/AAQ84170>, last visited on Feb. 27, 2012, 2 pages.

GenBank Accession No. AJ457070.2, *Cinnamomum tenuipilum* mRNA for Geraniol Synthase (GerS gene)., Yang, T.et al. (2005). "A Geraniol-Synthase Gene From *Cinnamum tenuipilum*," *Phytochemistry* 66(3):285-293, last updated on Apr. 15, 2005, located at <http://www.ncbi.nlm.nih.gov/nuccore/38092202>, last visited on Jun. 2, 2010, 2 pages.

GenBank Accession No. AY182241.2, *Malus X Domestica* (E, E)-Alpha-Farnesene Synthase (AFS1) mRNA, Complete cds., Pechous, S.W. et al. (2004). "Cloning and Functional Expression of an (E, E)-Alpha-Farnesene Synthase cDNA From Peel Tissue of Apple Fruit," *Planta* 219(1):84-94, last updated on May 4, 2004, located at <http://www.ncbi.nlm.nih.gov/nuccore/32265057>, last visited on Jun. 2, 2010, 2 pages.

GenBank Accession No. AY279379.1, *Melaleuca alternifolia* Putative Monoterpene Synthase mRNA, Complete cds., Shelton, D. et al. (2004). "Isolation and Partial Characterisation of a Putative Monoterpene Synthase From *Melaleuca alternifolia*," *Plant Physiol. Biochem.* 42(11):875-882, last updated on Mar. 11, 2005, located at <http://www.ncbi.nlm.nih.gov/nuccore/30984014>, last visited on Jun. 2, 2010, 2 pages.

GenBank Accession No. AY316691.1, *Pueraria montana* Var. Lobata Isoprene Synthase (IspS) Gene, Complete cds., Sharkey, T.D. et al. (2005). "Evolution of the Isoprene Biosynthetic Pathway in Kudzu," *Plant Physiol.* 137(2):700-712, last updated on Feb. 15, 2005, located at <http://www.ncbi.nlm.nih.gov/nuccore/35187003>, last visited on Jun. 2, 2010, 2 pages.

GenBank Accession No. AY341431.1, *Populus tremuloides* Isoprene Synthase (IspS) Gene, Completed cds., Sharkey, T.D. et al. (2005). "Evolution of the Isoprene Biosynthetic Pathway in Kudzu," *Plant Physiol.* 137(2):700-712, last updated Feb. 15, 2005, located at <http://www.ncbi.nlm.nih.gov/nuccore/AY341431>, last visited on Feb. 27, 2012, 2 pages.

GenBank Accession No. CAC35696.1, Isoprene Synthase (*Populus tremula X Populus alba*), Miller, B. et al. (2001). "First Isolation of an Isoprene Synthase Gene From Poplar and Successful Expression of the Gene in *Escherichia coli*," *Planta* 213(3):483-487, last updated on Apr. 15, 2005, located at <http://www.ncbi.nlm.nih.gov/protein/CAC35696>, last visited on Nov. 1, 2011, 1 page.

GenBank Accession No. D86235.1, *Trichoderma reesei* cbhl Gene for Cellobiohydrolase I, Upstream Region, Takashima, S. et al. (1996). "Analysis of Crel Binding Sites in the *Trichoderma reesei* cbhl Upstreat Region," *FEMS Microbiol. Lett.* 145(3):361-366, last updated on Oct. 29, 1997, located at <http://www.ncbi.nlm.nih.gov/nuccore/D86235>, last visited on Feb. 27, 2012, 2 pages.

GenBank Accession No. NC 003901.1, *Methanosarcina mazei* Ga1 Chromosome, Complete Genome, Deppenmeir, U. et al. (2002). "The Genome of *Methanosarcina mazei*: Evidence for Lateral Gene Transfer Between Bacteria and Archaea," *J. Mol. Microbiol. Biotechnol.* 4(4):453-461, last updated on May 11, 2011, located at <http://www.ncbi.nlm.nih.gov/nuccore/NC_003901.1>, last visited on Oct. 17, 2011, 360 pages.

\* cited by examiner

Figure 1

1-
*atg*tgtgcgacctcttctcaatttactcagattaccgagcataattcccgtcgttccgcaaactatcagccaaa
cctgtggaatttcgaattcctgcaatccctggagaacgacctgaaagtggaaaagctggaggagaaagc
gaccaaactggaggaagaagttcgctgcatgatcaaccgtgtagacacccagccgctgtccctgctgga
gctgatcgacgatgtgcagcgcctgggtctgacctacaaatttgaaaaagacatcattaaagccctggaa
aacatcgtactgctggacgaaaacaaaaagaacaaatctgacctgcacgcaaccgctctgtctttccgtct
gctgcgtcagcacggtttcgaggtttctcaggatgttttgagcgtttcaaggataaagaaggtggtttcagcg
gtgaactgaaaggtgacgtccaaggcctgctgagcctgtatgaagcgtcttacctgggtttcgagggtgag
aacctgctggaggaggcgcgtaccttttccatcacccacctgaagaacaacctgaaagaaggcattaata
ccaaggttgcagaacaagtgagccacgccctggaactgccatatcaccagcgtctgcaccgtctggagg
cacgttggttcctggataaatacgaaccgaaagaaccgcatcaccagctgctgctggagctggcgaagct
ggattttaacatggtacagaccctgcaccagaaagagctgcaagatctgtcccgctggtggaccgagatg
ggcctggctagcaaactggattttgtacgcgaccgcctgatggaagtttatttctgggcactgggtatggcgc
cagacccgcagtttggtgaatgtcgcaaagctgttactaaaatgtttggtctggtgacgatcatcgatgacgt
gtatgacgtttatggcactctggacgaactgcaactgttcaccgatgctgtagagcgctgggacgttaacgct
attaacaccctgccggactatatgaaactgtgtttcctggcactgtacaacaccgttaacgacacgtcctattc
tattctgaaagagaaaggtcataacaacctgtcctatctgacgaaaagctggcgtgaactgtgcaaagcct
ttctgcaagaggcgaaatggtccaacaacaaaattatcccggcttttctccaagtacctggaaaacgccag
cgtttcctcctccggtgtagcgctgctggcgccgtcttactttccgtatgccagcagcaggaagacatctccg
accacgcgctgcgttccctgaccgacttccatggtctggtgcgttctagctgcgttatcttccgcctgtgcaac
gatctggccacctctgcggcggagctggaacgtggcgagactaccaattctatcattagctacatgcacga
aaacgatggtaccagcgaggaacaggcccgcgaagaactgcgtaaactgatcgacgccgaatggaaa
aagatgaatcgtgaacgcgttagcgactccaccctgctgcctaaagcgttcatggaaatcgcagttaacat
ggcacgtgtttcccactgcacctaccagtatggcgatggtctgggtcgcccagactacgcgactgaaaacc
gcatcaaactgctgctgattgaccctttcccgattaaccagctgatgtatgtc
taactgcag
(SEQ ID NO:1)

Figure 3A 1-
gtttgacagcttatcatcgactgcacggtgcaccaatgcttctggcgtcaggcagccatcggaagctgtggtatg
gctgtgcaggtcgtaaatcactgcataattcgtgtcgctcaaggcgcactcccgttctggataatgttttttgcgcc
gacatcataacggttctggcaaatattctgaaatgagctgttgacaattaatcatccggctcgtataatgtgtgga
attgtgagcggataacaatttcacacaggaaacagcgccgctgagaaaaagcgaagcggcactgctcttta
acaatttatcagacaatctgtgtgggcactcgaccggaattatcgattaactttattattaaaaattaaagaggtat
atattaatgtatcgattaaata<u>aggagg</u>aataaaccATGtgtgcgacctcttctcaatttactcagattaccgag
cataattcccgtcgttccgcaaactatcagccaaacctgtggaatttcgaattcctgcaatccctggagaacga
cctgaaagtggaaaagctggaggagaaagcgaccaaactggaggaagaagttcgctgcatgatcaaccgt
gtagacacccagccgctgtccctgctggagctgatcgacgatgtgcagcgcctgggtctgacctacaaatttg
aaaaagacatcattaaagccctggaaaacatcgtactgctggacgaaaacaaaaagaacaaatctgacct
gcacgcaaccgctctgtctttccgtctgctgcgtcagcacggtttcgaggtttctcaggatgttttgagcgtttcaa
ggataaagaaggtggtttcagcggtgaactgaaaggtgacgtccaaggcctgctgagcctgtatgaagcgtct
tacctgggtttcgagggtgagaacctgctggaggaggcgcgtaccttttccatcacccacctgaagaacaacc
tgaaagaaggcattaataccaaggttgcagaacaagtgagccacgccctggaactgccatatcaccagcgt
ctgcaccgtctggaggcacgttggttcctggataaatacgaaccgaaagaaccgcatcaccagctgctgctg
gagctggcgaagctggattttaacatggtacagaccctgcaccagaaagagctgcaagatctgtcccgctgg
tggaccgagatgggcctggctagcaaactggattttgtacgcgaccgcctgatggaagtttatttctgggcactg
ggtatggcgccagacccgcagtttggtaatgtcgcaaagctgttactaaaatgtttggtctggtgacgatcatc
gatgacgtgtatgacgtttatggcactctggacgaactgcaactgttcaccgatgctgtagagcgctgggacgtt
aacgctattaacaccctgccggactatatgaaactgtgtttcctggcactgtacaacaccgttaacgacacgtc
ctattctattctgaaagagaaaggtcataacaacctgtcctatctgacgaaaagctggcgtgaactgtgcaaag
cctttctgcaagaggcgaaatggtccaacaacaaaattatcccggctttctccaagtacctggaaaacgccag
cgtttcctcctccggtgtagcgctgctggcgccgtcttacttttccgtatgccagcagcaggaagacatctccgac
cacgcgctgcgttccctgaccgacttccatggtctggtgcgttctagctgcgttatcttccgcctgtgcaacgatct
ggccacctctgcggcggagctggaacgtggcgagactaccaattctatcattagctacatgcacgaaaacga
tggtaccagcgaggaacaggcccgcgaagaactgcgtaaactgatcgacgccgaatggaaaaagatgaa
tcgtgaacgcgttagcgactccaccctgctgcctaaagcgttcatggaaatcgcagttaacatggcacgtgtttc
ccactgcacctaccagtatggcgatggtctgggtcgcccagactacgcgactgaaaaccgcatcaaactgct
gctgattgaccctttcccgattaaccagctgatgtatgtc*TAA*ctgcagctggtaccatatgggaattcgaagct
ttctagaacaaaaactcatctcagaagaggatctgaatagcgccgtcgaccatcatcatcatcatcattgagttt
aaacggtctccagcttggctgttttggcggatgagagaagattttcagcctgatacagattaaatcagaacgca
gaagcggtctgataaaacagaatttgcctggcggcagtagcgcggtggtcccacctgacccccatgccgaact
cagaagtgaaacgccgtagcgccgatggtagtgtggggtctccccatgcgagagtagggaactgccaggc
atcaaataaaacgaaaggctcagtcgaaagactgggcctttcgttttatctgttgtttgtcggtgaacgctctcctg
agtaggacaaatccgccgggagcggatttgaacgttgcgaagcaacggcccgg

Figure 3B agggtggcgggcaggacgcccgccataaactgccaggcatcaaattaagcagaaggccatcctgac
ggatggccttttgcgtttctacaaactcttttgtttattttctaaatacattcaaatatgtatccgctcatgagac
aataaccctgataaatgcttcaataatattgaaaaaggaagagtatgagtattcaacatttccgtgtcgccc
ttattccctttttgcggcattttgccttcctgttttgctcacccagaaacgctggtgaaagtaaaagatgctga
agatcagttgggtgcacgagtgggttacatcgaactggatctcaacagcggtaagatccttgagagtttc
gccccgaagaacgttttccaatgatgagcacttttaaagttctgctatgtggcgcggtattatcccgtgttgac
gccgggcaagagcaactcggtcgccgcatacactattctcagaatgacttggttgagtactcaccagtca
cagaaaagcatcttacggatggcatgacagtaagagaattatgcagtgctgccataaccatgagtgata
acactgcggccaacttacttctgacaacgatcggaggaccgaaggagctaaccgcttttttgcacaacat
ggggatcatgtaactcgccttgatcgttgggaaccggagctgaatgaagccataccaaacgacgagc
gtgacaccacgatgcctgtagcaatggcaacaacgttgcgcaaactattaactggcgaactacttactct
agcttcccggcaacaattaatagactggatggaggcggataaagttgcaggaccacttctgcgctcggc
ccttccggctggctggtttattgctgataaatctggagccggtgagcgtgggtctcgcggtatcattgcagca
ctggggccagatggtaagccctcccgtatcgtagttatctacacgacggggagtcaggcaactatggatg
aacgaaatagacagatcgctgagataggtgcctcactgattaagcattggtaactgtcagaccaagttta
ctcatatatactttagattgatttaaaacttcatttttaatttaaaaggatcaggtgaagatccttttgataatct
catgaccaaaatcccttaacgtgagttttcgttccactgagcgtcagaccccgtagaaaagatcaaagga
tcttcttgagatccttttttctgcgcgtaatctgctgcttgcaaacaaaaaaaccaccgctaccagcggtggt
ttgtttgccggatcaagagctaccaactctttttccgaaggtaactggcttcagcagagcgcagataccaa
atactgtccttctagtgtagccgtagttaggccaccacttcaagaactctgtagcaccgcctacatacctcg
ctctgctaatcctgttaccagtggctgctgccagtggcgataagtcgtgtcttaccgggttggactcaagac
gatagttaccggataaggcgcagcggtcgggctgaacggggggttcgtgcacacagcccagcttggag
cgaacgacctacaccgaactgagatacctacagcgtgagctatgagaaagcgccacgcttcccgaag
ggagaaaggcggacaggtatccggtaagcggcagggtcggaacaggagagcgcacgagggagctt
ccaggggggaaacgcctggtatctttatagtcctgtcgggtttcgccacctctgacttgagcgtcgatttttgtg
atgctcgtcaggggggcggagcctatggaaaaacgccagcaacgcggcctttttacggttcctggccttt
gctggccttttgctcacatgttctttcctgcgttatcccctgattctgtggataaccgtattaccgcctttgagtga
gctgataccgctcgccgcagccgaacgaccgagcgcagcgagtcagtgagcgaggaagcggaaga
gcgcctgatgcggtattttctccttacgcatctgtgcggtatttcacaccgcatatggtgcactctcagtacaa
tctgctctgatgccgcatagttaagccagtatacactccgctatcgctacgtgactgggtcatggctgcgcc
ccgacacccgccaacacccgctgacgcgccctgacgggcttgtctgctcccggcatccgcttacagaca
agctgtgaccgtctccgggagctgcatgtgtcagaggttttcaccgtcatcaccgaaacgcgcgaggca
gcagatcaattcgcgcgcgaaggcgaagcggcatgcatttacgttgacaccatcgaatggtgcaaaac
ctttcgcggtatggcatgatagcgcccggaagagagtcaattcagggtggtgaatgtgaaaccagtaac
gttatacgatgtcgcagagtatgccggtgtctcttatcagaccgtttcccgcgtggtgaaccaggccagcc
acgtttctgcgaaaacgcgggaaaagtggaagcggcgatggcggagctgaattacattcccaaccgc
gtggcacaacaactggcgggcaaacagtcgttgctgattggcgttgccacctccagtctggccctgcacg
cgccgtcgcaaattgtcgcggcgattaaatctcgcgccgatcaactgggtgccagcgtggtggtgtcgat
ggtagaacgaagcggcgtcgaagcctgtaaagcggcggtgcacaatcttctcgcgcaacgcgtcagtg
ggctgatcattaactatccgctggatgaccaggatgccattgctgtggaagctgcct

Figure 3C

Gcactaatgttccggcgttatttcttgatgtctctgaccagacacccatcaacagtattattttctc
ccatgaagacggtacgcgactgggcgtggagcatctggtcgcattgggtcaccagcaaat
cgcgctgttagcgggcccattaagttctgtctcggcgcgtctgcgtctggctggctggcataaa
tatctcactcgcaatcaaattcagccgatagcggaacgggaaggcgactggagtgccatgt
ccggttttcaacaaaccatgcaaatgctgaatgagggcatcgttcccactgcgatgctggttg
ccaacgatcagatggcgctgggcgcaatgcgcgccattaccgagtccgggctgcgcgttg
gtgcggatatctcggtagtgggatacgacgataccgaagacagctcatgttatatcccgccg
tcaaccaccatcaaacaggattttcgcctgctggggcaaaccagcgtggaccgcttgctgc
aactctctcagggccaggcggtgaagggcaatcagctgttgcccgtctcactggtgaaaag
aaaaaccaccctggcgcccaatacgcaaaccgcctctccccgcgcgttggccgattcatta
atgcagctggcacgacaggtttcccgactggaaagcgggcagtgagcgcaacgcaatta
atgtgagttagcgcgaattgatctg
(SEQ ID NO:2)

Figure 5A 1-
ttctcatgtttgacagcttatcatcgataagctttaatgcggtagtttatcacagttaaattgctaacgcagtca
ggcaccgtgtatgaaatctaacaatgcgctcatcgtcatcctcggcaccgtcacccctggatgctgtaggca
taggcttggttatgccggtactgccgggcctcttgcgggatatccggatatagttcctcctttcagcaaaaaa
cccctcaagacccgtttagaggccccaagggttatgctagttattgctcagcggtggcagcagccaact
cagcttcctttcgggctttgttagcagccggatccctgcagttagacatacatcagctggttaatcgggaaa
gggtcaatcagcagcagtttgatgcggttttcagtcgcgtagtctgggcgacccagaccatcgccatactg
gtaggtgcagtgggaaacacgtgccatgttaactgcgatttccatgaacgctttaggcagcagggtggag
tcgctaacgcgttcacgattcatcttttccattcggcgtcgatcagtttacgcagttcttcgcgggcctgttcct
cgctggtaccatcgttttcgtgcatgtagctaatgatagaattggtagtctcgccacgttccagctccgccgc
agaggtggccagatcgttgcacaggcggaagataacgcagctagaacgcaccagaccatggaagtc
ggtcagggaacgcagcgcgtggtcggagatgtcttcctgctgctggcatacggaaaagtaagacggcg
ccagcagcgctacaccggaggaggaaacgctggcgttttccaggtacttggagaaagccgggataattt
tgttgttggaccatttcgcctcttgcagaaaggctttgcacagttcacgccagcttttcgtcagataggacag
gttgttatgacctttctctttcagaatagaataggacgtgtcgttaacggtgttgtacagtgccaggaaacac
agtttcatatagtccggcagggtgttaatagcgttaacgtcccagcgctctacagcatcggtgaacagttgc
agttcgtccagagtgccataaacgtcatacacgtcatcgatgatcgtcaccagaccaaacattttagtaac
agctttgcgacattcaccaaactgcgggtctggcgccatacccagtgcccagaaataaacttccatcagg
cggtcgcgtacaaaatccagtttgctagccaggcccatctcggtccaccagcgggacagatcttgcagct
ctttctggtgcagggtctgtaccatgttaaaatccagcttcgccagctccagcagcagctggtgatgcggtt
ctttcggttcgtatttatccaggaaccaacgtgcctccagacggtgcagacgctggtgatatggcagttcca
gggcgtggctcacttgttctgcaaccttggtattaatgccttctttcaggttgttcttcaggtgggtgatggaaa
aggtacgcgcctcctccagcaggttctcaccctcgaaacccaggtaagacgcttcatacaggctcagca
ggccttggacgtcacctttcagttcaccgctgaaaccaccttctttatccttgaaacgctcaaaaacatcctg
agaaacctcgaaaccgtgctgacgcagcagacggaaagacagagcggttgcgtgcaggtcagatttgt
tcttttttgttttcgtccagcagtacgatgttttccagggctttaatgatgtcttttttcaaatttgtaggtcagaccca
ggcgctgcacatcgtcgatcagctccagcagggacagcggctgggtgtctacacggttgatcatgcagc
gaacttcttcctccagtttggtcgctttctcctccagcttttccactttcaggtcgttctccagggattgcaggaat
tcgaaattccacaggtttggctgatagtttgcggaacgacgggaattatgctcggtaatctgagtaaattga
gaagaggtcgcacacatatgacgaccttcgatatggccgctgctgtgatgatgatgatgatgatgatgatg
atggcccatggtatatctccttcttaaagttaaacaaaattatttctagaggggaattgttatccgctcacaatt
cccctatagtgagtcgtattaatttcgcgggatcgagatctcgatcctctacgccggacgcatcgtggccgg
catcaccggcgccacaggtgcggttgctggcgcctatatcgccgacatcaccgatggggaagatcggg
ctcgccacttcgggctcatgagcgcttgtttcggcgtgggtatggtggcaggccccgtggccgggggact
gttgggcgccatctccttgcatgcaccattccttgcggcggcggtgctcaacggcctcaacctactactgg
gctgcttcctaatgcaggagtcgcataagggagagcgtcgagatcccggacaccatcgaatggcgcaa
aacctttcgcggtatggcatgatagcgcccggaagagagtcaattcagggtggtgaatgtgaaaccagt
aacgttatacgatgtcgcagagtatgccggtgtctcttatcagaccgtttcccgcgtggtgaaccaggcca
gccacgtttctgcgaaaacgcgggaaaaagtggaagcggcgatggcggagctgaattacattcccaac
cgcgtggcacaacaactggcgggcaaacagtcgttgctgattggcgttgccacctccagtctggccctgc
acgcgccgtcgcaaattgtcgcggcgattaaatct

Figure 5B cgcgccgatcaactgggtgccagcgtggtggtgtcgatggtagaacgaagcggcgtcgaagcctgta
aagcggcggtgcacaatcttctcgcgcaacgcgtcagtgggctgatcattaactatccgctggatgacc
aggatgccattgctgtggaagctgcctgcactaatgttccggcgttatttcttgatgtctctgaccagacac
ccatcaacagtattattttctcccatgaagacggtacgcgactgggcgtggagcatctggtcgcattgggt
caccagcaaatcgcgctgttagcgggcccattaagttctgtctcggcgcgtctgcgtctggctggctggc
ataaatatctcactcgcaatcaaattcagccgatagcggaacgggaaggcgactggagtgccatgtcc
ggttttcaacaaaccatgcaaatgctgaatgagggcatcgttcccactgcgatgctggttgccaacgatc
agatggcgctgggcgcaatgcgcgccattaccgagtccgggctgcgcgttggtgcggatatctcggta
gtgggatacgacgataccgaagacagctcatgttatatcccgccgttaaccaccatcaaacaggatttt
cgcctgctggggcaaaccagcgtggaccgcttgctgcaactctctcagggccaggcggtgaagggca
atcagctgttgcccgtctcactggtgaaaagaaaaaccacctggcgcccaatacgcaaaccgcctct
ccccgcgcgttggccgattcattaatgcagctggcacgacaggtttcccgactggaaagcgggcagtg
agcgcaacgcaattaatgtaagttagctcactcattaggcaccgggatctcgaccgatgcccttgagag
ccttcaacccagtcagctccttccggtgggcgcggggcatgactatcgtcgccgcacttatgactgtcttc
tttatcatgcaactcgtaggacaggtgccggcagcgctctgggtcattttcggcgaggaccgctttcgctg
gagcgcgacgatgatcggcctgtcgcttgcggtattcggaatcttgcacgccctcgctcaagccttcgtc
actggtcccgccaccaaacgtttcggcgagaagcaggccattatcgccggcatggcggccgacgcg
ctgggctacgtcttgctggcgttcgcgacgcgaggctggatggccttccccattatgattcttctcgcttccg
gcggcatcgggatgcccgcgttgcaggccatgctgtccaggcaggtagatgacgaccatcagggaca
gcttcaaggatcgctcgcggctcttaccagcctaacttcgatcactggaccgctgatcgtcacggcgattt
atgccgcctcggcgagcacatggaacgggttggcatggattgtaggcgccgccctataccttgtctgcct
ccccgcgttgcgtcgcggtgcatggagccgggccacctcgacctgaatggaagccggcggcacctcg
ctaacggattcaccactccaagaattggagccaatcaattcttgcggagaactgtgaatgcgcaaacc
aacccttggcagaacatatccatcgcgtccgccatctccagcagccgcacgcggcgcatctcgggca
gcgttgggtcctggccacgggtgcgcatgatcgtgctcctgtcgttgaggacccggctaggctggcggg
gttgccttactggttagcagaatgaatcaccgatacgcgagcgaacgtgaagcgactgctgctgcaaa
acgtctgcgacctgagcaacaacatgaatggtcttcggtttccgtgtttcgtaaagtctggaaacgcgga
agtcagcgccctgcaccattatgttccggatctgcatcgcaggatgctgctggctaccctgtggaacacc
tacatctgtattaacgaagcgctggcattgaccctgagtgattttctctggtcccgccgcatccataccgc
cagttgtttaccctcacaacgttccagtaaccgggcatgttcatcatcagtaacccgtatcgtgagcatcct
ctctcgtttcatcggtatcattaccccccatgaacagaaatccccccttacacggaggcatcagtgaccaaa
caggaaaaaaccgcccttaacatggcccgctttatcagaagccagacattaacgcttctggagaaact
caacgagctggacgcggatgaacaggcagacatctgtgaatcgcttcacgaccacgctgatgagcttt
accgcagctgcctcgcgcgtttcggtgatgacggtgaaaacctctgacacatgcagctcccggagacg
gtcacagcttgtctgtaagcggatgccgggagcagacaagcccgtcagggcgcgtcagcgggtgttg
gcgggtgtcggggcgcagccatgacccagtcacgtagcgatagcggagtgtatactggcttaactatg
cggcatcagagcagattgtactgagagtgcaccatatatgcggtgtgaaataccgcacagatgcgtaa
ggagaaaataccgcatcaggcgctcttccgcttcctcgctcactgactcgctgcgctcggtcgttcggctg
cggcgagcggtatcagctcactcaaaggcggtaatacggttatccacagaatcaggggataacgcag
gaaagaacatgtgagcaaaaggccagcaaaaggccaggaaccgtaaaaaggccgcgttgctggc
gtttttccataggctccgcccccctgacgagcatcacaaaaatcgacgctcaagtcaga

Figure 5C ggtggcgaaacccgacaggactataaagataccaggcgtttccccctggaagctccctcgtgcgctctcct
gttccgaccctgccgcttaccggatacctgtccgcctttctcccttcgggaagcgtggcgctttctcatagctca
cgctgtaggtatctcagttcggtgtaggtcgttcgctccaagctgggctgtgtgcacgaaccccccgttcagc
ccgaccgctgcgccttatccggtaactatcgtcttgagtccaacccggtaagacacgacttatcgccactgg
cagcagccactggtaacaggattagcagagcgaggtatgtaggcggtgctacagagttcttgaagtggtg
gcctaactacggctacactagaaggacagtatttggtatctgcgctctgctgaagccagttaccttcggaaa
aagagttggtagctcttgatccggcaaacaaaccaccgctggtagcggtggtttttttgtttgcaagcagcag
attacgcgcagaaaaaaaggatctcaagaagatcctttgatcttttctacggggtctgacgctcagtggaac
gaaaactcacgttaagggattttggtcatgagattatcaaaaggatcttcacctagatccttttaaattaaaa
atgaagttttaaatcaatctaaagtatatatgagtaaacttggtctgacagttaccaatgcttaatcagtgagg
cacctatctcagcgatctgtctatttcgttcatccatagttgcctgactccccgtcgtgtagataactacgatacg
ggagggcttaccatctggccccagtgctgcaatgataccgcgagacccacgctcaccggctccagatttat
cagcaataaaccagccagccggaagggccgagcgcagaagtggtcctgcaactttatccgcctccatcc
agtctattaattgttgccgggaagctagagtaagtagttcgccagttaatagtttgcgcaacgttgttgccattg
ctgcaggcatcgtggtgtcacgctcgtcgtttggtatggcttcattcagctccggttcccaacgatcaaggcg
agttacatgatcccccatgttgtgcaaaaaagcggttagctccttcggtcctccgatcgttgtcagaagtaagt
tggccgcagtgttatcactcatggttatggcagcactgcataattctcttactgtcatgccatccgtaagatgctt
ttctgtgactggtgagtactcaaccaagtcattctgagaatagtgtatgcggcgaccgagttgctcttgcccgg
cgtcaacacgggataataccgcgccacatagcagaactttaaaagtgctcatcattggaaaacgttcttcg
gggcgaaaactctcaaggatcttaccgctgttgagatccagttcgatgtaacccactcgtgcacccaactg
atcttcagcatctttactttcaccagcgtttctgggtgagcaaaaacaggaaggcaaaatgccgcaaaaa
agggaataagggcgacacggaaatgttgaatactcatactcttccttttcaatattattgaagcatttatcagg
gttattgtctcatgagcggatacatatttgaatgtatttagaaaaataaacaaatagggggttccgcgcacattt
ccccgaaaagtgccacctgacgtctaagaaaccattattatcatgacattaacctataaaaataggcgtatc
acgaggccctttcgtcttcaagaa (SEQ ID NO:5)

Figure 7A 1-
cccgtcttactgtcgggaattcgcgttggccgattcattaatgcagctggcacgacaggtttcccgactggaa
agcgggcagtgagcgcaacgcaattaatgtgagttagctcactcattaggcaccccaggctttacactttat
gcttccggctcgtatgttgtgtggaattgtgagcggataacaatttcacacaggaaacagctatgaccatgat
tacgccaagcttgtatcgattaaataaggaggaataaaccatgtgtgcgacctcttctcaatttactcagatta
ccgagcataattcccgtcgttccgcaaactatcagccaaacctgtggaatttcgaattcctgcaatccctgga
gaacgacctgaaagtggaaaagctggaggagaaagcgaccaaactggaggaagaagttcgctgcatg
atcaaccgtgtagacacccagccgctgtccctgctggagctgatcgacgatgtgcagcgcctgggtctgac
ctacaaatttgaaaagacatcattaaagccctggaaaacatcgtactgctggacgaaaacaaaagaa
caaatctgacctgcacgcaaccgctctgtcttccgtctgctgcgtcagcacggtttcgaggtttctcaggatgt
ttttgagcgtttcaaggataaagaaggtggtttcagcggtgaactgaaaggtgacgtccaaggcctgctga
gcctgtatgaagcgtcttacctgggtttcgagggtgagaacctgctggaggaggcgcgtacctttttccatcac
ccacctgaagaacaacctgaaagaaggcattaataccaaggttgcagaacaagtgagccacgccctgg
aactgccatatcaccagcgtctgcaccgtctggaggcacgttggttcctggataaatacgaaccgaaaga
accgcatcaccagctgctgctggagctggcgaagctggattttaacatggtacagaccctgcaccagaaa
gagctgcaagatctgtcccgctggtggaccgagatgggcctggctagcaaactggattttgtacgcgaccg
cctgatggaagtttatttctgggcactgggtatggcgccagacccgcagtttggtaatgtcgcaaagctgtt
actaaaatgtttggtctggtgacgatcatcgatgacgtgtatgacgtttatggcactctggacgaactgcaact
gttcaccgatgctgtagagcgctgggacgttaacgctattaacaccctgccggactatatgaaactgtgtttc
ctggcactgtacaacaccgttaacgacacgtccattctattctgaaagagaaaggtcataacaacctgtcc
tatctgacgaaaagctggcgtgaactgtgcaaagcctttctgcaagaggcgaaatggtccaacaacaaa
attatcccggctttctccaagtacctggaaaacgccagcgtttcctcctccggtgtagcgctgctggcgccgt
cttacttttccgtatgccagcagcaggaagacatctccgaccacgcgctgcgttccctgaccgacttccatg
gtctggtgcgttctagctgcgttatcttccgcctgtcaacgatctggccacctctgcggcggagctggaacgt
ggcgagactaccaattctatcattagctacatgcacgaaaacgatggtaccagcgaggaacaggcccgc
gaagaactgcgtaaactgatcgacgccgaatggaaaaagatgaatcgtgaacgcgttagcgactccacc
ctgctgcctaaagcgttcatggaaatcgcagttaacatggcacgtgtttcccactgcacctaccagtatggc
gatggtctgggtcgcccagactacgcgactgaaaaccgcatcaaactgctgctgattgacccttcccgatt
aaccagctgatgtatgtctaactgcaggtcgactctagaggatccccgggtaccgagctcgaattcactgg
ccgtcgttttacaacgtcgtgactgggaaaaccctggcgttacccaacttaatcgccttgcagcacatcccc
ctttcgccagctggcgtaatagcgaagaggcccgcaccgatcgcccttcccaacagttgcgcagcctgaa
tggcgaatggcgcctgatgcggtattttctccttacgcatctgtgcggtatttcacaccgcatatggtgcactct
cagtacaatctgctctgatgccgcatagttaagccagccccgacacccgccaacacccgctgacgagctt
agtaaagccctcgctagattttaatgcggatgttgcgattacttcgccaactattgcgataacaagaaaaag
ccagcctttcatgatatatctcccaatttgtgtagggcttattatgcacgcttaaaataataaaagcagacttg
acctgatagtttggctgtgagcaattatgtgcttagtgcatcaacgcttgagttaagccgcgccgcgaagcg
gcgtcggcttgaacgaattgttagacattatttgccgactaccttggtgatctcgcctttcacgtagtggacaaa
ttcttccaactgatctgcgcgcgaggccaagcgatcttcttcttgtccaagataagcctgtctagcttcaagtat
gacgggctgatactgggccggcaggcgctccattgcccagtcggcagcgacatccttcggcgcgattttgc
cggttactgcgctgtaccaaatgcgggacaacgtaagcactacatttcgctcatcgccagcccagtcgggc
ggcgagttccatag

Figure 7B cgttaaggtttcatttagcgcctcaaatagatcctgttcaggaaccggatcaaagagttcctccgccgctg
gacctaccaaggcaacgctatgttctcttgcttttgtcagcaagatagccagatcaatgtcgatcgtggct
ggctcgaagatacctgcaagaatgtcattgcgctgccattctccaaattgcagttcgcgcttagctggata
acgccacggaatgatgtcgtcgtgcacaacaatggtgacttctacagcgcggagaatctcgctctctcc
aggggaagccgaagtttccaaaaggtcgttgatcaaagctcgccgcgttgtttcatcaagccttacggtc
accgtaaccagcaaatcaatatcactgtgtggcttcaggccgccatccactgcggagccgtacaaatgt
acggccagcaacgtcggttcgagatggcgctcgatgacgccaactacctctgatagttgagtcgatact
tcggcgatcaccgcttccctcatgatgtttaactttgttttagggcgactgccctgctgcgtaacatcgttgct
gctccataacatcaaacatcgacccacggcgtaacgcgcttgctgcttggatgcccgaggcatagact
gtaccccaaaaaaacagtcataacaagccatgaaaaccgccactgcgccgttaccaccgctgcgttc
ggtcaaggttctggaccagttgcgtgagcgcatacgctacttgcattacagcttacgaaccgaacaggc
ttatgtccactgggttcgtgccttcatccgtttccacggtgtgcgtcacccggcaaccttgggcagcagcg
aagtcgaggcatttctgtcctggctggcgaacgagcgcaaggtttcggtctccacgcatcgtcaggcatt
ggcggccttgctgttcttctacggcaaggtgctgtgcacggatctgccctggcttcaggagatcggaaga
cctcggccgtcgcggcgcttgccggtggtgctgaccccggatgaagtggttcgcatcctcggttttctgga
aggcgagcatcgtttgttcgcccagcttctgtatggaacgggcatgcggatcagtgagggtttgcaactg
cgggtcaaggatctggatttcgatcacggcacgatcatcgtgcgggagggcaagggctccaaggatc
gggccttgatgttacccgagagcttggcacccagcctgcgcgagcaggggaattaattcccacgggttt
tgctgcccgcaaacgggctgttctggtgttgctagtttgttatcagaatcgcagatccggcttcagccggttt
gccggctgaaagcgctatttcttccagaattgccatgatttttttcccacgggaggcgtcactggctcccgt
gttgtcggcagctttgattcgataagcagcatcgcctgtttcaggctgtctatgtgtgactgttgagctgtaa
caagttgtctcaggtgttcaatttcatgttctagttgctttgttttactggtttcacctgttctattaggtgttacatg
ctgttcatctgttacattgtcgatctgttcatggtgaacagctttgaatgcaccaaaaactcgtaaaagctct
gatgtatctatctttttacaccgttttcatctgtgcatatggacagttttccctttgatatgtaacggtgaacagt
tgttctacttttgtttgttagtcttgatgcttcactgatagatacaagagccataagaacctcagatccttccgt
atttagccagtatgttctctagtgtggttcgttgttttgcgtgagccatgagaacgaaccattgagatcatac
ttactttgcatgtcactcaaaaattttgcctcaaaactggtgagctgaattttttgcagttaaagcatcgtgtag
tgttttttcttagtccgttatgtaggtaggaatctgatgtaatggttgttggtattttgtcaccattcattttatctggt
tgttctcaagttcggttacgagatccatttgtctatctagttcaacttggaaaatcaacgtatcagtcgggcg
gcctcgcttatcaaccaccaatttcatattgctgtaagtgtttaaatctttacttattggtttcaaaacccattgg
ttaagccttttaaactcatggtagttattttcaagcattaacatgaacttaaattcatcaaggctaatctctata
tttgccttgtgagttttcttttgtgttagttcttttaataaccactcataaatcctcatagagtatttgttttcaaaag
acttaacatgttccagattatatttatgaatttttttaactggaaaagataaggcaatatctcttcactaaaa
actaattctaattttttcgcttgagaacttggcatagtttgtccactggaaaatctcaaagcctttaaccaaag
gattcctgatttccacagttctcgtcatcagctctctggttgctttagctaatacaccataagcattttccctact
gatgttcatcatctgagcgtattggttataagtgaacgataccgtccgttctttccttgtagggttttcaatcgt
ggggttgagtagtgccacacagcataaaattagcttggtttcatgctccgttaagtcatagcgactaatcg
ctagttcatttgctttgaaaacaactaattcagacatacatctcaattggtctaggtgattttaatcactatac
caattgagatgggctagtcaatgataattactagtccttttcctttgagttgtgggtatctgta

Figure 7C

Aattctgctagacctttgctggaaaacttgtaaattctgctagaccctctgtaaattccgctagacctttgtg
tgtttttttgtttatattcaagtggttataatttatagaataaagaaagaataaaaaaagataaaaagaat
agatcccagccctgtgtataactcactactttagtcagttccgcagtattacaaaaggatgtcgcaaac
gctgtttgctcctctacaaaacagaccttaaaaccctaaaggcttaagtagcaccctcgcaagctcgg
gcaaatcgctgaatattccttttgtctccgaccatcaggcacctgagtcgctgtctttttcgtgacattcagtt
cgctgcgctcacggctctggcagtgaatgggggtaaatggcactacaggcgcctttatggattcatgc
aaggaaactacccataatacaagaaaagcccgtcacgggcttctcagggcgttttatggcgggtctg
ctatgtggtgctatctgacttttgctgttcagcagttcctgccctctgattttccagtctgaccacttcggatta
tcccgtgacaggtcattcagactggctaatgcacccagtaaggcagcggtatcatcaacaggctta (SEQ ID NO:7)

Figure 12A 1-
gaattgctccattttcttctgctatcaaaataacagactcgtgattttccaaacgagctttcaaaaaagcctctgcc
ccttgcaaatcggatgcctgtctataaaattcccgatattggttaaacagcggcgcaatggcggccgcatctgat
gtctttgcttggcgaatgttcatcttatttcttcctccctctcaataattttttcattctatcccttttctgtaaagtttattttc
agaatacttttatcatcatgctttgaaaaaatatcacgataatatccattgttctcacggaagcacacgcaggtca
tttgaacgaatttttcgacaggaatttgccgggactcaggagcatttaacctaaaaaagcatgacatttcagcat
aatgaacatttactcatgtctattttcgttcttttctgtatgaaaatagttatttcgagtctctacggaaatagcgagag
atgatatacctaaatagagataaaatcatctcaaaaaaatgggtctactaaaatattattccatctattacaataa
attcacagaatagtcttttaagtaagtctactctgaattttttaaaaggagagggtaaagagtgtgtgcgacctctt
ctcaatttactcagattaccgagcataattcccgtcgttccgcaaactatcagccaaacctgtggaatttcgaatt
cctgcaatccctggagaacgacctgaaagtggaaaagctggaggagaaagcgaccaaactggaggaag
aagttcgctgcatgatcaaccgtgtagacacccagccgctgtccctgctggagctgatcgacgatgtgcagcg
cctgggtctgacctacaaatttgaaaaagacatcattaaagccctggaaaacatcgtactgctggacgaaaa
caaaaagaacaaatctgacctgcacgcaaccgctctgtctttccgtctgctgcgtcagcacggtttcgaggtttc
tcaggatgtttttgagcgtttcaaggataaagaaggtggtttcagcggtgaactgaaaggtgacgtccaaggcc
tgctgagcctgtatgaagcgtcttacctgggtttcgagggtgagaacctgctggaggaggcgcgtaccttttcca
tcacccacctgaagaacaacctgaaagaaggcattaataccaaggttgcagaacaagtgagccacgccct
ggaactgccatatcaccagcgtctgcaccgtctggaggcacgttggttcctggataaatacgaaccgaaaga
accgcatcaccagctgctgctggagctggcgaagctggattttaacatggtacagaccctgcaccagaaaga
gctgcaagatctgtcccgctggtggaccgagatgggcctggctagcaaactggattttgtacgcgaccgcctg
atggaagtttattctgggcactgggtatggcgccagacccgcagtttggtgaatgtcgcaaagctgttactaaa
atgtttggtctggtgacgatcatcgatgacgtgtatgacgtttatggcactctggacgaactgcaactgttcaccg
atgctgtagagcgctgggacgttaacgctattaacaccctgccggactatatgaaactgtgtttcctggcactgt
acaacaccgttaacgacacgtcctattctattctgaaagagaaaggtcataacaacctgtcctatctgacgaaa
agctggcgtgaactgtgcaaagcctttctgcaagaggcgaaatggtccaacaacaaaattatcccggctttctc
caagtacctggaaaacgccagcgtttcctcctccggtgtagcgctgctggcgccgtcttactttccgtatgccag
cagcaggaagacatctccgaccacgcgctgcgttccctgaccgacttccatggtctggtgcgttctagctgcgtt
atcttccgcctgtgcaacgatctggccacctctgcggcggagctggaacgtggcgagactaccaattctatcat
tagctacatgcacgaaaacgatggtaccagcgaggaacaggcccgcgaagaactgcgtaaactgatcgac
gccgaatggaaaagatgaatcgtgaacgcgttagcgactccaccctgctgccta aagcgttcatggaaatc
gcagttaacatggcacgtgtttcccactgcacctaccagtatggcgatggtctgggtcgcccagactacgcga
ctgaaaaccgcatcaaactgctgctgattgaccctttcccgattaaccagctgatgtatgtcta aaaaaaaccg
gccttggccccgccggttttttattattttttcttcctccgcatgttcaatccgctccataatcgacggatggctccctct
gaaaattttaacgagaaacggcgggttgacccggctcagtcccgtaacggccaagtcctgaaacgtctcaat
cgccgcttcccggtttccggtcagctcaatgccgtaacggtcggcggcgttttcctgataccgggagacggcatt
cgtaatcggatcctctagagtcgacctgcaggcatgcaagcttt gcctcgcgcgtttcggtgatgacggtgaaa
acctctgacacatgcagctcccggagacggtcacagcttgtctgtaagcggatgccgggagcagacaagcc
cgtcagggcgcgtcagcgggtgttggcgggtgtcggggcgcagccatgacccagtcacgtagcgata

Figure 12B gcggagtgtatactggcttaactatgcggcatcagagcagattgtactgagagtgcaccatatgcggtgt
gaaataccgcacagatgcgtaaggagaaataccgcatcaggcgctcttccgcttcctcgctcactga
ctcgctgcgctcggtcgttcggctgcggcgagcggtatcagctcactcaaaggcggtaatacggttatcc
acagaatcaggggataacgcaggaaagaacatgtgagcaaaaggccagcaaaaggccaggaac
cgtaaaaaggccgcgttgctggcgttttccataggctccgcccccctgacgagcatcacaaaaatcga
cgctcaagtcagaggtggcgaaacccgacaggactataaagataccaggcgtttccccctggaagct
ccctcgtgcgctctcctgttccgaccctgccgcttaccggatacctgtccgcctttctcccttcgggaagcgt
ggcgctttctcaatgctcacgctgtaggtatctcagttcggtgtaggtcgttcgctccaagctgggctgtgt
cacgaaccccccgttcagcccgaccgctgcgccttatccggtaactatcgtcttgagtccaacccggta
agacacgacttatcgccactggcagcagccactggtaacaggattagcagagcgaggtatgtaggcg
gtgctacagagttcttgaagtggtggcctaactacggctacactagaaggacagtatttggtatctgcgct
ctgctgaagccagttaccttcggaaaaagagttggtagctcttgatccggcaaacaaaccaccgctggt
agcggtggtttttttgtttgcaagcagcagattacgcgcagaaaaaaaggatctcaagaagatcctttgat
cttttctacggggtctgacgctcagtggaacgaaaactcacgttaagggattttggtcatgagattatcaa
aaaggatcgaagtcggttcagaaaaagaaggatatggatctggagctgtaatataaaaaccttcttcaa
ctaacggggcaggttagtgacattagaaaaccgactgtaaaaagtacagtcggcattatctcatattata
aaagccagtcattaggcctatctgacaattcctgaatagagttcataaacaatcctgcatgataaccatc
acaaacagaatgatgtacctgtaaagatagcggtaaatatattgaattacctttattaatgaattttcctgct
gtaataatgggtagaaggtaattactattattattgatatttaagttaaacccagtaaatgaagtccatgga
ataatagaaagagaaaaagcattttcaggtataggtgttgttgggaaacaatttaaaagaaccattatatt
ctctacatcagaaaggtataaatcataaaactctttgaagtcattcttacaggagtccaaataccagag
aatgtttagatacaccatcaaaaattgtataaagtggctctaacttatcccaataacctaactctccgtcg
ctattgtaaccagttctaaaagctgtatttgagtttatcacccttgtcactaagaaaataaatgcagggtaa
aatttatatccttcttgttttatgtttcggtataaaacactaatatcaatttctgtggttatactaaaagtcgtttgtt
ggttcaaataatgattaaatatctcttttctcttccaattgtctaaatcaattttattaaagttcatttgatatgcct
cctaaatttttatctaaagtgaatttaggaggcttacttgtctgctttcttcattagaatcaatccttttttaaagtc
aatattactgtaacataaatatatatttaaaaatatcccactttatccaattttcgttgttgaactaatgggtg
ctttagttgaagaataaagaccacattaaaaaatgtggtcttttgtgtttttttaaaggatttgagcgtacgcg
aaaaatccttttctttctttcttatcttgataataagggtaactattgccggttgtccattcatggctgaactctgc
ttcctctgttgacatgacacacatcatctcaatatccgataggggccatcagtctgacgaccaagagag
ccataaacaccaatagccttaacatcatccccatatttatccaatattcgttccttaatttcatgaacaatctt
cattctttcttctctagtcattattattggtccattcactattctcattcccttttcagataattttagatttgcttttcta
aataagaatatttggagagcaccgttcttattcagctattaataactcgtcttcctaagcatccttcaatccttt
taataacaattatagcatctaatcttcaacaaactggcccgtttgttgaactactctttaataaaataatttttc
cgttcccaattccacattgcaataatagaaaatccatcttcatcggcttttcgtcatcatctgtatgaatcaa
atcgccttcttctgtgtcatcaaggtttaattttttatgtatttcttttaacaaaccaccataggagattaaccttt
acggtgtaaaccttcctccaaatcagacaaacgtttcaaattctttcttcatcatcggtcataaaatccgta
tcctttacaggatattttgcagtttcgtcaattgccgattgtatatccgatttatatttattttcggtcgaatcattt
gaacttttacatttggatcatagtctaatttcattgccttttccaaaattgaatccattgttt

Figure 12C ttgattcacgtagttttctgttattctaaaataagttggttccacacataccattacatgcatgtgctgattata
agaattatctttattatttattgtcacatccgttgcacgcataaaaccaacaagatttttattaatttttttatatt
gcatcattcggcgaaatccttgagccatatctgtcaaactcttatttaattcttcgccatcataaacattttta
actgttaatgtgagaaacaaccaacgaactgttggcttttgtttaataacttcagcaacaaccttttgtgac
tgaatgccatgtttcattgctctcctccagttgcacattggacaaagcctggatttgcaaaaccacactcg
ataccactttctttcgcctgtttcacgattttgtttatactctaatatttcagcacaatcttttactctttcagccttt
ttaaattcaagaatatgcagaagttcaaagtaatcaacattagcgattttcttttctctccatggtctcacttt
tccacttttgtcttgtccactaaaacccttgattttcatctgaataaatgctactattaggacacataatatt
aaaagaaaccccccatctatttagttatttgtttagtcacttataactttaacagatggggttttttctgtgcaac
caattttaagggttttcaatactttaaaacacatacataccaacacttcaacgcacctttcagcaactaa
aataaaaatgacgttatttctatatgtatcaagataagaaagaacaagttcaaaaccatcaaaaaaag
acaccttttcaggtgctttttttattttataaactcattccctgatctcgacttcgttctttttttacctctcggttatg
agttagttcaaattcgttcttttaggttctaaatcgtgttttcttggaattgtgctgttttatcctttaccttgtcta
caaaccccttaaaaacgttttaaaggcttttaagccgtctgtacgttccttaag (SEQ ID NO:57)

Figure 13

ATGTGTGCAACCTCCTCCCAGTTTACTCAGATTACCGAGCATAATTCT
CGACGATCTGCTAACTACCAGCCGAACCTTTGGAACTTTGAGTTTCT
CCAGTCTCTCGAAAATGACCTGAAGGTGGAAAAGCTCGAGGAGAAG
GCGACCAAACTCGAGGAGGAGGTGCGATGTATGATCAACAGAGTTG
ACACCCAACCCCTGTCTTTGCTGGAGCTGATCGACGATGTGCAGCG
GTTGGGTTTGACTTATAAATTCGAGAAGGACATTATCAAGGCACTGG
AGAACATTGTGCTCCTCGACGAGAACAAGAAGAACAAGTCTGATCTT
CACGCTACCGCTCTCTTTCCGACTTCTTCGACAACACGGCTTCGA
GGTGTCGCAGGACGTCTTCGAGAGATTTAAGGACAAGGAGGGAGGA
TTTAGCGGCGAGCTGAAGGGAGACGTTCAGGGTCTTCTCTCCTTGT
ACGAGGCGTCCTACCTGGGATTCGAGGGAGAGAACCTCCTGGAGG
AAGCTCGTACATTTTCCATCACTCACCTTAAGAATAACCTTAAGGAGG
GAATTAACACCAAGGTGGCCGAGCAGGTTTCTCACGCCCTGGAGCT
CCCCTACCACCAACGGCTCCATAGACTGGAGGCTCGTTGGTTCCTG
GACAAATATGAGCCAAAGGAGCCTCATCATCAGTTGCTGTTGGAGTT
GGCCAAGCTGGACTTCAATATGGTTCAGACGCTGCACCAAAAGGAG
TTGCAGGACCTGTCTCGATGGTGGACCGAGATGGGATTGGCCTCGA
AGCTGGATTTTGTCCGTGACCGACTTATGGAGGTCTATTTTGGGCC
CTTGGAATGGCGCCTGACCCCAGTTCGGAGAGTGCCGGAAGGCG
GTGACGAAGATGTTCGGTCTTGTGACTATCATCGACGACGTCTACGA
TGTCTACGGCACACTCGACGAGTTGCAGCTGTTCACTGACGCCGTC
GAGCGATGGGATGTGAACGCCATTAATACTCTCCCTGACTATATGAA
GCTGTGCTTCCTGGCTCTGTACAACACTGTCAACGATACCTCGTACT
CTATCCTCAAGGAGAAGGGACACAACAATCTCTCCTACTTGACCAAA
TCCTGGCGAGAACTGTGCAAGGCTTTTCTGCAGGAGGCTAAATGGT
CCAATAACAAGATCATTCCTGCTTTTTCTAAATACCTGGAAAATGCCT
CGGTGTCGAGCTCTGGCGTCGCCCTTCTGGCCCCTTCCTACTTCTC
CGTCTGCCAGCAGCAGGAGGATATTTCCGATCATGCTCTTAGATCGC
TGACCGATTTTCACGGCCTCGTGCGATCTTCCTGCGTGATTTTCGG
TTGTGTAATGACCTTGCGACCTCTGCTGCTGAGCTGGAACGAGGCG
AGACTACAAATTCCATTATTTCTTACATGCACGAAAACGATGGAACAT
CTGAAGAACAGGCTAGAGAGGAACTGCGAAAGTTGATCGACGCCGA
GTGGAAGAAGATGAACAGAGAGCGGGTGTCCGACTCTACCCTGCTT
CCCAAGGCCTTCATGGAGATCGCCGTGAACATGGCTCGAGTTTCCC
ATTGTACTTACCAGTACGGTGACGGCCTGGGTCGTCCGGACTACGC
TACAGAGAACCGAATCAAGCTGCTGCTCATCGACCCCTTCCCTATCA
ACCAATTGATGTACGTGTAA (SEQ ID NO:8)

Figure 15A

```
   1 TCGACCGGTG AGAAGAACAG CATCGGGACA AGGGAAGGAA GAACAAAGAC AAAGAAAACA
  61 AAAGAAAGCA ATTGAAAACA AAACAAAACA ATTTTCATTC CTTCTCTTAT CATTCCTTTT
 121 CTTTTCTTTT CTCTCATTCA ACGCACTCCA TCGTATCCGT ATTCCTCTTA TTTTTTCTCT
 181 TTCTCTATAT CCATTTCTTT CTCTCTAGGT GTGTCCTCTC TCTCTCTTCA ATTTCTCTAC
 241 TCCGCATTCC AACGCATCCT TCCCCCAACC TCCCATTTCC TCCTTACGGC CCGATAGCGA
 301 TCGTCTTTCC CTCGCTATCA CTCGCTACCG GCCCCTCCTC TGCACCGTAA CCTCCTACGT
 361 ATTTACCATA TCATAAAGTT TTTTCCGACG CTTATCGCTG ACCCCCTGTC GCCCTCCTAT
 421 TGGCTTCCGG ATTATCTTCT TGTCCATAAG GTGATCCATG CTTCCTGAAG ATTCCCGAAA
 481 TGTGTCCACT TTGGCGGGGA ATCATTCCAT CCACTTCTTT CTCTCTCGCT TTCCTCATTC
 541 GGCGCTCCCC TTCCGCGTCT CATTGGTCTT CCGCTCCGTT TTTGCTTTGC CGATGTTACT
 601 TGGGGAGAGG TGCGATAATC CTTTCGCAAA AACTCGGTTT GACGCCTCCC ATGGTATAAA
 661 TAGTGGGTGG TGGACAGGTG CCTTCGCTTT TCTTTAAGCA AGAGAATCCC ATTGTCTTGA
 721 CTATCACGAA TTCACATACA TTATGAAGAT CACCGCTGTC ATTGCCCTTT TATTCTCACT
 781 TGCTGCTGCC TCACCTATTC CAGTTGCCGA TCCTGGTGTG GTTTCAGTTA GCAAGTCATA
 841 TGCTGATTTC CTTCGTGTTT ACCAAAGTTG GAACACTTTT GCTAATCCTG ATAGACCCAA
 901 CCTTAAGAAG AGAAATGATA CACCTGCAAG TGGATATCAA GTTGAAAAAG TCGTAATTTT
 961 GTCACGTCAC GGTGTTAGGG CCCCTACAAA AATGACTCAA ACCATGCGTG ATGTCACTCC
1021 TAATACATGG CCAGAATGGC CCGTTAAATT AGGATATATT ACACCAAGAG GTGAACACTT
1081 GATATCACTT ATGGGCGGTT TTTACCGTCA AAAATTCCAG CAACAAGGAA TCCTTTCTCA
1141 GGGCTCCTGT CCTACTCCTA ACTCCATATA TGTCTGGGCT GACGTCGATC AGCGTACTTT
1201 AAAAACTGGT GAAGCATTCC TTGCTGGTTT GGCACCACAA TGTGGCTTGA CAATTCATCA
1261 CCAACAAAAT CTTGAGAAAG CTGATCCTCT TTTTCATCCC GTTAAAGCTG GAACCTGCTC
1321 TATGGATAAA ACTCAAGTTC AACAAGCTGT TGAGAAGGAG GCACAAACTC CTATAGATAA
1381 TTTGAATCAA CATTACATCC CCTTTTTAGC TTTAATGAAT ACAACATTAA ATTTTAGTAC
1441 TTCTGCCTGG TGCCAAAAAC ACTCTGCTGA TAAATCCTGT GACCTAGGTT TATCCATGCC
1501 TTCTAAATTG TCCATAAAAG ATAATGGTAA CAAGGTCGCA TTGGATGGAG CTATTGGTCT
1561 ATCCTCTACT TTGGCCGAGA TTTTTCTTCT TGAATATGCT CAAGGCATGC CTCAAGCTGC
1621 TTGGGGTAAC ATCCACTCAG AGCAAGAGTG GGCTTCCTTG CTAAAGTTGC ATAATGTTCA
1681 ATTCGATTTG ATGGCCCGAA CACCTTATAT TGCTCGACAT AACGGTACTC CTTTATTGCA
1741 AGCTATATCA AATGCCCTTA ATCCCAACGC CACTGAATCA AAACTTCCAG ATATTTCACC
1801 TGATAACAAA ATATTGTTCA TTGCAGGTCA TGACACAAAT ATTGCTAATA TAGCCGGCAT
1861 GTTAAATATG CGTTGGACAT TACCAGGTCA ACCAGATAAT ACTCCTCCAG GTGGTGCCCT
1921 AGTATTTGAA CGTCTTGCTG ATAAAAGTGG AAAACAATAT GTTTCTGTAT CTATGGTTTA
1981 TCAAACACTA GAACAACTTC GATCACAGAC TCCCCTTTCT CTAAATCAGC CTGCCGGATC
2041 TGTTCAACTT AAAATTCCAG GTTGCAATGA TCAAACAGCC GAGGGTTACT GTCCTCTTTC
2101 CACTTTTACA AGAGTTGTTT CCCAATCTGT TGAACCTGGA TGCCAACTTC AATAATGAGG
2161 ATCCAAGTAA GGGAATGAGA ATGTGATCCA CTTTTAATTC CTAATGAATA CATGCCTATA
2221 GTTCTTTTCT TTTGTTCTTT ATGTCGTTTT TCGATGGTAC GGCCGTTGTC AATCTCAGTT
2281 TGTGTGCTTG GTTGCAGCTT GGTTTCAAAT CTGTTCATCT CATGAATCTT TTACCATTTC
2341 ACCACACGTT TATACCATTC TCTCATAGAA TCTTCATCAA ACCATCTCGG GGTTAGAGTG
2401 GAAAGAAAGT CTTGTTCTTT TATTTCCTTT TTTCCATCTT CAAGGCTTTT CTTTTCTTCC
2461 TCCTCCTCGT TCATCTTGAG GTTTGACGTG TCTGTTTAGA ATTTTGAGCT GTTGCAGCAT
2521 CTTATTTTTT GTTTTGCGAA AACGAAGCGC TTTACTCTCT TCATCAGTTG GACGATTGTA
2581 CCTTTGAAAA CCAACTACTT TTGCATGTTT TGTATAGAAA TCAATGATAT TAGAATCCCA
2641 TCCTTTAATT TCTTTCAAAG TAGTTGAGCT ATAGTTAAGT GTAAGGGCCC TACTGCGAAA
2701 GCATTTGCCA AGGATGTTTT CATTAATCAA GAACGAAAGT TAGGGGATCG AAGACGATCA
2761 GATACCGTCG TAGTCTTAAC CATAAACTAT GCCGACTAGG GATCGGGCAA TGTTTCATTT
2821 ATCGACTTGC TCGGCACCTT ACGAGAAATC AAAGTCTTTG GGTTCCGGGG GGAGTATGGT
2881 CGCAAGGCTG AAACTTAAAG GAATTGACGG AAGGGCACCA CAATGGAGTG GAGCCTGCGG
2941 CTTAATTTGA CTCAACACGG GGAAACTCAC CAGGTCCAGA CATAGTAAGG ATTGACAGAT
3001 TGAGAGCTCT TTCTTGATTC TATGGGTGGT GGTGCATGGC CGTTCTTAGT TGGTGGAGTG
3061 ATTTGTCTGC TTAATTGCGA TAACGAACGA GACCTTAACC TGCTAAATAG CTGGATCAGC
3121 CATTTTGGCT GATCATTAGC TTCTTAGAGG GACTATTGGC ATAAAGCCAA TGGAAGTTTG
3181 AGGCAATAAC AGGTCTGTGA TGCCCTTAGA TGTTCTGGGC CGCACGCGCG CTACACTGAC
3241 GGAGCCAACG AGTTGAAAAA AATCTTTTGA TTTTTTATCC TTGGCCGGAA GGTCTGGGTA
3301 ATCTTGTTAA ACTCCGTCGT GCTGGGGATA GAGCATTGCA ATTATTGCGG CCGCTCCTCA
3361 ATTCGATGTT GCAGATTTTA CAAGTTTTTA AAATGTATTT CATTATTACT TTTTATATGC
3421 CTAATAAAAA AGCCATAGTT TAATCTATAG ATAACTTTTT TTCCAGTGCA CTAACGGACG
```

Figure 15B

```
3481 TTACATTCCC ATACAAAACT GCGTAGTTAA AGCTAAGGAA AAGTTAATAT CATGTTAATT
3541 AAATACGCTA TTTACAATAA GACATTGAAC TCATTTATAT CGTTAATAT GAATAACCAA
3601 TTTCAGCGAA TTTTTAACAA ACATCGTTCA CCTCGTTTAA GGATATCTTG TGTATGGGGT
3661 GTTGACTTGC TTTATCGAAT AATTACCGTA CCTGTAATTG GCTTGCTGGA TATAGCGGTA
3721 GTCTAATATC TAGCAAAAAT CTTTTGGGTG AAAAGGCTTG CAATTTCACG ACACCGAACT
3781 ATTTGTCATT TTTTAATAAG GAAGTTTTCC ATAAATTCCT GTAATTCTCG GTTGATCTAA
3841 TTGAAAAGAG TAGTTTTGCA TCACGATGAG GAGGGCTTTT GTAGAAAGAA ATACGAACGA
3901 AACGAAAATC AGCGTTGCCA TCGCTTTGGA CAAAGCTCCC TTACCTGAAG AGTCGAATTT
3961 TATTGATGAA CTTATAACTT CCAAGCATGC AAACCAAAAG GGAGAACAAG TAATCCAAGT
4021 AGACACGGGA ATTGGATTCT TGGATCACAT GTATCATGCA CTGGCTAAAC ATGCAGGCTG
4081 GAGCTTACGA CTTTACTCAA GAGGTGATTT AATCATCGAT GATCATCACA CTGCAGAAGA
4141 TACTGCTATT GCACTTGGTA TTGCATTCAA GCAGGCTATG GGTAACTTTG CCGGCGTTAA
4201 AAGATTTGGA CATGCTTATT GTCCACTTGA CGAAGCTCTT TCTAGAAGCG TAGTTGACTT
4261 GTCGGGACGG CCCTATGCTG TTATCGATTT GGGATTAAAG CGTGAAAAGG TTGGGGAATT
4321 GTCCTGTGAA ATGATCCCTC ACTTACTATA TTCCTTTTCG GTAGCAGCTG GAATTACTTT
4381 GCATGTTACC TGCTTATATG GTAGTAATGA CCATCATCGT GCTGAAAGCG CTTTTAAATC
4441 TCTGGCTGTT GCCATGCGCG CGGCTACTAG TCTTACTGGA AGTTCTGAAG TCCCAAGCAC
4501 GAAGGGAGTG TTGTAAAGAT GAATTGGATT ATGTCAGGAA AAGAACGACA ATTTTGCATC
4561 CAAATTGTCT AAATTTTAGA GTTGCTTGAA AACAATAGAA CCTTACTTGC TTTATAATTA
4621 CGTTAATTAG AAGCGTTATC TCGTGAAGGA ATATAGTACG TAGCCGTATA AATTGAATTG
4681 AATGTTCAGC TTATAGAATA GAGACACTTT GCTGTTCAAT GCGTCGTCAC TTACCATACT
4741 CACTTTATTA TACGACTTTA AGTATAAACT CCGCGGTTAT GGTAAAATTA ATGATGCACA
4801 AACGTCCGAT TCCATATGGG TACACTACAA TTAAATACTT TTAAGCTGAT CCCCCACACA
4861 CCATAGCTTC AAAATGTTTC TACTCCTTTT TTACTCTTCC AGATTTTCTC GGACTCCGCG
4921 CATCGCCGTA CCACTTCAAA ACACCCAAGC ACAGCATACT AAATTTTCCC TCTTTCTTCC
4981 TCTAGGGTGT CGTTAATTAC CCGTACTAAA GGTTTGGAAA AGAAAAAAGA GACCGCCTCG
5041 TTTCTTTTTC TTCGTCGAAA AAGGCAATAA AAATTTTTAT CACGTTTCTT TTTCTTGAAA
5101 TTTTTTTTTT TAGTTTTTTT CTCTTTCAGT GACCTCCATT GATATTTAAG TTAATAAACG
5161 GTCTTCAATT TCTCAAGTTT CAGTTTCATT TTTCTTGTTC TATTACAACT TTTTTTACTT
5221 CTTGTTCATT AGAAAGAAAG CATAGCAATC TAATCTAAGG GCGGTGTTGA CAATTAATCA
5281 TCGGCATAGT ATATCGGCAT AGTATAATAC GACAAGGTGA GGAACTAAAC CATGGCCAAG
5341 TTGACCAGTG CCGTTCCGGT GCTCACCGCG CGCGACGTCG CCGGAGCGGT CGAGTTCTGG
5401 ACCGACCGGC TCGGGTTCTC CCGGGACTTC GTGGAGGACG ACTTCGCCGG TGTGGTCCGG
5461 GACGACGTGA CCCTGTTCAT CAGCGCGGTC CAGGACCAGG TGGTGCCGGA CAACACCCTG
5521 GCCTGGGTGT GGGTGCGCGG CCTGGACGAG CTGTACGCCG AGTGGTCGGA GGTCGTGTCC
5581 ACGAACTTCC GGGACGCCTC CGGGCCGGCC ATGACCGAGA TCGGCGAGCA GCCGTGGGGG
5641 CGGGAGTTCG CCCTGCGCGA CCCGGCCGGC AACTGCGTGC ACTTCGTGGC CGAGGAGCAG
5701 GACTGACACG TCCGACGGCG GCCCACGGGT CCCAGGCCTC GGAGATCCGT CCCCCTTTTC
5761 CTTTGTCGAT ATCATGTAAT TAGTTATGTC ACGCTTACAT TCACGCCCTC CCCCCACATC
5821 CGCTCTAACC GAAAAGGAAG GAGTTAGACA ACCTGAAGTC TAGGTCCCTA TTTATTTTTT
5881 TATAGTTATG TTAGTATTAA GAACGTTATT TATATTTCAA ATTTTTCTTT TTTTTCTGTA
5941 CAGACGCGAG CTTCCCAGTA AATGTGCCAT CTCGTAGGCA GAAAACGGTT CCCCCGTAGG
6001 GTCTCTCTCT TGGCCTCCTT TCTAGGTCGG GCTGATTGCT CTTGAAGCTC TCTAGGGGGG
6061 CTCACACCAT AGGCAGATAA CGTTCCCCAC CGGCTCGCCT CGTAAGCGCA CAAGGACTGC
6121 TCCCAAAGAT CCTAGGCGGG ATTTTGCCGA TTTCGGCCTA AAGGAACCGG AACACGTAGA
6181 AAGCCAGTCC GCAGAAACGG TGCTGACCCG GGATGAATGT CAGCTACTGG GCTATCTGGA
6241 CAAGGGAAAA CGCAAGCGCA AAGAGAAAGC AGGTAGCTTG CAGTGGGCTT ACATGGCGAT
6301 AGCTAGACTG GGCGGTTTTA TGGACAGCAA GCGAACCGGA ATTGCCAGCT GGGGCGCCCT
6361 CTGGTAAGGT TGGGAAGCCC TGCAAAGTAA ACTGGATGGC TTTCTTGCCG CCAAGGATCT
6421 GATGGCGCAG GGGATCAAGA TCTGATCAAG AGACAGGATG AGGATCGTTT CGCATGATTG
6481 AACAAGATGG ATTGCACGCA GGTTCTCCGG CCGCTTGGGT GGAGAGGCTA TTCGGCTATG
6541 ACTGGGCACA ACAGACAATC GGCTGCTCTG ATGCCGCCGT GTTCCGGCTG TCAGCGCAGG
6601 GGCGCCCGGT TCTTTTTGTC AAGACCGACC TGTCCGGTGC CCTGAATGAA CTGCAGGACG
6661 AGGCAGCGCG GCTATCGTGG CTGGCCACGA CGGGCGTTCC TTGCGCAGCT GTGCTCGACG
6721 TTGTCACTGA AGCGGGAAGG GACTGGCTGC TATTGGGCGA AGTGCCGGGG CAGGATCTCC
6781 TGTCATCTCG CCTTGCTCCT GCCGAGAAAG TATCCATCAT GGCTGATGCA ATGCGGCGGC
6841 TGCATACGCT TGATCCGGCT ACCTGCCCAT TCGACCACCA AGCGAAACAT CGCATCGAGC
6901 GAGCACGTAC TCGGATGGAA GCCGGTCTTG TCGATCAGGA TGATCTGGAC GAAGAGCATC
6961 AGGGGCTCGC GCCAGCCGAA CTGTTCGCCA GGCTCAAGGC GCGCATGCCC GACGGCGAGG
```

Figure 15C

```
7021 ATCTCGTCGT GATCCATGGC GATGCCTGCT TGCCGAATAT CATGGTGGAA AATGGCCGCT
7081 TTTCTGGATT CAACGACTGT GGCCGGCTGG GTGTGGCGGA CCGCTATCAG GACATAGCGT
7141 TGGATACCCG TGATATTGCT GAAGAGCTTG GCGGCGAATG GGCTGACCGC TTCCTCGTGC
7201 TTTACGGTAT CGCCGCTCCC GATTCGCAGC GCATCGCCTT CTATCGCCTT CTTGACGAGT
7261 TCTTCTGAAT TGAAAAAGGT ACCAAGTTTA CTCATATATA CTTTAGATTG ATTTAAAACT
7321 TCATTTTTAA TTTAAAAGGA TCTAGGTGAA GATCCTTTTT GATAATCTCA TGACCAAAAT
7381 CCCTTAACGT GAGTTTTCGT TCCACTGAGC GTCAGACCCC GTAGAAAAGA TCAAAGGATC
7441 TTCTTGAGAT CCTTTTTTTC TGCGCGTAAT CTGCTGCTTG CAAACAAAAA AACCACCGCT
7501 ACCAGCGGTG GTTTGTTTGC CGGATCAAGA GCTACCAACT CTTTTTCCGA AGGTAACTGG
7561 CTTCAGCAGA GCGCAGATAC CAAATACTGT CCTTCTAGTG TAGCCGTAGT TAGGCCACCA
7621 CTTCAAGAAC TCTGTAGCAC CGCCTACATA CCTCGCTCTG CTAATCCTGT TACCAGTGGC
7681 TGCTGCCAGT GGCGATAAGT CGTGTCTTAC CGGGTTGGAC TCAAGACGAT AGTTACCGGA
7741 TAAGGCGCAG CGGTCGGGCT GAACGGGGGG TTCGTGCACA CAGCCCAGCT TGGAGCGAAC
7801 GACCTACACC GAACTGAGAT ACCTACAGCG TGAGCATTGA GAAAGCGCCA CGCTTCCCGA
7861 AGGGAGAAAG GCGGACAGGT ATCCGGTAAG CGGCAGGGTC GGAACAGGAG AGCGCACGAG
7921 GGAGCTTCCA GGGGGAAACG CCTGGTATCT TTATAGTCCT GTCGGGTTTC GCCACCTCTG
7981 ACTTGAGCGT CGATTTTTGT GATGCTCGTC AGGGGGGCGG AGCCTATGGA AAAACGCCAG
8041 CAACGCGGCC TTTTTACGGT TCCTGGCCTT TTGCTGGCCT TTTGCTCACA TGTTCTTTCC
8101 TGCGTTATCC CCTGATTCTG TGGATAACCG TATTACCGCC TTTGAGTGAG CTGATACCGC
8161 TCGCCGCAGC CGAACGACCG AGCGCAGCGA G
```
(SEQ ID NO:11)

Figure 16

```
   1 GAATTCAAAA CAAAATGTGT GCAACCTCCT CCCAGTTTAC TCAGATTACC GAGCATAATT
  61 CTCGACGATC TGCTAACTAC CAGCCGAACC TTTGGAACTT TGAGTTTCTC CAGTCTCTCG
 121 AAAATGACCT GAAGGTGGAA AAGCTCGAGG AGAAGGCGAC CAAACTCGAG GAGGAGGTGC
 181 GATGTATGAT CAACAGAGTT GACACCCAAC CCCTGTCTTT GCTGGAGCTG ATCGACGATG
 241 TGCAGCGGTT GGGTTTGACT TATAAATTCG AGAAGGACAT TATCAAGGCA CTGGAGAACA
 301 TTGTGCTCCT CGACGAGAAC AAGAAGAACA AGTCTGATCT TCACGCTACC GCTCTCTCTT
 361 TCCGACTTCT TCGACAACAC GGCTTCGAGG TGTCGCAGGA CGTCTTCGAG AGATTTAAGG
 421 ACAAGGAGGG AGGATTTAGC GGCGAGCTGA AGGGAGACGT TCAGGGTCTT CTCTCCTTGT
 481 ACGAGGCGTC CTACCTGGGA TTCGAGGGAG AGAACCTCCT GGAGGAAGCT CGTACATTTT
 541 CCATCACTCA CCTTAAGAAT AACCTTAAGG AGGGAATTAA CACCAAGGTG GCCGAGCAGG
 601 TTTCTCACGC CCTGGAGCTC CCCTACCACC AACGGCTCCA TAGACTGGAG GCTCGTTGGT
 661 TCCTGGACAA ATATGAGCCA AAGGAGCCTC ATCATCAGTT GCTGTTGGAG TTGGCCAAGC
 721 TGGACTTCAA TATGGTTCAG ACGCTGCACC AAAAGGAGTT GCAGGACCTG TCTCGATGGT
 781 GGACCGAGAT GGGATTGGCC TCGAAGCTGG ATTTTGTCCG TGACCGACTT ATGGAGGTCT
 841 ATTTTTGGGC CCTTGGAATG GCGCCTGACC CCCAGTTCGG AGAGTGCCGG AAGGCGGTGA
 901 CGAAGATGTT CGGTCTTGTG ACTATCATCG ACGACGTCTA CGATGTCTAC GGCACACTCG
 961 ACGAGTTGCA GCTGTTCACT GACGCCGTCG AGCGATGGGA TGTGAACGCC ATTAATACTC
1021 TCCCTGACTA TATGAAGCTG TGCTTCCTGG CTCTGTACAA CACTGTCAAC GATACCTCGT
1081 ACTCTATCCT CAAGGAGAAG GGACACAACA ATCTCTCCTA CTTGACCAAA TCCTGGCGAG
1141 AACTGTGCAA GGCTTTTCTG CAGGAGGCTA ATGGTCCAA TAACAAGATC ATTCCTGCTT
1201 TTTCTAAATA CCTGGAAAAT GCCTCGGTGT CGAGCTCTGG CGTCGCCCTT CTGGCCCCTT
1261 CCTACTTCTC CGTCTGCCAG CAGCAGGAGG ATATTCCGA TCATGCTCTT AGATCGCTGA
1321 CCGATTTTCA CGGCCTCGTG CGATCTTCCT GCGTGATTTT TCGGTTGTGT AATGACCTTG
1381 CGACCTCTGC TGCTGAGCTG AACGAGGCG AGACTACAAA TTCCATTATT TCTTACATGC
1441 ACGAAAACGA TGGAACATCT GAAGAACAGG CTAGAGAGGA ACTGCGAAAG TTGATCGACG
1501 CCGAGTGGAA GAAGATGAAC AGAGAGCGGG TGTCCGACTC TACCCTGCTT CCCAAGGCCT
1561 TCATGGAGAT CGCCGTGAAC ATGGCTCGAG TTTCCCATTG TACTTACCAG TACGGTGACG
1621 GCCTGGGTCG TCCGGACTAC GCTACAGAGA ACCGAATCAA GCTGCTGCTC ATCGACCCCT
1681 TCCCTATCAA CCAATTGATG TACGTGTAAT AGTCTAGAGG ATCC
```
(SEQ ID NO:12)

Figure 17

```
   1 GAATTCAACA AAAATGTGCT CTGTTTCCAC TGAGAACGTG TCCTTTACTG AGACTGAGAC
  61 TGAAGCACGT AGAAGCGCCA ACTACGAACC CAACTCCTGG GATTATGACT TTCTGCTGTC
 121 TTCTGACACC GACGAGTCGA TCGAGGTTTA TAAGGATAAG GCCAAGAAAC TTGAGGCCGA
 181 GGTCAGACGA GAGATTAACA ACGAGAAGGC CGAGTTCCTG ACCCTTCTTG AGCTGATCGA
 241 CAACGTTCAA CGACTTGGTC TTGGTTACCG TTTCGAATCC GATATCCGAC GTGCATTGGA
 301 TCGATTTGTC TCGTCCGGAG GTTTCGATGG TGTGACTAAG ACGTCGCTGC ACGCCACAGC
 361 TCTTTCCTTC AGACTGTTGC GGCAGCATGG ATTTGAGGTT TCCCAGGAAG CCTTTTCTGG
 421 TTTCAAGGAT CAGAACGGAA ACTTTTTGGA GAATCTCAAG GAGGACACCA AGGCCATCCT
 481 GTCGTTGTAT GAGGCCTCGT TCCTGGCTCT TGAGGGCGAG AATATTCTGG ATGAGGCTCG
 541 GGTTTTCGCT ATTTCGCACC TGAAGGAGTT GTCGGAGGAA AAGATCGGAA AGGAACTGGC
 601 CGAGCAGGTC AACCATGCAC TTGAACTTCC CCTGCATCGA CGTACCCAGC GACTGGAGGC
 661 CGTGTGGAGC ATCGAGGCGT ACAGAAAAAA GGAGGATGCT AATCAGGTTC TGCTCGAACT
 721 CGCTATCCTC GACTATAACA TGATTCAGAG CGTGTACCAG CGTGACTTGC GAGAGACAAG
 781 CCGGTGGTGG CGACGGGTGG GACTGGCCAC GAAGCTCCAC TTTGCTAAAG ATCGATTGAT
 841 TGAGTCGTTC TACTGGGCAG TGGGTGTGGC CTTTGAGCCT CAGTACTCCG ACTGCCGAAA
 901 CTCCGTTGCA AAGATGTTTT CTTTTGTCAC TATCATCGAC GACATCTACG ATGTTTACGG
 961 CACTCTCGAT GAACTCGAAC TCTTCACGGA CGCTGTCGAG CGATGGGATG TGAATGCCAT
1021 TAATGATCTG CCAGATTATA TGAAGTTGTG TTTCTTGGCG CTCTACAACA CAATTAATGA
1081 AATTGCCTAC GACAACCTCA AGGACAAGGG AGAGAACATT CTGCCCTACC TTACTAAAGC
1141 CTGGGCCGAC CTGTGTAACG CCTTTTTGCA GGAAGCCAAG TGGCTCTATA ACAAATCTAC
1201 TCCTACATTT GATGACTACT CGGCAACGC TTGGAAGTCT TCCAGCGGCC CTCTCCAGTT
1261 GATCTTCGCT TACTTTGCAG TGGTCCAGAA CATCAAGAAA GAGGAGATTG AGAACCTCCA
1321 GAAGTATCAC GACATCATCT CCCGACCTTC GCACATCTTT CGACTGTGCA ATGACCTTGC
1381 CTCCGCATCC GCTGAGATTG CCCGAGGAGA AACAGCCAAT TCTGTGTCGT GTTACATGCG
1441 TACAAAGGGC ATCTCCGAGG AGCTGGCTAC CGAGTCTGTG ATGAACCTGA TCGATGAAAC
1501 CTGTAAGAAG ATGAACAAAG AGAAACTGGG CGGTTCTCTG TTCGCCAAAC CATTTGTTGA
1561 AACCGCGATC AATCTGGCTC GTCAGTCTCA TTGTACTTAC CATAACGGTG ACGCGCACAC
1621 TTCGCCGGAC GAATTGACCC GTAAGCGTGT GCTTTCGGTG ATTACCGAGC CGATCCTGCC
1681 GTTCGAAAGA TAATAGGATC C
```
(SEQ ID NO:13)

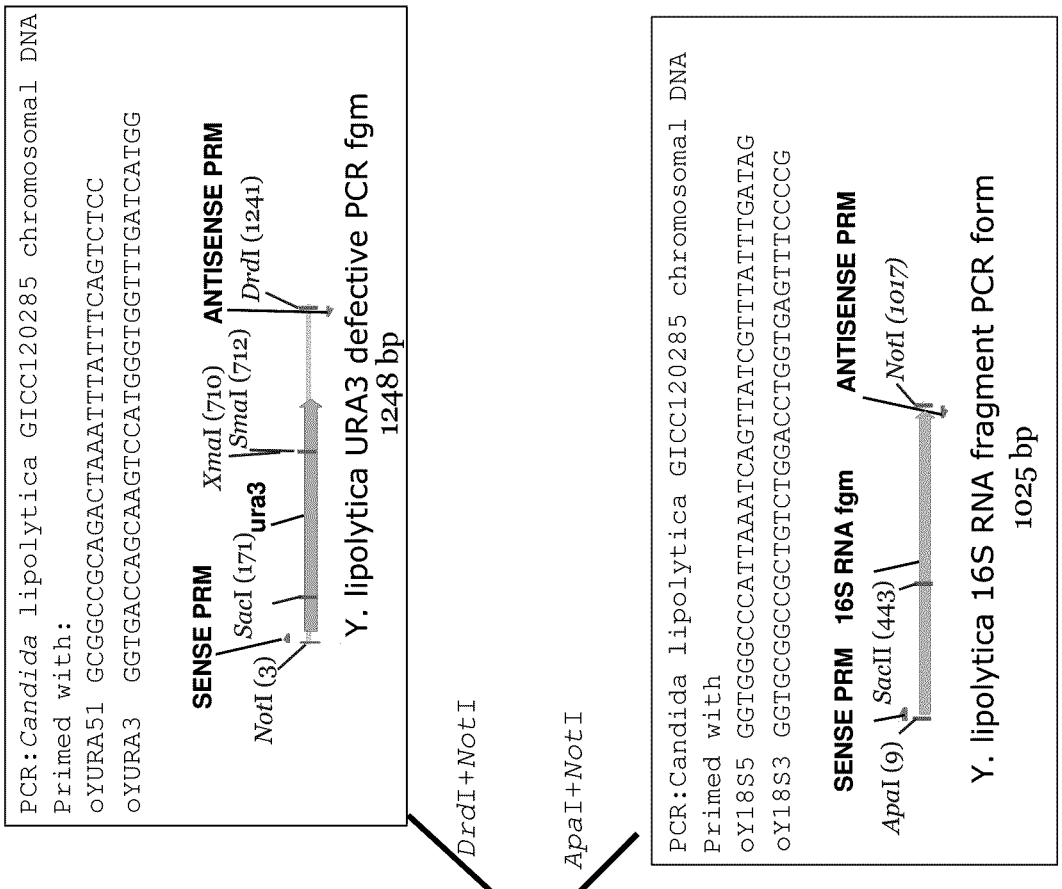
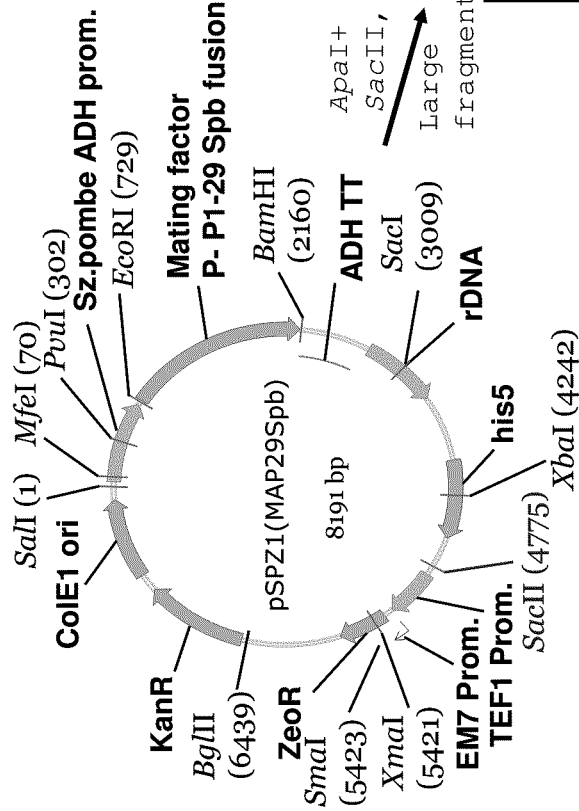
Figure 18A1

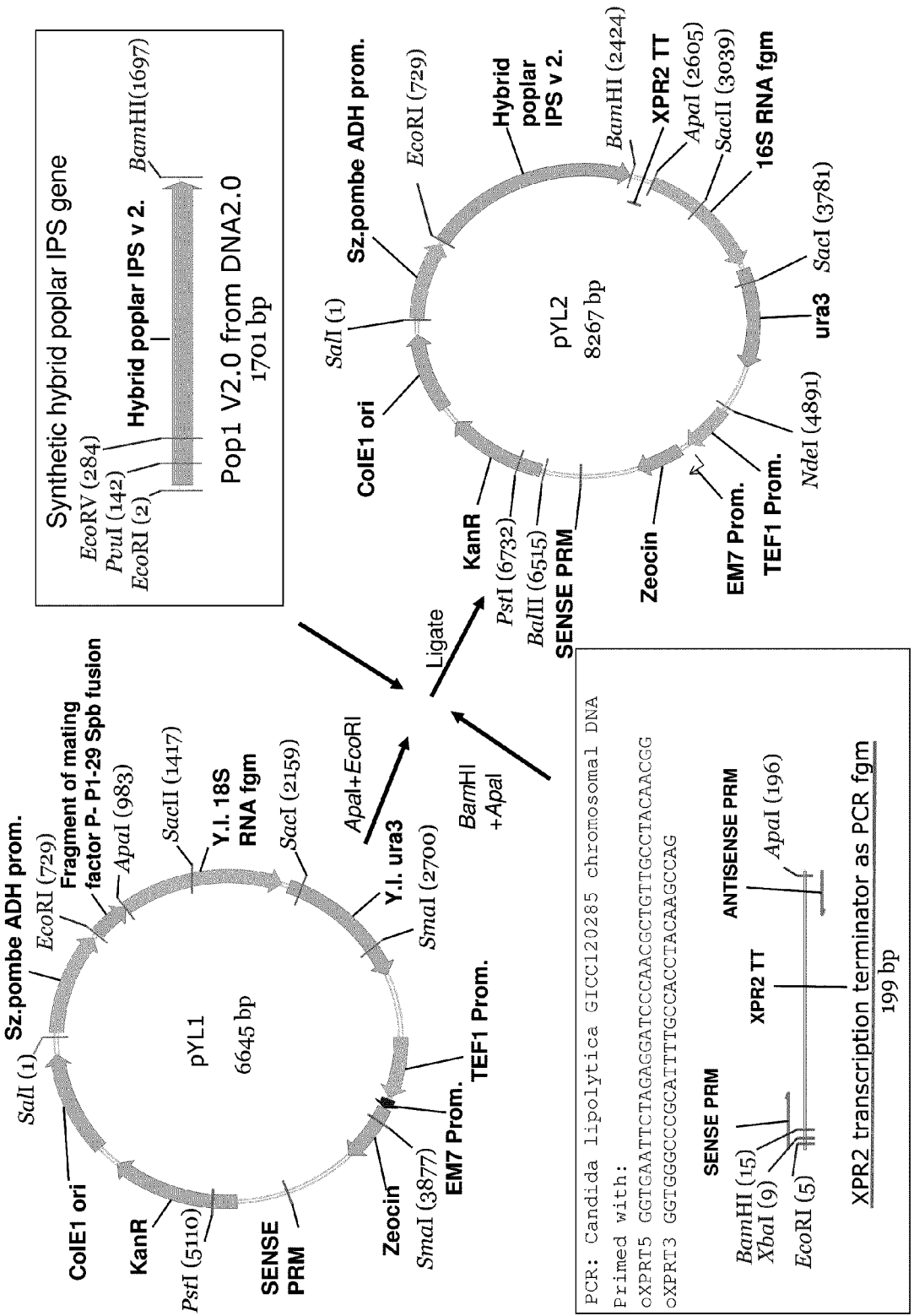
Figure 18A2

*Y. lipolytica* CLIB122:: pYLA(KZ1)

Figure 22A 1-
gctggtaccatatgggaattcgaagctttctagaacaaaaactcatctcagaagaggatctgaatagcgccgtc
gaccatcatcatcatcatcattgagtttaaacggtctccagcttggctgttttggcggatgagagaagattttcagcc
tgatacagattaaatcagaacgcagaagcggtctgataaaacagaatttgcctggcggcagtagcgcggtggt
cccacctgaccccatgccgaactcagaagtgaaacgccgtagcgccgatggtagtgtggggtctccccatgcg
agagtagggaactgccaggcatcaaataaaacgaaaggctcagtcgaaagactgggcctttcgttttatctgtt
gtttgtcggtaacgctctcctgagtaggacaaatccgccgggagcggatttgaacgttgcgaagcaacggcc
cggagggtggcgggcaggacgcccgccataaactgccaggcatcaaattaagcagaaggccatcctgacg
gatggcctttttgcgtttctacaaactcttttgtttattttctaaatacattcaaatatgtatccgcttaaccggaattgcc
agctggggcgccctctggtaaggttgggaagccctgcaaagtaaactggatggctttctcgccgccaaggatct
gatggcgcaggggatcaagctctgatcaagagacaggatgaggatcgtttcgcatgattgaacaagatggatt
gcacgcaggttctccggccgcttgggtggagaggctattcggctatgactgggcacaacagacaatcggctgct
ctgatgccgccgtgttccggctgtcagcgcaggggcgcccggttctttttgtcaagaccgacctgtccggtgccct
gaatgaactgcaagacgaggcagcgcggctatcgtggctggccacgacgggcgttccttgcgcagctgtgctc
gacgttgtcactgaagcgggaagggactggctgctattgggcgaagtgccggggcaggatcctgtcatctca
ccttgctcctgccgagaaagtatccatcatggctgatgcaatgcggcggctgcatacgcttgatccggctacctg
cccattcgaccaccaagcgaaacatcgcatcgagcgagcacgtactcggatggaagccggtcttgtcgatca
ggatgatctggacgaagagcatcaggggctcgcgccagccgaactgttcgccaggctcaaggcgagcatgc
ccgacggcgaggatctcgtcgtgacccatggcgatgcctgcttgccgaatatcatggtggaaaatggccgcttt
ctggattcatcgactgtggccggctgggtgtggcggaccgctatcaggacatagcgttggctacccgtgatattg
ctgaagagcttggcggcgaatgggctgaccgcttcctcgtgctttacggtatcgccgctcccgattcgcagcgca
tcgccttctatcgccttcttgacgagttcttctgacatgaccaaaatcccttaacgtgagttttcgttccactgagcgtc
agaccccgtagaaaagatcaaaggatcttcttgagatcctttttttctgcgcgtaatctgctgcttgcaaacaaaaa
aaccaccgctaccagcggtggtttgtttgccggatcaagagctaccaactcttttccgaaggtaactggcttcag
cagagcgcagataccaaatactgtccttctagtgtagccgtagttaggccaccacttcaagaactctgtagcacc
gcctacatacctcgctctgctaatcctgttaccagtggctgctgccagtggcgataagtcgtgtcttaccgggttgg
actcaagacgatagttaccggataaggcgcagcggtcgggctgaacggggggttcgtgcacacagcccagct
tggagcgaacgacctacaccgaactgagatacctacagcgtgagctatgagaaagcgccacgcttcccgaa
gggagaaaggcggacaggtatccggtaagcggcagggtcggaacaggagagcgcacgagggagcttcca
gggggaaacgcctggtatctttatagtcctgtcgggtttcgccacctctgacttgagcgtcgatttttgtgatgctcgt
caggggggcggagcctatggaaaaacgccagcaacgcggccttttttacggttcctggccttttgctggccttttgc
tcacatgttctttcctgcgttatccctgattctgtggataaccgtattaccgcctttgagtgagctgataccgctcgcc
gcagccgaacgaccgagcgcagcgagtcagtgagcgaggaagcggaagagcgcctgatgcggtattttctc
cttacgcatctgtgcggtatttcacaccgcatatggtgcactctcagtacaatctgctctgatgccgcatagttaagc
cagtatacactccgctatcgctacgtgactgggtcatggctgcgccccgacacccgccaacacccgctgacgc
gccctgacgggcttgtctgctcccggcatccgcttacagacaagctgtgaccgtctccgggagctgcatgtgtca
gaggttttcaccgtcatcaccgaaacgcgcgaggcagcagatcaattcgcgcgcgaaggcgaagcggcatg
catttacgttgacaccatcgaatggtgcaaaacctttcgcggtatggcatgatagcgcccggaaga

Figure 22B gagtcaattcagggtggtgaatgtgaaaccagtaacgttatacgatgtcgcagagtatgccggtgtctcttatc
agaccgtttcccgcgtggtgaaccaggccagccacgtttctgcgaaaacgcgggaaaaagtggaagcgg
cgatggcggagctgaattacattcccaaccgcgtggcacaacaactggcgggcaaacagtcgttgctgatt
ggcgttgccacctccagtctggccctgcacgcgccgtcgcaaattgtcgcggcgattaaatctcgcgccgat
caactgggtgccagcgtggtggtgtcgatggtagaacgaagcggcgtcgaagcctgtaaagcggcggtgc
acaatcttctcgcgcaacgcgtcagtgggctgatcattaactatccgctggatgaccaggatgccattgctgtg
gaagctgcctgcactaatgttccggcgttatttcttgatgtctctgaccagacacccatcaacagtattattttctc
ccatgaagacggtacgcgactgggcgtggagcatctggtcgcattgggtcaccagcaaatcgcgctgttag
cgggcccattaagttctgtctcggcgcgtctgcgtctggctggctggcataaatatctcactcgcaatcaaattc
agccgatagcggaacgggaaggcgactggagtgccatgtccggttttcaacaaaccatgcaaatgctgaa
tgagggcatcgttcccactgcgatgctggttgccaacgatcagatggcgctgggcgcaatgcgcgccattac
cgagtccgggctgcgcgttggtgcggatatctcggtagtgggatacgacgataccgaagacagctcatgtta
tatcccgccgtcaaccaccatcaaacaggattttcgcctgctggggcaaaccagcgtggaccgcttgctgca
actctctcagggccaggcggtgaagggcaatcagctgttcccgtctcactggtgaaaagaaaaaccacc
ctggcgcccaatacgcaaaccgcctctccccgcgcgttggccgattcattaatgcagctggcacgacaggtt
tcccgactggaaagcgggcagtgagcgcaacgcaattaatgtgagttagcgcgaattgatctggtttgacag
cttatcatcgactgcacggtgcaccaatgcttctggcgtcaggcagccatcggaagctgtggtatggctgtgc
aggtcgtaaatcactgcataattcgtgtcgctcaaggcgcactcccgttctggataatgttttttgcgccgacatc
ataacggttctggcaaatattctgaaatgagctgttgacaattaatcatccggctcgtataatgtgtggaattgtg
agcggataacaatttcacacaggaaacagcgccgctgagaaaaagcgaagcggcactgctctttaacaat
ttatcagacaatctgtgtgggcactcgaccggaattatcgattaactttattattaaaaattaaagaggtatatatt
aatgtatcgattaaataaggaggaataaaccatgtgtgcgacctcttctcaatttactcagattaccgagcata
attcccgtcgttccgcaaactatcagccaaacctgtggaatttcgaattcctgcaatccctggagaacgacctg
aaagtggaaaagctggaggagaaagcgaccaaactggaggaagaagttcgctgcatgatcaaccgtgt
agacacccagccgctgtccctgctggagctgatcgacgatgtgcagcgcctgggtctgacctacaaatttga
aaaagacatcattaaagccctggaaaacatcgtactgctggacgaaaacaaaagaacaaatctgacct
gcacgcaaccgctctgtctttccgtctgctgcgtcagcacggtttcgaggtttctcaggatgttttgagcgtttca
aggataaagaaggtggtttcagcggtgaactgaaaggtgacgtccaaggcctgctgagcctgtatgaagcg
tcttacctgggtttcgagggtgagaacctgctggaggaggcgcgtaccttttccatcacccacctgaagaaca
acctgaaagaaggcattaataccaaggttgcagaacaagtgagccacgccctggaactgccatatcacca
gcgtctgcaccgtctggaggcacgttggttcctggataaatacgaaccgaaagaaccgcatcaccagctgc
tgctggagctggcgaagctggattttaacatggtacagaccctgcaccagaaagagctgcaagatcgtccc
gctggtggaccgagatgggcctggctagcaaactggattttgtacgcgaccgcctgatggaagtttatttctgg
gcactgggtatggcgccagacccgcagtttggtgaatgtcgcaaagctgttactaaaatgtttggtctggtgac
gatcatcgatgacgtgtatgacgtttatggcactctggacgaactgcaactgttcaccgatgctgtagagcgct
gggacgttaacgctattaacaccctgccggactatatgaaactgtgtttcctggcactgtacaacaccgttaac
gacacgtcctattctattctgaaagagaaaggtcataacaacctgtcctatctgacgaaaagctggcgtgaa
ctgtgcaaagcctttctgcaagaggcgaaatggtccaacaacaaaattatcccggctttctccaagtacctgg
aaaacgccagcgtttcctcctccggtgtagcgctgctggcgccgtcttacttttccgta

Figure 22C tgccagcagcaggaagacatctccgaccacgcgctgcgttccctgaccgacttccatggtctggtgcgttctag
ctgcgttatcttccgcctgtgcaacgatctggccacctctgcggcggagctggaacgtggcgagactaccaatt
ctatcattagctacatgcacgaaaacgatggtaccagcgaggaacaggcccgcgaagaactgcgtaaactg
atcgacgccgaatggaaaaagatgaatcgtgaacgcgttagcgactccaccctgctgcctaaagcgttcatg
gaaatcgcagttaacatggcacgtgtttcccactgcacctaccagtatggcgatggtctgggtcgcccagacta
cgcgactgaaaaccgcatcaaactgctgctgattgacctttcccgattaaccagctgatgtatgtctaactgca
tcgcccttaggaggtaaaaaaaatgactgccgacaacaatagtatgccccatggtgcagtatctagttacgc
caaattagtgcaaaaccaaacacctgaagacattttggaagagtttcctgaaattattccattacaacaaagac
ctaatacccgatctagtgagacgtcaaatgacgaaagcggagaaacatgtttttctggtcatgatgaggagca
aattaagttaatgaatgaaaattgtattgttttggattgggacgataatgctattggtgccggtaccaagaaagttt
gtcatttaatggaaaatattgaaaagggtttactacatcgtgcattctccgtctttattttcaatgaacaaggtgaatt
acttttacaacaaagagccactgaaaaaataactttccctgatctttggactaacacatgctgctctcatccacta
tgtattgatgacgaattaggtttgaagggtaagctagacgataagattaagggcgctattactgcggcggtgag
aaaactagatcatgaattaggtattccagaagatgaaactaagacaaggggtaagtttcacttttaaacagaa
tccattacatggcaccaagcaatgaaccatggggtgaacatgaaattgattacatcctattttataagatcaacg
ctaaagaaaacttgactgtcaacccaaacgtcaatgaagttagagacttcaaatgggtttcaccaaatgatttg
aaaactatgtttgctgacccaagttacaagtttacgccttggtttaagattatttgcgagaattacttattcaactggt
gggagcaattagatgaccttctgaagtggaaaatgacaggcaaattcatagaatgctataacaacgcgtcct
gcattcgcccttaggaggtaaaaaaacatgagttttgatattgccaaatacccgaccctggcactggtcgactc
cacccaggagttacgactgttgccgaaagagagtttaccgaaactctgcgacgaactgcgccgctatttactc
gacagcgtgagccgttccagcgggcacttcgcctccgggctgggcacggtcgaactgaccgtggcgctgca
ctatgtctacaacaccccgtttgaccaattgatttgggatgtggggcatcaggcttatccgcataaaattttgacc
ggacgccgcgacaaaatcggcaccatccgtcagaaaggcggtctgcacccgttcccgtggcgcggcgaaa
gcgaatatgacgtattaagcgtcgggcattcatcaacctccatcagtgccggaattggtattgcggttgctgccg
aaaaagaaggcaaaaatcgccgcaccgtctgtgtcattggcgatggcgcgattaccgcaggcatggcgtttg
aagcgatgaatcacgcgggcgatatccgtcctgatatgctggtgattctcaacgacaatgaaatgtcgatttcc
gaaaatgtcggcgcgctcaacaaccatctggcacagctgctttccggtaagctttactcttcactgcgcgaagg
cgggaaaaaagttttctctggcgtgccgccaattaaagagctgctcaaacgcaccgaagaacatattaaagg
catggtagtgcctggcacgttgtttgaagagctgggctttaactacatcggcccggtggacggtcacgatgtgct
ggggcttatcaccacgctaaagaacatgcgcgacctgaaaggcccgcagttcctgcatatcatgaccaaaa
aaggtcgtggttatgaaccggcagaaaaagacccgatcactttccacgccgtgcctaaatttgatccctccag
cggttgtttgccgaaaagtagcggcggtttgccgagctattcaaaaatctttggcgactggttgtgcgaaacggc
agcgaaagacaacaagctgatggcgattactccggcgatgcgtgaaggttccggcatggtcgagttttcacgt
aaattcccggatcgctacttcgacgtggcaattgccgagcaacacgcggtgacctttgctgcgggtctggcgat
tggtgggtacaaacccattgtcgcgatttactccactttcctgcaacgcgcctatgatcaggtgctgcatgacgtg
gcgattcaaaagcttccggtcctgttcgccatcgaccgcgcgggcattgttggtgctgacggtcaaacccatca
gggtgcttttgatctctcttacctgcgctgcataccggaaatggtcattatgaccccgagcgatgaaaacgaatg
tcgccagatgctctataccggctatcactataacgatggcccgtcagcggtgcgctaccgcgtggcaacgcg
gtcgg

Figure 22D cgtggaactgacgccgctggaaaaactaccaattggcaaaggcattgtgaagcgtcgtggcgagaaactgg
cgatccttaactttggtacgctgatgccagaagcggcgaaagtcgccgaatcgctgaacgccacgctggtcg
atatgcgttttgtgaaaccgcttgatgaagcgttaattctggaaatggccgccagccatgaagcgctggtcacc
gtagaagaaaacgccattatgggcggcgcaggcagcggcgtgaacgaagtgctgatggcccatcgtaaac
cagtacccgtgctgaacattggcctgccggacttctttattccgcaaggaactcaggaagaaatgcgcgccga
actcggcctcgatgccgctggtatggaagccaaaatcaaggcctggctggcataactgca (SEQ ID NO:20)

Figure 25A

5'-
gtttgacagcttatcatcgactgcacggtgcaccaatgcttctggcgtcaggcagccatcggaagctgtggtatg
gctgtgcaggtcgtaaatcactgcataattcgtgtcgctcaaggcgcactcccgttctggataatgtttttgcgcc
gacatcataacggttctggcaaatattctgaaatgagctgttgacaattaatcatccggctcgtataatgtgtgga
attgtgagcggataacaatttcacacaggaaacagcgccgctgagaaaaagcgaagcggcactgctcttta
acaatttatcagacaatctgtgtgggcactcgaccggaattatcgattaactttattattaaaaattaaagaggtat
atattaatgtatcgattaaataaggaggaataaaccatggatccgagctcggatccactagtaacggccgcca
gtgtgctggaattcgcccttaggaggtaaaaaaacatgtcattaccgttcttaacttctgcaccgggaaggttat
tattttggtgaacactctgctgtgtacaacaagcctgccgtcgctgctagtgtgtctgcgttgagaacctacctgct
aataagcgagtcatctgcaccagatactattgaattggacttcccggacattagctttaatcataagtggtccatc
aatgatttcaatgccatcaccgaggatcaagtaaactcccaaaaattggccaaggctcaacaagccaccgat
ggcttgtctcaggaactcgttagtcttttggatccgttgttagctcaactatccgaatccttccactaccatgcagcg
ttttgtttcctgtatatgtttgtttgcctatgcccccatgccaagaatattaagttttctttaaagtctactttacccatcgg
tgctgggttgggctcaagcgcctctatttctgtatcactggccttagctatggcctacttggggggggttaataggat
ctaatgacttggaaaagctgtcagaaaacgataagcatatagtgaatcaatgggccttcataggtgaaagtg
tattcacggtacccttcaggaatagataacgctgtggccacttatggtaatgccctgctatttgaaaaagactc
acataatggaacaataaacacaaacaattttaagttcttagatgatttcccagccattccaatgatcctaacctat
actagaattccaaggtctacaaaagatcttgttgctcgcgttcgtgtgttggtcaccgagaaatttcctgaagttat
gaagccaattctagatgccatgggtgaatgtgccctacaaggcttagagatcatgactaagttaagtaaatgta
aaggcaccgatgacgaggctgtagaaactaataatgaactgtatgaacaactattggaattgataagaataa
atcatggactgcttgtctcaatcggtgtttctcatcctggattagaacttattaaaaatctgagcgatgatttgagaa
ttggctccacaaaacttaccggtgctggtggcggcggttgctctttgactttgttacgaagagacattactcaaga
gcaaattgacagcttcaaaaagaaattgcaagatgattttagttacgagacatttgaaacagacttgggtggga
ctggctgctgtttgttaagcgcaaaaaatttgaataaagatcttaaaatcaaatccctagtattccaattatttgaa
aataaaactaccacaaagcaacaaattgacgatctattattgccaggaaacacgaatttaccatggacttcat
aagctaatttgcgataggcctgcacccttaaggaggaaaaaaacatgtcagagttgagagccttcagtgccc
cagggaaagcgttactagctggtggatatttagtttagatacaaaatatgaagcatttgtagtcggattatcggc
aagaatgcatgctgtagcccatccttacggttcattgcaagggtctgataagtttgaagtgcgtgtgaaaagtaa
acaatttaaagatggggagtggctgtaccatataagtcctaaaagtggcttcattcctgtttcgataggcggatct
aagaacccttttcattgaaaaagttatcgctaacgtatttagctactttaaacctaacatggacgactactgcaata
gaaacttgttcgttattgatattttctctgatgatgcctaccattctcaggaggatagcgttaccgaacatcgtggca
acagaagattgagttttcattcgcacagaattgaagaagttcccaaaacagggctgggctcctcggcaggttta
gtcacagttttaactacagctttggcctccttttttgtatcggacctggaaaataatgtagacaaatatagagaagt
tattcataatttagcacaagttgctcattgtcaagctcagggtaaaattggaagcgggtttgatgtagcggcggc
agcatatggatctatcagatatagaagattcccacccgcattaatctctaatttgccagatattggaagtgctactt
acggcagtaaactggcgcatttggttgatgaagaagactggaatattacgattaaaagtaaccatttaccttcg
ggattaactttatggatgggcgatattaagaatggttcagaaacagtaaaactggtccagaaggtaaaaaatt
ggtatgattcgcatatgccagaaagcttgaaaata

Figure 25B tatacagaactcgatcatgcaaattctagatttatggatggactatctaaactagatcgcttacacgagactc
atgacgattacagcgatcagatatttgagtctcttgagaggaatgactgtacctgtcaaaagtatcctgaaat
cacagaagttagagatgcagttgccacaattagacgttcctttagaaaaataactaaagaatctggtgccg
atatcgaacctcccgtacaaactagcttattggatgattgccagaccttaaaaggagttcttacttgcttaatac
ctggtgctggtggttatgacgccattgcagtgattactaagcaagatgttgatcttagggctcaaaccgctaat
gacaaaagattttctaaggttcaatggctggatgtaactcaggctgactggggtgttaggaaagaaaaaga
tccggaaacttatcttgataaataacttaaggtagctgcatgcagaattcgcccttaaggaggaaaaaaaa
atgaccgtttacacagcatccgttaccgcacccgtcaacatcgcaacccttaagtattggggaaaaggg
acacgaagttgaatctgcccaccaattcgtccatatcagtgactttatcgcaagatgacctcagaacgttga
cctctgcggctactgcacctgagtttgaacgcgacactttgtggttaaatggagaaccacacagcatcgac
aatgaaagaactcaaaattgtctgcgcgacctacgccaattaagaaaggaaatggaatcgaaggacgc
ctcattgcccacattatctcaatggaaactccacattgtctccgaaaataactttcctacagcagctggtttag
cttcctccgctgctggctttgctgcattggtctctgcaattgctaagttataccaattaccacagtcaacttcaga
aatatctagaatagcaagaaaggggtctggttcagcttgtagatcgttgtttggcggatacgtggcctggga
aatgggaaaagctgaagatggtcatgattccatggcagtacaaatcgcagacagctctgactggcctcag
atgaaagcttgtgtcctagttgtcagcgatattaaaaaggatgtgagttccactcagggtatgcaattgaccgt
ggcaacctccgaactatttaaagaaagaattgaacatgtcgtaccaaagagatttgaagtcatgcgtaaag
ccattgttgaaaaagatttcgccacctttgcaaaggaaacaatgatggattccaactctttccatgccacatgt
ttggactctttccctccaatattctacatgaatgacacttccaagcgtatcatcagttggtgccacaccattaat
cagttttacggagaaacaatcgttgcatacacgtttgatgcaggtccaaatgctgtgttgtactacttagctga
aaatgagtcgaaactctttgcatttatctataaattgtttggctctgttcctggatgggacaagaaatttactact
gagcagcttgaggctttcaaccatcaatttgaatcatctaactttactgcacgtgaattggatcttgagttgcaa
aaggatgttgccagagtgattttaactcaagtcggttcaggcccacaagaaacaaacgaatctttgattgac
gcaaagactggtctaccaaaggaataagatcaattcgctgcatcgcccttaggaggtaaaaaaaaatga
ctgccgacaacaatagtatgccccatggtgcagtatctagttacgccaaattagtgcaaaaccaaacacct
gaagacattttggaagagtttcctgaaattattccattacaacaaagacctaatacccgatctagtgagacgt
caaatgacgaaagcggagaaacatgttttctggtcatgatgaggagcaaattaagttaatgaatgaaatt
gtattgttttggattgggacgataatgctattggtgccggtaccaagaaagtttgtcatttaatggaaaatattga
aaagggtttactacatcgtgcattctccgtctttattttcaatgaacaaggtgaattacttttacaacaaagagc
cactgaaaaaataactttccctgatctttggactaacacatgctgctctcatccactatgtattgatgacgaatt
aggtttgaagggtaagctagacgataagattaagggcgctattactgcggcggtgagaaaactagatcat
gaattaggtattccagaagatgaaactaagacaaggggtaagtttcacttttttaaacagaatccattacatg
gcaccaagcaatgaaccatggggtgaacatgaaattgattacatcctatttataagatcaacgctaaaga
aaacttgactgtcaacccaaacgtcaatgaagttagagacttcaaatgggtttccaaatgatttgaaaac
tatgtttgctgacccaagttacaagtttacgccttggtttaagattatttgcgagaattacttattcaactggtggg
agcaattagatgacctttctgaagtggaaaatgacaggcaaattcatagaatgctataacaacgcgtcctg
cattcgcccttaggaggtaaaaaaacatgtgtgcgacctcttctcaatttactcagattaccgagcataattcc
cgtcgttccgcaaactatcagccaaacctgtggaatttcgaattcctgcaatccctggagaacgacctgaa
agtggaaaagctggaggagaaagcgaccaaactggaggaagaagttcgctgcatg

Figure 25C atcaaccgtgtagacacccagccgctgtccctgctggagctgatcgacgatgtgcagcgcctgggtctgacc
tacaaatttgaaaaagacatcattaaagccctggaaaacatcgtactgctggacgaaaacaaaaagaaca
aatctgacctgcacgcaaccgctctgtctttccgtctgctgcgtcagcacggtttcgaggtttctcaggatgtttt
gagcgtttcaaggataaagaaggtggtttcagcggtgaactgaaaggtgacgtccaaggcctgctgagcct
gtatgaagcgtcttacctgggtttcgagggtgagaacctgctggaggaggcgcgtaccttttccatcacccac
ctgaagaacaacctgaaagaaggcattaataccaaggttgcagaacaagtgagccacgccctggaactg
ccatatcaccagcgtctgcaccgtctggaggcacgttggttcctggataaatacgaaccgaaagaaccgca
tcaccagctgctgctggagctggcgaagctggattttaacatggtacagaccctgcaccagaaagagctgc
aagatctgtcccgctggtggaccgagatgggcctggctagcaaactggattttgtacgcgaccgcctgatgg
aagtttatttctgggcactgggtatggcgccagacccgcagtttggtgaatgtcgcaaagctgttactaaaatgt
ttggtctggtgacgatcatcgatgacgtgtatgacgtttatggcactctggacgaactgcaactgttcaccgatg
ctgtagagcgctgggacgttaacgctattaacaccctgccggactatatgaaactgtgtttcctggcactgtac
aacaccgttaacgacacgtcctattctattctgaaagagaaaggtcataacaacctgtcctatctgacgaaaa
gctggcgtgaactgtgcaaagcctttctgcaagaggcgaaatggtccaacaacaaaattatcccggctttctc
caagtacctggaaaacgccagcgtttcctcctccggtgtagcgctgctggcgccgtcttacttttccgtatgcca
gcagcaggaagacatctccgaccacgcgctgcgttccctgaccgacttccatggtctggtgcgttctagctgc
gttatcttccgcctgtgcaacgatctggccacctctgcggcggagctggaacgtggcgagactaccaattcta
tcattagctacatgcacgaaaacgatggtaccagcgaggaacaggcccgcgaagaactgcgtaaactgat
cgacgccgaatggaaaaagatgaatcgtgaacgcgttagcgactccacccctgctgcctaaagcgttcatgg
aaatcgcagttaacatggcacgtgtttcccactgcacctaccagtatggcgatggtctgggtcgcccagacta
cgcgactgaaaaccgcatcaaactgctgctgattgacccttccccgattaaccagctgatgtatgtctaactgc
agctggtaccatatgggaattcgaagctttctagaacaaaaactcatctcagaagaggatctgaatagcgcc
gtcgaccatcatcatcatcatcattgagtttaaacggtctccagcttggctgttttggcggatgagagaagatttt
cagcctgatacagattaaatcagaacgcagaagcggtctgataaaacagaatttgcctggcggcagtagc
gcggtggtcccacctgaccccatgccgaactcagaagtgaaacgccgtagcgccgatggtagtgtggggt
ctccccatgcgagagtagggaactgccaggcatcaaataaaacgaaaggctcagtcgaaagactgggcc
tttcgttttatctgttgtttgtcggtgaacgctctcctgagtaggacaaatccgccgggagcggatttgaacgttgc
gaagcaacggcccggagggtggcgggcaggacgcccgccataaactgccaggcatcaaattaagcag
aaggccatcctgacggatggcctttttgcgtttctacaaactcttttttgtttatttttctaaatacattcaaatatgtatc
cgcttaaccggaattgccagctggggcgccctctggtaaggttgggaagccctgcaaagtaaactggatgg
ctttctcgccgccaaggatctgatggcgcaggggatcaagctctgatcaagagacaggatgaggatcgtttc
gcatgattgaacaagatggattgcacgcaggttctccggccgcttgggtggagaggctattcggctatgactg
ggcacaacagacaatcggctgctctgatgccgccgtgttccggctgtcagcgcaggggcgcccggttcttttt
gtcaagaccgacctgtccggtgccctgaatgaactgcaagacgaggcagcgcggctatcgtggctggcca
cgacgggcgttccttgcgcagctgtgctcgacgttgtcactgaagcgggaagggactggctgctattgggcg
aagtgccggggcaggatctcctgtcatctcaccttgctcctgccgagaaagtatccatcatggctgatgcaat
gcggcggctgcatacgcttgatccggctacctgcccattcgaccaccaagcgaaacatcgcatcgagcga
gcacgtactcggatggaagccggtcttgtcgatcaggatgatctggacgaagagcatcaggggctcgcgcc
agccgaactgttcgccaggctcaaggcgagcatgcccgacggcgaggatctcgtcgtgacccat

Figure 25D ggcgatgcctgcttgccgaatatcatggtggaaaatggccgcttttctggattcatcgactgtggccggctgggtgt
ggcggaccgctatcaggacatagcgttggctacccgtgatattgctgaagagcttggcggcgaatgggctgac
cgcttcctcgtgctttacggtatcgccgctcccgattcgcagcgcatcgccttctatcgccttcttgacgagttcttctg
acgcatgaccaaaatcccttaacgtgagttttcgttccactgagcgtcagaccccgtagaaaagatcaaaggat
cttcttgagatcctttttttctgcgcgtaatctgctgcttgcaaacaaaaaaaccaccgctaccagcggtggtttgttt
gccggatcaagagctaccaactctttttccgaaggtaactggcttcagcagagcgcagataccaaatactgtcct
tctagtgtagccgtagttaggccaccacttcaagaactctgtagcaccgcctacatacctcgctctgctaatcctgt
taccagtggctgctgccagtggcgataagtcgtgtcttaccgggttggactcaagacgatagttaccggataagg
cgcagcggtcgggctgaacggggggttcgtgcacacagcccagcttggagcgaacgacctacaccgaactg
agatacctacagcgtgagctatgagaaagcgccacgcttcccgaagggagaaaggcggacaggtatccggt
aagcggcagggtcggaacaggagagcgcacgagggagcttccaggggggaaacgcctggtatctttatagtc
ctgtcgggtttcgccacctctgacttgagcgtcgatttttgtgatgctcgtcaggggggcggagcctatggaaaaa
cgccagcaacgcggccttttttacggttcctggccttttgctggccttttgctcacatgttctttcctgcgttatcccctgat
tctgtggataaccgtattaccgcctttgagtgagctgataccgctcgccgcagccgaacgaccgagcgcagcg
agtcagtgagcgaggaagcggaagagcgcctgatgcggtattttctccttacgcatctgtgcggtatttcacacc
gcatatggtgcactctcagtacaatctgctctgatgccgcatagttaagccagtatacactccgctatcgctacgtg
actgggtcatggctgcgccccgacacccgccaacacccgctgacgcgccctgacgggcttgtctgctcccggc
atccgcttacagacaagctgtgaccgtctccgggagctgcatgtgtcagaggttttcaccgtcatcaccgaaacg
cgcgaggcagcagatcaattcgcgcgcgaaggcgaagcggcatgcatttacgttgacaccatcgaatggtgc
aaaacctttcgcggtatggcatgatagcgcccggaagagagtcaattcagggtggtgaatgtgaaaccagtaa
cgttatacgatgtcgcagagtatgccggtgtctcttatcagaccgtttccgcgtggtgaaccaggccagccacgt
ttctgcgaaaacgcgggaaaaagtggaagcggcgatggcggagctgaattacattcccaaccgcgtggcac
aacaactggcgggcaaacagtcgttgctgattggcgttgccacctccagtctggccctgcacgcgccgtcgcaa
attgtcgcggcgattaaatctcgcgccgatcaactgggtgccagcgtggtggtgtcgatggtagaacgaagcgg
cgtcgaagcctgtaaagcggcggtgcacaatcttctcgcgcaacgcgtcagtgggctgatcattaactatccgct
ggatgaccaggatgccattgctgtggaagctgcctgcactaatgttccggcgttatttcttgatgtctctgaccaga
cacccatcaacagtattattttctcccatgaagacggtacgcgactgggcgtggagcatctggtcgcattgggtca
ccagcaaatcgcgctgttagcgggcccattaagttctgtctcggcgcgtctgcgtctggctggctggcataaatat
ctcactcgcaatcaaattcagccgatagcggaacgggaaggcgactggagtgccatgtccggttttcaacaaa
ccatgcaaatgctgaatgagggcatcgttcccactgcgatgctggttgccaacgatcagatggcgctgggcgca
atgcgcgccattaccgagtccgggctgcgcgttggtgcggatatctcggtagtgggatacgacgataccgaag
acagctcatgttatatcccgccgtcaaccaccatcaaacaggattttcgcctgctggggcaaaccagcgtggac
cgcttgctgcaactctctcagggccaggcggtgaagggcaatcagctgttcccgtctcactggtgaaagaaa
aaccaccctggcgcccaatacgcaaaccgcctctccccgcgcgttggccgattcattaatgcagctggcacga
caggtttcccgactggaaagcgggcagtgagcgcaacgcaattaatgtgagttagcgcgaattgatctg (SEQ ID NO:33)

Figure 27A

5'-
cccgtcttactgtcgggaattcgcgttggccgattcattaatgcagattctgaaatgagctgttgacaattaatcatc
cggctcgtataatgtgtggaattgtgagcggataacaatttcacacaggaaacagcgccgctgagaaaagcg
aagcggcactgctctttaacaatttatcagacaatctgtgtgggcactcgaccggaattatcgattaactttattatta
aaaattaaagaggtatatattaatgtatcgattaaataaggaggaataaaccatggatccgagctcaggaggta
aaaaaacatgaaaacagtagttattattgatgcattacgaacaccaattggaaaatataaaggcagcttaagtc
aagtaagtgccgtagacttaggaacacatgttacaacacaacttttaaaaagacattccactatttctgaagaaa
ttgatcaagtaatctttggaaatgttttacaagctggaaatggccaaaatcccgcacgacaaatagcaataaac
agcggtttgtctcatgaaattcccgcaatgacggttaatgaggtctgcggatcaggaatgaaggccgttattttgg
cgaaacaattgattcaattaggagaagcggaagttttaattgctggcgggattgagaatatgtcccaagcaccta
aattacaacgttttaattacgaaacagaaagctacgatgcgcctttttctagtatgatgtatgatggattaacggatg
cctttagtggtcaggcaatgggcttaactgctgaaaatgtggccgaaaagtatcatgtaactagagaagagcaa
gatcaattttctgtacattcacaattaaaagcagctcaagcacaagcagaagggatattcgctgacgaaatagc
cccattagaagtatcaggaacgcttgtggagaaagatgaagggattcgccctaattcgagcgttgagaagcta
ggaacgcttaaaacagttttaaagaagacggtactgtaacagcagggaatgcatcaaccattaatgatgggg
cttctgctttgattattgcttcacaagaatatgccgaagcacacggtcttccttatttagctattattcgagacagtgtg
gaagtcggtattgatccagcctatatgggaatttcgccgattaaagccattcaaaaactgttagcgcgcaatcaa
cttactacggaagaaattgatctgtatgaaatcaacgaagcatttgcagcaacttcaatcgtggtccaaagaga
actggctttaccagaggaaaaggtcaacatttatggtggcggtatttcattaggtcatgcgattggtgccacaggt
gctcgtttattaacgagtttaagttatcaattaaatcaaaaagaaaagaaatatggagtggcttctttatgtatcggc
ggtggcttaggactcgctatgctactagagagacctcagcaaaaaaaaaacagccgattttatcaaatgagtcc
tgaggaacgcctggcttctcttcttaatgaaggccagatttctgctgatacaaaaaaagaatttgaaaatacggct
ttatcttcgcagattgccaatcatatgattgaaaatcaaatcagtgaaacagaagtgccgatgggcgttggcttac
atttaacagtggacgaaactgattatttggtaccaatggcgacagaagagccctcagttattgcggctttgagtaa
tggtgcaaaaatagcacaaggatttaaaacagtgaataacaacgcttaatgcgtggacaaatcgttttttacga
tgttgcagatcccgagtcattgattgataaactacaagtaagagaagcggaagttttcaacaagcagagttaag
ttatccatctatcgttaaacggggcggcggcttaagagatttgcaatatcgtacttttgatgaatcatttgtatctgtcg
acttttagtagatgttaaggatgcaatgggggcaaatatcgttaacgctatgttggaaggtgtggccgagttgttcc
gtgaatggtttgcggagcaaaagattttattcagtattttaagtaattatgccacggagtcggttgttacgatgaaaa
cggctattccagtttcacgtttaagtaaggggagcaatggccgggaaattgctgaaaaaattgttttagcttcacg
ctatgcttcattagatccttatcgggcagtcacgcataacaaaggaatcatgaatggcattgaagctgtagtttag
ctacaggaaatgatacacgcgctgttagcgcttcttgtcatgcttttgcggtgaaggaaggtcgctaccaaggctt
gactagttggacgctggatggcgaacaactaattggtgaaatttcagttccgcttgctttagccacggttggcggtg
ccacaaaagtcttacctaaatctcaagcagctgctgatttgttagcagtgacggatgcaaaagaactaagtcga
gtagtagcggctgttggtttggcacaaaatttagcggcgttacgggccttagtctctgaaggaattcaaaaagga
cacatggctctacaagcacgttctttagcgatgacggtcggagctactggtaaagaagttgaggcagtcgctca
acaattaaaacgtcaaaaaacgatgaaccaagaccgagccatggctatttt aaatgatttaagaaaacaataa
aggaggtaaaaaaacatgacaattgggat

Figure 27B tgataaaattagtttttttgtgccccccttattatattgatatgacggcactggctgaagccagaaatgtagaccctgg
aaaatttcatattggtattgggcaagaccaaatggcggtgaacccaatcagccaagatattgtgacatttgcagc
caatgccgcagaagcgatcttgaccaaagaagataaagaggccattgatatggtgattgtcgggactgagtcc
agtatcgatgagtcaaaagcggccgcagttgtcttacatcgtttaatggggattcaacctttcgctcgctctttcgaa
atcaaggaagcttgttacggagcaacagcaggcttacagttagctaagaatcacgtagccttacatccagataa
aaaagtcttggtcgtagcggcagatattgcaaaatatggcttaaattctggcggtgagcctacacaaggagctg
gggcggttgcaatgttagttgctagtgaaccgcgcattttggctttaaaagaggataatgtgatgctgacgcaaga
tatctatgacttttggcgtccaacaggccacccgtatcctatggtcgatggtcctttgtcaaacgaaacctacatcc
aatcttttgcccaagtctgggatgaacataaaaaacgaaccggtcttgattttgcagattatgatgctttagcgttcc
atattccttacacaaaaatgggcaaaaaagccttattagcaaaaatctccgaccaaactgaagcagaacagg
aacgaattttagcccgttatgaagaaagtatcgtctatagtcgtcgcgtaggaaacttgtatacggggttcactttatc
tgggactcatttcccttttagaaaatgcaacgactttaaccgcaggcaatcaaattggtttattcagttatggttctgg
tgctgtcgctgaattttttcactggtgaattagtagctggttatcaaaatcatttacaaaaagaaactcatttagcactg
ctggataatcggacagaactttctatcgctgaatatgaagccatgtttgcagaaactttagacacagacattgatc
aaacgttagaagatgaattaaaatatagtatttctgctattaataataccgttcgttcttatcgaaactaagagatctg
cagctggtaccatatgggaattcgaagcttgggcccgaacaaaaactcatctcagaagaggatctgaatagcg
ccgtcgaccatcatcatcatcatcattgagtttaaacggtctccagcttggctgttttggcggatgagagaagatttt
cagcctgatacagattaaatcagaacgcagaagcggtctgataaaacagaatttgcctggcggcagtagcgc
ggtggtcccacctgaccccatgccgaactcagaagtgaaacgccgtagcgccgatggtagtgtggggtctccc
catgcgagagtagggaactgccaggcatcaaataaaacgaaaggctcagtcgaaagactgggcctttcgtttt
atctgttgtttgtcggtgaacgctctcctgagtaggacaaatccgccgggagcggatttgaacgttgcgaagcaa
cggcccggagggtggcgggcaggacgcccgccataaactgccaggcatcaaattaagcagaaggccatcc
tgacggatggccttttgcgtttctacaaactcttttgtttatttttctaaatacattcaaatatgtatccgctcatgagac
aataaccctgataaatgcttcaataatctggcgtaatagcgaagaggcccgcaccgatcgcccttcccaacagt
tgcgcagcctgaatggcgaatggcgcctgatgcggtattttctccttacgcatctgtgcggtatttcacaccgcatat
ggtgcactctcagtacaatctgctctgatgccgcatagttaagccagccccgacacccgccaacacccgctga
cgagcttagtaaagccctcgctagattttaatgcggatgttgcgattacttcgccaactattgcgataacaagaaa
aagccagcctttcatgatatatctcccaatttgtgtagggcttattatgcacgcttaaaaataataaaagcagacttg
acctgatagtttggctgtgagcaattatgtgcttagtgcatcaacgcttgagttaagccgcgccgcgaagcggcg
tcggcttgaacgaattgttagacattatttgccgactaccttggtgatctcgcctttcacgtagtggacaaattcttcc
aactgatctgcgcgcgaggccaagcgatcttcttcttgtccaagataagcctgtctagcttcaagtatgacgggct
gatactgggccggcaggcgctccattgcccagtcggcagcgacatccttcggcgcgattttgccggttactgcgc
tgtaccaaatgcgggacaacgtaagcactacatttcgctcatcgccagcccagtcgggcggcgagttccatag
cgttaaggtttcatttagcgcctcaaatagatcctgttcaggaaccggatcaaagagttcctccgccgctggacct
accaaggcaacgctatgttctcttgcttttgtcagcaagatagccagatcaatgtcgatcgtggctggctcgaaga
tacctgcaagaatgtcattgcgctgccattctccaaattgcagttcgcgcttagctggataacgccacggaatgat
gtcgtcgtgcacaacaatggtgacttctacagcgcggagaatctcgctctctccaggggaagccgaagtttcca
aaaggtcgttgat

Figure 27C caaagctcgccgcgttgtttcatcaagccttacggtcaccgtaaccagcaaatcaatatcactgtgtggcttca
ggccgccatccactgcggagccgtacaaatgtacggccagcaacgtcggttcgagatggcgctcgatgac
gccaactacctctgatagttgagtcgatacttcggcgatcaccgcttccctcatgatgtttaactttgttttagggc
gactgccctgctgcgtaacatcgttgctgctccataacatcaaacatcgacccacggcgtaacgcgcttgctg
cttggatgcccgaggcatagactgtaccccaaaaaaacagtcataacaagccatgaaaaccgccactgc
gccgttaccaccgctgcgttcggtcaaggttctggaccagttgcgtgagcgcatacgctacttgcattacagct
tacgaaccgaacaggcttatgtccactgggttcgtgccttcatccgtttccacggtgtgcgtcacccggcaacc
ttgggcagcagcgaagtcgaggcatttctgtcctggctggcgaacgagcgcaaggtttcggtctccacgcat
cgtcaggcattggcggccttgctgttcttctacggcaaggtgctgtgcacggatctgccctggcttcaggagat
cggaagacctcggccgtcgcggcgcttgccggtggtgctgaccccggatgaagtggttcgcatcctcggtttt
ctggaaggcgagcatcgtttgttcgcccagcttctgtatggaacgggcatgcggatcagtgagggtttgcaac
tgcgggtcaaggatctggatttcgatcacggcacgatcatcgtgcgggagggcaagggctccaaggatcg
ggccttgatgttacccgagagcttggcacccagcctgcgcgagcaggggaattaattcccacgggttttgctg
cccgcaaacgggctgttctggtgttgctagtttgttatcagaatcgcagatccggcttcagccggtttgccggct
gaaagcgctatttcttccagaattgccatgattttttccccacggggaggcgtcactggctcccgtgttgtcggca
gctttgattcgataagcagcatcgcctgtttcaggctgtctatgtgtgactgttgagctgtaacaagttgtctcagg
tgttcaatttcatgttctagttgctttgtttttactggtttcacctgttctattaggtgttacatgctgttcatctgttacattgt
cgatctgttcatggtgaacagctttgaatgcaccaaaaactcgtaaaagctctgatgtatctatcttttttacacc
gttttcatctgtgcatatggacagttttccctttgatatgtaacggtgaacagttgttctacttttgtttgttagtcttgat
gcttcactgatagatacaagagccataagaacctcagatccttccgtatttagccagtatgttctctagtgtggtt
cgttgttttttgcgtgagccatgagaacgaaccattgagatcatacttactttgcatgtcactcaaaaattttgcctc
aaaactggtgagctgaattttttgcagttaaagcatcgtgtagtgttttttcttagtccgttatgtaggtaggaatctga
tgtaatggttgttggtattttgtcaccattcattttatctggttgttctcaagttcggttacgagatccatttgtctatcta
gttcaacttggaaaatcaacgtatcagtcgggcggcctcgcttatcaaccaccaatttcatattgctgtaagtgtt
taaatctttacttattggtttcaaaacccattggttaagccttttaaactcatggtagttattttcaagcattaacatg
aacttaaattcatcaaggctaatctctatatttgccttgtgagttttcttttgtgttagttcttttaataaccactcataaa
tcctcatagagtatttgttttcaaaagacttaacatgttccagattatattttatgaattttttttaactggaaaagataa
ggcaatatctcttcactaaaaactaattctaattttttcgcttgagaacttggcatagtttgtccactggaaaatctc
aaagcctttaaccaaaggattcctgatttccacagttctcgtcatcagctctctggttgctttagctaatacaccat
aagcattttccctactgatgttcatcatctgagcgtattggttataagtgaacgataccgtccgttcttccttgtag
ggttttcaatcgtggggttgagtagtgccacacagcataaaattagcttggtttcatgctccgttaagtcatagcg
actaatcgctagttcatttgctttgaaaacaactaattcagacatacatctcaattggtctaggtgattttaatcact
ataccaattgagatgggctagtcaatgataattactagtccttttcctttgagttgtgggtatctgtaaattctgcta
gacctttgctggaaaacttgtaaattctgctagaccctctgtaaattccgctagacctttgtgtgttttttttgtttatatt
caagtggttataatttatagaataaagaaagaataaaaaagataaaagaatagatcccagccctgtgtat
aactcactactttagtcagttccgcagtattacaaaaggatgtcgcaaacgctgtttgctcctctacaaaacag
accttaaaaccctaaaggcttaagtagcaccctcgcaagctcgggcaaatcgctgaatattccttttgtctccg
acc

Figure 27D

Atcaggcacctgagtcgctgtcttttcgtgacattcagttcgctgcgctcacggctctggcagtgaatgggggtaaat
ggcactacaggcgccttttatggattcatgcaaggaaactacccataatacaagaaaagcccgtcacgggcttctc
agggcgttttatggcgggtctgctatgtggtgctatctgacttttgctgttcagcagttcctgccctctgattttccagtctg
accacttcggattatcccgtgacaggtcattcagactggctaatgcacccagtaaggcagcggtatcatcaacagg
ctta (SEQ ID NO:46)

Figure 29A

5'-
tgtaacctttgctttcaaatgagtagaaataatgcacatccatgtttgtatcgtgcaaataaagtgtttcatccgtagga
aaaaatgactttagtatctgttccgcttttctgatgaaatgtgctccccgacaaaattgaatgaatcatggacatttgc
tggctttgatacagcgaaagcagccgttcctatgttatatatcggatttaacagcaggacaaaaaacaccatgaca
gccatcgtcacccacttattcacacgcacataaacctttcctgacttttggaacagatgatagctcatcaaaaatcc
cgccattgccaaataaatcgtatatggcattactgcaccataatcttttgagatttgattgggatatggcgcaagcag
caagacaagcagtccgataatcagcgtataaaataagcctagtaagatcttatccgttctccaatacagcttgaaa
aacactacattcaacgcaatgggaagagtgatgatgaaaaacagaaacacgaatgcaatcggctccatcccat
ccgggtattccttccaatacgaaagaaactaaaaatcatttgtacgatcggcaaactgacaacagcaaggtcg
aacgtataaaacttaccctttccgccatgatcacgcggcatcagcatatagtgaaaagccgtcagcagcacatat
ccgtataacaaaaaatgcagcagcggcagcagttcttttccgtcctctcttaagtaagcgctggtgaagtttgttgatt
gcacctggtgaataagttcaacagacactcccgccagcagcacaatccgcaatataacacccgccaagaacat
tgtgcgctgccggtttattttgggatgatgcaccaaaagatataagcccgccagaacaacaattgaccattgaatc
agcagggtgctttgtctgcttaatataaaataacgttcgaaatgcaatacataatgactgaataactccaacacga
acaacaactccattttcttctgctatcaaaataacagactcgtgattttccaaacgagctttcaaaaaagcctctgcc
ccttgcaaatcggatgcctgtctataaaattcccgatattggttaaacagcggcgcaatggcggccgcatctgatgt
ctttgcttggcgaatgttcatcttatttcttcctccctctcaataattttttcattctatccctttctgtaaagtttattttttcagaa
tacttttatcatcatgctttgaaaaaatatcacgataatatccattgttctcacggaagcacacgcaggtcatttgaac
gaattttttcgacaggaatttgccgggactcaggagcatttaacctaaaaaagcatgacatttcagcataatgaac
atttactcatgtctattttcgttcttttctgtatgaaaatagttatttcgagtctctacggaaatagcgagagatgatatacc
taaatagagataaaatcatctcaaaaaaatgggtctactaaaatattattccatctattacaataaattcacagaata
gtcttttaagtaagtctactctgaattttttttaaaaggagagggtaaagagtgtcattaccgttcttaacttctgcaccgg
gaaaggttattattttttggtgaacactctgctgtgtacaacaagcctgccgtcgctgctagtgtgtctgcgttgagaac
ctacctgctaataagcgagtcatctgcaccagatactattgaattggacttcccggacattagctttaatcataagtg
gtccatcaatgatttcaatgccatcaccgaggatcaagtaaactcccaaaaattggccaaggctcaacaagcca
ccgatggcttgtctcaggaactcgttagtcttttggatccgttgttagctcaactatccgaatccttccactaccatgca
gcgttttgtttcctgtatatgtttgtttgcctatgccccatgccaagaatattaagttttctttaaagtctactttacccatcg
gtgctggtttgggctcaagcgcctctatttctgtatcactggccttagctatggcctacttggggggttaataggatct
aatgacttggaaaagctgtcagaaaacgataagcatatagtgaatcaatgggccttcataggtgaaaagtgtattc
acggtaccccttcaggaatagataacgctgtggccacttatggtaatgccctgctatttgaaaaagactcacataat
ggaacaataaacacaaacaattttaagttcttagatgatttcccagccattccaatgatcctaacctatactagaatt
ccaaggtctacaaaagatcttgttgctcgcgttcgtgtgttggtcaccgagaaatttcctgaagttatgaagccaattc
tagatgccatgggtgaatgtgccctacaaggcttagagatcatgactaagttaagtaaatgtaaaggcaccgatg
acgaggctgtagaaactaataatgaactgtatgaacaactattggaattgataagaataaatcatggactgcttgt
ctcaatcggtgtttctcatcctggattagaacttattaaaaatctgagcgatgatttgagaattggctccacaaaactt
accggtgctggtggcggcggttgctctttgactttgttacgaagagacattactcaagagcaaattgacagcttcaa
aaagaaattgcaagatgattttagt

Figure 29B tacgagacatttgaaacagacttgggtgggactggctgctgtttgttaagcgcaaaaaatttgaataaagatcttaa
aatcaaatccctagtattccaattatttgaaaataaaactaccacaaagcaacaaattgacgatctattattgccag
gaaacacgaatttaccatggacttcataaaaggagagggtgtcagagttgagagccttcagtgccccagggaa
agcgttactagctggtggatatttagttttagatacaaaatatgaagcatttgtagtcggattatcggcaagaatgcat
gctgtagcccatccttacggttcattgcaagggtctgataagtttgaagtgcgtgtgaaaagtaaacaatttaaagat
ggggagtggctgtaccatataagtcctaaaagtggcttcattcctgtttcgataggcggatctaagaacccttttcattg
aaaaagttatcgctaacgtatttagctactttaaacctaacatggacgactactgcaatagaaacttgttcgttattga
tattttctctgatgatgcctaccattctcaggaggatagcgttaccgaacatcgtggcaacagaagattgagttttcatt
cgcacagaattgaagaagttcccaaaacagggctgggctcctcggcaggtttagtcacagttttaactacagcttt
ggcctccttttttgtatcggacctggaaaataatgtagacaaatatagagaagttattcataatttagcacaagttgct
cattgtcaagctcagggtaaaattggaagcgggtttgatgtagcggcggcagcatatggatctatcagatatagaa
gattcccacccgcattaatctctaatttgccagatattggaagtgctacttacggcagtaaactggcgcatttggttga
tgaagaagactggaatattacgattaaaagtaaccatttaccttcgggattaactttatggatgggcgatattaaga
atggttcagaaacagtaaaactggtccagaaggtaaaaaattggtatgattcgcatatgccagaaagcttgaaaa
tatatacagaactcgatcatgcaaattctagatttatggatggactatctaaactagatcgcttacacgagactcatg
acgattacagcgatcagatatttgagtctcttgagaggaatgactgtacctgtcaaaagtatcctgaaatcacaga
agttagagatgcagttgccacaattagacgttcctttagaaaaataactaaagaatctggtgccgatatcgaacct
cccgtacaaactagcttattggatgattgccagaccttaaaaggagttcttacttgcttaatacctggtgctggtggtta
tgacgccattgcagtgattactaagcaagatgttgatcttagggctcaaaccgctaatgacaaaagatttctaagg
ttcaatggctggatgtaactcaggctgactggggtgttaggaaagaaaaagatccggaaacttatcttgataaata
aaaggagagggtgaccgtttacacagcatccgttaccgcacccgtcaacatcgcaacccttaagtattgggga
aaagggacacgaagttgaatctgcccaccaattcgtccatatcagtgactttatcgcaagatgacctcagaacgtt
gacctctgcggctactgcacctgagtttgaacgcgacactttgtggttaaatggagaaccacacagcatcgacaa
tgaaagaactcaaaattgtctgcgcgacctacgccaattaagaaaggaaatggaatcgaaggacgcctcattgc
ccacattatctcaatggaaactccacattgtctccgaaaataactttcctacagcagctggtttagcttcctccgctgc
tggctttgctgcattggtctctgcaattgctaagttataccaattaccacagtcaacttcagaaatatctagaatagca
agaaaggggtctggttcagcttgtagatcgttgtttggcggatacgtggcctgggaaatgggaaaagctgaagat
ggtcatgattccatggcagtacaaatcgcagacagctctgactggcctcagatgaaagcttgtgtcctagttgtcag
cgatattaaaaaggatgtgagttccactcagggtatgcaattgaccgtggcaacctccgaactatttaaagaaag
aattgaacatgtcgtaccaaagagatttgaagtcatgcgtaaagccattgttgaaaaagatttcgccacctttgcaa
aggaaacaatgatggattccaactctttccatgccacatgtttggactctttccctccaatattctacatgaatgacac
ttccaagcgtatcatcagttggtgccacaccattaatcagttttacggagaaacaatcgttgcatacacgtttgatgc
aggtccaaatgctgtgttgtactacttagctgaaaatgagtcgaaactcttttgcatttatctataaattgtttggctctgtt
cctggatgggacaagaaatttactactgagcagcttgaggctttcaaccatcaatttgaatcatctaactttactgca
cgtgaattggatcttgagttgcaaaaggatgttgccagagtgattttaactcaagtcggttcaggcccacaagaaa
caaacgaatctttgattgacgcaaagactggtctaccaaaggaataaaaggagagggtgactgccgacaaca
atagtatgccccatggtgcagtatctagttacgccaaattagt

Figure 29C gcaaaaccaaacacctgaagacattttggaagagtttcctgaaattattccattacaacaaagacctaatacccg
atctagtgagacgtcaaatgacgaaagcggagaaacatgtttttctggtcatgatgaggagcaaattaagttaatg
aatgaaaattgtattgttttggattgggacgataatgctattggtgccggtaccaagaaagtttgtcatttaatggaaa
atattgaaaagggtttactacatcgtgcattctccgtctttattttcaatgaacaaggtgaattacttttacaacaaga
gccactgaaaaaataactttccctgatctttggactaacacatgctgctctcatccactatgtattgatgacgaattag
gtttgaagggtaagctagacgataagattaagggcgctattactgcggcggtgagaaaactagatcatgaattag
gtattccagaagatgaaactaagacaagggtaagtttcacttttaaacagaatccattacatggcaccaagca
atgaaccatggggtgaacatgaaattgattacatcctattttataagatcaacgctaaagaaaacttgactgtcaac
ccaaacgtcaatgaagttagagacttcaaatgggtttcaccaaatgatttgaaaactatgttgctgacccaagtta
caagtttacgccttggtttaagattatttgcgagaattacttattcaactggtgggagcaattagatgacctttctgaagt
ggaaaatgacaggcaaattcatagaatgctataaaaaaaaccggccttggccccgccggttttttattattttttcttcc
tccgcatgttcaatccgctccataatcgacggatggctccctctgaaaattttaacgagaaacggcgggttgaccc
ggctcagtcccgtaacggccaagtcctgaaacgtctcaatcgccgcttcccggtttccggtcagctcaatgccgta
acggtcggcggcgttttcctgataccgggagacggcattcgtaatttgaatacatacgaacaaattaataaagtga
aaaaaatacttcggaaacatttaaaaaataaccttattggtacttacatgtttggatcaggagttgagagtggacta
aaaccaaatagtgatcttgacttttagtcgtcgtatctgaaccattgacagatcaaagtaaagaaatacttatacaa
aaaattagacctatttcaaaaaaaataggagataaaagcaacttacgatatattgaattaacaattattattcagca
agaaatggtaccgtggaatcatcctcccaaacaagaatttatttatggagaatggttacaagagctttatgaacaa
ggatacattcctcagaaggaattaaattcagatttaaccataatgctttaccaagcaaaacgaaaaaataaaaga
atatacggaaattatgacttagaggaattactacctgatattccattttctgatgtgagaagagccattatggattcgtc
agaggaattaatagataattatcaggatgatgaaaccaactctatattaactttatgccgtatgattttaactatggac
acgggtaaaatcataccaaaagatattgcgggaaatgcagtggctgaatcttctccattagaacatagggagag
aattttgttagcagttcgtagttatcttggagagaatattgaatggactaatgaaaatgtaaatttaactataaactattt
aaataacagattaaaaaaattataatgtaacctttgctttcaaatgagtagaaataatgcacatccatgtttgtatcgt
gcaaataaagtgtttcatccgtaggaaaaaatgactttagtatctgttccgcttttttctgatgaaatgtgctccccgaca
aaattgaatgaatcatggacatttgctggctttgatacagcgaaagcagccgttcctatgttatatatcggatttaaca
gcaggacaaaaaacaccatgacagccatcgtcacccacttattcacacgcacataaacctttcctgactttgga
acagatgatagctcatcaaaaatcccgccattgccaaataaatcgtatatggcattactgcaccataatctttgag
atttgattgggatatggcgcaagcagcaagacaagcagtccgataatcagcgtataaaataagcctagtaagat
cttatccgttctccaatacagcttgaaaaacactacattcaacgcaatgggaagagtgatgatgaaaaacagaaa
cacgaatgcaatcggctccatcccatccgggtattccttccaatacgaaaagaaactaaaaatcatttgtacgatc
ggcaaactgacaacagcaaggtcgaacgtataaaacttacccttccgccatgatcacgcggcatcagcatata
gtgaaaagccgtcagcagcacatatccgtataacaaaaaatgcagcagcggcagcagttctttccgtcctctctt
aagtaagcgctggtgaagtttgttgattgcacctggtgaataagttcaacagacactcccgccagcagcacaatc
cgcaatataacacccgccaagaacattgtgcgctgccggtttattttgggatgatgcaccaaaagatataagccc
gccagaacaacaattgaccattgaatcagcagggtgctttgtctgcttaatataaaataacgttcgaaatgcaata
cataatgactgaataactccaacacgaacaacaaaagtgcgcatttt

Figure 29D

Ataaaagctaatgattcagtccacataattgatagacgaattctgctacaggtcacgtggctatgtgaaggatcgc
gcgtccagttaagagcaaaaacattgacaaaaaaatttatttatgctaaaatttactattaatatatttgtatgtataat
aagattctcctggccaggggaatcttatttttgtggaggatcatttcatgaggaaaaatgagtccagcttaacgtctc
taatttcagcttttgcccgtgcatatcacagccgatatgacacacctcttattttgatgattttatcgcaaaagatctcat
taacgaaaaagagtttatcgacatcagtaaaaatatgattcaagaaatatcgttttcaacaaagagatcgccgaa
cgtcttcaaaatgatcctgaaaaaatattaaaatgggttgcacaaatccagctgtctccaacgcccctagcacgtg
cttcttattgtgaaaaagtcttgcacaacgaattaatcctgggggcaaaacagtatgtcattcttggagcgggactg
gatactttctgctttcggcatccagaattagaaaacagcttacaggttttcgaggttgatcatccggccacacagca
attgaaaaaaaataagctgaaggatgcaaatctgacaattccgggtcatcttcattttgttcctatggatttcaccaa
aacgttttcgtatgatcctctcttagatgaaggatttaaaaacacaaaaacattcttcagccttctcggagtgtcttatt
atgtaacacgggaagaaaatgcaagcttgatcagcaatttattttctcatgtcccgcctggaagctctattgtttttgat
tatgcggacgaaacacttttacagcaaaagggacgtcgaatcgagttgaacatatggtgaagatggctgccgc
aagcggggaaccgatgaaatcatgtttcacttatcaagagattgaacatctg (SEQ ID NO:47)

Figure 31A

5'-
tagaaaaactcatcgagcatcaaatgaaactgcaatttattcatatcaggattatcaataccatattttgaaaaagc
cgtttctgtaatgaaggagaaaactcaccgaggcagttccataggatggcaagatcctggtatcggtctgcgattc
cgactcgtccaacatcaatacaacctattaatttccctcgtcaaaaataaggttatcaagtgagaaatcaccatg
agtgacgactgaatccggtgagaatggcaaaagtttatgcatttctttccagacttgttcaacaggccagccattac
gctcgtcatcaaaatcactcgcatcaaccaaaccgttattcattcgtgattgcgcctgagcgaggcgaaatacgcg
atcgctgttaaaaggacaattacaaacaggaatcgagtgcaaccggcgcaggaacactgccagcgcatcaac
aatattttcacctgaatcaggatattcttctaatacctggaacgctgtttttccggggatcgcagtggtgagtaaccatg
catcatcaggagtacggataaaatgcttgatggtcggaagtggcataaattccgtcagccagtttagtctgaccatc
tcatctgtaacatcattggcaacgctacctttgccatgtttcagaaacaactctggcgcatcgggcttcccatacaag
cgatagattgtcgcacctgattgcccgacattatcgcgagcccatttatacccatataaatcagcatccatgttggaa
tttaatcgcggcctcgacgtttcccgttgaatatggctcatattcttccttttcaatattattgaagcatttatcagggttatt
gtctcatgagcggatacatatttgaatgtatttagaaaaataaacaaatagggtcagtgttacaaccaattaacca
attctgaacattatcgcgagcccatttatacctgaatatggctcataacaccccttgtttgcctggcggcagtagcgc
ggtggtcccacctgacccatgccgaactcagaagtgaaacgccgtagcgccgatggtagtgtgggactccc
catgcgagagtagggaactgccaggcatcaaataaaacgaaaggctcagtcgaaagactgggcctttcgccc
gggctaattaggggggtgtcgccctttagtcgctgaacatgtgctctgtttctaccgagaacgtttccttcactgagacg
gaaaccgaggcacgtcgtagcgcgaactacgagccgaatagctgggactacgatttcctgctgtcttccgatact
gacgaatctattgaggtgtacaaagacaaagcaaagaaactggaggctgaagtgcgccgcgaaattaacaac
gagaaagctgaattcctgactctgctggagctgatcgataacgtacagcgcctgggtctgggttaccgcttcgaat
ctgatatccgtcgcgcactggatcgtttcgtaagcagcggcggtttcgatggcgtgaccaaaacgagcctgcacg
ctaccgcgctgtccttccgtctgctgcgtcagcacggcttcgaagtttctcaggaagcattctccggtttcaaagatc
aaaacggtaacttcctggaaaacctgaaagaagacactaaggcgatcctgagcctgtatgaggcaagctttctg
gccctggagggtgagaacatcctggatgaggcgcgcgtattcgccatctcccatctgaaagagctgtctgaaga
gaaaatcggtaaggaactggcagagcaggttaatcacgcactggaactgccgctgcatcgtcgtacccagcgtc
tggaggcggtttggtccatcgaagcgtaccgcaaaaaggaggatgctaaccaggttctgctggaactggccatc
ctggactacaacatgatccagtccgtttaccagcgtgatctgcgtgaaacctcccgttggtggcgccgtgtgggcct
ggcgaccaaactgcacttcgctaaggaccgcctgattgagtcttttactgggcagtcggcgttgcgttcgaacctc
agtattctgactgccgtaacagcgttgcgaaaatgttcagcttcgttactattatcgacgacatctacgacgtttacgg
tactctggacgagctggaactgtttaccgacgctgtcgaacgttgggatgttaacgccatcaacgatctgcctgact
acatgaaactgtgcttcctggcactgtataacacgatcaacgaaattgcatacgacaacctgaaagacaaaggt
gaaaacatcctgccgtacctgactaaagcgtgggcggatctgtgtaacgcttttctgcaagaagcgaaatggctgt
ataacaaatccactccgacctttgacgattatttcggcaatgcctggaaatccagctctggcccgctgcaactgatc
ttcgcttattttgcggttgtccaaaacatcaaaaaggaggaaattgaaaacctgcaaaaataccacgatatcatta
gccgtccttctcatatctttcgcctgtgcaacgacctggcaagcgcgtccgcagagatcgcacgtggcgaaaccg
ctaactctgtttcctgctacatgcgcaccaagggcatttccgaagagctggcaaccgagagcgtaatgaatctgat
cgacgaaacctgtaagaaaatgaacaaagaaaaactgggtggctccctgttcgctaaaccgttcgtagagactg
ctattaacct

Figure 31B ggcacgtcagagccactgcacctaccacaatggtgacgcacatactagcccggatgaactgactcgtaaacgt
gtactgtctgttatcaccgaaccgattctgccgttcgaacgttaactgcagcgtcaatcgaaagggcgacacaaa
atttattctaaatgcataataaatactgataacatcttatagtttgtattatattttgtattatcgttgacatgtataattttgat
atcaaaaactgattttcccttattattttcgagatttattttcttaattctctttaacaaactagaaatattgtatatacaaaa
aatcataaataatagatgaatagtttaattataggtgttcatcaatcgaaaaagcaacgtatcttatttaaagtgcgtt
gctttttctcatttataaggttaaataattctcatatatcaagcaaagtgacaggcgcccttaaatattctgacaaatg
ctctttccctaaactcccccccataaaaaaacccgccgaagcgggttttttacgttatttgcggattaacgattactcgtt
atcagaaccgcccaggggcccgagcttaagactggccgtcgttttacaacacagaaagagtttgtagaaacg
caaaaaggccatccgtcaggggccttctgcttagtttgatgcctggcagttccctactctcgccttccgcttcctcgct
cactgactcgctgcgctcggtcgttcggctgcggcgagcggtatcagctcactcaaaggcggtaatacggttatcc
acagaatcaggggataacgcaggaaagaacatgtgagcaaaaggccagcaaaaggccaggaaccgtaaa
aaggccgcgttgctggcgtttttccataggctccgcccccctgacgagcatcacaaaaatcgacgctcaagtcag
aggtggcgaaacccgacaggactataaagataccaggcgtttccccctggaagctccctcgtgcgctctcctgtt
ccgaccctgccgcttaccggatacctgtccgcctttctcccttcgggaagcgtggcgctttctcatagctcacgctgt
aggtatctcagttcggtgtaggtcgttcgctccaagctgggctgtgtgcacgaaccccccgttcagcccgaccgct
gcgccttatccggtaactatcgtcttgagtccaacccggtaagacacgacttatcgccactggcagcagccactg
gtaacaggattagcagagcgaggtatgtaggcggtgctacagagttcttgaagtggtgggctaactacggctaca
ctagaagaacagtatttggtatctgcgctctgctgaagccagttaccttcggaaaaagagttggtagctcttgatccg
gcaaacaaaccaccgctggtagcggtggttttttgtttgcaagcagcagattacgcgcagaaaaaaaggatctc
aagaagatcctttgatcttttctacggggtctgacgctcagtggaacgacgcgcgcgtaactcacgttaagggatttt
ggtcatgagcttgcgccgtcccgtcaagtcagcgtaatgctctgcttt (SEQ ID NO:48)

Figure 33A

5'-
gtttgacagcttatcatcgactgcacggtgcaccaatgcttctggcgtcaggcagccatcggaagctgtggtatg
gctgtgcaggtcgtaaatcactgcataattcgtgtcgctcaaggcgcactcccgttctggataatgttttttgcgccg
acatcataacggttctggcaaatattctgaaatgagctgttgacaattaatcatccggctcgtataatgtgtggaatt
gtgagcggataacaatttcacacaggaaacagcgccgctgagaaaaagcgaagcggcactgctctttaaca
atttatcagacaatctgtgtgggcactcgaccggaattatcgattaactttattattaaaaattaaagaggtatatatt
aatgtatcgattaaataaggaggaataaaccatgtgctctgtttctaccgagaacgtttccttcactgagacggaa
accgaggcacgtcgtagcgcgaactacgagccgaatagctgggactacgatttcctgctgtcttccgatactga
cgaatctattgaggtgtacaaagacaaagcaaagaaactggaggctgaagtgcgccgcgaaattaacaacg
agaaagctgaattcctgactctgctggagctgatcgataacgtacagcgcctgggtctgggttaccgcttcgaat
ctgatatccgtcgcgcactggatcgtttcgtaagcagcggcggtttcgatggcgtgaccaaaacgagcctgcac
gctaccgcgctgtccttccgtctgctgcgtcagcacggcttcgaagtttctcaggaagcattctccggtttcaaaga
tcaaaacggtaacttcctggaaaacctgaaagaagacactaaggcgatcctgagcctgtatgaggcaagcttt
ctggccctggagggtgagaacatcctggatgaggcgcgcgtattcgccatctcccatctgaaagagctgtctga
agagaaaatcggtaaggaactggcagagcaggttaatcacgcactggaactgccgctgcatcgtcgtaccca
gcgtctggaggcggtttggtccatcgaagcgtaccgcaaaaaggaggatgctaaccaggttctgctggaactg
gccatcctggactacaacatgatccagtccgtttaccagcgtgatctgcgtgaaacctcccgttggtggcgccgt
gtgggcctggcgaccaaactgcacttcgctaaggaccgcctgattgagtcttttactgggcagtcggcgttgcgtt
cgaacctcagtattctgactgccgtaacagcgttgcgaaaatgttcagcttcgttactattatcgacgacatctacg
acgtttacggtactctggacgagctggaactgtttaccgacgctgtcgaacgttgggatgttaacgccatcaacg
atctgcctgactacatgaaactgtgcttcctggcactgtataacacgatcaacgaaattgcatacgacaacctga
aagacaaaggtgaaaacatcctgccgtacctgactaaagcgtgggcggatctgtgtaacgcttttctgcaagaa
gcgaaatggctgtataacaaatccactccgaccttttgacgattatttcggcaatgcctggaaatccagctctggcc
cgctgcaactgatcttcgcttattttgcggttgtccaaaacatcaaaaaggaggaaattgaaaacctgcaaaaat
accacgatatcattagccgtccttctcatatctttcgcctgtgcaacgacctggcaagcgcgtccgcagagatcgc
acgtggcgaaaccgctaactctgtttcctgctacatgcgcaccaagggcatttccgaagagctggcaaccgag
agcgtaatgaatctgatcgacgaaacctgtaagaaaatgaacaaagaaaaactgggtggctccctgttcgcta
aaccgttcgtagagactgctattaacctggcacgtcagagccactgcacctaccacaatggtgacgcacatact
agcccggatgaactgactcgtaaacgtgtactgtctgttatcaccgaaccgattctgccgttcgaacgttaactgc
agctggtaccatatgggaattcgaagctttctagaacaaaaactcatctcagaagaggatctgaatagcgccgt
cgaccatcatcatcatcatcattgagtttaaacggtctccagcttggctgttttggcggatgagagaagattttcagc
ctgatacagattaaatcagaacgcagaagcggtctgataaaacagaatttgcctggcggcagtagcgcggtgg
tcccacctgaccccatgccgaactcagaagtgaaacgccgtagcgccgatggtagtgtggggtctccccatgc
gagagtagggaactgccaggcatcaaataaaacgaaaggctcagtcgaaagactgggcctttcgttttatctgt
tgtttgtcggtgaacgctctcctgagtaggacaaatccgccgggagcggatttgaacgttgcgaagcaacggcc
cggagggtggcgggcaggacgcccgccataaactgccaggcatcaaattaagcagaaggccatcctgacg
gatggcctttttgcgtttctacaaactctttttgttttattttctaaatacattcaaatatgtatccgctcatgagacaataa
ccctgataaatgcttcaataatattgaaaaaggaagagtatgagtattcaacatttc

Figure 33B cgtgtcgcccttattccctttttgcggcattttgccttcctgttttgctcacccagaaacgctggtgaaagtaaaagatg
ctgaagatcagttgggtgcacgagtgggttacatcgaactggatctcaacagcggtaagatccttgagagttttcgc
cccgaagaacgttttccaatgatgagcactttaaagttctgctatgtggcgcggtattatcccgtgttgacgccggc
aagagcaactcggtcgccgcatacactattctcagaatgacttggttgagtactcaccagtcacagaaagcatctt
acggatggcatgacagtaagagaattatgcagtgctgccataaccatgagtgataacactgcggccaacttacttct
gacaacgatcggaggaccgaaggagctaaccgctttttgcacaacatggggatcatgtaactcgccttgatcgtt
gggaaccggagctgaatgaagccataccaaacgacgagcgtgacaccacgatgcctgtagcaatggcaacaa
cgttgcgcaaactattaactggcgaactacttactctagcttcccggcaacaattaatagactggatggaggcggat
aaagttgcaggaccacttctgcgctcggcccttccggctggctggtttattgctgataaatctggagccggtgagcgt
gggtctcgcggtatcattgcagcactggggccagatggtaagccctcccgtatcgtagttatctacacgacgggga
gtcaggcaactatggatgaacgaaatagacagatcgctgagataggtgcctcactgattaagcattggtaactgtc
agaccaagtttactcatatatactttagattgatttaaaacttcatttttaatttaaaaggatctaggtgaagatcctttttga
taatctcatgaccaaaatcccttaacgtgagttttcgttccactgagcgtcagaccccgtagaaaagatcaaggat
cttcttgagatccttttttttctgcgcgtaatctgctgcttgcaaacaaaaaaaccaccgctaccagcggtggtttgtttgc
cggatcaagagctaccaactctttttccgaaggtaactggcttcagcagagcgcagataccaaatactgtccttcta
gtgtagccgtagttaggccaccacttcaagaactctgtagcaccgcctacatacctcgctctgctaatcctgttacca
gtggctgctgccagtggcgataagtcgtgtcttaccgggttggactcaagacgatagttaccggataaggcgcagc
ggtcgggctgaacggggggttcgtgcacacagcccagcttggagcgaacgacctacaccgaactgagataccta
cagcgtgagctatgagaaagcgccacgcttcccgaagggagaaaggcggacaggtatccggtaagcggcagg
gtcggaacaggagagcgcacgagggagcttccaggggggaaacgcctggtatctttatagtcctgtcgggtttcgcc
acctctgacttgagcgtcgatttttgtgatgctcgtcaggggggcggagcctatggaaaaacgccagcaacgcggc
cttttacggttcctggccttttgctggccttttgctcacatgttctttcctgcgttatcccctgattctgtggataaccgtattac
cgcctttgagtgagctgataccgctcgccgcagccgaacgaccgagcgcagcgagtcagtgagcgaggaagcg
gaagagcgcctgatgcggtattttctccttacgcatctgtgcggtatttcacaccgcatatggtgcactctcagtacaat
ctgctctgatgccgcatagttaagccagtatacactccgctatcgctacgtgactgggtcatggctgcgccccgaca
cccgccaacacccgctgacgcgccctgacgggcttgtctgctcccggcatccgcttacagacaagctgtgaccgtc
tccgggagctgcatgtgtcagaggttttcaccgtcatcaccgaaacgcgcgaggcagcagatcaattcgcgcgcg
aaggcgaagcggcatgcatttacgttgacaccatcgaatggtgcaaaacctttcgcggtatggcatgatagcgccc
ggaagagagtcaattcagggtggtgaatgtgaaaccagtaacgttatacgatgtcgcagagtatgccggtgtctctt
atcagaccgtttcccgcgtggtgaaccaggccagccacgtttctgcgaaaacgcgggaaaaagtggaagcggc
gatggcggagctgaattacattcccaaccgcgtggcacaacaactggcgggcaaacagtcgttgctgattggcgtt
gccacctccagtctggccctgcacgcgccgtcgcaaattgtcgcggcgattaaatctcgcgccgatcaactgggtg
ccagcgtggtggtgtcgatggtagaacgaagcggcgtcgaagcctgtaaagcggcggtgcacaatcttctcgcgc
aacgcgtcagtgggctgatcattaactatccgctggatgaccaggatgccattgctgtggaagctgcctgcactaat
gttccggcgttatttcttgatgtctctgaccagacacccatcaacagtattattttctcccatgaagacggtacgcgact
gggcgtggagcatctggtcgcattgggtcaccagcaaatcgcgctgttagcgggcccattaagttctgtctcggcgc
gtctgcgtctggctggctggcataaatatctcactcgcaatc

Figure 33C aaattcagccgatagcggaacgggaaggcgactggagtgccatgtccggttttcaacaaaccatgcaaatgctgaa
tgagggcatcgttcccactgcgatgctggttgccaacgatcagatggcgctgggcgcaatgcgcgccattaccgagt
ccgggctgcgcgttggtgcggatatctcggtagtgggatacgacgataccgaagacagctcatgttatatcccgccgt
caaccaccatcaaacaggattttcgcctgctggggcaaaccagcgtggaccgcttgctgcaactctctcagggcca
ggcggtgaagggcaatcagctgttgcccgtctcactggtgaaaagaaaaaccaccctggcgcccaatacgcaaac
cgcctctccccgcgcgttggccgattcattaatgcagctggcacgacaggtttcccgactggaaagcgggcagtgag
cgcaacgcaattaatgtgagttagcgcgaattgatctg (SEQ ID NO:49)

Figure 35A

5'-
ttgtctgctcccggcatccgcttacagacaagctgtgaccgtctccgggagctgcatgtgtcagaggttttcaccgtc
atcaccgaaacgcgcgaggcagcagatcaattcgcgcgcgaaggcgaagcggcatgcatttacgttgacacc
atcgaatggtgcaaaacctttcgcggtatggcatgatagcgcccggaagagagtcaattcagggtggtgaatgtg
aaaccagtaacgttatacgatgtcgcagagtatgccggtgtctcttatcagaccgtttcccgcgtggtgaaccagg
ccagccacgtttctgcgaaaacgcgggaaaaagtggaagcggcgatggcggagctgaattacattcccaacc
gcgtggcacaacaactggcgggcaaacagtcgttgctgattggcgttgccacctccagtctggccctgcacgcg
ccgtcgcaaattgtcgcggcgattaaatctcgcgccatcaactgggtgccagcgtggtggtgtcgatggtagaa
cgaagcggcgtcgaagcctgtaaagcggcggtgcacaatcttctcgcgcaacgcgtcagtgggctgatcattaa
ctatccgctggatgaccaggatgccattgctgtggaagctgcctgcactaatgttccggcgttatttcttgatgtctctg
accagacacccatcaacagtattattttctcccatgaagacggtacgcgactgggcgtggagcatctggtcgcatt
gggtcaccagcaaatcgcgctgttagcgggcccattaagttctgtctcggcgcgtctgcgtctggctggctggcata
aatatctcactcgcaatcaaattcagccgatagcggaacgggaaggcgactggagtgccatgtccggttttcaac
aaaccatgcaaatgctgaatgagggcatcgttcccactgcgatgctggttgccaacgatcagatggcgctgggc
gcaatgcgcgccattaccgagtccgggctgcgcgttggtgcggatatctcggtagtgggatacgacgataccga
agacagctcatgttatatcccgccgtcaaccaccatcaaacaggattttcgcctgctggggcaaaccagcgtgga
ccgcttgctgcaactctctcagggccaggcggtgaagggcaatcagctgttgcccgtctcactggtgaaaagaaa
aaccaccctggcgcccaatacgcaaaccgcctctccccgcgcgttggccgattcattaatgcagctggcacgac
aggtttcccgactggaaagcgggcagtgagcgcaacgcaattaatgtgagttagcgcgaattgatctggtttgac
agcttatcatcgactgcacggtgcaccaatgcttctggcgtcaggcagccatcggaagctgtggtatggctgtgca
ggtcgtaaatcactgcataattcgtgtcgctcaaggcgcactcccgttctggataatgttttttgcgccgacatcataa
cggttctggcaaatattctgaaatgagctgttgacaattaatcatccggctcgtataatgtgtggaattgtgagcggat
aacaatttcacacaggaaacagcgccgctgagaaaaagcgaagcggcactgctctttaacaatttatcagaca
atctgtgtgggcactcgaccggaattatcgattaactttattattaaaaattaaagaggtatatattaatgtatcgatta
aataaggaggaataaaccatgtgtgcgacctcttctcaatttactcagattaccgagcataattcccgtcgttccgc
aaactatcagccaaacctgtggaatttcgaattcctgcaatccctggagaacgacctgaaagtggaaaagctgg
aggagaaagcgaccaaactggaggaagaagttcgctgcatgatcaaccgtgtagacacccagccgctgtccct
gctggagctgatcgacgatgtgcagcgcctgggtctgacctacaaatttgaaaaagacatcattaaagccctgga
aaacatcgtactgctggacgaaaacaaaagaacaaatctgacctgcacgcaaccgctctgtctttccgtctgct
gcgtcagcacggtttcgaggtttctcaggatgttttgagcgtttcaaggataaagaaggtggtttcagcggtgaact
gaaaggtgacgtccaaggcctgctgagcctgtatgaagcgtcttacctgggtttcgaggtgagaacctgctgga
ggaggcgcgtacctttccatcacccacctgaagaacaacctgaaagaaggcattaataccaaggttgcagaac
aagtgagccacgccctggaactgccatatcaccagcgtctgcaccgtctggaggcacgttggttcctggataaat
acgaaccgaaagaaccgcatcaccagctgctgctggagctggcgaagctggattttaacatggtacagaccctg
caccagaaagagctgcaagatctgtcccgctggtggaccgagatgggcctggctagcaaactggattttgtacg
cgaccgcctgatggaagtttattctgggcactgggtatggcgccagacccgcagtttggtgaatgtcgcaaagct
gttactaaaatgtttggtctggtgacgatcatcgatgacgtgtatgacgt

Figure 35B ttatggcactctggacgaactgcaactgttcaccgatgctgtagagcgctgggacgttaacgctattaacaccct
gccggactatatgaaactgtgtttcctggcactgtacaacaccgttaacgacacgtcctattctattctgaaagag
aaaggtcataacaacctgtcctatctgacgaaaagctggcgtgaactgtgcaaagcctttctgcaagaggcg
aaatggtccaacaacaaaattatcccggctttctccaagtacctggaaaacgccagcgtttcctcctccggtgt
agcgctgctggcgccgtcttacttttccgtatgccagcagcaggaagacatctccgaccacgcgctgcgttccc
tgaccgacttccatggtctggtgcgttctagctgcgttatcttccgcctgtcaacgatctggccacctctgcggcg
gagctggaacgtggcgagactaccaattctatcattagctacatgcacgaaaacgatggtaccagcgagga
acaggcccgcgaagaactgcgtaaactgatcgacgccgaatggaaaaagatgaatcgtgaacgcgttagc
gactccaccctgctgcctaaagcgttcatggaaatcgcagttaacatggcacgtgtttcccactgcacctacca
gtatggcgatggtctgggtcgcccagactacgcgactgaaaaccgcatcaaactgctgctgattgacccttcc
cgattaaccagctgatgtatgtctaactgcatcgcccttaggaggtaaaaaaaaatgactgccgacaacaata
gtatgccccatggtgcagtatctagttacgccaaattagtgcaaaaccaaacacctgaagacattttggaaga
gtttcctgaaattattccattacaacaaagacctaatacccgatctagtgagacgtcaaatgacgaaagcgga
gaaacatgttttctggtcatgatgaggagcaaattaagttaatgaatgaaaattgtattgttttggattgggacgat
aatgctattggtgccggtaccaagaaagtttgtcatttaatggaaaatattgaaaagggtttactacatcgtgcatt
ctccgtctttatttcaatgaacaaggtgaattacttttacaacaaagagccactgaaaaaataactttccctgatc
tttggactaacacatgctgctctcatccactatgtattgatgacgaattaggtttgaagggtaagctagacgataa
gattaagggcgctattactgcggcggtgagaaaactagatcatgaattaggtattccagaagatgaaactaag
acaaggggtaagtttcacttttttaaacagaatccattacatggcaccaagcaatgaaccatggggtgaacatg
aaattgattacatcctattttataagatcaacgctaaagaaaacttgactgtcaacccaaacgtcaatgaagtta
gagacttcaaatgggtttcaccaaatgatttgaaaactatgtttgctgacccaagttacaagtttacgccttggttta
agattatttgcgagaattacttattcaactggtgggagcaattagatgaccttctgaagtggaaaatgacaggc
aaattcatagaatgctataacaacgcgtcctgcagctggtaccatatgggaattcgaagctttctagaacaaaa
actcatctcagaagaggatctgaatagcgccgtcgaccatcatcatcatcatcattgagtttaaacggtctccag
cttggctgttttggcggatgagagaagattttcagcctgatacagattaaatcagaacgcagaagcggtctgat
aaaacagaatttgcctggcggcagtagcgcggtggtcccacctgaccccatgccgaactcagaagtgaaac
gccgtagcgccgatggtagtgtggggtctcccatgcgagagtagggaactgccaggcatcaaataaaacg
aaaggctcagtcgaaagactgggcctttcgttttatctgttgtttgtcggtgaacgctctcctgagtaggacaaatc
cgccgggagcggatttgaacgttgcgaagcaacggcccggagggtggcgggcaggacgcccgccataaa
ctgccaggcatcaaattaagcagaaggccatcctgacggatggcctttttgcgtttctacaaactcttttgtttattt
ttctaaatacattcaaatatgtatccgcttaaccggaattgccagctggggcgccctctggtaaggttgggaagc
cctgcaaagtaaactggatggctttctcgccgccaaggatctgatggcgcaggggatcaagctctgatcaag
agacaggatgaggatcgtttcgcatgattgaacaagatggattgcacgcaggttctccggccgcttgggtgga
gaggctattcggctatgactgggcacaacagacaatcggctgctctgatgccgccgtgttccggctgtcagcg
caggggcgcccggttctttttgtcaagaccgacctgtccggtgccctgaatgaactgcaagacgaggcagcg
cggctatcgtggctggccacgacgggcgttccttgcgcagctgtgctcgacgttgtcactgaagcgggaaggg
actggctgctattgggcgaagtgccggggcaggatctcctgtcatctcaccttgctcctgccgagaaagtatcc
atcatggctgat

Figure 35C gcaatgcggcggctgcatacgcttgatccggctacctgcccattcgaccaccaagcgaaacatcgcatcgagcg
agcacgtactcggatggaagccggtcttgtcgatcaggatgatctggacgaagagcatcaggggctcgcgcca
gccgaactgttcgccaggctcaaggcgagcatgcccgacggcgaggatctcgtcgtgacccatggcgatgcct
gcttgccgaatatcatggtggaaaatggccgcttttctggattcatcgactgtggccggctgggtgtggcggaccgc
tatcaggacatagcgttggctacccgtgatattgctgaagagcttggcggcgaatgggctgaccgcttcctcgtgct
ttacggtatcgccgctcccgattcgcagcgcatcgccttctatcgccttcttgacgagttcttctgacatgaccaaaat
cccttaacgtgagttttcgttccactgagcgtcagaccccgtagaaaagatcaaggatcttcttgagatccttttttc
tgcgcgtaatctgctgcttgcaaacaaaaaaaccaccgctaccagcggtggtttgtttgccggatcaagagctacc
aactctttttccgaaggtaactggcttcagcagagcgcagataccaaatactgtccttctagtgtagccgtagttagg
ccaccacttcaagaactctgtagcaccgcctacatacctcgctctgctaatcctgttaccagtggctgctgccagtg
gcgataagtcgtgtcttaccgggttggactcaagacgatagttaccggataaggcgcagcggtcgggctgaacg
gggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacagg
agagcgcacgagggagcttccaggggga aacgcctggtatctttatagtcctgtcgggtttcgccacctctgactt
gagcgtcgatttttgtgatgctcgtcaggggggcggagcctatggaaaaacgccagcaacgcggcctttttacggt
tcctggccttttgctggccttttgctcacatgttctttcctgcgttatcccctgattctgtggataaccgtattaccgcctttg
agtgagctgataccgctcgccgcagccgaacgaccgagcgcagcgagtcagtgagcgaggaagcggaaga
gcgcctgatgcggtattttctccttacgcatctgtgcggtatttcacaccgcatatggtgcactctcagtacaatctgct
ctgatgccgcatagttaagccagtatacactccgctatcgctacgtgactgggtcatggctgcgccccgacacccg
ccaacacccgctgacgcgccctgacgggc (SEQ ID NO:50)

Figure 37A

5'-
ttgtctgctcccggcatccgcttacagacaagctgtgaccgtctccgggagctgcatgtgtcagaggttttcaccgtcat
caccgaaacgcgcgaggcagcagatcaattcgcgcgcgaaggcgaagcggcatgcatttacgttgacaccatcg
aatggtgcaaaaccttcgcggtatggcatgatagcgcccggaagagagtcaattcagggtggtgaatgtgaaacc
agtaacgttatacgatgtcgcagagtatgccggtgtctcttatcagaccgtttcccgcgtggtgaaccaggccagcca
cgtttctgcgaaaacgcgggaaaaagtggaagcggcgatggcggagctgaattacattcccaaccgcgtggcaca
acaactggcgggcaaacagtcgttgctgattggcgttgccacctccagtctggccctgcacgcgccgtcgcaaattgt
cgcggcgattaaatctcgcgccgatcaactgggtgccagcgtggtggtgtcgatggtagaacgaagcggcgtcgaa
gcctgtaaagcggcggtgcacaatcttctcgcgcaacgcgtcagtgggctgatcattaactatccgctggatgacca
ggatgccattgctgtggaagctgcctgcactaatgttccggcgttatttcttgatgtctctgaccagacacccatcaaca
gtattattttctcccatgaagacggtacgcgactgggcgtggagcatctggtcgcattgggtcaccagcaaatcgcgct
gttagcgggcccattaagttctgtctcggcgcgtctgcgtctggctggctggcataaatatctcactcgcaatcaaattc
agccgatagcggaacgggaaggcgactggagtgccatgtccggttttcaacaaaccatgcaaatgctgaatgagg
gcatcgttcccactgcgatgctggttgccaacgatcagatggcgctgggcgcaatgcgcgccattaccgagtccggg
ctgcgcgttggtgcggatatctcggtagtgggatacgacgataccgaagacagctcatgttatatcccgccgtcaacc
accatcaaacaggattttcgcctgctggggcaaaccagcgtggaccgcttgctgcaactctctcagggccaggcggt
gaagggcaatcagctgttgcccgtctcactggtgaaaagaaaaaccaccctggcgcccaatacgcaaaccgcctc
tccccgcgcgttggccgattcattaatgcagctggcacgacaggtttcccgactggaaagcgggcagtgagcgcaa
cgcaattaatgtgagttagcgcgaattgatctggtttgacagcttatcatcgactgcacggtgcaccaatgcttctggcgt
caggcagccatcggaagctgtggtatggctgtgcaggtcgtaaatcactgcataattcgtgtcgctcaaggcgcactc
ccgttctggataatgttttttgcgccgacatcataacggttctggcaaatattctgaaatgagctgttgacaattaatcatc
cggctcgtataatgtgtggaattgtgagcggataacaatttcacacaggaaacagcgccgctgagaaaaagcgaa
gcggcactgctctttaacaatttatcagacaatctgtgtgggcactcgaccggaattatcgattaactttattattaaaaat
taaagaggtatatattaatgtatcgattaaataaggaggaataaaccatgtgtgcgacctcttctcaatttactcagatta
ccgagcataattcccgtcgttccgcaaactatcagccaaacctgtggaatttcgaattcctgcaatccctggagaacg
acctgaaagtggaaaagctggaggagaaagcgaccaaactggaggaagaagttcgctgcatgatcaaccgtgta
gacacccagccgctgtccctgctggagctgatcgacgatgtgcagcgcctgggtctgacctacaaatttgaaaaag
acatcattaaagccctggaaaacatcgtactgctggacgaaaacaaaaagaacaaatctgacctgcacgcaacc
gctctgtctttccgtctgctgcgtcagcacggtttcgaggtttctcaggatgttttgagcgtttcaaggataaagaaggtg
gtttcagcggtgaactgaaaggtacgtccaaggcctgctgagcctgtatgaagcgtcttacctgggtttcgagggtg
agaacctgctggaggaggcgcgtaccttttccatcacccacctgaagaacaacctgaaagaaggcattaatacca
aggttgcagaacaagtgagccacgccctggaactgccatatcaccagcgtctgcaccgtctggaggcacgttggttc
ctggataaatacgaaccgaaagaaccgcatcaccagctgctgctggagctggcgaagctggattttaacatggtac
agaccctgcaccagaaagagctgcaagatctgtcccgctggtggaccgagatgggcctggctagcaaactggattt
tgtacgcgaccgcctgatggaagtttatttctgggcactgggtatggcgccagacccgcagtttggtaatgtcgcaaa
gctgttactaaaatgtttggtctggtgacgatcatcgatgacgtgtatgacgtttatggcactctggacgaactgcaactg
ttcaccgatgctgtagagcgctgggacgttaacgct

Figure 37B attaacaccctgccggactatatgaaactgtgtttcctggcactgtacaacaccgttaacgacacgtcctattctattc
tgaaagagaaaggtcataacaacctgtcctatctgacgaaaagctggcgtgaactgtgcaaagcctttctgcaag
aggcgaaatggtccaacaacaaaattatcccggctttctccaagtacctggaaaacgccagcgtttcctcctccg
gtgtagcgctgctggcgccgtcttacttttccgtatgccagcagcaggaagacatctccgaccacgcgctgcgttcc
ctgaccgacttccatggtctggtgcgttctagctgcgttatcttccgcctgtgcaacgatctggccacctctgcggcg
gagctggaacgtggcgagactaccaattctatcattagctacatgcacgaaaacgatggtaccagcgaggaac
aggcccgcgaagaactgcgtaaactgatcgacgccgaatggaaaaagatgaatcgtgaacgcgttagcgact
ccaccctgctgcctaaagcgttcatggaaatcgcagttaacatggcacgtgtttcccactgcacctaccagtatgg
cgatggtctgggtcgcccagactacgcgactgaaaaccgcatcaaactgctgctgattgaccctttcccgattaac
cagctgatgtatgtctaactgcattcgcccttaggaggtaaaaaaacatgagttttgatattgccaaatacccgacc
ctggcactggtcgactccacccaggagttacgactgttgccgaaagagagtttaccgaaactctgcgacgaactg
cgccgctatttactcgacagcgtgagccgttccagcgggcacttcgcctccgggctgggcacggtcgaactgacc
gtggcgctgcactatgtctacaacaccccgtttgaccaattgatttgggatgtggggcatcaggcttatccgcataa
aattttgaccggacgccgcgacaaaatcggcaccatccgtcagaaaggcggtctgcacccgttcccgtggcgc
ggcgaaagcgaatatgacgtattaagcgtcgggcattcatcaacctccatcagtgccggaattggtattgcggttg
ctgccgaaaaagaaggcaaaaatcgccgcaccgtctgtgtcattggcgatggcgcgattaccgcaggcatggc
gtttgaagcgatgaatcacgcgggcgatatccgtcctgatatgctggtgattctcaacgacaatgaaatgtcgatttc
cgaaaatgtcggcgcgctcaacaaccatctggcacagctgctttccggtaagctttactcttcactgcgcgaaggc
gggaaaaaagttttctctggcgtgccgccaattaaagagctgctcaaacgcaccgaagaacatattaaaggcat
ggtagtgcctggcacgttgtttgaagagctgggctttaactacatcggcccggtggacggtcacgatgtgctgggg
cttatcaccacgctaaagaacatgcgcgacctgaaaggcccgcagttcctgcatatcatgaccaaaaaaggtcg
tggttatgaaccggcagaaaaagacccgatcactttccacgccgtgcctaaatttgatccctccagcggttgtttgc
cgaaaagtagcggcggtttgccgagctattcaaaaatctttggcgactggttgtgcgaaacggcagcgaaagac
aacaagctgatggcgattactccggcgatgcgtgaaggttccggcatggtcgagttttcacgtaaattcccggatc
gctacttcgacgtggcaattgccgagcaacacgcggtgacctttgctgcgggtctggcgattggtgggtacaaac
ccattgtcgcgatttactccactttcctgcaacgcgcctatgatcaggtgctgcatgacgtggcgattcaaaagcttc
cggtcctgttcgccatcgaccgcgcgggcattgttggtgctgacggtcaaacccatcagggtgcttttgatctctctta
cctgcgctgcataccggaaatggtcattatgaccccgagcgatgaaaacgaatgtcgccagatgctctataccgg
ctatcactataacgatggcccgtcagcggtgcgctacccgcgtggcaacgcggtcggcgtggaactgacgccg
ctggaaaaactaccaattggcaaaggcattgtgaagcgtcgtggcgagaaactggcgatccttaactttggtacg
ctgatgccagaagcggcgaaagtcgccgaatcgctgaacgccacgctggtcgatatgcgttttgtgaaaccgctt
gatgaagcgttaattctggaaatggccgccagccatgaagcgctggtcaccgtagaagaaaacgccattatggg
cggcgcaggcagcggcgtgaacgaagtgctgatggcccatcgtaaaccagtacccgtgctgaacattggcctg
ccggacttctttattccgcaaggaactcaggaagaaatgcgcgccgaactcggcctcgatgccgctggtatggaa
gccaaaatcaaggcctggctggcataactgcagctggtaccatatgggaattcgaagctttctagaacaaaaact
catctcagaagaggatctgaatagcgccgtcgaccatcatcatcatcatcattgagtttaaacggtctccagcttgg
ctgttttggcggatgagagaagattttcagcctgatacagattaaatcagaacgcagaagcggtctgataaaaca
gaatttgcctggcggcagtagcgcg

Figure 37C gtggtcccacctgaccccatgccgaactcagaagtgaaacgccgtagcgccgatggtagtgtggggtctcc
ccatgcgagagtagggaactgccaggcatcaaataaaacgaaaggctcagtcgaaagactgggcctttc
gttttatctgttgtttgtcggtgaacgctctcctgagtaggacaaatccgccgggagcggatttgaacgttgcga
agcaacggcccggagggtggcgggcaggacgcccgccataaactgccaggcatcaaattaagcagaa
ggccatcctgacggatggcctttttgcgtttctacaaactcttttgtttattttctaaatacattcaaatatgtatccg
cttaaccggaattgccagctggggcgccctctggtaaggttgggaagccctgcaaagtaaactggatggctt
tctcgccgccaaggatctgatggcgcaggggatcaagctctgatcaagagacaggatgaggatcgtttcgc
atgattgaacaagatggattgcacgcaggttctccggccgcttgggtggagaggctattcggctatgactggg
cacaacagacaatcggctgctctgatgccgccgtgttccggctgtcagcgcaggggcgcccggttcttttgtc
aagaccgacctgtccggtgccctgaatgaactgcaagacgaggcagcgcggctatcgtggctggccacg
acgggcgttccttgcgcagctgtgctcgacgttgtcactgaagcgggaagggactggctgctattgggcgaa
gtgccggggcaggatctcctgtcatctcaccttgctcctgccgagaaagtatccatcatggctgatgcaatgc
ggcggctgcatacgcttgatccggctacctgcccattcgaccaccaagcgaaacatcgcatcgagcgagc
acgtactcggatggaagccggtcttgtcgatcaggatgatctggacgaagagcatcaggggctcgcgccag
ccgaactgttcgccaggctcaaggcgagcatgcccgacggcgaggatctcgtcgtgacccatggcgatgc
ctgcttgccgaatatcatggtggaaaatggccgcttttctggattcatcgactgtggccggctgggtgtggcgg
accgctatcaggacatagcgttggctacccgtgatattgctgaagagcttggcggcgaatgggctgaccgctt
cctcgtgctttacggtatcgccgctcccgattcgcagcgcatcgccttctatcgccttcttgacgagttcttctgac
gcatgaccaaaatcccttaacgtgagttttcgttccactgagcgtcagaccccgtagaaaagatcaaaggat
cttcttgagatcctttttttctgcgcgtaatctgctgcttgcaaacaaaaaaaccaccgctaccagcggtggtttgt
ttgccggatcaagagctaccaactcttttccgaaggtaactggcttcagcagagcgcagataccaaatactg
tccttctagtgtagccgtagttaggccaccacttcaagaactctgtagcaccgcctacatacctcgctctgctaa
tcctgttaccagtggctgctgccagtggcgataagtcgtgtcttaccgggttggactcaagacgatagttaccg
gataaggcgcagcggtcgggctgaacggggggttcgtgcacacagcccagcttggagcgaacgacctac
accgaactgagatacctacagcgtgagctatgagaaagcgccacgcttcccgaagggagaaaggcgga
caggtatccggtaagcggcagggtcggaacaggagagcgcacgagggagcttccaggggaaacgcc
tggtatctttatagtcctgtcgggtttcgccacctctgacttgagcgtcgatttttgtgatgctcgtcaggggggcg
gagcctatggaaaaacgccagcaacgcggcctttttacggttcctggccttttgctggccttttgctcacatgttc
tttcctgcgttatcccctgattctgtggataaccgtattaccgcctttgagtgagctgataccgctcgccgcagcc
gaacgaccgagcgcagcgagtcagtgagcgaggaagcggaagagcgcctgatgcggtattttctccttac
gcatctgtgcggtatttcacaccgcatatggtgcactctcagtacaatctgctctgatgccgcatagttaagcca
gtatacactccgctatcgctacgtgactgggtcatggctgcgccccgacacccgccaacacccgctgacgc
gccctgacgggc (SEQ ID NO:51)

Figure 39A

5'-
ctggcgtaatagcgaagaggcccgcaccgatcgcccttcccaacagttgcgcagcctgaatggcgaatggcgcc
tgatgcggtattttctccttacgcatctgtgcggtatttcacaccgcatatggtgcactctcagtacaatctgctctgatgc
cgcatagttaagccagccccgacacccgccaacacccgctgacgagcttagtaaagccctcgctagattttaatgc
ggatgttgcgattacttcgccaactattgcgataacaagaaaaagccagcctttcatgatatatctcccaatttgtgtag
ggcttattatgcacgcttaaaaataataaaagcagacttgacctgatagtttggctgtgagcaattatgtgcttagtgca
tctaacgcttgagttaagccgcgccgcgaagcggcgtcggcttgaacgaattgttagacattatttgccgactacctt
ggtgatctcgcctttcacgtagtggacaaattcttccaactgatctgcgcgcgaggccaagcgatcttcttcttgtccaa
gataagcctgtctagcttcaagtatgacgggctgatactgggccggcaggcgctccattgcccagtcggcagcgac
atccttcggcgcgattttgccggttactgcgctgtaccaaatgcgggacaacgtaagcactacatttcgctcatcgcc
agcccagtcgggcggcgagttccatagcgttaaggtttcatttagcgcctcaaatagatcctgttcaggaaccggat
caaagagttcctccgccgctggacctaccaaggcaacgctatgttctcttgcttttgtcagcaagatagccagatcaa
tgtcgatcgtggctggctcgaagatacctgcaagaatgtcattgcgctgccattctccaaattgcagttcgcgcttagc
tggataacgccacggaatgatgtcgtcgtgcacaacaatggtgacttctacagcgcggagaatctcgctctctcca
ggggaagccgaagtttccaaaaggtcgttgatcaaagctcgccgcgttgtttcatcaagccttacggtcaccgtaac
cagcaaatcaatatcactgtgtggcttcaggccgccatccactgcggagccgtacaaatgtacggccagcaacgt
cggttcgagatggcgctcgatgacgccaactacctctgatagttgagtcgatacttcggcgatcaccgcttccctcat
gatgtttaactttgttttagggcgactgccctgctgcgtaacatcgttgctgctccataacatcaaacatcgacccacgg
cgtaacgcgcttgctgcttggatgcccgaggcatagactgtaccccaaaaaaacagtcataacaagccatgaaa
accgccactgcgccgttaccaccgctgcgttcggtcaaggttctggaccagttgcgtgagcgcatacgctacttgca
ttacagcttacgaaccgaacaggcttatgtccactgggttcgtgccttcatccgttccacggtgtgcgtcacccggca
accttgggcagcagcgaagtcgaggcatttctgtcctggctggcaacgagcgcaaggtttcggtctccacgcatc
gtcaggcattggcggccttgctgttcttctacggcaaggtgctgtgcacggatctgccctggcttcaggagatcggaa
gacctcggccgtcgcggcgcttgccggtggtgctgaccccggatgaagtggttcgcatcctcggttttctggaaggc
gagcatcgtttgttcgcccagcttctgtatggaacgggcatgcggatcagtgagggtttgcaactgcgggtcaagga
tctggatttcgatcacggcacgatcatcgtgcgggagggcaaggctccaaggatcgggccttgatgttacccgag
agcttggcacccagcctgcgcgagcaggggaattaattcccacgggttttgctgccccgcaaacgggctgttctggtg
ttgctagtttgttatcagaatcgcagatccggcttcagccggtttgccggctgaaagcgctatttcttccagaattgccat
gatttttccccacgggaggcgtcactggctcccgtgttgtcggcagctttgattcgataagcagcatcgcctgtttcag
gctgtctatgtgtgactgttgagctgtaacaagttgtctcaggtgttcaatttcatgttctagttgctttgttttactggtttcac
ctgttctattaggtgttacatgctgttcatctgttacattgtcgatctgttcatggtgaacagctttgaatgcaccaaaaact
cgtaaaagctctgatgtatctatcttttttacaccgttttcatctgtgcatatggacagttttcccttgatatgtaacggtga
acagttgttctactttgtttgttagtcttgatgcttcactgatagatacaagagccataagaacctcagatccttccgtatt
tagccagtatgttctctagtgtggttcgttgttttgcgtgagccatgagaacgaaccattgagatcatacttactttgcat
gtcactcaaaaattttgcctcaaaactggtgagctgaattttttgcagttaaagcatcgtgtagtgttttcttagtccgttat
gtaggtaggaatctgatgtaatggttgttggtattttgtcaccattcattttatctggttgttctcaagttcgg

Figure 39B ttacgagatccatttgtctatctagttcaacttggaaaatcaacgtatcagtcgggcggcctcgcttatcaaccaccaatt
tcatattgctgtaagtgtttaaatctttacttattggtttcaaaacccattggttaagccttttaaactcatggtagttattttcaa
gcattaacatgaacttaaattcatcaaggctaatctctatatttgccttgtgagttttcttttgtgttagttcttttaataaccact
cataaatcctcatagagtatttgttttcaaaagacttaacatgttccagattatattttatgaattttttaactggaaaagata
aggcaatatctcttcactaaaaactaattctaattttttcgcttgagaacttggcatagtttgtccactggaaaatctcaaag
cctttaaccaaaggattcctgatttccacagttctcgtcatcagctctctggttgctttagctaatacaccataagcattttcc
ctactgatgttcatcatctgagcgtattggttataagtgaacgataccgtccgttctttccttgtagggttttcaatcgtgggg
ttgagtagtgccacacagcataaaattagcttggtttcatgctccgttaagtcatagcgactaatcgctagttcatttgcttt
gaaaacaactaattcagacatacatctcaattggtctaggtgattttaatcactataccaattgagatgggctagtcaat
gataattactagtccttttcctttgagttgtgggtatctgtaaattctgctagacctttgctggaaaacttgtaaattctgctag
accctctgtaaattccgctagacctttgtgtgttttttttgtttatattcaagtggttataatttatagaataaagaaagaataa
aaaagataaaaagaatagatcccagccctgtgtataactcactactttagtcagttccgcagtattacaaaaggatg
tcgcaaacgctgtttgctcctctacaaaacagaccttaaaaccctaaaggcttaagtagcaccctcgcaagctcggg
caaatcgctgaatattccttttgtctccgaccatcaggcacctgagtcgctgtcttttcgtgacattcagttcgctgcgctc
acggctctggcagtgaatgggggtaaatggcactacaggcgccttttatggattcatgcaaggaaactacccataat
acaagaaaagcccgtcacgggcttctcagggcgtttatggcgggtctgctatgtggtgctatctgacttttgctgttcag
cagttcctgccctctgattttccagtctgaccacttcggattatcccgtgacaggtcattcagactggctaatgcacccag
taaggcagcggtatcatcaacaggcttacccgtcttactgtcgggaattcgcgttggccgattcattaatgcagattctg
aaatgagctgttgacaattaatcatccggctcgtataatgtgtggaattgtgagcggataacaatttcacacaggaaac
agcgccgctgagaaaaagcgaagcggcactgctctttaacaatttatcagacaatctgtgtgggcactcgaccgga
attatcgattaactttattattaaaaattaaagaggtatatattaatgtatcgattaaataaggaggaataaaccatgtgtg
cgacctcttctcaatttactcagattaccgagcataattcccgtcgttccgcaaactatcagccaaacctgtggaatttcg
aattcctgcaatccctggagaacgacctgaaagtggaaaagctggaggagaaagcgaccaaactggaggaaga
agttcgctgcatgatcaaccgtgtagacacccagccgctgtccctgctggagctgatcgacgatgtgcagcgcctgg
gtctgacctacaaatttgaaaagacatcattaaagccctggaaaacatcgtactgctggacgaaaacaaaaaga
acaaatctgacctgcacgcaaccgctctgtcttccgtctgctgcgtcagcacggtttcgaggtttctcaggatgtttttga
gcgtttcaaggataaagaaggtggtttcagcggtgaactgaaaggtgacgtccaaggcctgctgagcctgtatgaag
cgtcttacctgggtttcgaggggtgagaacctgctggaggaggcgcgtaccttttccatcacccacctgaagaacaacc
tgaaagaaggcattaataccaaggttgcagaacaagtgagccacgccctggaactgccatatcaccagcgtctgc
accgtctggaggcacgttggttcctggataaatacgaaccgaaagaaccgcatcaccagctgctgctggagctggc
gaagctggattttaacatggtacagaccctgcaccagaaagagctgcaagatctgtcccgctggtggaccgagatg
ggcctggctagcaaactggattttgtacgcgaccgcctgatggaagtttattctgggcactgggtatggcgccagacc
cgcagtttggtgaatgtcgcaaagctgttactaaaatgtttggtctggtgacgatcatcgatgacgtgtatgacgtttatg
gcactctggacgaactgcaactgttcaccgatgctgtagagcgctgggacgttaacgctattaacaccctgccggact
atatgaaactgtgtttcctggcactgtacaacaccgttaacgacacgtcctattctattctgaaagagaaaggtcataac
aacctgtcct

Figure 39C atctgacgaaaagctggcgtgaactgtgcaaagcctttctgcaagaggcgaaatggtccaacaacaaaatta
tcccggctttctccaagtacctggaaaacgccagcgtttcctcctccggtgtagcgctgctggcgccgtcttacttt
tccgtatgccagcagcaggaagacatctccgaccacgcgctgcgttccctgaccgacttccatggtctggtgc
gttctagctgcgttatcttccgcctgtgcaacgatctggccacctctgcggcggagctggaacgtggcgagact
accaattctatcattagctacatgcacgaaaacgatggtaccagcgaggaacaggcccgcgaagaactgcg
taaactgatcgacgccaatggaaaaagatgaatcgtgaacgcgttagcgactccaccctgctgcctaaagc
gttcatggaaatcgcagttaacatggcacgtgtttcccactgcacctaccagtatggcgatggtctgggtcgccc
agactacgcgactgaaaaccgcatcaaactgctgctgattgacccttccccgattaaccagctgatgtatgtcta
actgcagctggtaccatatgggaattcgaagctttctagaacaaaaactcatctcagaagaggatctgaatag
cgccgtcgaccatcatcatcatcatcattgagtttaaacggtctccagcttggctgttttggcggatgagagaag
attttcagcctgatacagattaaatcagaacgcagaagcggtctgataaaacagaatttgcctggcggcagta
gcgcggtggtcccacctgaccccatgccgaactcagaagtgaaacgccgtagcgccgatggtagtgtgggg
tctccccatgcgagagtagggaactgccaggcatcaaataaaacgaaaggctcagtcgaaagactgggcct
ttcgttttatctgttgtttgtcggtgaacgctctcctgagtaggacaaatccgccgggagcggatttgaacgttgcg
aagcaacggcccggagggtggcgggcaggacgcccgccataaactgccaggcatcaaattaagcagaa
ggccatcctgacggatggcctttttgcgtttctacaaactcttttttgtttatttttctaaatacattcaaatatgtatccgc
tcatgagacaataaccctgataaatgcttcaataat (SEQ ID NO:52)

Figure 41A

5'-
cccgtcttactgtcgggaattcgcgttggccgattcattaatgcagattattgaagcatttatcagggttattgtctcatg
agcggatacatatttgaatgtatttagaaaaataaacaaaaagagtttgtagaaacgcaaaaaggccatccgtca
ggatggccttctgcttaatttgatgcctggcagtttatggcgggcgtcctgcccgccaccctccgggccgttgcttcg
caacgttcaaatccgctcccggcggatttgtcctactcaggagagcgttcaccgacaaacaacagataaaacga
aaggcccagtctttcgactgagcctttcgttttatttgatgcctggcagttccctactctcgcatggggagaccccaca
ctaccatcggcgctacggcgtttcacttctgagttcggcatggggtcaggtgggaccaccgcgctactgccgcca
ggcaaattctgttttatcagaccgcttctgcgttctgatttaatctgtatcaggctgaaaatcttctctcatccgccaaaa
cagccaagctggagaccgtttaaactcaatgatgatgatgatgatggtcgacggcgctattcagatcctcttctgag
atgagttttgttctagaaagcttcgaattcccatatggtaccagctgcagttagacatacatcagctggttaatcggg
aaagggtcaatcagcagcagtttgatgcggttttcagtcgcgtagtctgggcgacccagaccatcgccatactggt
aggtgcagtgggaaacacgtgccatgttaactgcgatttccatgaacgctttaggcagcagggtggagtcgctaa
cgcgttcacgattcatcttttccattcggcgtcgatcagtttacgcagttcttcgcgggcctgttcctcgctggtaccat
cgttttcgtgcatgtagctaatgatagaattggtagtctcgccacgttccagctccgccgcagaggtggccagatcg
ttgcacaggcggaagataacgcagctagaacgcaccagaccatggaagtcggtcagggaacgcagcgcgtg
gtcggagatgtcttcctgctgctggcatacggaaaagtaagacggcgccagcagcgctacaccggaggagga
aacgctggcgttttccaggtacttggagaaagccgggataattttgttgttggaccatttcgcctcttgcagaaaggct
ttgcacagttcacgccagcttttcgtcagataggacaggttgttatgacctttctctttcagaatagaataggacgtgtc
gttaacggtgttgtacagtgccaggaaacacagtttcatatagtccggcagggtgttaatagcgttaacgtcccagc
gctctacagcatcggtgaacagttgcagttcgtccagagtgccataaacgtcatacacgtcatcgatgatcgtcac
cagaccaaacattttagtaacagctttgcgacattcaccaaactgcgggtctggcgccatacccagtgcccagaa
ataaacttccatcaggcggtcgcgtacaaaatccagtttgctagccaggcccatctcggtccaccagcgggaca
gatcttgcagctctttctggtgcagggtctgtaccatgttaaaatccagcttcgccagctccagcagcagctggtgat
gcggttctttcggttcgtatttatccaggaaccaacgtgcctccagacggtgcagacgctggtgatatggcagttcc
agggcgtggctcacttgttctgcaaccttggtattaatgccttctttcaggttgttcttcaggtgggtgatggaaaaggt
acgcgcctcctccagcaggttctcaccctcgaaacccaggtaagacgcttcatacaggctcagcaggccttgga
cgtcacctttcagttcaccgctgaaaccaccttctttatccttgaaacgctcaaaaacatcctgagaaacctcgaaa
ccgtgctgacgcagcagacggaaagacagagcggttgcgtgcaggtcagatttgttctttttgttttcgtccagcagt
acgatgttttccagggctttaatgatgtcttttcaaatttgtaggtcagacccaggcgctgcacatcgtcgatcagctc
cagcagggacagcggctgggtgtctacacggttgatcatgcagcgaacttcttcctccagtttggtcgctttctcctc
cagcttttccactttcaggtcgttctccagggattgcaggaattcgaaattccacaggtttggctgatagtttgcggaa
cgacgggaattatgctcggtaatctgagtaaattgagaagaggtcgcacacatggtttattcctccttatttaatcgat
acattaatatatacctctttaattttaataataaagttaatcgataattccggtcgagtgcccacacagattgtctgata
aattgttaaagagcagtgccgcttcgcttttttctcagcggcgctgtttcctgtgtgaaattgttatccgctcacaattcca
cacattatacgagccggatgattaattgtcaacagctcatttcagaatctggcgtaatagcgaagaggcccgcac
cgatcgcccttcccaacagttgcgcagcctgaatggcgaatggcgcctgatgcggtattttctccttacgcatctgtg
cggtatttcacaccgcatatggtgcactctcagtacaatctgctc

Figure 41B tgatgccgcatagttaagccagccccgacacccgccaacacccgctgacgagcttagtaaagccctcgctagat
tttaatgcggatgttgcgattacttcgccaactattgcgataacaagaaaaagccagcctttcatgatatatctccca
atttgtgtagggcttattatgcacgcttaaaaataataaaagcagacttgacctgatagtttggctgtgagcaattatg
tgcttagtgcatctaacgcttgagttaagccgcgccgcgaagcggcgtcggcttgaacgaattgttagacattattg
ccgactaccttggtgatctcgcctttcacgtagtggacaaattcttccaactgatctgcgcgcgaggccaagcgatc
ttcttcttgtccaagataagcctgtctagcttcaagtatgacgggctgatactgggccggcaggcgctccattgccca
gtcggcagcgacatccttcggcgcgatttgccggttactgcgctgtaccaaatgcgggacaacgtaagcactac
atttcgctcatcgccagcccagtcgggcggcgagttccatagcgttaaggtttcatttagcgcctcaaatagatcctg
ttcaggaaccggatcaaagagttcctccgccgctggacctaccaaggcaacgctatgttctcttgctttgtcagca
agatagccagatcaatgtcgatcgtggctggctcgaagatacctgcaagaatgtcattgcgctgccattctccaaa
ttgcagttcgcgcttagctggataacgccacggaatgatgtcgtcgtgcacaacaatggtgacttctacagcgcgg
agaatctcgctctctccaggggaagccgaagtttccaaaaggtcgttgatcaaagctcgccgcgttgtttcatcaa
gccttacggtcaccgtaaccagcaaatcaatatcactgtgtggcttcaggccgccatccactgcggagccgtaca
aatgtacggccagcaacgtcggttcgagatggcgctcgatgacgccaactacctctgatagttgagtcgatacttc
ggcgatcaccgcttccctcatgatgtttaactttgttttagggcgactgccctgctgcgtaacatcgttgctgctccata
acatcaaacatcgacccacggcgtaacgcgcttgctgcttggatgcccgaggcatagactgtaccccaaaaaa
acagtcataacaagccatgaaaaccgccactgcgccgttaccaccgctgcgttcggtcaaggttctggaccagtt
gcgtgagcgcatacgctacttgcattacagcttacgaaccgaacaggcttatgtccactgggttcgtgccttcatcc
gtttccacggtgtgcgtcacccggcaaccttgggcagcagcgaagtcgaggcatttctgtcctggctggcgaacg
agcgcaaggtttcggtctccacgcatcgtcaggcattggcggccttgctgttcttctacggcaaggtgctgtgcacg
gatctgccctggcttcaggagatcggaagacctcggccgtcgcggcgcttgccggtggtgctgacccggatga
agtggttcgcatcctcggttttctggaaggcgagcatcgtttgttcgcccagcttctgtatggaacgggcatgcggat
cagtgagggtttgcaactgcgggtcaaggatctggatttcgatcacggcacgatcatcgtgcgggagggcaagg
gctccaaggatcgggccttgatgttacccgagagcttggcacccagcctgcgcgagcaggggaattaattccca
cgggttttgctgcccgcaaacgggctgttctggtgttgctagtttgttatcagaatcgcagatccggcttcagccggttt
gccggctgaaagcgctatttcttccagaattgccatgatttttttccccacgggaggcgtcactggctcccgtgttgtcg
gcagctttgattcgataagcagcatcgcctgtttcaggctgtctatgtgtgactgttgagctgtaacaagttgtctcagg
tgtttcaatttcatgttctagttgctttgttttactggtttcacctgttctattaggtgttacatgctgttcatctgttacattgtcga
tctgttcatggtgaacagctttgaatgcaccaaaaactcgtaaaagctctgatgtatctatcttttttacaccgttttcatc
tgtgcatatggacagttttcccttgatatgtaacggtgaacagttgttctacttttgtttgttagtcttgatgcttcactgata
gatacaagagccataagaacctcagatccttccgtatttagccagtatgttctctagtgtggttcgttgtttttgcgtga
gccatgagaacgaaccattgagatcatacttactttgcatgtcactcaaaaattttgcctcaaaactggtgagctga
attttttgcagttaaagcatcgtgtagtgtttttcttagtccgttatgtaggtaggaatctgatgtaatggttgttggtattttgt
caccattcattttttatctggttgttctcaagttcggttacgagatccatttgtctatctagttcaacttggaaaatcaacgta
tcagtcgggcggcctcgcttatcaaccaccaatttcatattgctgtaagtgtttaaatctttacttattggtttcaaaacc
cattggttaagccttttaaactcatggtagttattttcaagcattaacatgaacttaaattcatcaaggctaatctctatat
ttgc

Figure 41C cttgtgagttttcttttgtgttagttcttttaataaccactcataaatcctcatagagtatttgttttcaaaagacttaacatgttc
cagattatattttatgaattttttttaactggaaaagataaggcaatatctcttcactaaaaactaattctaattttttcgcttga
gaacttggcatagtttgtccactggaaaatctcaaagcctttaaccaaaggattcctgatttccacagttctcgtcatca
gctctctggttgctttagctaatacaccataagcattttccctactgatgttcatcatctgagcgtattggttataagtgaac
gataccgtccgttctttccttgtagggttttcaatcgtggggttgagtagtgccacacagcataaaattagcttggtttcat
gctccgttaagtcatagcgactaatcgctagttcatttgctttgaaaacaactaattcagacatacatctcaattggtcta
ggtgattttaatcactataccaattgagatgggctagtcaatgataattactagtccttttcctttgagttgtgggtatctgt
aaattctgctagacctttgctggaaaacttgtaaattctgctagaccctctgtaaattccgctagacctttgtgtgtttttttt
gtttatattcaagtggttataatttatagaataaagaaagaataaaaaaagataaaaagaatagatcccagccctgt
gtataactcactactttagtcagttccgcagtattacaaaaggatgtcgcaaacgctgtttgctcctctacaaaacaga
ccttaaaaccctaaaggcttaagtagcaccctcgcaagctcgggcaaatcgctgaatattccttttgtctccgaccat
caggcacctgagtcgctgtcttttcgtgacattcagttcgctgcgctcacggctctggcagtgaatgggggtaaatgg
cactacaggcgccttttatggattcatgcaaggaaactacccataatacaagaaaagcccgtcacgggcttctcag
ggcgtttatggcgggtctgctatgtggtgctatctgacttttttgctgttcagcagttcctgccctctgattttccagtctgac
cacttcggattatcccgtgacaggtcattcagactggctaatgcacccagtaaggcagcggtatcatcaacaggctt
a (SEQ ID NO:53)

Figure 43A

5'- ctggcgtaatagcgaagaggcccgcaccgatcgcccttcccaacagttgcgcagcctgaatggcgaatggcg
cctgatgcggtattttctccttacgcatctgtgcggtatttcacaccgcatatggtgcactctcagtacaatctgctctg
atgccgcatagttaagccagccccgacacccgccaacacccgctgacgagcttagtaaagccctcgctagatt
ttaatgcggatgttgcgattacttcgccaactattgcgataacaagaaaaagccagcctttcatgatatatctccca
atttgtgtagggcttattatgcacgcttaaaaataataaaagcagacttgacctgatagtttggctgtgagcaattat
gtgcttagtgcatctaacgcttgagttaagccgcgccgcgaagcggcgtcggcttgaacgaattgttagacattat
ttgccgactaccttggtgatctcgcctttcacgtagtggacaaattcttccaactgatctgcgcgcgaggccaagc
gatcttcttcttgtccaagataagcctgtctagcttcaagtatgacgggctgatactgggccggcaggcgctccatt
gcccagtcggcagcgacatccttcggcgcgattttgccggttactgcgctgtaccaaatgcgggacaacgtaag
cactacatttcgctcatcgccagcccagtcgggcggcgagttccatagcgttaaggtttcatttagcgcctcaaat
agatcctgttcaggaaccggatcaaagagttcctccgccgctggacctaccaaggcaacgctatgttctcttgctt
ttgtcagcaagatagccagatcaatgtcgatcgtggctggctcgaagatacctgcaagaatgtcattgcgctgcc
attctccaaattgcagttcgcgcttagctggataacgccacggaatgatgtcgtcgtgcacaacaatggtgacttc
tacagcgcggagaatctcgctctctccaggggaagccgaagtttccaaaaggtcgttgatcaaagctcgccgc
gttgtttcatcaagccttacggtcaccgtaaccagcaaatcaatatcactgtgtggcttcaggccgccatccactg
cggagccgtacaaatgtacggccagcaacgtcggttcgagatggcgctcgatgacgccaactacctctgatag
ttgagtcgatacttcggcgatcaccgcttccctcatgatgtttaactttgttttagggcgactgccctgctgcgtaacat
cgttgctgctccataacatcaaacatcgacccacggcgtaacgcgcttgctgcttggatgcccgaggcatagac
tgtaccccaaaaaaacagtcataacaagccatgaaaaccgccactgcgccgttaccaccgctgcgttcggtca
aggttctggaccagttgcgtgagcgcatacgctacttgcattacagcttacgaaccgaacaggcttatgtccactg
ggttcgtgccttcatccgtttccacggtgtgcgtcacccggcaaccttgggcagcagcgaagtcgaggcatttctg
tcctggctggcgaacgagcgcaaggtttcggtctccacgcatcgtcaggcattggcggccttgctgttcttctacg
gcaaggtgctgtgcacggatctgccctggcttcaggagatcggaagacctcggccgtcgcggcgcttgccggt
ggtgctgaccccggatgaagtggttcgcatcctcggttttctggaaggcgagcatcgtttgttcgcccagcttctgta
tggaacgggcatgcggatcagtgagggtttgcaactgcgggtcaaggatctggatttcgatcacggcacgatca
tcgtgcgggagggcaagggctccaaggatcgggccttgatgttacccgagagcttggcacccagcctgcgcg
agcagggggaattaattcccacgggttttgctgcccgcaaacgggctgttctggtgttgctagtttgttatcagaatcg
cagatccggcttcagccggtttgccggctgaaagcgctatttcttccagaattgccatgatttttccccacgggag
gcgtcactggctcccgtgttgtcggcagctttgattcgataagcagcatcgcctgtttcaggctgtctatgtgtgact
gttgagctgtaacaagttgtctcaggtgttcaatttcatgttctagttgctttgttttactggtttcacctgttcattaggtgt
tacatgctgttcatctgttacattgtcgatctgttcatggtgaacagctttgaatgcaccaaaaactcgtaaaagctct
gatgtatctatcttttttacaccgttttcatctgtgcatatggacagtttccctttgatatgtaacggtgaacagttgttct
acttttgtttgttagtcttgatgcttcactgatagatacaagagccataagaacctcagatccttccgtatttagccagt
atgttctctagtgtggttcgttgttttgcgtgagccatgagaacgaaccattgagatcatacttactttgcatgtcactc
aaaaattttgcctcaaaactggtgagctgaattttgcagttaaagcatcgtgtagtgttttcttagtccgttatgtagg
taggaatctgatgtaatggttgttggtattttgtcaccattcattttatctggttgttctcaagttcgg

Figure 43B ttacgagatccatttgtctatctagttcaacttggaaaatcaacgtatcagtcgggcggcctcgcttatcaaccacc
aatttcatattgctgtaagtgtttaaatctttacttattggtttcaaaacccattggttaagccttttaaactcatggtagtt
attttcaagcattaacatgaacttaaattcatcaaggctaatctctatatttgccttgtgagttttcttttgtgttagttctttt
aataaccactcataaatcctcatagagtatttgttttcaaaagacttaacatgttccagattatatttatgaatttttta
actggaaaagataaggcaatatctcttcactaaaaactaattctaattttttcgcttgagaacttggcatagtttgtcc
actggaaaatctcaaagcctttaaccaaaggattcctgatttccacagttctcgtcatcagctctctggttgctttagc
taatacaccataagcattttccctactgatgttcatcatctgagcgtattggttataagtgaacgataccgtccgttctt
tccttgtagggttttcaatcgtggggttgagtagtgccacacagcataaaattagcttggtttcatgctccgttaagtc
atagcgactaatcgctagttcatttgctttgaaaacaactaattcagacatacatctcaattggtctaggtgattttaa
tcactataccaattgagatgggctagtcaatgataattactagtccttttcctttgagttgtgggtatctgtaaattctgc
tagacctttgctggaaaacttgtaaattctgctagaccctctgtaaattccgctagacctttgtgtgtttttttttgtttatatt
caagtggttataatttatagaataaagaaagaataaaaaaagataaaaagaatagatcccagccctgtgtata
actcactactttagtcagttccgcagtattacaaaaggatgtcgcaaacgctgtttgctcctctacaaaacagacct
taaaaccctaaaggcttaagtagcaccctcgcaagctcgggcaaatcgctgaatattccttttgtctccgaccatc
aggcacctgagtcgctgtctttttcgtgacattcagttcgctgcgctcacggctctggcagtgaatgggggtaaatg
gcactacaggcgccttttatggattcatgcaaggaaactacccataatacaagaaaagcccgtcacgggcttct
cagggcgttttatggcgggtctgctatgtggtgctatctgacttttgctgttcagcagttcctgccctctgattttccagt
ctgaccacttcggattatcccgtgacaggtcattcagactggctaatgcacccagtaaggcagcggtatcatcaa
caggcttacccgtcttactgtcgggaattcgcgttggccgattcattaatgcagattctgaaatgagctgttgacaat
taatcatccggctcgtataatgtgtggaattgtgagcggataacaatttcacacaggaaacagcgccgctgaga
aaaagcgaagcggcactgctctttaacaatttatcagacaatctgtgtgggcactcgaccggaattatcgattaa
ctttattattaaaaattaaagaggtatatattaatgtatcgattaaataaggaggaataaaccatgtgtgcgacctct
tctcaatttactcagattaccgagcataattcccgtcgttccgcaaactatcagccaaacctgtggaatttcgaattc
ctgcaatccctggagaacgacctgaaagtggaaaagctggaggagaaagcgaccaaactggaggaagaa
gttcgctgcatgatcaaccgtgtagacacccagccgctgtccctgctggagctgatcgacgatgtgcagcgcct
gggtctgacctacaaatttgaaaagacatcattaaagccctggaaaacatcgtactgctggacgaaaacaaa
aagaacaaatctgacctgcacgcaaccgctctgtctttccgtctgctgcgtcagcacggtttcgaggtttctcagg
atgttttgagcgtttcaaggataaagaaggtggtttcagcggtgaactgaaaggtgacgtccaaggcctgctga
gcctgtatgaagcgtcttacctgggtttcgagggtgagaacctgctggaggaggcgcgtaccttttccatcaccca
cctgaagaacaacctgaaagaaggcattaataccaaggttgcagaacaagtgagccacgccctggaactgc
catatcaccagcgtctgcaccgtctggaggcacgttggttcctggataaatacgaaccgaaagaaccgcatca
ccagctgctgctggagctggcgaagctggattttaacatggtacagaccctgcaccagaaagagctgcaagat
ctgtcccgctggtggaccgagatgggcctggctagcaaactggattttgtacgcgaccgcctgatggaagtttatt
tctgggcactgggtatggcgccagacccgcagtttggtgaatgtcgcaaagctgttactaaaatgtttggtctggtg
acgatcatcgatgacgtgtatgacgtttatggcactctggacgaactgcaactgttcaccgatgctgtagagcgct
gggacgttaacgctattaacaccctgccggactatgaaactgtgtttcctggcactgtacaacaccgttaacga
cacgtcctattctattctgaaagagaaaggtcataacaacctgtcct

Figure 43C atctgacgaaaagctggcgtgaactgtgcaaagcctttctgcaagaggcgaaatggtccaacaacaaaatt
atcccggctttctccaagtacctggaaaacgccagcgtttcctcctccggtgtagcgctgctggcgccgtctta
cttttccgtatgccagcagcaggaagacatctccgaccacgcgctgcgttccctgaccgacttccatggtctg
gtgcgttctagctgcgttatcttccgcctgtgcaacgatctggccacctctgcggcggagctggaacgtggcg
agactaccaattctatcattagctacatgcacgaaaacgatggtaccagcgaggaacaggcccgcgaaga
actgcgtaaactgatcgacgccgaatggaaaaagatgaatcgtgaacgcgttagcgactccaccctgctgc
ctaaagcgttcatggaaatcgcagttaacatggcacgtgtttcccactgcacctaccagtatggcgatggtctg
ggtcgcccagactacgcgactgaaaaccgcatcaaactgctgctgattgaccctttcccgattaaccagctg
atgtatgtctaactgcatcgcccttaggaggtaaaaaaaaatgactgccgacaacaatagtatgccccatgg
tgcagtatctagttacgccaaattagtgcaaaaccaaacacctgaagacattttggaagagtttcctgaaatta
ttccattacaacaaagacctaatacccgatcagtgagacgtcaaatgacgaaagcggagaaacatgttttt
ctggtcatgatgaggagcaaattaagttaatgaatgaaattgtattgttttggattgggacgataatgctattgg
tgccggtaccaagaaagtttgtcatttaatggaaaatattgaaaagggtttactacatcgtgcattctccgtctttta
ttttcaatgaacaaggtgaattacttttacaacaaagagccactgaaaaaataactttccctgatctttggacta
acacatgctgctctcatccactatgtattgatgacgaattaggtttgaagggtaagctagacgataagattaag
ggcgctattactgcggcggtgagaaaactagatcatgaattaggtattccagaagatgaaactaagacaag
gggtaagtttcacttttttaaacagaatccattacatggcaccaagcaatgaaccatggggtgaacatgaaatt
gattacatcctatttataagatcaacgctaaagaaaacttgactgtcaacccaaacgtcaatgaagttagag
acttcaaatgggtttcaccaaatgatttgaaaactatgtttgctgacccaagttacaagtttacgccttggtttaag
attatttgcgagaattacttattcaactggtgggagcaattagatgacctttctgaagtggaaaatgacaggca
aattcatagaatgctataacgacgcgtcctgcagctggtaccatatgggaattcgaagctttctagaacgaaa
actcatctcagaagaggatctgaatagcgccgtcgaccatcatcatcatcatcattgagtttaaacggtctcca
gcttggctgtttttggcggatgagagaagattttcagcctgatacagattaaatcagaacgcagaagcggtctg
ataaaacagaatttgcctggcggcagtagcgcggtggtcccacctgaccccatgccgaactcagaagtga
aacgccgtagcgccgatggtagtgtggggtctcccatgcgagagtagggaactgccaggcatcaaataa
aacgaaaggctcagtcgaaagactgggcctttcgttttatctgttgtttgtcggtgaacgctctcctgagtagga
caaatccgccgggagcggatttgaacgttgcgaagcaacggcccggagggtggcgggcaggacgcccg
ccataaactgccaggcatcaaattaagcagaaggccatcctgacggatggccttttgcgtttctacaaactct
ttttgtttatttttctaaatacattcaaatatgtatccgctcatgagacaataaccctgataaatgcttcaataat (SEQ ID NO:54)

Figure 45A

5'- cccgtcttactgtcgggaattcgcgttggccgattcattaatgcagattattgaagcatttatcagggttattgtctcatg
agcggatacatatttgaatgtatttagaaaaataaacaaaaagagtttgtagaaacgcaaaaaggccatccgtca
ggatggccttctgcttaatttgatgcctggcagtttatggcgggcgtcctgcccgccaccctccgggccgttgcttcg
caacgttcaaatccgctcccggcggatttgtcctactcaggagagcgttcaccgacaaacaacagataaaacga
aaggcccagtctttcgactgagcctttcgttttatttgatgcctggcagttccctactctcgcatggggagaccccaca
ctaccatcggcgctacggcgtttcacttctgagttcggcatggggtcaggtgggaccaccgcgctactgccgcca
ggcaaattctgttttatcagaccgcttctgcgttctgatttaatctgtatcaggctgaaaatcttctctcatccgccaaaa
cagccaagctggagaccgtttaaactcaatgatgatgatgatgatggtcgacggcgctattcagatcctcttctgag
atgagttttttgttctagaaagcttcgaattcccatatggtaccagctgcagttatgccagccaggccttgattttggcttc
cataccagcggcatcgaggccgagttcggcgcgcatttcttcctgagttccttgcggaataaagaagtccggcag
gccaatgttcagcacgggtactggtttacgatgggccatcagcacttcgttcacgccgctgcctgcgccgcccata
atggcgttttcttctacggtgaccagcgcttcatggctggcggccatttccagaattaacgcttcatcaagcggtttca
caaaacgcatatcgaccagcgtggcgttcagcgattcggcgactttcgccgcttctggcatcagcgtaccaaagtt
aaggatcgccagtttctcgccacgacgcttcacaatgcctttgccaattggtagtttttccagcggcgtcagttccac
gccgaccgcgttgccacgcgggtagcgcaccgctgacgggccatcgttatagtgatagccggtatagagcatct
ggcgacattcgttttcatcgctcggggtcataatgaccatttccggtatgcagcgcaggtaagagagatcaaaagc
accctgatgggtttgaccgtcagcaccaacaatgcccgcgcggtcgatggcgaacaggaccggaagcttttgaa
tcgccacgtcatgcagcacctgatcataggcgcgttgcaggaaagtggagtaaatcgcgacaatgggtttgtacc
caccaatcgccagacccgcagcaaaggtcaccgcgtgttgctcggcaattgccacgtcgaagtagcgatccgg
gaatttacgtgaaaactcgaccatgccggaaccttcacgcatcgccggagtaatcgccatcagcttgttgtctttcg
ctgccgtttcgcacaaccagtcgccaaagattttgaatagctcggcaaaccgccgctactttcggcaaacaacc
gctggagggatcaaatttaggcacggcgtggaaagtgatcgggtcttttctgccggttcataaccacgaccttttttg
gtcatgatatgcaggaactgcgggcctttcaggtcgcgcatgttctttagcgtggtgataagccccagcacatcgtg
accgtccaccgggccgatgtagttaaagcccagctcttcaaacaacgtgccaggcactaccatgcctttaatatgt
tcttcggtgcgtttgagcagctctttaattggcggcacgccagagaaaacttttttcccgccttcgcgcagtgaagag
taaagcttaccggaaagcagctgtgccagatggttgttgagcgcgccgacattttcggaaatcgacatttcattgtc
gttgagaatcaccagcatatcaggacggatatcgcccgcgtgattcatcgcttcaaacgccatgcctgcggtaatc
gcgccatcgccaatgacacagacggtgcggcgattttttgccttcttttcggcagcaaccgcaataccaattccgg
cactgatggaggttgatgaatgcccgacgcttaatacgtcatattcgctttcgccgcgccacgggaacgggtgca
gaccgcctttctgacggatggtgccgattttgtcgcggcgtccggtcaaaattttatgcggataagcctgatgcccca
catcccaaatcaattggtcaaacggggtgttgtagacatagtgcagcgccacggtcagttcgaccgtgcccagcc
cggaggcgaagtgcccgctggaacggctcacgctgtcgagtaaatagcggcgcagttcgtcgcagagtttcggt
aaactctctttcggcaacagtcgtaactcctgggtggagtcgaccagtgccagggtcgggtatttggcaatatcaa
aactcatgtttttttacctcctaagggcgaatgcagttagacatacatcagctggttaatcgggaaagggtcaatca
gcagcagtttgatgcggtttcagtcgcgtagtctgggcgacccagaccatcgccatactggtaggtgcagtggga
aacacgtgccatgttaactgcgatttccatgaacgctttaggcagcagggtggagtcgctaacgcgttcacg

Figure 45B attcatcttttccattcggcgtcgatcagtttacgcagttcttcgcgggcctgttcctcgctggtaccatcgttttcgtgca
tgtagctaatgatagaattggtagtctcgccacgttccagctccgccgcagaggtggccagatcgttgcacaggc
ggaagataacgcagctagaacgcaccagaccatggaagtcggtcagggaacgcagcgcgtggtcggagatg
tcttcctgctgctggcatacggaaaagtaagacggcgccagcagcgctacaccggaggaggaaacgctggcgt
ttccaggtacttggagaaagccgggataattttgttgttggaccatttcgcctcttgcagaaaggctttgcacagttca
cgccagcttttcgtcagataggacaggttgttatgacctttctctttcagaatagaataggacgtgtcgttaacggtgtt
gtacagtgccaggaaacacagtttcatatagtccggcagggtgttaatagcgttaacgtcccagcgctctacagc
atcggtgaacagttgcagttcgtccagagtgccataaacgtcatacacgtcatcgatgatcgtcaccagaccaaa
cattttagtaacagctttgcgacattcaccaaactgcgggtctggcgccatacccagtgcccagaaataaacttcc
atcaggcggtcgcgtacaaaatccagtttgctagccaggcccatctcggtccaccagcgggacagatcttgcag
ctctttctggtgcagggtctgtaccatgttaaaatccagcttcgccagctccagcagcagctggtgatgcggttctttc
ggttcgtatttatccaggaaccaacgtgcctccagacggtgcagacgctggtgatatggcagttccagggcgtgg
ctcacttgttctgcaaccttggtattaatgccttcttcaggttgttcttcaggtgggtgatggaaaaggtacgcgcctcc
tccagcaggttctcaccctcgaaacccaggtaagacgcttcatacaggctcagcaggccttggacgtcacctttca
gttcaccgctgaaaccaccttctttatccttgaaacgctcaaaaacatcctgagaaacctcgaaaccgtgctgacg
cagcagacggaaagacagagcggttgcgtgcaggtcagatttgttcttttgttttcgtccagcagtacgatgttttcc
agggctttaatgatgtcttttcaaatttgtaggtcagacccaggcgctgcacatcgtcgatcagctccagcaggga
cagcggctgggtgtctacacggttgatcatgcagcgaacttcttcctccagtttggtcgctttctcctccagcttttcca
ctttcaggtcgttctcagggattgcaggaattcgaaattccacaggtttggctgatagtttgcggaacgacgggaa
ttatgctcggtaatctgagtaaattgagaagaggtcgcacacatggtttattcctccttatttaatcgatacattaatata
tacctctttaatttttaataataaagttaatcgataattccggtcgagtgcccacacagattgtctgataaattgttaaag
agcagtgccgcttcgcttttctcagcggcgctgtttcctgtgtgaaattgttatccgctcacaattccacacattatacg
agccggatgattaattgtcaacagctcatttcagaatctggcgtaatagcgaagaggcccgcaccgatcgcccttc
ccaacagttgcgcagcctgaatggcgaatggcgcctgatgcggtattttctccttacgcatctgtgcggtatttcaca
ccgcatatggtgcactctcagtacaatctgctctgatgccgcatagttaagccagccccgacacccgccaacacc
cgctgacgagcttagtaaagccctcgctagattttaatgcggatgttgcgattacttcgccaactattgcgataacaa
gaaaaagccagcctttcatgatatatctcccaatttgtgtagggcttattatgcacgcttaaaaataataaaagcag
acttgacctgatagtttggctgtgagcaattatgtgcttagtgcatcaacgcttgagttaagccgcgccgcgaagcg
gcgtcggcttgaacgaattgttagacattatttgccgactaccttggtgatctcgcctttcacgtagtggacaaattctt
ccaactgatctgcgcgcgaggccaagcgatcttcttcttgtccaagataagcctgtctagcttcaagtatgacgggc
tgatactgggccggcaggcgctccattgcccagtcggcagcgacatccttcggcgcgattttgccggttactgcgc
tgtaccaaatgcgggacaacgtaagcactacatttcgctcatcgccagcccagtcgggcggcgagttccatagc
gttaaggtttcatttagcgcctcaaatagatcctgttcaggaaccggatcaaagagttcctccgccgctggacctac
caaggcaacgctatgttctcttgctttgtcagcaagatagccagatcaatgtcgatcgtggctggctcgaagatac
ctgcaagaatgtcattgcgctgccattctccaaattgcagttcgcgcttagctggataacgccacggaatgatgtcg
tcgtgcacaacaatggtgacttctacagcgcggagaatctcgctctctccaggggaagccgaagtttccaaaag
gtcgttgatcaaagctcgccgcgttgtttcatcaagc

Figure 45C cttacggtcaccgtaaccagcaaatcaatatcactgtgtggcttcaggccgccatccactgcggagccgtaca
aatgtacggccagcaacgtcggttcgagatggcgctcgatgacgccaactacctctgatagttgagtcgatact
tcggcgatcaccgcttccctcatgatgtttaactttgttttagggcgactgccctgctgcgtaacatcgttgctgctc
cataacatcaaacatcgacccacggcgtaacgcgcttgctgcttggatgcccgaggcatagactgtacccca
aaaaaacagtcataacaagccatgaaaaccgccactgcgccgttaccaccgctgcgttcggtcaaggttctg
gaccagttgcgtgagcgcatacgctacttgcattacagcttacgaaccgaacaggcttatgtccactgggttcgt
gccttcatccgtttccacggtgtgcgtcacccggcaaccttgggcagcagcgaagtcgaggcatttctgtcctgg
ctggcgaacgagcgcaaggtttcggtctccacgcatcgtcaggcattggcggccttgctgttcttctacggcaa
ggtgctgtgcacggatctgccctggcttcaggagatcggaagacctcggccgtcgcggcgcttgccggtggtg
ctgaccccggatgaagtggttcgcatcctcggttttctggaaggcgagcatcgtttgttcgcccagcttctgtatgg
aacgggcatgcggatcagtgagggtttgcaactgcgggtcaaggatctggatttcgatcacggcacgatcatc
gtgcgggagggcaagggctccaaggatcgggccttgatgttacccgagagcttggcacccagcctgcgcga
gcaggggaattaattcccacgggttttgctgcccgcaaacgggctgttctggtgttgctagtttgttatcagaatcg
cagatccggcttcagccggtttgccggctgaaagcgctatttcttccagaattgccatgattttttccccacggga
ggcgtcactggctcccgtgttgtcggcagctttgattcgataagcagcatcgcctgtttcaggctgtctatgtgtga
ctgttgagctgtaacaagttgtctcaggtgttcaatttcatgttctagttgctttgttttactggtttcacctgttctattag
gtgttacatgctgttcatctgttacattgtcgatctgttcatggtgaacagctttgaatgcaccaaaaactcgtaaaa
gctctgatgtatctatctttttacaccgttttcatctgtgcatatggacagttttcccttttgatatgtaacggtgaacagt
tgttctactttttgtttgttagtcttgatgcttcactgatagatacaagagccataagaacctcagatccttccgtattta
gccagtatgttctctagtgtggttcgttgttttttgcgtgagccatgagaacgaaccattgagatcatacttactttgca
tgtcactcaaaaattttgcctcaaaactggtgagctgaattttttgcagttaaagcatcgtgtagtgttttcttagtcc
gttatgtaggtaggaatctgatgtaatggttgttggtattttgtcaccattcattttatctggttgttctcaagttcggtta
cgagatccatttgtctatctagttcaacttggaaaatcaacgtatcagtcgggcggcctcgcttatcaaccacca
atttcatattgctgtaagtgtttaaatctttacttattggtttcaaaacccattggttaagccttttaaactcatggtagtt
attttcaagcattaacatgaacttaaattcatcaaggctaatctctatatttgccttgtgagttttcttttgtgttagttcttt
taataaccactcataaatcctcatagagtatttgttttcaaaagacttaacatgttccagattatattttatgaatttttt
aactggaaaagataaggcaatatctcttcactaaaaactaattctaattttttcgcttgagaacttggcatagtttgt
ccactggaaaatctcaaagcctttaaccaaaggattcctgatttccacagttctcgtcatcagctctctggttgcttt
agctaatacaccataagcattttccctactgatgttcatcatctgagcgtattggttataagtgaacgataccgtcc
gttctttccttgtagggttttcaatcgtgggttgagtagtgccacacagcataaaattagcttggtttcatgctccgtt
aagtcatagcgactaatcgctagttcatttgctttgaaaacaactaattcagacatacatctcaattggtctaggtg
attttaatcactataccaattgagatgggctagtcaatgataattactagtccttttcctttgagttgtgggtatctgta
aattctgctagacctttgctggaaaacttgtaaattctgctagaccctctgtaaattccgctagacctttgtgtgttttt
ttgtttatattcaagtggttataatttatagaataaagaaagaataaaaaagataaaaagaatagatcccagc
cctgtgtataactcactactttagtcagttccgcagtattacaaaaggatgtcgcaaacgctgtttgctcctctaca
aaacagaccttaaaaccctaaaggcttaagtagcaccctcgcaagctcgggcaaatcgctgaatattccttttg
tctccgaccatcaggcacctgagtcgctgtcttttc

Figure 45D

Gtgacattcagttcgctgcgctcacggctctggcagtgaatgggggtaaatggcactacaggcgccttttatggatt
catgcaaggaaactacccataatacaagaaaagcccgtcacgggcttctcagggcgttttatggcgggtctgcta
tgtggtgctatctgacttttgctgttcagcagttcctgccctctgattttccagtctgaccacttcggattatcccgtgaca
ggtcattcagactggctaatgcacccagtaaggcagcggtatcatcaacaggctta (SEQ ID NO:55)

Figure 51A

5'- tcgctgcgctcggtcgttcggctgcggcgagcggtatcagctcactcaaaggcggtaatacggttatccacaga
atcaggggataacgcaggaaagaacatgtgagcaaaaggccagcaaaaggccaggaaccgtaaaaagg
ccgcgttgctggcgtttttccataggctccgcccccctgacgagcatcacaaaaatcgacgctcaagtcagaggt
ggcgaaacccgacaggactataaagataccaggcgtttccccctggaagctccctcgtgcgctctcctgttccg
accctgccgcttaccggatacctgtccgcctttctcccttcgggaagcgtggcgctttctcatagctcacgctgtag
gtatctcagttcggtgtaggtcgttcgctccaagctgggctgtgtgcacgaaccccccgttcagcccgaccgctgc
gccttatccggtaactatcgtcttgagtccaacccggtaagacacgacttatcgccactggcagcagccactggt
aacaggattagcagagcgaggtatgtaggcggtgctacagagttcttgaagtggtggcctaactacggctacac
tagaagaacagtatttggtatctgcgctctgctgaagccagttaccttcggaaaaagagttggtagctcttgatccg
gcaaacaaaccaccgctggtagcggtggtttttttgtttgcaagcagcagattacgcgcagaaaaaaaggatct
caagaagatcctttgatcttttctacggggtctgacgctcagtggaacgaaaactcacgttaagggattttggtcat
gagattatcaaaaaggatcttcacctagatccttttaaattaaaaatgaagttttaaatcaatctaaagtatatatga
gtaaacttggtctgacagttaccaatgcttaatcagtgaggcacctatctcagcgatctgtctatttcgttcatccata
gttgcctgactccccgtcgtgtagataactacgatacgggagggcttaccatctggccccagtgctgcaatgata
ccgcgagacccacgctcaccggctccagatttatcagcaataaaccagccagccggaagggccgagcgca
gaagtggtcctgcaactttatccgcctccatccagtctattaattgttgccgggaagctagagtaagtagttcgcca
gttaatagtttgcgcaacgttgttgccattgctacaggcatcgtggtgtcacgctcgtcgtttggtatggcttcattcag
ctccggttcccaacgatcaaggcgagttacatgatccccatgttgtgcaaaaaagcggttagctccttcggtcct
ccgatcgttgtcagaagtaagttggccgcagtgttatcactcatggttatggcagcactgcataattctcttactgtc
atgccatccgtaagatgcttttctgtgactggtgagtactcaaccaagtcattctgagaatagtgtatgcggcgacc
gagttgctcttgcccggcgtcaatacgggataataccgcgccacatagcagaactttaaaagtgctcatcattgg
aaaacgttcttcggggcgaaaactctcaaggatcttaccgctgttgagatccagttcgatgtaacccactcgtgca
cccaactgatcttcagcatcttttactttcaccagcgtttctgggtgagcaaaaacaggaaggcaaaatgccgca
aaaaagggaataagggcgacacggaaatgttgaatactcatactcttcctttttcaatattattgaagcatttatca
gggttattgtctcatgagcggatacatatttgaatgtatttagaaaaataaacaaatagggggttccgcgcacatttc
cccgaaaagtgccacctgacgtctaagaaaccattattatcatgacattaacctataaaaataggcgtatcacg
aggccctttcgtctcgcgcgtttcggtgatgacggtgaaaacctctgacacatgcagctcccggagacggtcac
agcttgtctgtaagcggatgccgggagcagacaagcccgtcagggcgcgtcagcgggtgttggcgggtgtcg
gggctggcttaactatgcggcatcagagcagattgtactgagagtgcaccatagatctggagctgtaatataaa
aaccttcttcaactaacggggcaggttagtgacattagaaaaccgactgtaaaaagtacagtcggcattatctca
tattataaaagccagtcattaggcctatctgacaattcctgaatagagttcataaacaatcctgcatgataaccatc
acaaacagaatgatgtacctgtaaagatagcggtaaatatattgaattacctttattaatgaattttcctgctgtaata
atgggtagaaggtaattactattattattgatatttaagttaaacccagtaaatgaagtccatgaataatagaaag
agaaaaagcattttcaggtataggtgttttgggaaacaatttccccgaaccattatatttctctacatcagaaaggt
ataaatcataaaactctttgaagtcattctttacaggagtccaaataccagagaatgttttagatacaccatcaaa
aattgtataaagtggctctaacttatcccaataacctaactctccgtcgctattgtaaccagttctaaaagctgtattt
gagtttatcacccttgtcactaagaaaataaatgcagggtaaaatttatatccttcttgtttttatgtttc

Figure 51B ggtataaaacactaatatcaatttctgtggttatactaaaagtcgtttgttggttcaaataatgattaaatatctc
ttttctcttccaattgtctaaatcaattttattaaagttcatttgatatgcctcctaaattttatctaaagtgaattta
ggaggcttacttgtctgctttcttcattagaatcaatccttttttaaaagtcaatattactgtaacataaatatatat
tttaaaaatatcccactttatccaattttcgtttgttgaactaatgggtgctttagttgaagaataaaagacctat
gcggtgtgaaataccgcacagatgcgtaaggagaaaataccgcatcaggcgccattcgccattcaggc
tgcgcaactgttgggaagggcgatcggtgcgggcctcttcgctattacgccagctggcgaaaggggat
gtgctgcaaggcgattaagttgggtaacgccagggttttcccagtcacgacgttgtaaaacgacggccag
tgccaagcttgcatgcctgcactccattttcttctgctatcaaaataacagactcgtgattttccaaacgagct
ttcaaaaaagcctctgccccttgcaaatcggatgcctgtctataaaattcccgatattggttaaacagcggc
gcaatggcggccgcatctgatgtctttgcttggcgaatgttcatcttatttcttcctccctctcaataattttttcatt
ctatccctttctgtaaagtttattttttcagaatactttatcatcatgctttgaaaaaatatcacgataatatccatt
gttctcacggaagcacacgcaggtcatttgaacgaattttttcgacaggaatttgccgggactcaggagca
tttaacctaaaaaagcatgacatttcagcataatgaacatttactcatgtctattttcgttcttttctgtatgaaaa
tagttatttcgagtctctacggaaatagcgagagatgatatacctaaatagagataaaatcatctcaaaaa
aatgggtctactaaaatattattccatcattacaataaattcacagaatagtcttttaagtaagtctactctga
atttttttaaaaggagagggtaaagagtgaaaacagtagttattattgatgcattacgaacaccaattggaa
aatataaaggcagcttaagtcaagtaagtgccgtagacttaggaacacatgttacaacacaactttttaaa
aagacattccactatttctgaagaaattgatcaagtaatctttggaaatgttttacaagctggaaatggccaa
aatcccgcacgacaaatagcaataaacagcggtttgtctcatgaaattcccgcaatgacggttaatgagg
tctgcggatcaggaatgaaggccgttatttttggcgaaacaattgattcaattaggagaagcggaagtttta
attgctggcgggattgagaatatgtcccaagcacctaaattacaacgttttaattacgaaacagaaagcta
cgatgcgccttttttctagtatgatgtatgatggattaacggatgcctttagtggtcaggcaatgggcttaactg
ctgaaaatgtggccgaaaagtatcatgtaactagagaagagcaagatcaattttctgtacattcacaatta
aaagcagctcaagcacaagcagaagggatattcgctgacgaaatagccccattagaagtatcaggaa
cgcttgtggagaaagatgaagggattcgccctaattcgagcgttgagaagctaggaacgcttaaaacag
ttttttaaagaagacggtactgtaacagcagggaatgcatcaaccattaatgatggggcttctgctttgattatt
gcttcacaagaatatgccgaagcacacggtcttccttatttagctattattcgagacagtgtggaagtcggt
attgatccagcctatatgggaatttcgccgattaaagccattcaaaaactgttagcgcgcaatcaacttact
acggaagaaattgatctgtatgaaatcaacgaagcatttgcagcaacttcaatcgtggtccaaagagaa
ctggctttaccagaggaaaaggtcaacatttatggtggcggtatttcattaggtcatgcgattggtgccaca
ggtgctcgtttattaacgagtttaagttatcaattaaatcaaaaagaaaagaaatatggagtggcttctttatg
tatcggcggtggcttaggactcgctatgctactagagagacctcagcaaaaaaaaaacagccgattttat
caaatgagtcctgaggaacgcctggcttctcttcttaatgaaggccagatttctgctgatacaaaaaaaga
atttgaaaatacggctttatcttcgcagattgccaatcatatgattgaaaatcaaatcagtgaaacagaagt
gccgatgggcgttggcttacatttaacagtggacgaaactgattatttggtaccaatggcgacagaagag
ccctcagttattgcggctttgagtaatggtgcaaaaatagcacaaggatttaaaacagtgaatcaacaac
gcttaatgcgtggacaaatcgttttttacgatgttgcagatcccgagtcattgattgataaactacaagtaag
agaagcggaagttttcaacaagcagagttaagttatccatctatcgttaaacggggcggcggcttaaga
gatttgcaatatcgtacttttgatgaatcatttgtatctgtcgacttttagtagatgttaaggatgcaatgggggg
caaatatcgttaacgctatgttggaaggtgtg

Figure 51C gccgagttgttccgtgaatggtttgcggagcaaaagatttattcagtattttaagtaattatgccacggagtcggttg
ttacgatgaaaacggctattccagtttcacgttaagtaaggggagcaatggccgggaaattgctgaaaaaattg
ttttagcttcacgctatgcttcattagatccttatcgggcagtcacgcataacaaaggaatcatgaatggcattgaa
gctgtagttttagctacaggaaatgatacacgcgctgttagcgcttcttgtcatgcttttgcggtgaaggaaggtcgc
taccaaggcttgactagttggacgctggatggcgaacaactaattggtgaaatttcagttccgcttgctttagccac
ggttggcggtgccacaaaagtcttacctaaatctcaagcagctgctgatttgttagcagtgacggatgcaaaaga
actaagtcgagtagtagcggctgttggtttggcacaaaatttagcggcgttacgggccttagtctctgaaggaatt
caaaaaggacacatggctctacaagcacgttctttagcgatgacggtcggagctactggtaaagaagttgagg
cagtcgctcaacaattaaaacgtcaaaaaacgatgaaccaagaccgagccatggctatttaaatgatttaaga
aaacaataaaaggagagggtgacaattgggattgataaaattagtttttttgtgcccccttattatattgatatgacg
gcactggctgaagccagaaatgtagaccctggaaaatttcatattggtattgggcaagaccaaatggcggtga
acccaatcagccaagatattgtgacatttgcagccaatgccgcagaagcgatcttgaccaaagaagataaag
aggccattgatatggtgattgtcgggactgagtccagtatcgatgagtcaaaagcggccgcagttgtcttacatcg
tttaatggggattcaacctttcgctcgctctttcgaaatcaaggaagcttgttacggagcaacagcaggcttacagt
tagctaagaatcacgtagccttacatccagataaaaaagtcttggtcgtagcggcagatattgcaaaatatggct
taaattctggcggtgagcctacacaaggagctggggcggttgcaatgttagttgctagtgaaccgcgcattttggc
tttaaaagaggataatgtgatgctgacgcaagatatctatgacttttggcgtccaacaggccacccgtatcctatg
gtcgatggtcctttgtcaaacgaaacctacatccaatcttttgcccaagtctgggatgaacataaaaaacgaacc
ggtcttgattttgcagattatgatgctttagcgttccatattccttacacaaaaatgggcaaaaaagccttattagca
aaaatctccgaccaaactgaagcagaacaggaacgaattttagcccgttatgaagaaagtatcgtctatagtcg
tcgcgtaggaaacttgtatacgggttcactttatctgggactcatttcccttttagaaaatgcaacgactttaaccgc
aggcaatcaaattggtttattcagttatggttctggtgctgtcgctgaattttcactggtgaattagtagctggttatca
aaatcatttacaaaaagaaactcatttagcactgctggataatcggacagaactttctatcgctgaatatgaagcc
atgtttgcagaaactttagacacagacattgatcaaacgttagaagatgaattaaaatatagtatttctgctattaat
aataccgttcgttcttatcgaaactaaaaaaaaccggccttggccccgccggtttttattattttttcttcctccgcatgt
tcaatccgctccataatcgacggatggctccctctgaaaattttaacgagaaacggcgggttgacccggctcagt
cccgtaacggccaagtcctgaaacgtctcaatcgccgcttcccggtttccggtcagctcaatgccgtaacggtcg
gcggcgttttcctgataccgggagacggcattcgtaatcgggatccccgggtaccgagctcgaattcgtaatcat
gtcatagctgtttcctgtgtgaaattgttatccgctcacaattccacacaacatacgagccggaagcataaagtgt
aaagcctggggtgcctaatgagtgagctaactcacattaattgcgttgcgctcactgcccgctttccagtcgggaa
acctgtcgtgccagctgcattaatgaatcggccaacgcgcggggagaggcggtttgcgtattgggcgctcttccg
cttcctcgctcactgac (SEQ ID NO:56)

Figure 75A

| Fuel Conc. (wt.%) | Oxidizer Conc. (wt.%) | Fuel Makeup Isoprene (wt.%) | Oxidizer Makeup H₂O (wt.%) | Oxidizer Makeup O₂ (wt.%) | Oxidizer Makeup N₂ (wt.%) | Concentration at Deflagration — Molar Concentration based on 100g of sample | | | | | Volumetric Concentrations based on ideal gas law | | | |
|---|---|---|---|---|---|---|---|---|---|---|---|---|---|---|
| | | | | | | Isoprene (mole) | H₂O (mole) | O₂ (mole) | N₂ (mole) | Total (mole) | Isoprene (vol. %) | O₂ (vol. %) | N₂ (vol. %) | H₂O (vol. %) |
| 3.10 | 96.90 | 100 | 0 | 12 | 88 | 4.56 | 0.00 | 36.34 | 304.54 | 345.44 | 1.32 | 10.52 | 88.16 | 0.00 |
| 3.10 | 96.90 | 100 | 0 | 13 | 87 | 4.56 | 0.00 | 39.37 | 301.08 | 345.01 | 1.32 | 11.41 | 87.27 | 0.00 |
| 3.10 | 96.90 | 100 | 0 | 14 | 86 | 4.56 | 0.00 | 42.39 | 297.62 | 344.57 | 1.32 | 12.30 | 86.37 | 0.00 |
| 3.10 | 96.90 | 100 | 0 | 15 | 85 | 4.56 | 0.00 | 45.42 | 294.16 | 344.14 | 1.32 | 13.20 | 85.48 | 0.00 |
| 3.10 | 96.90 | 100 | 0 | 16 | 84 | 4.56 | 0.00 | 48.45 | 290.70 | 343.71 | 1.33 | 14.10 | 84.58 | 0.00 |
| 3.10 | 96.90 | 100 | 0 | 17 | 83 | 4.56 | 0.00 | 51.48 | 287.24 | 343.28 | 1.33 | 15.00 | 83.68 | 0.00 |
| 3.10 | 96.90 | 100 | 0 | 21 | 79 | 4.56 | 0.00 | 63.59 | 273.40 | 341.55 | 1.33 | 18.62 | 80.05 | 0.00 |
| 3.50 | 96.50 | 100 | 0 | 11.1 | 88.9 | 5.15 | 0.00 | 33.47 | 306.39 | 345.01 | 1.49 | 9.70 | 88.81 | 0.00 |
| 4.40 | 95.60 | 100 | 0 | 12 | 88 | 6.47 | 0.00 | 35.85 | 300.46 | 342.78 | 1.89 | 10.46 | 87.65 | 0.00 |
| 5.50 | 94.50 | 100 | 0 | 13 | 87 | 8.09 | 0.00 | 38.39 | 293.63 | 340.10 | 2.38 | 11.29 | 86.33 | 0.00 |
| 6.60 | 93.40 | 100 | 0 | 14 | 86 | 9.71 | 0.00 | 40.86 | 286.87 | 337.44 | 2.88 | 12.11 | 85.01 | 0.00 |
| 7.60 | 92.40 | 100 | 0 | 15 | 85 | 11.18 | 0.00 | 43.31 | 280.50 | 334.99 | 3.34 | 12.93 | 83.73 | 0.00 |
| 8.50 | 91.50 | 100 | 0 | 16 | 84 | 12.50 | 0.00 | 45.75 | 274.50 | 332.75 | 3.76 | 13.75 | 82.49 | 0.00 |
| 9.60 | 90.40 | 100 | 0 | 17 | 83 | 14.12 | 0.00 | 48.03 | 267.97 | 330.11 | 4.28 | 14.55 | 81.18 | 0.00 |
| 13.50 | 86.50 | 100 | 0 | 21 | 79 | 19.85 | 0.00 | 56.77 | 244.05 | 320.67 | 6.19 | 17.70 | 76.11 | 0.00 |

Figure 76A

| Fuel Conc. (wt.%) | Oxidizer Conc. (wt.%) | Fuel Makeup | Oxidizer Makeup | | | Concentration at Deflagration | | | | | | | |
|---|---|---|---|---|---|---|---|---|---|---|---|---|---|
| | | | | | | Molar Concentration based on 100g of sample | | | | | Volumetric Concentrations based on ideal gas law | | |
| | | Isoprene (wt. %) | $H_2O$ (wt. %) | $O_2$ (wt. %) | $N_2$ (wt. %) | Isoprene (mole) | $H_2O$ (mole) | $O_2$ (mole) | $N_2$ (mole) | Total (mole) | Isoprene (vol. %) | $O_2$ (vol. %) | $N_2$ (vol. %) | $H_2O$ (vol. %) |
| 3.252 | 96.748 | 100 | 4 | 12 | 84 | 4.78 | 21.50 | 36.28 | 290.24 | 352.81 | 1.36 | 10.28 | 82.27 | 6.09 |
| 3.274 | 96.726 | 100 | 4 | 13 | 83 | 4.81 | 21.49 | 39.29 | 286.72 | 352.33 | 1.37 | 11.15 | 81.38 | 6.10 |
| 3.290 | 96.710 | 100 | 4 | 14 | 82 | 4.84 | 21.49 | 42.31 | 283.22 | 351.86 | 1.38 | 12.02 | 80.49 | 6.11 |
| 3.288 | 96.712 | 100 | 4 | 15 | 81 | 4.84 | 21.49 | 45.33 | 279.77 | 351.43 | 1.38 | 12.90 | 79.61 | 6.12 |
| 3.286 | 96.714 | 100 | 4 | 16 | 80 | 4.83 | 21.49 | 48.36 | 276.33 | 351.01 | 1.38 | 13.78 | 78.72 | 6.12 |
| 3.284 | 96.716 | 100 | 4 | 17 | 79 | 4.83 | 21.49 | 51.38 | 272.88 | 350.58 | 1.38 | 14.66 | 77.84 | 6.13 |
| 3.276 | 96.724 | 100 | 4 | 21 | 75 | 4.82 | 21.49 | 63.48 | 259.08 | 348.87 | 1.38 | 18.19 | 74.26 | 6.16 |
| 3.500 | 96.500 | 100 | 4 | 11.5 | 84.5 | 5.15 | 21.44 | 34.68 | 291.22 | 352.49 | 1.46 | 9.84 | 82.62 | 6.08 |
| 4.200 | 95.800 | 100 | 4 | 12 | 84 | 6.18 | 21.29 | 35.93 | 287.40 | 350.79 | 1.76 | 10.24 | 81.93 | 6.07 |
| 5.300 | 94.700 | 100 | 4 | 13 | 83 | 7.79 | 21.04 | 38.47 | 280.72 | 348.03 | 2.24 | 11.05 | 80.66 | 6.05 |
| 6.400 | 93.600 | 100 | 4 | 14 | 82 | 9.41 | 20.80 | 40.95 | 274.11 | 345.28 | 2.73 | 11.86 | 79.39 | 6.02 |
| 7.400 | 92.600 | 100 | 4 | 15 | 81 | 10.88 | 20.58 | 43.41 | 267.88 | 342.74 | 3.18 | 12.66 | 78.16 | 6.00 |
| 8.500 | 91.500 | 100 | 4 | 16 | 80 | 12.50 | 20.33 | 45.75 | 261.43 | 340.01 | 3.68 | 13.46 | 76.89 | 5.98 |
| 9.400 | 90.600 | 100 | 4 | 17 | 79 | 13.82 | 20.13 | 48.13 | 255.62 | 337.71 | 4.09 | 14.25 | 75.69 | 5.96 |
| 13.300 | 86.700 | 100 | 4 | 21 | 75 | 19.56 | 19.27 | 56.90 | 232.23 | 327.95 | 5.96 | 17.35 | 70.81 | 5.87 |

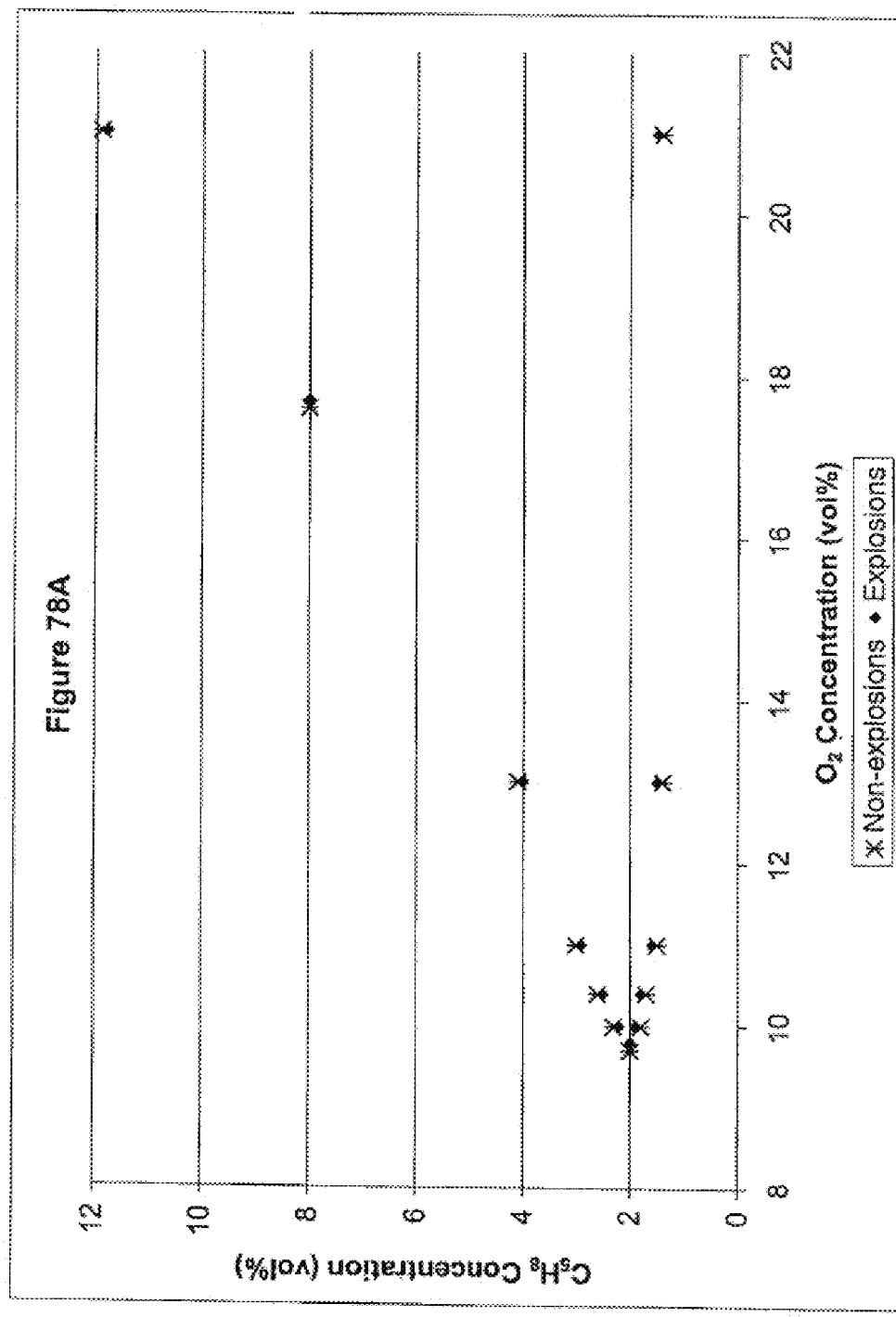

Figure 78B

| Explosions | | Non-explosions | |
|---|---|---|---|
| O₂ Concentration (vol. %) | C₅H₈ Concentration (vol. %) | O₂ Concentration (vol. %) | C₅H₈ Concentration (vol. %) |
| 21.0 | 1.5 | 21.0 | 1.4 |
| 13.0 | 1.5 | 13.0 | 1.4 |
| 11.0 | 1.6 | 11.0 | 1.5 |
| 10.4 | 1.8 | 10.4 | 1.7 |
| 10.0 | 1.9 | 10.0 | 1.8 |
| 9.8 | 2 | 9.7 | 2 |
| 10.0 | 2.2 | 10.0 | 2.3 |
| 10.4 | 2.5 | 10.4 | 2.6 |
| 11.0 | 2.9 | 11.0 | 3.0 |
| 13.0 | 4.0 | 13.0 | 4.1 |
| 17.7 | 8.0 | 17.6 | 8.0 |
| 21.0 | 11.8 | 21.0 | 11.9 |

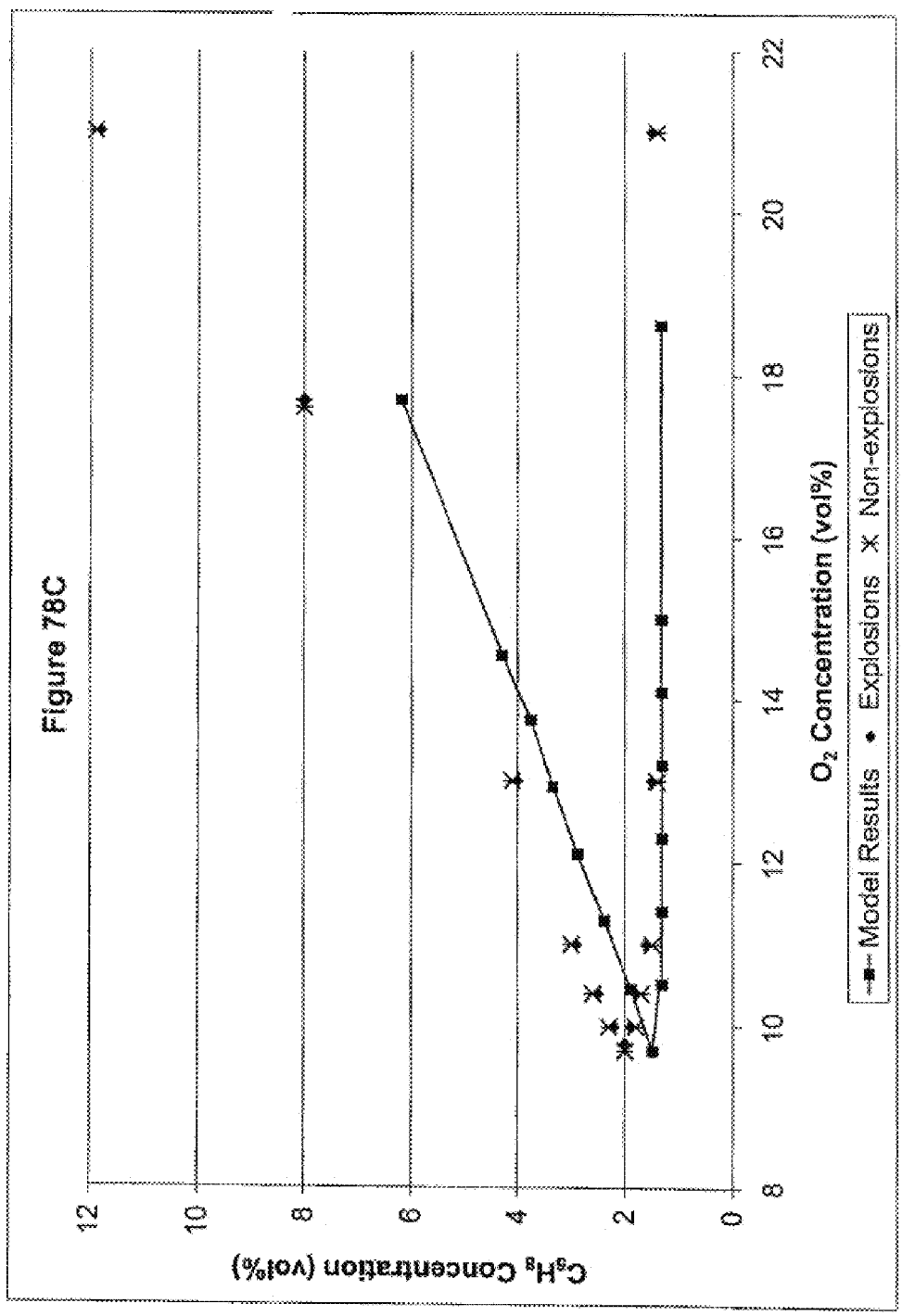

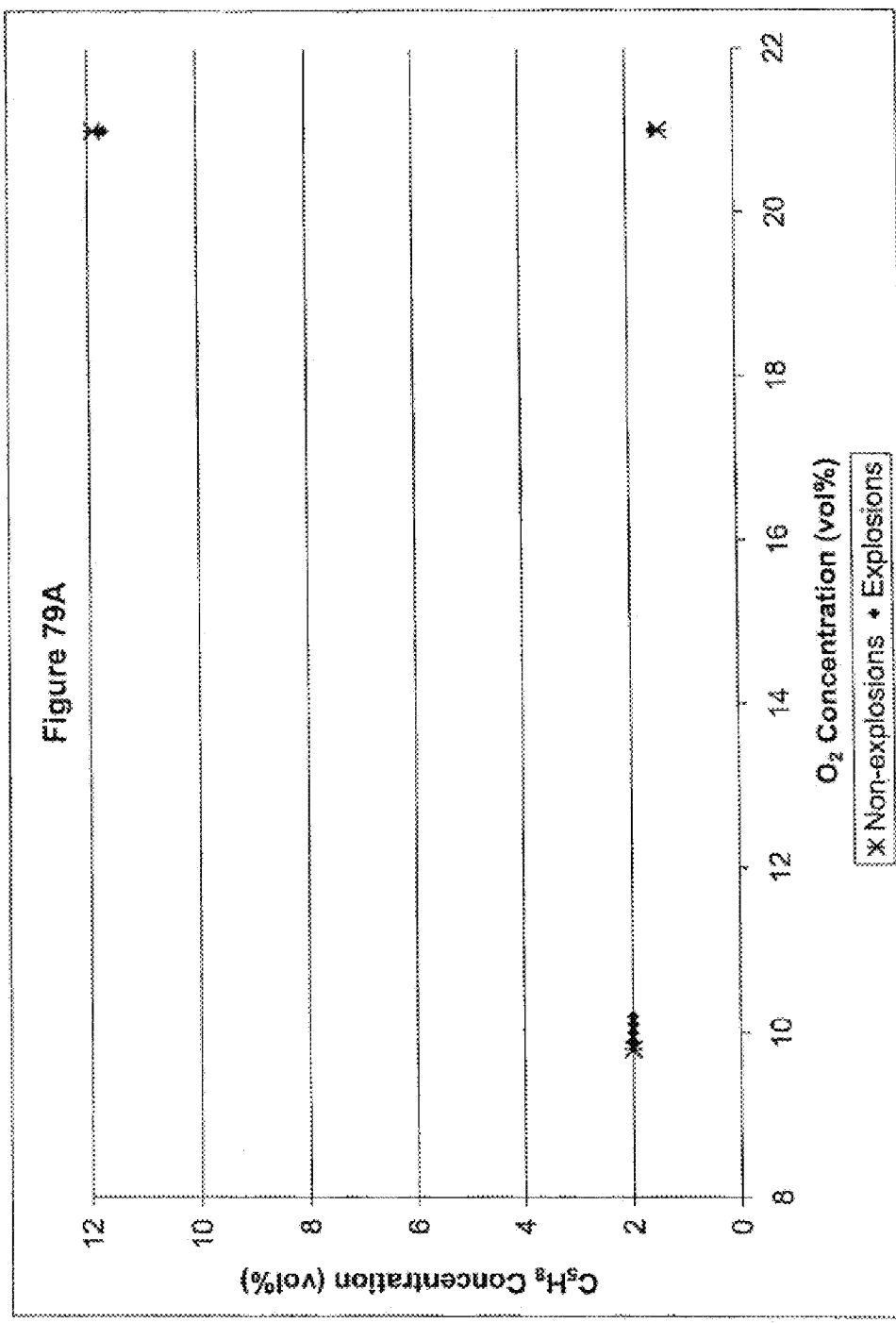

Figure 79B

| Explosions | | Non-explosions | |
|---|---|---|---|
| $O_2$ Concentration (vol. %) | $C_5H_8$ Concentration (vol. %) | $O_2$ Concentration (vol. %) | $C_5H_8$ Concentration (vol. %) |
| 21.0 | 11.7 | 21.0 | 11.9 |
| 21.0 | 11.8 | 21.0 | 11.9 |
| 21.0 | 11.8 | 21.0 | 11.9 |
| 21.0 | 1.5 | 21.0 | 1.4 |
| 21.0 | 1.5 | 21.0 | 1.4 |
| 10.2 | 2.0 | 21.0 | 1.4 |
| 10.1 | 2.0 | 9.8 | 2.0 |
| 10.0 | 2.0 | 9.8 | 2.0 |
| 9.9 | 2.0 | 9.8 | 2.0 |

Figure 80A

TEST SERIES 1

| Test | Data File Name | Temp °C | Initial Pressure bara | Partial Pressures C₃H₈ mbar | Partial Pressures N₂ mbar | Partial Pressures O₂ mbar | Concentrations C₃H₈ vol. % | Concentrations N₂ vol. % | Concentrations O₂ vol. % | Result | Pex bara |
|---|---|---|---|---|---|---|---|---|---|---|---|
| 1 | T11120700 | 40 | 1.012 | 12 | 787 | 213 | 1.2 | 77.8 | 21.0 | Non-Explosion | 1.05 |
| 2 | T11120701 | 40 | 1.016 | 16 | 787 | 213 | 1.6 | 77.5 | 21.0 | Explosion | 5.5 |
| 3 | T11120702 | 40 | 1.015 | 14 | 788 | 213 | 1.4 | 77.6 | 21.0 | Non-Explosion | <1.02 |
| 4 | T11120703 | 40 | 1.014 | 15 | 786 | 213 | 1.5 | 77.5 | 21.0 | Non-Explosion | <1.02 |
| 5 | T11120704 | 40 | 1.014 | 15 | 786 | 213 | 1.5 | 77.5 | 21.0 | Explosion | 4.31 |
| 6 | T11120705 | 40 | 1.017 | 18 | 785 | 214 | 1.8 | 77.2 | 21.0 | Explosion | 5.47 |
| 7 | T11120706 | 40 | 1.014 | 15 | 786 | 213 | 1.5 | 77.5 | 21.0 | Explosion | 4.51 |
| 8 | T11120707 | 40 | 1.014 | 14 | 787 | 213 | 1.4 | 77.6 | 21.0 | Non-Explosion | <1.02 |
| 9 | T11120708 | 40 | 1.014 | 14 | 787 | 213 | 1.4 | 77.6 | 21.0 | Non-Explosion | 1.05 |
| 10 | T11120709 | 40 | 1.015 | 102 | 700 | 213 | 10.0 | 69.0 | 21.0 | Explosion | 1.45 |
| 11 | T11120710 | 40 | 1.014 | 102 | 699 | 213 | 10.1 | 68.9 | 21.0 | Explosion | 1.39 |
| 12 | T11120711 | 40 | 1.014 | 106 | 695 | 213 | 10.5 | 68.5 | 21.0 | Explosion | 1.34 |
| 13 | T11120712 | 40 | 1.014 | 113 | 688 | 213 | 11.1 | 67.9 | 21.0 | Explosion | 1.29 |
| 14 | T11120713 | 40 | 1.014 | 122 | 679 | 213 | 12.0 | 67.0 | 21.0 | Non-Explosion | <1.02 |
| 15 | T11120714 | 40 | 1.014 | 117 | 684 | 213 | 11.5 | 67.5 | 21.0 | Explosion | 1.32 |
| 16 | T11120715 | 40 | 1.014 | 120 | 681 | 213 | 11.8 | 67.2 | 21.0 | Non-Explosion | 1.08 |
| 17 | T11130700 | 40 | 1.014 | 120 | 681 | 213 | 11.8 | 67.2 | 21.0 | Explosion | 1.09 |
| 18 | T11130701 | 40 | 1.014 | 121 | 680 | 213 | 11.9 | 67.1 | 21.0 | Non-Explosion | 1.07 |
| 19 | T11130702 | 40 | 1.015 | 121 | 681 | 213 | 11.9 | 67.1 | 21.0 | Non-Explosion | 1.06 |
| 20 | T11130703 | 40 | 1.015 | 121 | 681 | 213 | 11.9 | 67.1 | 21.0 | Non-Explosion | 1.07 |
| 21 | T11130704 | 40 | 1.015 | 30 | 853 | 132 | 3.0 | 84.0 | 13.0 | Explosion | 1.61 |
| 22 | T11130705 | 40 | 1.014 | 36 | 846 | 132 | 3.6 | 83.4 | 13.0 | Explosion | 1.28 |
| 23 | T11130706 | 40 | 1.014 | 39 | 843 | 132 | 3.8 | 83.1 | 13.0 | Explosion | 1.12 |
| 24 | T11130707 | 40 | 1.015 | 41 | 842 | 132 | 4.0 | 83.0 | 13.0 | Explosion | 1.09 |
| 25 | T11130708 | 40 | 1.014 | 42 | 840 | 132 | 4.1 | 82.8 | 13.0 | Non-Explosion | 1.06 |
| 26 | T11130709 | 40 | 1.015 | 42 | 841 | 132 | 4.1 | 82.9 | 13.0 | Non-Explosion | 1.06 |
| 27 | T11130710 | 40 | 1.014 | 42 | 840 | 132 | 4.1 | 82.8 | 13.0 | Non-Explosion | 1.05 |
| 28 | T11130711 | 40 | 1.014 | 15 | 867 | 132 | 1.5 | 85.5 | 13.0 | Non-Explosion | 1.03 |
| 29 | T11130712 | 40 | 1.014 | 16 | 866 | 132 | 1.6 | 85.4 | 13.0 | Explosion | 4.81 |
| 30 | T11130713 | 40 | 1.014 | 15 | 867 | 132 | 1.5 | 85.5 | 13.0 | Explosion | 4 |
| 31 | T11130714 | 40 | 1.014 | 14 | 868 | 132 | 1.4 | 85.6 | 13.0 | Non-Explosion | 1.03 |
| 32 | T11130715 | 40 | 1.014 | 14 | 868 | 132 | 1.4 | 85.6 | 13.0 | Non-Explosion | <1.02 |
| 33 | T11130716 | 40 | 1.014 | 14 | 868 | 132 | 1.4 | 85.6 | 13.0 | Non-Explosion | 1.03 |
| 34 | T11130717 | 40 | 1.015 | 20 | 883 | 112 | 2.0 | 87.0 | 11.0 | Explosion | 1.7 |
| 35 | T11130718 | 40 | 1.014 | 28 | 874 | 112 | 2.8 | 86.2 | 11.0 | Non-Explosion | 1.08 |
| 36 | T11130719 | 40 | 1.014 | 28 | 874 | 112 | 2.8 | 86.2 | 11.0 | Non-Explosion | 1.08 |
| 37 | T11130720 | 40 | 1.014 | 28 | 874 | 112 | 2.8 | 86.2 | 11.0 | Explosion | 1.13 |
| 38 | T11130721 | 40 | 1.015 | 29 | 874 | 112 | 2.9 | 86.1 | 11.0 | Non-Explosion | 1.08 |
| 39 | T11130722 | 40 | 1.014 | 29 | 873 | 112 | 2.9 | 86.1 | 11.0 | Explosion | 1.1 |

Figure 80B

| Test | Data File Name | Temp °C | Initial Pressure bara | Partial Pressures C₃H₈ mbar | Partial Pressures N₂ mbar | Partial Pressures O₂ mbar | Concentrations C₃H₈ vol.% | Concentrations N₂ vol.% | Concentrations O₂ vol.% | Result | Pex bara |
|---|---|---|---|---|---|---|---|---|---|---|---|
| 40 | T11130723 | 40 | 1.014 | 30 | 872 | 112 | 3.0 | 86.0 | 11.0 | Non-Explosion | 1.08 |
| 41 | T11130724 | 40 | 1.014 | 30 | 872 | 112 | 3.0 | 86.0 | 11.0 | Non-Explosion | 1.05 |
| 42 | T11130725 | 40 | 1.014 | 30 | 872 | 112 | 3.0 | 86.0 | 11.0 | Non-Explosion | 1.05 |
| 43 | T11130726 | 40 | 1.014 | 15 | 887 | 112 | 1.5 | 87.5 | 11.0 | Non-Explosion | <1.02 |
| 44 | T11130727 | 40 | 1.014 | 15 | 887 | 112 | 1.5 | 87.5 | 11.0 | Non-Explosion | <1.02 |
| 45 | T11140700 | 40 | 1.014 | 16 | 886 | 112 | 1.6 | 87.4 | 11.0 | Non-Explosion | <1.02 |
| 46 | T11140701 | 40 | 1.014 | 17 | 885 | 112 | 1.7 | 87.3 | 11.0 | Explosion | 1.81 |
| 47 | T11140702 | 40 | 1.014 | 16 | 886 | 112 | 1.6 | 87.4 | 11.0 | Explosion | 1.54 |
| 48 | T11140703 | 40 | 1.014 | 15 | 887 | 112 | 1.5 | 87.5 | 11.0 | Non-Explosion | <1.02 |
| 49 | T11140704 | 40 | 1.015 | 20 | 899 | 96 | 2.0 | 88.6 | 9.5 | Non-Explosion | 1.05 |
| 50 | T11140705 | 40 | 1.014 | 20 | 898 | 96 | 2.0 | 88.6 | 9.5 | Non-Explosion | 1.05 |
| 51 | T11140706 | 40 | 1.014 | 23 | 890 | 101 | 2.3 | 87.8 | 10.0 | Non-Explosion | 1.05 |
| 52 | T11140707 | 40 | 1.015 | 23 | 886 | 106 | 2.3 | 87.3 | 10.4 | Explosion | 1.19 |
| 53 | T11140708 | 40 | 1.014 | 25 | 884 | 105 | 2.5 | 87.2 | 10.4 | Explosion | 1.09 |
| 54 | T11140709 | 40 | 1.014 | 26 | 883 | 105 | 2.6 | 87.1 | 10.4 | Non-Explosion | 1.05 |
| 55 | T11140710 | 40 | 1.014 | 26 | 883 | 105 | 2.6 | 87.1 | 10.4 | Non-Explosion | 1.06 |
| 56 | T11140711 | 40 | 1.014 | 26 | 883 | 105 | 2.6 | 87.1 | 10.4 | Non-Explosion | 1.07 |
| 57 | T11140712 | 40 | 1.014 | 20 | 889 | 105 | 2.0 | 87.7 | 10.4 | Explosion | 1.21 |
| 58 | T11140713 | 40 | 1.014 | 17 | 892 | 105 | 1.7 | 88.0 | 10.4 | Non-Explosion | 1.04 |
| 59 | T11140714 | 40 | 1.014 | 18 | 891 | 105 | 1.8 | 87.9 | 10.4 | Explosion | 1.21 |
| 60 | T11140715 | 40 | 1.014 | 17 | 892 | 105 | 1.7 | 88.0 | 10.4 | Non-Explosion | 1.03 |
| 61 | T11140716 | 40 | 1.014 | 17 | 892 | 105 | 1.7 | 88.0 | 10.4 | Non-Explosion | 1.03 |
| 62 | T11140717 | 40 | 1.014 | 21 | 890 | 103 | 2.1 | 87.8 | 10.2 | Explosion | 1.1 |
| 63 | T11140718 | 40 | 1.014 | 21 | 891 | 102 | 2.1 | 87.9 | 10.1 | Explosion | 1.09 |
| 64 | T11140719 | 40 | 1.014 | 21 | 892 | 101 | 2.1 | 88.0 | 10.0 | Explosion | 1.09 |
| 65 | T11140720 | 40 | 1.014 | 22 | 891 | 101 | 2.2 | 87.9 | 10.0 | Explosion | 1.1 |
| 66 | T11140721 | 40 | 1.014 | 23 | 890 | 101 | 2.3 | 87.8 | 10.0 | Non-Explosion | 1.06 |
| 67 | T11140722 | 40 | 1.014 | 23 | 890 | 101 | 2.3 | 87.8 | 10.0 | Non-Explosion | 1.08 |
| 68 | T11140723 | 40 | 1.014 | 19 | 894 | 101 | 1.9 | 88.2 | 10.0 | Explosion | 1.12 |
| 69 | T11140724 | 40 | 1.014 | 18 | 895 | 101 | 1.8 | 88.3 | 10.0 | Non-Explosion | 1.06 |
| 70 | T11140725 | 40 | 1.014 | 18 | 895 | 101 | 1.8 | 88.3 | 10.0 | Non-Explosion | 1.03 |
| 71 | T11140726 | 40 | 1.014 | 18 | 895 | 101 | 1.8 | 88.3 | 10.0 | Non-Explosion | 1.04 |
| 72 | T11140727 | 40 | 1.014 | 20 | 895 | 99 | 2.0 | 88.3 | 9.8 | Non-Explosion | 1.08 |
| 73 | T11140728 | 40 | 1.014 | 20 | 895 | 99 | 2.0 | 88.3 | 9.8 | Explosion | 1.1 |
| 74 | T11140729 | 40 | 1.014 | 20 | 896 | 98 | 2.0 | 88.4 | 9.7 | Non-Explosion | 1.06 |
| 75 | T11140730 | 40 | 1.014 | 20 | 896 | 98 | 2.0 | 88.4 | 9.7 | Non-Explosion | 1.08 |
| 76 | T11140731 | 40 | 1.014 | 20 | 896 | 98 | 2.0 | 88.4 | 9.7 | Non-Explosion | 1.07 |
| 77 | T11140732 | 40 | 1.014 | 81 | 761 | 172 | 8.0 | 75.0 | 17.0 | Non-Explosion | 1.04 |
| 78 | T11140733 | 40 | 1.014 | 81 | 750 | 183 | 8.0 | 74.0 | 18.0 | Explosion | 1.3 |
| 79 | T11140734 | 40 | 1.014 | 81 | 754 | 179 | 8.0 | 74.4 | 17.7 | Explosion | 1.24 |
| 80 | T11140735 | 40 | 1.014 | 81 | 757 | 176 | 8.0 | 74.7 | 17.4 | Non-Explosion | 1.03 |
| 81 | T11140736 | 40 | 1.014 | 81 | 755 | 178 | 8.0 | 74.5 | 17.6 | Non-Explosion | 1.05 |
| 82 | T11140737 | 40 | 1.014 | 81 | 755 | 178 | 8.0 | 74.5 | 17.6 | Non-Explosion | 1.03 |
| 83 | T11140738 | 40 | 1.014 | 81 | 755 | 178 | 8.0 | 74.5 | 17.6 | Non-Explosion | 1.03 |

Figure 81

TEST SERIES 2

| Test | Data File Name | Temp °C | Initial Pressure bara | Partial Pressures | | | | Concentrations | | | | Result | Pex bara |
|---|---|---|---|---|---|---|---|---|---|---|---|---|---|
| | | | | $H_2O$ mbar | $C_3H_8$ mbar | $N_2$ mbar | $O_2$ mbar | $H_2O$ vol. % | $C_3H_8$ vol. % | $N_2$ vol. % | $O_2$ vol. % | | |
| 1 | T11150700 | 40 | 1.014 | 41 | 119 | 641 | 213 | 4.0 | 11.7 | 63.2 | 21.0 | Explosion | 1.33 |
| 2 | T11150701 | 40 | 1.014 | 40 | 121 | 640 | 213 | 3.9 | 11.9 | 63.1 | 21.0 | Non-explosion | 1.07 |
| 3 | T11150702 | 40 | 1.014 | 41 | 120 | 640 | 213 | 4.0 | 11.8 | 63.1 | 21.0 | Explosion | 1.09 |
| 4 | T11150703 | 40 | 1.014 | 40 | 121 | 640 | 213 | 3.9 | 11.9 | 63.1 | 21.0 | Non-explosion | 1.06 |
| 5 | T11150704 | 40 | 1.014 | 40 | 120 | 641 | 213 | 3.9 | 11.8 | 63.2 | 21.0 | Explosion | 1.09 |
| 6 | T11150705 | 40 | 1.014 | 40 | 121 | 640 | 213 | 3.9 | 11.9 | 63.1 | 21.0 | Non-explosion | 1.08 |
| 7 | T11150706 | 40 | 1.014 | 40 | 15 | 746 | 213 | 3.9 | 1.5 | 73.6 | 21.0 | Explosion | 4.68 |
| 8 | T11150707 | 40 | 1.014 | 41 | 15 | 745 | 213 | 4.0 | 1.5 | 73.5 | 21.0 | Explosion | 5.27 |
| 9 | T11150708 | 40 | 1.014 | 41 | 14 | 746 | 213 | 4.0 | 1.4 | 73.6 | 21.0 | Non-explosion | 1.03 |
| 10 | T11150709 | 40 | 1.014 | 42 | 14 | 745 | 213 | 4.1 | 1.4 | 73.5 | 21.0 | Non-explosion | 1.03 |
| 11 | T11160700 | 40 | 1.014 | 41 | 14 | 746 | 213 | 4.0 | 1.4 | 73.6 | 21.0 | Non-explosion | 1.03 |
| 12 | T11160701 | 40 | 1.014 | 41 | 20 | 850 | 103 | 4.0 | 2.0 | 83.8 | 10.2 | Explosion | 1.11 |
| 13 | T11160702 | 40 | 1.014 | 41 | 20 | 851 | 102 | 4.0 | 2.0 | 83.9 | 10.1 | Explosion | 1.11 |
| 14 | T11160703 | 40 | 1.014 | 41 | 20 | 852 | 101 | 4.0 | 2.0 | 84.0 | 10.0 | Explosion | 1.09 |
| 15 | T11160704 | 40 | 1.014 | 41 | 20 | 853 | 100 | 4.0 | 2.0 | 84.1 | 9.9 | Explosion | 1.09 |
| 16 | T11160705 | 40 | 1.014 | 41 | 20 | 854 | 99 | 4.0 | 2.0 | 84.2 | 9.8 | Non-explosion | 1.07 |
| 17 | T11160706 | 40 | 1.014 | 40 | 20 | 855 | 99 | 3.9 | 2.0 | 84.3 | 9.8 | Non-explosion | 1.06 |
| 18 | T11160707 | 40 | 1.014 | 41 | 20 | 854 | 99 | 4.0 | 2.0 | 84.2 | 9.8 | Non-explosion | 1.08 |

2-methyl-1,3-butadiene standard.

2-methyl-1,3-butadiene from recombinant *E. coli*

Figure 90
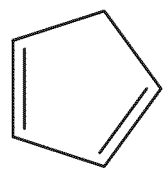
cyclopentadiene
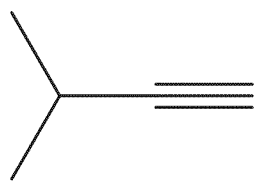
"isopryne" = 3-Me-1-butyne
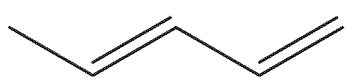
trans-piperylene
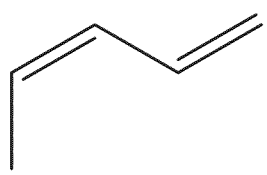
cis-piperylene
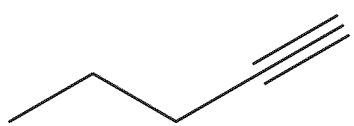
1-pentyne
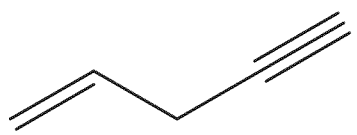
pent-4-ene-1-yne
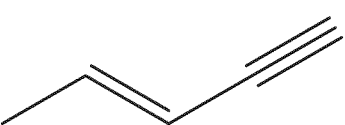
trans-pent-3-ene-1-yne
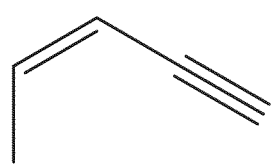
cis-pent-3-ene-1-yne

Figure 92A 1-
gtttgacagcttatcatcgactgcacggtgcaccaatgcttctggcgtcaggcagccatcggaagctgtggtatggctgtgcaggtc
gtaaatcactgcataattcgtgtcgctcaaggcgcactcccgttctggataatgtttttgcgccgacatcataacggttctggcaaata
ttctgaaatgagctgttgacaattaatcatccggctcgtataatgtgtggaattgtgagcggataacaatttcacacaggaaacagcg
ccgctgagaaaaagcgaagcggcactgctctttaacaatttatcagacaatctgtgtgggcactcgaccggaattatcgattaacttt
attattaaaattaaagaggtatatattaatgtatcgattaaataaggaggaataaaccatggatccgagctcaggaggtaaaaaa
acatgaaaacagtagttattattgatgcattacgaacaccaattggaaaatataaaggcagcttaagtcaagtaagtgccgtagact
taggaacacatgttacaacacaacttttaaaaagacattccactatttctgaagaaattgatcaagtaatctttggaaatgttttacaag
ctggaaatggccaaaatcccgcacgacaaatagcaataaacagcggtttgtctcatgaaattcccgcaatgacggttaatgaggt
ctgcggatcaggaatgaaggccgttattttggcgaaacaattgattcaattaggagaagcggaagttttaattgctggcgggattga
gaatatgtcccaagcacctaaattacaacgttttaattacgaaacagaaagctacgatgcgccttttctagtatgatgtatgatggatt
aacggatgcctttagtggtcaggcaatgggcttaactgctgaaaatgtggccgaaaagtatcatgtaactagagaagagcaagat
caattttctgtacattcacaattaaaagcagctcaagcacaagcagaagggatattcgctgacgaaatagccccattagaagtatc
aggaacgcttgtggagaaagatgaagggattcgccctaattcgagcgttgagaagctaggaacgcttaaaacagttttaaagaa
gacggtactgtaacagcagggaatgcatcaaccattaatgatggggcttctgctttgattattgcttcacaagaatatgccgaagca
cacggtcttccttatttagctattattcgagacagtgtggaagtcggtattgatccagcctatatgggaatttcgccgattaaagccattc
aaaaactgttagcgcgcaatcaacttactacggaagaaattgatctgtatgaaatcaacgaagcatttgcagcaacttcaatcgtg
gtccaaagagaactggctttaccagaggaaaaggtcaacatttatggtggcggtatttcattaggtcatgcgattggtgccacaggt
gctcgtttattaacgagtttaagttatcaattaaatcaaaagaaaagaaatatggagtggcttctttatgtatcggcggtggcttagga
ctcgctatgctactagagagacctcagcaaaaaaaaaacagccgattttatcaaatgagtcctgaggaacgcctggcttctcttctt
aatgaaggccagatttctgctgatacaaaaaaagaatttgaaaatacggctttatcttcgcagattgccaatcatatgattgaaaatc
aaatcagtgaaacagaagtgccgatgggcgttggcttacatttaacagtggacgaaactgattatttggtaccaatggcgacagaa
gagccctcagttattgcggctttgagtaatggtgcaaaaatagcacaaggattttaaaacagtgaatcaacaacgcttaatgcgtgg
acaaatcgttttttacgatgttgcagatcccgagtcattgattgataaactacaagtaagagaagcggaagttttcaacaagcagag
ttaagttatccatctatcgttaaacggggcggcggcttaagagatttgcaatatcgtacttttgatgaatcatttgtatctgtcgactttttag
tagatgttaaggatgcaatgggggcaaatatcgttaacgctatgttggaaggtgtggccgagttgttccgtgaatggtttgcggagca
aaagattttattcagtattttaagtaattatgccacggagtcggttgttacgatgaaaacggctattccagtttcacgtttaagtaagggg
agcaatggccgggaaattgctgaaaaaattgttttagcttcacgctatgcttcattagatccttatcgggcagtcacgcataacaaag
gaatcatgaatggcattgaagctgtagttttagctacaggaaatgatacacgcgctgttagcgcttcttgtcatgcttttgcggtgaagg
aaggtcgctaccaaggcttgactagttggacgctggatggcgaacaactaattggtgaaatttcagttccgcttgcttagccacggtt
ggcggtgccacaaaagtcttacctaaatctcaagcagctgctgatttgttagcagtgacggatgcaaaagaactaagtcgagtagt
agcggctgttggtttggcacaaaatttagcggcgttacgggccttagtctctgaaggaattcaaaaaggacacatggctctacaag
cacgttctttagcgatgacggtcggagctactggtaaagaagttgaggcagtcgctcaacaattaaaacgtcaaaaaacgatgaa
ccaagaccgagccatggctatttaaatgatttaagaaaacaataaggaggtaaaaaaacatgacaattgggattgataaaatt
agttttttgtgccccttattatattgatatgacggcactggctgaagccagaaatgtagaccctggaaaatttcatattggtattgggc
aagaccaaatggccggtgaacccaatcagccaagatattgtgacatttgcagccaatgccgcagaagcgatcttgaccaaagaa
gataaagaggccattgatatggtgattgtcgggactgagtccagtatcgatgagtcaaaagcggccgcagttgtcttacatcgtttaa
tggggattcaacctttcgctcgctctttcgaaatcaaggaagcttgttacggagcaacagcaggcttacagttagctaagaatcacgt
agccttacatccagataaaaaagtcttggtcgtagcggcagatattgcaaaatatggcttaaattctggcggtgagcctacacaag
gagctggggcggttgcaatgttagttgctagtgaaccgcgcattttggctttaaaagaggataatgtgatgctgacgcaagatatctat
gacttttggcgtccaacaggccacccgtatcctatggtcgatggtcctttgtcaaacgaaacctacatccaatcttttgcccaagtctg
ggatgaacataaaaaacgaaccggtcttgattttgcagattatgatgctttagcgttccatattccttacacaaaaatgggcaaaaaa
gccttattagcaaaaatctccgaccaaactgaagcagaacaggaacgaattttagcccgttatgaagaaagtatcgtctatagtcg
tcgcgtaggaaacttgtatacgggttcactttatctgggactcatttccctttagaaaatgcaacgactttaaccgcaggcaatcaaat
tggtttattcagttatggttctggtgctgtcgctgaattttcactggtgaattag

Figure 92B tagctggttatcaaaatcatttacaaaaagaaactcatttagcactgctggataatcggacagaactttctatcgctgaatatga
agccatgtttgcagaaactttagacacagacattgatcaaacgttagaagatgaattaaaatatagtatttctgctattaataata
ccgttcgttcttatcgaaactaagagatctgcagctggtaccatatgggaattcgaagcttgggcccgaacaaaaactcatct
cagaagaggatctgaatagcgccgtcgaccatcatcatcatcatcattgagtttaaacggtctccagcttggctgttttggcgg
atgagagaagattttcagcctgatacagattaaatcagaacgcagaagcggtctgataaaacagaatttgcctggcggcag
tagcgcggtggtcccacctgacccatgccgaactcagaagtgaaacgccgtagcgccgatggtagtgtggggtctcccc
atgcgagagtagggaactgccaggcatcaaataaaacgaaaggctcagtcgaaagactgggcctttcgttatctgttgttt
gtcggtgaacgctctcctgagtaggacaaatccgccggggagcggatttgaacgttgcgaagcaacggcccggagggtgg
cgggcaggacgccgccataaactgccaggcatcaaattaagcagaaggccatcctgacggatggcctttttgcgtttctac
aaactcttttgtttatttttctaaatacattcaaatatgtatccgctcatgagacaataaccctgataaatgcttcaataatattgaa
aaaggaagagtatgagtattcaacatttccgtgtcgcccttattccctttttgcggcattttgccttcctgttttgctcacccagaaa
cgctggtgaaagtaaaagatgctgaagatcagttgggtgcacgagtgggttacatcgaactggatctcaacagcggtaaga
tccttgagagttttcgccccgaagaacgttttccaatgatgagcacttttaaagttctgctatgtggcgcggtattatcccgtgttga
cgccgggcaagagcaactcggtcgccgcatacactattctcagaatgacttggttgagtactcaccagtcacagaaaagca
tcttacggatggcatgacagtaagagaattatgcagtgctgccataaccatgagtgataacactgcggccaacttacttctga
caacgatcggaggaccgaaggagctaaccgcttttttgcacaacatgggggatcatgtaactcgccttgatcgttgggaacc
ggagctgaatgaagccataccaaacgacgagcgtgacaccacgatgcctgtagcaatggcaacaacgttgcgcaaact
attaactggcgaactacttactctagcttcccggcaacaattaatagactggatggaggcggataaagttgcaggaccacttc
tgcgctcggcccttccggctggctggtttattgctgataaatctggagccggtgagcgtgggtctcgcggtatcattgcagcact
ggggccagatggtaagccctcccgtatcgtagttatctacacgacggggagtcaggcaactatggatgaacgaaatagac
agatcgctgagataggtgcctcactgattaagcattggtaactgtcagaccaagtttactcatatatactttagattgatttaaaa
cttcatttttaatttaaaaggatctaggtgaagatcctttttgataatctcatgaccaaaatcccttaacgtgagttttcgttccactga
gcgtcagaccccgtagaaaagatcaaaggatcttcttgagatccttttttctgcgcgtaatctgctgcttgcaaacaaaaaaa
ccaccgctaccagcggtggtttgtttgccggatcaagagctaccaactcttttccgaaggtaactggcttcagcagagcgca
gataccaaatactgtccttctagtgtagccgtagttaggccaccacttcaagaactctgtagcaccgcctacatacctcgctctg
ctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatac
ctacagcgtgagctatgagaaagcgccacgcttcccgaagggagaaaggcggacaggtatccggtaagcggcagggtc
ggaacaggagagcgcacgagggagcttccaggggaaacgcctggtatctttatagtcctgtcgggtttcgccacctctga
cttgagcgtcgatttttgtgatgctcgtcaggggggcggagcctatggaaaaacgccagcaacgcggcctttttacggttcctg
gccttttgctggccttttgctcacatgttcttcctgcgttatccctgattctgtggataaccgtattaccgcctttgagtgagctgata
ccgctcgccgcagccgaacgaccgagcgcagcgagtcagtgagcgaggaagcggaagagcgcctgatgcggtattttct
ccttacgcatctgtgcggtatttcacaccgcatatggtgcactctcagtacaatctgctctgatgccgcatagttaagccagtata
cactccgctatcgctacgtgactgggtcatggctgcgccccgacacccgccaacacccgctgacgcgccctgacgggcttg
tctgctcccggcatccgcttacagacaagctgtgaccgtctccgggagctgcatgtgtcagaggttttcaccgtcatcaccgaa
acgcgcgaggcagcagatcaattcgcgcgcgaaggcgaagcggcatgcatttacgttgacaccatcgaatggtgcaaaa
cctttcgcggtatggcatgatagcgcccggaagagagtcaattcagggtggtgaatgtgaaaccagtaacgttatacgatgtc
gcagagtatgccggtgtctcttatcagaccgtttcccgcgtggtgaaccaggccagccacgtttctgcgaaaacgcgggaaa
aagtggaagcggcgatggcggagctgaattacattcccaaccgcgtggcacaacaactggcgggcaaacagtcgttgct
gattggcgttgccacctccagtctggccctgcacgcgccgtcgcaaattgtcgcggcgattaaatctcgcgccgatcaactgg
gtgccagcgtggtggtgtcgatggtagaacgaagcggcgtcgaagcctgtaaagcggcggtgcacaatcttctcgcgcaa
cgcgtcagtgggctgatcattaactatccgctggatgaccaggatgccattgctgtggaagctgcctgcactaatgttccggcg
ttatttcttgatgtctctgaccagacacccatcaacagtattattttctcccatgaagacggtacgcgactgggcgtggagcatct
ggtcgcattgggtcaccagcaaatcgcgctgttagcgggcccattaagttctgtctcggcgcgtctgcgtctggctggctggca
taaatatctcactcgcaatcaaattcagccgatagcggaacgggaaggcgactggagtgccatgtccggttttcaacaaac
catgcaaatgctgaatgagggcatcg

Figure 92C ttcccactgcgatgctggttgccaacgatcagatggcgctgggcgcaatgcgcgccattaccgagtccgggctgcgcgttg
gtgcggatatctcggtagtgggatacgacgataccgaagacagctcatgttatatcccgccgtcaaccaccatcaaacag
gattttcgcctgctggggcaaaccagcgtggaccgcttgctgcaactctctcagggccaggcggtgaagggcaatcagct
gttgcccgtctcactggtgaaaagaaaaaccaccctggcgcccaatacgcaaaccgcctctccccgcgcgttggccgatt
cattaatgcagctggcacgacaggtttcccgactggaaagcgggcagtgagcgcaacgcaattaatgtgagttagcgcg
aattgatctg (SEQ ID NO:86)

Figure 103A cccgtcttactgtcgggaattcgcgttggccgattcattaatgcagattctgaaatgagctgttgacaattaatcatccggctcgt
ataatgtgtggaattgtgagcggataacaatttcacacaggaaacagcgccgctgagaaaaagcgaagcggcactgctctt
taacaatttatcagacaatctgtgtgggcactcgaccggaattatcgattaactttattattaaaaattaaagaggtatatattaat
gtatcgattaaataaggaggaataaaccatggatccgagctcaggaggtaaaaaaacatgaaaacagtagttattattgat
gcattacgaacaccaattggaaaatataaaggcagcttaagtcaagtaagtgccgtagacttaggaacacatgttacaaca
caacttttaaaaagacattccactatttctgaagaaattgatcaagtaatctttggaaatgttttacaagctggaaatggccaaa
atcccgcacgacaaatagcaataaacagcggtttgtctcatgaaatcccgcaatgacggttaatgaggtctgcggatcagg
aatgaaggccgttattttggcgaaacaattgattcaattaggagaagcggaagttttaattgctggcgggattgagaatatgtc
ccaagcacctaaattacaacgttttaattacgaaacagaaagctacgatgcgccttttctagtatgatgtatgatggattaacg
gatgcctttagtggtcaggcaatgggcttaactgctgaaaatgtggccgaaaagtatcatgtaactagagaagagcaagatc
aattttctgtacattcacaattaaaagcagctcaagcacaagcagaagggatattcgctgacgaaatagccccattagaagt
atcaggaacgcttgtggagaaagatgaagggattcgccctaattcgagcgttgagaagctaggaacgcttaaaacagttttt
aaagaagacggtactgtaacagcagggaatgcatcaaccattaatgatggggcttctgctttgattattgcttcacaagaatat
gccgaagcacacggtcttccttatttagctattattcgagacagtgtggaagtcggtattgatccagcctatatgggaatttcgcc
gattaaagccattcaaaaactgttagcgcgcaatcaacttactacggaagaaattgatctgtatgaaatcaacgaagcatttg
cagcaacttcaatcgtggtccaaagagaactggctttaccagaggaaaaggtcaacatttatggtggcggtatttcattaggtc
atgcgattggtgccacaggtgctcgtttattaacgagtttaagttatcaattaaatcaaaaagaaaagaaatatggagtggcttc
tttatgtatcggcggtggcttaggactcgctatgctactagagagacctcagcaaaaaaaaaacagccgattttatcaaatga
gtcctgaggaacgcctggcttctcttcttaatgaaggccagatttctgctgatacaaaaaaagaatttgaaaatacggctttatct
tcgcagattgccaatcatatgattgaaaatcaaatcagtgaaacagaagtgccgatgggcgttggcttacatttaacagtgga
cgaaactgattatttggtaccaatggcgacagaagagccctcagttattgcggctttgagtaatggtgcaaaaatagcacaa
ggatttaaaacagtgaatcaacaacgcttaatgcgtggacaaatcgttttttacgatgttgcagatcccgagtcattgattgata
aactacaagtaagagaagcggaagttttcaacaagcagagttaagttatccatctatcgttaaacggggcggcggcttaag
agatttgcaatatcgtactttgatgaatcatttgtatctgtcgactttttagtagatgttaaggatgcaatgggggcaaatatcgtta
acgctatgttggaaggtgtggccgagttgttccgtgaatggtttgcggagcaaaagatttattcagtattttaagtaattatgcca
cggagtcggttgttacgatgaaaacggctattccagtttcacgtttaagtaaggggagcaatggccgggaaattgctgaaaa
aattgttttagcttcacgctatgcttcattagatccttatcgggcagtcacgcataacaaaggaatcatgaatggcattgaagctg
tagttttagctacaggaaatgatacacgcgctgttagcgcttcttgtcatgcttttgcggtgaaggaaggtcgctaccaaggcttg
actagttggacgctggatggcgaacaactaattggtgaaatttcagttccgcttgctttagccacggttggcggtgccacaaaa
gtcttacctaaatctcaagcagctgctgatttgttagcagtgacggatgcaaaagaactaagtcgagtagtagcggctgttggt
ttggcacaaaatttagcggcgttacgggccttagtctctgaaggaattcaaaaaggacacatggctctacaagcacgttctta
gcgatgacggtcggagctactggtaaagaagttgaggcagtcgctcaacaattaaaacgtcaaaaaacgatgaaccaag
accgagccatggctattttaaatgatttaagaaaacaataaggaggtaaaaaaacatgacaattgggattgataaaattag
ttttttttgtgcccccttattatattgatatgacggcactggctgaagccagaaatgtagaccctggaaaatttcatattggtattggg
caagaccaaatggcggtgaacccaatcagccaagatattgtgacatttgcagccaatgccgcagaagcgatcttgaccaa
agaagataaagaggccattgatatggtgattgtcgggactgagtccagtatcgatgagtcaaaagcggccgcagttgtctta
catcgtttaatggggattcaacctttcgctcgtctttcgaaatcaaggaagcttgttacggagcaacagcaggcttacagttag
ctaagaatcacgtagccttacatccagataaaaaagtcttggtcgtagcggcagatattgcaaaatatggcttaaattctggcg
gtgagcctacacaaggagctggggcggttgcaatgttagttgctagtgaaccgcgcattttggctttaaaagaggataatgtg
atgctgacgcaagatatctatgactttggcgtccaacaggccacccgtatcctatggtcgatggtccttgtcaaacgaaacct
acatccaatcttttgcccaagtctgggatgaacataaaaaacgaaccggtcttgattttgcagattatgatgctttagcgttccat
attccttacacaaaaatgggcaaaaaagccttattagcaaaaatctccgaccaaactgaagcagaacaggaacgaattta
gcccgttatgaagaaagtatcgtctatagtcgtcgcgtaggaaacttgtatacgggttcactttatctgggactcatttcccttttag
aaaatgcaacgactttaaccgcaggcaatcaaattggtttattcagttatggttctggtgctgtcgctgaattttcactggtgaatt
agtagctggttatcaaaatcatttacaaaaagaaactcatttagcactgctggataatcggacagaactttctatcgctgaatat
gaagccatgtttgcagaaactttagacacagacattgatcaaacgtta

Figure 103B gaagatgaattaaaatatagtatttctgctattaataataccgttcgttcttatcgaaactaaagatctgcatcctgcattcgccct
taggaggtaaaaaaacatgtgtgcgacctcttctcaatttactcagattaccgagcataattcccgtcgttccgcaaactatc
agccaaacctgtggaatttcgaattcctgcaatccctggagaacgacctgaaagtggaaaagctggaggagaaagcga
ccaaactggaggaagaagttcgctgcatgatcaaccgtgtagacacccagccgctgtccctgctggagctgatcgacgat
gtgcagcgcctgggtctgacctacaaatttgaaaaagacatcattaaagccctggaaaacatcgtactgctggacgaaaa
caaaaagaacaaatctgacctgcacgcaaccgctctgtctttccgtctgctgcgtcagcacggtttcgaggtttctcaggatg
tttttgagcgtttcaaggataaagaaggtggtttcagcggtgaactgaaaggtgacgtccaaggcctgctgagcctgtatga
agcgtcttacctgggtttcgaggtgagaacctgctggaggaggcgcgtaccttttccatcacccacctgaagaacaacct
gaaagaaggcattaataccaaggttgcagaacaagtgagccacgccctggaactgccatatcaccagcgtctgcaccg
tctggaggcacgttggttcctggataaatacgaaccgaaagaaccgcatcaccagctgctgctggagctggcgaagctg
gattttaacatggtacagaccctgcaccagaaagagctgcaagatctgtcccgctggtggaccgagatgggcctggctag
caaactggattttgtacgcgaccgcctgatggaagtttatttctgggcactgggtatggcgccagacccgcagtttggtgaat
gtcgcaaagctgttactaaaatgtttggtctggtgacgatcatcgatgacgtgtatgacgtttatggcactctggacgaactgc
aactgttcaccgatgctgtagagcgctgggacgttaacgctattaaccaccctgccggactatatgaaactgtgtttcctggca
ctgtacaacaccgttaacgacacgtcctattcttattctgaaagagaaaggtcataacaacctgtcctatctgacgaaaagct
ggcgtgaactgtgcaaagcctttctgcaagaggcgaaatggtccaacaacaaaattatcccggctttctccaagtacctgg
aaaacgccagcgtttcctcctccggtgtagcgctgctggcgccgtcttacttttccgtatgccagcagcaggaagacatctcc
gaccacgcgctgcgttccctgaccgacttccatggtctggtgcgttctagctgcgttatcttccgcctgtgcaacgatctggcc
acctctgcggcggagctggaacgtggcgagactaccaattctatcattagctacatgcacgaaaacgatggtaccagcg
aggaacaggcccgcgaagaactgcgtaaactgatcgacgccgaatggaaaaagatgaatcgtgaacgcgttagcgac
tccaccctgctgcctaaagcgttcatggaaatcgcagttaacatggcacgtgtttcccactgcacctaccagtatggcgatg
gtctgggtcgcccagactacgcgactgaaaaccgcatcaaactgctgctgattgacccttttcccgattaaccagctgatgta
tgtctaactgcagctggtaccatatgggaattcgaagcttgggcccgaacaaaaactcatctcagaagaggatctgaatag
cgccgtcgaccatcatcatcatcatcattgagtttaaacggtctccagcttggctgttttggcggatgagagaagattttcagc
ctgatacagattaaatcagaacgcagaagcggtctgataaaacagaatttgcctggcggcagtagcgcggtggtcccac
ctgaccccatgccgaactcagaagtgaaacgccgtagcgccgatggtagtgtggggtctccccatgcgagagtaggga
actgccaggcatcaaataaaacgaaaggctcagtcgaaagactgggcctttcgttttatctgttgtttgtcggtgaacgctctc
ctgagtaggacaaatccgccgggagcggatttgaacgttgcgaagcaacggcccggagggtggcgggcaggacgcc
cgccataaactgccaggcatcaaattaagcagaaggccatcctgacggatggccttttgcgtttctacaaactctttttgttta
tttttctaaatacattcaaatatgtatccgctcatgagacaataaccctgataaatgcttcaataatctggcgtaatagcgaag
aggcccgcaccgatcgcccttcccaacagttgcgcagcctgaatggcgaatggcgcctgatgcggtattttctccttacgca
tctgtgcggtatttcacaccgcatatggtgcactctcagtacaatctgctctgatgccgcatagttaagccagccccgacacc
cgccaacacccgctgacgagcttagtaaagccctcgctagattttaatgcggatgttgcgattacttcgccaactattgcgat
aacaagaaaagccagcctttcatgatatatctcccaatttgtgtagggcttattatgcacgcttaaaaataataaaagcag
acttgacctgatagtttggctgtgagcaattatgtgcttagtgcatcaacgcttgagttaagccgcgccgcgaagcggcgtc
ggcttgaacgaattgttagacattatttgccgactaccttggtgatctcgcctttcacgtagtggacaaattcttccaactgatct
gcgcgcgaggccaagcgatcttcttcttgtccaagataagcctgtctagcttcaagtatgacgggctgatactgggccggc
aggcgctccattgcccagtcggcagcgacatccttcggcgcgattttgccggttactgcgctgtaccaaatgcgggacaac
gtaagcactacatttcgctcatcgccagcccagtcgggcggcgagttccatagcgttaaggtttcatttagcgcctcaaatag
atcctgttcaggaaccggatcaaagagttcctccgccgctggacctaccaaggcaacgctatgttctcttgcttttgtcagca
agatagccagatcaatgtcgatcgtggctggctcgaagatacctgcaagaatgtcattgcgctgccattctccaaattgcag
ttcgcgcttagctggataacgccacggaatgatgtcgtcgtgcacaacaatggtgacttctacagcgcggagaatctcgct
ctctccaggggaagccgaagtttccaaaaggtcgttgatcaaagctcgccgcgttgtttcatcaagccttacggtcaccgta
accagcaaatcaatatcactgtgtggcttcaggccgccatccactgcggagccgtacaaatgtacggccagcaacgtcg
gttcgagatggcgctcgatgacgccaactacctctgatagttgagtcgatacttcggcgatcaccgcttccctcatgatgttta
actttgtttagggcgactgccctgctgcgtaacatcgttgctgctccataacatcaaacatcgacccacggcgtaacgcgct
tgctgcttggat

Figure 103C gcccgaggcatagactgtaccccaaaaaaacagtcataacaagccatgaaaaccgccactgcgccgttacca
ccgctgcgttcggtcaaggttctggaccagttgcgtgagcgcatacgctacttgcattacagcttacgaaccgaaca
ggcttatgtccactgggttcgtgccttcatccgtttccacggtgtgcgtcacccggcaaccttgggcagcagcgaagt
cgaggcatttctgtcctggctggcgaacgagcgcaaggtttcggtctccacgcatcgtcaggcattggcggccttgc
tgttcttctacggcaaggtgctgtgcacggatctgccctggcttcaggagatcggaagacctcggccgtcgcggcg
cttgccggtggtgctgaccccggatgaagtggttcgcatcctcggttttctggaaggcgagcatcgtttgttcgcccag
cttctgtatggaacgggcatgcggatcagtgagggtttgcaactgcgggtcaaggatctggatttcgatcacggcac
gatcatcgtgcgggagggcaagggctccaaggatcgggccttgatgttacccgagagcttggcacccagcctgc
gcgagcaggggaattaattcccacgggttttgctgcccgcaaacgggctgttctggtgttgctagtttgttatcagaat
cgcagatccggcttcagccggtttgccggctgaaagcgctatttcttccagaattgccatgattttttccccacgggag
gcgtcactggctcccgtgttgtcggcagctttgattcgataagcagcatcgcctgtttcaggctgtctatgtgtgactgtt
gagctgtaacaagttgtctcaggtgttcaatttcatgttctagttgctttgttttactggtttcacctgttctattaggtgttaca
tgctgttcatctgttacattgtcgatcgttcatggtgaacagctttgaatgcaccaaaaactcgtaaaagctctgatgta
tctatctttttacaccgttttcatctgtgcatatggacagttttcctttgatatgtaacggtgaacagttgttctacttttgtttg
ttagtcttgatgcttcactgatagatacaagagccataagaacctcagatccttccgtatttagccagtatgttctctagt
gtggttcgttgttttttgcgtgagccatgagaacgaaccattgagatcatacttactttgcatgtcactcaaaaattttgcct
caaaactggtgagctgaattttttgcagttaaagcatcgtgtagtgtttttcttagtccgttatgtaggtaggaatctgatgt
aatggttgttggtattttgtcaccattcattttatctggttgttctcaagttcggttacgagatccatttgtctatctagttcaa
cttggaaaatcaacgtatcagtcgggcggcctcgcttatcaaccaccaatttcatattgctgtaagtgtttaaatcttta
cttattggtttcaaaacccattggttaagccttttaaactcatggtagttattttcaagcattaacatgaacttaaattcatc
aaggctaatctctatatttgccttgtgagttttcttttgtgttagttcttttaataaccactcataaatcctcatagagtatttgtt
ttcaaaagacttaacatgttccagattatattttatgaattttttttaactggaaaagataaggcaatatctcttcactaaaa
actaattctaattttttcgcttgagaacttggcatagtttgtccactggaaaatctcaaagcctttaaccaaaggattcctg
atttccacagttctcgtcatcagctctctggttgctttagctaatacaccataagcatttttccctactgatgttcatcatctg
agcgtattggttataagtgaacgataccgtccgttctttccttgtagggttttcaatcgtgggggttgagtagtgccacac
agcataaaattagcttggtttcatgctccgttaagtcatagcgactaatcgctagttcatttgctttgaaaacaactaatt
cagacatacatctcaattggtctaggtgattttaatcactataccaattgagatgggctagtcaatgataattactagtc
cttttcctttgagttgtgggtatctgtaaattctgctagacctttgctggaaaaacttgtaaattctgctagaccctctgtaaat
tccgctagacctttgtgtgtttttttgtttatattcaagtggttataatttatagaataaagaaagaataaaaaaagataa
aaagaatagatcccagccctgtgtataactcactactttagtcagttccgcagtattacaaaaggatgtcgcaaacg
ctgtttgctcctctacaaaacagaccttaaaaccctaaaggcttaagtagcaccctcgcaagctcgggcaaatcgc
tgaatattccttttgtctccgaccatcaggcacctgagtcgctgtcttttcgtgacattcagttcgctgcgctcacggctc
tggcagtgaatgggggtaaatggcactacaggcgccttttatggattcatgcaaggaaactacccataatacaag
aaaagcccgtcacgggcttctcagggcgtttatggcgggtctgctatgtggtgctatctgacttttgctgttcagcagt
tcctgccctctgattttccagtctgaccacttcggattatcccgtgacaggtcattcagactggctaatgcacccagta
aggcagcggtatcatcaacaggctta (SEQ ID NO:87)

Figure 108A 1-
caagaaaaatgccccgcttacgcagggcatccatttattactcaaccgtaaccgattttgccaggttacgcggctggtcaacg
tcggtgcctttgatcagcgcgacatggtaagccagcagctgcagcggaacggtgtagaagatcggtgcaatcacctcttcca
catgcggcatctcgatgatgtgcatgttatcgctacttacaaaacccgcatcctgatcggcgaagacatacaactgaccgcc
acgcgcgcgaacttcttcaatgttggatttcagtttttccagcaattcgttgttcggtgcaacaacaataaccggcatatcggcat
caattagcgccagcggaccgtgtttcagttcgccagcagcgtaggcttcagcgtgaatgtaagagatctctttcaacttcaatg
cgccttccagcgcgattgggtactgatcgccacggcccaggaacagcgcgtgatgtttgtcagagaaatcttctgccagcgc
ttcaatgcgtttgtcctgagacagcatctgctcaatacggctcggcagcgcctgcagaccatgcacgatgtcatgttcaatgga
ggcatccagacctttcaggcgagacagcttcgccaccagcatcaacagcacagttaactgagtggtgaatgctttagtggat
gccacgccgatttctgtacccgcgttggtcattagcgccagatcggattcgcgcaccagagaagaacccggaacgttacag
attgccagtgaaccaaggtaacccagctctttcgacagacgcaggccagccagggtatccgcggtttcgccagactgtgac
acgatcgcccttcccaacagttgcgcagcctatacgtacggcagtttaaggtttacacctataaaagagagagccgttatcgt
ctgtttgtggatgtacagagtgatattattgacacgccggggcgacggatggtgatcccctggccagtgcacgtctgctgtca
gataaagtctcccgtgaactttacccggtggtgcatatcggggatgaaagctggcgcatgatgaccaccgatatggccagtg
tgccggtctccgttatcggggaagaagtggctgatctcagccaccgcgaaaatgacatcaaaaacgccattaacctgatgtt
ctggggaatataaatgtcaggcatgagattatcaaaaaggatcttcacctagatccttttcacgtagaaagccagtccgcaga
aacggtgctgaccccggatgaatgtcagctactgggctatctggacaagggaaaacgcaagcgcaaagagaaagcagg
tagcttgcagtgggcttacatggcgatagctagactgggcggttttatggacagcaagcgaaccggaattgccagctggggc
gccctctggtaaggttgggaagccctgcaaagtaaactgatggctttctcgccgccaaggatctgatggcgcaggggatc
aagctctgatcaagagacaggatgaggatcgtttcgcatgattgaacaagatggattgcacgcaggttctccggccgcttgg
gtggagaggctattcggctatgactgggcacaacagacaatcggctgctctgatgccgccgtgttccggctgtcagcgcagg
ggcgcccggttcttttttgtcaagaccgacctgtccggtgccctgaatgaactgcaagacgaggcagcgcggctatcgtggct
ggccacgacgggcgttccttgcgcagctgtgctcgacgttgtcactgaagcggggaagggactggctgctattgggcgaagt
gccggggcaggatctcctgtcatctcaccttgctcctgccgagaaagtatccatcatggctgatgcaatgcggcggctgcata
cgcttgatccggctacctgcccattcgaccaccaagcgaaacatcgcatcgagcgagcacgtactcggatggaagccggt
cttgtcgatcaggatgatctggacgaagagcatcaggggctcgcgccagccgaactgttcgccaggctcaaggcgagcat
gcccgacggcgaggatctcgtcgtgacccatggcgatgcctgcttgccgaatatcatggtggaaaatggccgcttttctggatt
catcgactgtggccggctgggtgtggcggaccgctatcaggacatagcgttggctacccgtgatattgctgaagagcttggc
ggcgaatgggctgaccgcttcctcgtgctttacggtatcgccgctcccgattcgcagcgcatcgccttctatcgccttcttgacg
agttcttctgaattattaacgcttacaatttcctgatgcggtattttctccttacgcatctgtgcggtatttcacaccgcatacaggtg
gcacttttcggggaaatgtgcgcggaaccccctatttgtttatttttctaaatacattcaaatatgtatccgctcatgagacaataac
cctgataaatgcttcaataatagcacgtgaggagggccaccatggccaagttgaccagtgccgttccggtgctcaccgcgc
gcgacgtcgccggagcggtcgagttctggaccgaccggctcgggttctcccctagtaacggccgccagtgtgctggaattc
aggcagttcaacctgttgatagtacgtactaagctctcatgtttcacgtactaagctctcatgtttaacgtactaagctctcatgttt
aacgaactaaaccctcatggctaacgtactaagctctcatggctaacgtactaagctctcatgtttcacgtactaagctctcatg
tttgaacaataaaattaatataaatcagcaacttaaatagcctctaaggttttaagttttataagaaaaaaaagaatatataagg
cttttaaagcttttaaggtttaacggttgtggacaacaagccagggatgtaacgcactgagaagcccttagagcctctcaaag
caattttcagtgacacaggaacacttaacggctgacagcctgaattctgcagatatctgttttccactcttcgttcactttcgcca
ggtagctggtgaagacgaaggaagtcccggagccatctgcgcggcgtactacagcaatgttttgtgaaggcagtttcagac
ccggattcagtttggcgatggcttcatcatcccacttcttgatttgcccaggtagatgtcgccgagggtttaccatccagcacc
agttcgccagacttcagccctggaatgttaaccgccagcaccacgccgccaatcacggtcgggaactggaacagaccttc
ctgagccagttttcgtcagacagcggcgcgtcagaggcaccaaaatcaacggtattagcgataatctgttttacgccaccgg
aagaaccgatacctctggtagttaactttattaccggtttctttctggtaagtgtcagcccatttggcatacaccggcgcagggaa
ggttgcacctgcacctgtcaggcttgcttctgcaaacacagagaaagcactcatcgataaggtcgcggcgacaacagttgc
gacggtggtacgcataactttcataatgtcctgggaggattcataaagcattgtttgttggctacgagaagcaaaataggac
aaacaggtgacagttatatgtaaggaatatgacagttttatgacagagagataaagtcttcagtctgatttaaataagcgttgat
attcagtcaattacaaacattaataacg

Figure 108B aagagatgacagaaaaattttcattctgtgacagagaaaaagtagccgaagatgacggtttgtcacatggagttggcagga
tgtttgattaaaagcaattaaccctcactaaagggcggccgcgaagttcctattctctagaaagtataggaacttcattctaccg
ggtaggggaggcgcttttcccaaggcagtctggagcatgcgctttagcagccccgctgggcacttggcgctacacaagtgg
cctctggcctcgcacacattccacatccaccggtaggcgccaaccggctccgttctttggtggccccttcgcgccaccttccac
tcctcccctagtcaggaagttccccccccgccccgcagctcgcgtcgtgcaggacgtgacaaatggaagtagcacgtctcac
tagtctcgtgcagatggacagcaccgctgagcaatggaagcgggtaggcctttggggcagcggccaatagcagctttgctc
cttcgctttctgggctcagaggctgggaaggggtgggtccgggggcgggctcaggggcgggctcaggggcggggcgggc
gcccgaaggtcctccggaggcccggcattctgcacgcttcaaaagcgcacgtctgccgcgctgttctcctcttcctcatctccg
ggcctttcgacctgcagcagcacgtgttgacaattaatcatcggcatagtatatcggcatagtataatacgacaaggtgagga
actaaaccatggagaaaaaaatcactggatataccaccgttgatatatcccaatggcatcgtaaagaacattttgaggcattt
cagtcagttgctcaatgtacctataaccagaccgttcagctggatattacggcctttttaaagaccgtaaagaaaaataagca
caagttttatccggcctttattcacattcttgcccgcctgatgaatgctcatccggaattccgtatggcaatgaaagacggtgagc
tggtgatatgggatagtgttcacccttgttacaccgttttccatgagcaaactgaaacgttttcatcgctctggagtgaataccac
gacgatttccggcagtttctacacatatattcgcaagatgtggcgtgttacggtgaaaacctggcctatttccctaaagggtttatt
gagaatatgttttcgtctcagccaatccctgggtgagtttcaccagttttgatttaaacgtggccaatatggacaacttcttcgcc
cccgttttcaccatgggcaaatattatacgcaaggcgacaaggtgctgatgccgctggcgattcaggttcatcatgccgtttgt
gatggcttccatgtcggcagaatgcttaatgaattacaacagtactgcgatgagtggcagggcggggcgtaagcgggactct
ggggttcgaataaagaccgaccaagcgacgtctgagagctccctggccgaattcggtaccaataaaagagctttattttcatg
atctgtgtgttggttttttgtgtgcggcgcggaagttcctattctctagaaagtataggaacttcctcgagccctatagtgagtcgtatt
agcccttgacgatgccacatcctgagcaaataattcaaccactaattgtgagcggataacacaaggaggaaacagctatgt
cattaccgttcttaacttctgcaccgggaaaggttattattttggtgaacactctgctgtgtacaacaagcctgccgtcgctgcta
gtgtgtctgcgttgagaacctacctgctaataagcgagtcatctgcaccagatactattgaattggacttcccggacattagcttt
aatcataagtggtccatcaatgatttcaatgccatcaccgaggatcaagtaaactcccaaaaattggccaaggctcaacaa
gccaccgatggcttgtctcaggaactcgttagtctttttggatccgttgttagctcaactatccgaatccttccactaccatgcagc
gttttgtttcctgtatatgtttgtttgcctatgccccatgccaagaatattaagttttctttaaagtctactttacccatcggtgctgggtt
gggctcaagcgcctctatttctgtatcactggccttagctatggcctacttgggggggttaataggatctaatgacttggaaaag
ctgtcagaaaacgataagcatatagtgaatcaatgggccttcataggtgaaaagtgtattcacggtaccccttcaggaatag
ataacgctgtggccacttatggtaatgccctgctatttgaaaaagactcacataatggaacaataaacacaaacaatttaagt
tcttagatgatttcccagccattccaatgatcctaacctatactagaattccaaggtctacaaaagatcttgttgctcgcgttcgtgt
gttggtcaccgagaaatttcctgaagttatgaagccaattctagatgccatgggtgaatgtgccctacaaggcttagagatcat
gactaagttaagtaaatgtaaaggcaccgatgacgaggctgtagaaactaataatgaactgtatgaacaactattggaattg
ataagaataaatcatggactgcttgtctcaatcggtgtttctcatcctggattagaacttattaaaaatctgagcgatgatttgaga
attggctccacaaaacttaccggtgctggtggcggcggttgctctttgactttgttacgaagagacattactcaagagcaaattg
acagcttcaaaaagaaattgcaagatgattttagttacgagacatttgaaacagacttgggtgggactggctgctgtttgttaag
cgcaaaaaatttgaataaagatcttaaaatcaaatccctagtattccaattatttgaaaataaaactaccacaaagcaacaa
attgacgatctattattgccaggaaacacgaatttaccatggacttcataagctaatttgcgataggcctgcaccccttaaggag
gaaaaaaacatgtcagagttgagagccttcagtgccccagggaaagcgttactagctggtggatatttagttttagatacaaa
atatgaagcatttgtagtcggattatcggcaagaatgcatgctgtagcccatccttacggttcattgcaagggtctgataagtttg
aagtgcgtgtgaaaagtaaacaatttaaagatggggagtggctgtaccatataagtcctaaaagtggcttcattcctgtttcgat
aggcggatctaagaaccctttcattgaaaagttatcgctaacgtatttagctactttaaacctaacatggacgactactgcaat
agaaacttgttcgttattgatatttctctgatgatgccaccattctcaggaggatagcgttaccgaacatcgtggcaacagaag
attgagttttcattcgcacagaattgaagaagttcccaaaacagggctgggctcctcggcaggtttagtcacagttttaactaca
gctttggcctcctttttgtatcggacctggaaaataatgtagacaaatatagagaagttattcataatttagcacaagttgctcatt
gtcaagctcagggtaaaattggaagcgggtttgatgtagcggcggcagcatatggatctatcagatatagaagattcccacc
cgcattaatctctaatttgccagatattggaagtgctacttacggcagtaaactggcgcatttggttgatgaagaagactggaat
attacgattaaaagtaaccatttaccttc

Figure 108C gggattaactttatggatgggcgatattaagaatggttcagaaacagtaaaactggtccagaaggtaaaaaattggtatgatt
cgcatatgccagaaagcttgaaaatatatacagaactcgatcatgcaaattctagatttatggatggactatctaaactagatc
gcttacacgagactcatgacgattacagcgatcagatatttgagtctcttgagaggaatgactgtacctgtcaaaagtatcctg
aaatcacagaagttagagatgcagttgccacaattagacgttcctttagaaaaataactaaagaatctggtgccgatatcga
acctcccgtacaaactagcttattggatgattgccagaccttaaaaggagttcttacttgcttaatacctggtgctggtggttatga
cgccattgcagtgattactaagcaagatgttgatcttagggctcaaaccgctaatgacaaaagattttctaaggttcaatggctg
gatgtaactcaggctgactggggtgttaggaaagaaaaagatccggaaacttatcttgataaataacttaaggtagctgcatg
cagaattcgcccttaaggaggaaaaaaaaatgaccgtttacacagcatccgttaccgcacccgtcaacatcgcaacccta
agtattgggggaaaagggacacgaagttgaatctgcccaccaattcgtccatatcagtgactttatcgcaagatgacctcag
aacgttgacctctgcggctactgcacctgagtttgaacgcgacactttgtggttaaatggagaaccacacagcatcgacaat
gaaagaactcaaaattgtctgcgcgacctacgccaattaagaaaggaaatggaatcgaaggacgcctcattgcccacatt
atctcaatggaaactccacattgtctccgaaaataacttttcctacagcagctggtttagcttcctccgctgctggctttgctgcatt
ggtctctgcaattgctaagttataccaattaccacagtcaacttcagaaatatctagaatagcaagaaaggggtctggttcagc
ttgtagatcgttgtttggcggatacgtggcctgggaaatgggaaaagctgaagatggtcatgattccatggcagtacaaatcg
cagacagctctgactggcctcagatgaaagcttgtgtcctagttgtcagcgatattaaaaaggatgtgagttccactcagggta
tgcaattgaccgtggcaacctccgaactatttaaagaaagaattgaacatgtcgtaccaaagagatttgaagtcatgcgtaa
agccattgttgaaaaagatttcgccacctttgcaaaggaaacaatgatggattccaactctttccatgccacatgtttggactctt
tccctccaatattctacatgaatgacacttccaagcgtatcatcagttggtgccacaccattaatcagttttacggagaaacaat
cgttgcatacacgtttgatgcaggtccaaatgctgtgttgtactacttagctgaaaatgagtcgaaactctttgcatttatctataaa
ttgtttggctctgttcctggatgggacaagaaatttactactgagcagcttgaggctttcaaccatcaatttgaatcatctaacttta
ctgcacgtgaattggatcttgagttgcaaaaggatgttgccagagtgattttaactcaagtcggttcaggcccacaagaaaca
aacgaatctttgattgacgcaaagactggtctaccaaaggaataagatcaattcgctgcatcgcccttaggaggtaaaaaaa
aatgactgccgacaacaatagtatgccccatggtgcagtatctagttacgccaaattagtgcaaaaccaaacacctgaaga
catttttggaagagtttcctgaaattattccattacaacaaagacctaatacccgatcagtgagacgtcaaatgacgaaagcg
gagaaacatgttttctggtcatgatgaggagcaaattaagttaatgaatgaaaattgtattgttttggattgggacgataatgcta
ttggtgccggtaccaagaaagtttgtcatttaatggaaaatattgaaaagggtttactacatcgtgcattctccgtctttatttcaat
gaacaaggtgaattacttttacaacaaagagccactgaaaaaataactttccctgatctttggactaacacatgctgctctcat
ccactatgtattgatgacgaattaggtttgaagggtaagctagacgataagattaagggcgctattactgcggcggtgagaaa
actagatcatgaattaggtattccagaagatgaaactaagacaaggggtaagtttcacttttaaacagaatccattacatggc
accaagcaatgaaccatggggtgaacatgaaattgattacatcctatttataagatcaacgctaaagaaaacttgactgtca
acccaaacgtcaatgaagttagagacttcaaatgggtttcaccaaatgatttgaaaactatgtttgctgacccaagttacaagtt
tacgccttggtttaagattatttgcgagaattacttattcaactggtgggagcaattagatgacctttctgaagtggaaaatgaca
ggcaaattcatagaatgctataacaacgcgtctacaaataaaaaaggcacgtcagatgacgtgcctttttcttggggcc (SEQ ID NO:90)

Figure 110A 1-
gtgcggccgcaagcttgtcgacggagctcgaattcggatccctgcagttagacatacatcagctggttaatcgggaaagggtc
aatcagcagcagtttgatgcggttttcagtcgcgtagtctgggcgacccagaccatcgccatactggtaggtgcagtgggaaa
cacgtgccatgttaactgcgatttccatgaacgctttaggcagcagggtggagtcgctaacgcgttcacgattcatcttttccattc
ggcgtcgatcagtttacgcagttcttcgcgggcctgttcctcgctggtaccatcgttttcgtgcatgtagctaatgatagaattggta
gtctcgccacgttccagctccgccgcagaggtggccagatcgttgcacaggcggaagataacgcagctagaacgcaccag
accatggaagtcggtcagggaacgcagcgcgtggtcggagatgtcttcctgctgctggcatacggaaaagtaagacggcgc
cagcagcgctacaccggaggaggaaacgctggcgttttccaggtacttggagaaagccgggataattttgttgttggaccattt
cgcctcttgcagaaaggctttgcacagttcacgccagcttttcgtcagataggacaggttgttatgacctttctctttcagaatagaa
taggacgtgtcgttaacggtgttgtacagtgccaggaaacacagtttcatatagtccggcagggtgttaatagcgttaacgtccc
agcgctctacagcatcggtgaacagttgcagttcgtccagagtgccataaacgtcatacacgtcatcgatgatcgtcaccaga
ccaaacattttagtaacagctttgcgacattcaccaaactgcgggtctggcgccatacccagtgcccagaaataaacttccatc
aggcggtcgcgtacaaaatccagtttgctagccaggcccatctcggtccaccagcgggacagatcttcagctctttctggtgc
agggtctgtaccatgttaaaatccagcttcgccagctccagcagcagctggtgatgcggttctttcggttcgtatttatccaggaac
caacgtgcctccagacggtgcagacgctggtgatatggcagttccagggcgtggctcacttgttctgcaaccttggtattaatgc
cttctttcaggttgttcttcaggtgggtgatggaaaaggtacgcgcctcctccagcaggttctcaccctcgaaacccaggtaaga
cgcttcatacaggctcagcaggccttggacgtcacctttcagttcaccgctgaaaccaccttcttatccttgaaacgctcaaaaa
catcctgagaaacctcgaaaccgtgctgacgcagcagacggaaagacagagcggttgcgtgcaggtcagatttgttcttttgt
tttcgtccagcagtacgatgttttccagggctttaatgatgtcttttcaaatttgtaggtcagacccaggcgctgcacatcgtcgatc
agctccagcagggacagcggctggtgtctacacggttgatcatgcagcgaacttcttcctccagtttggtcgctttctcctccag
cttttccactttcaggtcgttctccagggattgcaggaattcgaaattccacaggtttggctgatagtttgcggaacgacgggaatt
atgctcggtaatctgagtaaattgagaagaggtcgcacacatggtatatctccttcttaaagttaaacaaaattatttctagaggg
gaattgttatccgctcacaattccctatagtgagtcgtattaatttcgcgggatcgagatctcgatcctctacgccggacgcatcg
tggccggcatcaccggcgccacaggtgcggttgctggcgcctatatcgccgacatcaccgatggggaagatcgggctcgcc
acttcgggctcatgagcgcttgtttcggcgtgggtatggtggcaggccccgtggccgggggactgttgggcgccatctccttgca
tgcaccattccttgcggcggcggtgctcaacggcctcaacctactactgggctgcttcctaatgcaggagtcgcataagggag
agcgtcgagatcccggacaccatcgaatggcgcaaaaccttcgcggtatggcatgatagcgcccggaagagagtcaattc
agggtggtgaatgtgaaaccagtaacgttatacgatgtcgcagagtatgccggtgtctcttatcagaccgtttcccgcgtggtga
accaggccagccacgtttctgcgaaaacgcgggaaaaagtggaagcggcgatggcggagctgaattacattcccaaccgc
gtggcacaacaactggcgggcaaacagtcgttgctgattggcgttgccacctccagtctggccctgcacgcgccgtcgcaaat
tgtcgcggcgattaaatctcgcgccgatcaactgggtgccagcgtggtggtgtcgatggtagaacgaagcggcgtcgaagcc
tgtaaagcggcggtgcacaatcttctcgcgcaacgcgtcagtgggctgatcattaactatccgctggatgaccaggatgccatt
gctgtggaagctgcctgcactaatgttccggcgttatttcttgatgtctctgaccagacacccatcaacagtattattttctcccatga
agacggtacgcgactgggcgtggagcatctggtcgcattgggtcaccagcaaatcgcgctgttagcgggcccattaagttctgt
ctcggcgcgtctgcgtctggctggctggcataaatatctcactcgcaatcaaattcagccgatagcggaacgggaaggcgact
ggagtgccatgtccggttttcaacaaaccatgcaaatgctgaatgagggcatcgttcccactgcgatgctggttgccaacgatc
agatggcgctgggcgcaatgcgcgccattaccgagtccgggctgcgcgttggtgcggatatctcggtagtgggatacgacga
taccgaagacagctcatgttatatcccgccgttaaccaccatcaaacaggattttcgcctgctggggcaaaccagcgtggacc
gcttgctgcaactctctcagggccaggcggtgaagggcaatcagctgttgcccgtctcactggtgaaaagaaaaaccaccct
ggcgcccaatacgcaaaccgcctctccccgcgcgttggccgattcattaatgcagctggcacgacaggtttcccgactggaa
agcgggcagtgagcgcaacgcaattaatgtaagttagctcactcattaggcaccgggatctcgaccgatgcccttgagagcct
tcaacccagtcagctccttccggtgggcgcggggcatgactatcgtcgccgcacttatgactgtcttctttatcatgcaactcgtag
gacaggtgccggcagcgctctgggtcattttcggcgaggaccgctttcgctggagcgcgacgatgatcggcctgtcgcttgcg
gtattcggaatcttgcacgccctcgctcaagccttcgtcactggtcccgccaccaaacgtttcggcgagaagcaggccattatc
gccggcatggcggccccacgggtgcgcatgatcgtgctcctg

Figure 110B tcgttgaggacccggctaggctggcggggttgccttactggttagcagaatgaatcaccgatacgcgagcgaacgtgaagcgact
gctgctgcaaaacgtctgcgacctgagcaacaacatgaatggtcttcggtttccgtgtttcgtaaagtctggaaacgcggaagtcag
cgccctgcaccattatgttccggatctgcatcgcaggatgctgctggctaccctgtggaacacctacatctgtattaacgaagcgctg
gcattgaccctgagtgattttctctggtcccgccgcatccataccgccagttgtttaccctcacaacgttccagtaaccgggcatgttc
atcatcagtaacccgtatcgtgagcatcctctctcgtttcatcggtatcattaccccccatgaacagaaatcccccttacacggaggca
tcagtgaccaaacaggaaaaaaccgcccttaacatggcccgctttatcagaagccagacattaacgcttctggagaaactcaac
gagctggacgcggatgaacaggcagacatctgtgaatcgcttcacgaccacgctgatgagctttaccgcagctgcctcgcgcgttt
cggtgatgacggtgaaaacctctgacacatgcagctcccggagacggtcacagcttgtctgtaagcggatgccgggagcagac
aagcccgtcagggcgcgtcagcgggtgttggcgggtgtcggggcgcagccatgacccagtcacgtagcgatagcggagtgtat
actggcttaactatgcggcatcagagcagattgtactgagagtgcaccatatatgcggtgtgaaataccgcacagatgcgtaagg
agaaaataccgcatcaggcgctcttccgcttcctcgctcactgactcgctgcgctcggtcgttcggctgcggcgagcggtatcagct
cactcaaaggcggtaatacggttatccacagaatcaggggataacgcaggaaagaacatgtgagcaaaaggccagcaaaag
gccaggaaccgtaaaaaggccgcgttgctggcgtttttccataggctccgcccccctgacgagcatcacaaaaatcgacgctca
agtcagaggtggcgaaacccgacaggactataaagataccaggcgtttccccctggaagctccctcgtgcgctctcctgttccga
ccctgccgcttaccggatacctgtccgcctttctcccttcgggaagcgtggcgctttctcatagctcacgctgtaggtatctcagttcggt
gtaggtcgttcgctccaagctgggctgtgtgcacgaaccccccgttcagcccgaccgctgcgccttatccggtaactatcgtcttgag
tccaacccggtaagacacgacttatcgccactggcagcagccactggtaacaggattagcagagcgaggtatgtaggcggtgct
acagagttcttgaagtggtggcctaactacggctacactagaaggacagtatttggtatctgcgctctgctgaagccagttaccttcg
gaaaaagagttggtagctcttgatccggcaaacaaaccaccgctggtagcggtggtttttttgtttgcaagcagcagattacgcgca
gaaaaaaaggatctcaagaagatcctttgatcttttctacggggtctgacgctcagtggaacgaaaactcacgttaagggattttggt
catgaacaataaaactgtctgcttacataaacagtaatacaaggggtgttatgagccatattcaacgggaaacgtcttgctctaggc
cgcgattaaattccaacatggatgctgatttatatgggtataaatgggctcgcgataatgtcgggcaatcaggtgcgacaatctatcg
attgtatgggaagcccgatgcgccagagttgtttctgaaacatggcaaaggtagcgttgccaatgatgttacagatgagatggtcag
actaaactggctgacggaatttatgcctcttccgaccatcaagcattttatccgtactcctgatgatgcatggttactcaccactgcgat
ccccgggaaaacagcattccaggtattagaagaatatcctgattcaggtgaaaatattgttgatgcgctggcagtgttcctgcgccg
gttgcattcgattcctgtttgtaattgtccttttaacagcgatcgcgtatttcgtctcgctcaggcgcaatcacgaatgaataacggtttggt
tgatgcgagtgattttgatgacgagcgtaatggctggcctgttgaacaagtctggaaagaaatgcataaacttttgccattctcaccg
gattcagtcgtcactcatggtgatttctcacttgataaccttatttttgacgaggggaaattaataggttgtattgatgttggacgagtcgg
aatcgcagaccgataccaggatcttgccatcctatggaactgcctcggtgagttttctccttcattacagaaacggcttttcaaaaat
atggtattgataatcctgatatgaataaattgcagtttcatttgatgctcgatgagttttctaagaattaattcatgagcggatacatatttg
aatgtatttagaaaaataaacaatagggttccgcgcacatttccccgaaaagtgccacctgaaattgtaaacgttaatattttgtta
aaattcgcgttaaattttgttaaatcagctcatttttaaccaataggccgaaatcggcaaatcccttataaatcaaaagaatagac
cgagatagggttgagtgttgttccagtttggaacaagagtccactattaaagaacgtggactccaacgtcaaagggcgaaaaacc
gtctatcagggcgatggcccactacgtgaaccatcaccctaatcaagttttttggggtcgaggtgccgtaaagcactaaatcggaa
ccctaaagggagcccccgatttagagcttgacggggaaagccggcgaacgtggcgagaaaggaagggaagaaagcgaaa
ggagcgggcgctagggcgctggcaagtgtagcggtcacgctgcgcgtaaccaccacacccgccgcgcttaatgcgccgctac
agggcgcgtcccattcgccaatccggatatagttcctcctttcagcaaaaaacccctcaagacccgtttagaggccccaaggggtt
atgctagttattgctcagcggtggcagcagccaactcagcttcctttcgggctttgttagcagccggatctcagtggtggtggtggtggt
gctcga (SEQ ID NO:101)

Figure 112B gcggccgcgcccttgacgatgccacatcctgagcaaataattcaaccactaattgtgagcggataacacaaggaggaaacagc
catggtatcctgttctgcgccgggtaagatttacctgttcggtgaacacgccgtagtttatggcgaaactgcaattgcgtgtgcggtgg
aactgcgtacccgtgttcgcgcggaactcaatgactctatcactattcagagccagatcggccgcaccggtctggatttcgaaaag
caccccttatgtgtctgcggtaattgagaaaatgcgcaaatctattcctattaacggtgttttcttgaccgtcgattccgacatcccggtgg
gctccggtctgggtagcagcgcagccgttactatcgcgtctattggtgcgctgaacgagctgttcggctttggcctcagcctgcaaga
aatcgctaaactgggccacgaaatcgaaattaaagtacagggtgccgcgtccccaaccgatacgtatgtttctaccttcggcggcg
tggttaccatcccggaacgtcgcaaactgaaaactccggactgcggcattgtgattggcgataccggcgttttctcctccaccaaag
agttagtagctaacgtacgtcagctgcgcgaaagctacccggatttgatcgaaccgctgatgacctctattggcaaaatctctcgtat
cggcgaacaactggttctgtctggcgactacgcatccatcggccgcctgatgaacgtcaaccagggtctcctggacgccctgggc
gttaacatcttagaactgagccagctgatctattccgctcgtgcggcaggtgcgtttggcgctaaaatcacgggcgctggcggcggt
ggctgtatggttgcgctgaccgctccggaaaaatgcaaccaagtggcagaagcggtagcaggcgctggcggtaaagtgactatc
actaaaccgaccgagcaaggtctgaaagtagattaagccttgacttaatagctgcttatttcgcccttatggtacctagtaggagga
aaaaaacatggaaatgcgtcaaccggctgtcgcaggtcaattctacccactgcgttgcgagaacctggaaaacgaactgaaac
gctgcttcgaaggcctggagatccgcgaacaagaagtgctgggcgcagtctgtccgcacgccggttatatgtactctggcaaagtt
gcggcgcacgtctatgccactctgccggaagctgatacctacgtaatcttcggcccgaaccacaccggctacggtagccctgtctc
tgtgagccgtgaaacttggaagaccccgttgggcaatatcgatgttgacctggaactggcggacggcttcctgggttccatcgtaga
tgcggatgaactcggtcacaaatacgaacactctatcgaagttcagctgccgtttctgcaataccgttttgaacgcgatttcaaaattc
tgccaatctgcatgggtatgcaagacgaagaaaccgcggtcgaagtaggtaacctgctggcggatctgatcagcgagtccggta
aacgtgctgtgatcatcgcaagctctgatttcacccactatgagacggctgaacgtgccaaagaaatcgattccgaagttattgattc
tatcctgaactttgacatctctggcatgtacgatcgcctgtatcgccgtaacgcctctgtttgcggttacggcccgatcaccgctatgct
gacggcaagcaaaaagctgggcggctctcgtgcgactttgctgaaatacgcaaacagcggtgacgtgtccggtgataaagacg
ctgtggtgggctacgccgccatcatcgttgagtaagctgattaaaggttaacagataggattcgtcatggatcctacaaggagga
aaaaaacatgaatgcttctaatgaaccggtgattctgaaactgggtggctctgctattaccgacaaaggtgcctacgaaggcgtag
ttaaggaagctgatttgctgcgcatcgcacaggaagttagcggtttccgtggcaagatgatcgtggttcatggtgctggtagcttcgg
ccatacgtacgcgaagaaatacggcctggaccgtaccttcgacccagagggcgcaattgttactcatgaatcgttaaaaagctc
gcctccaaagttgtaggtgctctgaatagcttcggcgtgcgtgctatcgcggtgcatcctatggactgcgcagtatgccgtaacggtc
gtatcgaaacgatgtatctggactccatcaagttaatgctggaaaaaggtctggtgccggttctgcacggcgacgtcgcaatggat
attgaactgggcacttgtatcctgtccggtgatcaaatcgttccttacctggccaaagaactgggtatctcccgcctcggcctgggca
gcgcagaggatggtgtgctggatatggagggcaaacctgtaccggaaatcacccagaaactttcgaagagttccgccactgca
tcggtggttctggttctactgatgtaaccggtggcatgctgggcaaagtgctggaacttctggaattgagcaaaaattcttccattacta
gctacattttcaacgctggtaaagcagacaacatctaccgctttctgaatggtgagtccatcggcactcgcatcagcccggacaag
cgtgtttaagctagttattaacctaaatgctctaaaccagttatgagctctacaaggaggaaaaaaacatgattaacactaccagcc
gccgcaaaattgaacacctgaaactctgcgcagaatccccggttgaagcgcgtcaggtatctgccggctttgaagacgttactctg
atccaccgcgctttaccggagctgaacatggatgaactggacctcagcgttgatttcctgggtaaacgcatcaaagcgccgttcctg
attgcgtctatcacgggtggtcacccagataccatcccggttaacgctgcgctggcagctgctgctgaggagctgggtgttggcatc
ggcgttggctctcagcgcgcggccattgatgatccgagccaggaagacagcttccgtgtagtgcgtgatgaagcccccagatgcgt
ttgtttatggcaacgtcggcgcagcacagatccgtcagtatggtgttgaaggtgttgaaaaactgatcgaaatgattgacgcagatg
ccttggcaatccacctgaactttctgcaagaagcggtccaaccggaaggtgaccgcgacgcgaccggttgcctggacatgattac
cgaaatttgctctcagattaaaactccggtaatcgtgaaagaaaccggtgcaggcattagccgtgaagatgcgattctgttccaga
aagctggcgtgagcgcaatcgacgttggcggcgcgggcggcacctcctgggctggcgtcgaggtctaccgtgctaaagaaagc
cgtgactctgttagcgagcgtttaggtgagctgttttgggatttcggcattccgacggtagcttctctgattgaatcccgcgtttccttgcc
gctgatcgcaaccggcggtatccgtaacggtctggacattgctaaaagcattgctctcggcgcaagcgctgccagcgccgctctg
ccgttcgttggtccgtccctggagggcaaagaatccgttgtacgtgtgctgagctgcatgctggaagaatttaaagcagcaatgttttt
gtgcggttgcggcaacatcaaaga

Figure 112C cctgcacaactctccagtagtggtaactggttggacccgcgaatacctggagcagcgcggttttaacgttaaggacctctccct
gccgggcaacgctctgtaagcttcaacgcgtctacaaataaaaaaggcacgtcagatgacgtgcctttttcttgtctaga
(SEQ ID NO:102)

Figure 113B gtttgacagcttatcatcgactgcacggtgcaccaatgcttctggcgtcaggcagccatcggaagctgtggtatggctgtgca
ggtcgtaaatcactgcataattcgtgtcgctcaaggcgcactcccgttctggataatgtttttgcgccgacatcataacggttctg
gcaaatattctgaaatgagctgttgacaattaatcatccggctcgtataatgtgtggaattgtgagcggataacaatttcacaca
ggaaacagcgccgctgagaaaaagcgaagcggcactgctctttaacaatttatcagacaatctgtgtgggcactcgaccg
gaattatcgattaactttattattaaaaattaaagaggtatatattaatgtatcgattaaataaggaggaataaaccatgtgtgcg
acctcttctcaatttactcagattaccgagcataattcccgtcgttccgcaaactatcagccaaacctgtggaatttcgaattcct
gcaatccctggagaacgacctgaaagtggaaaagctggaggagaaagcgaccaaactggaggaagaagttcgctgca
tgatcaaccgtgtagacacccagccgctgtcctgctggagctgatcgacgatgtgcagcgcctgggtctgacctacaaattt
gaaaaagacatcattaaagccctggaaaacatcgtactgctggacgaaaacaaaaagaacaaatctgacctgcacgca
accgctctgtctttccgtctgctgcgtcagcacggtttcgaggtttctcaggatgttttgagcgtttcaaggataaagaaggtggtt
tcagcggtgaactgaaaggtgacgtccaaggcctgctgagcctgtatgaagcgtcttacctgggtttcgagggtgagaacct
gctggaggaggcgcgtacctttccatcacccacctgaagaacaacctgaaagaaggcattaataccaaggttgcagaac
aagtgagccacgccctggaactgccatatcaccagcgtctgcaccgtctggaggcacgttggttcctggataaatacgaac
cgaaagaaccgcatcaccagctgctgctggagctggcgaagctggattttaacatggtacagaccctgcaccagaaaga
gctgcaagatctgtcccgctggtggaccgagatgggcctggctagcaaactggattttgtacgcgaccgcctgatggaagttt
atttctgggcactgggtatggcgccagacccgcagtttggtgaatgtcgcaaagctgttactaaaatgtttggtctggtgacgat
catcgatgacgtgtatgacgtttatggcactctggacgaactgcaactgttcaccgatgctgtagagcgctgggacgttaacg
ctattaacaccctgccggactatatgaaactgtgtttcctggcactgtacaacaccgttaacgacacgtcctattctattctgaaa
gagaaaggtcataacaacctgtcctatctgacgaaaagctggcgtgaactgtgcaaagcctttctgcaagaggcgaaatgg
tccaacaacaaaattatcccggctttctccaagtacctggaaaacgccagcgtttcctcctccggtgtagcgctgctggcgcc
gtcttacttttccgtatgccagcagcaggaagacatctccgaccacgcgctgcgttccctgaccgacttccatggtctggtgcgt
tctagctgcgttatcttccgcctgtgcaacgatctggccacctctgcggcggagctggaacgtggcgagactaccaattctatc
attagctacatgcacgaaaacgatggtaccagcgaggaacaggcccgcgaagaactgcgtaaactgatcgacgccgaa
tggaaaaagatgaatcgtgaacgcgttagcgactccaccctgctgcctaaagcgttcatggaaatcgcagttaacatggca
cgtgtttcccactgcacctaccagtatggcgatggtctgggtcgcccagactacgcgactgaaaaccgcatcaaactgctgct
gattgacccttttcccgattaaccagctgatgtatgtctaactgcataaaggaggtaaaaaaacatggtatcctgttctgcgccg
ggtaagatttacctgttcggtgaacacgccgtagtttatggcgaaactgcaattgcgtgtgcggtggaactgcgtacccgtgttc
gcgcggaactcaatgactctatcactattcagagccagatcggccgcaccggtctggatttcgaaaagcacccttatgtgtct
gcggtaattgagaaaatgcgcaaatctattcctattaacggtgttttcttgaccgtcgattccgacatcccggtgggctccggtct
gggtagcagcgcagccgttactatcgcgtcattggtgcgctgaacgagctgttcggctttggcctcagcctgcaagaaatcg
ctaaactgggccacgaaatcgaaattaaagtacagggtgccgcgtcccaaccgatacgtatgtttctaccttcggcggcgt
ggttaccatcccggaacgtcgcaaactgaaaactccggactgcggcattgtgattggcgataccggcgttttctcctccacca
aagagttagtagctaacgtacgtcagctgcgcgaaagctacccggatttgatcgaaccgctgatgacctctattggcaaaat
ctctcgtatcggcgaacaactggttctgtctggcgactacgcatccatcggccgcctgatgaacgtcaaccagggtctcctgg
acgccctgggcgttaacatcttagaactgagccagctgatctattccgctcgtgcggcaggtgcgtttggcgctaaaatcacg
ggcgctggcggcggtggctgtatggttgcgctgaccgctccggaaaaatgcaaccaagtggcagaagcggtagcaggcg
ctggcggtaaagtgactatcactaaaccgaccgagcaaggtctgaaagtagattaaagtctagttaaagtttaaacggtctcc
agcttggctgttttggcggatgagagaagattttcagcctgatacagattaaatcagaacgcagaagcggtctgataaaaca
gaatttgcctggcggcagtagcgcggtggtcccacctgaccccatgccgaactcagaagtgaaacgccgtagcgccgatg
gtagtgtggggtctccccatgcgagagtagggaactgccaggcatcaaataaaacgaaaggctcagtcgaaagactggg
cctttcgttttatctgttgtttgtcggtgaacgctctcctgagtaggacaaatccgccgggagcggatttgaacgttgcgaagcaa
cggcccggagggtggcgggcaggacgcccgccataaactgccaggcatcaaattaagcagaaggccatcctgacggat
ggcctttttgcgtttctacaaactcttttgtttatttttctaaatacattcaaatatgtatccgcttaaccggaattgccagctggggcg
ccctctggtaaggttgggaagccctgcaaagtaaactggatggctttctcgccgccaaggatctgatggcgcaggggatca
agctctgatcaagagacaggatgaggatcgtttcgcatgattgaacaagatggattgcacgcaggttctccggccgcttggt
ggagaggctattcggctatgactgggcacaa

Figure 113C cagacaatcggctgctctgatgccgccgtgttccggctgtcagcgcaggggcgcccggttcttttgtcaagaccgacctgtccgg
tgccctgaatgaactgcaagacgaggcagcgcggctatcgtggctggccacgacgggcgttccttgcgcagctgtgctcgacgt
tgtcactgaagcgggaagggactggctgctattgggcgaagtgccggggcaggatctcctgtcatctccccttgctcctgccgag
aaagtatccatcatggctgatgcaatgcggcggctgcatacgcttgatccggctacctgcccattcgaccaccaagcgaaacat
cgcatcgagcgagcacgtactcggatggaagccggtcttgtcgatcaggatgatctggacgaagagcatcaggggctcgcgc
cagccgaactgttcgccaggctcaaggcgagcatgcccgacggcgaggatctcgtcgtgacccatggcgatgcctgcttgccg
aatatcatggtggaaaatggccgcttttctggattcatcgactgtggccggctgggtgtggcggaccgctatcaggacatagcgtt
ggctacccgtgatattgctgaagagcttggcggcgaatgggctgaccgcttcctcgtgctttacggtatcgccgctcccgattcgca
gcgcatcgccttctatcgccttcttgacgagttcttctgacgcatgaccaaaatcccttaacgtgagttttcgttccactgagcgtcag
accccgtagaaaagatcaaaggatcttcttgagatccttttttctgcgcgtaatctgctgcttgcaaacaaaaaaaccaccgctac
cagcggtggtttgtttgccggatcaagagctaccaactcttttccgaaggtaactggcttcagcagagcgcagataccaaatact
gtccttctagtgtagccgtagttaggccaccacttcaagaactctgtagcaccgcctacatacctcgctctgctaatcctgttaccag
tggctgctgccagtggcgataagtcgtgtcttaccgggttggactcaagacgatagttaccggataaggcgcagcggtcgggct
gaacggggggttcgtgcacacagcccagcttggagcgaacgacctacaccgaactgagatacctacagcgtgagctatgag
aaagcgccacgcttcccgaagggagaaaggcggacaggtatccggtaagcggcagggtcggaacaggagagcgcacga
gggagcttccaggggggaaacgcctggtatctttatagtcctgtcgggtttcgccacctctgacttgagcgtcgattttgtgatgctcgt
cagggggcggagcctatggaaaaacgccagcaacgcggccttttacggttcctggccttttgctggccttttgctcacatgttctt
tcctgcgttatcccctgattctgtggataaccgtattaccgcctttgagtgagctgataccgctcgccgcagccgaacgaccgagc
gcagcgagtcagtgagcgaggaagcggaagagcgcctgatgcggtattttctccttacgcatctgtgcggtatttcacaccgcat
atggtgcactctcagtacaatctgctctgatgccgcatagttaagccagtatacactccgctatcgctacgtgactgggtcatggct
gcgccccgacacccgccaacacccgctgacgcgccctgacgggcttgtctgctcccggcatccgcttacagacaagctgtgac
cgtctccgggagctgcatgtgtcagaggttttcaccgtcatcaccgaaacgcgcgaggcagcagatcaattcgcgcgcgaagg
cgaagcggcatgcatttacgttgacaccatcgaatggtgcaaaacctttcgcggtatggcatgatagcgcccggaagagagtca
attcagggtggtgaatgtgaaaccagtaacgttatacgatgtcgcagagtatgccggtgtctcttatcagaccgtttcccgcgtggt
gaaccaggccagccacgtttctgcgaaaacgcgggaaaaagtggaagcggcgatggcggagctgaattacattcccaaccg
cgtggcacaacaactggcgggcaaacagtcgttgctgattggcgttgccacctccagtctggccctgcacgcgccgtcgcaaat
tgtcgcggcgattaaatctcgcgccgatcaactgggtgccagcgtggtggtcgatggtagaacgaagcggcgtcgaagcctg
taaagcggcggtgcacaatcttctcgcgcaacgcgtcagtgggctgatcattaactatccgctggatgaccaggatgccattgct
gtggaagctgcctgcactaatgttccggcgttattcttgatgtctctgaccagacacccatcaacagtattattttctcccatgaaga
cggtacgcgactgggcgtggagcatctggtcgcattgggtcaccagcaaatcgcgctgttagcgggcccattaagttctgtctcg
gcgcgtctgcgtctggctggctggcataaatatctcactcgcaatcaaattcagccgatagcggaacgggaaggcgactggagt
gccatgtccggttttcaacaaaccatgcaaatgctgaatgagggcatcgttcccactgcgatgctggttgccaacgatcagatgg
cgctggcgcaatgcgcgccattaccgagtccggctgcgcgttggtgcggatatctcggtagtgggatacgacgataccgaa
gacagctcatgttatatcccgccgtcaaccaccatcaaacaggattttcgcctgctggggcaaaccagcgtggaccgcttgctgc
aactctctcagggccaggcggtgaagggcaatcagctgttgcccgtctcactggtgaaaagaaaaaccaccctggcgcccaat
acgcaaaccgcctctccccgcgcgttggccgattcattaatgcagctggcacgacaggtttcccgactggaaagcgggcagtg
agcgcaacgcaattaatgtgagttagcgcgaattgatctg
(SEQ ID NO:103)

Figure 114B

```
aagggcgagctcaacgatccggctgctaacaaagcccgaaaggaagctgagttggctgctgccaccgctgagcaataact
agcataaccccttggggcctctaaacgggtcttgaggagttttttgctgaaaggaggaactatatccggatatcccgcaagagg
cccggcagtaccggcataaccaagcctatgcctacagcatccagggtgacggtgccgaggatgacgatgagcgcattgtta
gatttcatacacggtgcctgactgcgttagcaatttaactgtgataaactaccgcattaaagcttatcgatgataagctgtcaaac
atgagaattaattcttgaagacgaaagggcctcgtgatacgcctattttataggttaatgtcatgataataatggtttcttagacgtc
aggtggcacttttcggggaaatgtgcgcggaaccccctatttgtttattttctaaatacattcaaatatgtatccgctcatgagacaat
aaccctgataaatgcttcaataatattgaaaaaggaagagtatgattgaacaagatggattgcacgcaggttctccggccgctt
gggtggagaggctattcggctatgactgggcacaactgacaatcggctgctctgatgccgccgtgttccggctgtcagcgcag
gggcgcccggttctttttgtcaagaccgacctgtccggtgccctgaatgaactgcaggacgaggcagcgcggctatcgtggct
ggccacgacgggcgttccttgcgcagctgtgctcgacgttgtcactgaagcgggaagggactggctgctattgggcgaagtgc
cggggcaggatctcctgtcatctcaccttgctcctgccgagaaagtatccatcatggctgatgcaatgcggcggctgcatacgct
tgatccggctacctgcccattcgaccaccaagcgaaacatcgcatcgagcgggcacgtactcggatggaagccggtcttgtc
gatcaggatgatctggacgaagagcatcaggggctcgcgccagccgaactgttcgccaggctcaaggcgcgcatgcccga
cggcgaggatctcgtcgtgacacatggcgatgcctgcttgccgaatatcatggtggaaaatggccgcttttctggattcatcgact
gtggccggctgggtgtggcggaccgctatcaggacatagcgttggctacccgtgatattgctgaagagcttggcggcgaatgg
gctgaccgcttcctcgtgctttacggtatcgccgctcccgattcgcagcgcatcgccttctatcgccttcttgacgagttcttctgagc
gggactctggggttcgaaatgaccgaccaagcgacgcctaactgtcagaccaagtttactcatatatactttagattgatttaaa
acttcattttaatttaaaaggatctaggtgaagatccttttgataatctcatgaccaaaatcccttaacgtgagttttcgttccactga
gcgtcagaccccgtagaaaagatcaaaggatcttcttgagatcctttttttctgcgcgtaatctgctgcttgcaaacaaaaaaacc
accgctaccagcggtggtttgtttgccggatcaagagctaccaactcttttccgaaggtaactggcttcagcagagcgcagata
ccaaatactgtccttctagtgtagccgtagttaggccaccacttcaagaactctgtagcaccgcctacatacctcgctctgctaat
cctgttaccagtggctgctgccagtggcgataagtcgtgtcttaccgggttggactcaagacgatagttaccggataaggcgca
gcggtcgggctgaacggggggttcgtgcacacagcccagcttggagcgaacgacctacaccgaactgagatacctacagc
gtgagctatgagaaagcgccacgcttcccgaagggagaaaggcggacaggtatccggtaagcggcagggtcggaacag
gagagcgcacgagggagcttccaggggaaacgcctggtatctttatagtcctgtcgggtttcgccacctctgacttgagcgtc
gatttttgtgatgctcgtcaggggggcggagcctatggaaaaacgccagcaacgcggcctttttacggttcctggccttttgctgg
ccttttgctcacatgttctttcctgcgttatcccctgattctgtggataaccgtattaccgcctttgagtgagctgataccgctcgccgc
agccgaacgaccgagcgcagcgagtcagtgagcgaggaagcggaagagcgcctgatgcggtattttctccttacgcatctgt
gcggtatttcacaccgcaatggtgcactctcagtacaatctgctctgatgccgcatagttaagccagtatacactccgctatcgct
acgtgactgggtcatggctgcgccccgacacccgccaacacccgctgacgcgccctgacgggcttgtctgctcccggcatcc
gcttacagacaagctgtgaccgtctccgggagctgcatgtgcagaggttttcaccgtcatcaccgaaacgcgcgaggcagct
gcggtaaagctcatcagcgtggtcgtgaagcgattcacagatgtctgcctgttcatccgcgtccagctcgttgagtttctccagaa
gcgttaatgtctggcttctgataaagcgggccatgttaagggcggttttttcctgtttggtcactgatgcctccgtgtaaggggga ttt
ctgttcatgggggtaatgataccgatgaaacgagagaggatgctcacgatacgggttactgatgatgaacatgcccggttactg
gaacgttgtgagggtaaacaactggcggtatggatgcggcgggaccagagaaaaatcactcagggtcaatgccagcgcttc
gttaatacagatgtaggtgttccacagggtagccagcagcatcctgcgatgcagatccggaacataatggtgcagggcgctg
acttccgcgtttccagactttacgaaacacggaaaccgaagaccattcatgttgttgctcaggtcgcagacgttttgcagcagca
gtcgcttcacgttcgctcgcgtatcggtgattcattctgctaaccagtaaggcaaccccgccagcctagccgggtcctcaacga
caggagcacgatcatgcgcacccgtggccaggacccaacgctgcccgagatgcgccgcgtgcggctgctggagatggcg
gacgcgatggatatgttctgccaagggttggtttgcgcattcacagttctccgcaagaattgattggctccaattcttggagtggtg
aatccgttagcgaggtgccgccggcttccattcaggtcgaggtggcccggctccatgcaccgcgacgcaacgcggggaggc
agacaaggtatagggcggcgcctacaatccatgccaacccgttccatgtgctcgccgaggcggcataaatcgccgtgacga
tcagcggtccaatgatcgaagttaggctggtaagagccgcgagcgatccttgaagctgtccctgatggtcgtcatctacctgcct
ggacagcatggcctgcaacgcgggcatcccgatgccgccggaagcgagaagaatcataatggggaaggccatccagcct
cgcgtcgcgaacgccagcaagacgtagcccagcgcgt
```

Figure 114C cggccgccatgccggcgataatggcctgcttctcgccgaaacgtttggtggcgggaccagtgacgaaggctt
gagcgagggcgtgcaagattccgaataccgcaagcgacaggccgatcatcgtcgcgctccagcgaaagc
ggtcctcgccgaaaatgacccagagcgctgccggcacctgtcctacgagttgcatgataaagaagacagtc
ataagtgcggcgacgatagtcatgccccgcgcccaccggaaggagctgactggttgaaggctctcaaggg
catcggtcgagatcccggtgcctaatgagtgagctaacttacattaattgcgttgcgctcactgcccgctttccag
tcgggaaacctgtcgtgccagctgcattaatgaatcggccaacgcgcggggagaggcggtttgcgtattggg
cgccagggtggttttctttcaccagtgagacgggcaacagctgattgcccttcaccgcctggccctgagaga
gttgcagcaagcggtccacgctggtttgccccagcaggcgaaaatcctgtttgatggtggttaacggcgggat
ataacatgagctgtcttcggtatcgtcgtatcccactaccgagatatccgcaccaacgcgcagcccggactcg
gtaatggcgcgcattgcgcccagcgccatctgatcgttggcaaccagcatcgcagtgggaacgatgccctcat
tcagcatttgcatggtttgttgaaaaccggacatggcactccagtcgccttcccgttccgctatcggctgaatttga
ttgcgagtgagatatttatgccagccagccagacgcagacgcgccgagacagaacttaatgggcccgctaa
cagcgcgatttgctggtgacccaatgcgaccagatgctccacgcccagtcgcgtaccgtcttcatgggagaaa
ataatactgttgatgggtgtctggtcagagacatcaagaaataacgccggaacattagtgcaggcagcttca
cagcaatggcatcctggtcatccagcggatagttaatgatcagcccactgacgcgttgcgcgagaagattgtg
caccgccgctttacaggcttcgacgccgcttcgttctaccatcgacaccaccacgctggcacccagttgatcgg
cgcgagatttaatcgccgcgacaatttgcgacggcgcgtgcagggccagactggaggtggcaacgccaatc
agcaacgactgtttgcccgccagttgttgtgccacgcggttgggaatgtaattcagctccgccatcgccgcttcc
acttttccgcgttttcgcagaaacgtggcctggccttggttcaccacgcgggaaacggtctgataagagacacc
ggcatactctgcgacatcgtataacgttactggtttcacattcaccaccctgaattgactctcttccgggcgctatc
atgccataccgcgaaaggttttgcgccattcgatggtgtccgggatctcgacgctctccttatgcgactcctgca
ttaggaagcagcccagtagtaggttgaggccgttgagcaccgccgccgcaaggaatggtgcatgcaagga
gatggcgcccaacagtcccccggccacggggcctgccaccatacccacgccgaaacaagcgctcatgag
cccgaagtggcgagcccgatcttcccatcggtgatgtcggcgatataggcgccagcaaccgcacctgtggc
gccggtgatgccggccacgatgcgtccggcgtagaggatcgagatctcgatcccgcgaaattaatacgactc
actatagggaattgtgagcggataacaattcccctctagaaataattttgtttaactttaagaaggagatataca
tatgcggggttctcatcatcatcatcatcatggtatggctagcatgactggtggacagcaaatgggtcgggatct
gtacgacgatgacgataaggatcatcccttcaccatggtatcctgttctgcgccgggtaagatttacctgttcggt
gaacacgccgtagtttatggcgaaactgcaattgcgtgtgcggtggaactgcgtacccgtgttcgcgcggaact
caatgactctatcactattcagagccagatcggccgcaccggtctggatttcgaaaagcaccttatgtgtctgc
ggtaattgagaaaatgcgcaaatctattcctattaacggtgttttcttgaccgtcgattccgacatcccggtgggct
ccggtctgggtagcagcgcagccgttactatcgcgtctattggtgcgctgaacgagctgttcggctttggcctca
gcctgcaagaaatcgctaaactgggccacgaaatcgaattaaagtacagggtgccgcgtccccaaccgat
acgtatgtttctaccttcggcggcgtggttaccatcccggaacgtcgcaaactgaaaactccggactgcggcat
tgtgattggcgataccggcgttttctcctccaccaaagagttagtagctaacgtacgtcagctgcgcgaaagcta
cccggatttgatcgaaccgctgatgacctctattggcaaaatctctcgtatcggcgaacaactggttcgtctggc
gactacgcatccatcggccgcctgatgaacgtcaaccagggtctcctggacgccctgggcgttaacatcttag
aactgagccagctgatcattccgctcgtgcggcaggtgcgtttggcgctaaaatcacgggcgctggcggcgg
tggctgtatggttgcgctgaccgctccggaaaaatgcaaccaagtggcagaagcggtagcaggcgctggcg
gtaaagtgactatcactaaaccgaccgagcaaggtctgaaagtagattaa
(SEQ ID NO:104)

Figure 117B

>kudzu isoprene synthase codon-optimized for yeast in pDONR221:19430
gaattcaaaatgtgtgcaacttcatcccaattcactcaaatcacagagcataattctagacgttcagctaactaccaaccaa
atctgtggaattttgaatttcttcaatcccttgaaaatgatttgaaagtggaaaagttggaggaaaaagccacaaaactaga
ggaagaagttagatgtatgataaacagagtagatacacaacctctgtcactactagaattgattgacgatgtccagaggct
gggtttaacatataagttcgaaaaggatataatcaaagccttagaaaacatagtccttctagatgaaaacaagaagaata
agtctgacttgcacgcaaccgctctgagttttagattgctgagacaacatggttttgaagtaagtcaagatgtgtttgaaaggtt
caaagacaaagagggaggattctcaggagaattaaagggagatgtgcagggtctgttgtcattgtacgaggccagttattt
ggggtttgaaggggaaaatctactagaggaggccagaaccttctctataacccatctgaagaataacttgaaagaaggc
atcaatacaaaagtggctgaacaagtttcacatgcattggaattgccctaccaccaaagacttcatagacttgaagccaga
tggttttggacaagtatgaaccaaggagcctcaccatcaactttattggaattagcaaaactggattttaacatggttcag
acattacaccagaaagaattgcaggacctatcaagatggtggacggagatgggtttagccagcaagttagatttcgttaga
gatagattgatggaagtttacttttgggcactgggaatggcaccagatcctcaatttggtgaatgtagaaaggcagttacaa
agatgtttggtctagtaacaatcattgatgatgtttatgatgtgtacggaactttggatgaattacaactattcaccgacgcagtt
gaacgttgggatgtaaacgcaataaacacgttgcctgattatatgaagctgtgttttctggcattgtacaacacagtcaatga
cacttcttactccattttaaaggagaaagggcataacaatctatcctatttgacaaaatcatggagggagttatgcaaagcat
tccttcaagaagctaagtggtctaacaataagataatcccagcattctccaagtatcttgaaaacgcttccgtatcctcctccg
gtgtggccctactagcaccatcatatttttccgtctgccagcagcaggaagatatctctgatcatgctttgagatccttaacag
attttcatggtctagtcagatcctcttgcgtgattttcagattgtgcaatgatttggctacttcagccgcagagttagagagggt
gaaaccacgaactcaattattagttatatgcacgagaatgatggaacatccgaagaacaagcccgtgaagaattaagaa
aactgatcgatgctgaatggaagaagatgaatagagaaagagtttccgacagcactttgctgcctaaggcattcatggag
atagctgttaacatggctagggtttcacactgtacataccaatacggggacggtcttggaaggcccgactacgccactgaa
aatagaattaaactgctactgattgatcctttccccattaaccagttaatgtacgtgtaatagggatccgaattc
(SEQ ID NO:112)

Figure 117C

>pDW14
acggattagaagccgccgagcgggtgacagccctccgaaggaagactctcctccgtgcgtcctcgtcttcaccggtcgcgttcctga
aacgcagatgtgcctcgcgccgcactgctccgaacaataaagattctacaatactagcttttatggttatgaagaggaaaaattggca
gtaacctggccccacaaaccttcaaatgaacgaatcaaattaacaaccataggatgataatgcgattagttttttagccttatttctggg
gtaattaatcagcgaagcgatgattttttgatctattaacagatatataaatgcaaaaactgcataaccactttaactaatactttcaacatt
ttcggtttgtattacttcttattcaaatgtaataaaagtatcaacaaaaaattgttaatatacctctatactttaacgtcaaggagaaaaaac
cccggatcggactactagcagctgtaatacgactcactatagggaatattaagctatcaaacaagtttgtacaaaaaagcaggctga
attcaaa<u>atgtgtgcaacttcatcccaattcactcaaatcacagagcataattctagacgttcagctaactaccaaccaaatctgtgga</u>
<u>attttgaatttcttcaatcccttgaaaatgatttgaaagtggaaaagttggaggaaaaagccacaaaactagaggaagaagttagatg</u>
<u>tatgataaacagagtagatacacaacctctgtcactactagaattgattgacgatgtccagaggctgggtttaacatataagttcgaaa</u>
<u>aggatataatcaaagccttagaaaacatagtccttctagatgaaaacaagaagaataagtctgacttgcacgcaaccgctctgagtt</u>
<u>ttagattgctgagacaacatggttttgaagtaagtcaagatgtgtttgaaaggttcaaagacaaagagggaggattctcaggagaatt</u>
<u>aaagggagatgtgcagggtctgttgtcattgtacgaggccagttatttgggtttgaaggggaaaatctactagaggaggccagaac</u>
<u>cttctctataacccatctgaagaataacttgaaagaaggcatcaatacaaaagtggctgaacaagtttcacatgcattggaattgccct</u>
<u>accaccaaagacttcatagacttgaagccagatggttttggacaagtatgaaccaaaggagcctcaccatcaactttattggaatta</u>
<u>gcaaaactggattttaacatggttcagacattacaccagaaagaattgcaggacctatcaagatggtggacggagatgggtttagcc</u>
<u>agcaagttagatttcgttagagatagattgatggaagtttacttttgggcactgggaatggcaccagatcctcaatttggtgaatgtaga</u>
<u>aaggcagttacaaagatgtttggtctagtaacaatcattgatgatgtttatgatgtgtacggaactttggatgaattacaactattcaccga</u>
<u>cgcagttgaacgttgggatgtaaacgcaataaacacgttgcctgattatatgaagctgtgttttctggcattgtacaacacagtcaatga</u>
<u>cacttcttactccatttttaaaggagaaagggcataacaatctatcctatttgacaaaatcatggagggagttatgcaaagcattccttca</u>
<u>agaagctaagtggtctaacaataagataatcccagcattctccaagtatcttgaaaacgcttccgtatcctcctccggtgtggccctact</u>
<u>agcaccatcatatttttccgtctgccagcagcaggaagatatctctgatcatgctttgagatccttaacagatttttcatggtctagtcagat</u>
<u>cctcttgcgtgattttcagattgtgcaatgatttggctacttcagccgcagagttagagaggggtgaaaccacgaactcaattattagtta</u>
<u>tatgcacgagaatgatggaacatccgaagaacaagcccgtgaagaattaagaaaactgatcgatgctgaatggaagaagatgaa</u>
<u>tagagaaagagtttccgacagcactttgctgcctaaa</u>a<u>gcattcatggagatagctgttaacatggctagggtttcacactgtacatacc</u>
<u>aatacggggacggtcttggaaggcccgactacgccactgaaaatagaattaaactgctactgattgatcctttcccccattaaccagtt</u>
aatgtacgtgtaatagggatccgaattcacccagctttcttgtacaaagtggttcgatctagagggcccttcgaaggtaagcctatccct
aaccctctcctcggtctcgattctacgcgtaccggtcatcatcaccatcaccattgagtttaaacccgctgatcctagagggccgcatc
atgtaattagttatgtcacgcttacattcacgcccctcccccacatccgctctaaccgaaaaggaaggagttagacaacctgaagtct
aggtcccctatttattttttatagttatgttagtattaagaacgttatttatatttcaaattttctttttttctgtacagacgcgtgtacgcatgtaac
attatactgaaaaccttgcttgagaaggttttgggacgctcgaaggctttaatttgcaagctgcggccctgcattaatgaatcggccaac
gcgcggggagaggcggtttgcgtattgggcgctcttccgcttcctcgctcactgactcgctgcgctcggtcgttcggctgcggcgagc
ggtatcagctcactcaaaggcggtaatacggttatccacagaatcaggggataacgcaggaaagaacatgtgagcaaaaggcc
agcaaaagcccaggaaccgtaaaaaggccgcgttgctggcgttttccataggctccgcccccctgacgagcatcacaaaaatcg
acgctcaagtcagaggtggcgaaacccgacaggactataaagataccaggcgtttccccctggaagctccctcgtgcgctctcctg
ttccgaccctgccgcttaccggatacctgtccgcctttctcccttcgggaagcgtggcgctttctcatagctcacgctgtaggtatctcagt
tcggtgtaggtcgttcgctccaagctgggctgtgtgcacgaaccccccgttcagcccgaccgctgcgccttatccggtaactatcgtctt
gagtccaacccggtaagacacgacttatcgccactggcagcagccactggtaacaggattagcagagcgaggtatgtaggcggt
gctacagagttcttgaagtggtggcctaactacggctacactagaaggacagtatttggtatctgcgctctgctgaagccagttaccttc
ggaaaaagagttggtagctcttgatccggcaaacaaaccaccgctggtagcggtggtttttttgtttgcaagcagcagattacgcgca
gaaaaaaggatctcaagaagatcctttgatcttttctacggggtctgacgctcagtggaacgaaaactcacgttaagggattttggtc
atgagattatcaaaaaggatcttcacctagatccttttaaattaaaaatgaagttttaaatcaatctaaagtatatatgagtaaacttggtc
tgacagttaccaatgcttaatcagtgaggcacctatctcagcgatctgtctatttcgttcatccatagttgcctgactccccgtcgtgtagat
aactacgatacgggagcgcttaccatctggccccagtgctgcaatgataccgcgagacccacgctcaccggctccagatttatcag
caataaaccagccagccggaagggccgagcgcagaagtggtcctgcaactttatccgcctccatccagtctattaattgttgccggg
aagctagagtaagtagttcgccagttaatagttt

Figure 117D

```
gcgcaacgttgttggcattgctacaggcatcgtggtgtcactctcgtcgtttggtatggcttcattcagctccggttcccaacgatcaaggc
gagttacatgatccccatgttgtgcaaaaaagcggttagctccttcggtcctccgatcgttgtcagaagtaagttggccgcagtgttatca
ctcatggttatggcagcactgcataattctcttactgtcatgccatccgtaagatgcttttctgtgactggtgagtactcaaccaagtcattctg
agaatagtgtatgcggcgaccgagttgctcttgcccggcgtcaatacgggataatagtgtatcacatagcagaactttaaaagtgctcat
cattggaaaacgttcttcggggcgaaaactctcaaggatcttaccgctgttgagatccagttcgatgtaacccactcgtgcacccaactg
atcttcagcatctttacttttcaccagcgtttctgggtgagcaaaaacaggaaggcaaaatgccgcaaaaaagggaataagggcgac
acggaaatgttgaatactcatactcttccttttcaatgggtaataactgatataattaaattgaagctctaatttgtgagtttagtatacatgca
tttacttataatacagttttttagttttgctggccgcatcttctcaaatatgcttcccagcctgcttttctgtaacgttcaccctctaccttagcatcc
cttcctttgcaaatagtcctcttccaacaataataatgtcagatcctgtagagaccacatcatccacggttctatactgttgacccaatgc
gtctcccttgtcatctaaacccacaccgggtgtcataatcaaccaatcgtaaccttcatctcttccacccatgtctctttgagcaataaagc
cgataacaaaatctttgtcgctcttcgcaatgtcaacagtacccttagtatattctccagtagatagggagcccttgcatgacaattctgcta
acatcaaaaggcctctaggttcctttgttacttcttctgccgcctgcttcaaaccgctaacaatacctgggcccaccacaccgtgtgcattc
gtaatgtctgcccattctgctattctgtatacacccgcagagtactgcaatttgactgtattaccaatgtcagcaaattttctgtcttcgaagag
taaaaaattgtacttggcggataatgcctttagcggcttaactgtgccctccatggaaaaatcagtcaagatatccacatgtgtttttagtaa
acaaattttgggacctaatgcttcaactaactccagtaattccttggtggtacgaacatccaatgaagcacacaagtttgtttgcttttcgtg
catgatattaaatagcttggcagcaacaggactaggatgagtagcagcacgttccttatatgtagctttcgacatgatttatcttcgtttcctg
caggtttttgttctgtgcagttgggttaagaatactgggcaatttcatgtttcttcaacactacatatgcgtatatataccaatctaagtctgtgct
ccttccttcgttcttccttctgttcggagattaccgaatcaaaaaaatttcaaagaaaccgaaatcaaaaaaaagaataaaaaaaaaat
gatgaattgaattgaaaagctagcttatcgatgataagctgtcaaagatgagaattaattccacggactatagactatactagatactcc
gtctactgtacgatacacttccgctcaggtccttgtcctttaacgaggccttaccactcttttgttactctattgatccagctcagcaaaggca
gtgtgatctaagattctatcttcgcgatgtagtaaaactagctagaccgagaaagagactagaaatgcaaaaggcacttctacaatgg
ctgccatcattattatccgatgtgacgctgcagcttctcaatgatattcgaatacgctttgaggagatacagcctaatatccgacaaactgtt
ttacagatttacgatcgtacttgttacccatcattgaattttgaacatccgaacctgggagttttccctgaaacagatagtatatttgaacctgt
ataataatatatagtctagcgctttacggaagacaatgtatgtatttcggttcctggagaaactattgcatctattgcataggtaatcttgcac
gtcgcatccccggttcattttctgcgtttccatcttgcacttcaatagcatatctttgttaacgaagcatctgtgcttcattttgtagaacaaaaat
gcaacgcgagagcgctaattttcaaacaaagaatctgagctgcattttacagaacagaaatgcaacgcgaaagcgctattttacca
acgaagaatctgtgcttcattttgtaaaacaaaaatgcaacgcgacgagagcgctaattttcaaacaaagaatctgagctgcatttta
cagaacagaaatgcaacgcgagagcgctattttaccaacaaagaatctatacttcttttttgttctacaaaaatgcatcccgagagcgct
attttctaacaaagcatcttagattactttttctcctttgtgcgctctataatgcagtctcttgataacttttgcactgtaggtccgttaaggtta
gaagaaggctactttggtgtctattttctcttccataaaaaaagcctgactccacttcccgcgtttactgattactagcgaagctgcgggtgc
atttttcaagataaaggcatccccgattatattctataccgatgtggattgcgcatactttgtgaacagaaagtgatagcgttgatgattctt
cattggtcagaaaattatgaacggtttcttctattttgtctctatatactacgtataggaaatgtttacatttttcgtattgttttcgattcactctatga
atagttcttactacaattttttgtctaaagagtaatactagagataaacataaaaaatgtagaggtcgagtttagatgcaagttcaaggag
cgaaaggtggatgggtaggttatatagggatatagcacagagatatatagcaaagagatactttttgagcaatgtttgtggaagcggtatt
cgcaatgggaagctccaccccggttgataatcagaaaagccccaaaaacaggaagattgtataagcaaatatttaaattgtaaacgtt
aatatttgttaaaattcgcgttaaattttgttaaatcagctcatttttaacgaatagcccgaaatcggcaaaatcccttataaatcaaaag
aatagaccgagataggttgagtgttgttccagtttccaacaagagtccactattaaagaacgtggactccaacgtcaaagggcgaaa
aagggtctatcagggcgatggcccactacgtgaaccatcacctaatcaagttttttggggtcgaggtgccgtaaagcagtaaatcgg
aagggtaaacggatgcccccatttagagcttgacggggaaagccggcgaacgtggcgagaaaggaagggaagaaagcgaaag
gagcggggggctagggcggtgggaagtgtaggggtcacgctgggcgtaaccaccacacccgccgcgcttaatggggcgctacagg
gcgcgtggggatgatccactagt
```
(SEQ ID NO:113)

Figure 119
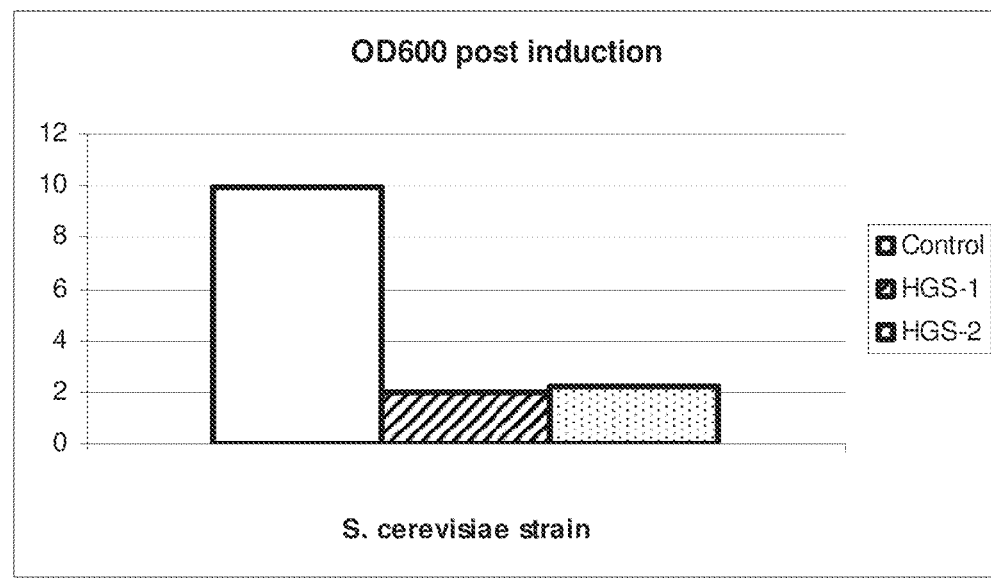
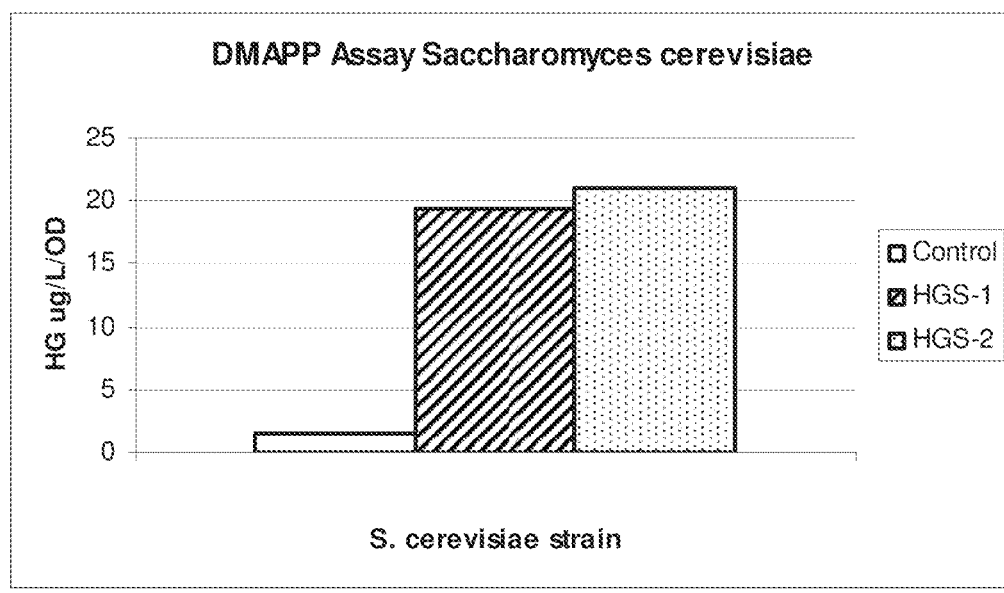

CONVERSION OF PRENYL DERIVATIVES TO ISOPRENE

CROSS-REFERENCE TO RELATED APPLICATIONS

This applications claims priority to U.S. Provisional Patent Application 61/097,204, filed on Sep. 15, 2008, the entire contents of which are hereby incorporated by reference in its entirety.

BACKGROUND OF THE INVENTION

Isoprene(2-methyl-1,3-butadiene) is the critical starting material for a variety of synthetic polymers, most notably synthetic rubbers. Isoprene is naturally produced by a variety of microbial, plant, and animal species. In particular, two pathways have been identified for the biosynthesis of isoprene: the mevalonate (MVA) pathway and the non-mevalonate (DXP) pathway. However, the yield of isoprene from naturally-occurring organisms is commercially unattractive. About 800,000 tons per year of cis-polyisoprene are produced from the polymerization of isoprene; most of this polyisoprene is used in the tire and rubber industry. Isoprene is also copolymerized for use as a synthetic elastomer in other products such as footwear, mechanical products, medical products, sporting goods, and latex.

Currently, the tire and rubber industry is based on the use of natural and synthetic rubber. Natural rubber is obtained from the milky juice of rubber trees or plants found in the rainforests of Africa. Synthetic rubber is based primarily on butadiene polymers. For these polymers, butadiene is obtained as a co-product from ethylene and propylene manufacture.

While isoprene can be obtained by fractionating petroleum, the purification of this material is expensive and time-consuming. Petroleum cracking of the C5 stream of hydrocarbons produces only about 15% isoprene. Thus, more economical methods for producing isoprene are needed. In particular, methods that produce isoprene at rates, titers, and purity that are sufficient to meet the demands of a robust commercial process are desirable. Also desired are systems for producing isoprene from inexpensive starting materials.

BRIEF SUMMARY OF THE INVENTION

The present invention also provides, inter alia, compositions, cells, systems and methods of producing isoprene. In one aspect, the invention provides for methods of producing isoprene comprising (a) culturing cells under suitable culture conditions for the production of a prenyl derivative, and wherein the cells comprise a heterologous nucleic acid that encodes an isoprene synthase polypeptide in operable combination with a promoter; (b) recovering said prenyl derivative; and (c) dehydrating or decarboxylating said prenyl derivative to produce isoprene. In some embodiments, the prenyl derivative is a compound of Formula (I):

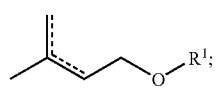
(I)

wherein $R^1$ is hydrogen or —C(O)$R^2$; and $R^2$ is $C_1$-$C_5$ linear or branched alkyl. In some embodiments, the prenyl derivative is a compound of Formula (II):

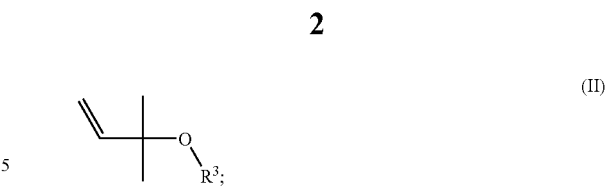

wherein $R^3$ is hydrogen or —C(O)$R^4$; and $R^4$ is $C_1$-$C_5$ linear or branched alkyl. In some embodiments, the prenyl derivative is a C5 unsaturated alcohol or a $C_1$-$C_5$ linear or branched acyl ester thereof. In some embodiments, the method comprises contacting said prenyl derivative with a catalyst such that isoprene is produced by dehydration or decarboxylation of said prenyl derivative. In some embodiments, the catalyst is an inorganic acid catalyst (e.g. HCl, HBr, $H_2SO_4$, or $H_3PO_4$), a solid acid catalyst (e.g. activated alumina, a zeolite, or an inorganic acid on an inert carrier), an organic acid catalyst (e.g. p-toluenesulfonic acid or trifluoromethane sulfonic acid), or an organic acid resin (e.g. Nafion or other fluorosulfonic acid resin). In some embodiments, the catalyst is on a solid support. In some embodiments, the catalyst is in solution. In a preferred embodiment, the catalyst is an acidic salt solution. In some embodiments, the catalyst is optionally buffered with additional salts. In some embodiments, the prenyl derivative is recovered from fermentation off-gas of the cultured cells using a process selected from the group consisting of distillation, gas-stripping, two-phase recovery, and pervaporation. In some embodiments, the prenyl derivative is a prenyl alcohol. In some embodiments, the prenyl alcohol is converted to an acetyl ester prior to gas stripping. In some preferred embodiments, the prenyl alcohol comprises one or both of prenol and isoprenol. In some embodiments, the prenyl derivative is an acetyl ester. In some embodiments, the prenyl derivative is 3-methyl-3-buten-1-ol, 3-methyl-2-butene-1-ol, 3-methyl-3-buten-1-yl acetate, 3-methyl-2-buten-1-yl acetate, or 2-methyl-3-buten-2-ol. In some embodiments, the cells further comprise one or both of an IDI polypeptide and an MVA pathway enzyme.

In addition, the present invention provides methods of producing isoprene, the method comprising (a) culturing cells in culture medium under suitable culture conditions for the production of isoprene, wherein said culture medium comprises a prenyl derivative, and wherein said cells comprise a heterologous nucleic acid that encodes an isoprene synthase polypeptide in operable combination with a promoter; and (b) producing said isoprene. In some embodiments, the prenyl derivative is a compound of Formula (I):

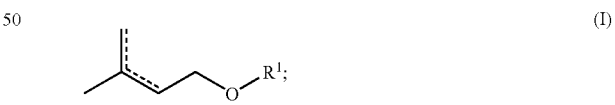
(I)

wherein $R^1$ is hydrogen or —C(O)$R^2$; and $R^2$ is $C_1$-$C_5$ linear or branched alkyl. In some embodiments, the prenyl derivative is a compound of Formula (II):

(II)

wherein $R^3$ is hydrogen or —C(O)$R^4$; and $R^4$ is $C_1$-$C_5$ linear or branched alkyl. In some embodiments, the prenyl derivative is a C5 unsaturated alcohol or a $C_1$-$C_5$ linear or branched acyl ester thereof. In some embodiments, the cells are bacterial cells or yeast cells. In some embodiments, the cells are selected from the group consisting of *E. coli, P. citrea, B. subtilis, T. reesei, Y. lipolytica*, and *S. cerevisiae*. In some embodiments, the prenyl derivative is a prenyl alcohol. In some embodiments, the prenyl alcohol comprises one or both of prenol and isoprenol. In some embodiments, the prenyl derivative is an acetyl ester. In some embodiments, the prenyl derivative is 3-methyl-3-buten-1-ol, 3-methyl-2-butene-1-ol, 3-methyl-3-buten-1-yl acetate, 3-methyl-2-buten-1-yl acetate, or 2-methyl-3-buten-2-ol. In some embodiments, the cells further comprise one or both of an IDI polypeptide and an MVA pathway enzyme. In some embodiments, the cells further comprise prenol kinase activity. In some embodiments, the cells further comprise isoprene synthase.

In one aspect, the invention features cells in culture that produce isoprene. In some embodiments, the invention provides cells in culture that produce greater than about 400 nmole of isoprene/gram wet weight of the cells/hour (nmole/$g_{wcm}$/hr) of isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, alcohol, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions.

In some embodiments, the invention provides cells in culture that convert more than about 0.002% of the carbon in a cell culture medium into isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, alcohol, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions.

In some embodiments, the invention provides cells in culture that comprise a heterologous nucleic acid encoding an isoprene synthase polypeptide. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, alcohol, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions.

In one aspect, the invention features methods of producing isoprene, such as methods of using any of the cells described herein to produce isoprene. In some embodiments, the method involves culturing cells under conditions sufficient to produce greater than about 400 nmole/$g_{wcm}$/hr of isoprene. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, alcohol, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions. In various embodiments, the amount of isoprene produced (such as the total amount of isoprene produced or the amount of isoprene produced per liter of broth per hour per $OD_{600}$) during stationary phase is greater than or about 2 or more times the amount of isoprene produced during the growth phase for the same length of time. In some embodiments, the gas phase comprises greater than or about 9.5% (volume) oxygen, and the concentration of isoprene in the gas phase is less than the lower flammability limit or greater than the upper flammability limit. In particular embodiments, (i) the concentration of isoprene in the gas phase is less than the lower flammability limit or greater than the upper flammability limit, and (ii) the cells produce greater than about 400 nmole/$g_{wcm}$/hr of isoprene.

In some embodiments, the method includes culturing cells under conditions sufficient to convert more than about 0.002% of the carbon (mol/mol) in a cell culture medium into isoprene. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, alcohol, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions.

In some embodiments, isoprene is only produced in stationary phase. In some embodiments, isoprene is produced in both the growth phase and stationary phase. In various embodiments, the amount of isoprene produced (such as the total amount of isoprene produced or the amount of isoprene produced per liter of broth per hour per $OD_{600}$) during stationary phase is greater than or about 2, 3, 4, 5, 10, 20, 30, 40, 50, or more times the amount of isoprene produced during the growth phase for the same length of time.

In one aspect, the invention features compositions and systems that comprise isoprene. In some embodiments, the composition comprises greater than or about 2, 5, 10, 20, 30, 40, 50, 60, 70, 80, 90, 100, 200, 300, 400, 500, 600, 700, 800, 900, or 1000 mg of isoprene. In some embodiments, the composition comprises greater than or about 2, 5, 10, 20, 30, 40, 50, 60, 70, 80, 90, 100 g of isoprene (w/w) of the volatile organic fraction of the composition is isoprene.

In some embodiments, the composition comprises greater than or about 99.90, 99.92, 99.94, 99.96, 99.98, or 100% isoprene by weight compared to the total weight of all C5 hydrocarbons in the composition. In some embodiments, the composition comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol) by weight compared to the total weight of all C5 hydrocarbons in the composition. In some embodiments, the composition has less than or about 0.12, 0.10, 0.08, 0.06, 0.04, 0.02, 0.01, 0.005, 0.001, 0.0005, 0.0001, 0.00005, or 0.00001% for 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol) by weight compared to the total weight of all C5 hydrocarbons in the composition. In particular embodiments, the composition has greater than about 2 mg of isoprene and has greater than or about 99.90, 99.92, 99.94, 99.96, 99.98, or 100% isoprene by weight compared to the total weight of all C5 hydrocarbons in the composition.

In some embodiments, the composition has less than or about 50, 40, 30, 20, 10, 5, 1, 0.5, 0.1, 0.05, 0.01, or 0.005 ug/L of a compound that inhibits the polymerization of isoprene for any compound in the composition that inhibits the polymerization of isoprene. In particular embodiments the composition also has greater than about 2 mg of isoprene.

In some embodiments, the composition has one or more compounds selected from the group consisting of ethanol, acetone, C5 prenyl alcohols, and isoprenoid compounds with 10 or more carbon atoms. In some embodiments, the composition has greater than or about 0.005, 0.01, 0.05, 0.1, 0.5, 1, 5, 10, 20, 30, 40, 60, 80, 100, or 120 ug/L of ethanol, acetone, a C5 prenyl alcohol (such as 3-methyl-3-buten-1-ol or 3-methyl-2-buten-1-ol), or any two or more of the foregoing. In particular embodiments, the composition has greater than about 2 mg of isoprene and has one or more compounds selected from the group consisting of ethanol, acetone, C5 prenyl alcohols, and isoprenoid compounds with 10 or more carbon atoms.

In some embodiments, the composition includes isoprene and one or more second compounds selected from the group consisting of 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, and 2,3-cycloheptenolpyridine. In various embodiments, the amount of one of these second components relative to the amount of isoprene in units of percentage by weight (i.e., weight of the component divided by the weight of isoprene times 100) is at greater than or about 0.01, 0.02, 0.05, 0.1, 0.5, 1, 5, 10, 20, 30, 40, 50, 60, 70, 80, 90, 100, or 110% (w/w).

In some embodiments, the composition comprises (i) a gas phase that comprises isoprene and (ii) cells in culture that produce greater than about 400 nmole/$g_{wcm}$/hr of isoprene. In some embodiments, the composition comprises a closed system, and the gas phase comprises greater than or about 5. 10, 20, 30, 40, 50, 60, 70, 80, 90, 100 ug/L of isoprene when normalized to 1 mL of 1 $OD_{600}$ cultured for 1 hour. In some embodiments, the composition comprises an open system, and the gas phase comprises greater than or about 5, 10, 20, 30, 40, 50, 60, 70, 80, 90, 100 ug/L of isoprene when sparged at a rate of 1 vvm. In some embodiments, the volatile organic fraction of the gas phase comprises greater than or about 99.90, 99.92, 99.94, 99.96, 99.98, or 100% isoprene by weight compared to the total weight of all C5 hydrocarbons in the volatile organic fraction. In some embodiments, the volatile organic fraction of the gas phase comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol) by weight compared to the total weight of all C5 hydrocarbons in the volatile organic fraction. In some embodiments, the volatile organic fraction of the gas phase has less than or about 0.12, 0.10, 0.08, 0.06, 0.04, 0.02, 0.01, 0.005, 0.001, 0.0005, 0.0001, 0.00005, or 0.00001% for 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol) by weight compared to the total weight of all C5 hydrocarbons in the volatile organic fraction. In particular embodiments, the volatile organic fraction of the gas phase has greater than about 2 mg of isoprene and has greater than or about 99.90, 99.92, 99.94, 99.96, 99.98, or 100% isoprene by weight compared to the total weight of all C5 hydrocarbons in the volatile organic fraction.

In some embodiments, the volatile organic fraction of the gas phase has less than or about 50, 40, 30, 20, 10, 5, 1, 0.5, 0.1, 0.05, 0.01, or 0.005 ug/L of a compound that inhibits the polymerization of isoprene for any compound in the volatile organic fraction of the gas phase that inhibits the polymerization of isoprene. In particular embodiments the volatile organic fraction of the gas phase also has greater than about 2 mg of isoprene.

In some embodiments, the volatile organic fraction of the gas phase has one or more compounds selected from the group consisting of ethanol, acetone, C5 prenyl alcohols, and isoprenoid compounds with 10 or more carbon atoms. In some embodiments, the volatile organic fraction of the gas phase has greater than or about 0.005, 0.01, 0.05, 0.1, 0.5, 1, 5, 10, 20, 30, 40, 60, 80, 100, or 120 ug/L of ethanol, acetone, a C5 prenyl alcohol (such as 3-methyl-3-buten-1-ol or 3-methyl-2-buten-1-ol), or any two or more of the foregoing. In particular embodiments, the volatile organic fraction of the gas phase has greater than about 2 mg of isoprene and has one or more compounds selected from the group consisting of ethanol, acetone, C5 prenyl alcohols, and isoprenoid compounds with 10 or more carbon atoms.

In some embodiments, the volatile organic fraction of the gas phase has includes isoprene and one or more second compounds selected from the group consisting of 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, and 2,3-cycloheptenolpyridine. In various embodiments, the amount of one of these second components relative to amount of isoprene in units of percentage by weight (i.e., weight of the component divided by the weight of isoprene times 100) is at greater than or about 0.01, 0.02, 0.05, 0.1, 0.5, 1, 5, 10, 20, 30, 40, 50, 60, 70, 80, 90, 100, or 110% (w/w) in the volatile organic fraction of the gas phase.

In some embodiments of any of the compositions of the invention, at least a portion of the isoprene is in a gas phase. In some embodiments, at least a portion of the isoprene is in a liquid phase (such as a condensate). In some embodiments, at least a portion of the isoprene is in a solid phase. In some embodiments, at least a portion of the isoprene is adsorbed to a solid support, such as a support that includes silica and/or activated carbon. In some embodiments, the composition includes ethanol. In some embodiments, the composition includes between about 75 to about 90% by weight of ethanol, such as between about 75 to about 80%, about 80 to about 85%, or about 85 to about 90% by weight of ethanol. In some embodiments, the composition includes between about 4 to about 15% by weight of isoprene, such as between about 4 to about 8%, about 8 to about 12%, or about 12 to about 15% by weight of isoprene.

In some embodiments, the invention also features systems that include any of the cells and/or compositions described herein. In some embodiments, the system includes a reactor that chamber comprises cells in culture that produce greater than about 400, 500, 600, 700, 800, 900, 1,000, 1,250, 1,500, 1,750, 2,000, 2,500, 3,000, 4,000, 5,000, or more nmole/$g_{wcm}$/hr isoprene. In some embodiments, the system is not a closed system. In some embodiments, at least a portion of the isoprene is removed from the system. In some embodiments, the system includes a gas phase comprising isoprene. In various embodiments, the gas phase comprises any of the compositions described herein.

In one aspect, the invention provides a tire comprising polyisoprene. In some embodiments, the polyisoprene is produced by (i) polymerizing isoprene in any of the compositions described herein or (ii) polymerizing isoprene recovered from any of the compositions described herein. In some embodiments, the polyisoprene comprises cis-1,4-polyisoprene. In another aspect, the invention provides methods of manufacturing a tire wherein the improvement comprises using any one or more the compositions, cells, systems and/or methods described herein to produce isoprene for the manufacture of the tire.

In some embodiments of any of the compositions, systems, and methods of the invention, a nonflammable concentration of isoprene in the gas phase is produced. In some embodiments, the gas phase comprises less than about 9.5% (volume) oxygen. In some embodiments, the gas phase comprises greater than or about 9.5% (volume) oxygen, and the concentration of isoprene in the gas phase is less than the lower flammability limit or greater than the upper flammability limit. In some embodiments, the portion of the gas phase other than isoprene comprises between about 0% to about 100% (volume) oxygen, such as between about 10% to about 100% (volume) oxygen. In some embodiments, the portion of the gas phase other than isoprene comprises between about 0% to about 99% (volume) nitrogen. In some embodiments, the portion of the gas phase other than isoprene comprises between about 1% to about 50% (volume) $CO_2$.

In some embodiments of any of the aspects of the invention, the cells in culture produce isoprene at greater than or about 400, 500, 600, 700, 800, 900, 1,000, 1,250, 1,500, 1,750, 2,000, 2,500, 3,000, 4,000, 5,000, or more nmole/$g_{wcm}$/hr isoprene. In some embodiments of any of the aspects of the invention, the cells in culture convert greater than or about 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6%, or more of the carbon in the cell culture medium into isoprene. In some embodiments of any of the aspects of the invention, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments of any of the aspects of the invention, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). Other exemplary rates of isoprene production and total amounts of isoprene production are disclosed herein.

In some embodiments of any of the aspects of the invention, the cells further comprise a heterologous nucleic acid encoding an IDI polypeptide. In some embodiments of any of the aspects of the invention, the cells further comprise an insertion of a copy of an endogenous nucleic acid encoding an IDI polypeptide. In some embodiments of any of the aspects of the invention, the cells further comprise a heterologous nucleic acid encoding a DXS polypeptide. In some embodiments of any of the aspects of the invention, the cells further comprise an insertion of a copy of an endogenous nucleic acid encoding a DXS polypeptide. In some embodiments of any of the aspects of the invention, the cells further comprise one or more nucleic acids encoding an IDI polypeptide and a DXS polypeptide. In some embodiments of any of the aspects of the invention, one nucleic acid encodes the isoprene synthase polypeptide, IDI polypeptide, and DXS polypeptide. In some embodiments of any of the aspects of the invention, one vector encodes the isoprene synthase polypeptide, IDI polypeptide, and DXS polypeptide. In some embodiments, the vector comprises a selective marker, such as an antibiotic resistance nucleic acid.

In some embodiments of any of the aspects of the invention, the heterologous isoprene synthase nucleic acid is operably linked to a T7 promoter, such as a T7 promoter contained in a medium or high copy plasmid. In some embodiments of any of the aspects of the invention, the heterologous isoprene synthase nucleic acid is operably linked to a Trc promoter, such as a Trc promoter contained in a medium or high copy plasmid. In some embodiments of any of the aspects of the invention, the heterologous isoprene synthase nucleic acid is operably linked to a Lac promoter, such as a Lac promoter contained in a low copy plasmid. In some embodiments of any of the aspects of the invention, the heterologous isoprene synthase nucleic acid is operably linked to an endogenous promoter, such as an endogenous alkaline serine protease promoter. In some embodiments, the heterologous isoprene synthase nucleic acid integrates into a chromosome of the cells without a selective marker.

In some embodiments, one or more MVA pathway, IDI, DXP, or isoprene synthase nucleic acids are placed under the control of a promoter or factor that is more active in stationary phase than in the growth phase. For example, one or more MVA pathway, IDI, DXP, or isoprene synthase nucleic acids may be placed under control of a stationary phase sigma factor, such as RpoS. In some embodiments, one or more MVA pathway, IDI, DXP, or isoprene synthase nucleic acids are placed under control of a promoter inducible in stationary phase, such as a promoter inducible by a response regulator active in stationary phase.

In some embodiments of any of the aspects of the invention, at least a portion of the cells maintain the heterologous isoprene synthase nucleic acid for at least or about 5, 10, 20, 40, 50, 60, 65, or more cell divisions in a continuous culture (such as a continuous culture without dilution). In some embodiments of any of the aspects of the invention, the nucleic acid comprising the isoprene synthase, IDI, or DXS nucleic acid also comprises a selective marker, such as an antibiotic resistance nucleic acid.

In some embodiments of any of the aspects of the invention, the cells further comprise a heterologous nucleic acid encoding an MVA pathway polypeptide (such as an MVA pathway polypeptide from *Saccharomyces cerevisia* or *Enterococcus faecalis*). In some embodiments of any of the aspects of the invention, the cells further comprise an insertion of a copy of an endogenous nucleic acid encoding an MVA pathway polypeptide (such as an MVA pathway polypeptide from *Saccharomyces cerevisia* or *Enterococcus faecalis*). In some embodiments of any of the aspects of the invention, the cells comprise an isoprene synthase, DXS, and MVA pathway nucleic acid. In some embodiments of any of the aspects of the invention, the cells comprise an isoprene synthase nucleic acid, a DXS nucleic acid, an IDI nucleic acid, and a MVA pathway nucleic (in addition to the IDI nucleic acid).

In some embodiments of any of the aspects of the invention, the isoprene synthase polypeptide is a polypeptide from a plant such as *Pueraria* (e.g., *Pueraria montana* or *Pueraria lobata*) or *Populus* (e.g., *Populus tremuloides, Populus alba, Populus nigra, Populus trichocarpa*, or the hybrid, *Populus alba* x *Populus tremula*).

In some embodiments of any of the aspects of the invention, the cells are bacterial cells, such as gram-positive bacterial cells (e.g., *Bacillus* cells such as *Bacillus subtilis* cells or *Streptomyces* cells such as *Streptomyces lividans, Streptomyces coelicolor*, or *Streptomyces griseus* cells). In some embodiments of any of the aspects of the invention, the cells are gram-negative bacterial cells (e.g., *Escherichia* cells such as *Escherichia coli* cells or *Pantoea* cells such as *Pantoea citrea* cells). In some embodiments of any of the aspects of the invention, the cells are fungal, cells such as filamentous fungal cells (e.g., *Trichoderma* cells such as *Trichoderma reesei* cells or *Aspergillus* cells such as *Aspergillus oryzae* and *Aspergillus niger*) or yeast cells (e.g., *Yarrowia* cells such as *Yarrowia lipolytica* cells).

In some embodiments of any of the aspects of the invention, the microbial polypeptide carbon source includes one or more polypeptides from yeast or bacteria. In some embodiments of any of the aspects of the invention, the plant polypeptide carbon source includes one or more polypeptides from soy, corn, canola, jatropha, palm, peanut, sunflower, coconut, mustard, rapeseed, cottonseed, palm kernel, olive, safflower, sesame, or linseed.

In one aspect, the invention features a product produced by any of the compositions or methods of the invention.

BRIEF DESCRIPTION OF THE DRAWINGS

FIG. 1 is the nucleotide sequence of a kudzu isoprene synthase gene codon-optimized for expression in *E. coli* (SEQ ID NO:1). The atg start codon is in italics, the stop codon is in bold and the added PstI site is underlined.

FIG. 3 is the nucleotide sequence of pTrcKudzu (SEQ ID NO:2). The RBS is underlined, the kudzu isoprene synthase start codon is in bold capitol letters and the stop codon is in bold, capitol, italics letters. The vector backbone is pTrcHis2B.

FIG. 5 is the nucleotide sequence of pETNHisKudzu (SEQ ID NO:5).

FIG. 7 is the nucleotide sequence of pCL-lac-Kudzu (SEQ ID NO:7).

FIG. 12 is the nucleotide sequence of pBS Kudzu #2 (SEQ ID NO:57).

FIG. 13 is the nucleotide sequence of kudzu isoprene synthase codon-optimized for expression in *Yarrowia* (SEQ ID NO:8).

FIG. 15 is the nucleotide sequence of vector pSPZ1 (MAP29Spb) (SEQ ID NO:11).

FIG. 16 is the nucleotide sequence of the synthetic kudzu (*Pueraria montana*) isoprene gene codon-optimized for expression in *Yarrowia* (SEQ ID NO:12).

FIG. 17 is the nucleotide sequence of the synthetic hybrid poplar (*Populus alba* x *Populus tremula*) isoprene synthase gene (SEQ ID NO:13). The ATG start codon is in bold and the stop codon is underlined.

FIGS. 18A1 and 18A2 show a schematic outlining construction of vectors pYLA 1, pYL1 and pYL2 (SEQ ID NO: 79; SEQ ID NO: 77; SEQ ID NO: 76; SEQ ID NO: 75; SEQ ID NO: 74; and SEQ ID NO: 73).

FIG. 22 is the nucleotide sequence of pTrcKudzu yIDI DXS Kan (SEQ ID NO:20).

FIG. 25 is a nucleotide sequence of pTrcKKDyIkIS kan (SEQ ID NO:33).

FIGS. 27A-27D is a nucleotide sequence of pCL PtrcUpperPathway (SEQ ID NO:46).

FIG. 29 is a nucleotide sequence of cassette containing the lower MVA pathway and yeast idi for integration into the B. subtilis chromosome at the nprE locus (SEQ ID NO:47).

FIG. 31 is a nucleotide sequence of p9796-poplar (SEQ ID NO:48).

FIG. 33 is a nucleotide sequence of pTrcPoplar (SEQ ID NO:49).

FIG. 35 is a nucleotide sequence of pTrcKudzu yIDI Kan (SEQ ID NO:50).

FIG. 37 is a nucleotide sequence of pTrcKudzuDXS Kan (SEQ ID NO:51).

FIG. 39 is a nucleotide sequence of pCL PtrcKudzu (SEQ ID NO:52).

FIG. 41 is a nucleotide sequence of pCL PtrcKudzu A3 (SEQ ID NO:53).

FIG. 43 is a nucleotide sequence of pCL PtrcKudzu yIDI (SEQ ID NO:54).

FIG. 45 is a nucleotide sequence of pCL PtrcKudzu DXS (SEQ ID NO:55).

FIG. 51 is the nucleotide sequence of pJMupperpathway2 (SEQ ID NO:56).

FIG. 75A is a table of the conversion of the CAFT Model results from weight percent to volume percent for series A.

FIG. 76A is a table of the conversion of the CAFT Model results from weight percent to volume percent for series B.

FIG. 78A is a graph of the flammability Curve for Test Series 1: 0% Steam, 0 psig, and 40° C.

FIG. 78B is a table summarizing the explosion and non-explosion data points for Test Series 1.

FIG. 78C is a graph of the flammability curve for Test Series 1 compared with the CAFT Model.

FIG. 79A is a graph of the flammability curve for Test Series 2: 4% Steam, 0 psig, and 40° C.

FIG. 79B is a table summarizing the explosion and non-explosion data points for Test Series 2.

FIGS. 80A and 80B are a table of the detailed experimental conditions and results for Test Series 1.

FIG. 81 is a table of the detailed experimental conditions and results for Test Series 2.

FIG. 87D is an expansion of FIG. 87C.

Figure 88A:
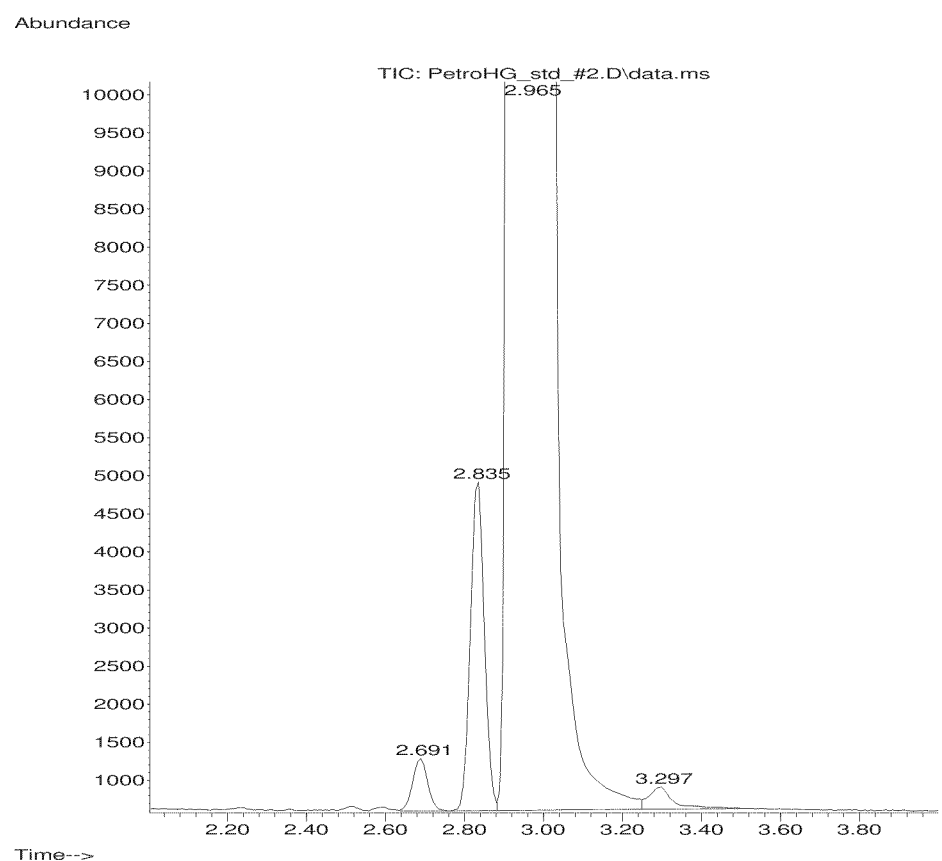
Figure 88B:
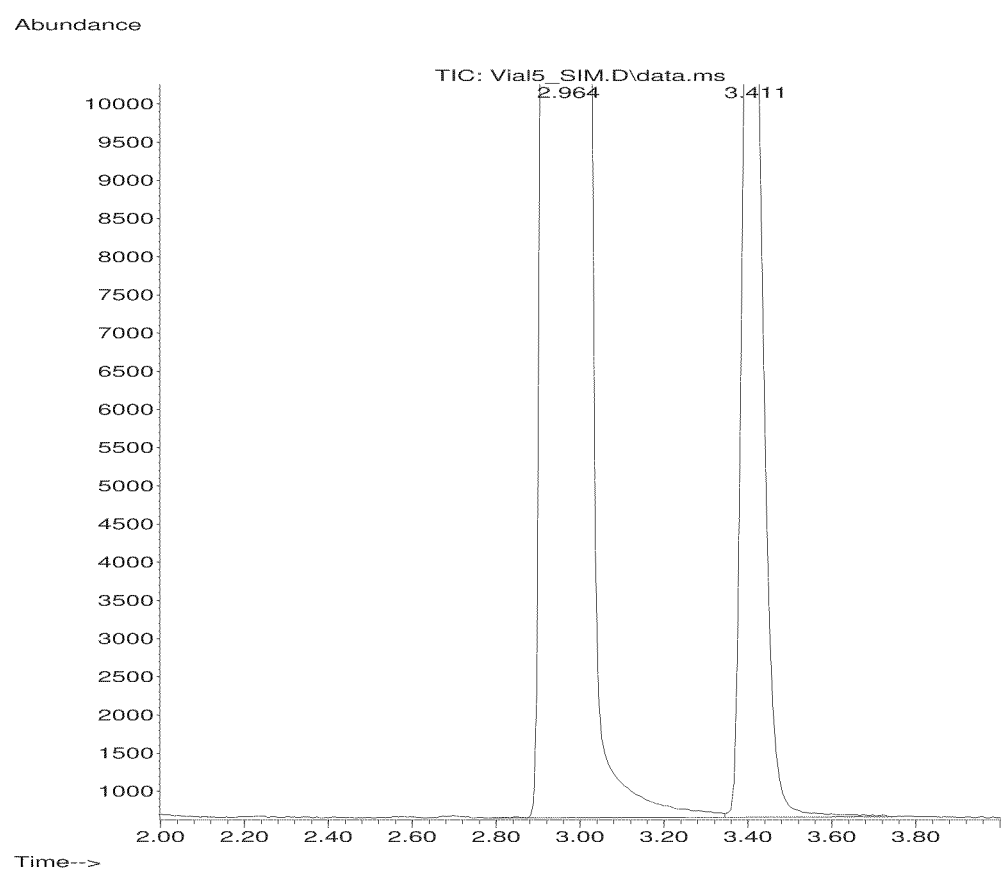

FIGS. 88A and 88B are GC/MS chromatogram comparing C5 hydrocarbons from petroleum-derived isoprene (FIG. 88A) and biologically produced isoprene (FIG. 88B). The standard contains three C5 hydrocarbon impurities eluting around the main isoprene peak (FIG. 88A). In contrast, biologically produced isoprene contains amounts of ethanol and acetone (run time of 3.41 minutes) (FIG. 88A).

Figure 89:
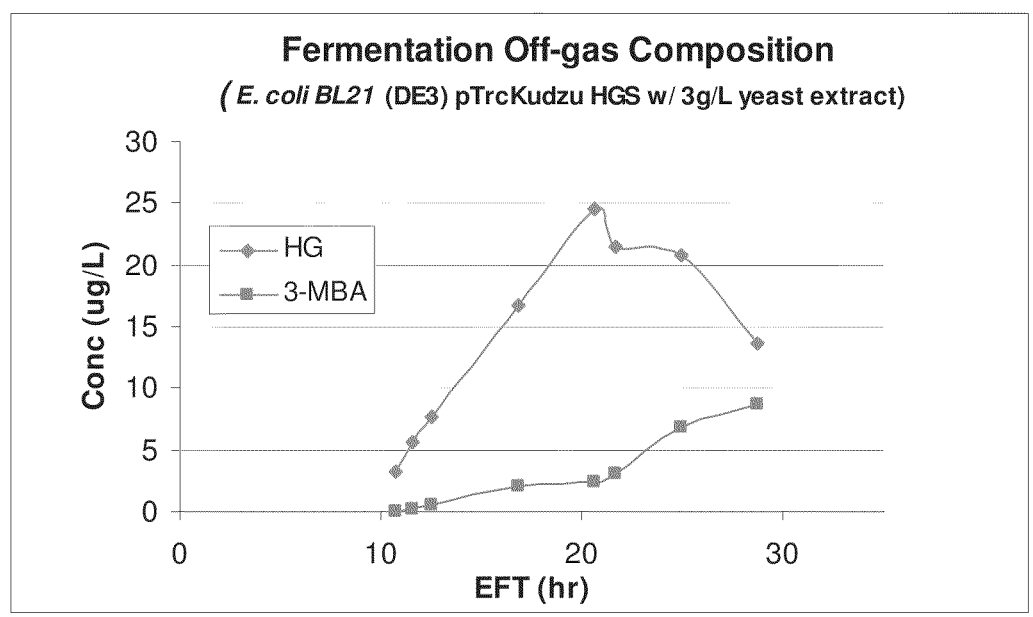

FIG. 89 is a graph of the analysis of fermentation off-gas of an *E. coli* BL21(DE3) pTrcIS strain expressing a Kudzu isoprene synthase and fed glucose with 3 g/L yeast extract.

FIG. 90 shows the structures of several impurities that are structurally similar to isoprene and may also act as polymerization catalyst poisons.

Figure 91:
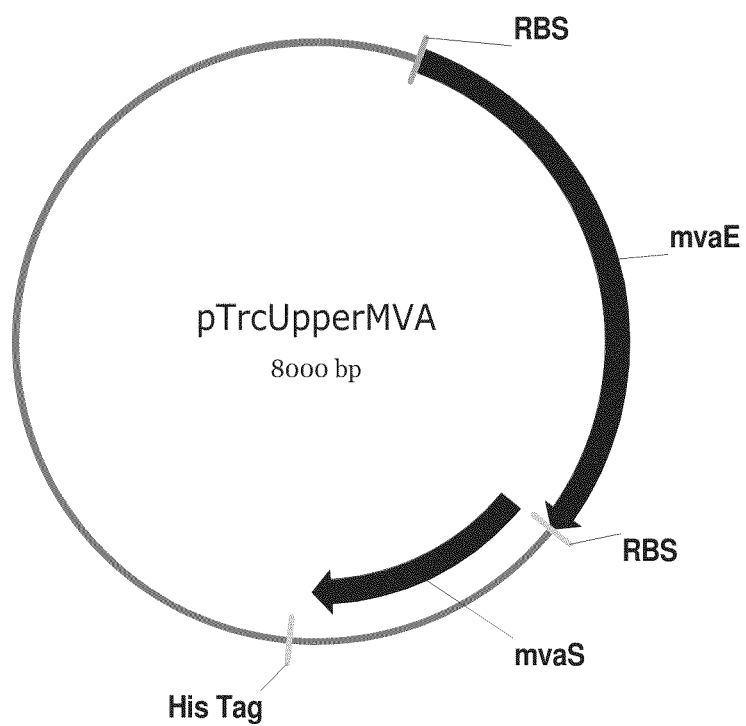

FIG. 91 is a map of pTrcHis2AUpperPathway (also called pTrcUpperMVA).

FIGS. 92A-92C are the nucleotide sequence of pTrcHis2AUpperPathway (also called pTrcUpperMVA) (SEQ ID NO:86).

Figure 93:
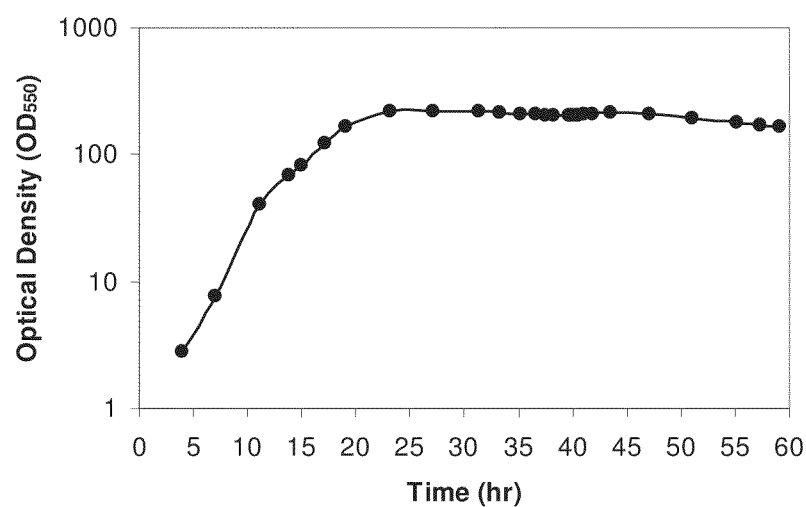

FIG. 93 is a time course of optical density within the 15-L bioreactor fed with glucose.

Figure 94:
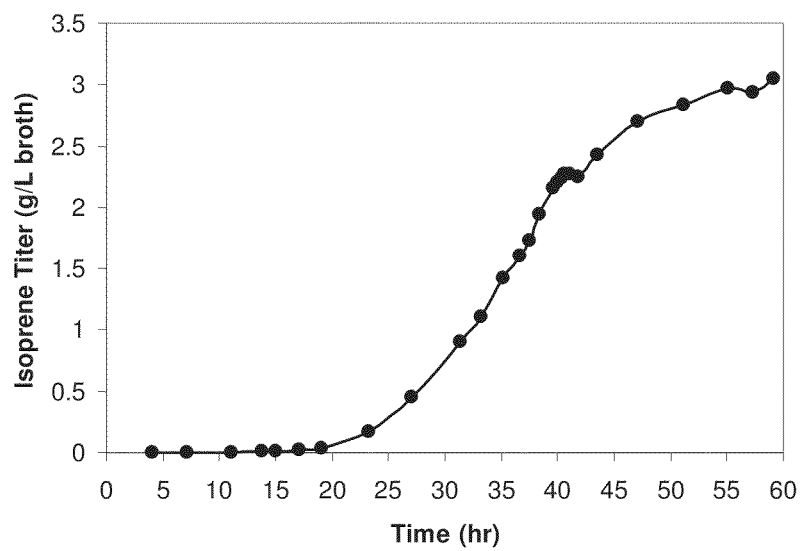

FIG. 94 is a time course of isoprene titer within the 15-L bioreactor fed with glucose. The titer is defined as the amount of isoprene produced per liter of fermentation broth.

Figure 95:
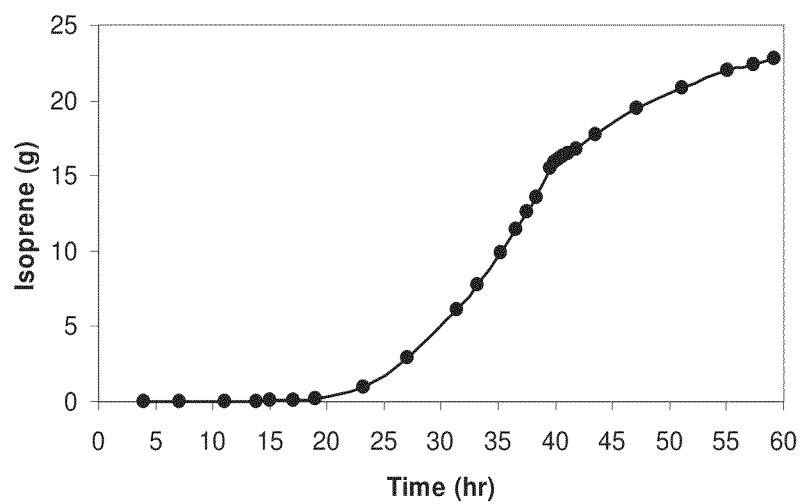

FIG. 95 is a time course of total isoprene produced from the 15-L bioreactor fed with glucose.

Figure 96:
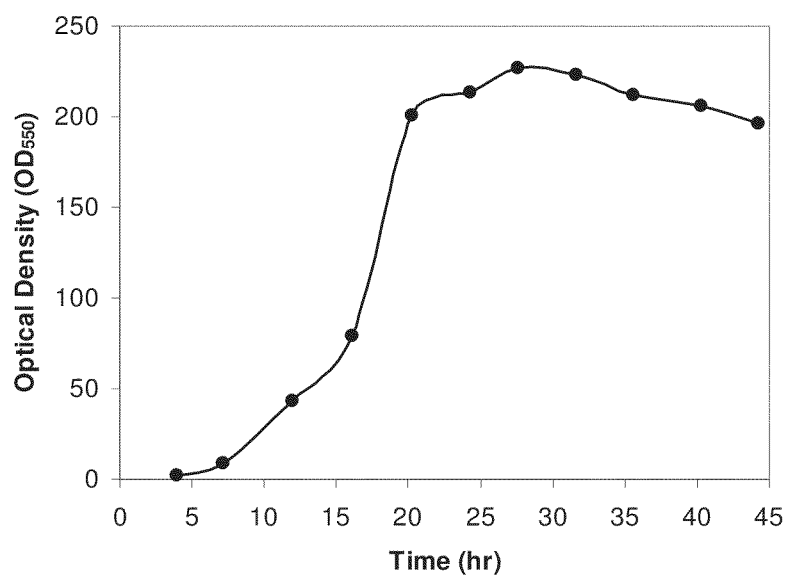

FIG. 96 is a time course of optical density within the 15-L bioreactor fed with invert sugar.

Figure 97:
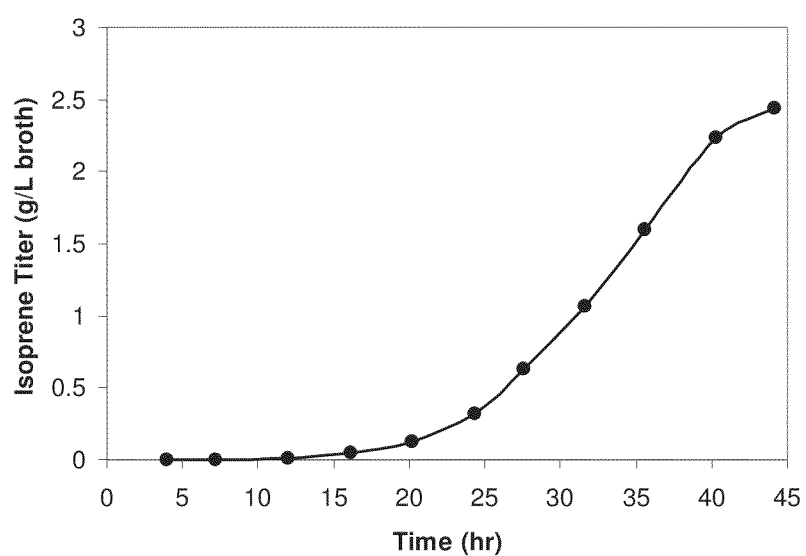

FIG. 97 is a time course of isoprene titer within the 15-L bioreactor fed with invert sugar. The titer is defined as the amount of isoprene produced per liter of fermentation broth.

Figure 98:
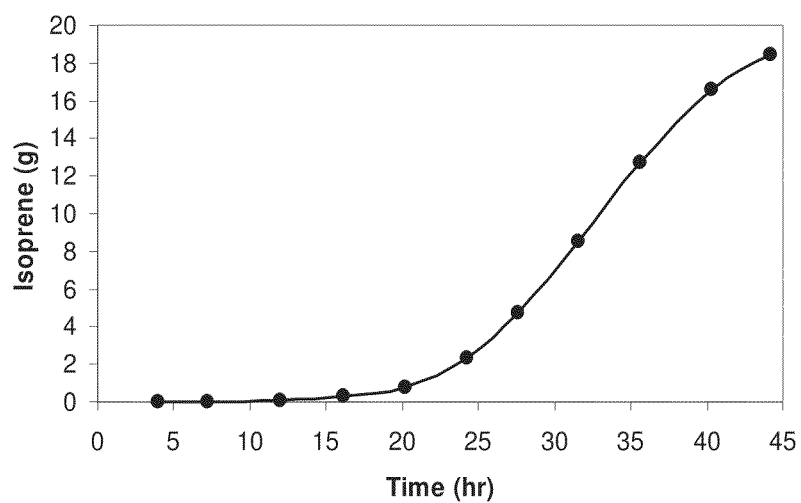

FIG. 98 is a time course of total isoprene produced from the 15-L bioreactor fed with invert sugar.

Figure 99:
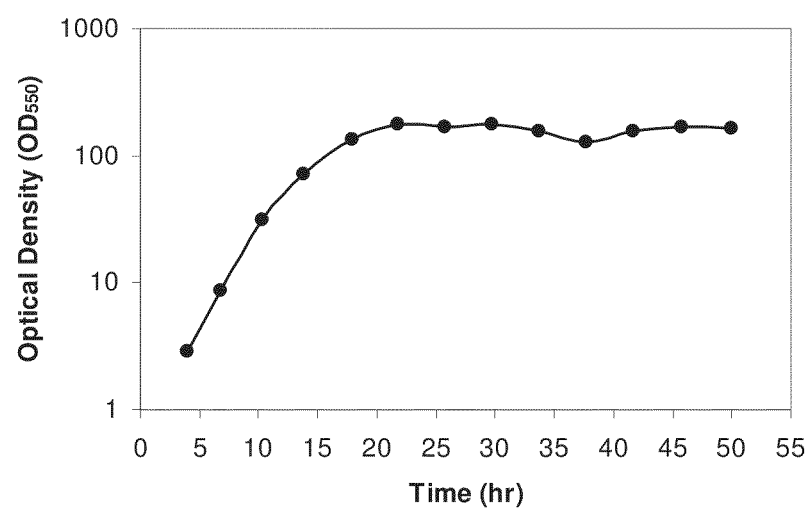

FIG. 99 is a time course of optical density within the 15-L bioreactor fed with glucose.

Figure 100:
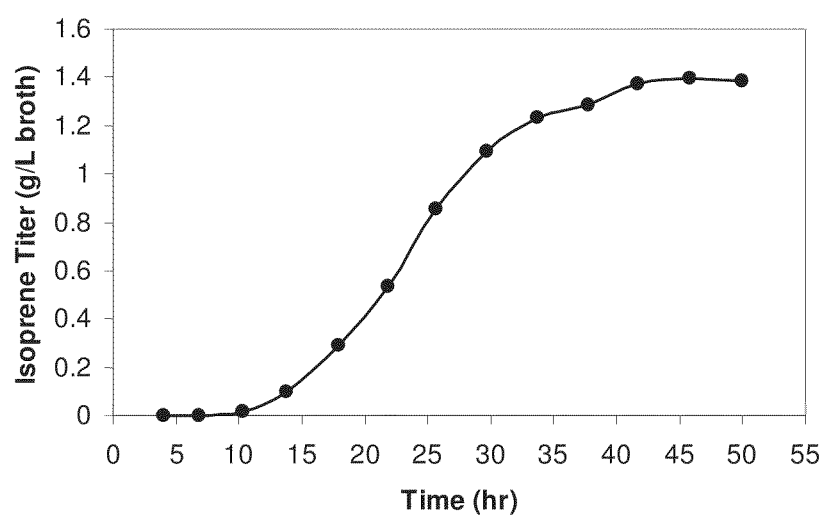

FIG. 100 is a time course of isoprene titer within the 15-L bioreactor fed with glucose. The titer is defined as the amount of isoprene produced per liter of fermentation broth.

Figure 101:
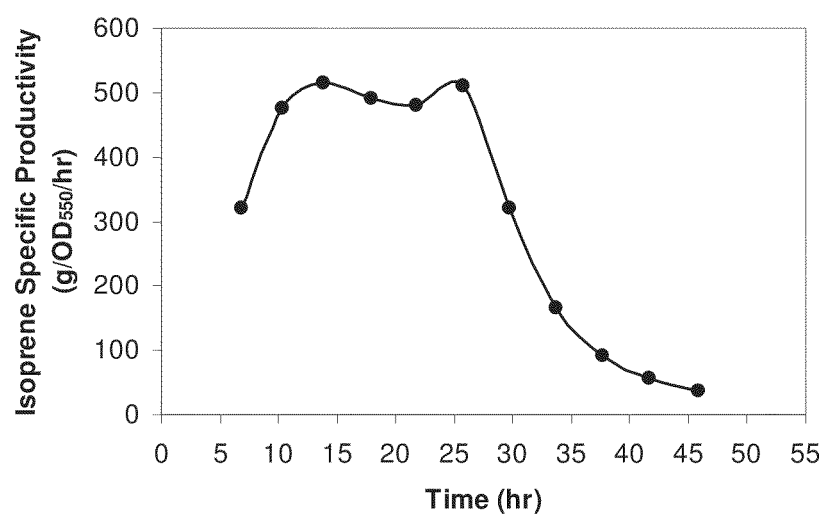

FIG. 101 is a time course of isoprene specific activity from the 15-L bioreactor fed with glucose.

Figure 102:
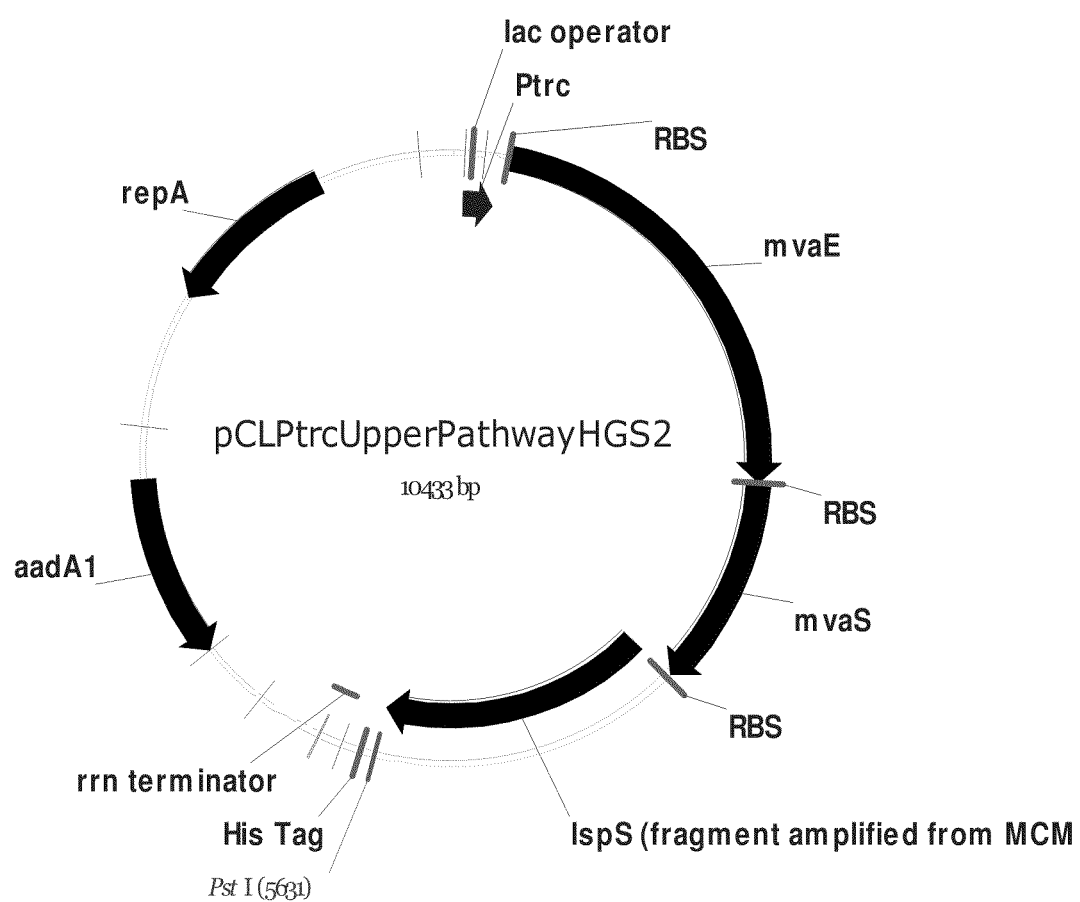

FIG. 102 is a map of pCLPtrcUpperPathwayHGS2 (also referred to as pCL UpperHGS2).

FIGS. 103A-103C are the nucleotide sequence of pCLPtrcUpperPathwayHGS2 (SEQ ID NO:87).

Figure 104:
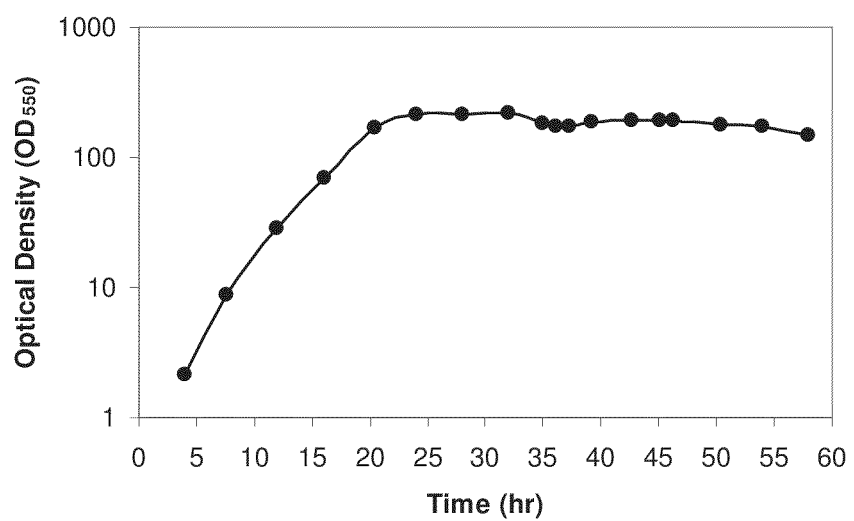

FIG. 104 is a time course of optical density within the 15-L bioreactor fed with glucose.

Figure 105:
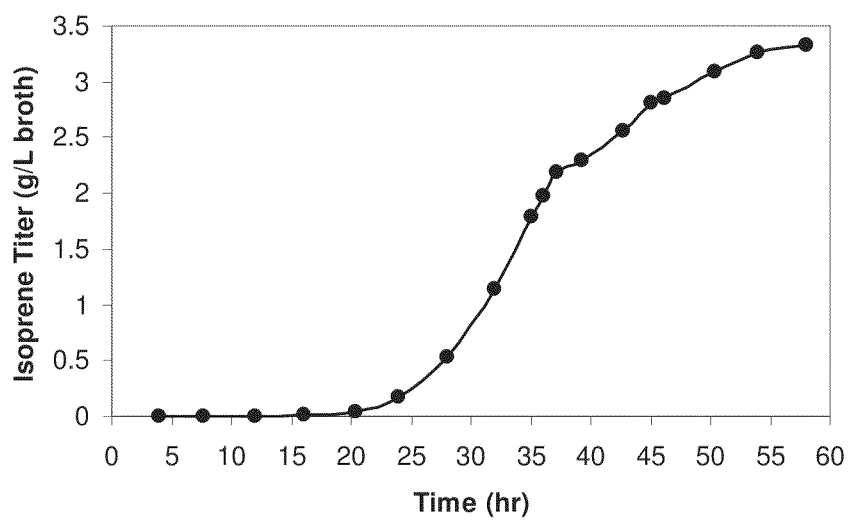

FIG. 105 is a time course of isoprene titer within the 15-L bioreactor fed with glucose. The titer is defined as the amount of isoprene produced per liter of fermentation broth.

Figure 106:
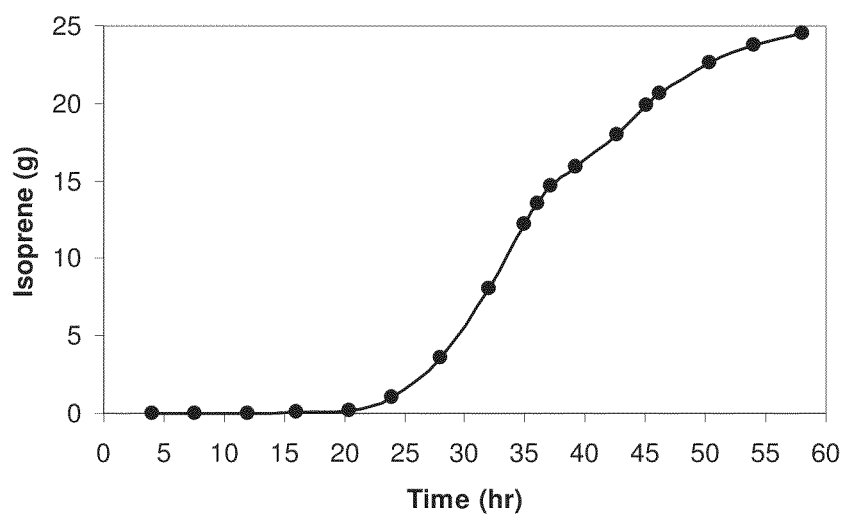

FIG. 106 is a time course of total isoprene produced from the 15-L bioreactor fed with glucose.

Figure 107:
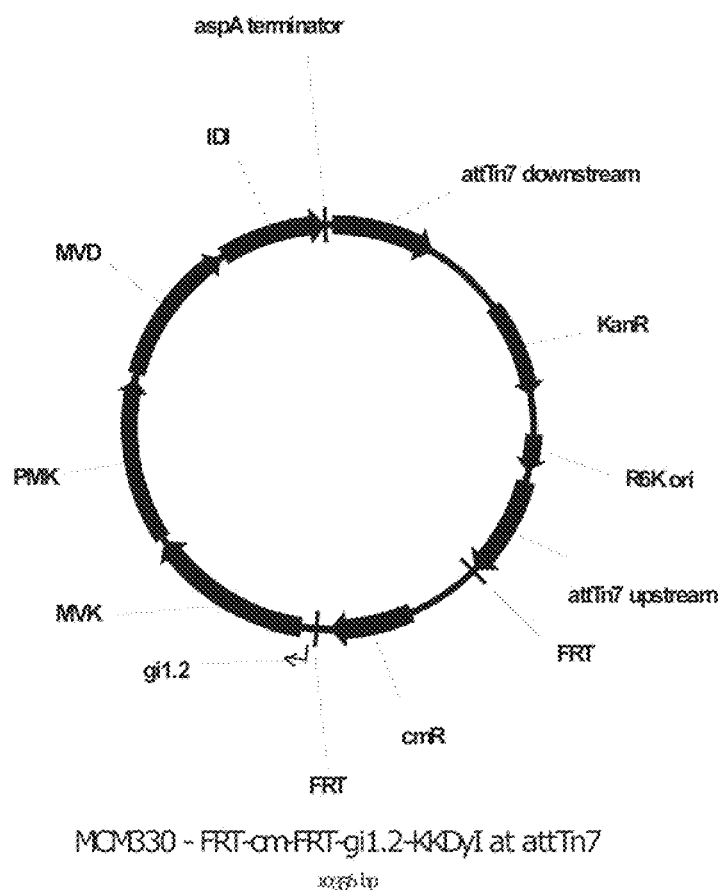

FIG. 107 is a map of plasmid MCM330.

FIGS. 108A-108C are the nucleotide sequence of plasmid MCM330 (SEQ ID NO:90).

Figure 109:
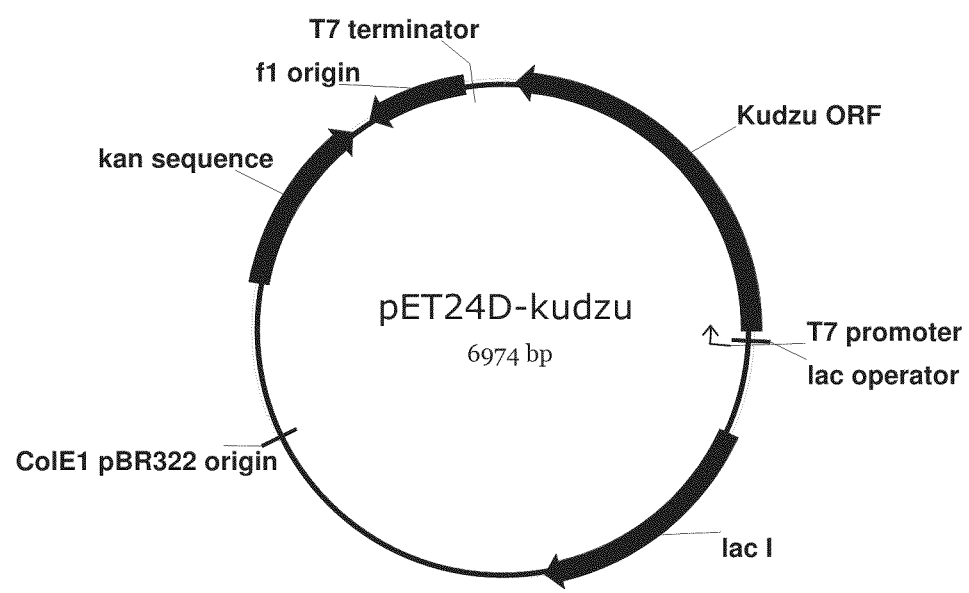

FIG. 109 is a map of pET24D-Kudzu.

FIGS. 110A and 110B are the nucleotide sequence of pET24D-Kudzu (SEQ ID NO:101).

Figure 111A:
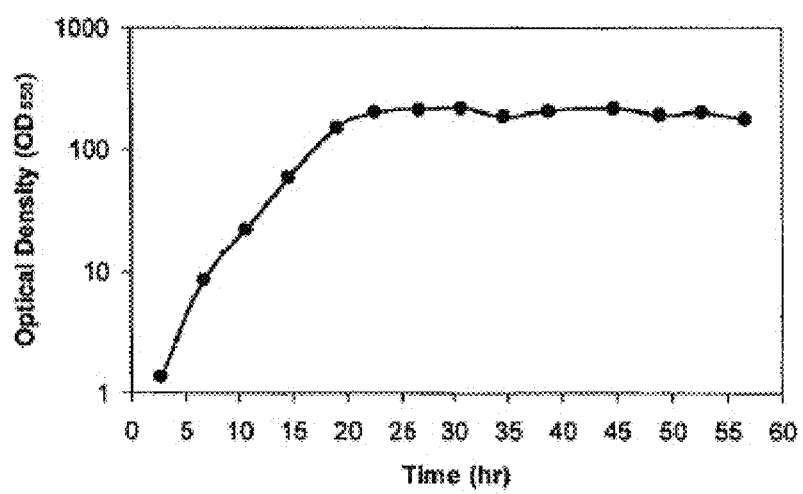
Figure 111B:
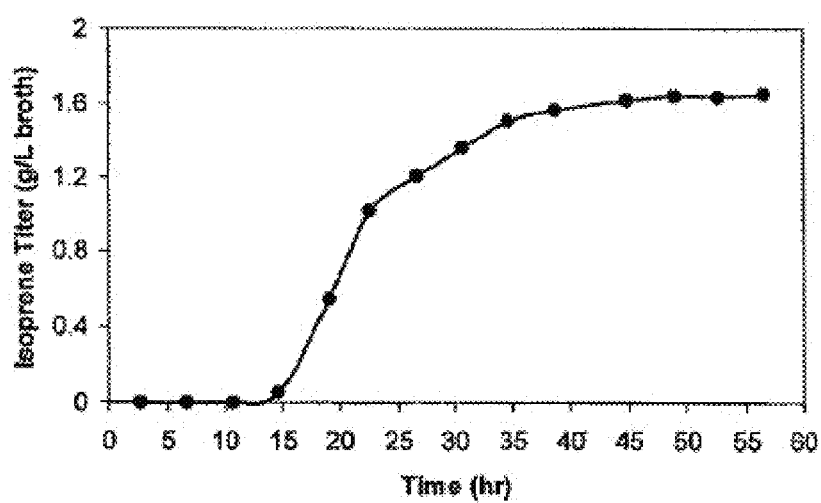
Figure 111C:
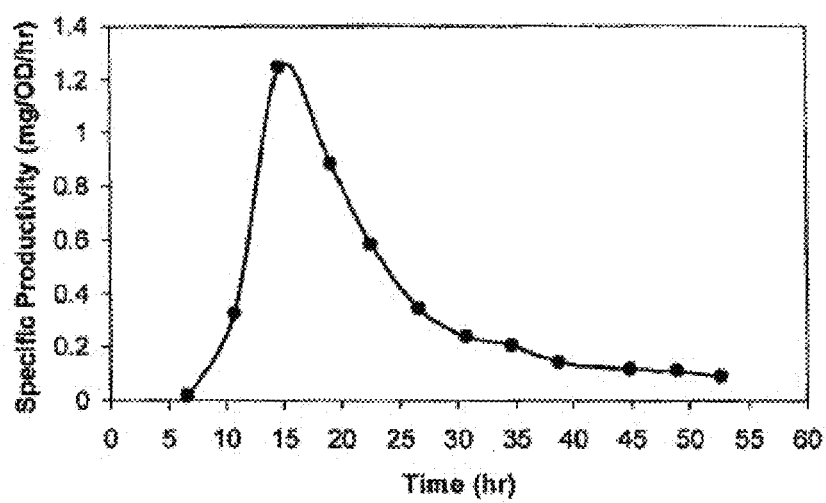

FIG. 111A is a time course of optical density within the 15-L bioreactor fed with glucose. FIG. 111B is a time course of isoprene titer within the 15-L bioreactor fed with glucose. The titer is defined as the amount of isoprene produced per liter of fermentation broth. FIG. 111C is a time course of specific productivity of isoprene in the 15-L bioreactor fed with glucose.

Figure 112A:
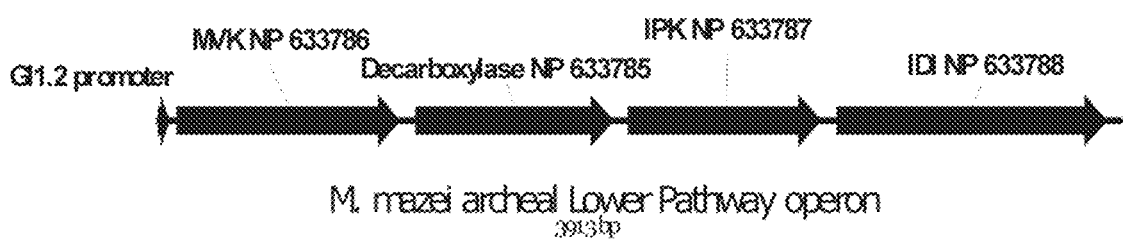

FIG. 112A provides a map of the *M. mazei* archeal lower pathway operon. FIGS. 112B and 112C provide the nucleotide sequence of the *M. mazei* archeal lower pathway operon (SEQ ID NO:102).

Figure 113A:
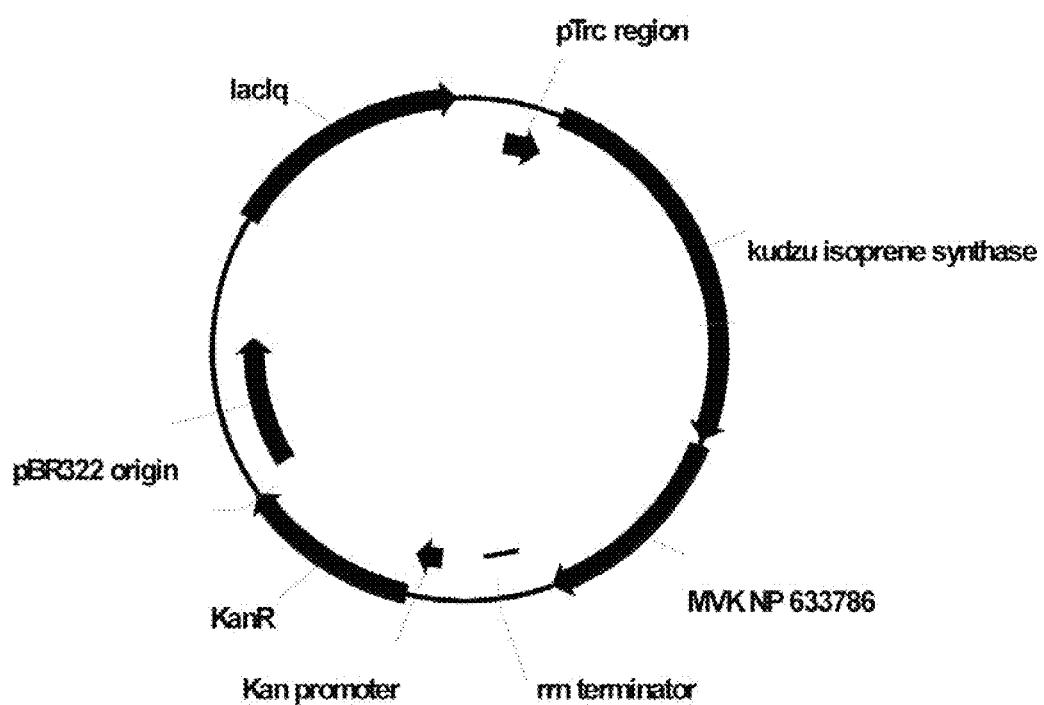

FIG. 113A provides a map of MCM382—pTrcKudzuMVK(mazei). FIGS. 113B and 113C provide the nucleotide sequence of MCM382—pTrcKudzuMVK(mazei) (SEQ ID NO:103).

Figure 114A:
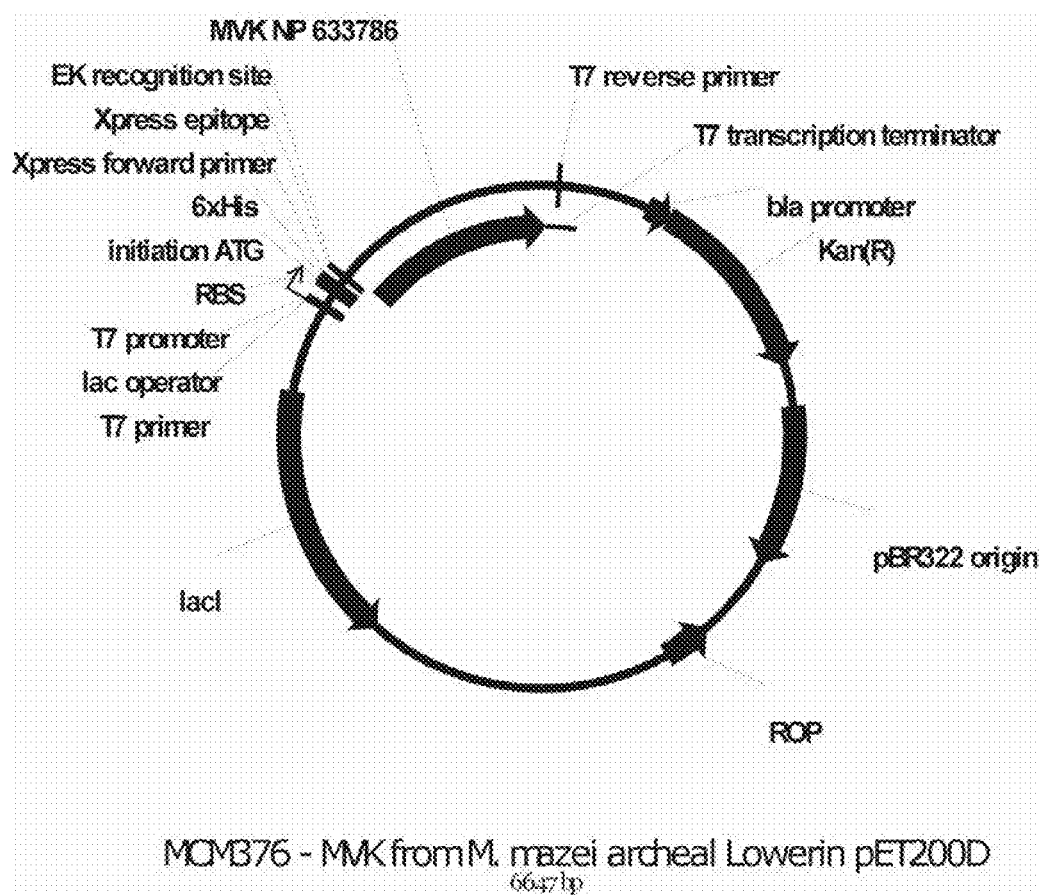

FIG. 114A provides a map of MCM376—MVK from *M. mazei* archeal Lowerin pET200D. FIGS. 114B and 114C provide the nucleotide sequence of MCM376—MVK from *M. mazei* archeal Lowerin pET200D (SEQ ID NO:104).

Figure 115A:
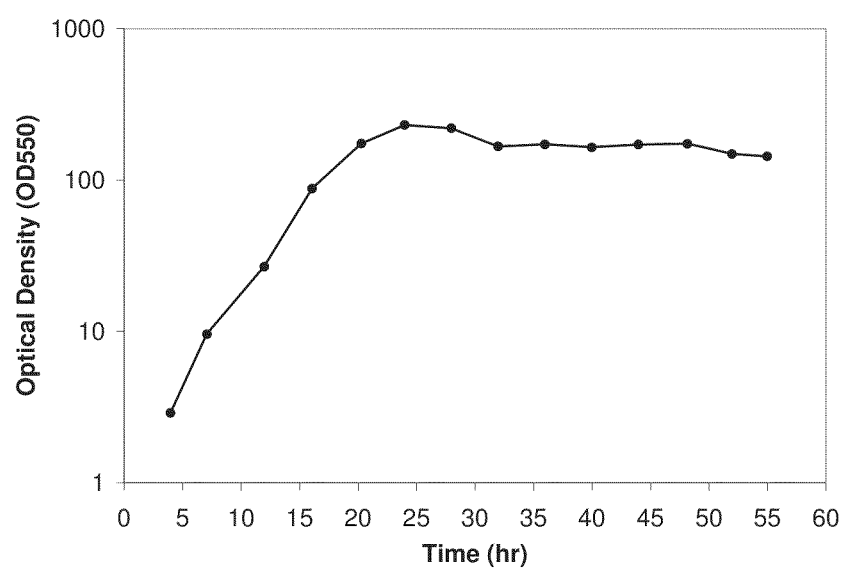
Figure 115B:
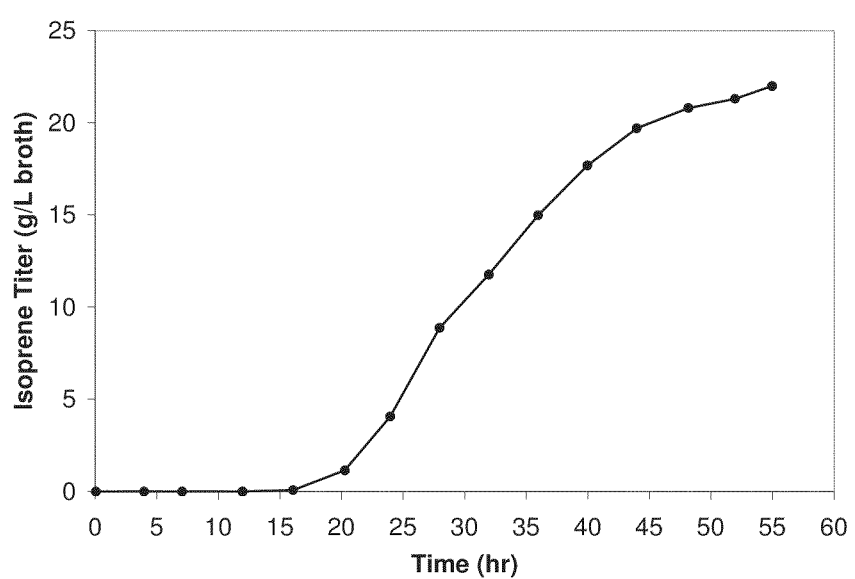
Figure 115C:
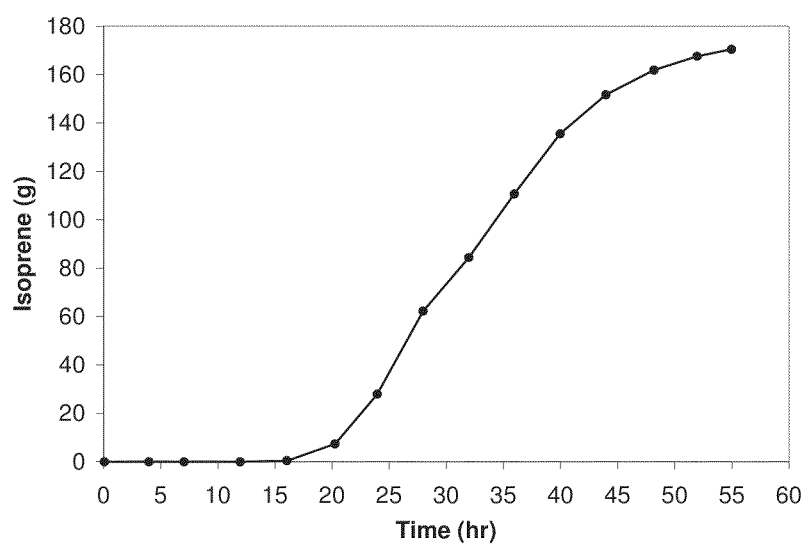

FIG. 115A provides a time course of optical density within the 15-L bioreactor fed with glucose. FIG. 115B provides a time course of isoprene titer within the 15-L bioreactor fed with glucose, in which titer is defined as the amount of isoprene produced per liter of fermentation broth. FIG. 115C provides a time course of total isoprene produced from the 15-L bioreactor fed with glucose.

Figure 116:
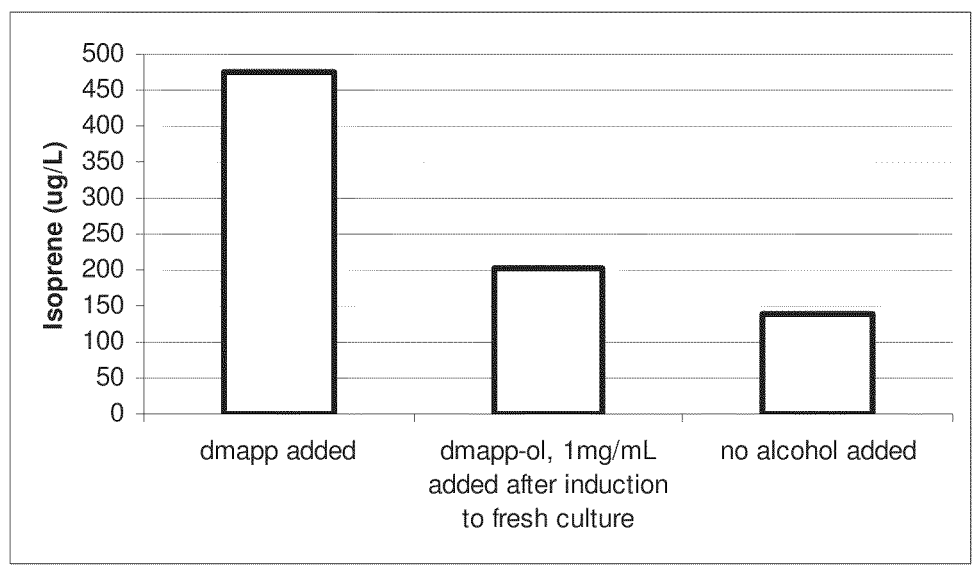

FIG. 116 provides a graph showing the production of isoprene from dimethyl allyl alcohol by recombinant *E. coli* engineered to express kudzu isoprene synthase.

Figure 117A:
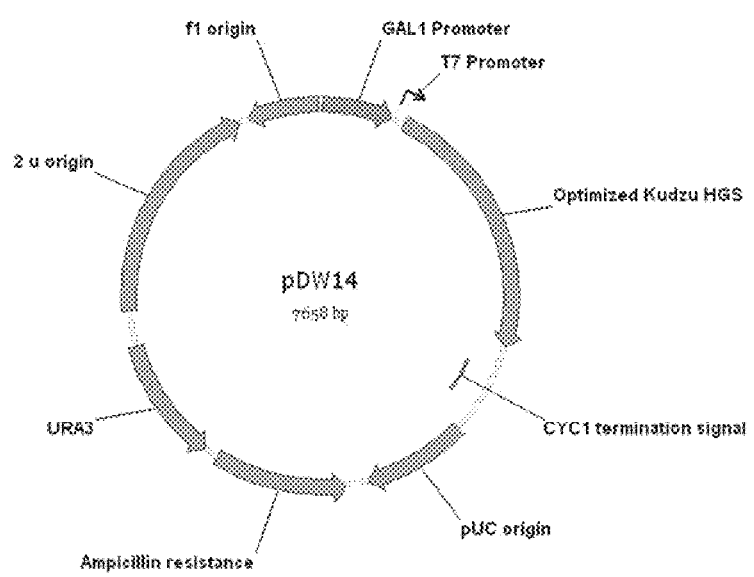

FIG. 117A provides a map of plasmid pDW14. FIG. 117B provides the nucleotide sequence of kudzu isoprene synthase that has been codon-optimized for expression in yeast (SEQ ID NO:112). FIGS. 117C and 117D provide the nucleotide sequence of plasmid pDW14 (SEQ ID NO:113).

Figure 118:
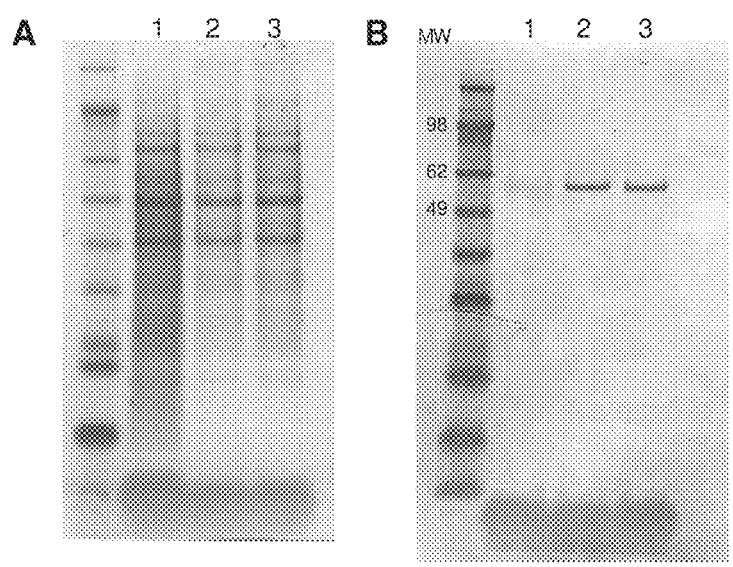

FIGS. 118A and 118B provide an SDS-PAGE gel and a western blot respectively, demonstrating production of isoprene synthase by recombinant yeast. A 4-12% bis tris gel (Novex, Invitrogen) of lysates obtained from yeast cell strains harboring pDW14 or pYES-DEST52 prepared after induction with galactose was stained with SimplyBlue SafeStain (Invitrogen). The western blot was prepared using the WesternBreeze kit (Invitrogen). Lanes are as follows: 1) INVSc-1+pYES-DEST52; 2) INVSc-1+pDW14 (isolate 1); and 3) INVSc-1+pDW14 (isolate 2). The MW (kDa) of the SeeBlue Plus 2 molecular weight standards is shown.

FIGS. 119A and 119B provide graphs showing the growth of galactose-induced INVSc-1 yeast cells harboring pDW14 or pYES-DEST52 and their production of isoprene in the headspace as determined by the DMAPP assay, respectively. Specific activity was calculated as ug isoprene/L/OD. Samples are as follows: Control, INVSc-1+pYES-DEST52; HGS-1, INVSc-1+pDW14 (isolate 1); and HGS-2, INVSc-1+pDW14 (isolate 2).

Figure 120:
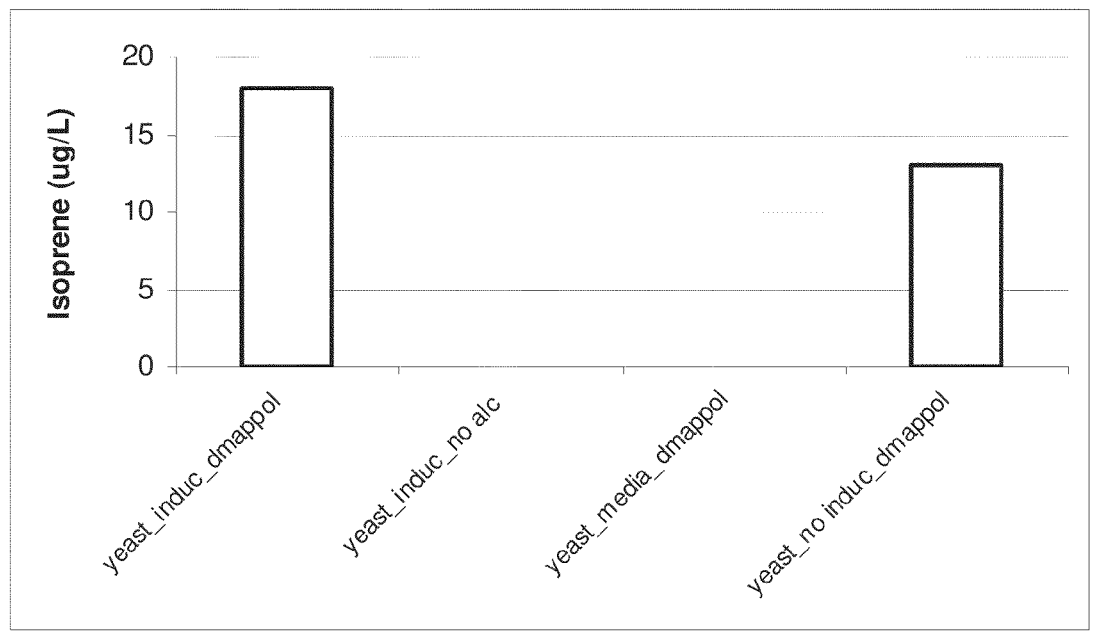

FIG. 120 provides a graph showing the production of isoprene from dimethyl allyl alcohol by recombinant *S. cerevisiae* engineered to express kudzu isoprene synthase.

DETAILED DESCRIPTION OF THE INVENTION

In one aspect, the invention features compositions and methods for the production of isoprene in increased amounts and/or purity. As used herein, the term "isoprene" or "2-methyl-1,3-butadiene" (CAS#78-79-5) refers to the direct and final volatile C5 hydrocarbon product from the elimination of pyrophosphate from 3,3-dimethylallyl pyrophosphate (DMAPP), and does not involve the linking or polymerization of one or more isopentenyl diphosphate (IPP) molecules to one or more DMAPP molecules.

The vast majority of isoprene is derived from petrochemical sources as an impure C5 hydrocarbon fraction which requires extensive purification before the material is suitable for polymerization. Several impurities are particularly problematic given their structural similarity to isoprene and the fact that they can act as polymerization catalyst poisons. Such compounds include 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne (FIG. 90) and 3-hexen-1-ol, 3-hexen-1-yl acetate, limonene, geraniol (trans-3,7-dimethyl-2,6-octadien-1-ol) and citronellol (3,7-dimethyl-6-octen-1-ol). In some embodiments, the isoprene composition of the invention is substantially free of any contaminating unsaturated C5 hydrocarbons. As described further in Example 10, no detectable amount of unsaturated C5 hydrocarbons other than isoprene (such as 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne) was found in isoprene compositions produced using the methods described herein. Some isoprene compositions produced using the methods described herein contain ethanol, acetone, and C5 prenyl alcohols as determined by GC/MS analysis. All of these components are far more readily removed from the isoprene stream than the isomeric C5 hydrocarbon fractions that are present in isoprene compositions derived from petrochemical sources. Accordingly, in some embodiments, the isoprene compositions of the invention require minimal treatment in order to be of polymerization grade.

In one aspect, compositions and methods of the invention increase the rate of isoprene production and increase the total amount of isoprene that is produced. For example, cell culture systems that generate $4.8 \times 10^4$ nmole/$g_{wcm}$/hr of isoprene have been produced (Table 1). The efficiency of these systems is demonstrated by the conversion of about 2.2% of the carbon that the cells consume from a cell culture medium into isoprene. As shown in the Examples and Table 2, approximately 3 g of isoprene per liter of broth was generated. If desired, even greater amounts of isoprene can be obtained using other conditions, such as those described herein. In some embodiments, a renewable carbon source is used for the production of isoprene. In some embodiments, the production of isoprene is decoupled from the growth of the cells. In some embodiments, the concentrations of isoprene and any oxidants are within the nonflammable ranges to reduce or eliminate the risk that a fire may occur during production or recovery of isoprene. The compositions and methods of the present invention are desirable because they allow high isoprene yield per cell, high carbon yield, high isoprene purity, high productivity, low energy usage, low production cost and investment, and minimal side reactions. This efficient, large scale, biosynthetic process for isoprene production provides an isoprene source for synthetic isoprene-based rubber and provides a desirable, low-cost alternative to using natural rubber.

As discussed further below, the amount of isoprene produced by cells can be greatly increased by introducing a heterologous nucleic acid encoding an isoprene synthase polypeptide (e.g., a plant isoprene synthase polypeptide) into the cells. Isoprene synthase polypeptides convert dimethylallyl diphosphate (DMAPP) into isoprene. As shown in the Examples, a heterologous *Pueraria Montana* (kudzu) isoprene synthase polypeptide was expressed in a variety of host cells, such as *Escherichia coli, Panteoa citrea, Bacillus subtilis, Yarrowia lipolytica*, and *Trichoderma reesei*. All of these cells produced more isoprene than the corresponding cells without the heterologous isoprene synthase polypeptide. As illustrated in Tables 1 and 2, large amounts of isoprene are produced using the methods described herein. For example, *B. subtilis* cells with a heterologous isoprene synthase nucleic acid produced approximately 10-fold more isoprene in a 14 liter fermentor than the corresponding control *B. subtilis* cells without the heterologous nucleic acid (Table 2). The production of 300 mg of isoprene per liter of broth (mg/L, wherein the volume of broth includes both the volume of the cell medium and the volume of the cells) by *E. coli* and 30 mg/L by *B. subtilis* in fermentors indicates that significant amounts of isoprene can be generated (Table 2). If desired, isoprene can be produced on an even larger scale or other conditions described herein can be used to further increase the amount of isoprene. The vectors listed in Tables 1 and 2 and the experimental conditions are described in further detail below and in the Examples section.

TABLE 1

Exemplary yields of isoprene from a shake flask using the cell cultures and methods of the invention. The assay for measuring isoprene production is described in Example I, part II. For this assay, a sample was removed at one or more time points from the shake flask and cultured for 30 minutes. The amount of isoprene produced in this sample was then measured. The headspace concentration and specific rate of isoprene production are listed in Table 1 and described further herein.

| | Isoprene Production in a Headspace vial* | |
|---|---|---|
| Strain | Headspace concentration ($\mu g/L_{gas}$) | Specific Rate $\mu g/L_{broth}/hr/OD$ (nmol/$g_{wcm}$/hr) |
| *E. coli* BL21/pTrcKudzu IS | 1.40 | 53.2 (781.2) |
| *E. coli* BL21/pCL DXS yidi Kudzu IS | 7.61 | 289.1 (4.25 × 10³) |

TABLE 1-continued

Exemplary yields of isoprene from a shake flask using the cell cultures and methods of the invention. The assay for measuring isoprene production is described in Example I, part II. For this assay, a sample was removed at one or more time points from the shake flask and cultured for 30 minutes. The amount of isoprene produced in this sample was then measured. The headspace concentration and specific rate of isoprene production are listed in Table 1 and described further herein.

| | Isoprene Production in a Headspace vial* | |
|---|---|---|
| Strain | Headspace concentration ($\mu g/L_{gas}$) | Specific Rate $\mu g/L_{broth}/hr/OD$ (nmol/$g_{wcm}$/hr) |
| *E. coli* BL21/MCM127 with kudzu IS and entire MVA pathway | 23.0 | 874.1 (12.8 × 10³) |
| *E. coli* BL21/pET N-HisKudzu IS | 1.49 | 56.6 (831.1) |
| *Pantoea citrea*/pTrcKudzu IS | 0.66 | 25.1 (368.6) |
| *E. coli* w/ Poplar IS [Miller (2001)] | — | 5.6 (82.2) |
| *Bacillis licheniformis* Fall U.S. Pat. No. 5,849,970 | — | 4.2 (61.4) |
| *Yarrowia lipolytica* with kudzu isoprene synthase | ~0.05 µg/L | ~2 (~30) |
| *Trichoderma reesei* with kudzu isoprene synthase | ~0.05 µg/L | ~2 (~30) |
| *E. coli* BL21/pTrcKKD$_y$I$_k$IS with kudzu IS and lower MVA pathway | 85.9 | 3.2 × 10³ (4.8 × 10⁴) |

*Normalized to 1 mL of 1 $OD_{600}$, cultured for 1 hour in a sealed headspace vial with a liquid to headspace volume ratio of 1:19.

TABLE 2

Exemplary yields of isoprene in a fermentor using the cell cultures and methods of the invention. The assay for measuring isoprene production is described in Example I, part II. For this assay, a sample of the off-gas of the fermentor was taken and analyzed for the amount of isoprene. The peak headspace concentration (which is the highest headspace concentration during the fermentation), titer (which is the cumulative, total amount of isoprene produced per liter of broth), and peak specific rate of isoprene production (which is the highest specific rate during the fermentation) are listed in Table 2 and described further herein.

| | Isoprene Production in Fermentors | | |
|---|---|---|---|
| Strain | Peak Headspace concentration** (ug/$L_{gas}$) | Titer (mg/$L_{broth}$) | Peak Specific rate $\mu g/L_{broth}/$ hr/OD (nmol/$g_{wcm}$/hr) |
| *E. coli* BL21/pTrcKudzu with Kudzu IS | 52 | 41.2 | 37 (543.3) |
| *E. coli* FM5/pTrcKudzu IS | 3 | 3.5 | 21.4 (308.1) |
| *E. coli* BL21/triple strain (DXS, yidi, IS) | 285 | 300 | 240 (3.52 × 10³) |
| *E. coli* FM5/triple strain (DXS, yidi, IS) | 50.8 | 29 | 180.8 (2.65 × 10³) |
| *E. coli*/MCM127 with Kudzu IS and entire MVA pathway | 3815 | 3044 | 992.5 (1.46 × 10⁴) |
| *E. coli* BL21/pCLPtrc UpperPathway gi1.2 integrated lower pathway pTrcKudzu | 2418 | 1640 | 1248 (1.83 × 10⁴) |
| *E. coli* BL21/MCM401 with 4 × 50 µM IPTG | 13991 | 23805 | 3733 (5.49 × 10⁴) |
| *E. coli* BL21/MCM401 with 2 × 100 µM IPTG | 22375 | 19541 | 5839.5 (8.59 × 10⁴) |
| *E. coli* BL21/pCLPtrc UpperPathwayHGS2-pTrcKKDyIkIS | 3500 | 3300 | 1088 (1.60 × 10⁴) |

TABLE 2-continued

Exemplary yields of isoprene in a fermentor using the cell cultures and methods of the invention. The assay for measuring isoprene production is described in Example I, part II. For this assay, a sample of the off-gas of the fermentor was taken and analyzed for the amount of isoprene. The peak headspace concentration (which is the highest headspace concentration during the fermentation), titer (which is the cumulative, total amount of isoprene produced per liter of broth), and peak specific rate of isoprene production (which is the highest specific rate during the fermentation) are listed in Table 2 and described further herein.

| | Isoprene Production in Fermentors | | |
|---|---|---|---|
| Strain | Peak Headspace concentration** ($ug/L_{gas}$) | Titer ($mg/L_{broth}$) | Peak Specific rate $\mu g/L_{broth}/$ hr/OD (nmol/ $g_{wcm}$/hr) |
| *Bacillus subtilis* wild-type | 1.5 | 2.5 | 0.8 (11.7) |
| *Bacillus* pBS Kudzu IS | 16.6 | ~30 (over 100 hrs) | 5 (73.4) |
| *Bacillus Marburg* 6051 [Wagner and Fall (1999)] | 2.04 | 0.61 | 24.5 (359.8) |
| *Bacillus Marburg* 6051 Fall U.S. Pat. No. 5,849,970 | 0.7 | 0.15 | 6.8 (100) |

**Normalized to an off-gas flow rate of 1 vvm (1 volume off-gas per 1 $L_{broth}$ per minute).

Additionally, isoprene production by cells that contain a heterologous isoprene synthase nucleic acid can be enhanced by increasing the amount of a 1-deoxy-D-xylulose-5-phosphate synthase (DXS) polypeptide and/or an isopentenyl diphosphate isomerase (IDI) polypeptide expressed by the cells. For example, a DXS nucleic acid and/or an IDI nucleic acid can be introduced into the cells. The DXS nucleic acid may be a heterologous nucleic acid or a duplicate copy of an endogenous nucleic acid. Similarly, the IDI nucleic acid may be a heterologous nucleic acid or a duplicate copy of an endogenous nucleic acid. In some embodiments, the amount of DXS and/or IDI polypeptide is increased by replacing the endogenous DXS and/or IDI promoters or regulatory regions with other promoters and/or regulatory regions that result in greater transcription of the DXS and/or IDI nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

Figure 19A:
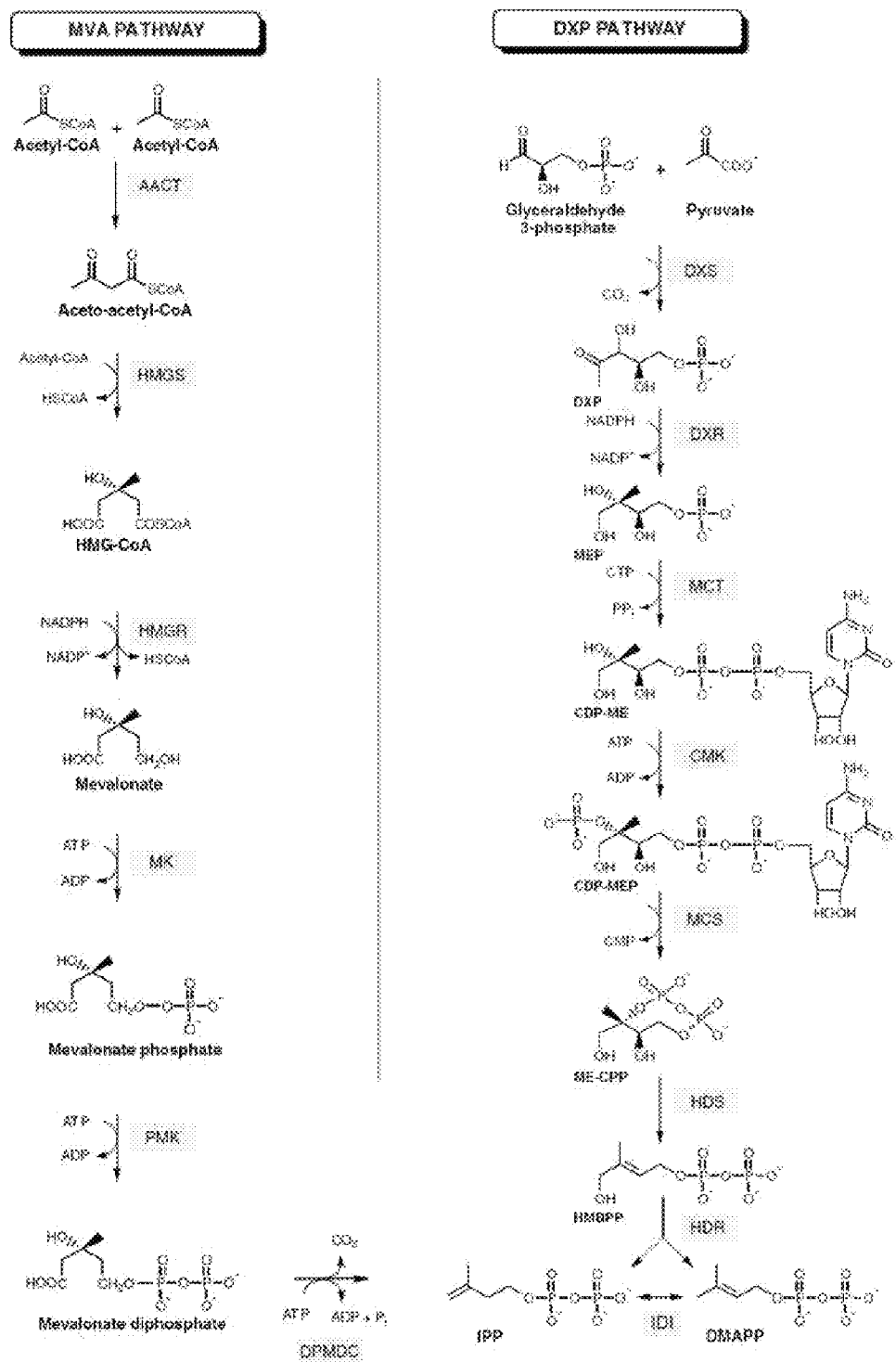
FIG. 19A shows the MVA and DXP metabolic pathways for isoprene (based on F. Bouvier et al., Progress in Lipid Res. 44: 357-429, 2005). The following description includes alternative names for each polypeptide in the pathways and a reference that discloses an assay for measuring the activity of the indicated polypeptide (each of these references are each hereby incorporated by reference in their entireties, particularly with respect to assays for polypeptide activity for polypeptides in the MVA and DXP pathways). Mevalonate Pathway: AACT; Acetyl-CoA acetyltransferase, MvaE, EC 2.3.1.9. Assay: J. Bacteriol., 184: 2116-2122, 2002; HMGS; Hydroxymethylglutaryl-CoA synthase, MvaS, EC 2.3.3.10. Assay: J. Bacteriol., 184: 4065-4070, 2002; HMGR; 3-Hydroxy-3-methylglutaryl-CoA reductase, MvaE, EC 1.1.1.34. Assay: J. Bacteriol., 184: 2116-2122, 2002; MVK; Mevalonate kinase, ERG12, EC 2.7.1.36. Assay: Curr Genet 19:9-14, 1991. PMK; Phosphomevalonate kinase, ERG8, EC 2.7.4.2, Assay: Mol Cell Biol., 11:620-631, 1991; DPMDC; Diphosphomevalonate decarboxylase, MVD1, EC 4.1.1.33. Assay: Biochemistry, 33:13355-13362, 1994; IDI; Isopentenyl-diphosphate delta-isomerase, IDI1, EC 5.3.3.2. Assay: J. Biol. Chem. 264:19169-19175, 1989. DXP Pathway: DXS; 1-Deoxyxylulose-5-phosphate synthase, dxs, EC 2.2.1.7. Assay: PNAS, 94:12857-62, 1997; DXR; 1-Deoxy-D-xylulose 5-phosphate reductoisomerase, dxr, EC 2.2.1.7. Assay: Eur. J. Biochem. 269:4446-4457, 2002; MCT; 4-Diphosphocytidyl-2C-methyl-D-erythritol synthase, IspD, EC 2.7.7.60. Assay: PNAS, 97: 6451-6456, 2000; CMK; 4-Diphosphocytidyl-2-C-methyl-D-erythritol kinase, IspE, EC 2.7.1.148. Assay: PNAS, 97:1062-1067, 2000; MCS; 2C-Methyl-D-erythritol 2,4-cyclodiphosphate synthase, IspF, EC 4.6.1.12. Assay: PNAS, 96:11758-11763, 1999; HDS; 1-Hydroxy-2-methyl-2-(E)-butenyl 4-diphosphate synthase, ispG, EC 1.17.4.3. Assay: J. Org. Chem., 70:9168-9174, 2005; HDR; 1-Hydroxy-2-methyl-2-(E)-butenyl 4-diphosphate reductase, IspH, EC 1.17.1.2. Assay: JACS, 126:12847-12855, 2004.

The encoded DXS and IDI polypeptides are part of the DXP pathway for the biosynthesis of isoprene (FIG. 19A). DXS polypeptides convert pyruvate and D-glyceraldehyde-3-phosphate into 1-deoxy-D-xylulose-5-phosphate. While not intending to be bound by any particular theory, it is believed that increasing the amount of DXS polypeptide increases the flow of carbon through the DXP pathway, leading to greater isoprene production. IDI polypeptides catalyze the interconversion of isopentenyl diphosphate (IPP) and dimethylallyl diphosphate (DMAPP). While not intending to be bound by any particular theory, it is believed that increasing the amount of IDI polypeptide in cells increases the amount (and conversion rate) of IPP that is converted into DMAPP, which in turn is converted into isoprene.

For example, fermentation of *E. coli* cells with a kudzu isoprene synthase, *S. cerevisia* IDI, and *E. coli* DXS nucleic acids was used to produce isoprene. The levels of isoprene varied from 50 to 300 μg/L over a time period of 15 hours (Example 7, part VII).

In some embodiments, the presence of heterologous or extra endogenous isoprene synthase, IDI, and DXS nucleic acids causes cells to grow more reproducibly or remain viable for longer compared to the corresponding cell with only one or two of these heterologous or extra endogenous nucleic acids. For example, cells containing heterologous isoprene synthase, IDI, and DXS nucleic acids grew better than cells with only heterologous isoprene synthase and DXS nucleic acids or with only a heterologous isoprene synthase nucleic acid. Also, heterologous isoprene synthase, IDI, and DXS nucleic acids were successfully operably linked to a strong promoter on a high copy plasmid that was maintained by *E. coli* cells, suggesting that large amounts of these polypeptides could be expressed in the cells without causing an excessive amount of toxicity to the cells. While not intending to be bound to a particular theory, it is believed that the presence of heterologous or extra endogenous isoprene synthase and IDI nucleic acids may reduce the amount of one or more potentially toxic intermediates that would otherwise accumulate if only a heterologous or extra endogenous DXS nucleic acid was present in the cells.

Figure 19B:
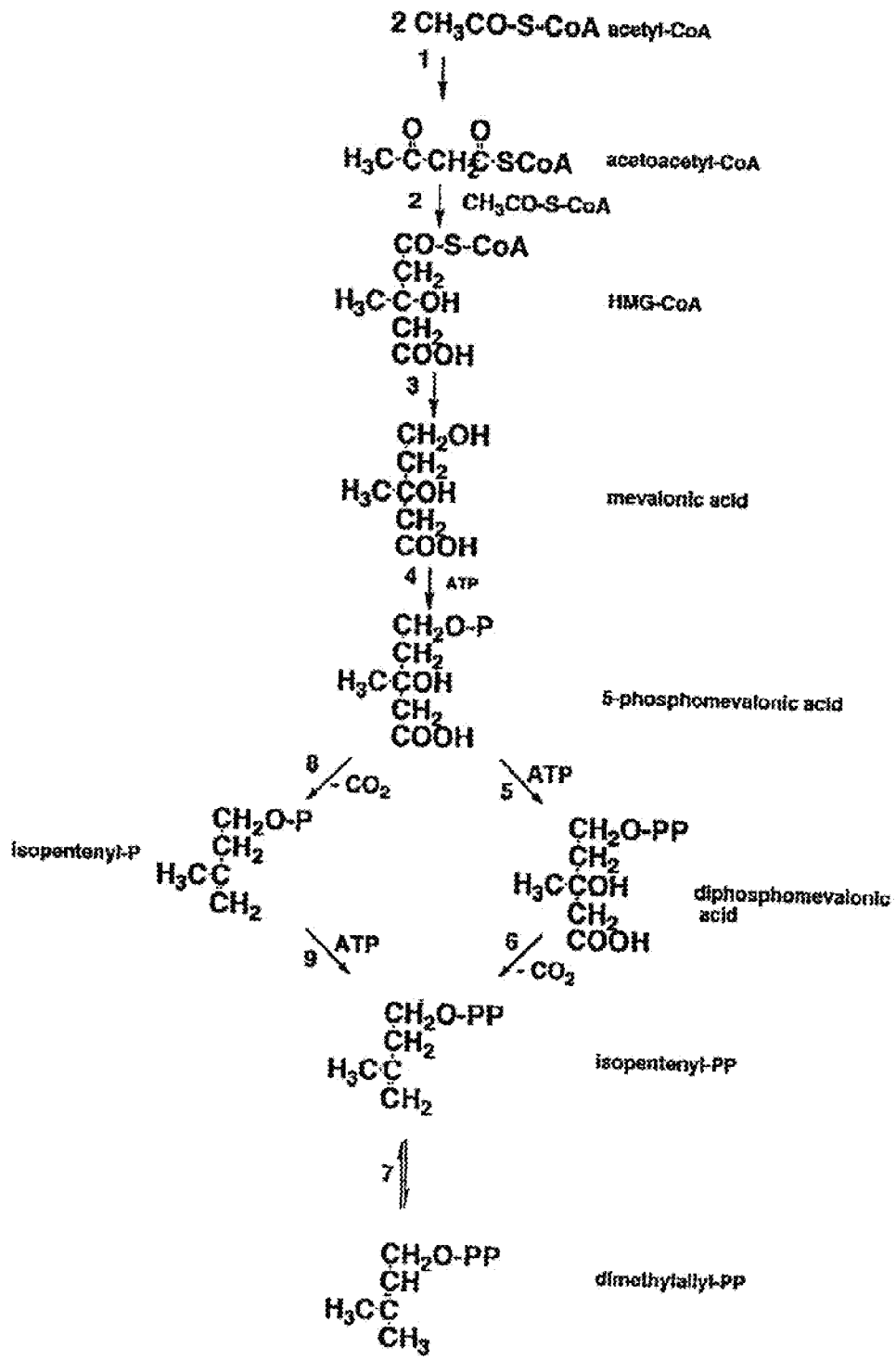
FIG. 19B illustrates the classical and modified MVA pathways. 1, acetyl-CoA acetyltransferase (AACT); 2, HMG-CoA synthase (HMGS); 3, HMG-CoA reductase (HMGR); 4, mevalonate kinase (MVK); 5, phosphomevalonate kinase (PMK); 6, diphosphomevalonate decarboxylase (MVD or DPMDC); 7, isopentenyl diphosphate isomerase (IDI); 8, phosphomevalonate decarboxylase (PMDC); 9, isopentenyl phosphate kinase (IPK). The classical MVA pathway proceeds from reaction 1 through reaction 7 via reactions 5 and 6, while a modified MVA pathway goes through reactions 8 and 9. P and PP in the structural formula are phosphate and pyrophosphate, respectively. This figure was taken from Koga and Morii, *Microbiology and Mol. Biology Reviews*, 71:97-120, 2007, which is incorporated by reference in its entirety, particular with respect to nucleic acids and polypetides of the modified MVA pathway. The modified MVA pathway is present, for example, in some archaeal organisms, such as *Methanosarcina mazei*.

In some embodiments, the production of isoprene by cells by cells that contain a heterologous isoprene synthase nucleic acid is augmented by increasing the amount of a MVA polypeptide expressed by the cells (FIGS. 19A and 19B). Exemplary MVA pathways polypeptides include any of the following polypeptides: acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. For example, one or more MVA pathway nucleic acids can be introduced into the cells. In some embodiments, the cells contain the upper MVA pathway, which includes AA-CoA thiolase, HMG-CoA synthase, and HMG-CoA reductase nucleic acids. In some embodiments, the cells contain the lower MVA pathway, which includes MVK, PMK, MVD, and IDI nucleic acids. In some embodiments, the cells contain an entire MVA pathway that includes AA-CoA thiolase, HMG-CoA synthase, HMG-CoA reductase, MVK, PMK, MVD, and IDI nucleic acids. In some embodiments, the cells contain an entire MVA pathway that includes AA-CoA thiolase, HMG-CoA synthase, HMG-CoA reductase, MVK, PMDC, IPK, and IDI nucleic acids. The MVA pathway nucleic acids may be heterologous nucleic acids or duplicate copies of endogenous nucleic acids. In some embodiments, the amount of one or more MVA pathway polypeptides is increased by replacing the endogenous promoters or regulatory regions for the MVA pathway nucleic acids with other promoters and/or regulatory regions that result in greater transcription of the MVA pathway nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

For example, *E. coli* cells containing a nucleic acid encoding a kudzu isoprene synthase polypeptide and nucleic acids encoding *Saccharomyces cerevisia* MVK, PMK, MVD, and IDI polypeptides generated isoprene at a rate of $6.67 \times 10^{-4}$ mol/$L_{broth}$/OD$_{600}$/hr (see Example 8). Additionally, a 14 liter fermentation of *E. coli* cells with nucleic acids encoding *Enterococcus faecalis* AA-CoA thiolase, HMG-CoA synthase, and HMG-CoA reductase polypeptides produced 22 grams of mevalonic acid (an intermediate of the MVA pathway). A shake flask of these cells produced 2-4 grams of mevalonic acid per liter. These results indicate that heterologous MVA pathways nucleic acids are active in *E. coli*. *E. coli* cells that contain nucleic acids for both the upper MVA pathway and the lower MVA pathway as well as a kudzu isoprene synthase (strain MCM 127) produced significantly more isoprene (874 ug/L) compared to *E. coli* cells with nucleic acids for only the lower MVA pathway and the kudzu isoprene synthase (strain MCM 131) (see Table 3 and Example 8, part VIII).

In some embodiments, at least a portion of the cells maintain the heterologous isoprene synthase, DXS, IDI, and/or MVA pathway nucleic acid for at least about 5, 10, 20, 50, 75, 100, 200, 300, or more cell divisions in a continuous culture (such as a continuous culture without dilution). In some embodiments of any of the aspects of the invention, the nucleic acid comprising the heterologous or duplicate copy of an endogenous isoprene synthase, DXS, IDI, and/or MVA pathway nucleic acid also comprises a selective marker, such as a kanamycin, ampicillin, carbenicillin, gentamicin, hygromycin, phleomycin, bleomycin, neomycin, or chloramphenicol antibiotic resistance nucleic acid.

Figure 48A:
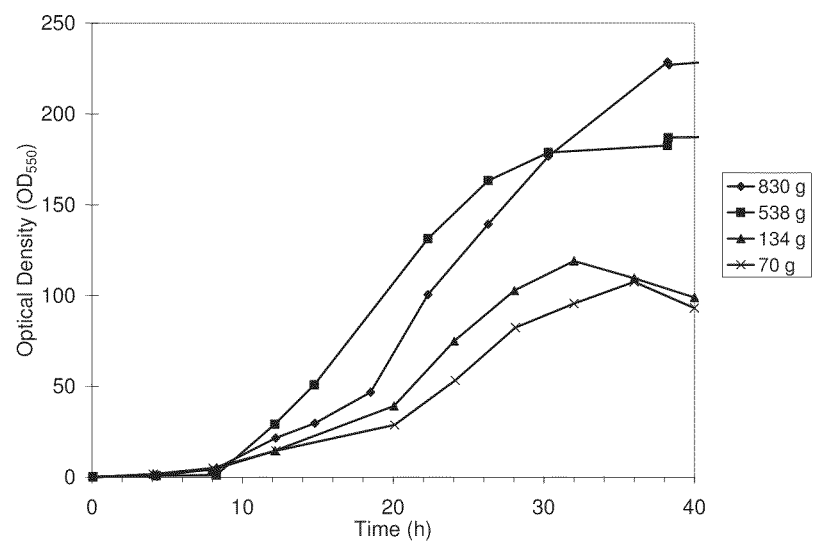
FIG. 48 shows graphs demonstrating the effect of yeast extract of isoprene production. Panel A shows the time course of optical density within fermentors fed with varying amounts of yeast extract. Panel B shows the time course of isoprene titer within fermentors fed with varying amounts of yeast extract. The titer is defined as the amount of isoprene produced per liter of fermentation broth. Panel C shows the effect of yeast extract on isoprene production in E. coli grown in fed-batch culture.
Figure 48B:
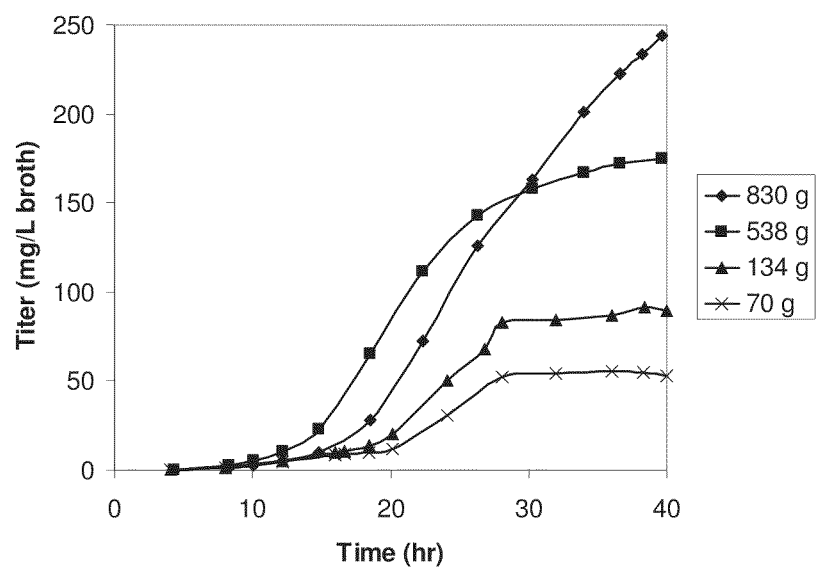
Figure 48C:
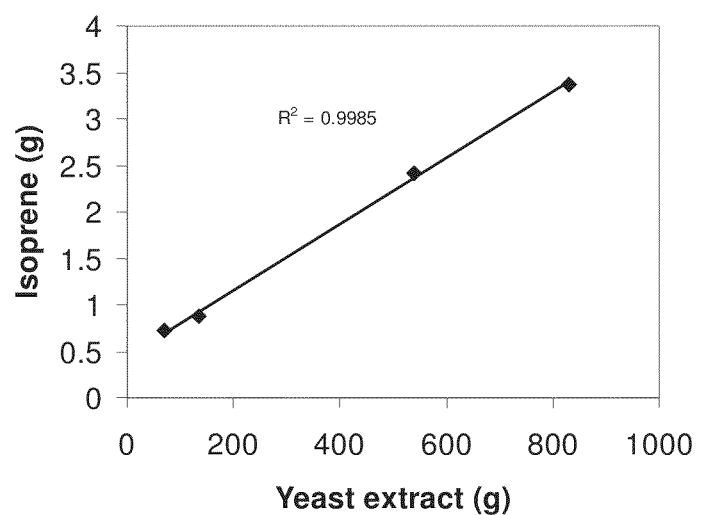

As indicated in Example 7, part VI, the amount of isoprene produced can be further increased by adding yeast extract to the cell culture medium. In this example, the amount of isoprene produced was linearly proportional to the amount of yeast extract in the cell medium for the concentrations tested (FIG. 48C). Additionally, approximately 0.11 grams of isoprene per liter of broth was produced from a cell medium with yeast extract and glucose (Example 7, part VIII). Both of these experiments used E. coli cells with kudzu isoprene synthase, *S. cerevisia* IDI, and *E. coli* DXS nucleic acids to produce isoprene. Increasing the amount of yeast extract in the presence of glucose resulted in more isoprene being produced than increasing the amount of glucose in the presence of yeast extract. Also, increasing the amount of yeast extract allowed the cells to produce a high level of isoprene for a longer length of time and improved the health of the cells.

Figure 46A:
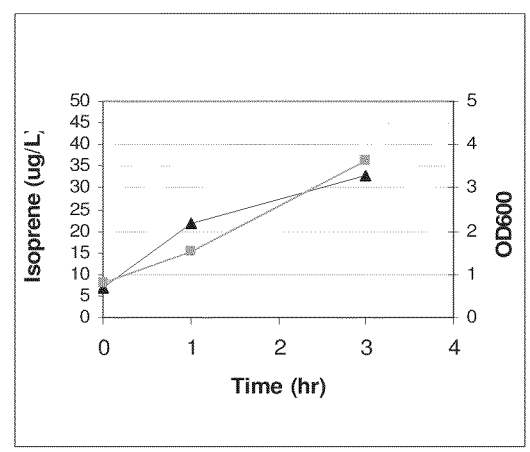
FIG. 46 shows graphs representing isoprene production from biomass feedstocks. Panel A shows isoprene production from corn stover, Panel B shows isoprene production from bagasse, Panel C shows isoprene production from softwood pulp, Panel D shows isoprene production from glucose, and Panel E shows isoprene production from cells with no additional feedstock. Grey squares represent $OD_{600}$ measurements of the cultures at the indicated times post-inoculation and black triangles represent isoprene production at the indicated times post-inoculation.
Figure 46B:
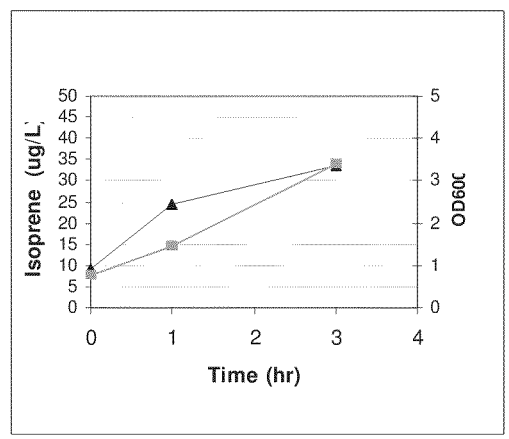
Figure 46C:
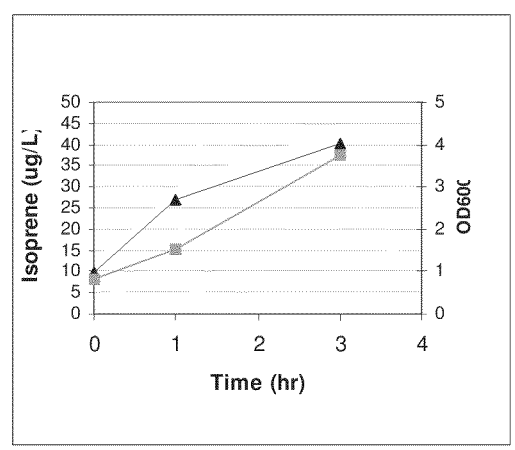
Figure 46D:
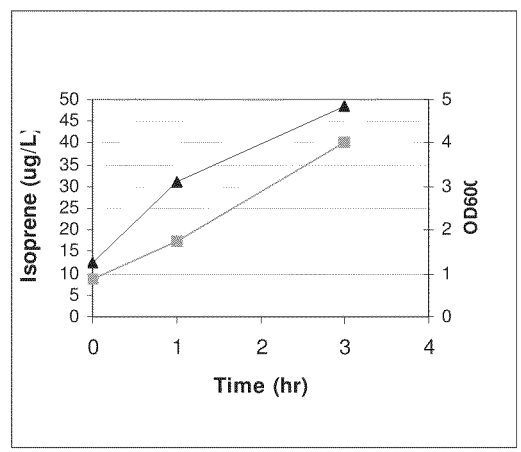
Figure 46E:
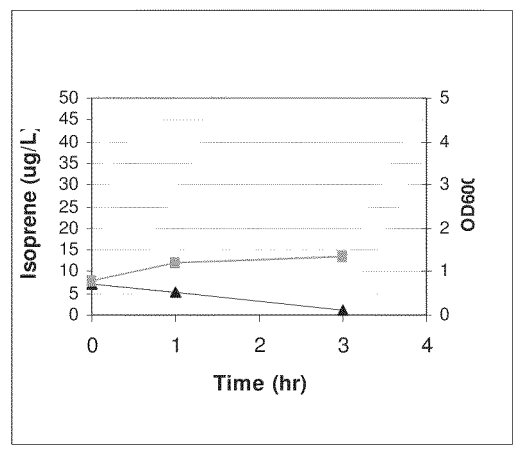
Figure 47A:
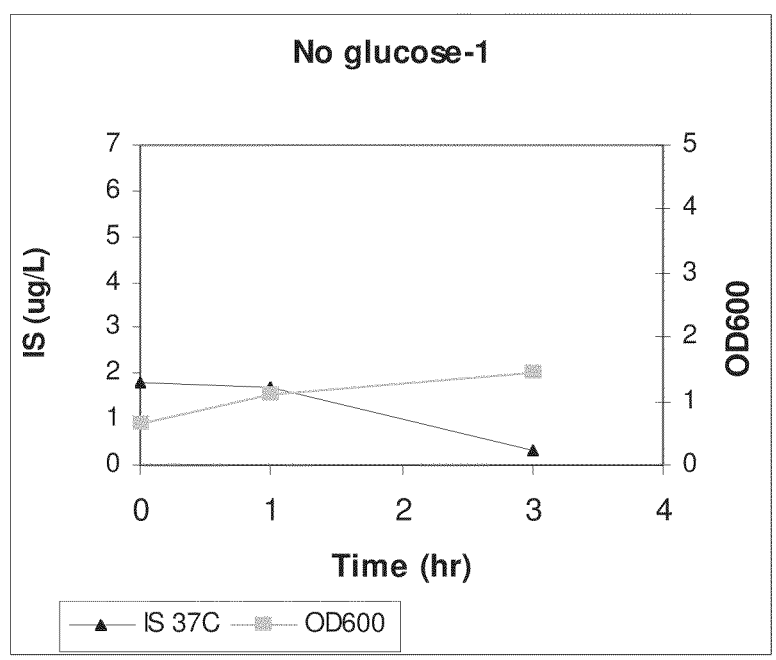
FIG. 47A shows a graph representing isoprene production by BL21(λDE3) pTrcKudzu yIDI DXS (kan) in a culture with no glucose added. Squares represent $OD_{600}$, and triangles represent isoprene produced (μg/ml).
Figure 47B:
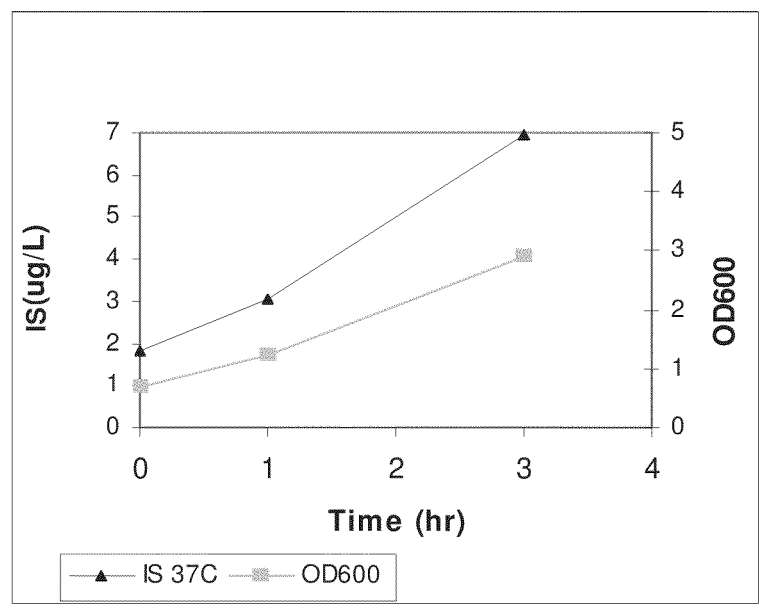
FIG. 47B shows a graph representing isoprene production from 1% glucose feedstock invert sugar by BL21(λDE3) pTrcKudzu yIDI DXS (kan). Squares represent $OD_{600}$, and triangles represent isoprene produced (μg/ml).
Figure 47C:
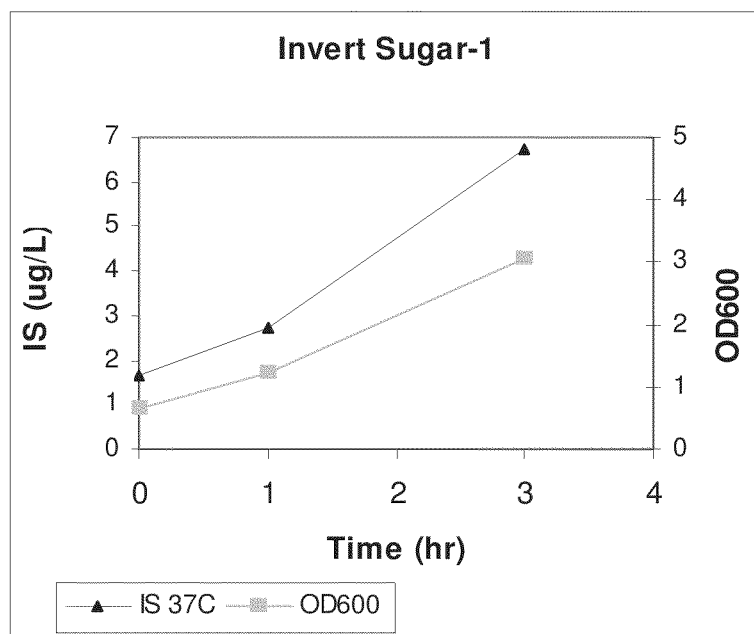
FIG. 47C shows a graph representing isoprene production from 1% invert sugar feedstock by BL21(λDE3) pTrcKudzu yIDI DXS (kan). Squares represent $OD_{600}$, and triangles represent isoprene produced (μg/ml).
Figure 47D:
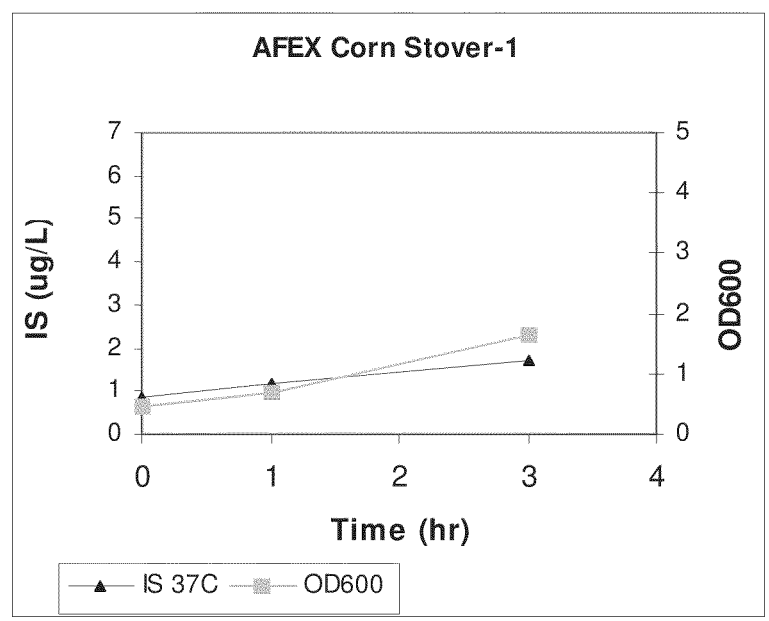
FIG. 47D shows a graph representing isoprene production from 1% AFEX corn stover feedstock by BL21(λDE3) pTrcKudzu yIDI DXS (kan). Squares represent $OD_{600}$, and triangles represent isoprene produced (μg/ml).

Isoprene production was also demonstrated using three types of hydrolyzed biomass (bagasse, corn stover, and soft wood pulp) as the carbon source (FIGS. 46A-C). *E. coli* cells with kudzu isoprene synthase, *S. cerevisia* IDI, and *E. coli* DXS nucleic acids produced as much isoprene from these hydrolyzed biomass carbon sources as from the equivalent amount of glucose (e.g., 1% glucose, w/v). If desired, any other biomass carbon source can be used in the compositions and methods of the invention. Biomass carbon sources are desirable because they are cheaper than many conventional cell mediums, thereby facilitating the economical production of isoprene.

Additionally, invert sugar was shown to function as a carbon source for the generation of isoprene (FIGS. 47C and 96-98). For example, 2.4 g/L of isoprene was produced from cells expressing MVA pathway polypeptides and a Kudzu isoprene synthase (Example 8, part XV). Glycerol was as also used as a carbon source for the generation of 2.2 mg/L of isoprene from cells expressing a Kudzu isoprene synthase (Example 8, part XIV). Expressing a DXS nucleic acid, an IDI nucleic acid, and/or one or more MVA pathway nucleic acids (such as nucleic acids encoding the entire MVA pathway) in addition to an isoprene synthase nucleic acid may increase the production of isoprene from glycerol.

In some embodiments, an oil is included in the cell medium. For example, *B. subtilis* cells containing a kudzu isoprene synthase nucleic acid produced isoprene when cultured in a cell medium containing an oil and a source of glucose (Example 4, part III). In some embodiments, more than one oil (such as 2, 3, 4, 5, or more oils) is included in the cell medium. While not intending to be bound to any particular theory, it is believed that (i) the oil may increase the amount of carbon in the cells that is available for conversion to isoprene, (ii) the oil may increase the amount of acetyl-CoA in the cells, thereby increasing the carbon flow through the MVA pathway, and/or (ii) the oil may provide extra nutrients to the cells, which is desirable since a lot of the carbon in the cells is converted to isoprene rather than other products. In some embodiments, cells that are cultured in a cell medium containing oil naturally use the MVA pathway to produce isoprene or are genetically modified to contain nucleic acids for the entire MVA pathway. In some embodiments, the oil is partially or completely hydrolyzed before being added to the cell culture medium to facilitate the use of the oil by the host cells.

One of the major hurdles to commercial production of small molecules such as isoprene in cells (e.g., bacteria) is the decoupling of production of the molecule from growth of the cells. In some embodiments for the commercially viable production of isoprene, a significant amount of the carbon from the feedstock is converted to isoprene, rather than to the growth and maintenance of the cells ("carbon efficiency"). In various embodiments, the cells convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene. In particular embodiments, a significant portion of the carbon from the feedstock that is converted to downstream products is converted to isoprene. As described further in Example 11, *E. coli* cells expressing MVA pathway and kudzu isoprene synthase nucleic acids exhibited decoupling of the production of isoprene or the intermediate mevalonic acid from growth, resulting in high carbon efficiency. In particular, mevalonic acid was formed from cells expressing the upper MVA pathway from *Enterococcus faecalis*. Isoprene was formed from cells expressing the upper MVA pathway from *Enterococcus faecalis*, the lower MVA pathway from *Saccharomyces cerevisiae*, and the isoprene synthase from *Pueraria montana* (Kudzu). This decoupling of isoprene or mevalonic acid production from growth was demonstrated in four different strains of *E. coli*: BL21(λDE3), BL21(λDE3) Tuner, FM5, and MG1655. The first two *E. coli* strains are B strains, and the latter two are K12 strains. Decoupling of production from growth was also demonstrated in a variant of MG1655 with ack and pta genes deleted. This variant also demonstrated less production of acetate.

Exemplary Polypeptides and Nucleic Acids

Various isoprene synthase, DXS, IDI, and/or MVA pathway polypeptides and nucleic acids can be used in the compositions and methods of the invention.

As used herein, "polypeptides" includes polypeptides, proteins, peptides, fragments of polypeptides, and fusion polypeptides. In some embodiments, the fusion polypeptide includes part or all of a first polypeptide (e.g., an isoprene synthase, DXS, IDI, or MVA pathway polypeptide or catalytically active fragment thereof) and may optionally include part or all of a second polypeptide (e.g., a peptide that facilitates purification or detection of the fusion polypeptide, such as a His-tag). In some embodiments, the fusion polypeptide has an activity of two or more MVA pathway polypeptides (such as AA-CoA thiolase and HMG-CoA reductase polypeptides). In some embodiments, the polypeptide is a naturally-occurring polypeptide (such as the polypeptide encoded by an *Enterococcus faecalis* mvaE nucleic acid) that has an activity of two or more MVA pathway polypeptides.

In various embodiments, a polypeptide has at least or about 50, 100, 150, 175, 200, 250, 300, 350, 400, or more amino acids. In some embodiments, the polypeptide fragment contains at least or about 25, 50, 75, 100, 150, 200, 300, or more contiguous amino acids from a full-length polypeptide and has at least or about 5%, 10%, 20%, 30%, 40%, 50%, 60%, 70%, 80%, 90%, 95%, or 100% of an activity of a corresponding full-length polypeptide. In particular embodiments the polypeptide includes a segment of or the entire amino acid sequence of any naturally-occurring isoprene synthase, DXS, IDI, or MVA pathway polypeptide. In some embodiments, the polypeptide has one or more mutations compared to the sequence of a wild-type (i.e., a sequence occurring in nature) isoprene synthase, DXS, IDI, or MVA pathway polypeptide.

In some embodiments, the polypeptide is an isolated polypeptide. As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

In some embodiments, the polypeptide is a heterologous polypeptide. By "heterologous polypeptide" is meant a polypeptide whose amino acid sequence is not identical to that of another polypeptide naturally expressed in the same host cell. In particular, a heterologous polypeptide is not identical to a wild-type nucleic acid that is found in the same host cell in nature.

As used herein, a "nucleic acid" refers to two or more deoxyribonucleotides and/or ribonucleotides in either single or double-stranded form. In some embodiments, the nucleic acid is a recombinant nucleic acid. By "recombinant nucleic acid" means a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences. In various embodiments, a nucleic acid is a recombinant nucleic acid. In some embodiments, an isoprene synthase, DXS, IDI, or MVA pathway nucleic acid is operably linked to another nucleic acid encoding all or a portion of another polypeptide such that the recombinant nucleic acid encodes a fusion polypeptide that includes an isoprene synthase, DXS, IDI, or MVA pathway polypeptide and all or part of another polypeptide (e.g., a peptide that facilitates purification or detection of the fusion polypeptide, such as a His-tag). In some embodiments, part or all of a recombinant nucleic acid is chemically synthesized. It is to be understood that mutations, including single nucleotide mutations, can occur within a nucleic acid as defined herein.

In some embodiments, the nucleic acid is a heterologous nucleic acid. By "heterologous nucleic acid" is meant a nucleic acid whose nucleic acid sequence is not identical to that of another nucleic acid naturally found in the same host cell.

In particular embodiments the nucleic acid includes a segment of or the entire nucleic acid sequence of any naturally-occurring isoprene synthase, DXS, IDI, or MVA pathway nucleic acid. In some embodiments, the nucleic acid includes at least or about 50, 100, 150, 200, 300, 400, 500, 600, 700, 800, or more contiguous nucleotides from a naturally-occurring isoprene synthase nucleic acid DXS, IDI, or MVA pathway nucleic acid. In some embodiments, the nucleic acid has one or more mutations compared to the sequence of a wild-type (i.e., a sequence occurring in nature) isoprene synthase, DXS, IDI, or MVA pathway nucleic acid. In some embodiments, the nucleic acid has one or more mutations (e.g., a silent mutation) that increase the transcription or translation of isoprene synthase, DXS, IDI, or MVA pathway nucleic acid. In some embodiments, the nucleic acid is a degenerate variant of any nucleic acid encoding an isoprene synthase, DXS, IDI, or MVA pathway polypeptide.

"Codon degeneracy" refers to divergence in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a nucleic acid for improved expression in a host cell, it is desirable in some embodiments to design the nucleic acid such that its frequency of codon usage approaches the frequency of preferred codon usage of the host cell.

The accession numbers of exemplary isoprene synthase, DXS, IDI, and/or MVA pathway polypeptides and nucleic acids are listed in Appendix 1 (the accession numbers of Appendix 1 and their corresponding sequences are herein incorporated by reference in their entireties, particularly with respect to the amino acid and nucleic acid sequences of isoprene synthase, DXS, IDI, and/or MVA pathway polypeptides and nucleic acids). The Kegg database also contains the amino acid and nucleic acid sequences of numerous exemplary isoprene synthase, DXS, IDI, and/or MVA pathway polypeptides and nucleic acids (see, for example, the worldwide web at "genome.jp/kegg/pathway/map/map00100.html" and the sequences therein, which are each hereby incorporated by reference in their entireties, particularly with respect to the amino acid and nucleic acid sequences of isoprene synthase, DXS, IDI, and/or MVA pathway polypeptides and nucleic acids). In some embodiments, one or more of the isoprene synthase, DXS, IDI, and/or MVA pathway polypeptides and/or nucleic acids have a sequence identical to a sequence publicly available on Dec. 12, 2007 or Sep. 14, 2008 such as any of the sequences that correspond to any of the accession numbers in Appendix 1 or any of the sequences present in the Kegg database. Additional exemplary isoprene synthase, DXS, IDI, and/or MVA pathway polypeptides and nucleic acids are described further below.

Exemplary Isoprene Synthase Polypeptides and Nucleic Acids

As noted above, isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Standard methods can be used to determine whether a polypeptide has isoprene synthase polypeptide activity by measuring the ability of the polypeptide to convert DMAPP into isoprene in vitro, in a cell extract, or in vivo. In an exemplary assay, cell extracts are prepared by growing a strain (e.g., the *E. coli*/pTrcKudzu strain described herein) in the shake flask method as described in Example 1. After induction is complete, approximately 10 mL of cells are pelleted by centrifugation at 7000×g for 10 minutes and resuspended in 5 ml of PEB without glycerol. The cells are lysed using a French Pressure cell using standard procedures. Alternatively the cells are treated with lysozyme (Ready-Lyse lysozyme solution; EpiCentre) after a freeze/thaw at −80° C.

Isoprene synthase polypeptide activity in the cell extract can be measured, for example, as described in Silver et al., J. Biol. Chem. 270:13010-13016, 1995 and references therein, which are each hereby incorporated by reference in their entireties, particularly with respect to assays for isoprene synthase polypeptide activity. DMAPP (Sigma) is evaporated to dryness under a stream of nitrogen and rehydrated to a concentration of 100 mM in 100 mM potassium phosphate buffer pH 8.2 and stored at −20° C. To perform the assay, a solution of 5 μL of 1M $MgCl_2$, 1 mM (250 μg/ml) DMAPP, 65 μL of Plant Extract Buffer (PEB) (50 mM Tris-HCl, pH 8.0, 20 mM $MgCl_2$, 5% glycerol, and 2 mM DTT) is added to 25 μL of cell extract in a 20 ml Headspace vial with a metal screw cap and teflon coated silicon septum (Agilent Technologies) and cultured at 37° C. for 15 minutes with shaking. The reaction is quenched by adding 200 μL of 250 mM EDTA and quantified by GC/MS as described in Example 1, part II.

Exemplary isoprene synthase nucleic acids include nucleic acids that encode a polypeptide, fragment of a polypeptide, peptide, or fusion polypeptide that has at least one activity of an isoprene synthase polypeptide. Exemplary isoprene synthase polypeptides and nucleic acids include naturally-occurring polypeptides and nucleic acids from any of the source organisms described herein as well as mutant polypeptides and nucleic acids derived from any of the source organisms described herein.

In some embodiments, the isoprene synthase polypeptide or nucleic acid is from the family Fabaceae, such as the Faboideae subfamily. In some embodiments, the isoprene synthase polypeptide or nucleic acid is a polypeptide or nucleic acid from *Pueraria montana* (kudzu) (Sharkey et al., Plant Physiology 137: 700-712, 2005), *Pueraria lobata*, poplar (such as *Populus alba, Populus nigra, Populus trichocarpa,* or *Populus alba* x *tremula* (CAC35696) Miller et al., Planta 213: 483-487, 2001) aspen (such as *Populus tremuloides*) Silver et al., JBC 270(22): 13010-1316, 1995), or English Oak (*Quercus robur*) (Zimmer et al., WO 98/02550), which are each hereby incorporated by reference in their entireties, particularly with respect to isoprene synthase nucleic acids and the expression of isoprene synthase polypeptides. Suitable isoprene synthases include, but are not limited to, those identified by Genbank Accession Nos. AY341431, AY316691, AY279379, AJ457070, and AY182241, which are each hereby incorporated by reference in their entireties, particularly with respect to sequences of isoprene synthase nucleic acids and polypeptides. In some embodiments, the isoprene synthase polypeptide or nucleic acid is not a naturally-occurring polypeptide or nucleic acid from *Quercus robur* (i.e., the isoprene synthase polypeptide or nucleic acid is an isoprene synthase polypeptide or nucleic acid other than a naturally-occurring polypeptide or nucleic acid from *Quercus robur*). In some embodiments, the isoprene synthase nucleic acid or polypeptide is a naturally-occurring polypeptide or nucleic acid from poplar. In some embodiments, the isoprene synthase nucleic acid or polypeptide is not a naturally-occurring polypeptide or nucleic acid from poplar.

Exemplary DXS Polypeptides and Nucleic Acids

As noted above, 1-deoxy-D-xylulose-5-phosphate synthase (DXS) polypeptides convert pyruvate and D-glyceraldehyde-3-phosphate into 1-deoxy-D-xylulose-5-phosphate. Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS nucleic acids include nucleic acids that encode a polypeptide, fragment of a polypeptide, peptide, or fusion polypeptide that has at least one activity of a DXS polypeptide. Exemplary DXS polypeptides and nucleic acids include naturally-occurring polypeptides and nucleic acids from any of the source organisms described herein as well as mutant polypeptides and nucleic acids derived from any of the source organisms described herein.

Exemplary IDI Polypeptides and Nucleic Acids

Isopentenyl diphosphate isomerase polypeptides (isopentenyl-diphosphate delta-isomerase or IDI) catalyses the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Exemplary MVA Pathway Polypeptides and Nucleic Acids

Exemplary MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein as well as mutant polypeptides and nucleic acids derived from any of the source organisms described herein.

In particular, acetyl-CoA acetyltransferase polypeptides (AA-CoA thiolase or AACT) convert two molecules of acetyl-CoA into acetoacetyl-CoA. Standard methods (such as those described herein) can be used to determine whether a polypeptide has AA-CoA thiolase polypeptide activity by measuring the ability of the polypeptide to convert two molecules of acetyl-CoA into acetoacetyl-CoA in vitro, in a cell extract, or in vivo.

3-hydroxy-3-methylglutaryl-CoA synthase (HMG-CoA synthase or HMGS) polypeptides convert acetoacetyl-CoA into 3-hydroxy-3-methylglutaryl-CoA. Standard methods (such as those described herein) can be used to determine whether a polypeptide has HMG-CoA synthase polypeptide activity by measuring the ability of the polypeptide to convert acetoacetyl-CoA into 3-hydroxy-3-methylglutaryl-CoA in vitro, in a cell extract, or in vivo.

3-hydroxy-3-methylglutaryl-CoA reductase (HMG-CoA reductase or HMGR) polypeptides convert 3-hydroxy-3-methylglutaryl-CoA into mevalonate. Standard methods (such as those described herein) can be used to determine whether a polypeptide has HMG-CoA reductase polypeptide activity by measuring the ability of the polypeptide to convert 3-hydroxy-3-methylglutaryl-CoA into mevalonate in vitro, in a cell extract, or in vivo.

Mevalonate kinase (MVK) polypeptides phosphorylates mevalonate to form mevalonate-5-phosphate. Standard methods (such as those described herein) can be used to determine whether a polypeptide has MVK polypeptide activity by measuring the ability of the polypeptide to convert mevalonate into mevalonate-5-phosphate in vitro, in a cell extract, or in vivo.

Phosphomevalonate kinase (PMK) polypeptides phosphorylates mevalonate-5-phosphate to form mevalonate-5-diphosphate. Standard methods (such as those described herein) can be used to determine whether a polypeptide has PMK polypeptide activity by measuring the ability of the polypeptide to convert mevalonate-5-phosphate into mevalonate-5-diphosphate in vitro, in a cell extract, or in vivo.

Diphosphomevalonte decarboxylase (MVD or DPMDC) polypeptides convert mevalonate-5-diphosphate into isopentenyl diphosphate (IPP). Standard methods (such as those described herein) can be used to determine whether a polypeptide has MVD polypeptide activity by measuring the ability of the polypeptide to convert mevalonate-5-diphosphate into IPP in vitro, in a cell extract, or in vivo.

Phosphomevalonate decarboxylase (PMDC) polypeptides convert mevalonate-5-phosphate into isopentenyl phosphate (IP). Standard methods (such as those described herein) can be used to determine whether a polypeptide has PMDC polypeptide activity by measuring the ability of the polypeptide to convert mevalonate-5-phosphate into IP in vitro, in a cell extract, or in vivo.

Isopentenyl phosphate kinase (IPK) polypeptides phosphorylate isopentyl phosphate (IP) to form isopentenyl diphosphate (IPP). Standard methods (such as those described herein) can be used to determine whether a polypeptide has IPK polypeptide activity by measuring the ability of the polypeptide to convert IP into IPP in vitro, in a cell extract, or in vivo.

Exemplary IDI polypeptides and nucleic acids are described above.

Exemplary Methods for Isolating Nucleic Acids

Isoprene synthase, DXS, IDI, and/or MVA pathway nucleic acids can be isolated using standard methods. Methods of obtaining desired nucleic acids from a source organism of interest (such as a bacterial genome) are common and well known in the art of molecular biology (see, for example, WO 2004/033646 and references cited therein, which are each hereby incorporated by reference in their entireties, particularly with respect to the isolation of nucleic acids of interest). For example, if the sequence of the nucleic acid is known (such as any of the known nucleic acids described herein), suitable genomic libraries may be created by restriction endonuclease digestion and may be screened with probes complementary to the desired nucleic acid sequence. Once the sequence is isolated, the DNA may be amplified using standard primer directed amplification methods such as polymerase chain reaction (PCR) (U.S. Pat. No. 4,683,202, which is incorporated by reference in its entirety, particularly with respect to PCR methods) to obtain amounts of DNA suitable for transformation using appropriate vectors.

Alternatively, isoprene synthase, DXS, IDI, and/or MVA pathway nucleic acids (such as any isoprene synthase, DXS, IDI, and/or MVA pathway nucleic acids with a known nucleic acid sequence) can be chemically synthesized using standard methods.

Additional isoprene synthase, DXS, IDI, or MVA pathway polypeptides and nucleic acids which may be suitable for use in the compositions and methods described herein can be identified using standard methods. For example, cosmid libraries of the chromosomal DNA of organisms known to produce isoprene naturally can be constructed in organisms such as *E. coli*, and then screened for isoprene production. In particular, cosmid libraries may be created where large segments of genomic DNA (35-45 kb) are packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the heterologous DNA. In addition to the cos sequence, these vectors also contain an origin of replication such as ColEI and drug resistance markers such as a nucleic acid resistant to ampicillin or neomycin. Methods of using cosmid vectors for the transformation of suitable bacterial hosts are well described in Sambrook et al., Molecular Cloning: A Laboratory Manual, $2^{nd}$ ed., Cold Spring Harbor, 1989, which is hereby incorporated by reference in its entirety, particularly with respect to transformation methods.

Typically to clone cosmids, heterologous DNA is isolated using the appropriate restriction endonucleases and ligated adjacent to the cos region of the cosmid vector using the appropriate ligases. Cosmid vectors containing the linearized heterologous DNA are then reacted with a DNA packaging vehicle such as bacteriophage. During the packaging process, the cos sites are cleaved and the heterologous DNA is packaged into the head portion of the bacterial viral particle. These particles are then used to transfect suitable host cells such as *E. coli*. Once injected into the cell, the heterologous DNA circularizes under the influence of the cos sticky ends. In this manner, large segments of heterologous DNA can be introduced and expressed in host cells.

Additional methods for obtaining isoprene synthase, DXS, IDI, and/or MVA pathway nucleic acids include screening a metagenomic library by assay (such as the headspace assay described herein) or by PCR using primers directed against nucleotides encoding for a length of conserved amino acids (for example, at least 3 conserved amino acids). Conserved amino acids can be identified by aligning amino acid sequences of known isoprene synthase, DXS, IDI, and/or MVA pathway polypeptides. Conserved amino acids for isoprene synthase polypeptides can be identified based on aligned sequences of known isoprene synthase polypeptides. An organism found to produce isoprene naturally can be subjected to standard protein purification methods (which are well known in the art) and the resulting purified polypeptide can be sequenced using standard methods. Other methods are found in the literature (see, for example, Julsing et al., *Applied. Microbiol. Biotechnol.* 75: 1377-84, 2007; Withers et al., *Appl Environ Microbiol.* 73(19):6277-83, 2007, which are each hereby incorporated by reference in their entireties, particularly with respect to identification of nucleic acids involved in the synthesis of isoprene).

Additionally, standard sequence alignment and/or structure prediction programs can be used to identify additional DXS, IDI, or MVA pathway polypeptides and nucleic acids based on the similarity of their primary and/or predicted polypeptide secondary structure with that of known DXS, IDI, or MVA pathway polypeptides and nucleic acids. Standard databases such as the swissprot-trembl database (worldwide web at "expasy.org", Swiss Institute of Bioinformatics Swiss-Prot group CMU-1 rue Michel Servet CH-1211 Geneva 4, Switzerland) can also be used to identify isoprene synthase, DXS, IDI, or MVA pathway polypeptides and nucleic acids. The secondary and/or tertiary structure of an isoprene synthase, DXS, IDI, or MVA pathway polypeptide can be predicted using the default settings of standard structure prediction programs, such as PredictProtein (630 West, 168 Street, BB217, New York, N.Y. 10032, USA). Alternatively, the actual secondary and/or tertiary structure of an isoprene synthase, DXS, IDI, or MVA pathway polypeptide can be determined using standard methods. Additional isoprene synthase, DXS, IDI, or MVA pathway nucleic acids can also be identified by hybridization to probes generated from known isoprene synthase, DXS, IDI, or MVA pathway nucleic acids.

Exemplary Promoters and Vectors

Any of the isoprene synthase, DXS, IDI, or MVA pathway nucleic acid described herein can be included in one or more vectors. Accordingly, the invention also features vectors with one more nucleic acids encoding any of the isoprene synthase, DXS, IDI, or MVA pathway polypeptides that are described herein. As used herein, a "vector" means a construct that is capable of delivering, and desirably expressing one or more nucleic acids of interest in a host cell. Examples of vectors include, but are not limited to, plasmids, viral vectors, DNA or RNA expression vectors, cosmids, and phage vectors. In some embodiments, the vector contains a nucleic acid under the control of an expression control sequence.

As used herein, an "expression control sequence" means a nucleic acid sequence that directs transcription of a nucleic acid of interest. An expression control sequence can be a promoter, such as a constitutive or an inducible promoter, or an enhancer. An "inducible promoter" is a promoter that is active under environmental or developmental regulation. The expression control sequence is operably linked to the nucleic acid segment to be transcribed.

In some embodiments, the vector contains a selective marker. The term "selective marker" refers to a nucleic acid capable of expression in a host cell that allows for ease of selection of those host cells containing an introduced nucleic acid or vector. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. Exemplary nutritional selective markers include those markers known in the art as amdS, argB, and pyr4. Markers useful in vector systems for transformation of Trichoderma are known in the art (see, e.g., Finkelstein, Chapter 6 in Biotechnology of Filamentous Fungi, Finkelstein et al., Eds. Butterworth-Heinemann, Boston, Mass., Chap. 6., 1992; and Kinghorn et al., Applied Molecular Genetics of Filamentous Fungi, Blackie Academic and Professional, Chapman and Hall, London, 1992, which are each hereby incorporated by reference in their entireties, particularly with respect to selective markers). In some embodiments, the selective marker is the amdS nucleic acid, which encodes the enzyme acetamidase, allowing transformed cells to grow on acetamide as a nitrogen source. The use of an A. nidulans amdS nucleic acid as a selective marker is described in Kelley et al., EMBO J. 4:475-479, 1985 and Penttila et al., Gene 61:155-164, 1987 (which are each hereby incorporated by reference in their entireties, particularly with respect to selective markers). In some embodiments, an isoprene synthase, DXS, IDI, or MVA pathway nucleic acid integrates into a chromosome of the cells without a selective marker.

Suitable vectors are those which are compatible with the host cell employed. Suitable vectors can be derived, for example, from a bacterium, a virus (such as bacteriophage T7 or a M-13 derived phage), a cosmid, a yeast, or a plant. Protocols for obtaining and using such vectors are known to those in the art (see, for example, Sambrook et al., Molecular Cloning: A Laboratory Manual, $2^{nd}$ ed., Cold Spring Harbor, 1989, which is hereby incorporated by reference in its entirety, particularly with respect to the use of vectors).

Promoters are well known in the art. Any promoter that functions in the host cell can be used for expression of an isoprene synthase, DXS, IDI, or MVA pathway nucleic acid in the host cell. Initiation control regions or promoters, which are useful to drive expression of isoprene synthase, DXS, IDI, or MVA pathway nucleic acids in various host cells are numerous and familiar to those skilled in the art (see, for example, WO 2004/033646 and references cited therein, which are each hereby incorporated by reference in their entireties, particularly with respect to vectors for the expression of nucleic acids of interest). Virtually any promoter capable of driving these nucleic acids is suitable for the present invention including, but not limited to, CYC1, HIS3, GAL1, GAL10, ADH1, PGK, PHO5, GAPDH, ADCI, TRP1, URA3, LEU2, ENO, and TPI (useful for expression in Saccharomyces); AOX1 (useful for expression in Pichia); and lac, trp, $\lambda P_L$, $\lambda P_R$, T7, tac, and trc (useful for expression in E. coli).

In some embodiments, a glucose isomerase promoter is used (see, for example, U.S. Pat. No. 7,132,527 and references cited therein, which are each hereby incorporated by reference in their entireties, particularly with respect promoters and plasmid systems for expressing polypeptides of interest). Reported glucose isomerase promoter mutants can be used to vary the level of expression of the polypeptide encoded by a nucleic acid operably linked to the glucose isomerase promoter (U.S. Pat. No. 7,132,527). In various embodiments, the glucose isomerase promoter is contained in a low, medium, or high copy plasmid (U.S. Pat. No. 7,132, 527).

In various embodiments, an isoprene synthase, DXS, IDI, and/or MVA pathway nucleic acid is contained in a low copy plasmid (e.g., a plasmid that is maintained at about 1 to about 4 copies per cell), medium copy plasmid (e.g., a plasmid that is maintained at about 10 to about 15 copies per cell), or high copy plasmid (e.g., a plasmid that is maintained at about 50 or more copies per cell). In some embodiments, the heterologous or extra endogenous isoprene synthase, DXS, IDI, or MVA pathway nucleic acid is operably linked to a T7 promoter. In some embodiments, the heterologous or extra endogenous isoprene synthase, DXS, IDI, or MVA pathway nucleic acid operably linked to a T7 promoter is contained in a medium or high copy plasmid. In some embodiments, the heterologous or extra endogenous isoprene synthase, DXS, IDI, or MVA pathway nucleic acid is operably linked to a Trc promoter. In some embodiments, the heterologous or extra endogenous isoprene synthase, DXS, IDI, or MVA pathway nucleic acid operably linked to a Trc promoter is contained in a medium or high copy plasmid. In some embodiments, the heterologous or extra endogenous isoprene synthase, DXS, IDI, or MVA pathway nucleic acid is operably linked to a Lac promoter. In some embodiments, the heterologous or extra endogenous isoprene synthase, DXS, IDI, or MVA pathway nucleic acid operably linked to a Lac promoter is contained in a low copy plasmid. In some embodiments, the heterologous or extra endogenous isoprene synthase, DXS, IDI, or MVA pathway nucleic acid is operably linked to an endogenous promoter, such as an endogenous *Escherichia, Panteoa, Bacillus, Yarrowia, Streptomyces*, or *Trichoderma* promoter or an endogenous alkaline serine protease, isoprene synthase, DXS, IDI, or MVA pathway promoter. In some embodiments, the heterologous or extra endogenous isoprene synthase, DXS, IDI, or MVA pathway nucleic acid operably linked to an endogenous promoter is contained in a high copy plasmid. In some embodiments, the vector is a replicating plasmid that does not integrate into a chromosome in the cells. In some embodiments, part or all of the vector integrates into a chromosome in the cells.

In some embodiments, the vector is any vector which when introduced into a fungal host cell is integrated into the host cell genome and is replicated. Reference is made to the Fungal Genetics Stock Center Catalogue of Strains (FGSC, the world-wide web at "fgsc.net" and the references cited therein, which are each hereby incorporated by reference in their entireties, particularly with respect to vectors) for a list of vectors. Additional examples of suitable expression and/or integration vectors are provided in Sambrook et al., Molecular Cloning: A Laboratory Manual, $2^{nd}$ ed., Cold Spring Harbor, 1989, Current Protocols in Molecular Biology (F. M. Ausubel et al. (eds) 1987, Supplement 30, section 7.7.18); van den Hondel et al. in Bennett and Lasure (Eds.) More Gene Manipulations in Fungi, Academic Press pp. 396-428, 1991; and U.S. Pat. No. 5,874,276, which are each hereby incorporated by reference in their entireties, particularly with respect to vectors. Particularly useful vectors include pFB6, pBR322, PUC18, pUC100, and pENTR/D.

In some embodiments, an isoprene synthase, DXS, IDI, or MVA pathway nucleic acid is operably linked to a suitable promoter that shows transcriptional activity in a fungal host cell. The promoter may be derived from one or more nucleic acids encoding a polypeptide that is either endogenous or heterologous to the host cell. In some embodiments, the promoter is useful in a *Trichoderma* host. Suitable non-limiting examples of promoters include cbh1, cbh2, egl1, egl2, pepA, hfb1, hfb2, xyn1, and amy. In some embodiments, the promoter is one that is native to the host cell. For example, in some embodiments when *T. reesei* is the host, the promoter is a native *T. reesei* promoter. In some embodiments, the promoter is *T. reesei* cbh1, which is an inducible promoter and has been deposited in GenBank under Accession No. D86235, which is incorporated by reference in its entirety, particularly with respect to promoters. In some embodiments, the promoter is one that is heterologous to the fungal host cell. Other examples of useful promoters include promoters from the genes of *A. awamori* and *A. niger* glucoamylase (glaA) (Nunberg et al., *Mol. Cell Biol.* 4:2306-2315, 1984 and Boel et al., *EMBO J.* 3:1581-1585, 1984, which are each hereby incorporated by reference in their entireties, particularly with respect to promoters); *Aspergillus niger* alpha amylases, *Aspergillus oryzae* TAKA amylase, *T. reesei* xln1, and the *T. reesei* cellobiohydrolase 1 (EP 137280, which is incorporated by reference in its entirety, particularly with respect to promoters).

In some embodiments, the expression vector also includes a termination sequence. Termination control regions may also be derived from various genes native to the host cell. In some embodiments, the termination sequence and the promoter sequence are derived from the same source. In another embodiment, the termination sequence is endogenous to the host cell. A particularly suitable terminator sequence is cbh1 derived from a *Trichoderma* strain (such as *T. reesei*). Other useful fungal terminators include the terminator from an *A. niger* or *A. awamori* glucoamylase nucleic acid (Nunberg et al., *Mol. Cell Biol.* 4:2306-2315, 1984 and Boel et al., *EMBO J.* 3:1581-1585, 1984; which are each hereby incorporated by reference in their entireties, particularly with respect to fungal terminators). Optionally, a termination site may be included. For effective expression of the polypeptides, DNA encoding the polypeptide are linked operably through initiation codons to selected expression control regions such that expression results in the formation of the appropriate messenger RNA.

In some embodiments, the promoter, coding, region, and terminator all originate from the isoprene synthase, DXS, IDI, or MVA pathway nucleic acid to be expressed. In some embodiments, the coding region for an isoprene synthase, DXS, IDI, or MVA pathway nucleic acid is inserted into a general-purpose expression vector such that it is under the transcriptional control of the expression construct promoter and terminator sequences. In some embodiments, genes or part thereof are inserted downstream of the strong cbh1 promoter.

An isoprene synthase, DXS, IDI, or MVA pathway nucleic acid can be incorporated into a vector, such as an expression vector, using standard techniques (Sambrook et al., Molecular Cloning: A Laboratory Manual, Cold Spring Harbor, 1982, which is hereby incorporated by reference in its entirety, particularly with respect to the screening of appropriate DNA sequences and the construction of vectors). Methods used to ligate the DNA construct comprising a nucleic acid of interest (such as an isoprene synthase, DXS, IDI, or MVA pathway nucleic acid), a promoter, a terminator, and other sequences and to insert them into a suitable vector are well known in the art. For example, restriction enzymes can be used to cleave the isoprene synthase, DXS, IDI, or MVA pathway nucleic acid and the vector. Then, the compatible ends of the cleaved isoprene synthase, DXS, IDI, or MVA pathway nucleic acid and the cleaved vector can be ligated. Linking is generally accomplished by ligation at convenient restriction sites. If such sites do not exist, the synthetic oligonucleotide linkers are used in accordance with conventional practice (see, Sambrook et al., Molecular Cloning: A Laboratory Manual, $2^{nd}$ ed., Cold Spring Harbor, 1989, and Bennett and Lasure, More Gene Manipulations in Fungi, Academic Press, San Diego, pp 70-76, 1991, which are each hereby incorporated by reference in their entireties, particularly with respect to oligonucleotide linkers). Additionally, vectors can be constructed using known recombination techniques (e.g., Invitrogen Life Technologies, Gateway Technology).

In some embodiments, it may be desirable to over-express isoprene synthase, DXS, IDI, or MVA pathway nucleic acids at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for over-expressing desired polypeptides are common and well known in the art of molecular biology and examples may be found in Sambrook et al., Molecular Cloning: A Laboratory Manual, 2<sup>nd</sup> ed., Cold Spring Harbor, 1989, which is hereby incorporated by reference in its entirety, particularly with respect to cloning techniques.

The following resources include descriptions of additional general methodology useful in accordance with the invention: Kreigler, Gene Transfer and Expression; A Laboratory Manual, 1990 and Ausubel et al., Eds. Current Protocols in Molecular Biology, 1994, which are each hereby incorporated by reference in their entireties, particularly with respect to molecular biology and cloning techniques.

Exemplary Source Organisms

Isoprene synthase, DXS, IDI, or MVA pathway nucleic acids (and their encoded polypeptides) can be obtained from any organism that naturally contains isoprene synthase, DXS, IDI, and/or MVA pathway nucleic acids. As noted above, isoprene is formed naturally by a variety of organisms, such as bacteria, yeast, plants, and animals. Organisms contain the MVA pathway, DXP pathway, or both the MVA and DXP pathways for producing isoprene (FIGS. 19A and 19B). Thus, DXS nucleic acids can be obtained, e.g., from any organism that contains the DXP pathway or contains both the MVA and DXP pathways. IDI and isoprene synthase nucleic acids can be obtained, e.g., from any organism that contains the MVA pathway, DXP pathway, or both the MVA and DXP pathways. MVA pathway nucleic acids can be obtained, e.g., from any organism that contains the MVA pathway or contains both the MVA and DXP pathways.

In some embodiments, the nucleic acid sequence of the isoprene synthase, DXS, IDI, or MVA pathway nucleic is identical to the sequence of a nucleic acid that is produced by any of the following organisms in nature. In some embodiments, the amino acid sequence of the isoprene synthase, DXS, IDI, or MVA pathway polypeptide is identical to the sequence of a polypeptide that is produced by any of the following organisms in nature. In some embodiments, the isoprene synthase, DXS, IDI, or MVA pathway nucleic acid or polypeptide is a mutant nucleic acid or polypeptide derived from any of the organisms described herein. As used herein, "derived from" refers to the source of the nucleic acid or polypeptide into which one or more mutations is introduced. For example, a polypeptide that is "derived from a plant polypeptide" refers to polypeptide of interest that results from introducing one or more mutations into the sequence of a wild-type (i.e., a sequence occurring in nature) plant polypeptide.

In some embodiments, the source organism is a fungus, examples of which are species of *Aspergillus* such as *A. oryzae* and *A. niger*, species of *Saccharomyces* such as *S. cerevisiae*, species of *Schizosaccharomyces* such as *S. pombe*, and species of *Trichoderma* such as *T. reesei*. In some embodiments, the source organism is a filamentous fungal cell. The term "filamentous fungi" refers to all filamentous forms of the subdivision Eumycotina (see, Alexopoulos, C. J. (1962), Introductory Mycology, Wiley, N.Y.). These fungi are characterized by a vegetative mycelium with a cell wall composed of chitin, cellulose, and other complex polysaccharides. The filamentous fungi are morphologically, physiologically, and genetically distinct from yeasts. Vegetative growth by filamentous fungi is by hyphal elongation and carbon catabolism is obligatory aerobic. The filamentous fungal parent cell may be a cell of a species of, but not limited to, *Trichoderma*, (e.g., *Trichoderma reesei*, the asexual morph of *Hypocrea jecorina*, previously classified as *T. longibrachiatum, Trichoderma viride, Trichoderma koningii, Trichoderma harzianum*) (Sheir-Neirs et al., Appl. Microbiol. Biotechnol 20: 46-53, 1984; ATCC No. 56765 and ATCC No. 26921); *Penicillium* sp., *Humicola* sp. (e.g., *H. insolens, H. lanuginose*, or *H. grisea*); *Chrysosporium* sp. (e.g., *C. lucknowense*), *Gliocladium* sp., *Aspergillus* sp. (e.g., *A. oryzae, A. niger, A. sojae, A. japonicus, A. nidulans*, or *A. awamori*) (Ward et al., Appl. Microbiol. Biotechnol. 39: 7380743, 1993 and Goedegebuur et al., Genet 41: 89-98, 2002), *Fusarium* sp., (e.g., *F. roseum, F. graminum F. cerealis, F. oxysporuim*, or *F. venenatum*), *Neurospora* sp., (e.g., *N. crassa*), *Hypocrea* sp., *Mucor* sp., (e.g., *M. miehei*), *Rhizopus* sp. and *Emericella* sp. (see also, Innis et al., Sci. 228: 21-26, 1985). The term "*Trichoderma*" or "*Trichoderma* sp." or "*Trichoderma* spp." refer to any fungal genus previously or currently classified as *Trichoderma*.

In some embodiments, the fungus is *A. nidulans, A. awamori, A. oryzae, A. aculeatus, A. niger, A. japonicus, T. reesei, T. viride, F. oxysporum*, or *F. solani*. *Aspergillus* strains are disclosed in Ward et al., Appl. Microbiol. Biotechnol. 39:738-743, 1993 and Goedegebuur et al., Curr Gene 41:89-98, 2002, which are each hereby incorporated by reference in their entireties, particularly with respect to fungi. In particular embodiments, the fungus is a strain of *Trichoderma*, such as a strain of *T. reesei*. Strains of *T. reesei* are known and non-limiting examples include ATCC No. 13631, ATCC No. 26921, ATCC No. 56764, ATCC No. 56765, ATCC No. 56767, and NRRL 15709, which are each hereby incorporated by reference in their entireties, particularly with respect to strains of *T. reesei*. In some embodiments, the host strain is a derivative of RL-P37. RL-P37 is disclosed in Sheir-Neiss et al., Appl. Microbiol. Biotechnology 20:46-53, 1984, which is hereby incorporated by reference in its entirety, particularly with respect to strains of *T. reesei*.

In some embodiments, the source organism is a yeast, such as *Saccharomyces* sp., *Schizosaccharomyces* sp., *Pichia* sp., or *Candida* sp.

In some embodiments, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, or strains of *Escherichia* such as *E. coli*.

As used herein, "the genus Bacillus" includes all species within the genus "*Bacillus*," as known to those of skill in the art, including but not limited to *B. subtilis, B. lichemformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus Bacillus continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

In some embodiments, the source organism is a gram-positive bacterium. Non-limiting examples include strains of *Streptomyces* (e.g., *S. lividans, S. coelicolor*, or *S. griseus*) and *Bacillus*. In some embodiments, the source organism is a gram-negative bacterium, such as *E. coli* or *Pseudomonas* sp.

In some embodiments, the source organism is a plant, such as a plant from the family Fabaceae, such as the Faboideae subfamily. In some embodiments, the source organism is kudzu, poplar (such as *Populus alba* x *tremula* CAC35696), aspen (such as *Populus tremuloides*), or *Quercus robur*.

In some embodiments, the source organism is an algae, such as a green algae, red algae, glaucophytes, chlorarachniophytes, euglenids, chromista, or dinoflagellates.

In some embodiments, the source organism is a cyanobacteria, such as cyanobacteria classified into any of the following groups based on morphology: *Chroococcales, Pleurocapsales, Oscillatoriales, Nostocales*, or *Stigonematales*.

Exemplary Host Cells

A variety of host cells can be used to express isoprene synthase, DXS, IDI, and/or MVA pathway polypeptides and to produce isoprene in the methods of the claimed invention. Exemplary host cells include cells from any of the organisms listed in the prior section under the heading "Exemplary Source Organisms." The host cell may be a cell that naturally produces isoprene or a cell that does not naturally produce isoprene. In some embodiments, the host cell naturally produces isoprene using the DXP pathway, and an isoprene synthase, DXS, and/or IDI nucleic acid is added to enhance production of isoprene using this pathway. In some embodiments, the host cell naturally produces isoprene using the MVA pathway, and an isoprene synthase and/or one or more MVA pathway nucleic acids are added to enhance production of isoprene using this pathway. In some embodiments, the host cell naturally produces isoprene using the DXP pathway and one or more MVA pathway nucleic acids are added to produce isoprene using part or all of the MVA pathway as well as the DXP pathway. In some embodiments, the host cell naturally produces isoprene using both the DXP and MVA pathways and one or more isoprene synthase, DXS, IDI, or MVA pathway nucleic acids are added to enhance production of isoprene by one or both of these pathways.

Exemplary Transformation Methods

Isoprene synthase, DXS, IDI, and/or MVA pathway nucleic acids or vectors containing them can be inserted into a host cell (e.g., a plant cell, a fungal cell, a yeast cell, or a bacterial cell described herein) using standard techniques for expression of the encoded isoprene synthase, DXS, IDI, and/or MVA pathway polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds) Chapter 9, 1987; Sambrook et al., Molecular Cloning: A Laboratory Manual, $2^{nd}$ ed., Cold Spring Harbor, 1989; and Campbell et al., *Curr. Genet.* 16:53-56, 1989, which are each hereby incorporated by reference in their entireties, particularly with respect to transformation methods). The expression of heterologous polypeptide in *Trichoderma* is described in U.S. Pat. No. 6,022,725; U.S. Pat. No. 6,268,328; U.S. Pat. No. 7,262,041; WO 2005/001036; Harkki et al.; *Enzyme Microb. Technol.* 13:227-233, 1991; Harkki et al., *Bio Technol.* 7:596-603, 1989; EP 244,234; EP 215,594; and Nevalainen et al., "*The Molecular Biology of Trichoderma and its Application to the Expression of Both Homologous and Heterologous Genes*," in Molecular Industrial Mycology, Eds. Leong and Berka, Marcel Dekker Inc., NY pp. 129-148, 1992, which are each hereby incorporated by reference in their entireties, particularly with respect to transformation and expression methods). Reference is also made to Cao et al., (*Sci.* 9:991-1001, 2000; EP 238023; and Yelton et al., *Proceedings. Natl. Acad. Sci. USA* 81:1470-1474, 1984 (which are each hereby incorporated by reference in their entireties, particularly with respect to transformation methods) for transformation of *Aspergillus* strains. The introduced nucleic acids may be integrated into chromosomal DNA or maintained as extrachromosomal replicating sequences.

Any method known in the art may be used to select transformants. In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on a solid non-selective medium (e.g., a medium that lacks acetamide), harvesting spores from this culture medium, and determining the percentage of these spores which subsequently germinate and grow on selective medium containing acetamide.

In some embodiments, fungal cells are transformed by a process involving protoplast formation and transformation of the protoplasts followed by regeneration of the cell wall in a known manner. In one specific embodiment, the preparation of *Trichoderma* sp. for transformation involves the preparation of protoplasts from fungal mycelia (see, Campbell et al., *Curr. Genet.* 16:53-56, 1989, which is incorporated by reference in its entirety, particularly with respect to transformation methods). In some embodiments, the mycelia are obtained from germinated vegetative spores. The mycelia are treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M. It is desirable to use about a 1.2 M solution of sorbitol in the suspension medium.

Uptake of DNA into the host *Trichoderma* sp. strain is dependent upon the calcium ion concentration. Generally, between about 10 mM $CaCl_2$ and 50 mM $CaCl_2$ is used in an uptake solution. In addition to the calcium ion in the uptake solution, other compounds generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). While not intending to be bound to any particular theory, it is believed that the polyethylene glycol acts to fuse the cell membranes, thus permitting the contents of the medium to be delivered into the cytoplasm of the *Trichoderma* sp. strain and the plasmid DNA to be transferred to the nucleus. This fusion frequently leaves multiple copies of the plasmid DNA integrated into the host chromosome.

Usually a suspension containing the *Trichoderma* sp. protoplasts or cells that have been subjected to a permeability treatment at a density of $10^5$ to $10^7$/mL (such as $2\times10^6$/mL) are used in the transformation. A volume of 100 μL of these protoplasts or cells in an appropriate solution (e.g., 1.2 M sorbitol and 50 mM $CaCl_2$) are mixed with the desired DNA. Generally, a high concentration of PEG is added to the uptake solution. From 0.1 to 1 volume of 25% PEG 4000 can be added to the protoplast suspension. In some embodiments, about 0.25 volumes are added to the protoplast suspension. Additives such as dimethyl sulfoxide, heparin, spermidine, potassium chloride, and the like may also be added to the uptake solution and aid in transformation. Similar procedures are available for other fungal host cells (see, e.g., U.S. Pat. Nos. 6,022,725 and 6,268,328, which are each hereby incorporated by reference in their entireties, particularly with respect to transformation methods).

Generally, the mixture is then cultured at approximately 0° C. for a period of between 10 to 30 minutes. Additional PEG is then added to the mixture to further enhance the uptake of the desired nucleic acid sequence. The 25% PEG 4000 is generally added in volumes of 5 to 15 times the volume of the transformation mixture; however, greater and lesser volumes may be suitable. The 25% PEG 4000 is desirably about 10 times the volume of the transformation mixture. After the PEG is added, the transformation mixture is then cultured either at room temperature or on ice before the addition of a sorbitol and $CaCl_2$ solution. The protoplast suspension is then further added to molten aliquots of a growth medium. When the growth medium includes a growth selection (e.g., acetamide or an antibiotic) it permits the growth of transformants only.

The transformation of bacterial cells may be performed according to conventional methods, e.g., as described in Sambrook et al., Molecular Cloning: A Laboratory Manual, Cold Spring Harbor, 1982, which is hereby incorporated by reference in its entirety, particularly with respect to transformation methods.

Exemplary Cell Culture Media

The invention also includes a cell or a population of cells in culture that produce isoprene. By "cells in culture" is meant two or more cells in a solution (e.g., a cell medium) that allows the cells to undergo one or more cell divisions. "Cells in culture" do not include plant cells that are part of a living, multicellular plant containing cells that have differentiated into plant tissues. In various embodiments, the cell culture includes at least or about 10, 20, 50, 100, 200, 500, 1,000, 5,000, 10,000 or more cells.

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

In some embodiments, the carbon source is a carbohydrate (such as monosaccharide, disaccharide, oligosaccharide, or polysaccharids), invert sugar (e.g., enzymatically treated sucrose syrup), glycerol, glycerine (e.g., a glycerine byproduct of a biodiesel or soap-making process), dihydroxyacetone, one-carbon source, oil (e.g., a plant or vegetable oil such as corn, palm, or soybean oil), animal fat, animal oil, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as a carbon source other than a carbohydrate (e.g., glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria. In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the concentration of the carbohydrate is at least or about 5 grams per liter of broth (g/L, wherein the volume of broth includes both the volume of the cell medium and the volume of the cells), such as at least or about 10, 15, 20, 30, 40, 50, 60, 80, 100, 150, 200, 300, 400, or more g/L. In some embodiments, the concentration of the carbohydrate is between about 50 and about 400 g/L, such as between about 100 and about 360 g/L, between about 120 and about 360 g/L, or between about 200 and about 300 g/L. In some embodiments, this concentration of carbohydrate includes the total amount of carbohydrate that is added before and/or during the culturing of the host cells.

In some embodiments, the cells are cultured under limited glucose conditions. By "limited glucose conditions" is meant that the amount of glucose that is added is less than or about 105% (such as about 100%) of the amount of glucose that is consumed by the cells. In particular embodiments, the amount of glucose that is added to the culture medium is approximately the same as the amount of glucose that is consumed by the cells during a specific period of time. In some embodiments, the rate of cell growth is controlled by limiting the amount of added glucose such that the cells grow at the rate that can be supported by the amount of glucose in the cell medium. In some embodiments, glucose does not accumulate during the time the cells are cultured. In various embodiments, the cells are cultured under limited glucose conditions for greater than or about 1, 2, 3, 5, 10, 15, 20, 25, 30, 35, 40, 50, 60, or 70 hours. In various embodiments, the cells are cultured under limited glucose conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited glucose conditions may allow more favorable regulation of the cells.

In some embodiments, the cells are cultured in the presence of an excess of glucose. In particular embodiments, the amount of glucose that is added is greater than about 105% (such as about or greater than 110, 120, 150, 175, 200, 250, 300, 400, or 500%) or more of the amount of glucose that is consumed by the cells during a specific period of time. In some embodiments, glucose accumulates during the time the cells are cultured.

Exemplary lipids are any substance containing one or more fatty acids that are C4 and above fatty acids that are saturated, unsaturated, or branched.

Exemplary oils are lipids that are liquid at room temperature. In some embodiments, the lipid contains one or more C4 or above fatty acids (e.g., contains one or more saturated, unsaturated, or branched fatty acid with four or more carbons). In some embodiments, the oil is obtained from soy, corn, canola, jatropha, palm, peanut, sunflower, coconut, mustard, rapeseed, cottonseed, palm kernel, olive, safflower, sesame, linseed, oleagineous microbial cells, Chinese tallow, or any combination of two or more of the foregoing.

Exemplary fatty acids include compounds of the formula RCOOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitelaidic acid, and arachidonic acid.

Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more $C_{12}$-$C_{22}$ fatty acids, such as a $C_{12}$ saturated fatty acid, a $C_{14}$ saturated fatty acid, a $C_{16}$ saturated fatty acid, a $C_{18}$ saturated fatty acid, a $C_{20}$ saturated fatty acid, or a $C_{22}$ saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerols are fatty acid esters of glycerol.

In some embodiments, the concentration of the lipid, oil, fat, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, oil, fat, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, oil, fat, fatty acid, monoglyceride, diglyceride, or triglyceride that is added before and/or during the culturing of the host cells. In some embodiments, the carbon source includes both (i) a lipid, oil, fat, fatty acid, monoglyceride, diglyceride, or triglyceride and (ii) a carbohydrate, such as glucose. In some embodiments, the ratio of the lipid, oil, fat, fatty acid, monoglyceride, diglyceride, or triglyceride to the carbohydrate is about 1:1 on a carbon basis (i.e., one carbon in the lipid, oil, fat, fatty acid, monoglyceride, diglyceride, or triglyceride per carbohydrate carbon). In particular embodiments, the amount of the lipid, oil, fat, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., *Bioresource Technology* 96 (18): 2014-2018, 2005; U.S. Pat. No. 6,176,176; U.S. Pat. No. 6,106,888; which are each hereby incorporated by reference in their entireties, particularly with respect to the pretreatment of renewable carbon sources). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., *Bioresource Technology* 96 (18): 2014-2018, 2005). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry to dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., *Agric. Biol. Chem.*, 53(2) 541-543, 1989, which is hereby incorporated by reference in its entirety, particularly with respect to carbon sources) and in bacteria (Hunter et. al., *Biochemistry*, 24, 4148-4155, 1985, which is hereby incorporated by reference in its entirety, particularly with respect to carbon sources). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, *Bacterial Metabolism*, Second Edition, Springer-Verlag: New York, 1986, which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate. Likewise, the serine pathway assimilates the one-carbon compound into the glycolytic pathway via methylene-tetrahydrofolate.

In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth Cl Compd., [Int. Symp.]*, $7^{th}$ ed., 415-32. Editors: Murrell et al., Publisher: Intercept, Andover, UK, 1993, which is hereby incorporated by reference in its entirety, particularly with respect to carbon sources). Similarly, various species of *Candida* metabolize alanine or oleic acid (Sulter et al., *Arch. Microbiol.* 153(5), 485-9, 1990, which is hereby incorporated by reference in its entirety, particularly with respect to carbon sources).

In some embodiments, cells are cultured in a standard medium containing physiological salts and nutrients (see, e.g., Pourquie, J. et al., Biochemistry and Genetics of Cellulose Degradation, eds. Aubert et al., Academic Press, pp. 71-86, 1988 and Ilmen et al., *Appl. Environ. Microbiol.* 63:1298-1306, 1997, which are each hereby incorporated by reference in their entireties, particularly with respect to cell media). Exemplary growth media are common commercially prepared media such as Luria Bertani (LB) broth, Sabouraud Dextrose (SD) broth, or Yeast medium (YM) broth. Other defined or synthetic growth media may also be used, and the appropriate medium for growth of particular host cells are known by someone skilled in the art of microbiology or fermentation science.

In addition to an appropriate carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein, which are each hereby incorporated by reference in their entireties, particularly with respect cell medias and cell culture conditions). In some embodiments where an isoprene synthase, DXS, IDI, and/or MVA pathway nucleic acid is under the control of an inducible promoter, the inducing agent (e.g., a sugar, metal salt or antimicrobial), is desirably added to the medium at a concentration effective to induce expression of an isoprene synthase, DXS, IDI, and/or MVA pathway polypeptide. In some embodiments, cell medium has an antibiotic (such as kanamycin) that corresponds to the antibiotic resistance nucleic acid (such as a kanamycin resistance nucleic acid) on a vector that has one or more DXS, IDI, or MVA pathway nucleic acids.

Exemplary Cell Culture Conditions

Materials and methods suitable for the maintenance and growth of bacterial cultures are well known in the art. Exemplary techniques may be found in *Manual of Methods for General Bacteriology* Gerhardt et al., eds), American Society for Microbiology, Washington, D.C. (1994) or Brock in *Biotechnology: A Textbook of Industrial Microbiology*, Second Edition (1989) Sinauer Associates, Inc., Sunderland, Mass., which are each hereby incorporated by reference in their entireties, particularly with respect to cell culture techniques. In some embodiments, the cells are cultured in a culture medium under conditions permitting the expression of one or more isoprene synthase, DXS, IDI, or MVA pathway polypeptides encoded by a nucleic acid inserted into the host cells.

Standard cell culture conditions can be used to culture the cells (see, for example, WO 2004/033646 and references cited therein, which are each hereby incorporated by reference in their entireties, particularly with respect to cell culture and fermentation conditions). Cells are grown and maintained at an appropriate temperature, gas mixture, and pH (such as at about 20 to about 37° C., at about 6% to about 84% $CO_2$, and at a pH between about 5 to about 9). In some embodiments, cells are grown at 35° C. in an appropriate cell medium. In some embodiments, e.g., cultures are cultured at approximately 28° C. in appropriate medium in shake cultures or fermentors until desired amount of isoprene production is achieved. In some embodiments, the pH ranges for fermentation are between about pH 5.0 to about pH 9.0 (such as about pH 6.0 to about pH 8.0 or about 6.5 to about 7.0). Reactions may be performed under aerobic, anoxic, or anaerobic conditions based on the requirements of the host cells. Exemplary culture conditions for a given filamentous fungus are known in the art and may be found in the scientific literature and/or from the source of the fungi such as the American Type Culture Collection and Fungal Genetics Stock Center.

In various embodiments, the cells are grown using any known mode of fermentation, such as batch, fed-batch, or continuous processes. In some embodiments, a batch method of fermentation is used. Classical batch fermentation is a closed system where the composition of the media is set at the beginning of the fermentation and is not subject to artificial alterations during the fermentation. Thus, at the beginning of the fermentation the cell medium is inoculated with the desired host cells and fermentation is permitted to occur adding nothing to the system. Typically, however, "batch" fermentation is batch with respect to the addition of carbon source and attempts are often made at controlling factors such as pH and oxygen concentration. In batch systems, the metabolite and biomass compositions of the system change constantly until the time the fermentation is stopped. Within batch cultures, cells moderate through a static lag phase to a high growth log phase and finally to a stationary phase where growth rate is diminished or halted. In some embodiments, cells in log phase are responsible for the bulk of the isoprene production. In some embodiments, cells in stationary phase produce isoprene.

In some embodiments, a variation on the standard batch system is used, such as the Fed-Batch system. Fed-Batch fermentation processes comprise a typical batch system with the exception that the carbon source is added in increments as the fermentation progresses. Fed-Batch systems are useful when catabolite repression is apt to inhibit the metabolism of the cells and where it is desirable to have limited amounts of carbon source in the cell medium. Fed-batch fermentations may be performed with the carbon source (e.g., glucose) in a limited or excess amount. Measurement of the actual carbon source concentration in Fed-Batch systems is difficult and is therefore estimated on the basis of the changes of measurable factors such as pH, dissolved oxygen, and the partial pressure of waste gases such as $CO_2$. Batch and Fed-Batch fermentations are common and well known in the art and examples may be found in Brock, Biotechnology: *A Textbook of Industrial Microbiology*, Second Edition (1989) Sinauer Associates, Inc., which is hereby incorporated by reference in its entirety, particularly with respect to cell culture and fermentation conditions.

In some embodiments, continuous fermentation methods are used. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or isoprene production. For example, one method maintains a limiting nutrient such as the carbon source or nitrogen level at a fixed rate and allows all other parameters to moderate. In other systems, a number of factors affecting growth can be altered continuously while the cell concentration (e.g., the concentration measured by media turbidity) is kept constant. Continuous systems strive to maintain steady state growth conditions. Thus, the cell loss due to media being drawn off is balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, Biotechnology: *A Textbook of Industrial Microbiology*, Second Edition (1989) Sinauer Associates, Inc., which is hereby incorporated by reference in its entirety, particularly with respect to cell culture and fermentation conditions.

In some embodiments, cells are immobilized on a substrate as whole cell catalysts and subjected to fermentation conditions for isoprene production.

In some embodiments, bottles of liquid culture are placed in shakers in order to introduce oxygen to the liquid and maintain the uniformity of the culture. In some embodiments, an incubator is used to control the temperature, humidity, shake speed, and/or other conditions in which a culture is grown. The simplest incubators are insulated boxes with an adjustable heater, typically going up to ~65° C. More elaborate incubators can also include the ability to lower the temperature (via refrigeration), or the ability to control humidity or $CO_2$ levels. Most incubators include a timer; some can also be programmed to cycle through different temperatures, humidity levels, etc. Incubators can vary in size from tabletop to units the size of small rooms.

If desired, a portion or all of the cell medium can be changed to replenish nutrients and/or avoid the build up of potentially harmful metabolic byproducts and dead cells. In the case of suspension cultures, cells can be separated from the media by centrifuging or filtering the suspension culture and then resuspending the cells in fresh media. In the case of adherent cultures, the media can be removed directly by aspiration and replaced. In some embodiments, the cell medium allows at least a portion of the cells to divide for at least or about 5, 10, 20, 40, 50, 60, 65, or more cell divisions in a continuous culture (such as a continuous culture without dilution).

In some embodiments, a constitutive or leaky promoter (such as a Trc promoter) is used and a compound (such as IPTG) is not added to induce expression of the isoprene synthase, DXS, IDI, or MVA pathway nucleic acid(s) operably linked to the promoter. In some embodiments, a compound (such as IPTG) is added to induce expression of the isoprene synthase, DXS, IDI, or MVA pathway nucleic acid(s) operably linked to the promoter.

Exemplary Methods for Decoupling Isoprene Production from Cell Growth

Desirably, carbon from the feedstock is converted to isoprene rather than to the growth and maintenance of the cells. In some embodiments, the cells are grown to a low to medium $OD_{600}$, then production of isoprene is started or increased. This strategy permits a large portion of the carbon to be converted to isoprene.

In some embodiments, cells reach an optical density such that they no longer divide or divide extremely slowly, but continue to make isoprene for several hours (such as about 2, 4, 6, 8, 10, 15, 20, 25, 30, or more hours). For example, FIGS. 60A-67C illustrate that cells may continue to produce a substantial amount of mevalonic acid or isoprene after the cells reach an optical density such that they no longer divide or divide extremely slowly. In some cases, the optical density at 550 nm decreases over time (such as a decrease in the optical density after the cells are no longer in an exponential growth phase due to cell lysis), and the cells continue to produce a substantial amount of mevalonic acid or isoprene. In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr) during this time period. In some embodiments, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some embodiments, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth ($mg/L_{broth}$, wherein the volume of broth includes the volume of the cells and the cell medium) during this time period. In some embodiments, the amount of isoprene is between about 2 to about 5,000 $mg/L_{broth}$, such as between about 2 to about 100 $mg/L_{broth}$, about 100 to about 500 $mg/L_{broth}$, about 500 to about 1,000 $mg/L_{broth}$, about 1,000 to about 2,000 $mg/L_{broth}$, or about 2,000 to about 5,000 $mg/L_{broth}$. In some embodiments, the amount of isoprene is between about 20 to about 5,000 $mg/L_{broth}$, about 100 to about 5,000 $mg/L_{broth}$, about 200 to about 2,000 $mg/L_{broth}$, about 200 to about 1,000 $mg/L_{broth}$, about 300 to about 1,000 $mg/L_{broth}$, or about 400 to about 1,000 $mg/L_{broth}$.

In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene during this time period. In some embodiments, the percent conversion of carbon into isoprene is between such as about 0.002 to about 4.0%, about 0.002 to about 3.0%, about 0.002 to about 2.0%, about 0.002 to about 1.6%, about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. In some embodiments, the percent conversion of carbon into isoprene is between about 0.002 to about 0.4%, 0.002 to about 0.16%, 0.04 to about 0.16%, about 0.005 to about 0.3%, about 0.01 to about 0.3%, or about 0.05 to about 0.3%.

In some embodiments, isoprene is only produced in stationary phase. In some embodiments, isoprene is produced in both the growth phase and stationary phase. In various embodiments, the amount of isoprene produced (such as the total amount of isoprene produced or the amount of isoprene produced per liter of broth per hour per $OD_{600}$) during stationary phase is greater than or about 2, 3, 4, 5, 10, 20, 30, 40, 50, or more times the amount of isoprene produced during the growth phase for the same length of time. In various embodiments, greater than or about 5, 10, 20, 30, 40, 50, 60, 70, 80, 90, 95, 99% or more of the total amount of isoprene that is produced (such as the production of isoprene during a fermentation for a certain amount of time, such as 20 hours) is produced while the cells are in stationary phase. In various embodiments, greater than or about 5, 10, 20, 30, 40, 50, 60, 70, 80, 90, 95, 99% or more of the total amount of isoprene that is produced (such as the production of isoprene during a fermentation for a certain amount of time, such as 20 hours) is produced while the cells divide slowly or not at all such that the optical density at 550 nm of the cells increases by less than or about 50% (such as by less than or about 40, 30, 20, 10, 5, or 0%). In some embodiments, isoprene is only produced in the growth phase.

In some embodiments, one or more MVA pathway, IDI, DXP, or isoprene synthase nucleic acids are placed under the control of a promoter or factor that is more active in stationary phase than in the growth phase. For example, one or more MVA pathway, IDI, DXP, or isoprene synthase nucleic acids may be placed under control of a stationary phase sigma factor, such as RpoS. In some embodiments, one or more MVA pathway, IDI, DXP, or isoprene synthase nucleic acids are placed under control of a promoter inducible in stationary phase, such as a promoter inducible by a response regulator active in stationary phase.

Production of Isoprene within Safe Operating Ranges

The production of isoprene within safe operating levels according to its flammability characteristics simplifies the design and construction of commercial facilities, vastly improves the ability to operate safely, and limits the potential for fires to occur. In particular, the optimal ranges for the production of isoprene are within the safe zone, i.e., the nonflammable range of isoprene concentrations. In one such aspect, the invention features a method for the production of isoprene within the nonflammable range of isoprene concentrations (outside the flammability envelope of isoprene).

Thus, computer modeling and experimental testing were used to determine the flammability limits of isoprene (such as isoprene in the presence of $O_2$, $N_2$, $CO_2$, or any combination of two or more of the foregoing gases) in order to ensure process safety. The flammability envelope is characterized by the lower flammability limit (LFL), the upper flammability limit (UFL), the limiting oxygen concentration (LOC), and the limiting temperature. For a system to be flammable, a minimum amount of fuel (such as isoprene) must be in the presence of a minimum amount of oxidant, typically oxygen. The LFL is the minimum amount of isoprene that must be present to sustain burning, while the UFL is the maximum amount of isoprene that can be present. Above this limit, the mixture is fuel rich and the fraction of oxygen is too low to have a flammable mixture. The LOC indicates the minimum fraction of oxygen that must also be present to have a flammable mixture. The limiting temperature is based on the flash point of isoprene and is that lowest temperature at which combustion of isoprene can propagate. These limits are specific to the concentration of isoprene, type and concentration of oxidant, inerts present in the system, temperature, and pressure of the system. Compositions that fall within the limits of the flammability envelope propagate combustion and require additional safety precautions in both the design and operation of process equipment.

The following conditions were tested using computer simulation and mathematical analysis and experimental testing. If desired, other conditions (such as other temperature, pressure, and permanent gas compositions) may be tested using the methods described herein to determine the LFL, UFL, and LOC concentrations.

(1) Computer Simulation and Mathematical Analysis

Test Suite 1:

isoprene: 0 wt %-14 wt %

$O_2$: 6 wt %-21 wt %

$N_2$: 79 wt %-94 wt %

Test Suite 2:

isoprene: 0 wt %-14 wt %

$O_2$: 6 wt %-21 wt %

$N_2$: 79 wt %-94 wt %

Saturated with $H_2O$

Test Suite 3:

isoprene: 0 wt %-14 wt %

$O_2$: 6 wt %-21 wt %

$N_2$: 79 wt %-94 wt %

$CO_2$: 5 wt %-30 wt %

(2) Experimental Testing for Final Determination of Flammability Limits
Test Suite 1:
isoprene: 0 wt %-14 wt %
$O_2$: 6 wt %-21 wt %
$N_2$: 79 wt %-94 wt %
Test Suite 2:
isoprene: 0 wt %-14 wt %
$O_2$: 6 wt %-21 wt %
$N_2$: 79 wt %-94 wt %
Saturated with $H_2O$ Simulation software was used to give an estimate of the flammability characteristics of the system for several different testing conditions. $CO_2$ showed no significant affect on the system's flammability limits. Test suites 1 and 2 were confirmed by experimental testing. The modeling results were in-line with the experimental test results. Only slight variations were found with the addition of water.

The LOC was determined to be 9.5 vol % for an isoprene, $O_2$, $N_2$, and $CO_2$ mixture at 40° C. and 1 atmosphere. The addition of up to 30% $CO_2$ did not significantly affect the flammability characteristics of an isoprene, $O_2$, and $N_2$ mixture. Only slight variations in flammability characteristics were shown between a dry and water saturated isoprene, $O_2$, and $N_2$ system. The limiting temperature is about −54° C. Temperatures below about −54° C. are too low to propagate combustion of isoprene.

In some embodiments, the LFL of isoprene ranges from about 1.5 vol.% to about 2.0 vol %, and the UFL of isoprene ranges from about 2.0 vol. % to about 12.0 vol. %, depending on the amount of oxygen in the system. In some embodiments, the LOC is about 9.5 vol % oxygen. In some embodiments, the LFL of isoprene is between about 1.5 vol. % to about 2.0 vol %, the UFL of isoprene is between about 2.0 vol. % to about 12.0 vol. %, and the LOC is about 9.5 vol % oxygen when the temperature is between about 25° C. to about 55° C. (such as about 40° C.) and the pressure is between about 1 atmosphere and 3 atmospheres.

In some embodiments, isoprene is produced in the presence of less than about 9.5 vol % oxygen (that is, below the LOC required to have a flammable mixture of isoprene). In some embodiments in which isoprene is produced in the presence of greater than or about 9.5 vol % oxygen, the isoprene concentration is below the LFL (such as below about 1.5 vol. %). For example, the amount of isoprene can be kept below the LFL by diluting the isoprene composition with an inert gas (e.g., by continuously or periodically adding an inert gas such as nitrogen to keep the isoprene composition below the LFL). In some embodiments in which isoprene is produced in the presence of greater than or about 9.5 vol % oxygen, the isoprene concentration is above the UFL (such as above about 12 vol. %). For example, the amount of isoprene can be kept above the UFL by using a system (such as any of the cell culture systems described herein) that produces isoprene at a concentration above the UFL. If desired, a relatively low level of oxygen can be used so that the UFL is also relatively low. In this case, a lower isoprene concentration is needed to remain above the UFL.

In some embodiments in which isoprene is produced in the presence of greater than or about 9.5 vol % oxygen, the isoprene concentration is within the flammability envelope (such as between the LFL and the UFL). In some embodiments when the isoprene concentration may fall within the flammability envelope, one or more steps are performed to reduce the probability of a fire or explosion. For example, one or more sources of ignition (such as any materials that may generate a spark) can be avoided. In some embodiments, one or more steps are performed to reduce the amount of time that the concentration of isoprene remains within the flammability envelope. In some embodiments, a sensor is used to detect when the concentration of isoprene is close to or within the flammability envelope. If desired, the concentration of isoprene can be measured at one or more time points during the culturing of cells, and the cell culture conditions and/or the amount of inert gas can be adjusted using standard methods if the concentration of isoprene is close to or within the flammability envelope. In particular embodiments, the cell culture conditions (such as fermentation conditions) are adjusted to either decrease the concentration of isoprene below the LFL or increase the concentration of isoprene above the UFL. In some embodiments, the amount of isoprene is kept below the LFL by diluting the isoprene composition with an inert gas (such as by continuously or periodically adding an inert gas to keep the isoprene composition below the LFL).

In some embodiments, the amount of flammable volatiles other than isoprene (such as one or more sugars) is at least about 2, 5, 10, 50, 75, or 100-fold less than the amount of isoprene produced. In some embodiments, the portion of the gas phase other than isoprene gas comprises between about 0% to about 100% (volume) oxygen, such as between about 0% to about 10%, about 10% to about 20%, about 20% to about 30%, about 30% to about 40%, about 40% to about 50%, about 50% to about 60%, about 60% to about 70%, about 70% to about 80%, about 90% to about 90%, or about 90% to about 100% (volume) oxygen. In some embodiments, the portion of the gas phase other than isoprene gas comprises between about 0% to about 99% (volume) nitrogen, such as between about 0% to about 10%, about 10% to about 20%, about 20% to about 30%, about 30% to about 40%, about 40% to about 50%, about 50% to about 60%, about 60% to about 70%, about 70% to about 80%, about 90% to about 90%, or about 90% to about 99% (volume) nitrogen.

In some embodiments, the portion of the gas phase other than isoprene gas comprises between about 1% to about 50% (volume) $CO_2$, such as between about 1% to about 10%, about 10% to about 20%, about 20% to about 30%, about 30% to about 40%, or about 40% to about 50% (volume) $CO_2$.

In some embodiments, an isoprene composition also contains ethanol. For example, ethanol may be used for extractive distillation of isoprene, resulting in compositions (such as intermediate product streams) that include both ethanol and isoprene. Desirably, the amount of ethanol is outside the flammability envelope for ethanol. The LOC of ethanol is about 8.7 vol %, and the LFL for ethanol is about 3.3 vol % at standard conditions, such as about 1 atmosphere and about 60° F. (NFPA 69 *Standard on Explosion Prevention Systems*, 2008 edition, which is hereby incorporated by reference in its entirety, particularly with respect to LOC, LFL, and UFL values). In some embodiments, compositions that include isoprene and ethanol are produced in the presence of less than the LOC required to have a flammable mixture of ethanol (such as less than about 8.7% vol %). In some embodiments in which compositions that include isoprene and ethanol are produced in the presence of greater than or about the LOC required to have a flammable mixture of ethanol, the ethanol concentration is below the LFL (such as less than about 3.3 vol. %).

In various embodiments, the amount of oxidant (such as oxygen) is below the LOC of any fuel in the system (such as isoprene or ethanol). In various embodiments, the amount of oxidant (such as oxygen) is less than about 60, 40, 30, 20, 10, or 5% of the LOC of isoprene or ethanol. In various embodiments, the amount of oxidant (such as oxygen) is less than the LOC of isoprene or ethanol by at least 2, 4, 5, or more absolute percentage points (vol %). In particular embodiments, the amount of oxygen is at least 2 absolute percentage points (vol %) less than the LOC of isoprene or ethanol (such as an oxygen concentration of less than 7.5 vol % when the LOC of isoprene is 9.5 vol %). In various embodiments, the amount of fuel (such as isoprene or ethanol) is less than or about 25, 20, 15, 10, or 5% of the LFL for that fuel.

Exemplary Production of Isoprene

In some embodiments, the cells are cultured in a culture medium under conditions permitting the production of isoprene by the cells. By "peak absolute productivity" is meant the maximum absolute amount of isoprene in the off-gas during the culturing of cells for a particular period of time (e.g., the culturing of cells during a particular fermentation run). By "peak absolute productivity time point" is meant the time point during a fermentation run when the absolute amount of isoprene in the off-gas is at a maximum during the culturing of cells for a particular period of time (e.g., the culturing of cells during a particular fermentation run). In some embodiments, the isoprene amount is measured at the peak absolute productivity time point. In some embodiments, the peak absolute productivity for the cells is about any of the isoprene amounts disclosed herein.

By "peak specific productivity" is meant the maximum amount of isoprene produced per cell during the culturing of cells for a particular period of time (e.g., the culturing of cells during a particular fermentation run). By "peak specific productivity time point" is meant the time point during the culturing of cells for a particular period of time (e.g., the culturing of cells during a particular fermentation run) when the amount of isoprene produced per cell is at a maximum. The specific productivity is determined by dividing the total productivity by the amount of cells, as determined by optical density at 600 nm (OD600). In some embodiments, the isoprene amount is measured at the peak specific productivity time point. In some embodiments, the peak specific productivity for the cells is about any of the isoprene amounts per cell disclosed herein.

By "cumulative total productivity" is meant the cumulative, total amount of isoprene produced during the culturing of cells for a particular period of time (e.g., the culturing of cells during a particular fermentation run). In some embodiments, the cumulative, total amount of isoprene is measured. In some embodiments, the cumulative total productivity for the cells is about any of the isoprene amounts disclosed herein.

By "relative detector response" refers to the ratio between the detector response (such as the GC/MS area) for one compound (such as isoprene) to the detector response (such as the GC/MS area) of one or more compounds (such as all C5 hydrocarbons). The detector response may be measured as described herein, such as the GC/MS analysis performed with an Agilent 6890 GC/MS system fitted with an Agilent HP-5MS GC/MS column (30 m×250 μm; 0.25 μm film thickness). If desired, the relative detector response can be converted to a weight percentage using the response factors for each of the compounds. This response factor is a measure of how much signal is generated for a given amount of a particular compound (that is, how sensitive the detector is to a particular compound). This response factor can be used as a correction factor to convert the relative detector response to a weight percentage when the detector has different sensitivities to the compounds being compared. Alternatively, the weight percentage can be approximated by assuming that the response factors are the same for the compounds being compared. Thus, the weight percentage can be assumed to be approximately the same as the relative detector response.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/ gram of cells for the wet weight of the cells/hour (nmole/ $g_{wcm}$/hr). In some embodiments, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/ $g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some embodiments, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/ hr, about 300 to about 1,000 nmole/$g_{wcm}$/hr, or about 400 to about 1,000 nmole/$g_{wcm}$/hr.

The amount of isoprene in units of nmole/$g_{wcm}$/hr can be measured as disclosed in U.S. Pat. No. 5,849,970, which is hereby incorporated by reference in its entirety, particularly with respect to the measurement of isoprene production. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, for example, Greenberg et al, *Atmos. Environ.* 27A: 2689-2692, 1993; Silver et al., *Plant Physiol.* 97:1588-1591, 1991, which are each hereby incorporated by reference in their entireties, particularly with respect to the measurement of isoprene production). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some embodiments, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h. The amount of isoprene in ng/$g_{wcm}$/h can be calculated by multiplying the value for isoprene production in the units of nmole/ $g_{wcm}$/hr discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/L$_{broth}$, wherein the volume of broth includes the volume of the cells and the cell medium). In some embodiments, the amount of isoprene is between about 2 to about 5,000 mg/L$_{broth}$, such as between about 2 to about 100 mg/L$_{broth}$, about 100 to about 500 mg/L$_{broth}$, about 500 to about 1,000 mg/L$_{broth}$, about 1,000 to about 2,000 mg/L$_{broth}$, or about 2,000 to about 5,000 mg/L$_{broth}$. In some embodiments, the amount of isoprene is between about 20 to about 5,000 mg/L$_{broth}$, about 100 to about 5,000 mg/L$_{broth}$, about 200 to about 2,000 mg/L$_{broth}$, about 200 to about 1,000 mg/L$_{broth}$, about 300 to about 1,000 mg/L$_{broth}$, or about 400 to about 1,000 mg/L$_{broth}$.

The specific productivity of isoprene in mg of isoprene/L of headspace from shake flask or similar cultures can be measured by taking a 1 ml sample from the cell culture at an OD$_{600}$ value of approximately 1.0, putting it in a 20 mL vial, incubating for 30 minutes, and then measuring the amount of isoprene in the headspace (as described, for example, in Example I, part II). If the OD$_{600}$ value is not 1.0, then the measurement can be normalized to an OD$_{600}$ value of 1.0 by dividing by the OD$_{600}$ value. The value of mg isoprene/L headspace can be converted to mg/L$_{broth}$/hr/OD$_{600}$ of culture broth by multiplying by a factor of 38. The value in units of mg/L$_{broth}$/hr/OD$_{600}$ can be multiplied by the number of hours and the OD$_{600}$ value to obtain the cumulative titer in units of mg of isoprene/L of broth.

The instantaneous isoprene production rate in mg/L$_{broth}$/hr in a fermentor can be measured by taking a sample of the fermentor off-gas, analyzing it for the amount of isoprene (in units such as mg of isoprene per L$_{gas}$) as described, for example, in Example I, part II and multiplying this value by the rate at which off-gas is passed though each liter of broth (e.g., at 1 vvm (volume of air/volume of broth/minute) this is 60 L$_{gas}$ per hour). Thus, an off-gas level of 1 mg/L$_{gas}$ corresponds to an instantaneous production rate of 60 mg/L$_{broth}$/hr at air flow of 1 vvm. If desired, the value in the units mg/L$_{broth}$/hr can be divided by the OD$_{600}$ value to obtain the specific rate in units of mg/L$_{broth}$/hr/OD. The average value of mg isoprene/L$_{gas}$ can be converted to the total product productivity (grams of isoprene per liter of fermentation broth, mg/L$_{broth}$) by multiplying this average off-gas isoprene concentration by the total amount of off-gas sparged per liter of fermentation broth during the fermentation. Thus, an average off-gas isoprene concentration of 0.5 mg/L$_{broth}$/hr over 10 hours at 1 vvm corresponds to a total product concentration of 300 mg isoprene/L$_{broth}$.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene. In some embodiments, the percent conversion of carbon into isoprene is between such as about 0.002 to about 4.0%, about 0.002 to about 3.0%, about 0.002 to about 2.0%, about 0.002 to about 1.6%, about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. In some embodiments, the percent conversion of carbon into isoprene is between about 0.002 to about 0.4%, 0.002 to about 0.16%, 0.04 to about 0.16%, about 0.005 to about 0.3%, about 0.01 to about 0.3%, or about 0.05 to about 0.3%.

The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

$$\text{Carbon Yield} = (\text{moles carbon in isoprene produced})/(\text{moles carbon in carbon source})*100 \quad \text{Equation 1}$$

For this calculation, yeast extract can be assumed to contain 50% w/w carbon. As an example, for the 500 liter described in Example 7, part VIII, the percent conversion of carbon into isoprene can be calculated as shown in Equation 2.

$$\text{Carbon Yield} = (39.1 \text{ g isoprene} * 1/68.1 \text{ mol/g} * 5 \text{ C/mol})/[(181221 \text{ g glucose} * 1/180 \text{ mol/g} * 6 \text{ C/mol}) + (17780 \text{ g yeast extract} * 0.5 * 1/12 \text{ mol/g})] * 100 = 0.042\% \quad \text{Equation 2}$$

For the two 500 liter fermentations described herein (Example 7, parts VII and VIII), the percent conversion of carbon into isoprene was between 0.04-0.06%. A 0.11-0.16% carbon yield has been achieved using 14 liter systems as described herein. Example 11, part V describes the 1.53% conversion of carbon to isoprene using the methods described herein.

One skilled in the art can readily convert the rates of isoprene production or amount of isoprene produced into any other units. Exemplary equations are listed below for interconverting between units.

Units for Rate of Isoprene production (total and specific)

$$1 \text{ g isoprene}/L_{broth}/\text{hr} = 14.7 \text{ mmol isoprene}/L_{broth}/\text{hr} \text{ (total volumetric rate)} \quad \text{Equation 3}$$

$$1 \text{ nmol isoprene}/g_{wcm}/\text{hr} = 1 \text{ nmol isoprene}/L_{broth}/\text{hr}/OD_{600} \text{ (This conversion assumes that one liter of broth with an } OD_{600} \text{ value of 1 has a wet cell weight of 1 gram.)} \quad \text{Equation 4}$$

$$1 \text{ nmol isoprene}/g_{wcm}/\text{hr} = 68.1 \text{ ng isoprene}/g_{wcm}/\text{hr} \text{ (given the molecular weight of isoprene)} \quad \text{Equation 5}$$

$$1 \text{ nmol isoprene}/L_{gas} O_2/\text{hr} = 90 \text{ nmol isoprene}/L_{broth}/\text{hr (at an } O_2 \text{ flow rate of 90 L/hr per L of culture broth)} \quad \text{Equation 6}$$

$$1 \text{ ug isoprene}/L_{gas} \text{ isoprene in off-gas} = 60 \text{ ug isoprene}/L_{broth}/\text{hr at a flow rate of 60 } L_{gas} \text{ per } L_{broth} \text{ (1 vvm)} \quad \text{Equation 7}$$

Units for Titer (Total and Specific)

$$1 \text{ nmol isoprene/mg cell protein} = 150 \text{ nmol isoprene}/L_{broth}/OD_{600} \text{ (This conversion assumes that one liter of broth with an } OD_{600} \text{ value of 1 has a total cell protein of approximately 150 mg) (specific productivity)} \quad \text{Equation 8}$$

$$1 \text{ g isoprene}/L_{broth} = 14.7 \text{ mmol isoprene}/L_{broth} \text{ (total titer)} \quad \text{Equation 9}$$

If desired, Equation 10 can be used to convert any of the units that include the wet weight of the cells into the corresponding units that include the dry weight of the cells.

$$\text{Dry weight of cells} = (\text{wet weight of cells})/3.3 \quad \text{Equation 10}$$

If desired, Equation 11 can be used to convert between units of ppm and ug/L. In particular, "ppm" means parts per million defined in terms of ug/g (w/w). Concentrations of gases can also be expressed on a volumetric basis using "ppmv" (parts per million by volume), defined in terms of uL/L (vol/vol). Conversion of ug/L to ppm (e.g., ug of analyte per g of gas) can be performed by determining the mass per L of off-gas (i.e., the density of the gas). For example, a liter of air at standard temperature and pressure (STP; 101.3 kPa (1 bar) and 273.15K) has a density of approximately 1.29 g/L. Thus, a concentration of 1 ppm (ug/g) equals 1.29 ug/L at STP (equation 11). The conversion of ppm (ug/g) to ug/L is a function of pressure, temperature, and overall composition of the off-gas.

> 1 ppm (ug/g) equals 1.29 ug/L at standard temperature and pressure (STP; 101.3 kPa (1 bar) and 273.15K). Equation 11

Conversion of ug/L to ppmv (e.g., uL of analyte per L of gas) can be performed using the Universal Gas Law (equation 12). For example, an off-gas concentration of 1000 ug/L$_{gas}$ corresponds to 14.7 umol/L$_{gas}$. The universal gas constant is 0.082057 K$^{-1}$ mol$^{-1}$, so using equation 12, the volume occupied by 14.7 umol of HG at STP is equal to 0.329 mL. Therefore, the concentration of 1000 ug/L HG is equal to 329 ppmv or 0.0329% (v/v) at STP.

> PV=nRT, where "P" is pressure, "V" is volume, "n" is moles of gas, "R" is the Universal gas constant, and "T" is temperature in Kelvin. Equation 12

The amount of impurities in isoprene compositions are typically measured herein on a weight per volume (w/v) basis in units such as ug/L. If desired, measurements in units of ug/L can be converted to units of mg/m$^3$ using equation 13.

> 1 ug/L=1 mg/m$^3$ Equation 13

In some embodiments encompassed by the invention, a cell comprising a heterologous nucleic acid encoding an isoprene synthase polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase polypeptide.

In some embodiments encompassed by the invention, a cell comprising a heterologous nucleic acid encoding an isoprene synthase polypeptide and one or more heterologous nucleic acids encoding a DXS, IDI, and/or MVA pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

In some embodiments, the isoprene composition comprises greater than or about 99.90, 99.92, 99.94, 99.96, 99.98, or 100% isoprene by weight compared to the total weight of all C5 hydrocarbons in the composition. In some embodiments, the composition has a relative detector response of greater than or about 99.90, 99.91, 99.92, 99.93, 99.94, 99.95, 99.96, 99.97, 99.98, 99.99, or 100% for isoprene compared to the detector response for all C5 hydrocarbons in the composition. In some embodiments, the isoprene composition comprises between about 99.90 to about 99.92, about 99.92 to about 99.94, about 99.94 to about 99.96, about 99.96 to about 99.98, about 99.98 to 100% isoprene by weight compared to the total weight of all C5 hydrocarbons in the composition.

In some embodiments, the isoprene composition comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne) by weight compared to the total weight of all C5 hydrocarbons in the composition. In some embodiments, the composition has a relative detector response of less than or about 0.12, 0.10, 0.08, 0.06, 0.04, 0.02, 0.01, 0.005, 0.001, 0.0005, 0.0001, 0.00005, or 0.00001% for C5 hydrocarbons other than isoprene compared to the detector response for all C5 hydrocarbons in the composition. In some embodiments, the composition has a relative detector response of less than or about 0.12, 0.10, 0.08, 0.06, 0.04, 0.02, 0.01, 0.005, 0.001, 0.0005, 0.0001, 0.00005, or 0.00001% for 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne compared to the detector response for all C5 hydrocarbons in the composition. In some embodiments, the isoprene composition comprises between about 0.02 to about 0.04%, about 0.04 to about 0.06%, about 0.06 to 0.08%, about 0.08 to 0.10%, or about 0.10 to about 0.12% C5 hydrocarbons other than isoprene (such 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne) by weight compared to the total weight of all C5 hydrocarbons in the composition.

In some embodiments, the isoprene composition comprises less than or about 50, 40, 30, 20, 10, 5, 1, 0.5, 0.1, 0.05, 0.01, or 0.005 ug/L of a compound that inhibits the polymerization of isoprene for any compound in the composition that inhibits the polymerization of isoprene. In some embodiments, the isoprene composition comprises between about 0.005 to about 50, such as about 0.01 to about 10, about 0.01 to about 5, about 0.01 to about 1, about 0.01 to about 0.5, or about 0.01 to about 0.005 ug/L of a compound that inhibits the polymerization of isoprene for any compound in the composition that inhibits the polymerization of isoprene. In some embodiments, the isoprene composition comprises less than or about 50, 40, 30, 20, 10, 5, 1, 0.5, 0.1, 0.05, 0.01, or 0.005 ug/L of a hydrocarbon other than isoprene (such 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne). In some embodiments, the isoprene composition comprises between about 0.005 to about 50, such as about 0.01 to about 10, about 0.01 to about 5, about 0.01 to about 1, about 0.01 to about 0.5, or about 0.01 to about 0.005 ug/L of a hydrocarbon other than isoprene. In some embodiments, the isoprene composition comprises less than or about 50, 40, 30, 20, 10, 5, 1, 0.5, 0.1, 0.05, 0.01, or 0.005 ug/L of a protein or fatty acid (such as a protein or fatty acid that is naturally associated with natural rubber).

In some embodiments, the isoprene composition comprises less than or about 10, 5, 1, 0.8, 0.5, 0.1, 0.05, 0.01, or 0.005 ppm of alpha acetylenes, piperylenes, acetonitrile, or 1,3-cyclopentadiene. In some embodiments, the isoprene composition comprises less than or about 5, 1, 0.5, 0.1, 0.05, 0.01, or 0.005 ppm of sulfur or allenes. In some embodiments, the isoprene composition comprises less than or about 30, 20, 15, 10, 5, 1, 0.5, 0.1, 0.05, 0.01, or 0.005 ppm of all acetylenes (such as pentyne-1, butyne-2, 2MB1-3yne, and 1-pentyne-4yne). In some embodiments, the isoprene composition comprises less than or about 2000, 1000, 500, 200, 100, 50, 40, 30, 20, 10, 5, 1, 0.5, 0.1, 0.05, 0.01, or 0.005 ppm of isoprene dimers, such as cyclic isoprene dimmers (e.g., cyclic C10 compounds derived from the dimerization of two isoprene units).

In some embodiments, the isoprene composition includes ethanol, acetone, a C5 prenyl alcohol (such as 3-methyl-3-buten-1-ol or 3-methyl-2-buten-1-ol), or any two or more of the foregoing. In particular embodiments, the isoprene composition comprises greater than or about 0.005, 0.01, 0.05, 0.1, 0.5, 1, 5, 10, 20, 30, 40, 60, 80, 100, or 120 ug/L of ethanol, acetone, a C5 prenyl alcohol (such as 3-methyl-3-buten-1-ol or 3-methyl-2-buten-1-ol), or any two or more of the foregoing. In some embodiments, the isoprene composition comprises between about 0.005 to about 120, such as about 0.01 to about 80, about 0.01 to about 60, about 0.01 to about 40, about 0.01 to about 30, about 0.01 to about 20, about 0.01 to about 10, about 0.1 to about 80, about 0.1 to about 60, about 0.1 to about 40, about 5 to about 80, about 5 to about 60, or about 5 to about 40 ug/L of ethanol, acetone, a C5 prenyl alcohol, or any two or more of the foregoing.

In some embodiments, the isoprene composition includes one or more of the following components: 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, 2,3-cycloheptenolpyridine, or a linear isoprene polymer (such as a linear isoprene dimer or a linear isoprene trimer derived from the polymerization of multiple isoprene units). In various embodiments, the amount of one of these components relative to amount of isoprene in units of percentage by weight (i.e., weight of the component divided by the weight of isoprene times 100) is greater than or about 0.01, 0.02, 0.05, 0.1, 0.5, 1, 5, 10, 20, 30, 40, 50, 60, 70, 80, 90, 100, or 110% (w/w). In some embodiments, the relative detector response for the second compound compared to the detector response for isoprene is greater than or about 0.01, 0.02, 0.05, 0.1, 0.5, 1, 5, 10, 20, 30, 40, 50, 60, 70, 80, 90, 100, or 110%. In various embodiments, the amount of one of these components relative to amount of isoprene in units of percentage by weight (i.e., weight of the component divided by the weight of isoprene times 100) is between about 0.01 to about 105% (w/w), such as about 0.01 to about 90, about 0.01 to about 80, about 0.01 to about 50, about 0.01 to about 20, about 0.01 to about 10, about 0.02 to about 50, about 0.05 to about 50, about 0.1 to about 50, or 0.1 to about 20% (w/w).

In some embodiments, the isoprene composition includes one or more of the following: an alcohol, an aldehyde, or a ketone (such as any of the alcohols, aldehyes, or ketones described herein). In some embodiments, the isoprene composition includes (i) an alcohol and an aldehyde, (ii) an alcohol and a ketone, (iii) an aldehyde and a ketone, or (iv) an alcohol, an aldehyde, and a ketone.

In some embodiments, the isoprene composition contains one or more of the following: methanol, acetaldehyde, ethanol, methanethiol, 1-butanol, 3-methyl-1-propanol, acetone, acetic acid, 2-butanone, 2-methyl-1-butanol, or indole. In some embodiments, the isoprene composition contains 1 ppm or more of one or more of the following: methanol, acetaldehyde, ethanol, methanethiol, 1-butanol, 3-methyl-1-propanol, acetone, acetic acid, 2-butanone, 2-methyl-1-butanol, or indole. In some embodiments, the concentration of more of one or more of the following: methanol, acetaldehyde, ethanol, methanethiol, 1-butanol, 3-methyl-1-propanol, acetone, acetic acid, 2-butanone, 2-methyl-1-butanol, or indole, is between about 1 to about 10,000 ppm in an isoprene composition (such as off-gas before it is purified). In some embodiments, the isoprene composition (such as off-gas after it has undergone one or more purification steps) includes one or more of the following: methanol, acetaldehyde, ethanol, methanethiol, 1-butanol, 3-methyl-1-propanol, acetone, acetic acid, 2-butanone, 2-methyl-1-butanol, or indole, at a concentration between about 1 to about 100 ppm, such as about 1 to about 10 ppm, about 10 to about 20 ppm, about 20 to about 30 ppm, about 30 to about 40 ppm, about 40 to about 50 ppm, about 50 to about 60 ppm, about 60 to about 70 ppm, about 70 to about 80 ppm, about 80 to about 90 ppm, or about 90 to about 100 ppm. Volatile organic compounds from cell cultures (such as volatile organic compounds in the headspace of cell cultures) can be analyzed using standard methods such as those described herein or other standard methods such as proton transfer reaction-mass spectrometry (see, for example, Bunge et al., *Applied and Environmental Microbiology*, 74(7):2179-2186, 2008 which is hereby incorporated by reference in its entirety, particular with respect to the analysis of volatile organic compounds).

In some embodiments, the composition comprises greater than about 2 mg of isoprene, such as greater than or about 5, 10, 20, 30, 40, 50, 60, 70, 80, 90, 100, 200, 300, 400, 500, 600, 700, 800, 900, or 1000 mg of isoprene. In some embodiments, the composition comprises greater than or about 2, 5, 10, 20, 30, 40, 50, 60, 70, 80, 90, 100 g of isoprene. In some embodiments, the amount of isoprene in the composition is between about 2 to about 5,000 mg, such as between about 2 to about 100 mg, about 100 to about 500 mg, about 500 to about 1,000 mg, about 1,000 to about 2,000 mg, or about 2,000 to about 5,000 mg. In some embodiments, the amount of isoprene in the composition is between about 20 to about 5,000 mg, about 100 to about 5,000 mg, about 200 to about 2,000 mg, about 200 to about 1,000 mg, about 300 to about 1,000 mg, or about 400 to about 1,000 mg. In some embodiments, greater than or about 20, 25, 30, 40, 50, 60, 70, 80, 90, or 95% by weight of the volatile organic fraction of the composition is isoprene.

In some embodiments, the composition includes ethanol. In some embodiments, the composition includes between about 75 to about 90% by weight of ethanol, such as between about 75 to about 80%, about 80 to about 85%, or about 85 to about 90% by weight of ethanol. In some embodiments in which the composition includes ethanol, the composition also includes between about 4 to about 15% by weight of isoprene, such as between about 4 to about 8%, about 8 to about 12%, or about 12 to about 15% by weight of isoprene.

In some embodiments encompassed by the invention, a cell comprising one or more heterologous nucleic acids encoding an isoprene synthase polypeptide, DXS polypeptide, IDI polypeptide, and/or MVA pathway polypeptide produces an amount of an isoprenoid compound (such as a compound with 10 or more carbon atoms that is formed from the reaction of one or more IPP molecules with one or more DMAPP molecules) that is greater than or about 2-fold, 3-fold, 5-fold, 10-fold, 25-fold, 50-fold, 100-fold, 150-fold, 200-fold, 400-fold, or greater than the amount of the isoprenoid compound produced from a corresponding cell grown under essentially the same conditions without the one or more heterologous nucleic acids. In some embodiments encompassed by the invention, a cell comprising one or more heterologous nucleic acids encoding an isoprene synthase polypeptide, DXS polypeptide, IDI polypeptide, and/or MVA pathway polypeptide produces an amount of a C5 prenyl alcohol (such as 3-methyl-3-buten-1-ol or 3-methyl-2-buten-1-ol) that is greater than or about 2-fold, 3-fold, 5-fold, 10-fold, 25-fold, 50-fold, 100-fold, 150-fold, 200-fold, 400-fold, or greater than the amount of the C5 prenyl alcohol produced from a corresponding cell grown under essentially the same conditions without the one or more heterologous nucleic acids.

Exemplary Isoprene Purification Methods

In some embodiments, any of the methods described herein further include recovering the isoprene. For example, the isoprene produced using the compositions and methods of the invention can be recovered using standard techniques. such as gas stripping, membrane enhanced separation, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029, which are each hereby incorporated by reference in their entireties, particularly with respect to isoprene recovery and purification methods). In particular embodiments, extractive distillation with an alcohol (such as ethanol, methanol, propanol, or a combination thereof) is used to recover the isoprene. In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation (such as condensation due to exposure to a condensation coil or do to an increase in pressure). In some embodiments, membrane enrichment of a dilute isoprene vapor stream above the dew point of the vapor resulting in the condensation of liquid isoprene. In some embodiments, the isoprene is compressed and condensed.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent.

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

In some embodiments, at least a portion of the gas phase remaining after one or more recovery steps for the removal of isoprene is recycled by introducing the gas phase into a cell culture system (such as a fermentor) for the production of isoprene.

In some embodiments, any of the methods described herein further include polymerizing the isoprene. For example, standard methods can be used to polymerize the purified isoprene to form cis-polyisoprene or other down stream products using standard methods. Accordingly, the invention also features a tire comprising polyisoprene, such as cis-1,4-polyisoprene and/or trans-1,4-polyisoprene made from any of the isoprene compositions disclosed herein.

Exemplary Methods for Recovery of Prenyl Derivatives

In some embodiments, the methods of the present invention include recovering the prenyl derivatives of Formula (I):

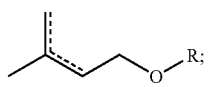

(I)

wherein R is —C(O)R¹; and
R¹ is $C_1$-$C_5$ linear or branched alkyl;
from fermentation off-gas of recombinant host cells. In some embodiments, the prenyl derivative is a prenyl alcohol or acetyl ester thereof. Production of prenyl alcohols is achieved by the methods and compositions of Example 10. However, the compositions and methods of the present invention are not limited to the use of this particular cell line or prenyl derivative. Other suitable compositions and methods for producing prenyl alcohols are provided by U.S. Application No. 61/134,094, filed Jul. 2, 2008 herein incorporated by reference in its entirety. Additional compositions and methods for producing prenyl alcohols are provided by U.S. Pat. No. 6,689,593, and EP 1 354 956.

Prenyl derivatives, such as prenyl alcohols, may be removed from the fermentation broth by a number of techniques well known in the art including but not limited to distillation, gas-stripping, two-phase recovery, and pervaporation. A description and comparison of several of these techniques as applied to butanol recovery from fermentations are provided in Groot et al., *Process Biochemistry*, 27:61-75 (1992). As used herein the term "prenyl alcohol" refers to alcohols derived from C5 isoprenyl units, including C5, C10, C15 and higher alcohols. The term "C5 prenyl alcohol" refers to the unsaturated C5 alcohols 3-methyl-2-buten-1-ol (prenol, DMAPP-ol) and 3-methyl-3-buten-1-ol (isoprenol, IPP-ol). The term "prenol" refers specifically to 3-methyl-2-buten-1-ol, also referred to a 3,3-dimethylallyl alcohol or DMAPP-ol, while the term "isoprenol" refers specifically to 3-methyl-3-buten-1-ol, also referred to as IPP-ol.

Distillation may be used to purify the prenyl derivatives, such as prenyl alcohols, from the fermentation broth. An entrainer may be optionally added to the distillation to enhance separation of the desired product from the bulk medium and may include benzene, toluene, cyclohexane, iso-octane, pentane, carbon tetrachloride, trichloroethylene, diethyl ether, 1-butanol, ethyl acetate, and other organic solvents or mixtures of solvents. The term "entrainer" refers to a component that is added to a distillation mixture to modify the separation characteristics of the material to be separated from the bulk medium. A successful entrainer may form one or more binary and/or ternary azeotropes with water and may have a very low solubility with water. The term "azeotrope" refers to a liquid mixture that is characterized by a constant minimum or maximum boiling point that is lower or higher than that of any of the pure components and that distills without change in composition. Distillation is generally described in Doherty and Malone, *Conceptual Design of Distillation Systems*, McGraw-Hill, New York (2001).

Gas stripping removes volatile compounds from fermentation broth by passing a flow of stripping gas through the fermentor culture or through an external stripping column to form an enriched stripping gas. Examples of stripping gases include helium, argon, carbon dioxide, hydrogen, nitrogen, or mixture of such gases in any desired ratio. The desired product may be condensed from the enriched stripping gas, and the stripping gas may be recycled. The flow rate of the gas may be dependent on such factors such as configuration of the system, volatility of the desired product, and solvent concentration in the fermentor. The enriched stripping gas stream may also be further treated with distillation to produce the product in the desired purity.

Two-phase partitioning bioreactors have been developed to separate hydrophobic products or reactants from growing cultures in the aqueous phase. Generally, an organic solvent such as dodecane is added to the culture medium and is present during fermentation. The solubility of the organic solvent is preferably low, so as to not adversely affect the microorganisms in the fermentation broth. The hydrophobic product extracts into the organic layer during fermentation which is attractive in systems where the product inhibits further production. The organic layer may be separated from the fermentation broth and the product may be isolated by distillation or evaporation of the organic solvent. Alternatively, an ionic liquid may be used in place of the organic solvent. Use of such bioreactors is described in Newman et al., *Biotech and Bioeng*, 95:684-691 (2006).

Pervaporation refers to a process in which a mixture of miscible components is placed in contact with one side of a membrane. A concentration gradient is created by applying a vacuum use or purge gas on the other side of the membrane. The components permeate through the membrane and evaporate into the vapor phase. The vapor or "permeate" is then condensed and the desired product collected. Different species in the fermentation broth will have different affinities for the membrane and diffusion rates through the membrane; therefore, components at low concentration in the feed may be highly enriched in the permeate. The membrane may be a non-porous polymeric membrane or a molecularly porous inorganic membrane. A review of the technique is provided in Vane, *J Chem Technol Biotechnol*, 80:603-629 (2005).

Exemplary Chemical Methods for Conversion of Prenyl Derivatives to Isoprene

In some embodiments, the methods of the present invention further include chemically synthesizing isoprene from biologically-obtained prenyl derivatives. In some embodiments, the prenyl derivative is a compound of Formula (I):

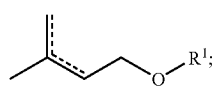

(I)

wherein $R^1$ is hydrogen or —C(O)$R^2$; and $R^2$ is $C_1$-$C_5$ linear or branched alkyl. In some embodiments, the prenyl derivative is a compound of Formula (II):

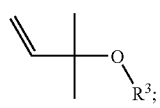

(II)

wherein $R^3$ is hydrogen or —C(O)$R^4$, and $R^4$ is $C_1$-$C_5$ linear or branched alkyl. In some embodiments, the prenyl derivative is a C5 unsaturated alcohol or a $C_1$-$C_5$ linear or branched acyl ester thereof. In some embodiments, the prenyl derivative is a prenyl alcohol (e.g., 3-methyl-3-buten-1-ol, CAS Registry No. 763-32-6, isoprenol; and 3-methyl-2-buten-1-ol, CAS Registry No. 556-82-1, prenol). In some embodiments, the prenyl derivative is an acyl ester (e.g. 3-methyl-3-buten-1-yl acetate and 3-methyl-2-buten-1-yl acetate). In some embodiments, the prenyl derivative is 2-methyl-3-buten-2-ol. In some embodiments, chemical synthesis of isoprene from one or more biologically-obtained prenyl derivatives is achieved by use of a catalyst. In some embodiments, the catalyst is an inorganic acid catalyst (e.g. HCl, HBr, $H_2SO_4$, or $H_3PO_4$), a solid acid catalyst (e.g. activated alumina, a zeolite, or an inorganic acid on an inert carrier), an organic acid catalyst (e.g. p-toluenesulfonic acid or trifluoromethane sulfonic acid), or an organic acid resin (e.g. Nafion or other fluorosulfonic acid resin). In some embodiments, the catalyst is on a solid support. In some embodiments, the catalyst is in solution. In a preferred embodiment, the catalyst is an acidic salt solution. In some embodiments, the catalyst is optionally buffered with additional salts.

For instance, production of isoprene from isoprenol is accomplished by dehydration of isoprenol in an acidic salt (e.g., HCl/NaCl) solution as known in the art (Weitz and Loser, "Isoprene," in Ullmann's Encyclopedia of Industrial Chemistry, 7th edition, electronic release, Wiley-VCH Verlag GMBH, Weinheim, pp. 1-20, 2005; and U.S. Pat. No. 3,792,104 to Mueller). Briefly, a solution containing sodium chloride, water and hydrochloric acid is placed in a reaction (e.g., dehydration) vessel equipped with a reflux condenser (operated at 45° C.), which is connected to a descending condenser (operated at −10° C.). The descending condenser causes condensation of the isoprene product and the isopentenols. The prenyl alcohol(s) are metered to the stirred dehydration vessel (heated at 95° C.) to produce a condensate comprising isoprene. The aqueous phase is continuously recycled to the dehydration vessel, while the organic phase is neutralized with a concentrated aqueous sodium carbonate solution and separated to pure isoprene and isopentonols in a continuous fractionating column. The aqueous phase is removed from the dehydrator at intervals of one hour to keep the liquid at its original level. Common salt and hydrochloric acid are replenished. At one hour intervals, the higher-boiling oligomers are removed from the dehydrator.

Exemplary Biological Methods for Conversion of Prenyl Derivatives to Isoprene

In some embodiments, the methods of the present invention further include producing isoprene from prenyl derivatives, such as prenyl alcohols, of petrochemical or biological origin by feeding the prenyl derivatives to host cells having isoprene synthase and prenol kinase activity. The prenyl derivatives may be as defined in any of the embodiments herein described. In some embodiments, the prenol kinase activity results in an increase in isoprene production by at least about 10, 20, 25, 30, 40, 50, 60, 70, 80, 90, or 100% compared to host cells lacking prenol kinase activity. In some embodiments, the host cells are capable of converting a prenyl derivative, such as a prenyl alcohol, to a diphosphate derivative (e.g. IPP or DMAPP) in one or more sequential steps. In some particularly preferred embodiments, the cells further comprise one or both of an IDI polypeptide and an MVA pathway enzyme. In some embodiments, the IDI polypeptide is overexpressed. In some embodiments the host cells are recombinant host cells comprising a heterologous isoprene synthase enzyme. In further embodiments, the host cells overexpress an enzyme having prenol kinase activity. In some embodiments, the host cells comprise prenol kinase activity, an IDI polypeptide, and an isoprene synthase. In some embodiments, the host cells are capable of converting a prenyl derivative, such as a prenyl alcohol, to a diphosphate derivative (e.g. IPP or DMAPP), optionally converting IPP to DMAPP, and converting DMAPP to isoprene in one or more sequential steps. Suitable host cells include but are not limited to bacterial cells and yeast cells.

In one embodiment, the host cells are recombinant *E. coli* that express heterologous integrated lower and upper MVA pathway enzymes as well as a plant isoprene synthase. Briefly, the bacterial host cells are grown in culture medium that is supplemented with dimethyl allyl alcohol. Isoprene produced by the recombinant bacteria is recoverable from the fermentation off-gas (See, FIG. 116).

In another embodiment, the host cells are recombinant *S. cerevisiae* that express a plant isoprene synthase. Briefly, the yeast host cells are grown in culture medium containing raffinose and galactose, as well as dimethyl allyl alcohol. Isoprene produced by the recombinant yeast is recoverable from the fermentation off-gas (See, FIG. 120).

In another embodiment, the methods of the present invention further include producing isoprene from prenyl derivatives, such as prenyl alcohols, of biological origin, wherein host cells having isoprene synthase and prenol kinase activity a) release a prenyl derivative; b) reuptake the released prenyl derivative, and c) produce isoprene. The prenyl derivatives may be as defined in any of the embodiments herein described. In some embodiments, the prenol kinase activity results in an increase in isoprene production by at least about 10, 20, 25, 30, 40, 50, 60, 70, 80, 90, or 100% compared to host cells lacking prenol kinase activity. In some embodiments, the host cells are capable of converting a prenyl derivative, such as a prenyl alcohol, to a diphosphate derivative (e.g. IPP or DMAPP). In some particularly preferred embodiments, the cells further comprise one or both of an IDI polypeptide and an MVA pathway enzyme. In some embodiments, the IDI polypeptide is overexpressed. In some embodiments the host cells are recombinant host cells comprising a heterologous isoprene synthase enzyme. In further embodiments, the host cells overexpress an enzyme having prenol kinase activity. In some embodiments, the host cells comprise prenol kinase activity, an IDI polypeptide, and an isoprene synthase. Suitable host cells include but are not limited to bacterial cells and yeast cells.

EXAMPLES

The examples, which are intended to be purely exemplary of the invention and should therefore not be considered to limit the invention in any way, also describe and detail aspects and embodiments of the invention discussed above. Unless indicated otherwise, temperature is in degrees Centigrade and pressure is at or near atmospheric. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Example 1

Production of Isoprene in *Escherichia coli* Expressing Recombinant Kudzu Isoprene Synthase I. Construction of Vectors for Expression of the Kudzu Isoprene Synthase in *E. coli*

Figure 2:
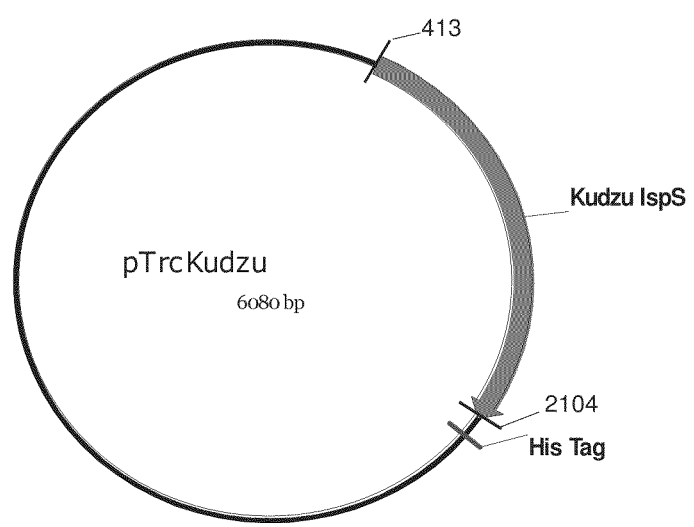
FIG. 2 is a map of pTrcKudzu.

The protein sequence for the kudzu (*Pueraria montana*) isoprene synthase gene (IspS) is obtained from GenBank (AAQ84170). A kudzu isoprene synthase gene, optimized for *E. coli* codon usage, is purchased from DNA2.0 (SEQ ID NO:1). The isoprene synthase gene is removed from the supplied plasmid by restriction endonuclease digestion with BspLU11I/PstI, gel-purified, and ligated into pTrcHis2B (Invitrogen) that had been digested with NcoI/PstI. The construct is designed such that the stop codon in the isoprene synthase gene 5' to the PstI site. As a result, when the construct is expressed the His-Tag is not attached to the isoprene synthase protein. The resulting plasmid, pTrcKudzu, is verified by sequencing (FIGS. 2 and 3).

Figure 4:
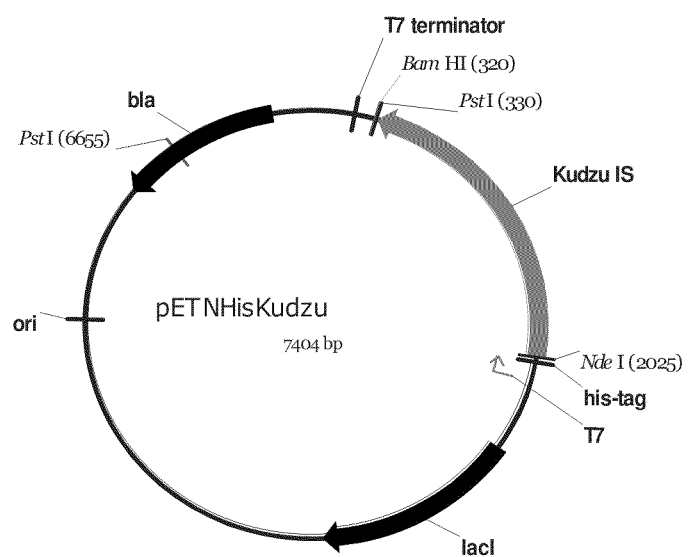
FIG. 4 is a map of pETNHisKudzu.

The isoprene synthase gene is also cloned into pET16b (Novagen). In this case, the isoprene synthase gene is inserted into pET16b such that the recombinant isoprene synthase protein contains the N-terminal His tag. The isoprene synthase gene is amplified from pTrcKudzu by PCR using the primer set pET-His-Kudzu-2F: 5'-CGTGAGATCATATGT-GTGCGACCTCTTCTCAATTTAC (SEQ ID NO:3) and pET-His-Kudzu-R: 5'-CGGTCGACGGATCCCTGCAGT-TAGACATACATCAGCTG (SEQ ID NO:4). These primers add an NdeI site at the 5'-end and a BamH1 site at the 3' end of the gene respectively. The plasmid pTrcKudzu, described above, is used as template DNA, Herculase polymerase (Stratagene) iss used according to manufacture's directions, and primers are added at a concentration of 10 pMols. The PCR is carried out in a total volume of 25 µl. The PCR product is digested with NdeI/BamH1 and cloned into pET16b digested with the same enzymes. The ligation mix is transformed into *E. coli* Top10 (Invitrogen) and the correct clone selected by sequencing. The resulting plasmid, in which the kudzu isoprene synthase gene is expressed from the T7 promoter, is designated pETNHisKudzu (FIGS. 4 and 5).

Figure 6:
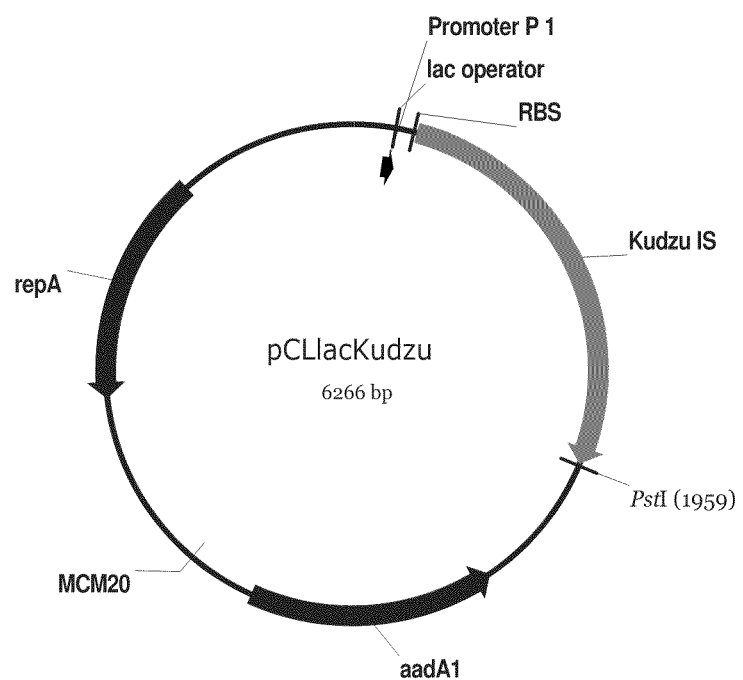
FIG. 6 is a map of pCL-lac-Kudzu.
Figure 8A:
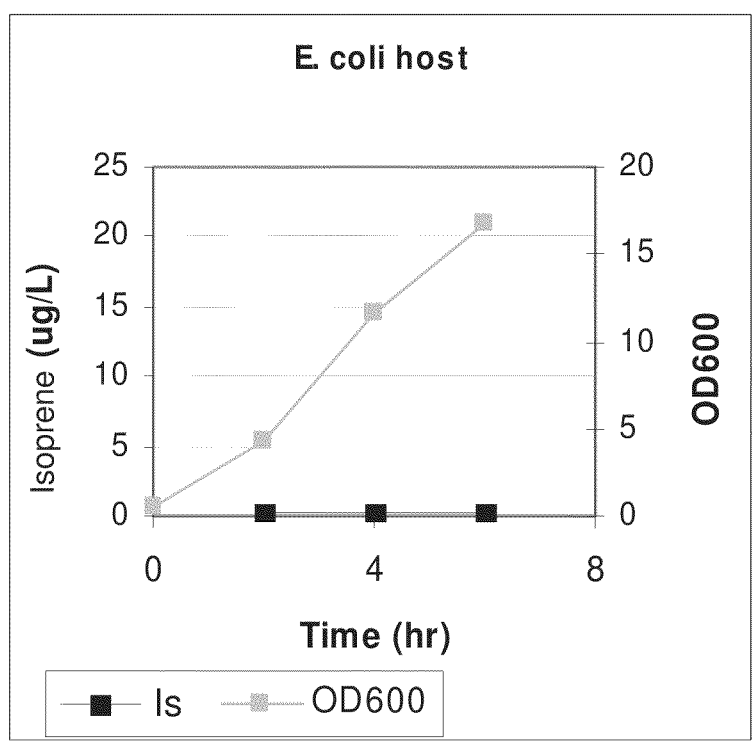
FIG. 8A is a graph showing the production of isoprene in *E. coli* BL21 cells with no vector.
Figure 8B:
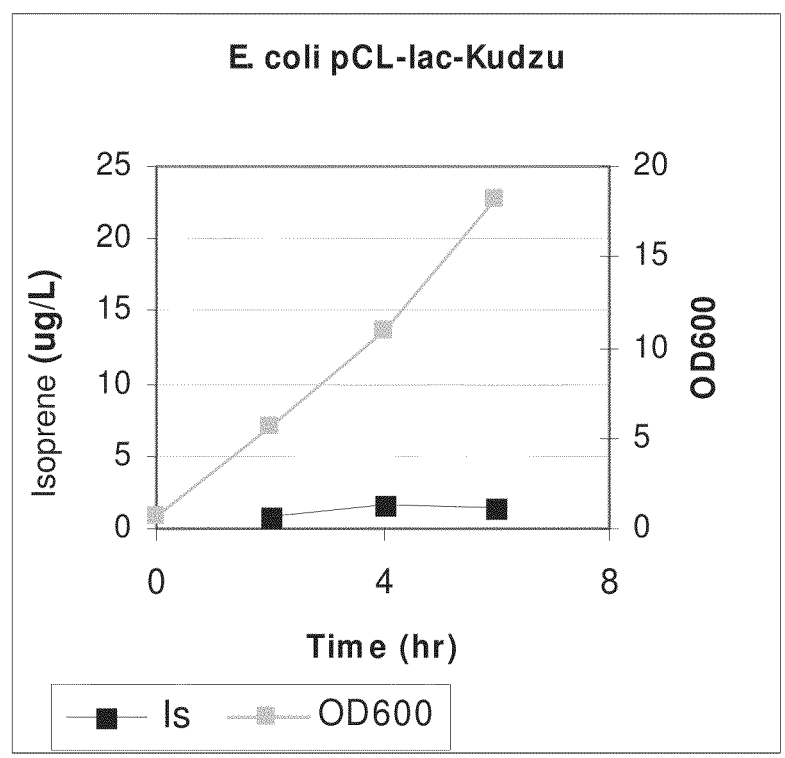
FIG. 8B is a graph showing the production of isoprene in *E. coli* BL21 cells with pCL-lac-Kudzu.
Figure 8C:
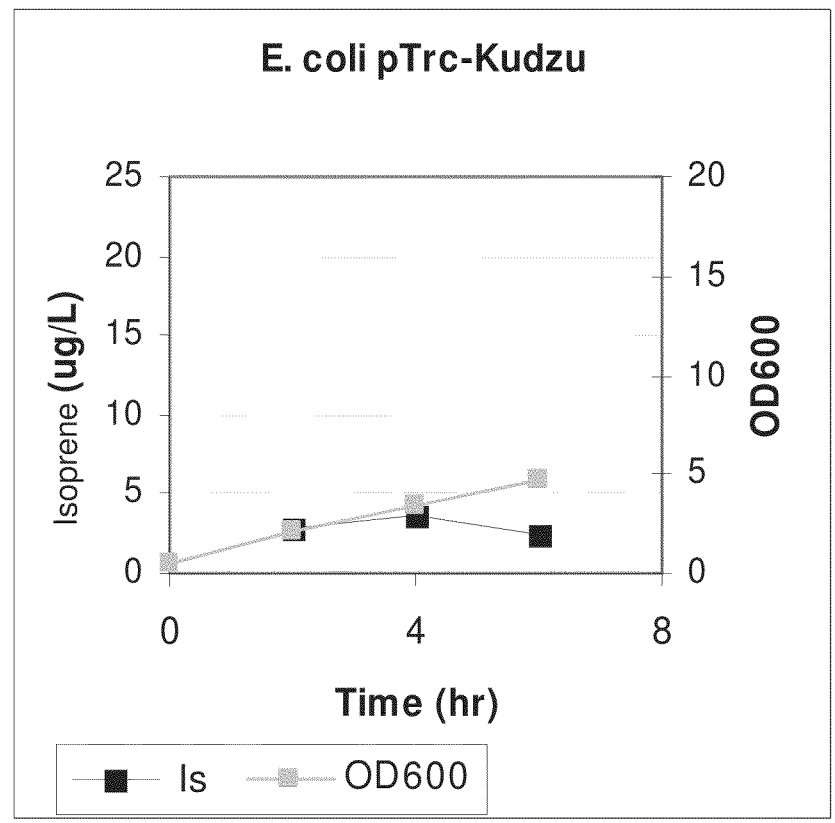
FIG. 8C is a graph showing the production of isoprene in *E. coli* BL21 cells with pTrcKudzu.
Figure 8D:
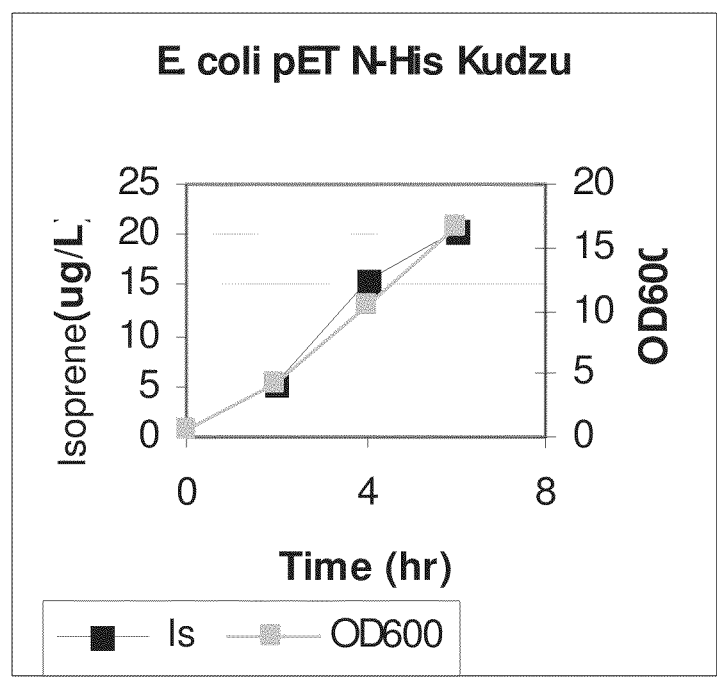
FIG. 8D is a graph showing the production of isoprene in *E. coli* BL21 cells with pETN-HisKudzu.

The kudzu isoprene synthase gene is also cloned into the low copy number plasmid pCL1920. Primers are used to amplify the kudzu isoprene synthase gene from pTrcKudzu described above. The forward primer adds a HindIII site and an *E. coli* consensus RBS to the 5' end. The PstI cloning site is already present in pTrcKudzu just 3' of the stop codon so the reverse primer is constructed such that the final PCR product includes the PstI site. The sequences of the primers are: HindIII-rbs-Kudzu F: 5'-CATATGAAAGCTTGTATCGAT-TAAATAAGGAGGAATAAACC (SEQ ID NO:6) and BamH1-Kudzu R:

5'-CGGTCGACGGATCCCTGCAGTTAGA-CATACATCAGCTG (SEQ ID NO:4). The PCR product is amplified using Herculase polymerase with primers at a concentration of 10 pmol and with 1 ng of template DNA (pTrcKudzu). The amplification protocol includes 30 cycles of (95° C. for 1 minute, 60° C. for 1 minute, 72° C. for 2 minutes). The product is digested with HindIII and PstI and ligated into pCL1920 which has also been digested with HindIII and PstI. The ligation mix is transformed into *E. coli* Top10. Several transformants are checked by sequencing. The resulting plasmid is designated pCL-lac-Kudzu (FIGS. 6 and 7).

II. Determination of Isoprene Production

For the shake flask cultures, one ml of a culture is transferred from shake flasks to 20 ml CTC headspace vials (Agilent vial cat#5188 2753; cap cat#5188 2759). The cap is screwed on tightly and the vials incubated at the equivalent temperature with shaking at 250 rpm. After 30 minutes the vials are removed from the incubator and analyzed as described below (see Table 1 for some experimental values from this assay).

In cases where isoprene production in fermentors is determined, samples are taken from the off-gas of the fermentor and analyzed directly as described below (see Table 2 for some experimental values from this assay).

The analysis is performed using an Agilent 6890 GC/MS system interfaced with a CTC Analytics (Switzerland) CombiPAL autosampler operating in headspace mode. An Agilent HP-5MS GC/MS column (30 m×0.25 mm; 0.25 μm film thickness) is used for separation of analytes. The sampler is set up to inject 500 μL of headspace gas. The GC/MS method utilizes helium as the carrier gas at a flow of 1 ml/min. The injection port is held at 250° C. with a split ratio of 50:1. The oven temperature is held at 37° C. for the 2 minute duration of the analysis. The Agilent 5793N mass selective detector is run in single ion monitoring (SIM) mode on m/z 67. The detector is switched off from 1.4 to 1.7 minutes to allow the elution of permanent gases. Under these conditions isoprene (2-methyl-1,3-butadiene) is observed to elute at 1.78 minutes. A calibration table is used to quantify the absolute amount of isoprene and is found to be linear from 1 μg/L to 2000 μg/L. The limit of detection is estimated to be 50 to 100 ng/L using this method.

III. Production of Isoprene in Shake Flasks Containing *E. coli* Cells Expressing Recombinant Isoprene Synthase The vectors described above are introduced to *E. coli* strain BL21 (Novagen) to produce strains BL21/ptrcKudzu, BL21/pCL-lac-Kudzu and BL21/pETHisKudzu. The strains are spread for isolation onto LA (Luria agar)+carbenicillin (50 μg/ml) and incubated overnight at 37° C. Single colonies are inoculated into 250 ml baffled shake flasks containing 20 ml Luria Bertani broth (LB) and carbenicillin (100 μg/ml). Cultures are grown overnight at 20° C. with shaking at 200 rpm. The $OD_{600}$ of the overnight cultures are measured and the cultures are diluted into a 250 ml baffled shake flask containing 30 ml MagicMedia (Invitrogen)+carbenicillin (100 μg/ml) to an $OD_{600}$~0.05. The culture is incubated at 30° C. with shaking at 200 rpm. When the $OD_{600}$~0.5-0.8, 400 μM IPTG is added and the cells are incubated for a further 6 hours at 30° C. with shaking at 200 rpm. At 0, 2, 4 and 6 hours after induction with IPTG, 1 ml aliquots of the cultures are collected, the $OD_{600}$ is determined and the amount of isoprene produced is measured as described above. Results are shown in FIG. 8.

IV. Production of Isoprene from BL21/ptrcKudzu in 14 Liter Fermentation

Large scale production of isoprene from *E. coli* containing the recombinant kudzu isoprene synthase gene is determined from a fed-batch culture. The recipe for the fermentation media (TM2) per liter of fermentation medium is as follows: $K_2HPO_4$ 13.6 g, $KH_2PO_4$ 13.6 g, $MgSO4*7H_2O$ 2 g, citric acid monohydrate 2 g, ferric ammonium citrate 0.3 g, $(NH_4)_2SO_4$ 3.2 g, yeast extract 5 g, 1000× Modified Trace Metal Solution 1 ml. All of the components are added together and dissolved in $diH_2O$. The pH is adjusted to 6.8 with potassium hydroxide (KOH) and q.s. to volume. The final product is filter sterilized with 0.22μ filter (only, do not autoclave).

The recipe for 1000× Modified Trace Metal Solution is as follows: citric acid*$H_2O$ 40 g, $MnSO_4*H_2O$ 30 g, NaCl 10 g, $FeSO_4*7H_2O$ 1 g, $CoCl_2*6H_2O$ 1 g, $CuSO_4*5H_2O$ 100 mg, $H_3BO_3$ 100 mg, $NaMoO_4*2H_2O$ 100 mg. Each component is one at a time in $diH_2O$, pH to 3.0 with HCl/NaOH, then q.s. to volume and filter sterilized with a 0.22μ filter.

Figure 9A:
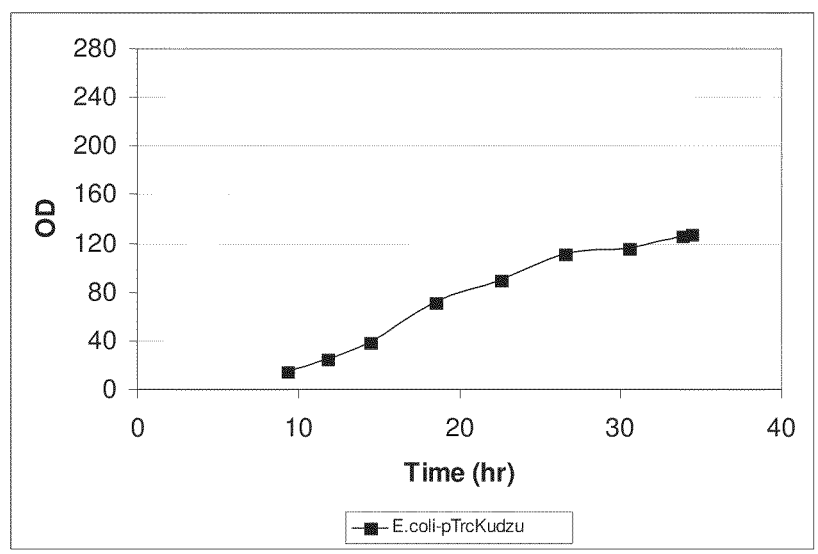
FIG. 9A is a graph showing OD over time of fermentation of *E. coli* BL21/pTrcKudzu in a 14 liter fed batch fermentation.
Figure 9B:
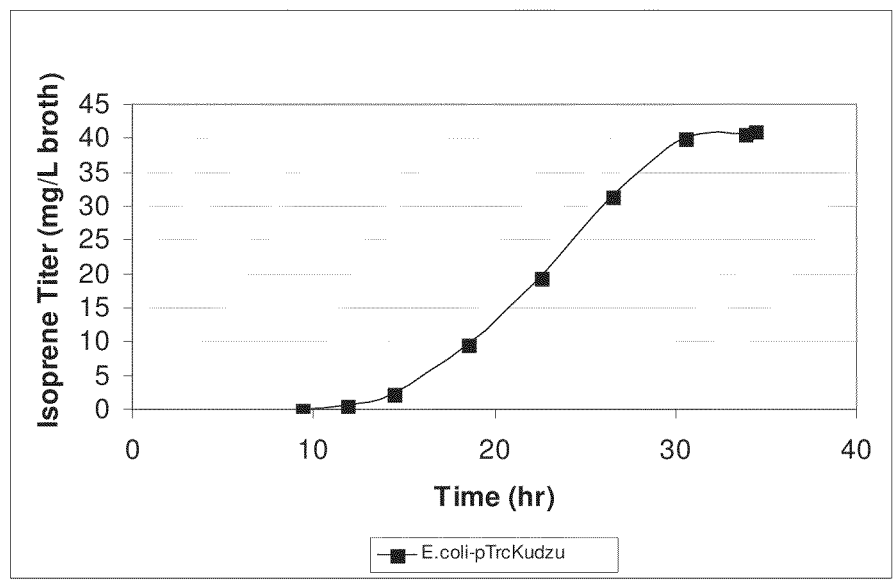
FIG. 9B is a graph showing isoprene production over time of fermentation of *E. coli* BL21/pTrcKudzu in a 14 liter fed batch fermentation.

This experiment is carried out in 14 L bioreactor to monitor isoprene formation from glucose at the desired fermentation, pH 6.7 and temperature 34° C. An inoculum of *E. coli* strain BL21/ptrcKudzu taken from a frozen vial is prepared in soytone-yeast extract-glucose medium. After the inoculum grows to $OD_{550}$=0.6, two 600 ml flasks are centrifuged and the contents resuspended in 70 ml supernatant to transfer the cell pellet (70 ml of OD 3.1 material) to the bioreactor. At various times after inoculation, samples are removed and the amount of isoprene produced is determined as described above. Results are shown in FIG. 9.

Example 2

Figure 30:
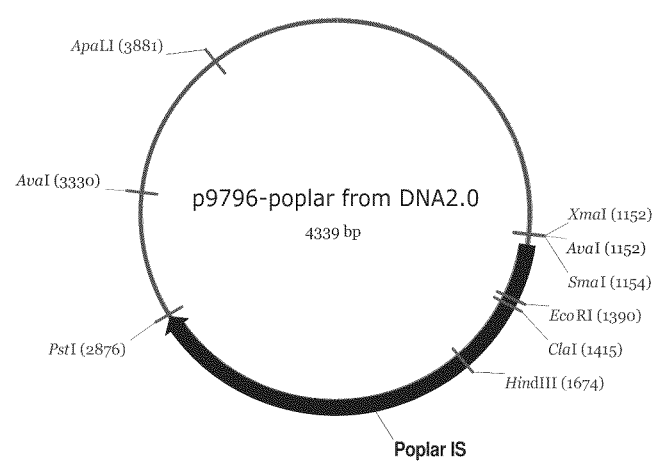
FIG. 30 is a map of p9796-poplar.
Figure 32:
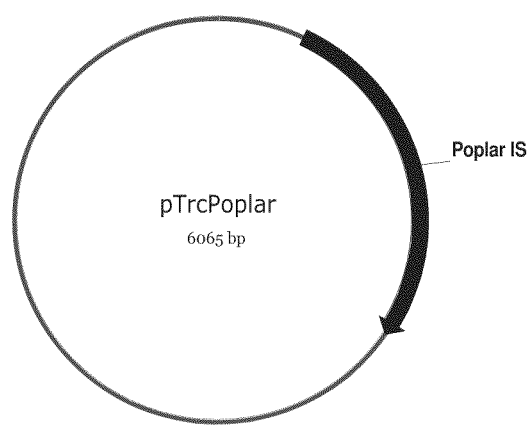
FIG. 32 is a map of pTrcPoplar.

Production of Isoprene in *Escherichia coli* Expressing Recombinant Poplar Isoprene Synthase The protein sequence for the poplar (*Populus alba* x *Populus tremula*) isoprene synthase (Schnitzler, J-P, et al. (2005) *Planta* 222:777-786) is obtained from GenBank (CAC35696). A gene, codon optimized for *E. coli*, is purchased from DNA2.0 (p9796-poplar, FIGS. 30 and 31). The isoprene synthase gene is removed from the supplied plasmid by restriction endonuclease digestion with BspLU11/PstI, gel-purified, and ligated into pTrcHis2B that had been digested with NcoI/PstI. The construct is cloned such that the stop codon in the insert is before the PstI site, which results in a construct in which the His-Tag is not attached to the isoprene synthase protein. The resulting plasmid pTrcPoplar (FIGS. 32 and 33), is verified by sequencing.

Example 3

Figure 10A:
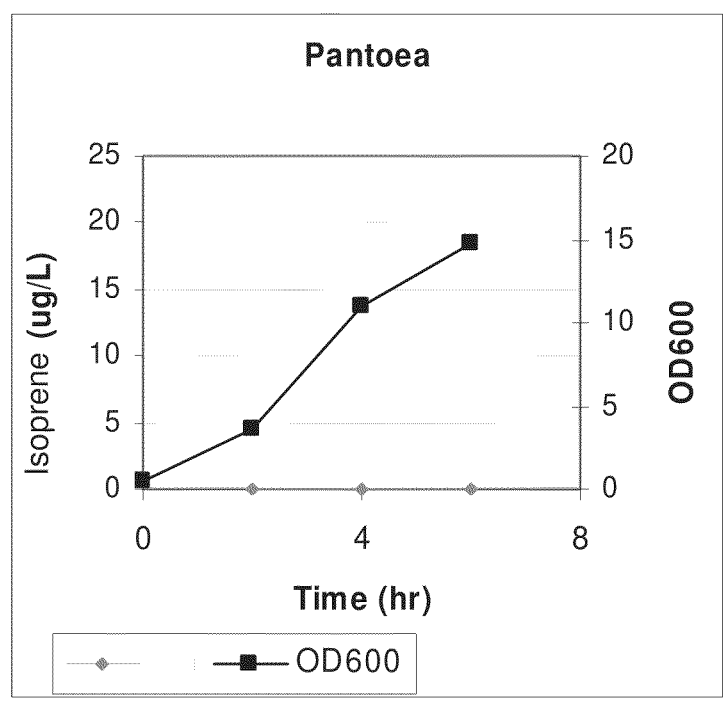
FIG. 10A is a graph showing the production of isoprene in *Panteoa citrea*. Control cells without recombinant kudzu isoprene synthase. Grey diamonds represent isoprene synthesis, black squares represent $OD_{600}$.
Figure 10B:
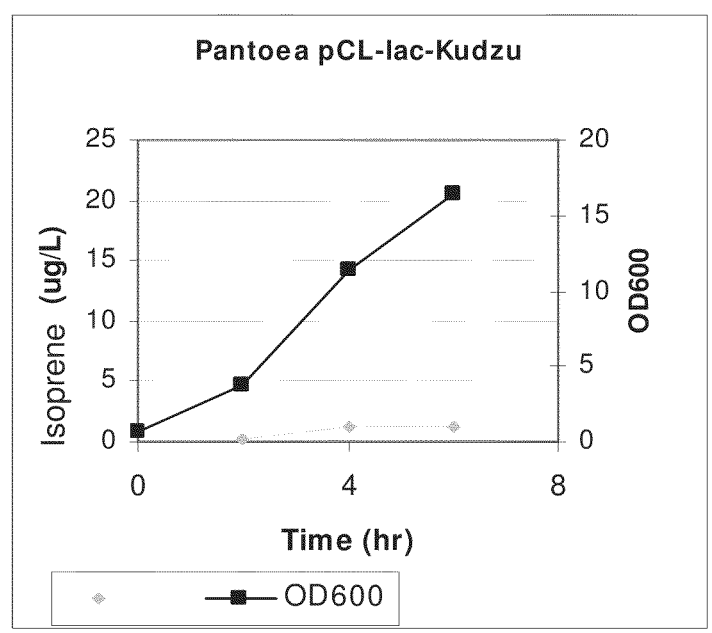
FIG. 10B is a graph showing the production of isoprene in *Panteoa citrea* expressing pCL-lac Kudzu. Grey diamonds represent isoprene synthesis, black squares represent $OD_{600}$.
Figure 10C:
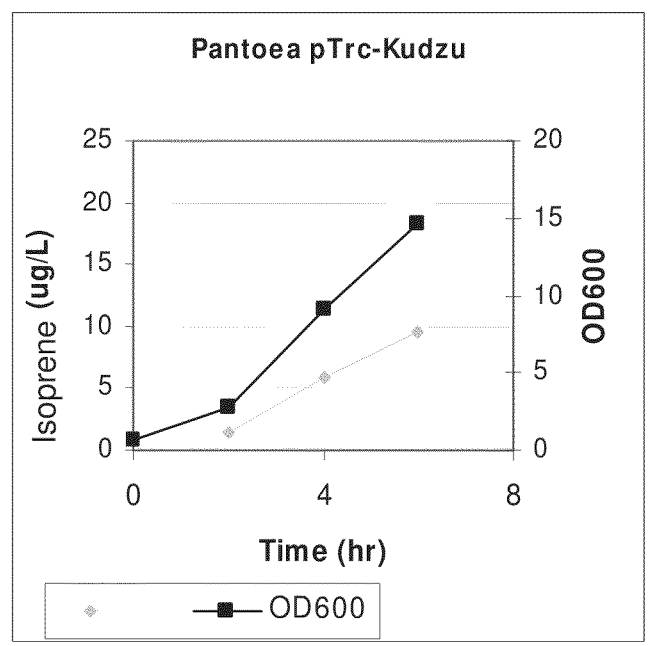
FIG. 10C is a graph showing the production of isoprene in *Panteoa citrea* expressing pTrcKudzu. Grey diamonds represent isoprene synthesis, black squares represent $OD_{600}$.

Production of Isoprene in *Panteoa citrea* Expressing Recombinant Kudzu Isoprene Synthase The pTrcKudzu and pCL-lac Kudzu plasmids described in Example 1 are electroporated into *P. citrea* (U.S. Pat. No. 7,241,587). Transformants are selected on LA containing carbenicillin (200 μg/ml) or spectinomycin (50 μg/ml) respectively. Production of isoprene from shake flasks and determination of the amount of isoprene produced is performed as described in Example 1 for *E. coli* strains expressing recombinant kudzu isoprene synthase. Results are shown in FIG. 10.

Example 4

Production of Isoprene in *Bacillus subtilis* Expressing Recombinant Kudzu Isoprene Synthase I. Construction of a *B. subtilis* Replicating Plasmid for the Expression of Kudzu Isoprene Synthase The kudzu isoprene synthase gene is expressed in *Bacillus subtilis* aprEnprE Pxyl-comK strain (BG3594comK) using a replicating plasmid (pBS19 with a chloramphenicol resistance cassette) under control of the aprE promoter. The isoprene synthase gene, the aprE promoter and the transcription terminator are amplified separately and fused using PCR. The construct is then cloned into pBS19 and transformed into *B. subtilis*.

a) Amplification of the aprE Promoter

The aprE promoter is amplified from chromosomal DNA from *Bacillus subtilis* using the following primers:

```
CF 797 (+) Start aprE promoter MfeI
                                  (SEQ ID NO: 58)
5'-GACATCAATTGCTCCATTTTCTTCTGCTATC CF 07-43 (-) Fuse aprE promoter to Kudzu ispS
                                  (SEQ ID NO: 59)
5'-ATTGAGAAGAGGTCGCACACACTCTTTACCCTCTCCTTTTA
``` b) Amplification of the Isoprene Synthase Gene

The kudzu isoprene synthase gene is amplified from plasmid pTrcKudzu (SEQ ID NO:2). The gene is codon optimized for *E. coli* and synthesized by DNA 2.0. The following primers are used:

```
CF 07-42 (+) Fuse the aprE promoter to kudzu
isoprene synthase gene (GTG start codon)
                                  (SEQ ID NO: 60)
5'-TAAAAGGAGAGGGTAAAGAGTGTGTGCGACCTCTTCTCAAT CF 07-45 (-) Fuse the 3' end of kudzu isoprene
synthase gene to the terminator
                                  (SEQ ID NO: 61)
CCAAGGCCGGTTTTTTTAGACATACATCAGCTGGTTAATC
``` c) Amplification of the Transcription Terminator

The terminator from the alkaline serine protease of *Bacillus amyliquefaciens* is amplified from a previously sequenced plasmid pJHPms382 using the following primers:

```
CF 07-44 (+) Fuse the 3' end of kudzu isoprene
synthase to the terminator
                                  (SEQ ID NO: 62)
5'-GATTAACCAGCTGATGTATGTCTAAAAAAAACCGGCCTTGG CF 07-46 (-) End of B. amyliquefaciens terminator
(BamHI)
                                  (SEQ ID NO: 63)
5'-GACATGACGGATCCGATTACGAATGCCGTCTC
```

The kudzu fragment is fused to the terminator fragment using PCR with the following primers:

```
CF 07-42 (+) Fuse the aprE promoter to kudzu
isoprene synthase gene (GTG start codon)
                                  (SEQ ID NO: 60)
5'-TAAAAGGAGAGGGTAAAGAGTGTGTGCGACCTCTTCTCAAT.

CF 07-46 (-) End of B. amyliquefaciens terminator
(BamHI)
                                  (SEQ ID NO: 63)
5'-GACATGACGGATCCGATTACGAATGCCGTCTC.
```

The kudzu-terminator fragment is fused to the promoter fragment using PCR with the following primers:

```
CF 797 (+) Start aprE promoter MfeI
                                  (SEQ ID NO: 64)
5'-GACATCAATTGCTCCATTTTCTTCTGCTATC CF 07-46 (-) End of B. amyliquefaciens terminator
(BamHI)
                                  (SEQ ID NO: 63)
5'-GACATGACGGATCCGATTACGAATGCCGTCTC
```

The fusion PCR fragment is purified using a Qiagen kit and digested with the restriction enzymes MfeI and BamHI. This digested DNA fragment is gel purified using a Qiagen kit and ligated to a vector known as pBS19, which has been digested with EcoRI and BamHI and gel purified.

The ligation mix is transformed into *E. coli* Top 10 cells and colonies are selected on LA+50 carbenicillin plates. A total of six colonies are chosen and grown overnight in LB+50 carbenicillin and then plasmids are isolated using a Qiagen kit. The plasmids are digested with EcoRI and BamHI to check for inserts and three of the correct plasmids are sent in for sequencing with the following primers:

```
CF 149 (+) EcoRI start of aprE promoter
                                  (SEQ ID NO: 65)
5'-GACATGAATTCCTCCATTTTCTTCTGC CF 847 (+) Sequence in pXX 049 (end of aprE
promoter)
                                  (SEQ ID NO: 66)
5'-AGGAGAGGGTAAAGAGTGAG CF 07-45 (-) Fuse the 3' end of kudzu
isoprene synthase to the terminator
                                  (SEQ ID NO: 61)
5'-CCAAGGCCGGTTTTTTTAGACATACATCAGCTGGTTAATC CF 07-48 (+) Sequencing primer for kudzu isoprene
synthase
                                  (SEQ ID NO: 67)
5'-CTTTTCCATCACCCACCTGAAG CF 07-49 (+) Sequencing in kudzu isoprene synthase
                                  (SEQ ID NO: 68)
5'-GGCGAAATGGTCCAACAACAAAATTATC
```

Figure 52:
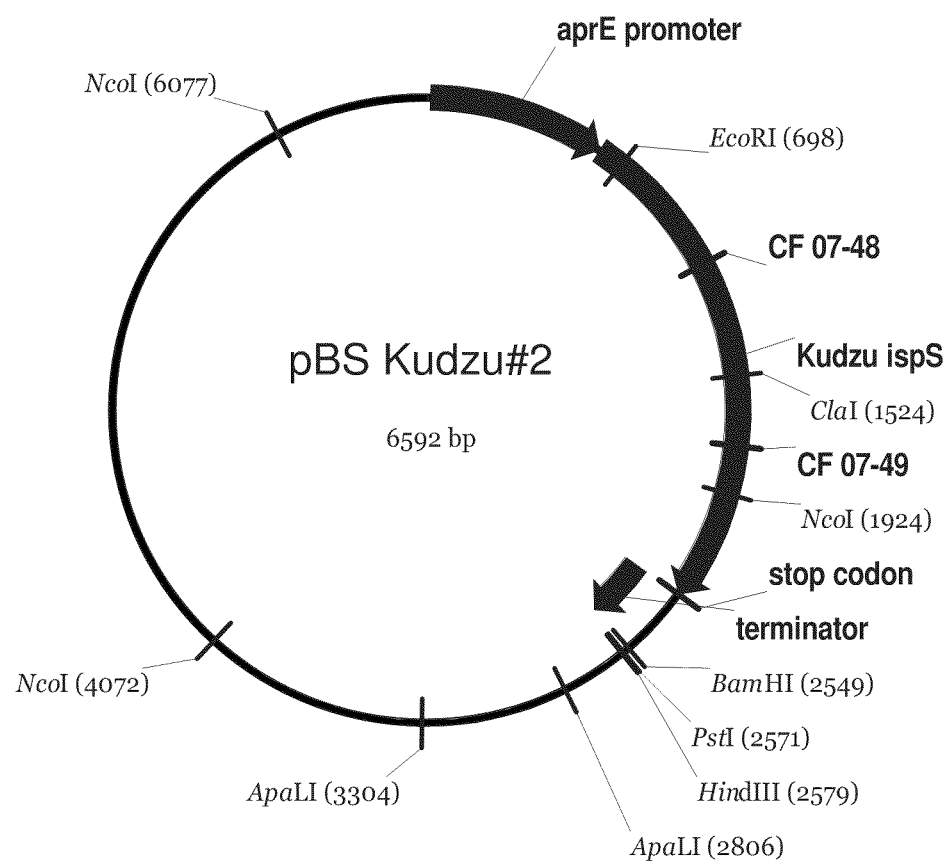
FIG. 52 is a map of pBS Kudzu #2.

The plasmid designated pBS Kudzu #2 (FIGS. 52 and 12) is correct by sequencing and is transformed into BG 3594 comK, a *Bacillus subtilis* host strain. Selection is done on LA+5 chloramphenicol plates. A transformant is chosen and struck to single colonies on LA+5 chloramphenicol, then grown in LB+5 chloramphenicol until it reaches an $OD_{600}$ of 1.5. It is stored frozen in a vial at −80° C. in the presence of glycerol. The resulting strain is designated CF 443.

Figure 11:
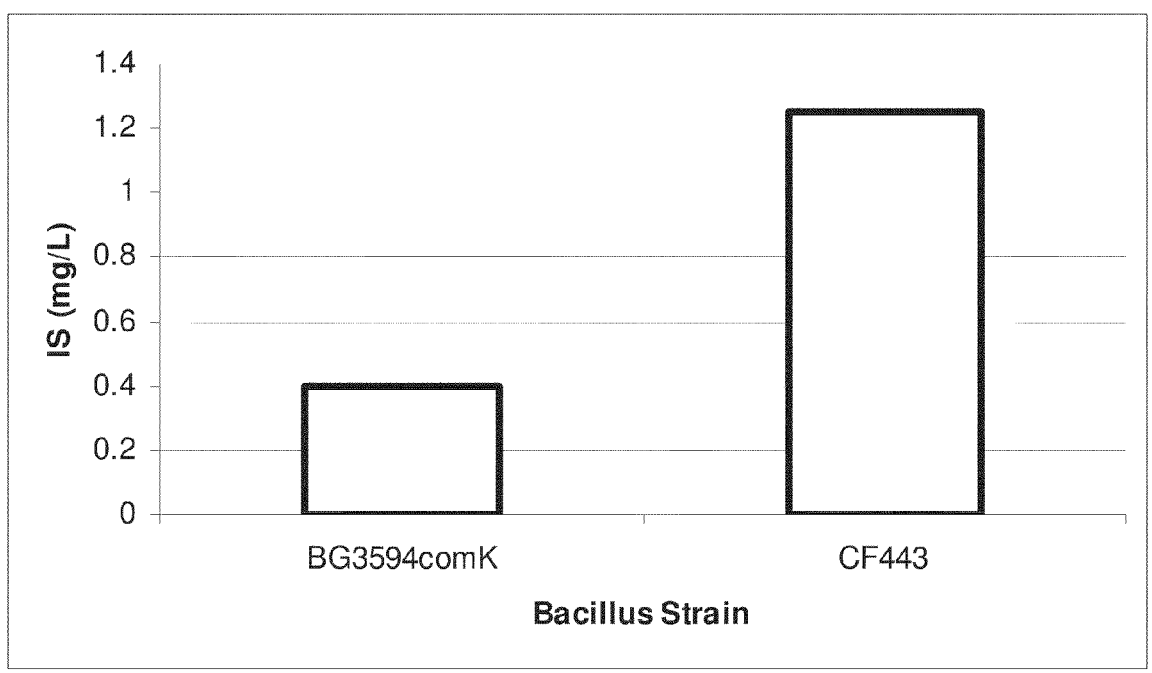
FIG. 11 is a graph showing the production of isoprene in *Bacillus subtilis* expressing recombinant isoprene synthase. BG3594comK is a *B. subtilis* strain without plasmid (native isoprene production). CF443-BG3594comK is a *B. subtilis* strain with pBSKudzu (recombinant isoprene production). IS on the y-axis indicates isoprene.

II. Production of Isoprene in Shake Flasks Containing *B. subtilis* Cells Expressing Recombinant Isoprene Synthase Overnight cultures are inoculated with a single colony of CF 443 from a LA+Chloramphenicol (Cm, 25 μg/ml). Cultures are grown in LB+Cm at 37° C. with shaking at 200 rpm. These overnight cultures (1 ml) are used to inoculate 250 ml baffled shake flasks containing 25 ml Grants II media and chloramphenicol at a final concentration of 25 μg/ml. Grants II Media recipe is 10 g soytone, 3 ml 1M $K_2HPO_4$, 75 g glucose, 3.6 g urea, 100 ml 10× MOPS, q.s. to 1 L with $H_2O$, pH 7.2; 10× MOPS recipe was 83.72 g MOPS, 7.17 g tricine, 12 g KOH pellets, 10 ml 0.276M $K_2SO_4$ solution, 10 ml 0.528M $MgCl_2$ solution, 29.22 g NaCl, 100 ml 100× micronutrients, q.s. to 1 L with $H_2O$; and 100×micronutrients recipe is 1.47 g $CaCl_2*2H_2O$, 0.4 g $FeSO_4*7H_2O$, 0.1 g $MnSO_4*H_2O$, 0.1 g $ZnSO_4*H_2O$, 0.1 g $CoCl_2*6H_2O$, 0.1 g $Na_2MoO_4*2H_2O$, q.s. to 1 L with $H_2O$. Shake flasks are incubated at 37° C. and samples are taken at 18, 24, and 44 hours. At 18 hours the headspaces of CF443 and the control strain are sampled. This represents 18 hours of accumulation of isoprene. The amount of isoprene is determined by gas chromatography as described in Example 1. Production of isoprene is enhanced significantly by expressing recombinant isoprene synthase (FIG. 11).

III. Production of Isoprene by CF443 in 14 L Fermentation

Figure 53A:
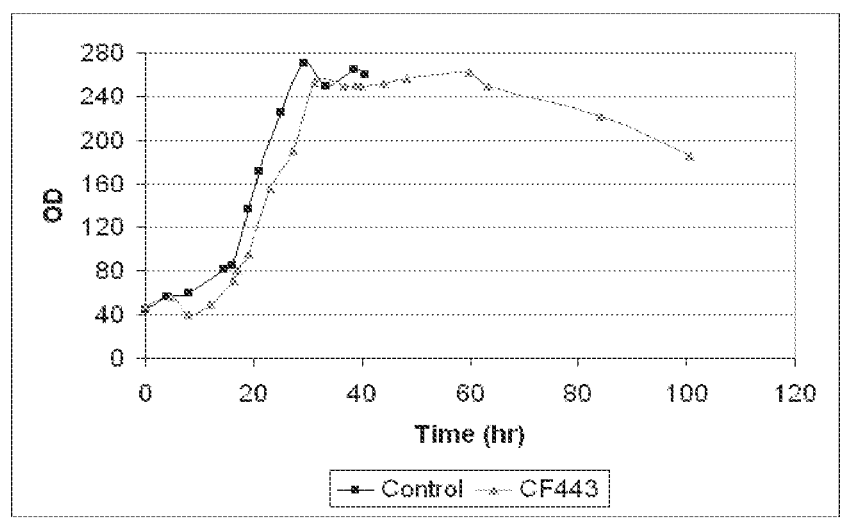
FIG. 53A is a graph showing growth during fermentation time of Bacillus expressing recombinant kudzu isoprene synthase in 14 liter fed batch fermentation. Black diamonds represent a control strain (BG3594comK) without recombinant isoprene synthase (native isoprene production) and grey triangles represent Bacillus with pBSKudzu (recombinant isoprene production).
Figure 53B:
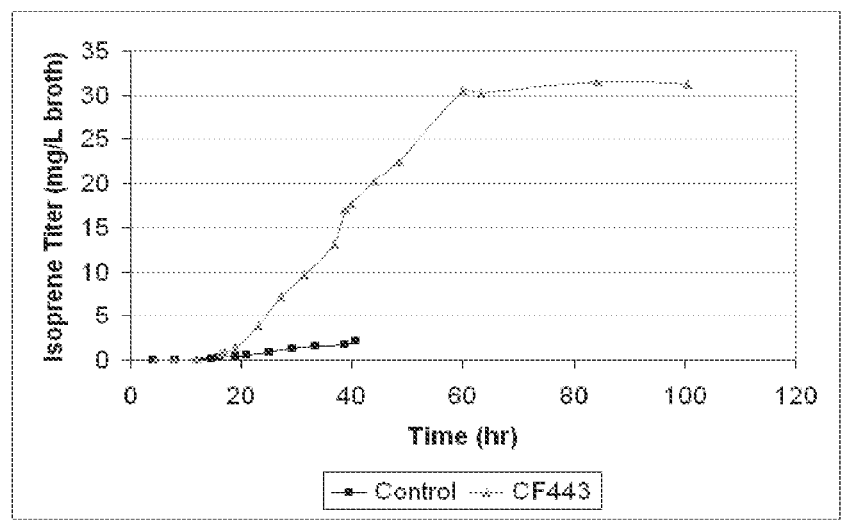
FIG. 53B is a graph showing isoprene production during fermentation time of Bacillus expressing recombinant kudzu isoprene synthase in 14 liter fed batch fermentation. Black diamonds represent a control strain (BG3594comK) without recombinant isoprene synthase (native isoprene production) and grey triangles represent Bacillus with pBSKudzu (recombinant isoprene production).

Large scale production of isoprene from *B. subtilis* containing the recombinant kudzu isoprene synthase gene on a replication plasmid is determined from a fed-batch culture. *Bacillus* strain CF 443, expressing a kudzu isoprene synthase gene, or control stain which does not express a kudzu isoprene synthase gene are cultivated by conventional fed-batch fermentation in a nutrient medium containing soy meal (Cargill), sodium and potassium phosphate, magnesium sulfate and a solution of citric acid, ferric chloride and manganese chloride. Prior to fermentation the media is macerated for 90 minutes using a mixture of enzymes including cellulases, hemicellulases and pectinases (see, WO95/04134). 14-L batch fermentations are fed with 60% wt/wt glucose (Cargill DE99 dextrose, ADM Versadex greens or Danisco invert sugar) and 99% wt/wt oil (Western Family soy oil, where the 99% wt/wt is the concentration of oil before it was added to the cell culture medium). Feed is started when glucose in the batch is non-detectable. The feed rate is ramped over several hours and is adjusted to add oil on an equal carbon basis. The pH is controlled at 6.8-7.4 using 28% w/v ammonium hydroxide. In case of foaming, antifoam agent is added to the media. The fermentation temperature is controlled at 37° C. and the fermentation culture is agitated at 750 rpm. Various other parameters such as pH, DO%, airflow, and pressure are monitored throughout the entire process. The DO% is maintained above 20. Samples are taken over the time course of 36 hours and analyzed for cell growth ($OD_{550}$) and isoprene production. Results of these experiments are presented in FIGS. 53A and 53B.

IV. Integration of the Kudzu Isoprene Synthase (ispS) in *B. subtilis*.

The kudzu isoprene synthase gene is cloned in an integrating plasmid (pJH101-cmpR) under the control of the aprE promoter. Under the conditions tested, no isoprene is detected.

Example 5

Production of Isoprene in *Trichoderma reesei* Expressing Recombinant Kudzu Isoprene Synthase I. Construction of Vectors for Expression of the Kudzu Isoprene Synthase in *T. reesei*

The *Yarrowia lipolytica* codon-optimized kudzu IS gene is synthesized by DNA 2.0 (SEQ ID NO:8) (FIG. 13). This plasmid serves as the template for the following PCR amplification reaction: 1 µl plasmid template (20 ng/ul), 1 µl Primer EL-945 (10 uM) 5'-GCTTATGGATCCTCTAGACTATTA-CACGTACATCAATTGG (SEQ ID NO:9), 1 µl Primer EL-965 (10 uM) 5'-CACCATGTGTGCAACCTCCTC-CCAGTTTAC (SEQ ID NO:10), 1 µl dNTP (10 mM), 5 µl 10× PfuUltra II Fusion HS DNA Polymerase Buffer, 1 µl PfuUltra II Fusion HS DNA Polymerase, 40 µl water in a total reaction volume of 50 µl. The forward primer contains an additional 4 nucleotides at the 5'-end that do not correspond to the *Y. lipolytica* codon-optimized kudzu isoprene synthase gene, but is required for cloning into the pENTR/D-TOPO vector. The reverse primer contains an additional 21 nucleotides at the 5'-end that do not correspond to the *Y. lipolytica* codon-optimized kudzu isoprene synthase gene, but are inserted for cloning into other vector backbones. Using the MJ Research PTC-200 Thermocycler, the PCR reaction is performed as follows: 95° C. for 2 minutes (first cycle only), 95° C. for 30 seconds, 55° C. for 30 seconds, 72° C. for 30 seconds (repeat for 27 cycles), 72° C. for 1 minute after the last cycle. The PCR product is analyzed on a 1.2% E-gel to confirm successful amplification of the *Y. lipolytica* codon-optimized kudzu isoprene synthase gene.

The PCR product is then cloned using the TOPO pENTR/D-TOPO Cloning Kit following manufacturer's protocol: 1 µl PCR reaction, 1 µl Salt solution, 1 µl TOPO pENTR/D-TOPO vector and 3 µl water in a total reaction volume of 6 µl. The reaction is incubated at room temperature for 5 minutes. One microliter of TOPO reaction is transformed into TOP10 chemically competent *E. coli* cells. The transformants are selected on LA+50 µg/ml kanamycin plates. Several colonies are picked and each is inoculated into a 5 ml tube containing LB+50 µg/mlkanamycin and the cultures grown overnight at 37° C. with shaking at 200 rpm. Plasmids are isolated from the overnight culture tubes using QIAprep Spin Miniprep Kit, following manufacturer's protocol. Several plasmids are sequenced to verify that the DNA sequence is correct.

A single pENTR/D-TOPO plasmid encoding a *Y. lipolytica* codon-optimized kudzu isoprene synthase gene is used for Gateway Cloning into a custom-made pTrex3g vector. Construction of pTrex3g is described in WO 2005/001036 A2. The reaction is performed following manufacturer's protocol for the Gateway LR Clonase II Enzyme Mix Kit (Invitrogen): 1 µl *Y. lipolytica* codon-optimized kudzu isoprene synthase gene pENTR/D-TOPO donor vector, 1 µl pTrex3g destination vector, 6 µl TE buffer, pH 8.0 in a total reaction volume of 8 µl. The reaction is incubated at room temperature for 1 hour and then 1 µl proteinase K solution is added and the incubation continued at 37° C. for 10 minutes. Then 1 µl of reaction is transformed into TOP10 chemically competent *E. coli* cells. The transformants are selected on LA+50 µg/ml carbenicillin plates. Several colonies are picked and each is inoculated into a 5 ml tube containing LB+50 µl g/ml carbenicillin and the cultures are grown overnight at 37° C. with shaking at 200 rpm. Plasmids are isolated from the overnight culture tubes using QIAprep Spin Miniprep Kit (Qiagen, Inc.), following manufacturer's protocol. Several plasmids are sequenced to verify that the DNA sequence was correct.

Figure 14:
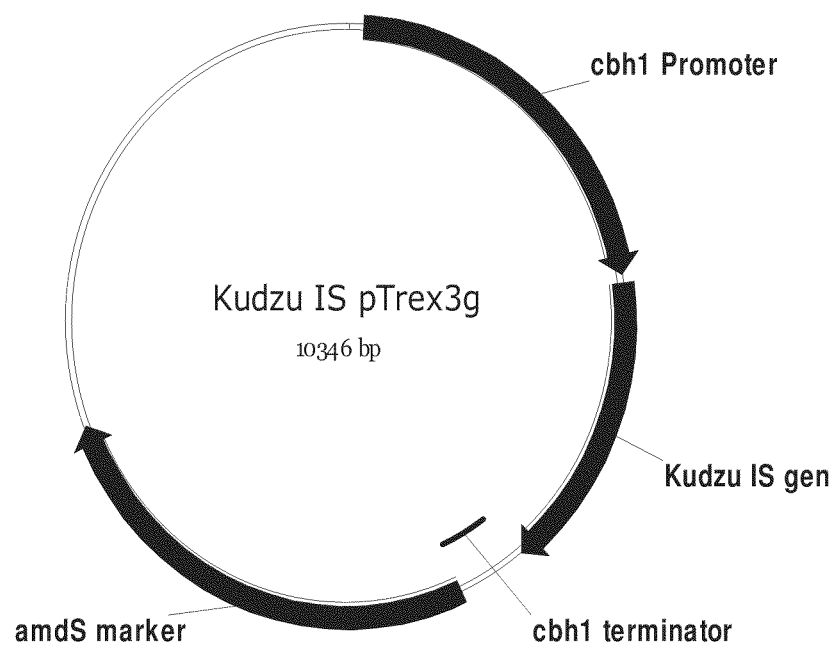
FIG. 14 is a map of pTrex3g comprising a kudzu isoprene synthase gene codon-optimized for expression in *Yarrowia*.

Biolistic transformation of *Y. lipolytica* codon-optimized kudzu isoprene synthase pTrex3g plasmid (FIG. 14) into a quad delete *Trichoderma reesei* strain is performed using the Biolistic PDS-1000/HE Particle Delivery System (see WO 2005/001036 A2). Isolation of stable transformants and shake flask evaluation is performed using protocol listed in Example 11 of patent publication WO 2005/001036 A2.

II. Production of isoprene in recombinant strains of *T. reesei*

One ml of 15 and 36 hour old cultures of isoprene synthase transformants described above are transferred to head space vials. The vials are sealed and incubated for 5 hours at 30° C. Head space gas is measured and isoprene is identified by the method described in Example 1. Two of the transformants show traces of isoprene. The amount of isoprene can be increased by a 14 hour incubation. The two positive samples show isoprene at levels of about 0.5 µg/L for the 14 hour incubation. The untransformed control shows no detectable levels of isoprene. This experiment shows that *T. reesei* is capable of producing isoprene from endogenous precursor when supplied with an exogenous isoprene synthase.

Example 6

Production of Isoprene in *Yarrowia lipolytica* Expressing Recombinant Kudzu Isoprene Synthase I. Construction of Vectors for Expression of the Kudzu Isoprene Synthase in *Y. lipolytica*.

The starting point for the construction of vectors for the expression of the kudzu isoprene synthase gene in *Yarrowia lipolytica* is the vector pSPZ1(MAP29Spb). The complete sequence of this vector (SEQ ID No:11) is shown in FIG. 15.

The following fragments are amplified by PCR using chromosomal DNA of a *Y. lipolytica* strain GICC 120285 as the template: a promotorless form of the URA3 gene, a fragment of 18S ribosomal RNA gene, a transcription terminator of the Y. lipolytica XPR2 gene and two DNA fragments containing the promoters of XPR2 and ICL1 genes. The following PCR primers are used:

ICL1 3
(SEQ ID NO: 69)
5'-GGTGAATTCAGTCTACTGGGGATTCCCAAATCTATATATACTGCAGGTGAC

ICL1 5
(SEQ ID NO: 70)
5'-GCAGGTGGGAAACTATGCACTCC

XPR3
(SEQ ID NO: 71)
5'-CCTGAATTCTGTTGGATTGGAGGATTGGATAGTGGG

XPR5
(SEQ ID NO: 72)
5'-GGTGTCGACGTACGGTCGAGCTTATTGACC

XPRT3
(SEQ ID NO: 73)
5'-GGTGGGCCCGCATTTTGCCACCTACAAGCCAG

XPRT 5
(SEQ ID NO: 74)
5'-GGTGAATTCTAGAGGATCCCAACGCTGTTGCCTACAACGG

Y18S3
(SEQ ID NO: 75)
5'-GGTGCGGCCGCTGTCTGGACCTGGTGAGTTTCCCCG

Y18S 5
(SEQ ID NO: 76)
5'-GGTGGGCCCATTAAATCAGTTATCGTTTATTTGATAG

YURA3
(SEQ ID NO: 77)
5'-GGTGACCAGCAAGTCCATGGGTGGTTTGATCATGG

YURA 50
(SEQ ID NO: 78)
5'-GGTGCGGCCGCCTTTGGAGTACGACTCCAACTATG

YURA 51
(SEQ ID NO: 79)
5'-GCGGCCGCAGACTAAATTTATTTCAGTCTCC

For PCR amplification the PfuUltraII polymerase (Stratagene), supplier-provided buffer and dNTPs, 2.5 µM primers and the indicated template DNA are used as per the manufacturer's instructions. The amplification is done using the following cycle: 95° C. for 1 min; 34× (95° C. for 30 sec; 55° C. for 30 sec; 72° C. for 3 min) and 10 min at 72° C. followed by a 4° C. incubation.

Figure 18B:
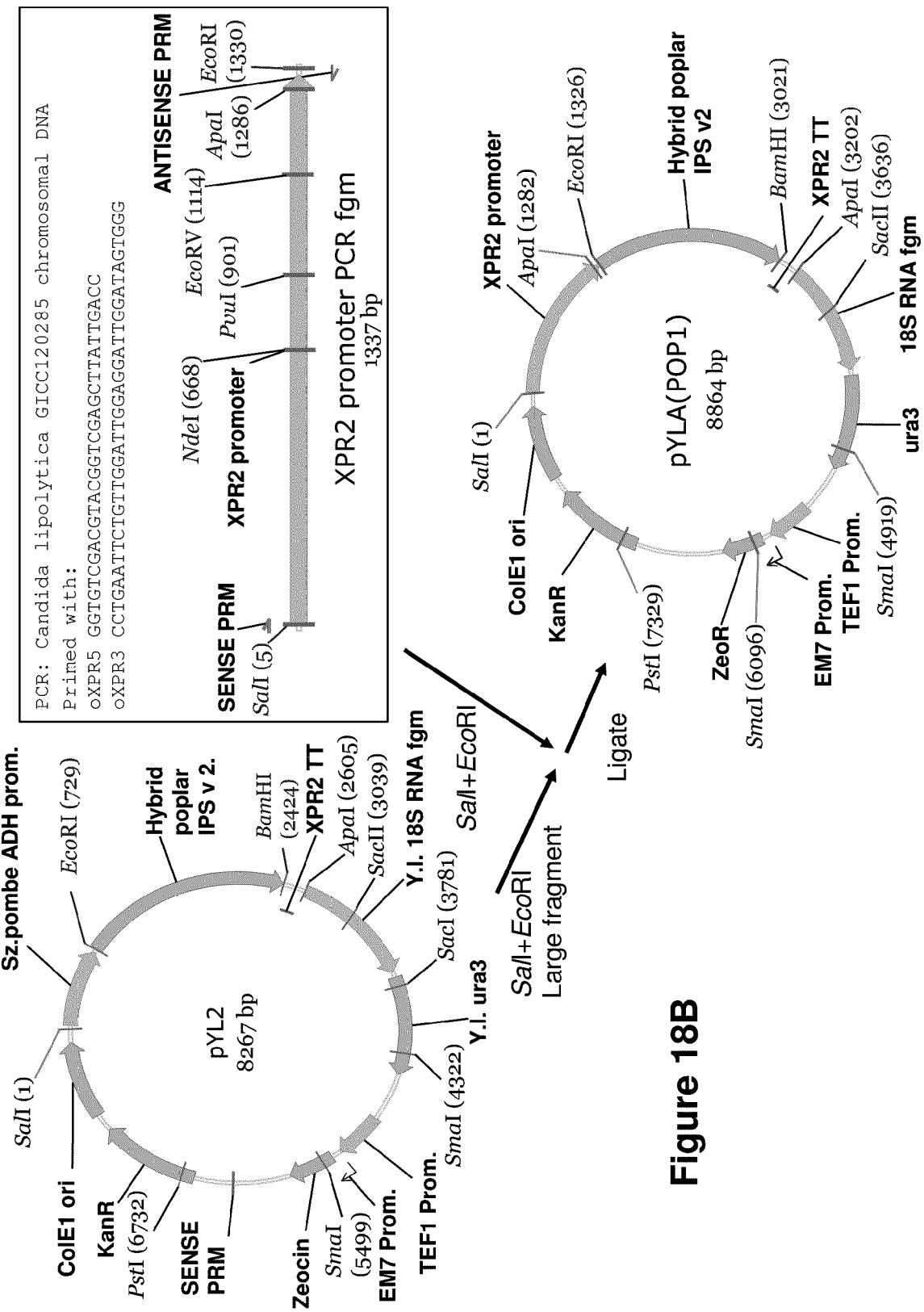
FIG. 18B shows a schematic outlining construction of the vector pYLA(POP1) (SEQ ID NO:72 and SEQ ID NO: 71).
Figure 18C:
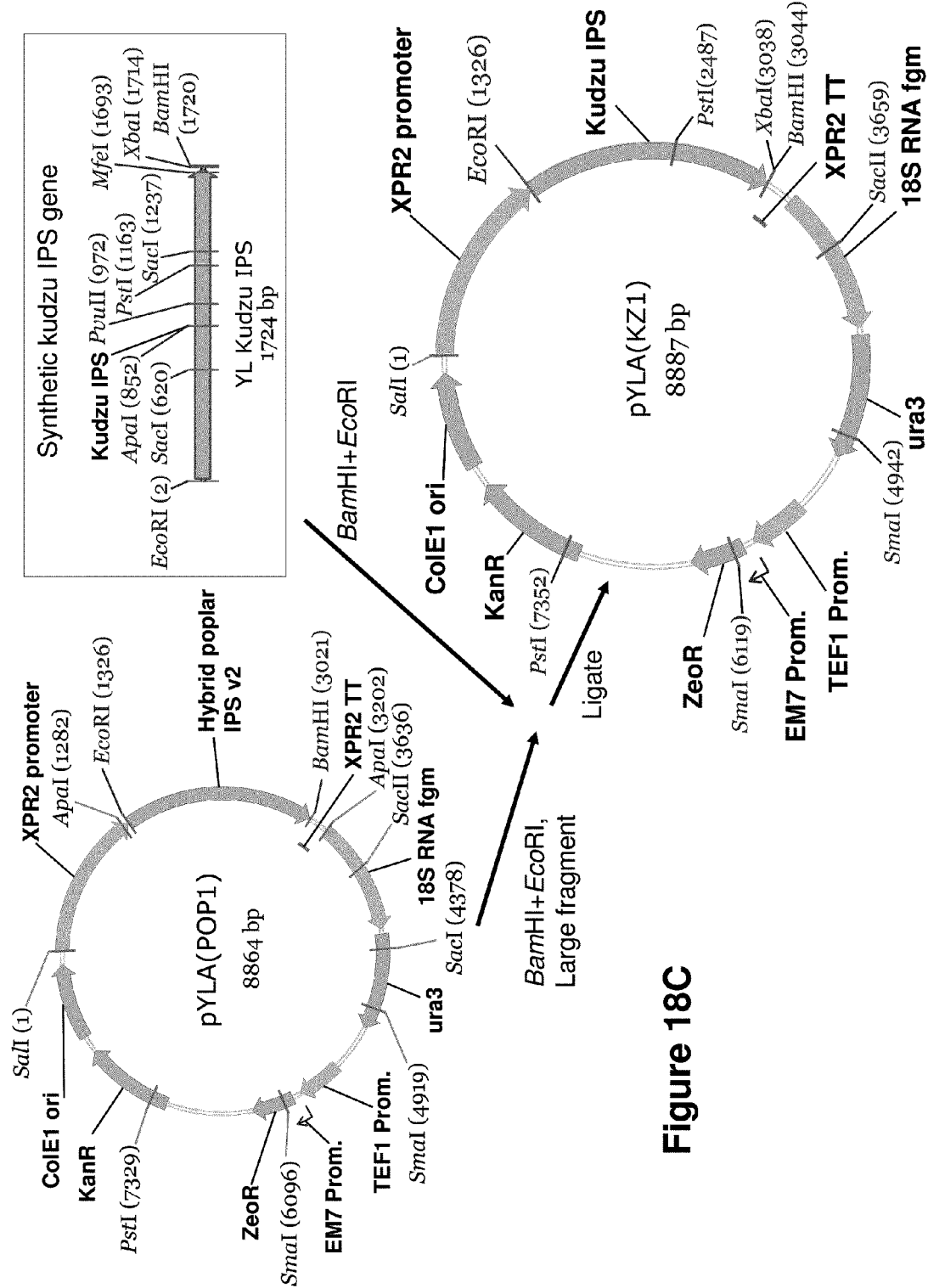
FIG. 18C shows a schematic outlining construction of the vector pYLA(KZ1)
Figure 18D:
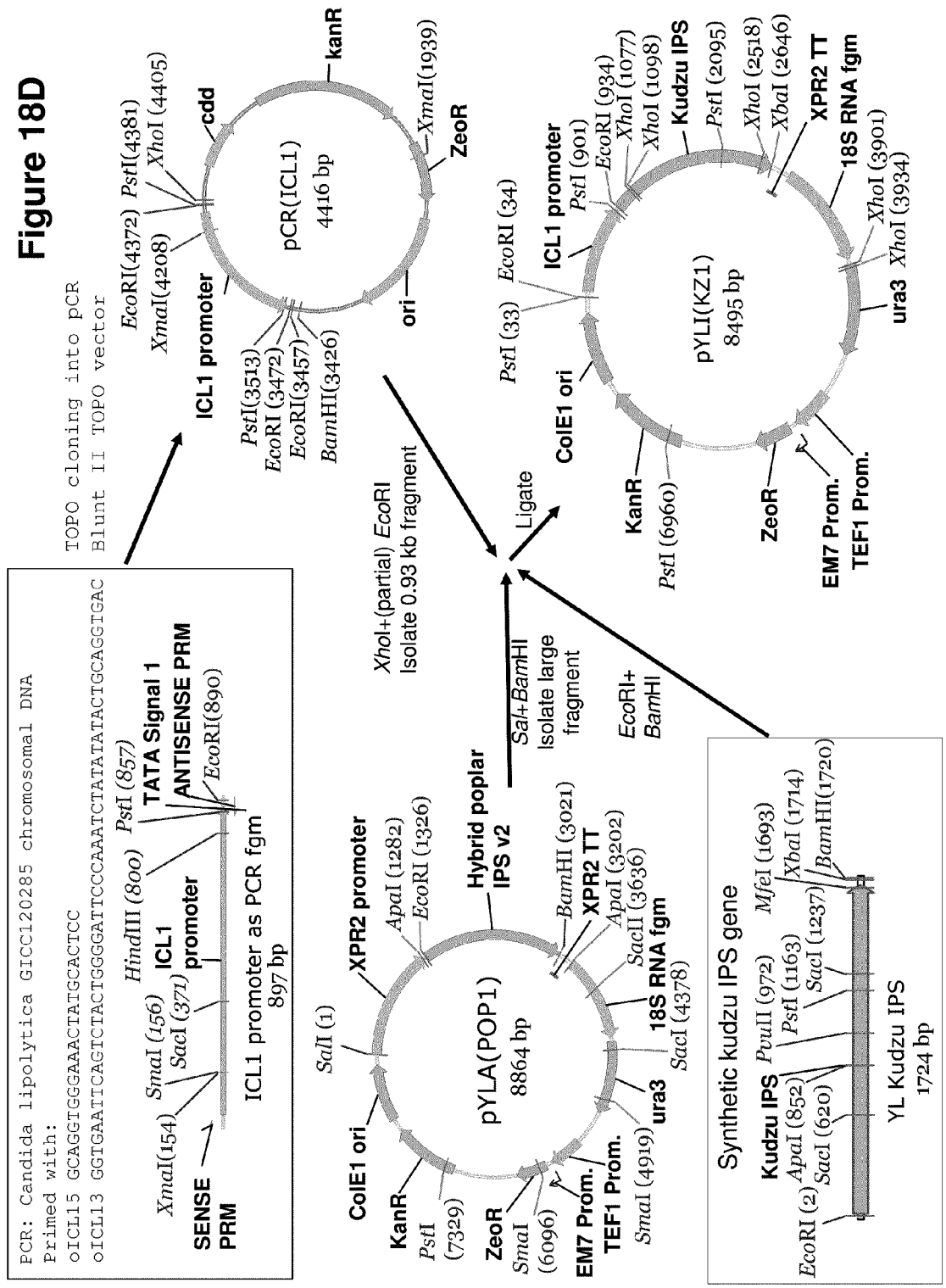
FIG. 18D shows a schematic outlining construction of the vector pYLI(KZ1) (SEQ ID NO: 70 and SEQ ID NO: 69).
Figure 18E:
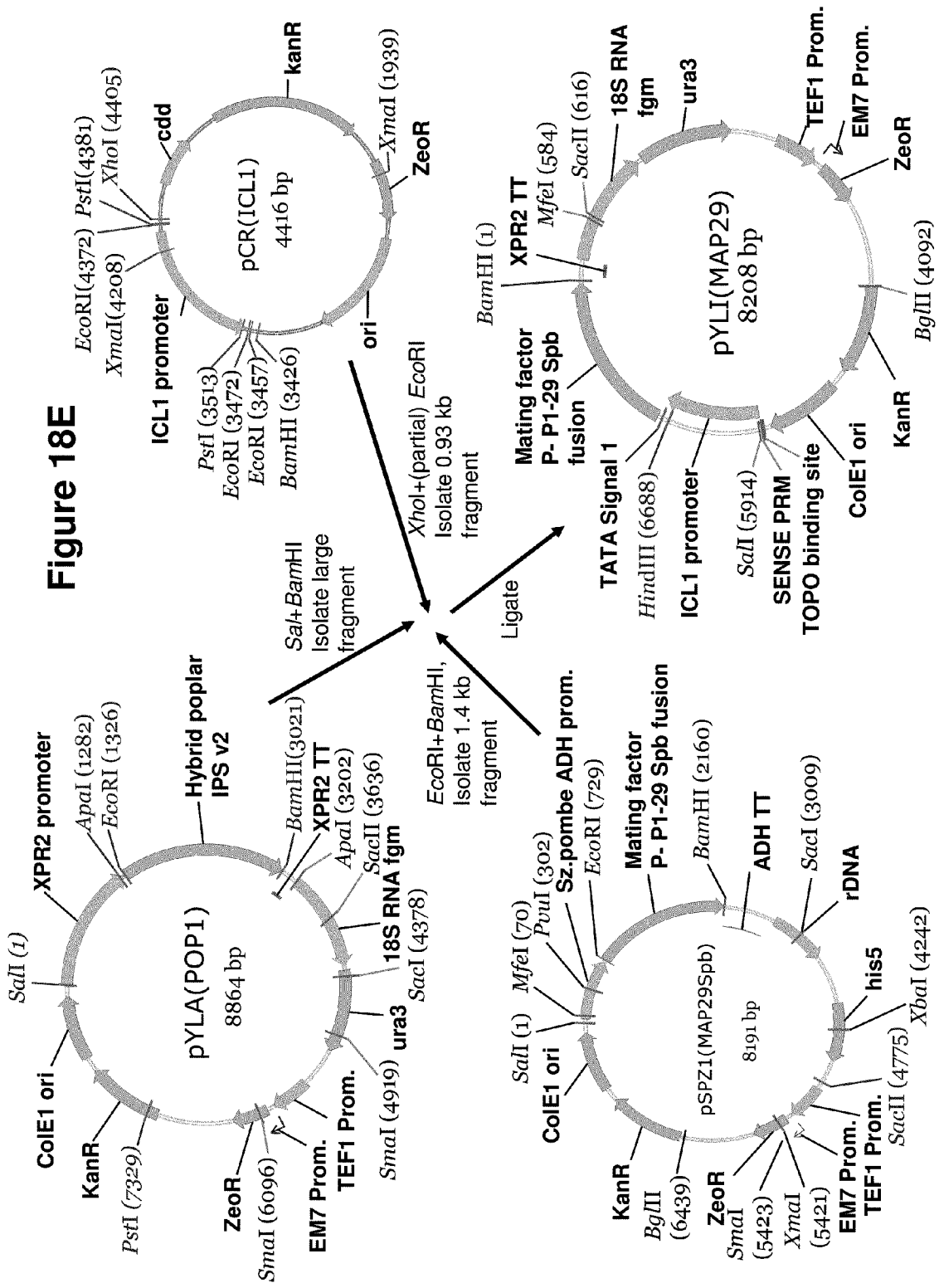
FIG. 18E shows a schematic outlining construction of the vector pYLI(MAP29)
Figure 18F:
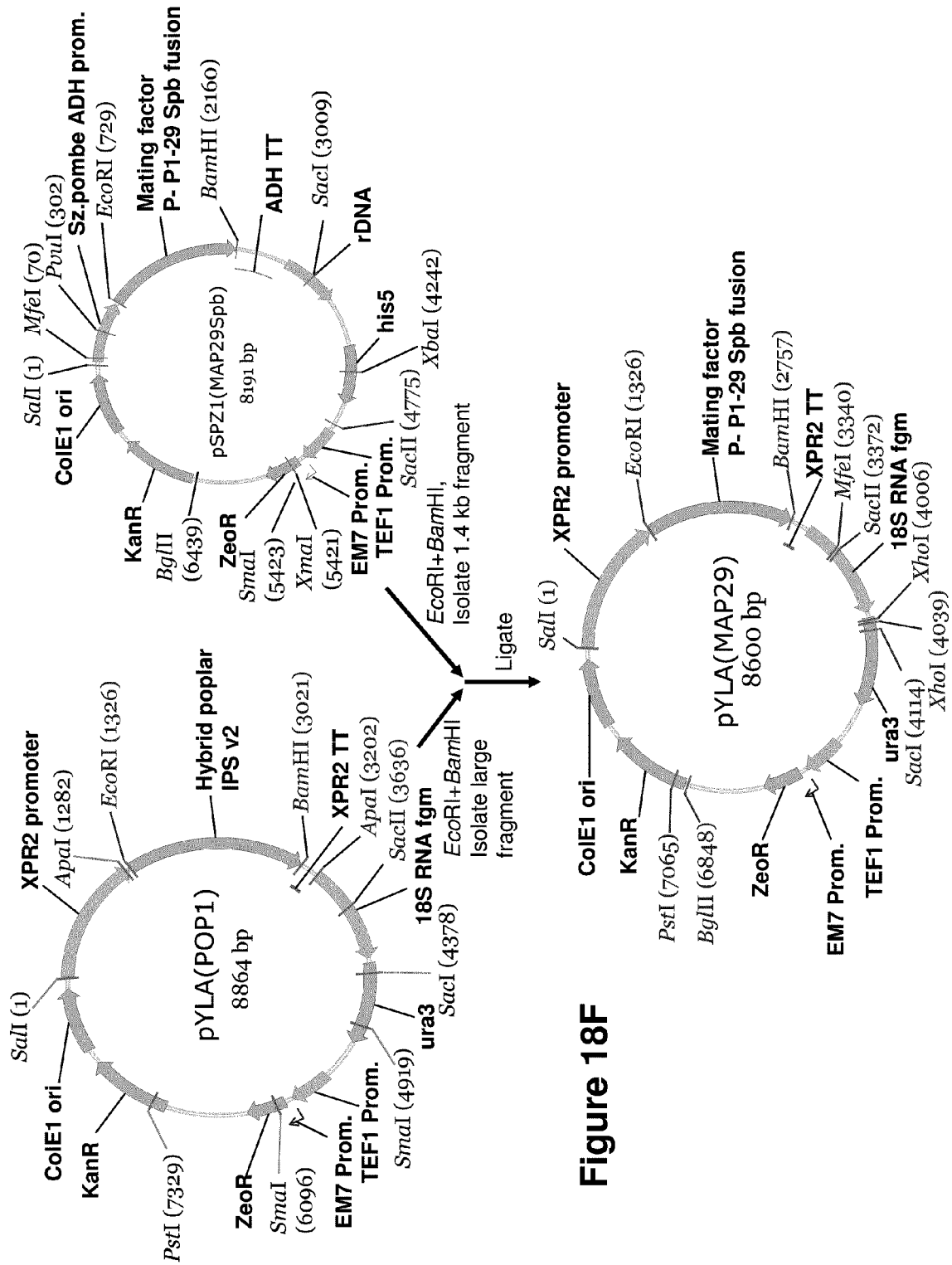
FIG. 18F shows a schematic outlining construction of the vector pYLA(MAP29)

Synthetic DNA molecules encoding the kudzu isoprene synthase gene, codon-optimized for expression in *Yarrowia*, are obtained from DNA 2.0 (FIG. 16; SEQ ID NO:12). Full detail of the construction scheme of the plasmids pYLA (KZ1) and pYLI(KZ1) carrying the synthetic kudzu isoprene synthase gene under control of XPR2 and ICL1 promoters respectively is presented in FIG. 18. Control plasmids in which a mating factor gene (MAP29) is inserted in place of an isoprene synthase gene are also constructed (FIGS. 18E and 18F).

A similar cloning procedure can be used to express a poplar (*Populus alba×Populus tremula*) isoprene synthase gene. The sequence of the poplar isoprene is described in Miller B. et al. (2001) *Planta* 213, 483-487 and shown in FIG. 17 (SEQ ID NO:13). A construction scheme for the generation of the plasmids pYLA(POP1) and pYLI(POP1) carrying synthetic poplar isoprene synthase gene under control of XPR2 and ICL1 promoters respectively is presented in FIGS. 18A and B.

II. Production of Isoprene by Recombinant Strains of *E. lipolytica*.

Vectors pYLA(KZ1), pYLI(KZ1), pYLA(MAP29) and pYLI(MAP29) are digested with SacII and used to transform the strain *Y. lipolytica* CLIB 122 by a standard lithium acetate/polyethylene glycol procedure to uridine prototrophy. Briefly, the yeast cells grown in YEPD (1% yeast extract, 2% peptone, 2% glucose) overnight, are collected by centrifugation (4000 rpm, 10 min), washed once with sterile water and suspended in 0.1 M lithium acetate, pH 6.0. Two hundred µl aliquots of the cell suspension are mixed with linearized plasmid DNA solution (10-20 µg), incubated for 10 minutes at room temperature and mixed with 1 ml of 50% PEG 4000 in the same buffer. The suspensions are further incubated for 1 hour at room temperature followed by a 2 minutes heat shock at 42° C. Cells are then plated on SC his leu plates (0.67% yeast nitrogen base, 2% glucose, 100 mg/L each of leucine and histidine). Transformants appear after 3-4 days of incubation at 30° C.

Figure 20A:
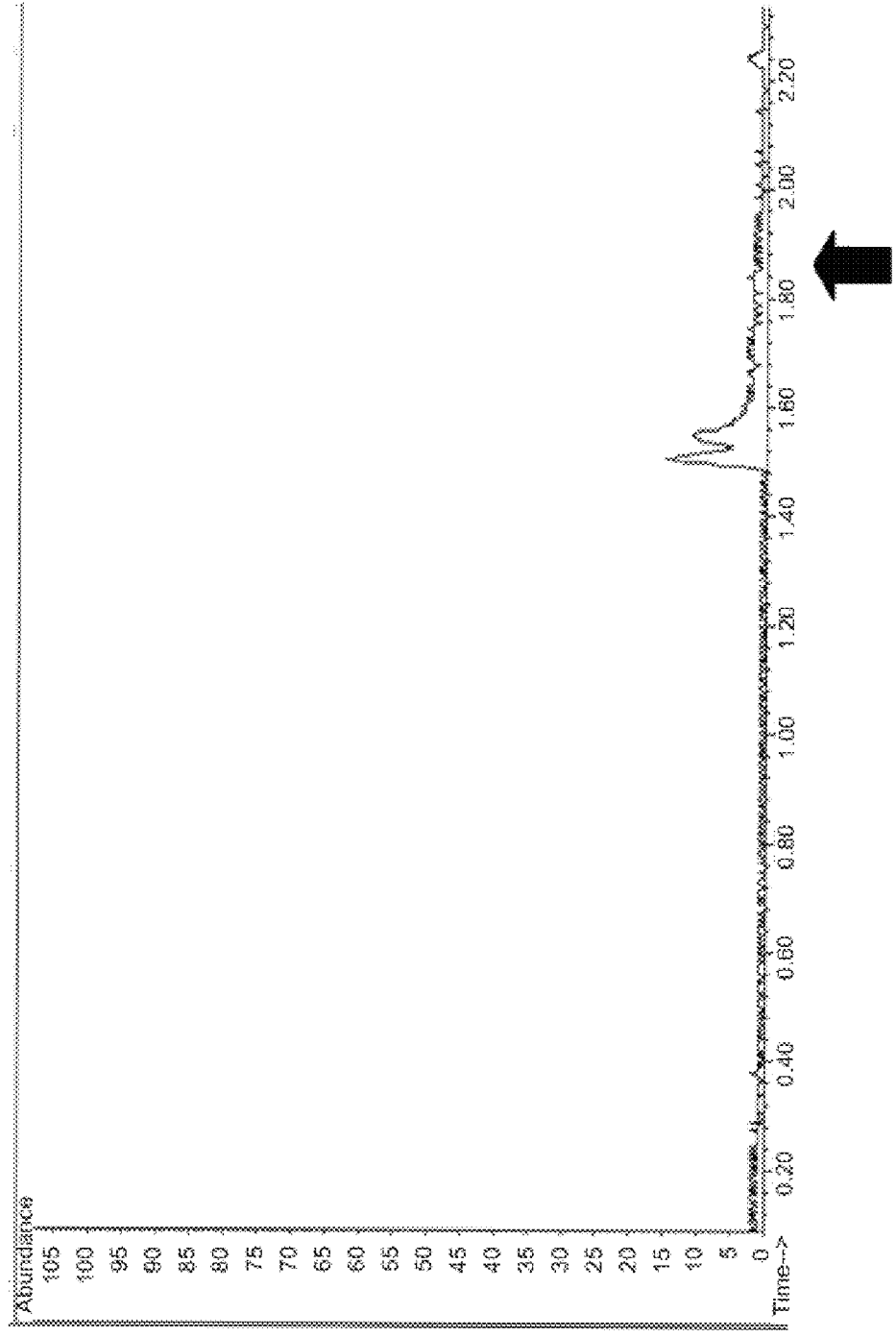
FIG. 20 shows graphs representing results of the GC-MS analysis of isoprene production by recombinant *Y. lipolytica* strains without (left) or with (right) a kudzu isoprene synthase gene. The arrows indicate the elution time of the authentic isoprene standard.
Figure 20B:
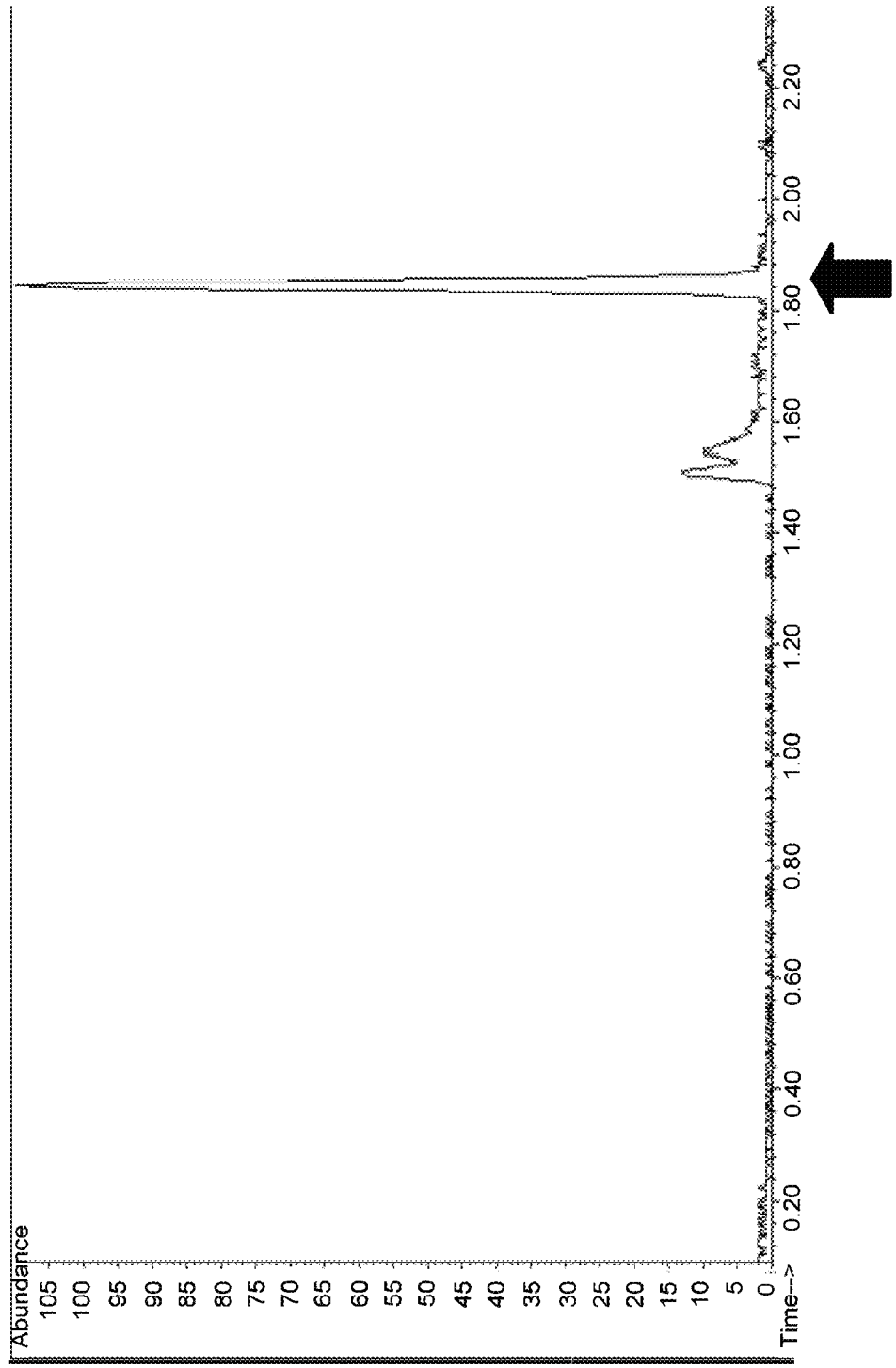

Three isolates from the pYLA(KZ1) transformation, three isolates from the pYLI(KZ1) transformation, two isolates from the pYLA(MAP29) transformation and two isolates from the pYLI(MAP29) transformation are grown for 24 hours in YEP7 medium (1% yeast extract, 2% peptone, pH 7.0) at 30° C. with shaking. Cells from 10 ml of culture are collected by centrifugation, resuspended in 3 ml of fresh YEP7 and placed into 15 ml screw cap vials. The vials are incubated overnight at room temperature with gentle (60 rpm) shaking. Isoprene content in the headspace of these vials is analyzed by gas chromatography using mass-spectrometric detector as described in Example 1. All transformants obtained with pYLA(KZ1) and pYLI(KZ1) produce readily detectable amounts of isoprene (0.5 µg/L to 1 µg/L, FIG. 20). No isoprene is detected in the headspace of the control strains carrying phytase gene instead of an isoprene synthase gene.

Example 7

Production of Isoprene in *E. coli* Expressing Kudzu Isoprene Synthase and idi, or dxs, or idi and dxs I. Construction of Vectors Encoding Kudzu Isoprene Synthase and idi, or dxs, or idi and dxs for the Production of Isoprene in *E. coli* i) Construction of pTrcKudzuKan

The bla gene of pTrcKudzu (described in Example 1) is replaced with the gene conferring kanamycin resistance. To remove the bla gene, pTrcKudzu is digested with BspHI, treated with Shrimp Alkaline Phosphatase (SAP), heat killed at 65° C., then end-filled with Klenow fragment and dNTPs. The 5 kbp large fragment is purified from an agarose gel and ligated to the kan$^r$ gene which has been PCR amplified from pCR-Blunt-II-TOPO using primers MCM22 5'-GATCAAGCTTAACCGGAATTGCCAGCTG (SEQ ID NO:14) and MCM23 5'-GATCCGATCGTCAGAAGAACTCGTCAAGAAGGC (SEQ ID NO:15), digested with HindIII and PvuI, and end-filled. A transformant carrying a plasmid conferring kanamycin resistance (pTrcKudzuKan) is selected on LA containing kanamycin 50 µg/ml.

ii) Construction of pTrcKudzu yIDI Kan pTrcKudzuKan is digested with PstI, treated with SAP, heat killed and gel purified. It is ligated to a PCR product encoding idi from *S. cerevisiae* with a synthetic RBS. The primers for PCR are NsiI-YIDI 1 F 5'-CATCAATGCATCGCCCTTAGGAGGTAAAAAAAAATGAC (SEQ ID NO:16) and PstI-YIDI 1 R 5'-CCTTCTGCAGGACGCGTTGTTATAGC (SEQ ID NO:17); and the template is *S. cer-*

Figure 34:
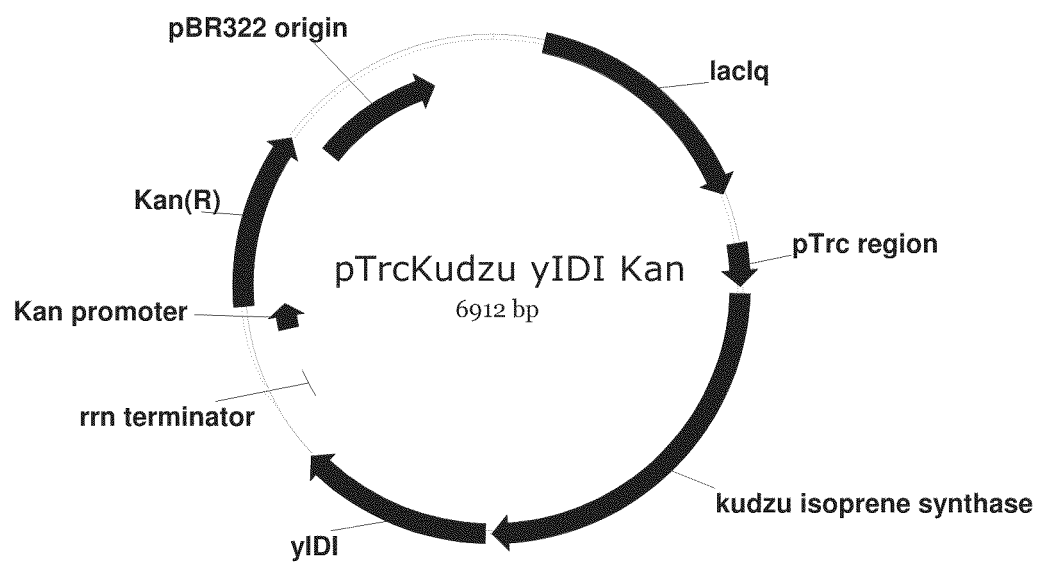
FIG. 34 is a map of pTrcKudzu yIDI Kan.

*evisiae* genomic DNA. The PCR product is digested with NsiI and PstI and gel purified prior to ligation. The ligation mixture is transformed into chemically competent TOP10 cells and selected on LA containing 50 µg/ml kanamycin. Several transformants are isolated and sequenced and the resulting plasmid is called pTrcKudzu-yIDI(kan) (FIGS. 34 and 35).

iii) Construction of pTrcKudzu DXS Kan

Figure 21:
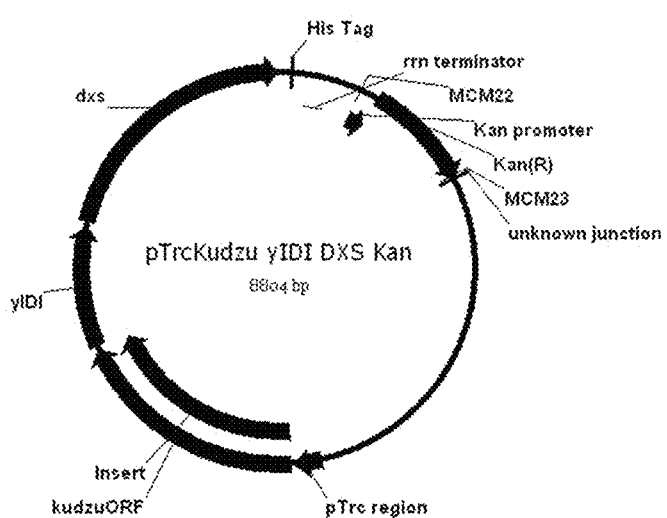
FIG. 21 is a map of pTrcKudzu yIDI DXS Kan.
Figure 36:
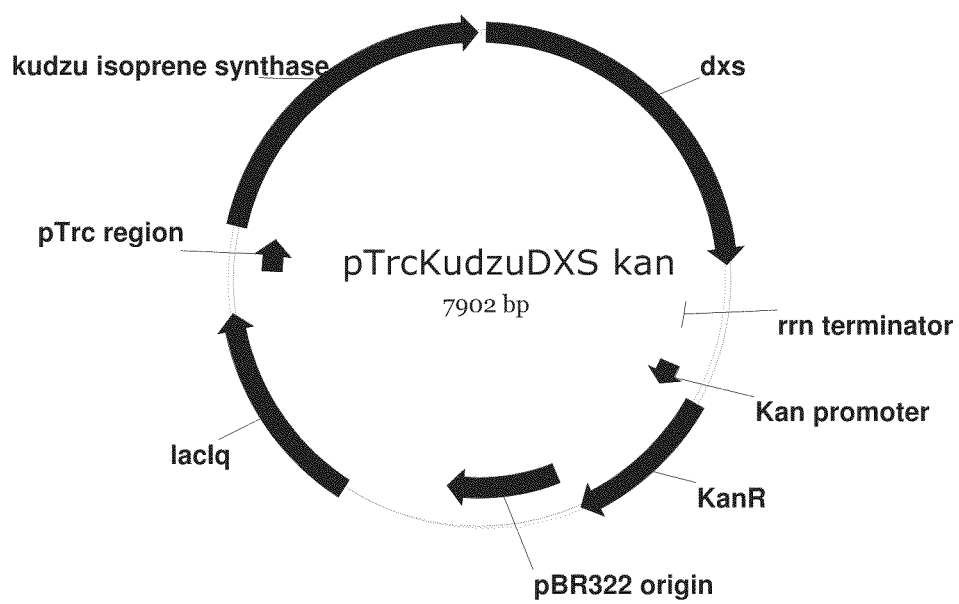
FIG. 36 is a map of pTrcKudzuDXS Kan.
Figure 38:
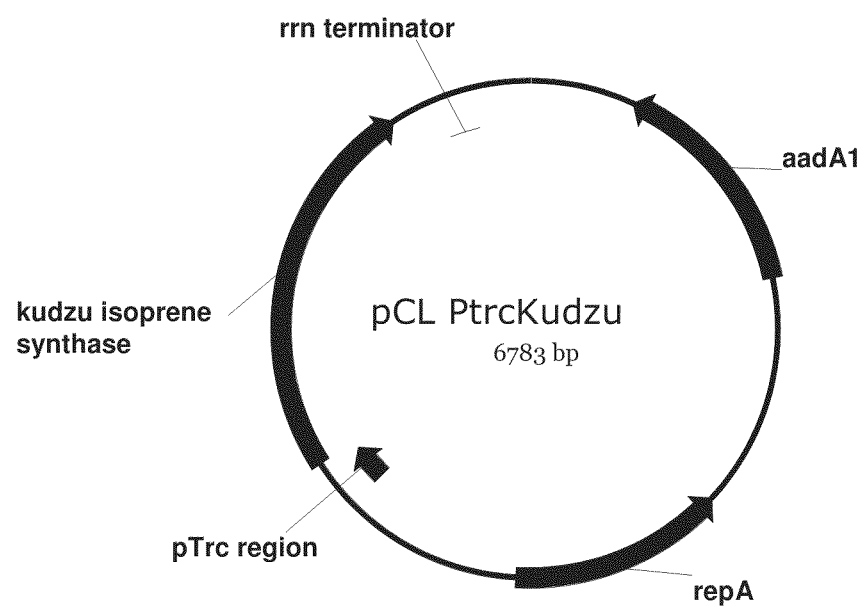
FIG. 38 is a map of pCL PtrcKudzu.
Figure 40:
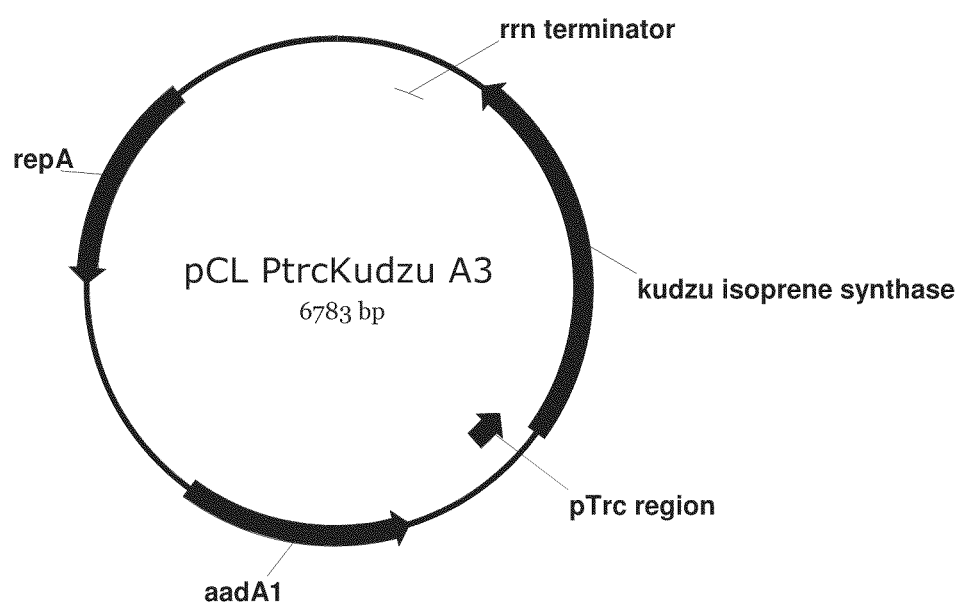
FIG. 40 is a map of pCL PtrcKudzu A3.

Plasmid pTrcKudzuKan is digested with PstI, treated with SAP, heat killed and gel purified. It is ligated to a PCR product encoding dxs from *E. coli* with a synthetic RBS. The primers for PCR are MCM 13 5'-GATCATGCATTCGCCCTTAG-GAGGTAAAAAAACATGAGTTTTGATAT-TGCCAAATAC CCG (SEQ ID NO:18) and MCM14 5'-CATGCTGCAGTTATGCCAGCCAGGCCTTGAT (SEQ ID NO:19); and the template is *E. coli* genomic DNA. The PCR product is digested with NsiI and PstI and gel purified prior to ligation. The resulting transformation reaction is transformed into TOP10 cells and selected on LA with kanamycin 50 µg/ml. Several transformants are isolated and sequenced and the resulting plasmid is called pTrcKudzu-DXS(kan) (FIGS. 36 and 37).

iv) Construction of pTrcKudzu-yIDI-dxs (kan)

pTrcKudzu-yIDI(kan) is digested with PstI, treated with SAP, heat killed and gel purified. It is ligated to a PCR product encoding *E. coli* dxs with a synthetic RBS (primers MCM13 5'-GATCATGCATTCGCCCTTAGGAGG-TAAAAAAACATGAGTTTTGATATTGCCAAATAC CCG (SEQ ID NO:18) and MCM14 5'-CATGCTGCAGTTATGC-CAGCCAGGCCTTGAT (SEQ ID NO:19); template TOP10 cells) which have been digested with NsiI and PstI and gel purified. The final plasmid is called pTrcKudzu-yIDI-dxs (kan) (FIGS. 21 and 22).

v) Construction of pCL PtrcKudzu

A fragment of DNA containing the promoter, structural gene and terminator from Example 1 above is digested from pTrcKudzu using SspI and gel purified. It is ligated to pCL1920 which has been digested with PvuII, treated with SAP and heat killed. The resulting ligation mixture was transformed into TOP10 cells and selected in LA containing spectinomycin 50 µg/ml. Several clones are isolated and sequenced and two are selected. pCL PtrcKudzu and pCL PtrcKudzu (A3) have the insert in opposite orientations (FIGS. 38-41).

vi) Construction of pCL PtrcKudzu yIDI

Figure 42:
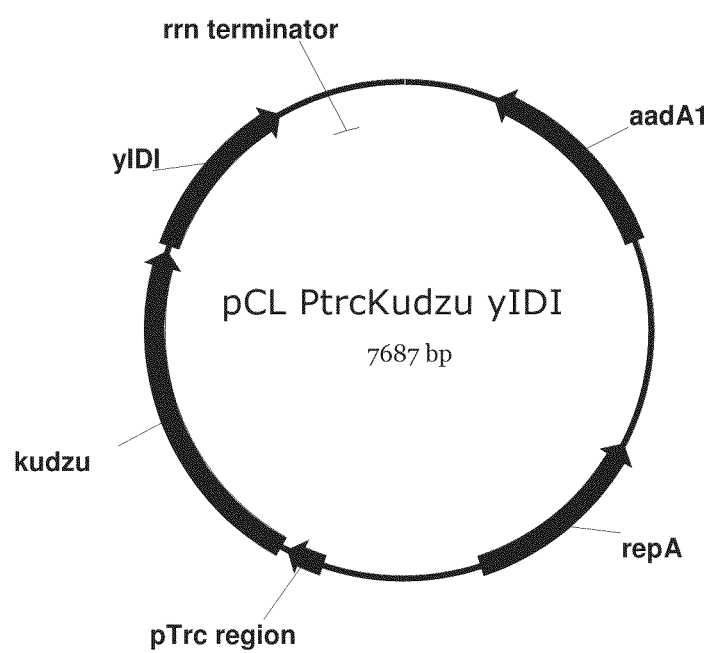
FIG. 42 is a map of pCL PtrcKudzu yIDI.

The NsiI-PstI digested, gel purified, IDI PCR amplicon from (ii) above is ligated into pCL PtrcKudzu which has been digested with PstI, treated with SAP, and heat killed. The ligation mixture is transformed into TOP10 cells and selected in LA containing spectinomycin 50 µg/ml. Several clones are isolated and sequenced and the resulting plasmid is called pCL PtrcKudzu yIDI (FIGS. 42 and 43).

vii) Construction of pCL PtrcKudzu DXS

Figure 44:
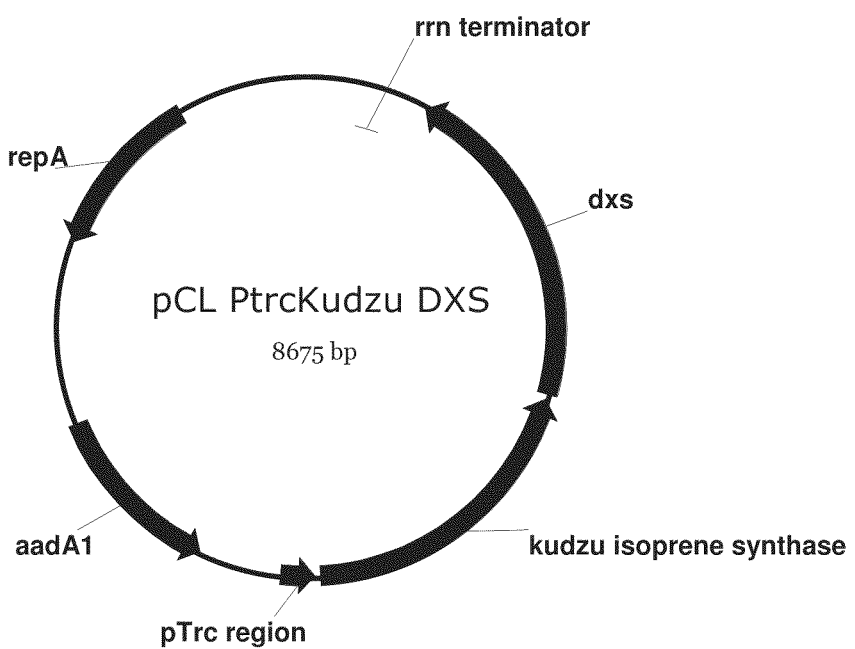
FIG. 44 is a map of pCL PtrcKudzu DXS.

The NsiI-PstI digested, gel purified, DXS PCR amplicon from (iii) above is ligated into pCL PtrcKudzu (A3) which has been digested with PstI, treated with SAP, and heat killed. The ligation mixture is transformed into TOP10 cells and selected in LA containing spectinomycin 50 µg/ml. Several clones are isolated and sequenced and the resulting plasmid is called pCL PtrcKudzu DXS (FIGS. 44 and 45).

II. Measurement of Isoprene in Headspace from Cultures Expressing Kudzu Isoprene Synthase, idi, and/or dxs at Different Copy Numbers.

Cultures of *E. coli* BL21(λDE3) previously transformed with plasmids pTrcKudzu(kan) (A), pTrcKudzu-yIDI kan (B), pTrcKudzu-DXS kan (C), pTrcKudzu-yIDI-DXS kan (D) are grown in LB kanamycin 50 µg/mL. Cultures of pCL PtrcKudzu (E), pCL PtrcKudzu, pCL PtrcKudzu-yIDI (F) and pCL PtrcKudzu-DXS (G) are grown in LB spectinomycin 50 µg/mL. Cultures are induced with 400 µM IPTG at time 0 ($OD_{600}$ approximately 0.5) and samples taken for isoprene headspace measurement (see Example 1). Results are shown in FIG. 23A-23G.

Figure 23A:
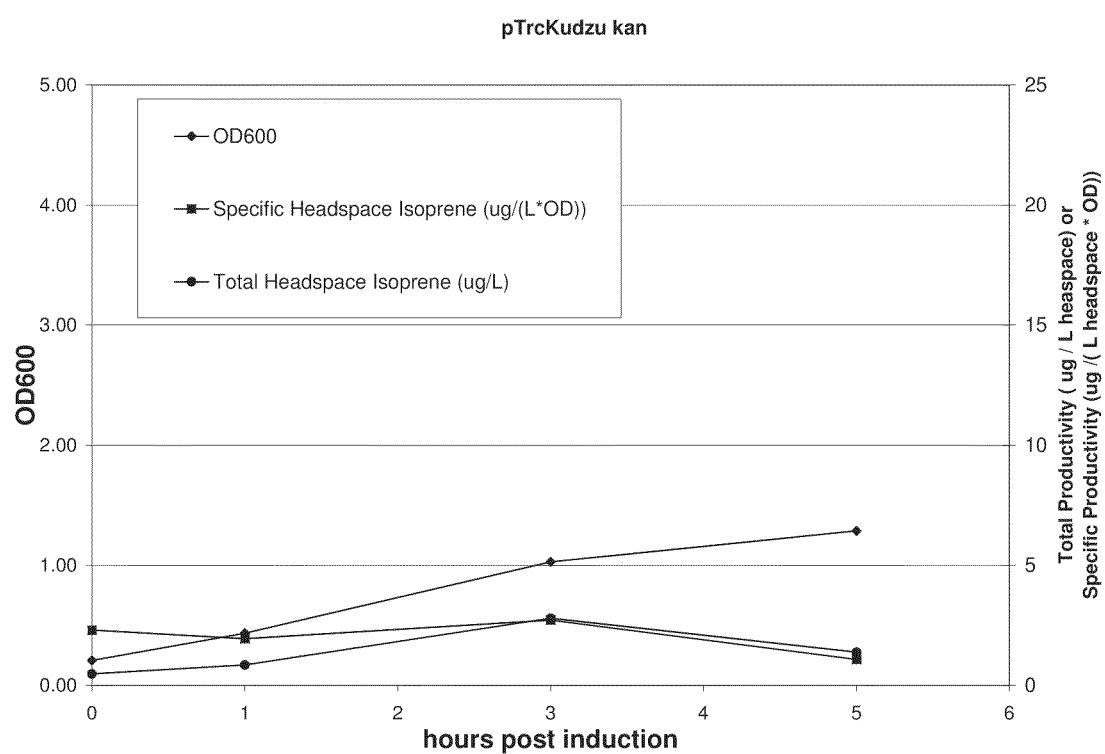
FIG. 23A is a graph showing production of isoprene from glucose in BL21/pTrcKudzukan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23B:
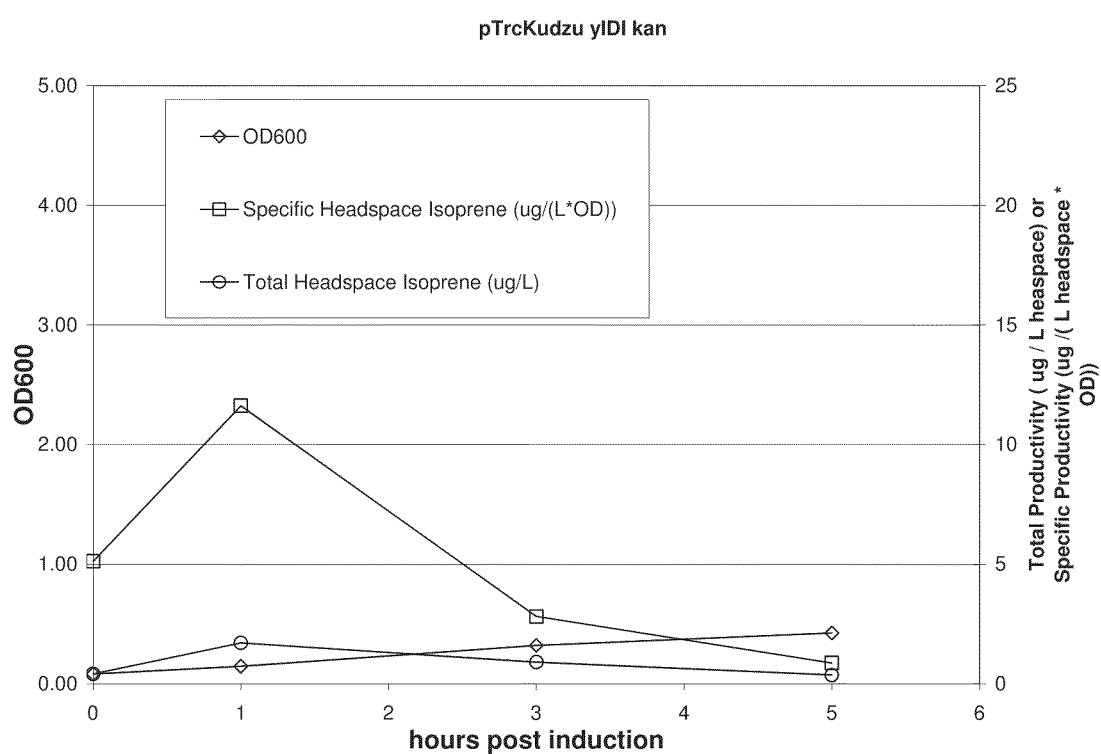
FIG. 23B is a graph showing production of isoprene from glucose in BL21/pTrcKudzu yIDI kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23C:
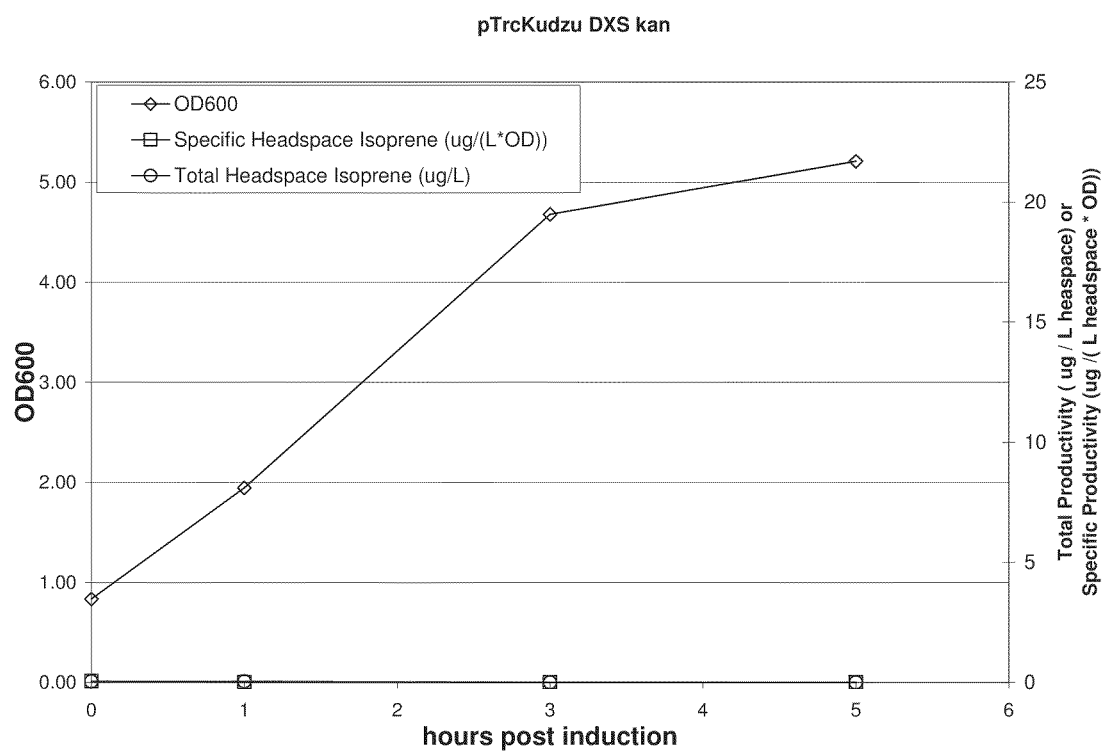
FIG. 23C is a graph showing production of isoprene from glucose in BL21/pTrcKudzu DXS kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23D:
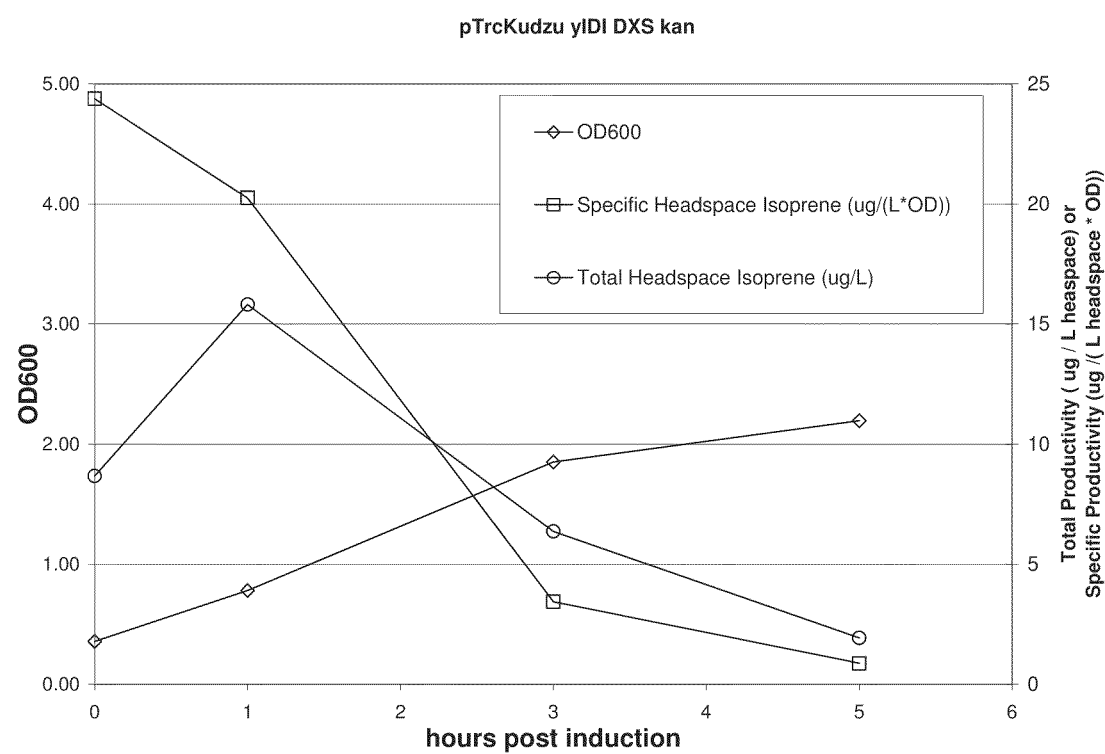
FIG. 23D is a graph showing production of isoprene from glucose in BL21/pTrcKudzu yIDI DXS kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23E:
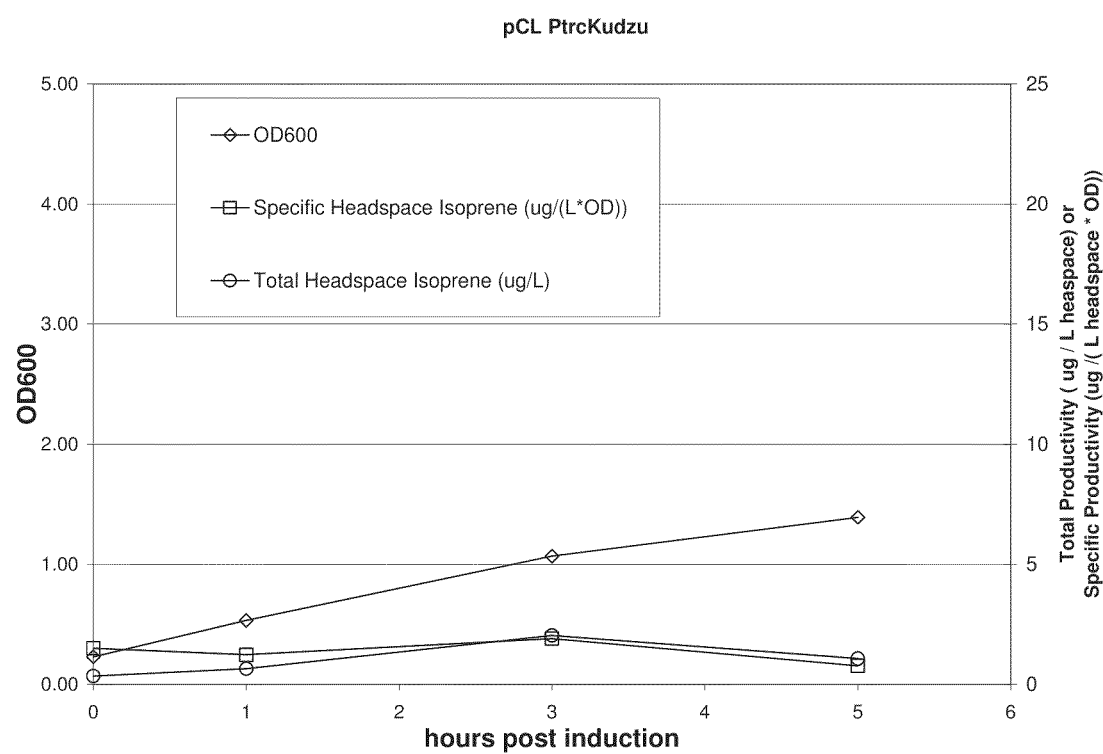
FIG. 23E is a graph showing production of isoprene from glucose in BL21/pCL PtrcKudzu. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23F:
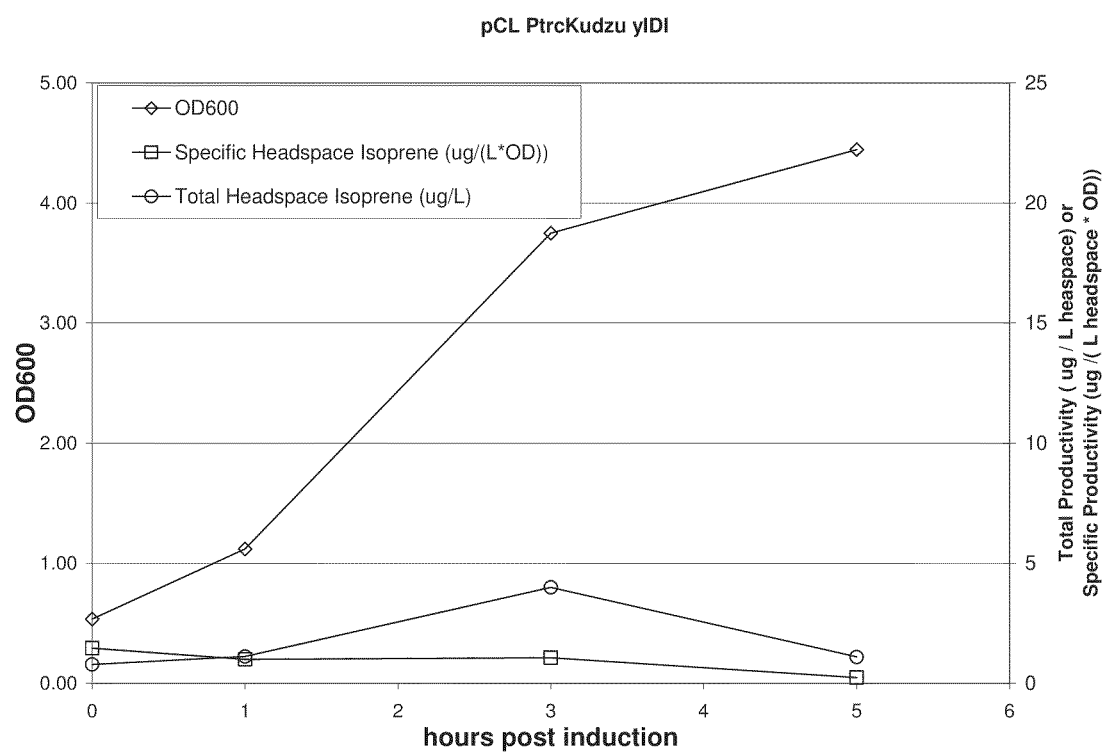
FIG. 23F is a graph showing production of isoprene from glucose in BL21/pCL PtrcKudzu yIDI. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23G:
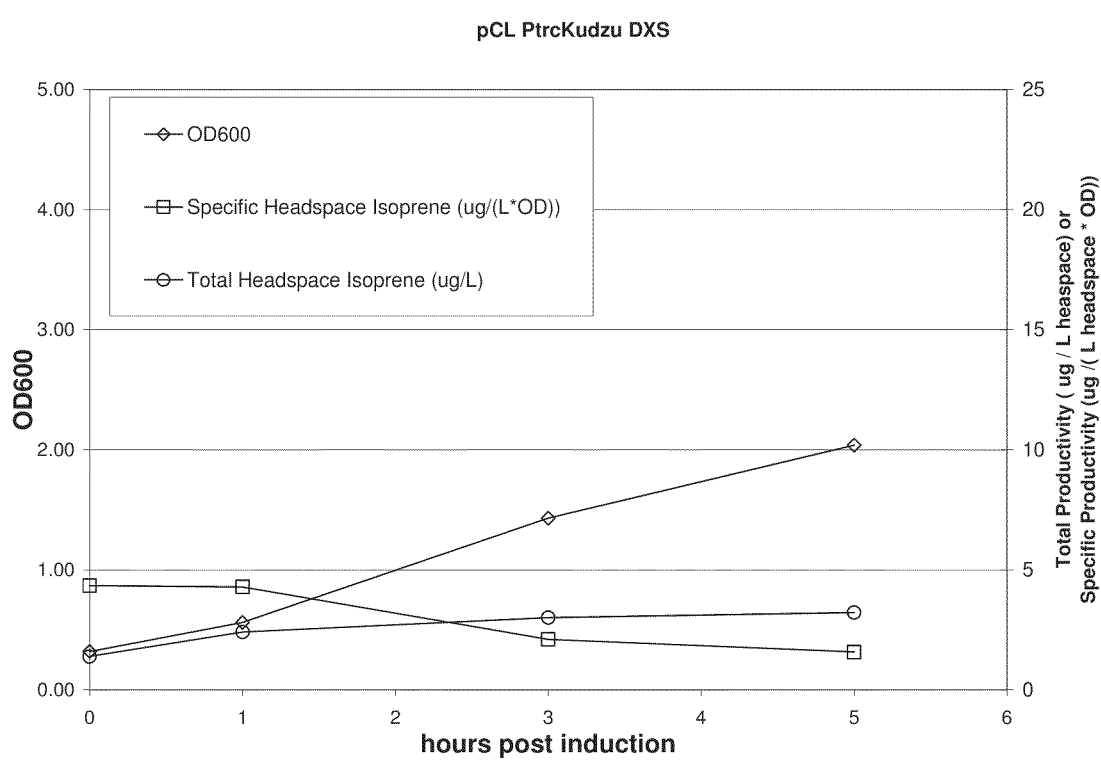
FIG. 23G is a graph showing production of isoprene from glucose in BL21/pCL PtrcKudzu DXS. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23H:
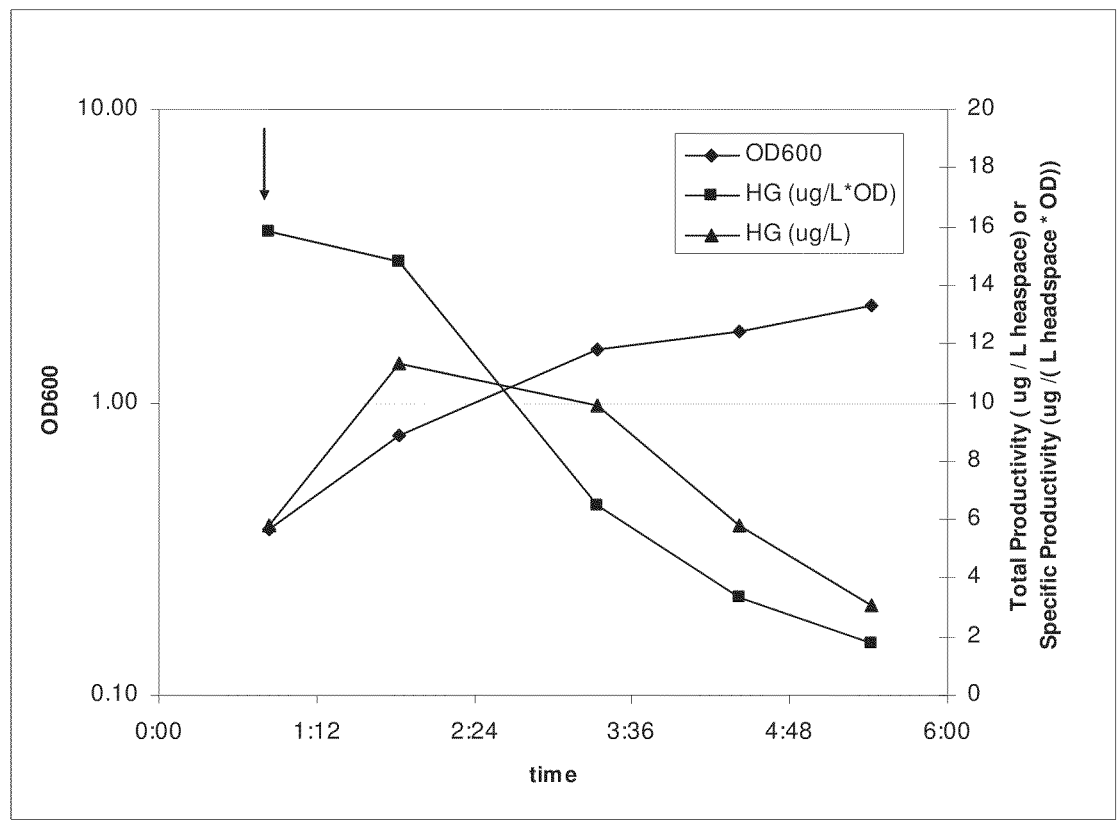
FIG. 23H is a graph showing production of isoprene from glucose in BL21/pTrcKudzuIDIDXSkan. The arrow indicates the time of induction with IPTG (400 μmol). The x-axis is time after inoculation; the y-axis is OD600 and the y2-axis is total productivity of isoprene (μg/L headspace or specific productivity (μg/L headspace/OD). Diamonds represent OD600, triangles represent total isoprene productivity (μg/L) and squares represent specific productivity of isoprene (μg/L/OD).

Plasmid pTrcKudzu-yIDI-dxs (kan) was introduced into *E. coli* strain BL21 by transformation. The resulting strain BL21/pTrc Kudzu IDI DXS is grown overnight in LB containing kanamycin (50 µg/ml) at 20° C. and used to inoculate shake flasks of TM3 (13.6 g $K_2PO_4$, 13.6 g $KH_2PO_4$, 2.0 g $MgSO_4.7H_2O$), 2.0 g citric acid monohydrate, 0.3 g ferric ammonium citrate, 3.2 g $(NH_4)_2SO_4$, 0.2 g yeast extract, 1.0 ml 1000× Modified Trace Metal Solution, adjusted to pH 6.8 and q.s. to $H_2O$, and filter sterilized) containing 1% glucose. Flasks are incubated at 30° C. until an $OD_{600}$ of 0.8 is reached, and then induced with 400 µM IPTG. Samples are taken at various times after induction and the amount of isoprene in the head space is measured as described in Example 1. Results are shown in FIG. 23H.

III. Production of Isoprene from Biomass in *E. coli*/pTrcKudzu yIDI DXS

The strain BL21 pTrcKudzuIDIDXS is tested for the ability to generate isoprene from three types of biomass; bagasse, corn stover and soft wood pulp with glucose as a control. Hydrolysates of the biomass are prepared by enzymatic hydrolysis (Brown, L and Torget, R., 1996, NREL standard assay method Lap-009 "Enzymatic Saccharification of Lignocellulosic Biomass") and used at a dilution based upon glucose equivalents. In this example, glucose equivalents are equal to 1% glucose. A single colony from a plate freshly transformed cells of BL21(DE3) pTrcKudzu yIDI DXS (kan) is used to inoculate 5 ml of LB plus kanamycin (50 µg/ml). The culture is incubated overnight at 25° C. with shaking. The following day the overnight culture is diluted to an $OD_{600}$ of 0.05 in 25 ml of TM3+0.2% YE+1% feedstock. The feedstock is corn stover, bagasse, or softwood pulp. Glucose is used as a positive control and no glucose is used as a negative control. Cultures are incubated at 30° C. with shaking at 180 rpm. The culture is monitored for $OD_{600}$ and when it reaches an $OD_{600}$ of ~0.8, cultures are analyzed at 1 and 3 hours for isoprene production as described in Example 1. Cultures are not induced. All cultures containing added feedstock produce isoprene equivalent to those of the glucose positive control. Experiments are done in duplicate and are shown in FIG. 46.

IV. Production of Isoprene from Invert Sugar in *E. coli*/pTrcKudzuIDIDXS

A single colony from a plate freshly transformed cells of BL21(λDE3)/pTrcKudzu yIDI DXS (kan) is used to inoculate 5 mL of LB+kanamycin (50 µg/ml). The culture is incubated overnight at 25° C. with shaking. The following day the overnight culture is diluted to an $OD_{600}$ of 0.05 in 25 ml of TM3+0.2% YE+1% feedstock. Feedstock is glucose, inverted glucose or corn stover. The invert sugar feedstock (Danisco Invert Sugar) is prepared by enzymatically treating sucrose syrup. AFEX corn stover is prepared as described below (Part V). The cells are grown at 30° C. and the first sample is measured when the cultures reach an $OD_{600}$~0.8-1.0 (0 hour). The cultures are analyzed for growth as measured by $OD_{600}$ and for isoprene production as in Example 1 at 0, 1 and 3 hours. Results are shown in FIG. 47.

V. Preparation of Hydrolysate from AFEX Pretreated Corn Stover

AFEX pretreated corn stover is obtained from Michigan Biotechnology Institute. The pretreatment conditions are 60% moisture, 1:1 ammonia loading, and 90° C. for 30 minutes, then air dried. The moisture content in the AFEX pretreated corn stover is 21.27%. The contents of glucan and xylan in the AFEX pretreated corn stover are 31.7% and 19.1% (dry basis), respectively. The saccharification process is as follows; 20 g of AFEX pretreated corn stover is added into a 500 ml flask with 5 ml of 1 M sodium citrate buffer pH 4.8, 2.25 ml of Accellerase 1000, 0.1 ml of Grindamyl H121 (Danisco xylanase product from *Aspergillus niger* for breadmaking industry), and 72.65 ml of DI water. The flask is put in an orbital shaker and incubated at 50° C. for 96 hours. One sample is taken from the shaker and analyzed using HPLC. The hydrolysate contained 38.5 g/l of glucose, 21.8 g/l of xylose, and 10.3 g/l of oligomers of glucose and/or xylose.

VI. The Effect of Yeast Extract on Isoprene Production in *E. coli* Grown in Fed-Batch Culture Fermentation is performed at the 14-L scale as previously described with *E. coli* cells containing the pTrcKudzu yIDI DXS plasmid described above. Yeast extract (Bio Springer, Montreal, Quebec, Canada) is fed at an exponential rate. The total amount of yeast extract delivered to the fermentor is varied between 70-830 g during the 40 hour fermentation. Optical density of the fermentation broth is measured at a wavelength of 550 nm. The final optical density within the fermentors is proportional to the amount of yeast extract added (FIG. 48A). The isoprene level in the off-gas from the fermentor is determined as previously described. The isoprene titer increases over the course of the fermentation (FIG. 48B). The amount of isoprene produced is linearly proportional to the amount of fed yeast extract (FIG. 48C).

VII. Production of Isoprene in 500 L Fermentation of pTrcKudzu DXS yIDI

A 500 liter fermentation of *E. coli* cells with a kudzu isoprene synthase, *S. cerevisiae* IDI, and *E. coli* DXS nucleic acids (*E. coli* BL21(λDE3) pTrc Kudzu dxs yidi) is used to produce isoprene. The levels of isoprene varied from 50 to 300 μg/L over a time period of 15 hours. On the basis of the average isoprene concentrations, the average flow through the device and the extent of isoprene breakthrough, the amount of isoprene collected is calculated to be approximately 17 g.

VIII. Production of Isoprene in 500 L Fermentation of *E. coli* Grown in Fed-Batch Culture Medium Recipe (per liter fermentation medium): $K_2HPO_4$ 7.5 g, $MgSO_4.7H_2O$ 2 g, citric acid monohydrate 2 g, ferric ammonium citrate 0.3 g, yeast extract 0.5 g, 1000× Modified Trace Metal Solution 1 ml. All of the components are added together and dissolved in $diH_2O$. This solution is autoclaved. The pH is adjusted to 7.0 with ammonium gas ($NH_3$) and q.s. to volume. Glucose 10 g, thiamine.HCl 0.1 g, and antibiotic are added after sterilization and pH adjustment.

1000× Modified Trace Metal Solution: citric acid.$H_2O$ 40 g, $MnSO_4.H_2O$ 30 g, NaCl 10 g, $FeSO_4.7H_2O$ 1 g, $CoCl_2.6H_2O$ 1 g, $ZnSO_4.7H_2O$ 1 g, $CuSO_4.5H_2O$ 100 mg, $H_3BO_3$ 100 mg, $NaMoO_4.2H_2O$ 100 mg. Each component is dissolved one at a time in DI $H_2O$, pH to 3.0 with HCl/NaOH, then q.s. to volume and filter sterilized with 0.22 micron filter.

Fermentation is performed in a 500-L bioreactor with *E. coli* cells containing the pTrcKudzu yIDI DXS plasmid. This experiment is carried out to monitor isoprene formation from glucose and yeast extract at the desired fermentation pH 7.0 and temperature 30° C. An inoculum of *E. coli* strain taken from a frozen vial is prepared in soytone-yeast extract-glucose medium. After the inoculum grows to OD 0.15, measured at 550 nm, 20 ml is used to inoculate a bioreactor containing 2.5-L soytone-yeast extract-glucose medium. The 2.5-L bioreactor is grown at 30° C. to OD 1.0 and 2.0-L is transferred to the 500-L bioreactor.

Figure 49A:
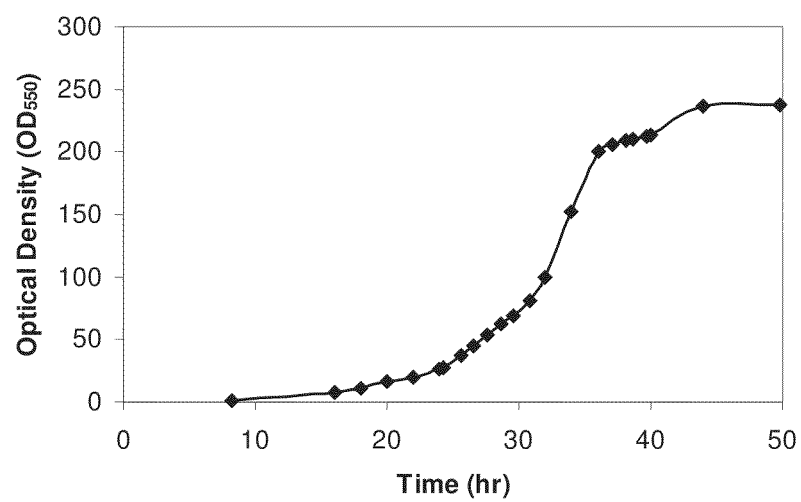
FIG. 49 shows graphs demonstrating isoprene production from a 500 L bioreactor with E. coli cells containing the pTrcKudzu+yIDI+DXS plasmid. Panel A shows the time course of optical density within the 500-L bioreactor fed with glucose and yeast extract. Panel B shows the time course of isoprene titer within the 500-L bioreactor fed with glucose and yeast extract. The titer is defined as the amount of isoprene produced per liter of fermentation broth. Panel C shows the time course of total isoprene produced from the 500-L bioreactor fed with glucose and yeast extract.
Figure 49B:
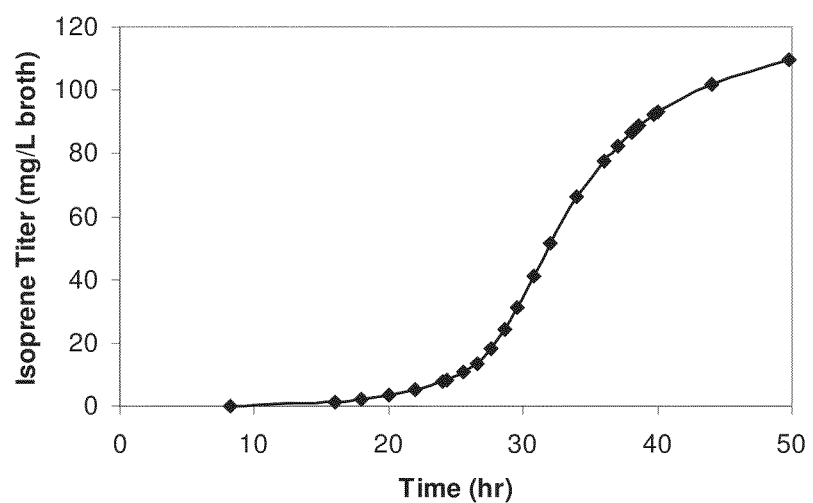
Figure 49C:
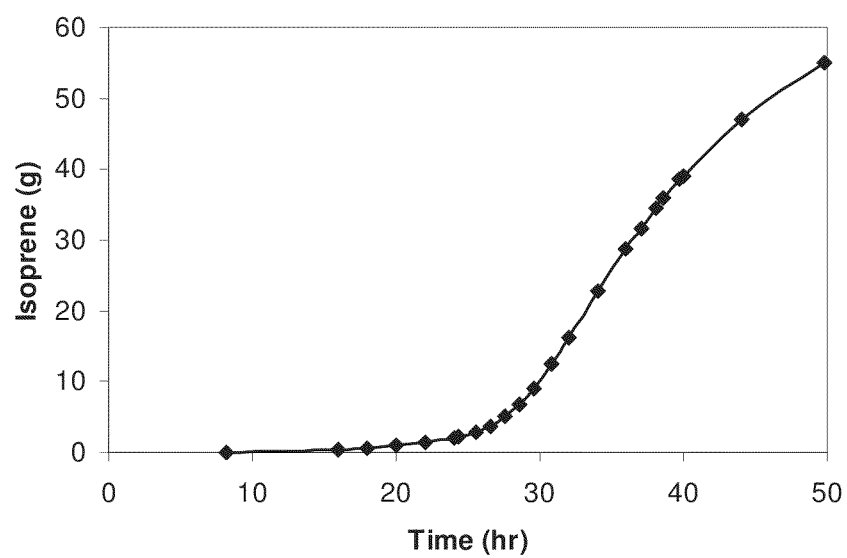

Yeast extract (Bio Springer, Montreal, Quebec, Canada) and glucose are fed at exponential rates. The total amount of glucose and yeast extract delivered to the bioreactor during the 50 hour fermentation is 181.2 kg and 17.6 kg, respectively. The optical density within the bioreactor over time is shown in FIG. 49A. The isoprene level in the off-gas from the bioreactor is determined as previously described. The isoprene titer increases over the course of the fermentation (FIG. 49B). The total amount of isoprene produced during the 50 hour fermentation is 55.1 g and the time course of production is shown in FIG. 49C.

Example 8

Production of Isoprene in *E. coli* Expressing Heterologous Isoprene Synthase and Mevalonic Acid Pathway Genes I. Cloning the Lower MVA Pathway The strategy for cloning the lower mevalonic pathway is as follows. Four genes of the mevalonic acid biosynthesis pathway; mevalonate kinase (MVK), phosphomevalonate kinase (PMK), diphosphomevalonte decarboxylase (MVD) and isopentenyl diphosphate isomerase genes are amplified by PCR from *S. cerevisiae* chromosomal DNA and cloned individually into the pCR BluntII TOPO plasmid (Invitrogen). In some cases, the idi gene is amplified from *E. coli* chromosomal DNA. The primers are designed such that an *E. coli* consensus RBS (AGGAGGT (SEQ ID NO:80) or AAGGAGG (SEQ ID NO:81)) is inserted at the 5' end, 8 bp upstream of the start codon and a PstI site is added at the 3' end. The genes are then cloned one by one into the pTrcHis2B vector until the entire pathway is assembled.

Chromosomal DNA from *S. cerevisiae* S288C is obtained from ATCC (ATCC 204508D). The MVK gene is amplified from the chromosome of *S. cerevisiae* using primers MVKF (5'-AGGAGGTAAAAAAACATGTCATTACCGT-TCTTAACTTCTGC, SEQ ID NO:21) and MVK-PstI-R (5'-ATGGCTGCAGGCCTATCGCAAATTAGCT-TATGAAGTCCATGGTAAATTCGTG, SEQ ID NO:22) using PfuTurbo as per manufacturer's instructions. The correct sized PCR product (1370 bp) is identified by electrophoresis through a 1.2% E-gel (Invitrogen) and cloned into pZeroBLUNT TOPO. The resulting plasmid is designated pMVK1. The plasmid pMVK1 is digested with SacI and Taq1 restriction endonucleases and the fragment is gel purified and ligated into pTrcHis2B digested with SacI and BstBI. The resulting plasmid is named pTrcMVK1.

The second gene in the mevalonic acid biosynthesis pathway, PMK, is amplified by PCR using primers: PstI-PMK1 R (5'-GAATTCGCCCTTCTGCAGCTACC, SEQ ID NO:23) and BsiHKA I-PMK1 F (5'-CGACTGGTGCACCCTTAAG-GAGGAAAAAAACATGTCAG, SEQ ID NO:24). The PCR reaction is performed using Pfu Turbo polymerase (Stratagene) as per manufacturer's instructions. The correct sized product (1387 bp) is digested with PstI and BsiHKI and ligated into pTrcMVK1 digested with PstI. The resulting plasmid is named pTrcKK. The MVD and the idi genes are cloned in the same manner. PCR is carried out using the primer pairs PstI-MVD 1 R (5'-GTGCTGGAATTCGCCCT-TCTGCAGC, SEQ ID NO:25) and NsiI-MVD 1 F (5'-GTA-GATGCATGCAGAATTCGCCCTTAAGGAGG, SEQ ID NO:26) to amplify the MVD gene and PstI-YIDI 1 R (5'-CCTTCTGCAGGACGCGTTGTTATAGC, SEQ ID NO:27) and NsiI-YIDI 1 F (5'-CATCAATGCATCGCCCTTAG-GAGGTAAAAAAAAATGAC, SEQ ID NO:28) to amplify the yIDI gene. In some cases the IPP isomerase gene, idi from *E. coli* is used. To amplify idi from *E. coli* chromosomal DNA, the following primer set is used: PstI-CIDI 1 R (5'-GTGTGATGGATATCTGCAGAATTCG, SEQ ID NO:29)

and NsiI-CIDI 1 F (5'-CATCAATGCATCGCCCTTAG-GAGGTAAAAAAACATG, SEQ ID NO:30). Template DNA is chromosomal DNA isolated by standard methods from *E. coli* FM5 (WO 96/35796 and WO 2004/033646, which are each hereby incorporated by reference in their entireties, particularly with respect to isolation of nucleic acids). The final plasmids are named pKKDIy for the construct encoding the yeast idi gene or pKKDIc for the construct encoding the *E. coli* idi gene. The plasmids are transformed into *E. coli* hosts BL21 for subsequent analysis. In some cases the isoprene synthase from kudzu is cloned into pKKDIy yielding plasmid pKKDIyIS.

The lower MVA pathway is also cloned into pTrc containing a kanamycin antibiotic resistance marker. The plasmid pTrcKKDIy is digested with restriction endonucleases ApaI and PstI, the 5930 bp fragment is separated on a 1.2% agarose E-gel and purified using the Qiagen Gel Purification kit according to the manufacturer's instructions. The plasmid pTrcKudzuKan, described in Example 7, is digested with restriction endonucleases ApaI and PstI, and the 3338 bp fragment containing the vector is purified from a 1.2% E-gel using the Qiagen Gel Purification kit. The 3338 bp vector fragment and the 5930 bp lower MVA pathway fragment are ligated using the Roche Quick Ligation kit. The ligation mix is transformed into *E. coli* TOP10 cells and tranformants were grown at 37° C. overnight with selection on LA containing kanamycin (50 µg/ml). The transformants are verified by restriction enzyme digestion and one is frozen as a stock. The plasmid is designated pTrcKanKKDIy.

II. Cloning a Kudzu Isoprene Synthase Gene into pTrcKanKKDIy

The kudzu isoprene synthase gene is amplified by PCR from pTrcKudzu, described in Example 1, using primers MCM50 5'-GATCATGCATTCGCCCTTAGGAGG-TAAAAAAACATGTGTGCGACCTCTTCTCAATTT ACT (SEQ ID NO:31) and MCM53 5'-CGGTCGACGGATCCCT-GCAGTTAGACATACATCAGCTG (SEQ ID NO:32). The resulting PCR fragment is cloned into pCR2.1 and transformed into *E. coli* TOP10. This fragment contains the coding sequence for kudzu isoprene synthase and an upstream region containing a RBS from *E. coli*. Transformants are incubated overnight at 37° C. with selection on LA containing carbenicillin (50 µg/ml). The correct insertion of the fragment is verified by sequencing and this strain is designated MCM93.

Figure 24:
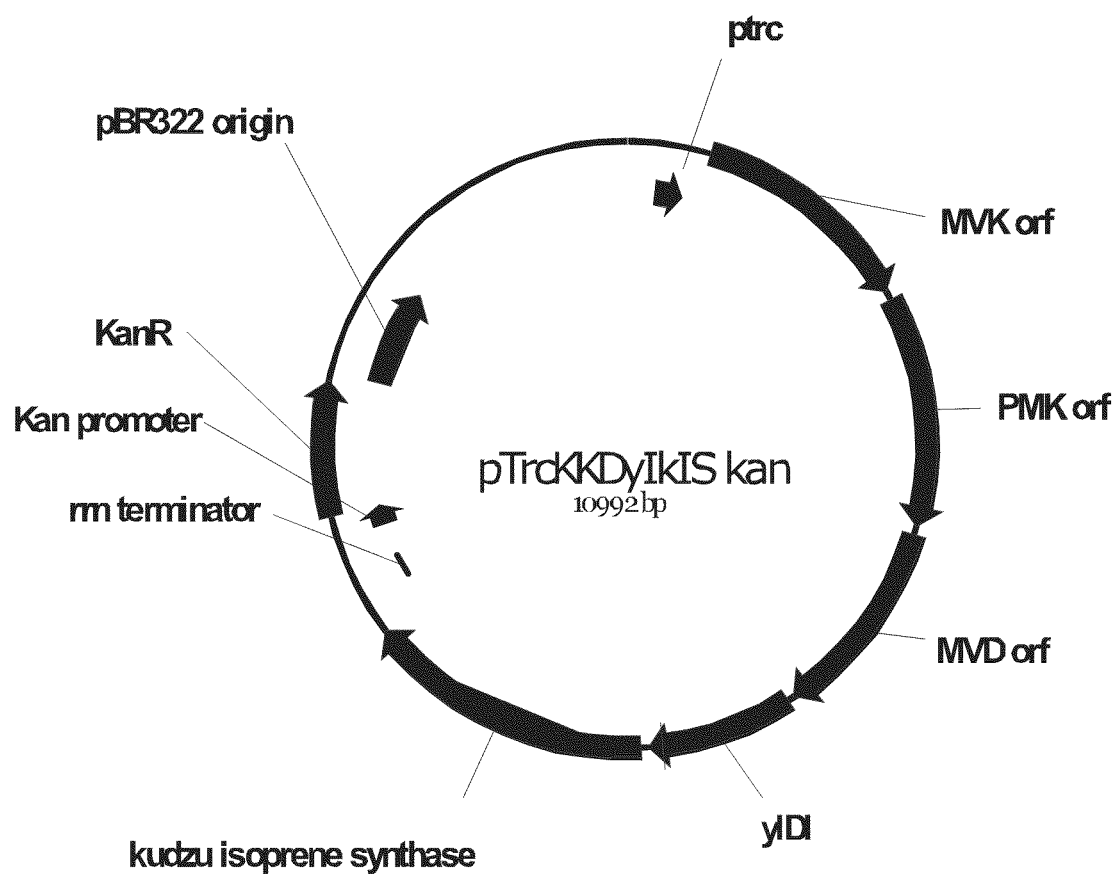
FIG. 24 is a map of pTrcKKDyIkIS kan.
Figure 26:
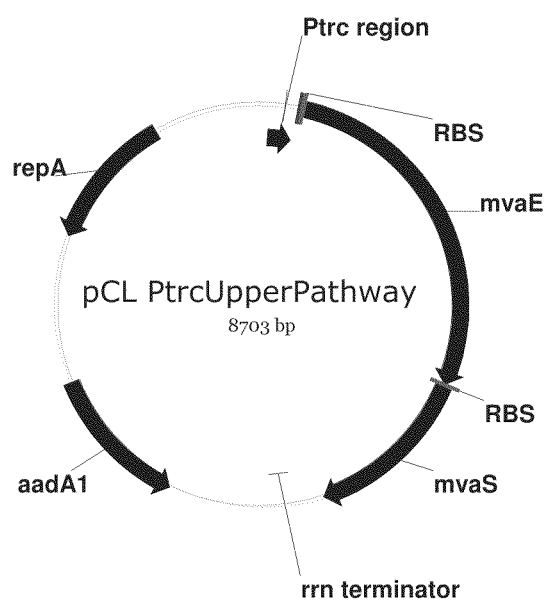
FIG. 26 is a map of pCL PtrcUpperPathway.

The plasmid from strain MCM93 is digested with restriction endonucleases NsiI and PstI to liberate a 1724 bp insert containing the RBS and kudzu isoprene synthase. The 1724 bp fragment is separated on a 1.2% agarose E-gel and purified using the Qiagen Gel Purification kit according to the manufacturer's instructions. Plasmid pTrcKanKKDIy is digested with the restriction endonuclease PstI, treated with SAP for 30 minutes at 37° C. and purified using the Qiagen PCR cleanup kit. The plasmid and kudzu isoprene synthase encoding DNA fragment are ligated using the Roche Quick Ligation kit. The ligation mix is transformed into *E. coli* TOP10 cells and transformants are grown overnight at 37° C. with selection on LA containing Kanamycin at 50 µg/ml. The correct transformant is verified by restriction digestion and the plasmid is designated pTrcKKDyIkISKan (FIGS. 24 and 25). This plasmid is transformed into BL21(λDE3) cells (Invitrogen).

III. Isoprene Production from Mevalonate in *E. coli* Expressing the Recombinant Lower Mevalonate Pathway and Isoprene Synthase from Kudzu Strain BL21/pTrcKKDyIkISKan is cultured in MOPS medium (Neidhardt et al., (1974) *J. Bacteriology* 119:736-747) adjusted to pH 7.1 and supplemented with 0.5% glucose and 0.5% mevalonic acid. A control culture is also set up using identical conditions but without the addition of 0.5% mevalonic acid. The culture is started from an overnight seed culture with a 1% inoculum and induced with 500 µM IPTG when the culture has reached an $OD_{600}$ of 0.3 to 0.5. The cultures are grown at 30° C. with shaking at 250 rpm. The production of isoprene is analyzed 3 hours after induction by using the head space assay described in Example 1. Maximum production of isoprene is $6.67 \times 10^{-4}$ $mol/L_{broth}/OD_{600}/hr$ where $L_{broth}$ is the volume of broth and includes both the volume of the cell medium and the volume of the cells. The control culture not supplemented with mevalonic acid does not produce measurable isoprene.

IV. Cloning the Upper MVA Pathway

The upper mevalonate biosynthetic pathway, comprising two genes encoding three enzymatic activities, is cloned from *Enterococcus faecalis*. The mvaE gene encodes a protein with the enzymatic activities of both acetyl-CoA acetyltransferase and 3-hydroxy-3-methylglutaryl-CoA (HMG-CoA) reductase, the first and third proteins in the pathway, and the mvaS gene encodes the second enzyme in the pathway, HMG-CoA synthase. The mvaE gene is amplified from *E. faecalis* genomic DNA (ATCC 700802D-5) with an *E. coli* ribosome binding site and a spacer in front using the following primers:

```
CF 07-60 (+) Start of mvaE w/ RBS + ATG start
codon SacI
                                  (SEQ ID NO: 34)
5'-GAGACATGAGCTCAGGAGGTAAAAAAACATGAAAACAGTAGTTATT
ATTG CF 07-62 (-) Fuse mvaE to mvaS with RBS in between
                                  (SEQ ID NO: 35)
5'-TTTATCAATCCCAATTGTCATGTTTTTTTACCTCCTTTATTGTTTT
CTTAAATC
```

The mvaS gene is amplified from *E. faecalis* genomic DNA (ATCC 700802D-5) with a RBS and spacer from *E. coli* in front using the following primers:

```
CF 07-61 (+) Fuse mvaE to mvaS with RBS in between
                                  (SEQ ID NO: 36)
5'-GATTTAAGAAAACAATAAAGGAGG-
TAAAAAAACATGACAATTGGGATTG
ATAAA CF 07-102 (-) End of mvaS gene BglII
                                  (SEQ ID NO: 37)
5'-GACATGACATAGATCTTTAGTTTCGATAAGAACGAACGGT
```

The PCR fragments are fused together with PCR using the following primers:

```
CF 07-60 (+) Start of mvaE w/ RBS + ATG start
codon SacI
                                  (SEQ ID NO: 34)
5'-GAGACATGAGCTCAGGAGGTAAAAAAACATGAAAACAGTAGTTATT
ATTG CF 07-102 (-) End of mvaS gene BglII
                                  (SEQ ID NO: 37)
5'-GACATGACATAGATCTTTAGTTTCGATAAGAACGAACGGT
```

The fusion PCR fragment is purified using a Qiagen kit and digested with the restriction enzymes SacI and BglII. This digested DNA fragment is gel purified using a Qiagen kit and ligated into the commercially available vector pTrcHis2A, which has been digested with SacI and BglII and gel purified.

The ligation mix is transformed into *E. coli* Top 10 cells and colonies are selected on LA+50 µg/ml carbenicillin plates. A total of six colonies are chosen and grown overnight in LB+50 μg/ml carbenicillin and plasmids are isolated using a Qiagen kit. The plasmids are digested with SacI and BglII to check for inserts and one correct plasmid is sequenced with the following primers:

```
CF 07-58 (+) Start of mvaE gene
                                  (SEQ ID NO: 38)
5'-ATGAAAACAGTAGTTATTATTGATGC CF 07-59 (-) End of mvaE gene
                                  (SEQ ID NO: 39)
5'-ATGTTATTGTTTTCTTAAATCATTTAAAATAGC CF 07-82 (+) Start of mvaS gene
                                  (SEQ ID NO: 40)
5'-ATGACAATTGGGATTGATAAAATTAG CF 07-83 (-) End of mvaS gene
                                  (SEQ ID NO: 41)
5'-TTAGTTTCGATAAGAACGAACGGT CF 07-86 (+) Sequence in mvaE
                                  (SEQ ID NO: 42)
5'-GAAATAGCCCCATTAGAAGTATC CF 07-87 (+) Sequence in mvaE
                                  (SEQ ID NO: 43)
5'-TTGCCAATCATATGATTGAAAATC CF 07-88 (+) Sequence in mvaE
                                  (SEQ ID NO: 44)
5'-GCTATGCTTCATTAGATCCTTATCG CF 07-89 (+) Sequence mvaS
                                  (SEQ ID NO: 45)
5'-GAAACCTACATCCAATCTTTTGCCC
```

The plasmid called pTrcHis2AUpperPathway#1 is correct by sequencing and is transformed into the commercially available *E. coli* strain BL21. Selection is done on LA+50 μg/ml carbenicillin. Two transformants are chosen and grown in LB+50 μg/ml carbenicillin until they reach an $OD_{600}$ of 1.5. Both strains are frozen in a vial at −80° C. in the presence of glycerol. Strains are designated CF 449 for pTrcHis2AUpperPathway#1 in BL21, isolate #1 and CF 450 for pTrcHis2AUpperPathway#1 in BL21, isolate #2. Both clones are found to behave identically when analyzed.

V. Cloning of UpperMVA Pathway into pCL1920

The plasmid pTrcHis2AUpperPathway is digested with the restriction endonuclease SspI to release a fragment containing pTrc-mvaE-mvaS-(His tag)-terminator. In this fragment, the His-tag is not translated. This blunt ended 4.5 kbp fragment is purified from a 1.2% E-gel using the Qiagen Gel Purification kit. A dephosphorylated, blunt ended 4.2 kbp fragment from pCL1920 is prepared by digesting the vector with the restriction endonuclease PvuII, treating with SAP and gel purifying from a 1.2% E-gel using the Qiagen Gel Purification kit. The two fragments are ligated using the Roche Quick Ligation Kit and transformed into TOP10 chemically competent cells. Transformants are selected on LA containing spectinomycin (50 μg/ml). A correct colony is identified by screening for the presence of the insert by PCR. The plasmid is designated pCL PtrcUpperPathway (FIGS. 26 and 27A-27D).

VI. Strains Expressing the Combined Upper and Lower Mevalonic Acid Pathways

To obtain a strain with a complete mevalonic acid pathway plus kudzu isoprene synthase, plasmids pTrcKKDyIkISKan and pCLpTrcUpperPathway are both transformed into BL21 (λDE3) competent cells (Invitrogen) and transformants are selected on LA containing kanamycin (50 μg/ml) and Spectinomycin (50 μg/ml). The transformants are checked by plasmid prep to ensure that both plasmids are retained in the host. The strain is designated MCM127.

VII. Production of Mevalonic Acid from Glucose in *E. coli*/ pUpperpathway

Single colonies of the BL21/pTrcHis2A-mvaE/mvaS or FM5/p pTrcHis2A-mvaE/mvaS are inoculated into LB+carbenicillin (100 μg/ml) and are grown overnight at 37° C. with shaking at 200 rpm. These cultures are diluted into 50 ml medium in 250 ml baffled flasks to an $OD_{600}$ of 0.1. The medium is TM3+1 or 2% glucose+carbenicillin (100 ug/ml) or TM3+1% glucose+hydrolyzed soy oil+carbenicillin (100 ug/ml) or TM3+biomass (prepared bagasse, corn stover or switchgrass). Cultures are grown at 30° C. with shaking at 200 rpm for approximately 2-3 hours until an $OD_{600}$ of 0.4 is reached. At this point the expression from the mvaE mvaS construct is induced by the addition of IPTG (400 μM). Cultures are incubated for a further 20 or 40 hours with samples taken at 2 hour intervals to 6 hour post induction and then at 24, 36 and 48 hours as needed. Sampling is done by removing 1 ml of culture, measuring the $OD_{600}$, pelleting the cells in a microfuge, removing the supernatant and analyzing it for mevalonic acid.

A 14 liter fermentation of *E. coli* cells with nucleic acids encoding *Enterococcus faecalis* AA-CoA thiolase, HMG-CoA synthase, and HMG-CoA reductase polypeptides produce 22 grams of mevalonic acid with TM3 medium and 2% glucose as the cell medium. A shake flask of these cells produces 2-4 grams of mevalonic acid per liter with LB medium and 1% glucose as the cell culture medium. The production of mevalonic acid in these strains indicates that the MVA pathway was functional in *E. coli*.

VIII. Production of isoprene from *E. coli* BL21 Containing the Upper and Lower MVA Pathway Plus Kudzu Isoprene Synthase.

The following strains are created by transforming in various combinations of plasmids containing the upper and lower MVA pathway and the kudzu isoprene synthase gene as described above and the plasmids containing the idi, dxs, and dxr and isoprene synthase genes described in Example 7. The host cells used are chemically competent BL21(λDE3) and the transformations are done by standard methods. Transformants are selected on L agar containing kanamycin (50 μg/ml) or kanamycin plus spectinomycin (both at a concentration of 50 μg/ml). Plates were grown at 37° C. The resulting strains are designated as follows:

Grown on Kanamycin plus Spectinomycin (50 μg/ml each)
MCM127–pCL Upper MVA+pTrcKKDyIkIS (kan) in BL21 (λDE3)
MCM131–pCL1920+pTrcKKDyIkIS (kan) in BL21(λDE3)
MCM125–pCL Upper MVA+pTrcHis2B (kan) in BL21 (λDE3)

Grown on Kanamycin (50 μg/ml)
MCM64–pTrcKudzu yIDI DXS (kan) in BL21(λDE3)
MCM50–pTrcKudzu (kan) in BL21(λDE3)
MCM123–pTrcKudzu yIDI DXS DXR (kan) in BL21 (λDE3)

The above strains are streaked from freezer stocks to LA+appropriate antibiotic and grown overnight at 37° C. A single colony from each plate is used to inoculate shake flasks (25 ml LB+the appropriate antibiotic). The flasks are incubated at 22° C. overnight with shaking at 200 rpm. The next morning the flasks are transferred to a 37° C. incubator and grown for a further 4.5 hours with shaking at 200 rpm. The 25 ml cultures are centrifuged to pellet the cells and the cells are resuspended in 5 ml LB+the appropriate antibiotic. The cultures are then diluted into 25 ml LB+1% glucose+the appropriate antibiotic to an $OD_{600}$ of 0.1. Two flasks for each strain are set up, one set for induction with IPTG (800 µM) the second set is not induced. The cultures are incubated at 37° C. with shaking at 250 rpm. One set of the cultures are induced after 1.50 hours (immediately following sampling time point 1). At each sampling time point, the $OD_{600}$ is measured and the amount of isoprene determined as described in Example 1. Results are presented in Table 8-1. The amount of isoprene made is presented as the amount at the peak production for the particular strain.

TABLE 8-1

Production of Isoprene in *E. coli* Strains

| Strain | Isoprene (µg/liter/OD/hr) |
|---|---|
| MCM50 | 23.8 |
| MCM64 | 289 |
| MCM125 | ND |
| MCM131 | Trace |
| MCM127 | 874 |

ND: not detected
Trace: peak present but not integrable.

IX. Analysis of Mevalonic Acid

Mevalonolactone (1.0 g, 7.7 mmol) (CAS#503-48-0) is supplied from Sigma-Aldrich (WI, USA) as a syrup that is dissolved in water (7.7 mL) and is treated with potassium hydroxide (7.7 mmol) in order to generate the potassium salt of mevalonic acid. The conversion to mevalonic acid is confirmed by $^1$H NMR analysis. Samples for HPLC analysis are prepared by centrifugation at 14,000 rpm for 5 minutes to remove cells, followed by the addition of a 300 µl aliquot of supernatant to 900 µl of $H_2O$. Perchloric acid (36 µl of a 70% solution) is then added followed by mixing and cooling on ice for 5 minutes. The samples are then centrifuged again (14,000 rpm for 5 mM) and the supernatant transferred to HPLC. Mevalonic acid standards (20, 10, 5, 1 and 0.5 g/L) are prepared in the same fashion. Analysis of mevalonic acid (20 uL injection volume) is performed by HPLC using a BioRad Aminex 87-H+column (300 mm by 7.0 mm) eluted with 5 mM sulfuric acid at 0.6 mL/min with refractive index (RI) detection. Under these conditions mevalonic acid elutes as the lactone form at 18.5 minutes.

X. Production of Isoprene from *E. coli* BL21 Containing the Upper MVA Pathway Plus Kudzu Isoprene Synthase A 15-L scale fermentation of *E. coli* expressing mevalonic acid pathway polypeptides and Kudzu isoprene synthase is used to produce isoprene from cells in fed-batch culture. This experiment demonstrates that growing cells under glucose limiting conditions results in the production of 2.2 g/L of isoprene.

Medium Recipe (per liter fermentation medium): The medium is generated using the following components per liter fermentation medium: $K_2HPO_4$ 7.5 g, $MgSO_4.7H_2O$ 2 g, citric acid monohydrate 2 g, ferric ammonium citrate 0.3 g, yeast extract 0.5 g, and 1000× modified trace metal solution 1 ml. All of the components are added together and dissolved in $diH_2O$. This solution is autoclaved. The pH is adjusted to 7.0 with ammonium hydroxide (30%) and q.s. to volume. Glucose 10 g, thiamine.HCl 0.1 g, and antibiotics are added after sterilization and pH adjustment.

1000× Modified Trace Metal Solution: The 1000× modified trace metal solution is generated using the following components: citric acid.$H_2O$ 40 g, $MnSO_4.H_2O$ 30 g, NaCl 10 g, $FeSO_4.7H_2O$ 1 g, $CoCl_2.6H_2O$ 1 g, $ZnSO_4.7H_2O$ 1 g, $CuSO_4.5H_2O$ 100 mg, $H_3BO_3$ 100 mg, and $NaMoO_4.2H_2O$ 100 mg. Each component is dissolved one at a time in $diH_2O$, pH to 3.0 with HCl/NaOH, then q.s. to volume, and filter sterilized with a 0.22 micron filter.

Fermentation is performed in a 15-L bioreactor with BL21 (DE3) *E. coli* cells containing the pCL PtrcUpperPathway (FIG. 26) and pTrcKKDyIkIS plasmids. This experiment is carried out to monitor isoprene formation from glucose at the desired fermentation pH 7.0 and temperature 30° C. An inoculum of *E. coli* strain taken from a frozen vial is streaked onto an LB broth agar plate (with antibiotics) and incubated at 37° C. A single colony is inoculated into soytone-yeast extract-glucose medium. After the inoculum grows to OD 1.0 when measured at 550 nm, 500 mL is used to inoculate a 15-L bioreactor containing an initial working volume of 5 L.

Figure 54:
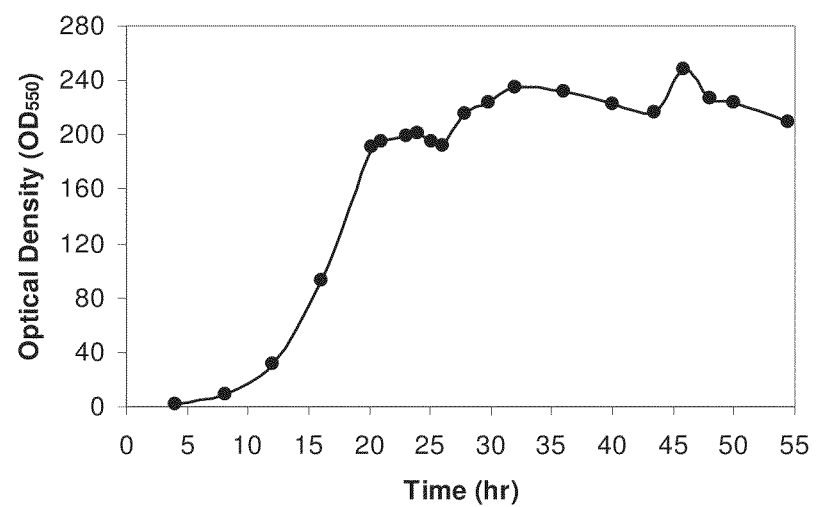
FIG. 54 is a time course of optical density within the 15-L bioreactor fed with glucose.
Figure 55:
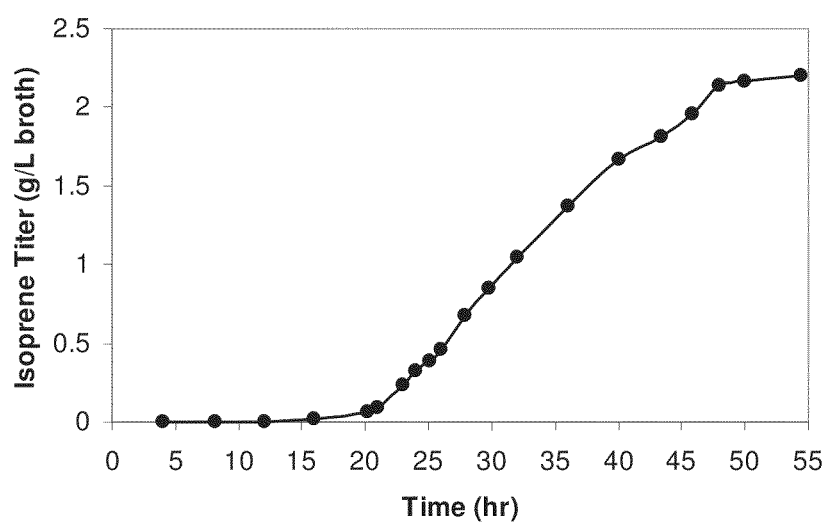
FIG. 55 is a time course of isoprene titer within the 15-L bioreactor fed with glucose. The titer is defined as the amount of isoprene produced per liter of fermentation broth.
Figure 56:
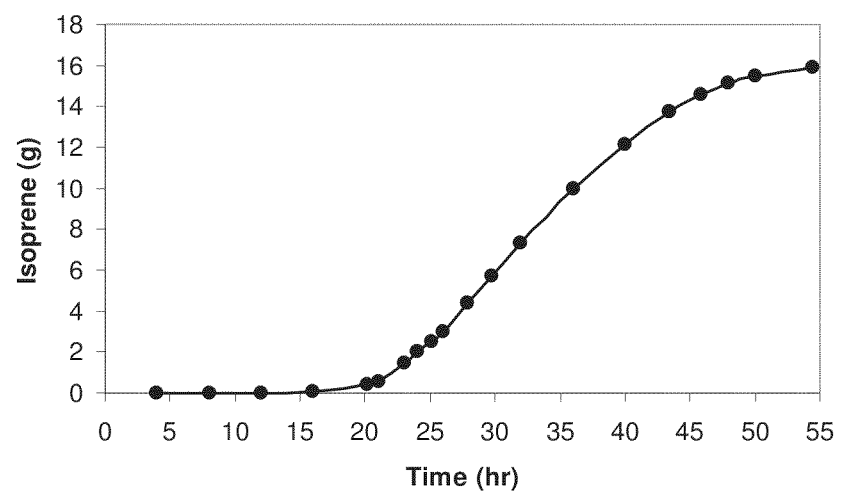
FIG. 56 is a time course of total isoprene produced from the 15-L bioreactor fed with glucose.

Glucose is fed at an exponential rate until cells reach the stationary phase. After this time the glucose feed is decreased to meet metabolic demands. The total amount of glucose delivered to the bioreactor during the 54 hour fermentation is 3.7 kg. Induction is achieved by adding isopropyl-beta-D-1-thiogalactopyranoside (IPTG). The IPTG concentration is brought to 25 uM when the optical density at 550 nm ($OD_{550}$) reaches a value of 10. The IPTG concentration is raised to 50 uM when $OD_{550}$ reached 190. IPTG concentration is raised to 100 uM at 38 hours of fermentation. The $OD_{550}$ profile within the bioreactor over time is shown in FIG. 54. The isoprene level in the off gas from the bioreactor is determined as described herein. The isoprene titer increases over the course of the fermentation to a final value of 2.2 g/L (FIG. 55). The total amount of isoprene produced during the 54 hour fermentation is 15.9 g, and the time course of production is shown in FIG. 56.

XI. Isoprene Fermentation from *E. coli* Expressing Genes from the Mevalonic Acid Pathway and Grown in Fed-Batch Culture at the 15-L Scale A 15-L scale fermentation of *E. coli* expressing mevalonic acid pathway polypeptides and Kudzu isoprene synthase is used to produce isoprene from cells in fed-batch culture. This experiment demonstrates that growing cells under glucose limiting conditions results in the production of 3.0 g/L of isoprene.

Medium Recipe (per liter fermentation medium): The medium is generated using the following components per liter fermentation medium: $K_2HPO_4$ 7.5 g, $MgSO_4.7H_2O$ 2 g, citric acid monohydrate 2 g, ferric ammonium citrate 0.3 g, yeast extract 0.5 g, and 1000× Modified Trace Metal Solution 1 ml. All of the components sre added together and dissolved in $diH_2O$. This solution is autoclaved. The pH is adjusted to 7.0 with ammonium hydroxide (30%) and q.s. to volume. Glucose 10 g, thiamine.HCl 0.1 g, and antibiotics are added after sterilization and pH adjustment.

1000× Modified Trace Metal Solution: The 1000× modified trace metal solution is generated using the following components: citric acid.$H_2O$ 40 g, $MnSO_4.H_2O$ 30 g, NaCl 10 g, $FeSO_4.7H_2O$ 1 g, $CoCl_2.6H_2O$ 1 g, $ZnSO_4.7H_2O$ 1 g, $CuSO_4.5H_2O$ 100 mg, $H_3BO_3$ 100 mg, and $NaMoO_4.2H_2O$ 100 mg. Each component is dissolved one at a time in $diH_2O$, pH to 3.0 with HCl/NaOH, then q.s. to volume, and filter sterilized with a 0.22 micron filter.

Fermentation is performed in a 15-L bioreactor with BL21 (DE3) *E. coli* cells containing the pCL PtrcUpperMVA and pTrc KKDyIkIS plasmids. This experiment is carried out to monitor isoprene formation from glucose at the desired fermentation pH 7.0 and temperature 30° C. An inoculum of *E. coli* strain taken from a frozen vial is streaked onto an LB broth agar plate (with antibiotics) and incubated at 37° C. A single colony is inoculated into tryptone-yeast extract medium. After the inoculum grows to OD 1.0, measured at 550 nm, 500 mL is used to inoculate a 15-L bioreactor containing an initial working volume of 5 L.

Glucose is fed at an exponential rate until cells reach the stationary phase. After this time, the glucose feed is decreased to meet metabolic demands. The total amount of glucose delivered to the bioreactor during the 59 hour fermentation is 2.2 kg. Induction is achieved by adding IPTG. The IPTG concentration is brought to 25 uM when the optical density at 550 nm ($OD_{550}$) reaches a value of 10. The IPTG concentration is raised to 50 uM when $OD_{550}$ reaches 190. The $OD_{550}$ profile within the bioreactor over time is shown in FIG. 93. The isoprene level in the off gas from the bioreactor is determined as described herein. The isoprene titer increases over the course of the fermentation to a final value of 3.0 g/L (FIG. 94). The total amount of isoprene produced during the 59 hour fermentation is 22.8 g, and the time course of production is shown in FIG. 95. The molar yield of utilized carbon that goes into producing isoprene during fermentation is 2.2%. The weight percent yield of isoprene from glucose is 1.0%.

XII. Isoprene Fermentation from *E. coli* Expressing Genes from the Mevalonic Acid Pathway and Grown in Fed-Batch-culture at the 15-L Scale A 15-L scale fermentation of *E. coli* expressing mevalonic acid pathway polypeptides, *Pueraria lobata* isoprene synthase, and Kudzu isoprene synthase is used to produce isoprene from cells in fed-batch culture. This experiment demonstrates that growing cells under glucose limiting conditions results in the production of 3.3 g/L of isoprene.

i) Construction of pCLPtrcUpperPathwayHGS2

The gene encoding isoprene synthase from *Pueraria lobata* is PCR-amplified using primers NsiI-RBS-HGS F (CTTGATGCATCCTGCATTCGCCCTTAGGAGG, SEQ ID NO:88) and pTrcR (CCAGGCAAATTCTGTTTTAT-CAG, SEQ ID NO:89), and pTrcKKDyIkIS as a template. The PCR product thus obtained is restriction-digested with NsiI and PstI and gel-purified. The plasmid pCL PtrcUpperPathway is restriction-digested with PstI and dephosphorylated using rAPid alkaline phosphatase (Roche) according to manufacturer's instructions.

These DNA fragments are ligated together and the ligation reaction is transformed into *E. coli* Top10 chemcially competent cells (Invitrogen), plated on L agar containing spectinomycin (50 μg/ml) and incubated overnight at 37° C. Plasmid DNA is prepared from 6 clones using the Qiaquick Spin Mini-prep kit. The plasmid DNA is digested with restriction enzymes EcoRV and MluI to identify a clone in which the insert has the right orientation (i.e., the gene oriented in the same way as the pTrc promoter).

The resulting correct plasmid is designated pCLPtrcUpperPathwayHGS2. This plasmid is assayed using the headspace assay described herein and found to produce isoprene in *E. coli* Top10, thus validating the functionality of the gene. The plasmid is transformed into BL21(λDE3) containing pTrcKKDyIkIS to yield the strain BL21/pCLPtrcUpperPathwayHGS2-pTrcKKDyIkIS. This strain has an extra copy of the isoprene synthase compared to the BL21/pCL PtrcUpperMVA and pTrc KKDyIkIS strain (Example 8, part XI). This strain also has increased expression and activity of HMGS compared to the BL21/pCL PtrcUpperMVA and pTrc KKDyIkIS strain used in Example 8, part XI.

ii) Isoprene Fermentation from *E. coli* Expressing pCLPtrcUpperPathwayHGS2-pTrcKKDyIkIS and Grown in Fed-Batch Culture at the 15-L Scale Medium Recipe (per liter fermentation medium): The medium is generated using the following components per liter fermentation medium: $K_2HPO_4$ 7.5 g, $MgSO_4.7H_2O$ 2 g, citric acid monohydrate 2 g, ferric ammonium citrate 0.3 g, yeast extract 0.5 g, and 1000× modified trace metal solution 1 ml. All of the components are added together and dissolved in $diH_2O$. This solution is autoclaved. The pH is adjusted to 7.0 with ammonium hydroxide (30%) and q.s. to volume. Glucose 10 g, thiamine.HCl 0.1 g, and antibiotics were added after sterilization and pH adjustment.

1000× Modified Trace Metal Solution: The 1000× modified trace metal solution is generated using the following components: citric acid.$H_2O$ 40 g, $MnSO_4.H_2O$ 30 g, NaCl 10 g, $FeSO_4.7H_2O$ 1 g, $CoCl_2.6H_2O$ 1 g, $ZnSO_4.7H_2O$ 1 g, $CuSO_4.5H_2O$ 100 mg, $H_3BO_3$ 100 mg, and $NaMoO_4.2H_2O$ 100 mg. Each component is dissolved one at a time in Di $H_2O$, pH to 3.0 with HCl/NaOH, then q.s. to volume and filter sterilized with 0.22 micron filter.

Fermentation is performed in a 15-L bioreactor with BL21 (DE3) *E. coli* cells containing the pCLPtrcUpperPathwayHGS2 and pTrc KKDyIkIS plasmids. This experiment is carried out to monitor isoprene formation from glucose at the desired fermentation pH 7.0 and temperature 30° C. An inoculum of *E. coli* strain taken from a frozen vial is streaked onto an LB broth agar plate (with antibiotics) and incubated at 37° C. A single colony is inoculated into tryptone-yeast extract medium. After the inoculum grows to OD 1.0 measured at 550 nm, 500 mL is used to inoculate a 15-L bioreactor containing an initial working volume of 5 L.

Glucose is fed at an exponential rate until cells reach the stationary phase. After this time the glucose feed is decreased to meet metabolic demands. The total amount of glucose delivered to the bioreactor during the 58 hour fermentation is 2.1 kg. Induction is achieved by adding IPTG. The IPTG concentration is brought to 25 uM when the optical density at 550 nm ($OD_{550}$) reach a value of 9. The IPTG concentration is raised to 50 uM when $OD_{550}$ reached 170. The $OD_{550}$ profile within the bioreactor over time is shown in FIG. 104. The isoprene level in the off gas from the bioreactor is determined as described herein. The isoprene titer increases over the course of the fermentation to a final value of 3.3 g/L (FIG. 105). The total amount of isoprene produced during the 58 hour fermentation is 24.5 g and the time course of production is shown in FIG. 106. The molar yield of utilized carbon that goes into producing isoprene during fermentation is 2.5%. The weight percent yield of isoprene from glucose is 1.2%. Analysis shows that the activity of the isoprene synthase is increased by approximately 3-4 times that compared to BL21 expressing CL PtrcUpperMVA and pTrc KKDyIkIS plasmids (data not shown).

XIII. Chromosomal Integration of the Lower Mevalonate Pathway in *E. coli*.

A synthetic operon containing mevalonate kinase, mevalonate phosphate kinase, mevalonate pyrophosphate decarboxylase, and the IPP isomerase is integerated into the chromosome of *E. coli*. If desired, expression may be altered by integrating different promoters 5' of the operon. Table 8-2 lists primers used for this experiment.

TABLE 8-2

PRIMERS

| Primer (Description) | Sequence |
|---|---|
| MCM78 (attTn7 up rev for integration construct) | gcatgctcgagcggccgcTTTTAATCAAACATCCTGCCAA CTC (SEQ ID NO: 91) |
| MCM79 (attTn7 down rev for integration construct) | gatcgaagggcgatcgTGTCACAGTCTGGCGAAACCG (SEQ ID NO: 92) |
| MCM88 (attTn7 up forw for integration construct) | ctgaattctgcagatatcTGTTTTTCCACTCTTCGTTCACTT T (SEQ ID NO: 93) |
| MCM89 (attTn7 down forw for integration construct) | tctagagggcccAAGAAAAATGCCCCGCTTACG (SEQ ID NO: 94) |
| MCM104 (GI1.2 promoter - MVK) | Gatcgcggccgcgcccttgacgatgccacatcctgagcaaataattcaaccac taattgtgagcggataacacaaggaggaaacagctatgtcattaccgttcttaact tc (SEQ ID NO: 95) |
| MCM105 (aspA terminator - yIDI) | Gatcgggccccaagaaaaaaggcacgtcatctgacgtgccttttttatttgtaga cgcgttgttatagcattcta (SEQ ID NO: 96) |
| MCM120 (forw of attTn7: attTn7 homology, GB marker homology) | aaagtagccgaagatgacggtttgtcacatggagttggcaggatgtttgattaaa agcAATTAACCCTCACTAAAGGGCGG (SEQ ID NO: 97) |
| MCM127 (Rev complement of 1.2 GI: GB marker homology (extra long), promoter, RBS, ATG) | AGAGTGTTCACCAAAAATAATAACCTTTCCCGG TGCAgaagttaagaacggtaatgacatagctgtttcctccttgtgttatccgct cacaattagtggttgaatttatttgctcaggatgtggcatcgtcaagggcTAAT ACGACTCACTATAGGGCTCG (SEQ ID NO: 98) | i) Target Vector Construction

The attTn7 site is selected for integration. Regions of homology upstream (attTn7 up) (primers MCM78 and MCM79) and downstream (attTn7 down) (primers MCM88 and MCM89) are amplified by PCR from MG1655 cells. A 50 uL reaction with 1 uL 10 uM primers, 3 uL ddH2O, 45 uL Invitrogen Platinum PCR Supermix High Fidelity, and a scraped colony of MG1655 is denatured for 2:00 at 94° C., cycled 25 times (2:00 at 94° C., 0:30 at 50° C., and 1:00 at 68° C.), extended for 7:00 at 72° C., and cooled to 4° C. This resulting DNA is cloned into pCR2.1 (Invitrogen) according to the manufacturer's instructions, resulting in plasmids MCM278 (attTn7 up) and MCM252 (attTn7 down). The 832 bp Apai-Pvui fragment digested and gel purified from MCM252 is cloned into Apai-Pvui digested and gel purified plasmid pR6K, creating plasmid MCM276. The 825 bp PstI-NotI fragment digested and gel purified from MCM278 is cloned into PstI-NotI digested and gel purified MCM276, creating plasmid MCM281.

ii) Cloning of Lower Pathway and Promoter

MVK-PMK-MVD-IDI genes are amplified from pTrcK-KDyIkIS with primers MCM104 and MCM105 using Roche Expand Long PCR System according to the manufacturer's instructions. This product is digested with NotI and ApaI and cloned into MCM281 which has been digested with NotI and ApaI and gel purified. Primers MCM120 and MCM127 are used to amplify CMR cassette from the GeneBridges FRT-gb2-Cm-FRT template DNA using Stratagene Pfu Ultra II. A PCR program of denaturing at 95° C. for 4:00, 5 cycles of 95° C. for 0:20, 55° C. for 0:20, 72° C. for 2:00, 25 cycles of 95° C. for 0:20, 58° C. for 0:20, 72° C. for 2:00, 72° C. for 10:00, and then cooling to 4° C. is used with four 50 uL PCR reactions containing 1 uL ~10 ng/uL template, 1 uL each primer, 1.25 uL 10 mM dNTPs, 5 uL 10× buffer, 1 uL enzyme, and 39.75 uL ddH20. Reactions are pooled, purified on a Qiagen PCR cleanup column, and used to electroporate water-washed Pir1 cells containing plasmid MCM296. Electroporation is carried out in 2 mM cuvettes at 2.5V and 200 ohms. Electroporation reactions are recovered in LB for 3 hr at 30° C. Transformant MCM330 is selected on LA with CMPS, Kan50 (FIGS. 107 and 108A-108C).

iii) Integration into E. coli Chromosome

Miniprepped DNA (Qiaquick Spin kit) from MCM330 is digested with SnaBI and used to electroporate BL21(DE3) (Novagen) or MG1655 containing GeneBridges plasmid pRedET Carb. Cells are grown at 30° C. to ~OD1 then induced with 0.4% L-arabinose at 37° C. for 1.5 hours. These cells are washed three times in 4° C. ddH$_2$O before electroporation with 2 uL of DNA. Integrants are selected on L agar containing chloramphenicol (5 ug/ml) and subsequently confirmed to not grow on L agar+Kanamycin (50 ug/ml). BL21 integrant MCM331 and MG1655 integrant MCM333 are frozen.

iv) Construction of pET24D-Kudzu Encoding Kudzu Isoprene Synthase

The kudzu isoprene synthase gene is subcloned into the pET24d vector (Novagen) from the pCR2.1 vector (Invitrogen). In particular, the kudzu isoprene synthase gene is amplified from the pTrcKudzu template DNA using primers MCM50 5'-GATCATGCAT TCGCCCTTAG GAGG-TAAAAA AACATGTGTG CGACCTCTTC TCAATT-TACT (SEQ ID NO:99) and MCM53 5'-CGGTCGACGG ATCCCTGCAG TTAGACATAC ATCAGCTG (SEQ ID NO:100). PCR reactions are carried out using Taq DNA Polymerase (Invitrogen), and the resulting PCR product is cloned into pCR2.1-TOPO TA cloning vector (Invitrogen), and transformed into E. coli Top10 chemically competent cells (Invitrogen). Transformants are plated on L agar containing carbenicillin (50 μg/ml) and incubated overnight at 37° C. Five ml Luria Broth cultures containing carbenicillin 50 μg/ml are inoculated with single transformants and grown overnight at 37° C. Five colonies are screened for the correct insert by sequencing of plasmid DNA isolated from 1 ml of liquid culture (Luria Broth) and purified using the QIAprep Spin Mini-prep Kit (Qiagen). The resulting plasmid, designated MCM93, contains the kudzu isoprene synthase coding sequence in a pCR2.1 backbone.

The kudzu coding sequence is removed by restriction endonuclease digestion with PciI and BamH1 (Roche) and gel purified using the QIAquick Gel Extraction kit (Qiagen). The pET24d vector DNA is digested with NcoI and BamHI (Roche), treated with shrimp alkaline phosphatase (Roche), and purified using the QIAprep Spin Mini-prep Kit (Qiagen). The kudzu isoprene synthase fragment is ligated to the NcoI/BamH1 digested pET24d using the Rapid DNA Ligation Kit (Roche) at a 5:1 fragment to vector ratio in a total volume of 20 μl. A portion of the ligation mixture (5 μl) is transformed into *E. coli* Top 10 chemically competent cells and plated on L agar containing kanamycin (50 μg/ml). The correct transformant is confirmed by sequencing and transformed into chemically competent BL21(λDE3)pLysS cells (Novagen). A single colony is selected after overnight growth at 37° C. on L agar containing kanamycin (50 μg/ml). A map of the resulting plasmid designated as pET24D-Kudzu is shown in FIG. 109. The sequence of pET24D-Kudzu (SEQ ID NO:101) is shown in FIGS. 110A and 110B. Isoprene synthase activity is confirmed using a headspace assay.

v) Production Strains

Strains MCM331 and MCM333 are cotransformed with plasmids pCLPtrcupperpathway and either pTrcKudzu or pETKudzu, resulting in the strains shown in Table 8-3.

TABLE 8-3

Production Strains

| Background | Integrated Lower | Upper MVA plasmid | IpS plasmid | Production Stain |
|---|---|---|---|---|
| BL21(DE3) | MCM331 | pCLPtrcUpper Pathway | pTrcKudzu | MCM343 |
| BL21(DE3) | MCM331 | pCLPtrcUpper Pathway | pET24D-Kudzu | MCM335 |
| MG1655 | MCM333 | pCLPtrcUpper Pathway | pTrcKudzu | MCM345 | vi) Isoprene Fermentation from *E. coli* Expressing Genes from the Mevalonic Acid Pathway and Grown in Red-Batch Culture at the 15-L Scale.

Medium Recipe (per liter fermentation medium): The medium is generated using the following components per liter fermentation medium: $K_2HPO_4$ 7.5 g, $MgSO_4.7H_2O$ 2 g, citric acid monohydrate 2 g, ferric ammonium citrate 0.3 g, yeast extract 0.5 g, and 1000× modified trace metal solution 1 ml. All of the components are added together and dissolved in diH2O. This solution is autoclaved. The pH is adjusted to 7.0 with ammonium hydroxide (30%) and q.s. to volume. Glucose 10 g, thiamine.HCl 0.1 g, and antibiotics are added after sterilization and pH adjustment.

1000× Modified Trace Metal Solution: The 1000× modified trace metal solution is generated using the following components: citric acid.$H_2O$ 40 g, $MnSO_4.H_2O$ 30 g, NaCl 10 g, $FeSO_4.7H_2$ 1 g, $CoCl_2.6H_2O$ 1 g, $ZnSO_4.7H_2O$ 1 g, $CuSO_4.5H_2$ 100 mg, $H_3BO_3$ 100 mg, and $NaMoO_4.2H_2O$ 100 mg. Each component is dissolved one at a time in Di $H_2O$, pH to 3.0 with HCl/NaOH, then q.s. to volume and filter sterilized with a 0.22 micron filter.

Fermentation is performed in a 15-L bioreactor with BL21 (DE3) *E. coli* cells containing the gi1.2 integrated lower MVA pathway described above and the pCL PtrcUpperMVA and pTrcKudzu plasmids. This experiment is carried out to monitor isoprene formation from glucose at the desired fermentation pH 7.0 and temperature 30° C. An inoculum of *E. coli* strain taken from a frozen vial is streaked onto an LB broth agar plate (with antibiotics) and incubated at 37° C. A single colony is inoculated into tryptone-yeast extract medium. After the inoculum grows to OD 1.0, measured at 550 nm, 500 mL is used to inoculate a 15-L bioreactor containing an initial working volume of 5 L.

Glucose is fed at an exponential rate until cells reach the stationary phase. After this time, the glucose feed is decreased to meet metabolic demands. The total amount of glucose delivered to the bioreactor during the 57 hour fermentation is 3.9 kg. Induction is achieved by adding IPTG. The IPTG concentration is brought to 100 uM when the carbon dioxide evolution rate reaches 100 mmol/L/hr. The $OD_{550}$ profile within the bioreactor over time is shown in FIG. 111A. The isoprene level in the off gas from the bioreactor is determined as described herein. The isoprene titer increases over the course of the fermentation to a final value of 1.6 g/L (FIG. 111B). The specific productivity of isoprene over the course of the fermentation is shown in FIG. 111C and peaks at 1.2 mg/OD/hr. The total amount of isoprene produced during the 57 hour fermentation is 16.2 g. The molar yield of utilized carbon that goes into producing isoprene during fermentation is 0.9%. The weight percent yield of isoprene from glucose is 0.4%.

XIV. Production of Isoprene from *E. coli* BL21 Containing the Kudzu Isoprene Synthase Using Glycerol as a Carbon Source A 15-L scale fermentation of *E. coli* expressing Kudzu isoprene synthase is used to produce isoprene from cells fed glycerol in fed-batch culture. This experiment demonstrates that growing cells in the presence of glycerol (without glucose) results in the production of 2.2 mg/L of isoprene.

Medium Recipe (per liter fermentation medium): The medium is generated using the following components per liter fermentation medium: $K_2HPO_4$ 7.5 g, $MgSO_4.7H_2O$ 2 g, citric acid monohydrate 2 g, ferric ammonium citrate 0.3 g, and 1000× modified trace metal solution 1 ml. All of the components are added together and dissolved in di$H_2O$. This solution is autoclaved. The pH is adjusted to 7.0 with ammonium hydroxide (30%) and q.s. to volume. Glycerol 5.1 g, thiamine.HCl 0.1 g, and antibiotics are added after sterilization and pH adjustment.

1000× Modified Trace Metal Solution: The medium is generated using the following components per liter fermentation medium: citric acid.$H_2O$ 40 g, $MnSO_4.H_2O$ 30 g, NaCl 10 g, $FeSO_4.7H_2O$ 1 g, $CoCl_2.6H_2O$ 1 g, $ZnSO_4.7H_2O$ 1 g, $CuSO_4.5H_2O$ 100 mg, $H_3BO_3$ 100 mg, and $NaMoO_4.2H_2O$ 100 mg. Each component is dissolved one at a time in di$H_2O$, pH to 3.0 with HCl/NaOH, then q.s. to volume and filter sterilized with a 0.22 micron filter.

Fermentation is performed in a 15-L bioreactor with BL21 (DE3) *E. coli* cells containing the pTrcKudzu plasmid. This experiment is carried out to monitor isoprene formation from glycerol at the desired fermentation pH 7.0 and temperature 35° C. An inoculum of *E. coli* strain taken from a frozen vial is streaked onto an LA broth agar plate (with antibiotics) and incubated at 37° C. A single colony is inoculated into soytone-yeast extract-glucose medium and grown at 35° C. After the inoculum grows to OD 1.0, measured at 550 nm, 600 mL is used to inoculate a 7.5-L bioreactor.

Figure 57:
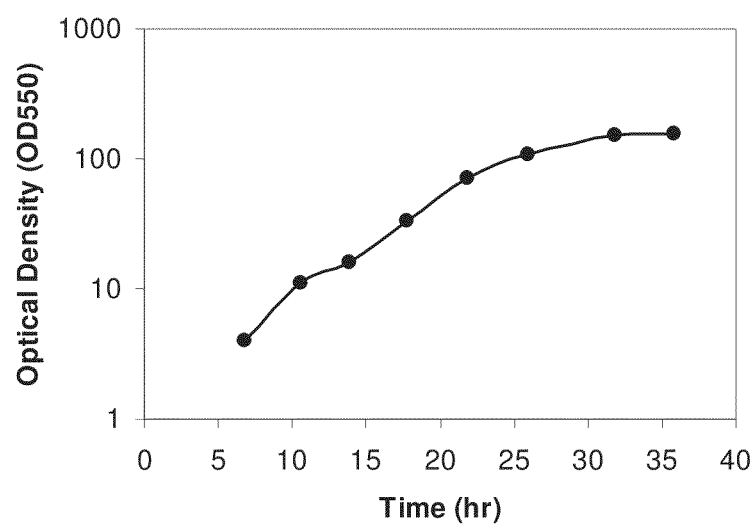
FIG. 57 is a time course of optical density within the 15-L bioreactor fed with glycerol.
Figure 58:
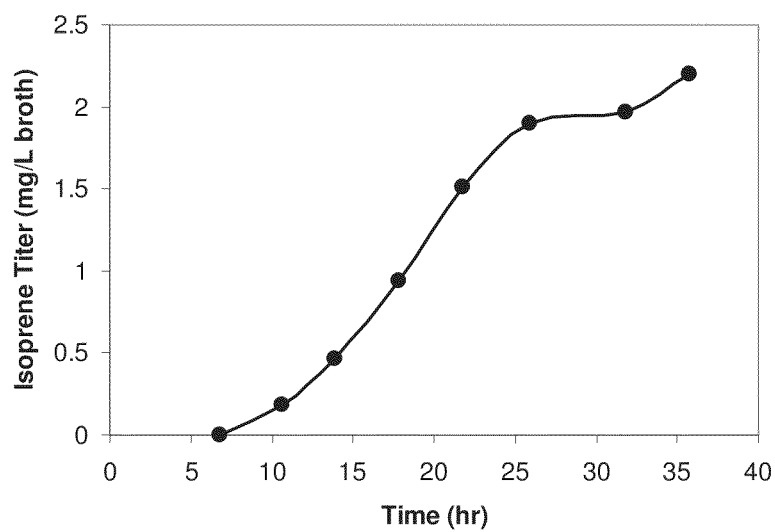
FIG. 58 is a time course of isoprene titer within the 15-L bioreactor fed with glycerol. The titer is defined as the amount of isoprene produced per liter of fermentation broth.
Figure 59:
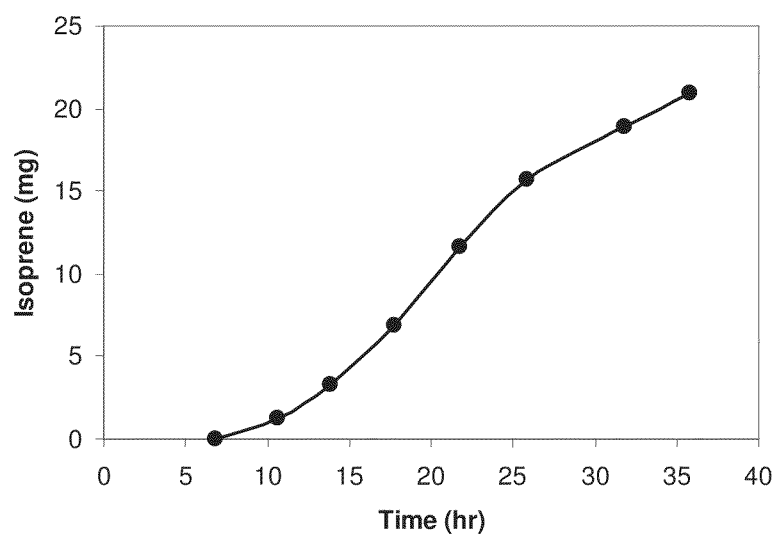
FIG. 59 is a time course of total isoprene produced from the 15-L bioreactor fed with glycerol.

Glycerol is fed at an exponential rate until cells reach an optical density at 550 nm ($OD_{550}$) of 153. The total amount of glycerol delivered to the bioreactor during the 36 hour fermentation is 1.7 kg. Other than the glucose in the inoculum, no glucose is added to the bioreactor. Induction is achieved by adding IPTG. The IPTG concentration is brought to 20 uM when the $OD_{550}$ reached a value of 50. The $OD_{550}$ profile within the bioreactor over time is shown in FIG. 57. The isoprene level in the off gas from the bioreactor is determined as described herein. The isoprene titer increases over the course of the fermentation to a final value of 2.2 mg/L (FIG. 58). The total amount of isoprene produced during the 54 hour fermentation is 20.9 mg, and the time course of production is shown in FIG. 59.

XV. Isoprene Fermentation from *E. coli* Expressing Genes from the Mevalonic Acid Pathway and Grown in Fed-Batch Culture at the 15-L Scale Using Invert Sugar as a Carbon Source A 15-L scale fermentation of *E. coli* expressing mevalonic acid pathway polypeptides and Kudzu isoprene synthase is used to produce isoprene from cells fed invert sugar in fed-batch culture. This experiment demonstrates that growing cells in the presence of invert sugar results in the production of 2.4 g/L of isoprene.

Medium Recipe (per liter fermentation medium): The medium is generated using the following components per liter fermentation medium: $K_2HPO_4$ 7.5 g, $MgSO_4 \cdot 7H_2O$ 2 g, citric acid monohydrate 2 g, ferric ammonium citrate 0.3 g, yeast extract 0.5 g, and 1000× Modified Trace Metal Solution 1 ml. All of the components are added together and dissolved in $diH_2O$. This solution is autoclaved. The pH is adjusted to 7.0 with ammonium hydroxide (30%) and q.s. to volume. Invert sugar 10 g, thiamine.HCl 0.1 g, and antibiotics are added after sterilization and pH adjustment.

1000× Modified Trace Metal Solution: The 1000× modified trace metal solution is generated using the following components: citric acid.$H_2O$ 40 g, $MnSO_4 \cdot H_2O$ 30 g, NaCl 10 g, $FeSO_4 \cdot 7H_2O$ 1 g, $CoCl_2 \cdot 6H_2O$ 1 g, $ZnSO_4 \cdot 7H_2O$ 1 g, $CuSO_4 \cdot 5H_2O$ 100 mg, $H_3BO_3$ 100 mg, and $NaMoO_4 \cdot 2H_2O$ 100 mg. Each component is dissolved one at a time in Di $H_2O$, pH to 3.0 with HCl/NaOH, then q.s. to volume and filter sterilized with 0.22 micron filter.

Fermentation is performed in a 15-L bioreactor with BL21 (DE3) *E. coli* cells containing the pCL PtrcUpperMVA and pTrc KKDyIkIS plasmids. This experiment is carried out to monitor isoprene formation from invert sugar at the desired fermentation pH 7.0 and temperature 30° C. An inoculum of *E. coli* strain taken from a frozen vial is streaked onto an LB broth agar plate (with antibiotics) and incubated at 37° C. A single colony is inoculated into tryptone-yeast extract medium. After the inoculum grows to OD 1.0, measured at 550 nm, 500 mL is used to inoculate a 15-L bioreactor containing an initial working volume of 5 L.

Invert sugar is fed at an exponential rate until cells reached the stationary phase. After this time the invert sugar feed is decreased to meet metabolic demands. The total amount of invert sugar delivered to the bioreactor during the 44 hour fermentation is 2.4 kg. Induction is achieved by adding IPTG. The IPTG concentration is brought to 25 uM when the optical density at 550 nm ($OD_{550}$) reaches a value of 9. The IPTG concentration is raised to 50 uM when $OD_{550}$ reaches 200. The $OD_{550}$ profile within the bioreactor over time is shown in FIG. 96. The isoprene level in the off gas from the bioreactor is determined as described herein. The isoprene titer increases over the course of the fermentation to a final value of 2.4 g/L (FIG. 97). The total amount of isoprene produced during the 44 hour fermentation is 18.4 g and the time course of production is shown in FIG. 98. The molar yield of utilized carbon that goes into producing isoprene during fermentation is 1.7%. The weight percent yield of isoprene from glucose is 0.8%.

Example 9

Construction of the Upper and Lower MVA Pathway for Integration into *Bacillus subtilis*

I. Construction of the Upper MVA pathway in *B. subtilis*

The upper pathway from *Enterococcus faecalis* is integrated into *B. subtilis* under control of the aprE promoter. The upper pathway consists of two genes; mvaE, which encodes for AACT and HMGR, and mvaS, which encodes for HMGS. The two genes are fused together with a stop codon in between, an RBS site in front of mvaS, and are under the control of the aprE promoter. A terminator is situated after the mvaE gene. The chloramphenicol resistance marker is cloned after the mvaE gene and the construct is integrated at the aprE locus by double cross over using flanking regions of homology.

Four DNA fragments are amplified by PCR such that they contain overhangs that will allow them to be fused together by a PCR reaction. PCR amplifications are carried out using Herculase polymerase according to manufacturer's instructions.

```
1. PaprE
CF 07-134 (+) Start of aprE promoter PstI
                                        (SEQ ID NO: 82)
5'-GACATCTGCAGCTCCATTTTCTTCTGC.

CF 07-94 (-) Fuse PaprE to mvaE
                                        (SEQ ID NO: 83)
5'-CAATAATAACTACTGTTTTCACTCTTTACCCTCTCCTTTTAA
Template: Bacillus subtilis chromosomal DNA 2. mvaE
CF 07-93 (+) fuse mvaE to the aprE promoter
(GTG start codon)
                                        (SEQ ID NO: 84)
5'-TTAAAAGGAGAGGGTAAAGAGTGAAAACAGTAGTTATTATTG.

CF 07-62 (-) Fuse mvaE to mvaS with RBS in between
                                        (SEQ ID NO: 35)
5'-TTTATCAATCCCAATTGTCATGTTTTTTTACCTCCTTTATTG
TTTTCTTAAATC.
Template: Enterococcus faecalis chromosomal DNA
(from ATCC)

3. mvaS
CF 07-61 (+) Fuse mvaE to mvaS with RBS in between
                                        (SEQ ID NO: 36)
5'-GATTTAAGAAAACAATAAAGGAGGTAAAAAAACATGACAATTGGGAT
TGATAAA.

CF 07-124 (-) Fuse the end of mvaS to the
terminator
                                        (SEQ ID NO: 85)
5'-CGGGGCCAAGGCCGGTTTTTTTTAGTTTCGATAAGAACGAACGGT
Template: Enterococcus faecalis chromosomal DNA.

4. B. amyliquefaciens alkaline serine protease
terminator
CF 07-123 (+) Fuse the end of mvaS to the
terminator
                                        (SEQ ID NO: 114)
5'-ACCGTTCGTTCTTATCGAAACTAAAAAAAACCGGCCTTGGCCCCG.

CF 07-46 (-) End of B. amyliquefaciens terminator
BamHI
                                        (SEQ ID NO: 63)
5'-GACATGACGGATCCGATTACGAATGCCGTCTC.
Template: Bacillus amyliquefaciens chromosomal DNA PCR Fusion Reactions
5. Fuse mvaE to mvaS
CF 07-93 (+) fuse mvaE to the aprE promoter
(GTG start codon)
                                        (SEQ ID NO: 84)
5'-TTAAAAGGAGAGGGTAAAGAGTGAAAACAGTAGTTATTATTG.

CF 07-124 (-) Fuse the end of mvaS to the
terminator
                                        (SEQ ID NO: 85)
5'-CGGGGCCAAGGCCGGTTTTTTTTAGTTTCGATAAGAACGAACGGT.
Template: #2 and 3 from above
```

-continued

6. Fuse mvaE-mvaS to aprE promoter
CF 07-134 (+) Start of aprE promoter PstI
(SEQ ID NO: 82)
5'-GACATCTGCAGCTCCATTTTCTTCTGC CF 07-124 (-) Fuse the end of mvaS to the terminator
(SEQ ID NO: 85)
5'-CGGGGCCAAGGCCGGTTTTTTTTAGTTTCGATAAGAACGAACGGT.
Template #1 and #4 from above 7. Fuse PaprE-mvaE-mvaS to terminator
CF 07-134 (+) Start of aprE promoter PstI
(SEQ ID NO: 82)
5'-GACATCTGCAGCTCCATTTTCTTCTGC.

CF 07-46 (-) End of B. amyliquefaciens terminator BamHI
(SEQ ID NO: 63)
5'-GACATGACGGATCCGATTACGAATGCCGTCTC.
Template: #4 and #6

Figure 50:
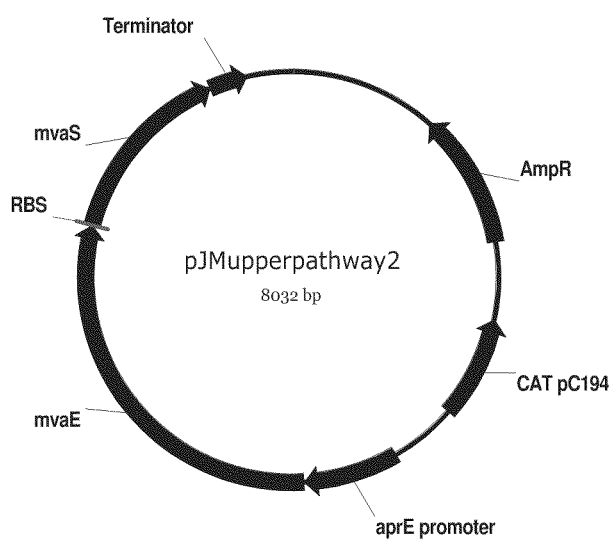
FIG. 50 is a map of pJMupperpathway2.

The product is digested with restriction endonucleases PstI/BamHI and ligated to pJM102 (Perego, M. 1993. Integrational vectors for genetic manipulation in *Bacillus subtilis*, p. 615-624. In A. L. Sonenshein, J. A. Hoch, and R. Losick (ed.), Bacillus subtilis and other gram-positive bacteria: biochemistry, physiology, and molecular genetics. American Society for Microbiology, Washington, D.C.) which is digested with PstI/BamHI. The ligation is transformed into *E. coli* TOP 10 chemically competent cells and transformants are selected on LA containing carbenicillin (50 μg/ml). The correct plasmid is identified by sequencing and is designated pJMUpperpathway2 (FIGS. 50 and 51). Purified plasmid DNA is transformed into *Bacillus subtilis* aprEnprE PxylcomK and transformants are selected on L agar containing chloramphenicol (5 μg/ml). A correct colony is selected and is plated sequentially on L agar containing chloramphenicol 10, 15 and 25 μg/ml to amplify the number of copies of the cassette containing the upper pathway.

The resulting strain is tested for mevalonic acid production by growing in LB containing 1% glucose and 1%. Cultures are analyzed by GC for the production of mevalonic acid. This strain is used subsequently as a host for the integration of the lower mevalonic acid pathway.

The following primers are used to sequence the various constructs above.

```
Sequencing primers:
CF 07-134 (+) Start of aprE promoter PstI
                                    (SEQ ID NO: 82)
5'-GACATCTGCAGCTCCATTTTCTTCTGC CF 07-58 (+) Start of mvaE gene
                                    (SEQ ID NO: 38)
5'-ATGAAAACAGTAGTTATTATTGATGC CF 07-59 (-) End of mvaE gene
                                    (SEQ ID NO: 39)
5'-ATGTTATTGTTTTCTTAAATCATTTAAAATAGC CF 07-82 (+) Start of mvaS gene
                                    (SEQ ID NO: 40)
5'-ATGACAATTGGGATTGATAAAATTAG CF 07-83 (-) End of mvaS gene
                                    (SEQ ID NO: 41)
5'-TTAGTTTCGATAAGAACGAACGGT CF 07-86 (+) Sequence in mvaE
                                    (SEQ ID NO: 42)
5'-GAAATAGCCCCATTAGAAGTATC CF 07-87 (+) Sequence in mvaE
                                    (SEQ ID NO: 43)
5'-TTGCCAATCATATGATTGAAAATC CF 07-88 (+) Sequence in mvaE
                                    (SEQ ID NO: 44)
5'-GCTATGCTTCATTAGATCCTTATCG CF 07-89 (+) Sequence mvaS
                                    (SEQ ID NO: 45)
5'-GAAACCTACATCCAATCTTTTGCCC
```

Transformants are selected on LA containing chloramphenicol at a concentration of 5 μg/ml. One colony is confirmed to have the correct integration by sequencing and is plated on LA containing increasing concentrations of chloramphenicol over several days, to a final level of 25 μg/ml. This results in amplification of the cassette containing the genes of interest. The resulting strain is designated CF 455: pJMupperpathway#1×*Bacillus subtilis* aprEnprE Pxyl comK (amplified to grow on LA containing chloramphenicol 25 μg/ml).

II. Construction of the Lower MVA Pathway in *Bacillus subtilis*

Figure 28:
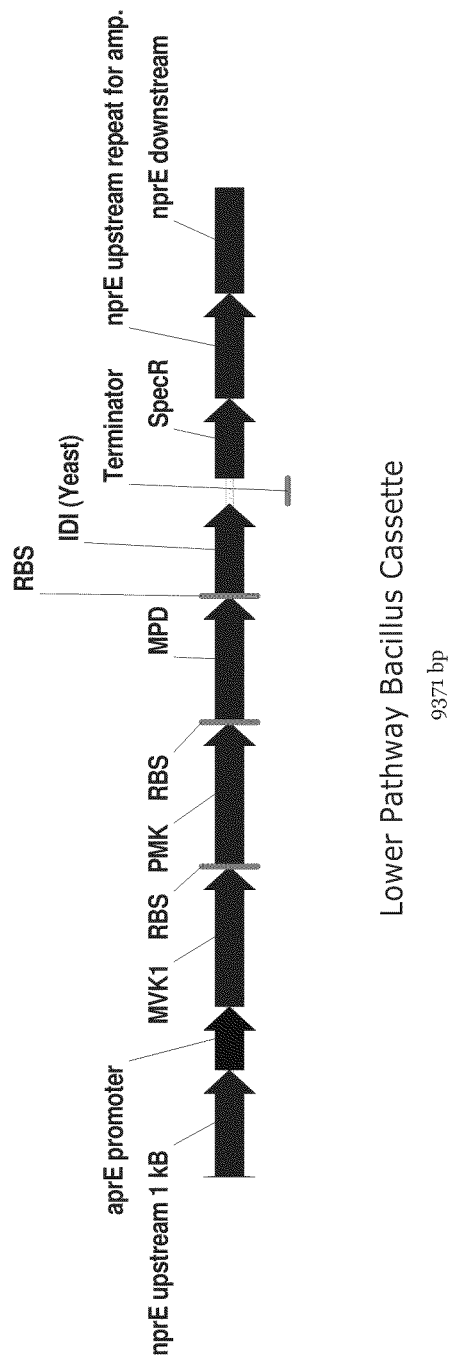
FIG. 28 shows a map of the cassette containing the lower MVA pathway and yeast idi for integration into the B. subtilis chromosome at the nprE locus. nprE upstream/downstream indicates 1 kb each of sequence from the nprE locus for integration. aprE promoter (alkaline serine protease promoter) indicates the promoter (−35, −10, +1 transcription start site, RBS) of the aprE gene. MVK1 indicates the yeast mevalonate kinase gene. RBS-PMK indicates the yeast phosphomevalonte kinase gene with a Bacillus RBS upstream of the start site. RBS-MPD indicates the yeast diphosphomevalonate decarboxylase gene with a Bacillus RBS upstream of the start site. RBS-IDI indicates the yeast idi gene with a Bacillus RBS upstream of the start site. Terminator indicates the terminator alkaline serine protease transcription terminator from B. amyliquefaciens. SpecR indicates the spectinomycin resistance marker. "nprE upstream repeat for amp." indicates a direct repeat of the upstream region used for amplification.

The lower MVA pathway, consisting of the genes mvk1, pmk, mpd and idi are combined in a cassette consisting of flanking DNA regions from the nprE region of the *B. subtilis* chromosome (site of integration), the aprE promoter, and the spectinomycin resistance marker (see FIGS. 28 and 29). This cassette is synthesized by DNA2.0 and is integrated into the chromosome of *B. subtilis* containing the upper MVA pathway integrated at the aprE locus. The kudzu isoprene synthase gene is expressed from the replicating plasmid described in Example 4 and is transformed into the strain with both upper and lower pathways integrated.

Example 10

Exemplary Isoprene Compositions and Methods of Making Them

I. Compositional Analysis of Fermentation Off-Gas Containing Isoprene

A 14 L scale fermentation is performed with a recombinant *E. coli* BL21(DE3) strain containing two plasmids (pCL upperMev; pTrcKKDyIkIS encoding the full mevalonate pathway for isoprenoid precursor biosynthesis, an isoprenyl pyrophosphate isomerase from yeast, and an isoprene synthase from Kudzu. Fermentation off-gas from the 14 L tank is collected into 20 mL headspace vials at around the time of peak isoprene productivity (27.9 hours elapsed fermentation time, "EFT") and analyzed by headspace GC/MS for volatile components.

Headspace analysis is performed with an Agilent 6890 GC/MS system fitted with an Agilent HP-5MS GC/MS column (30 m×250 μm; 0.25 μm film thickness). A combiPAL autoinjector is used for sampling 500 uL aliquots from 20 mL headspace vials. The GC/MS method utilizes helium as the carrier gas at a flow of 1 mL/min. The injection port is held at 250° C. with a split ratio of 50:1. The oven temperature is held at 37° C. for an initial 2 minute period, followed by an increase to 237° C. at a rate of 25° C./min for a total method time of 10 minutes. The Agilent 5793N mass selective detector scans from m/z 29 to m/z 300. The limit of detection of this system is approximately 0.1 ug/$L_{gas}$ or approximately 0.1 ppm. If desired, more sensitive equipment with a lower limit of detection may be used.

Figure 86A:
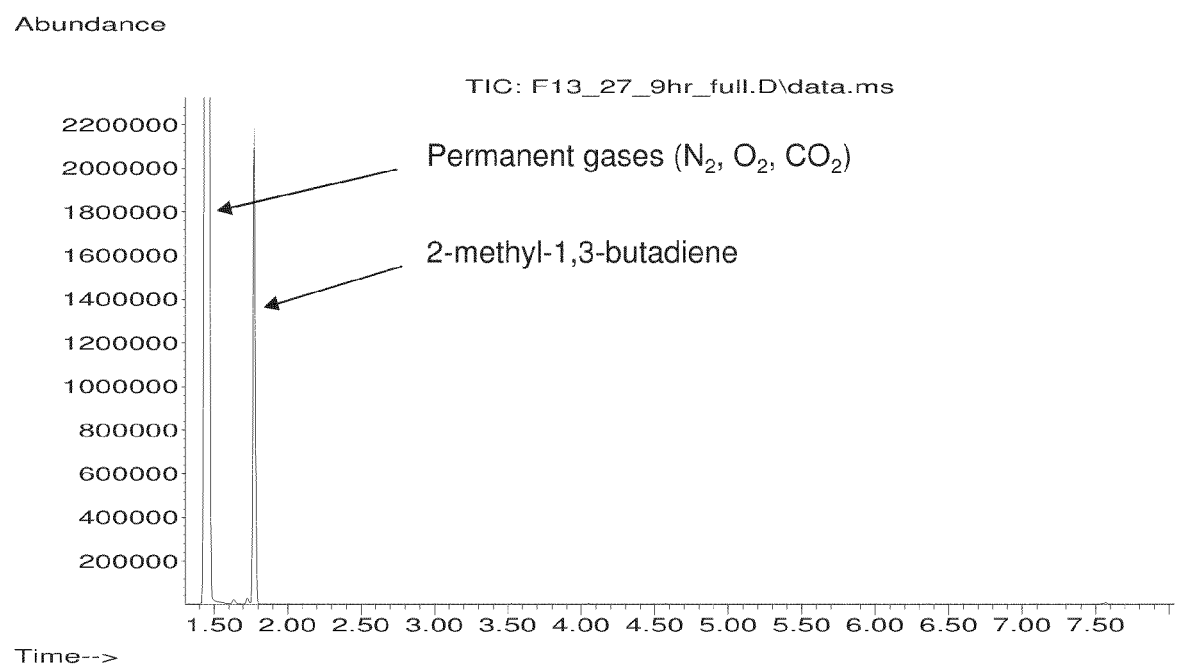
FIG. 86A is a GC/MS chromatogram of fermentation off-gas.
Figure 86B:
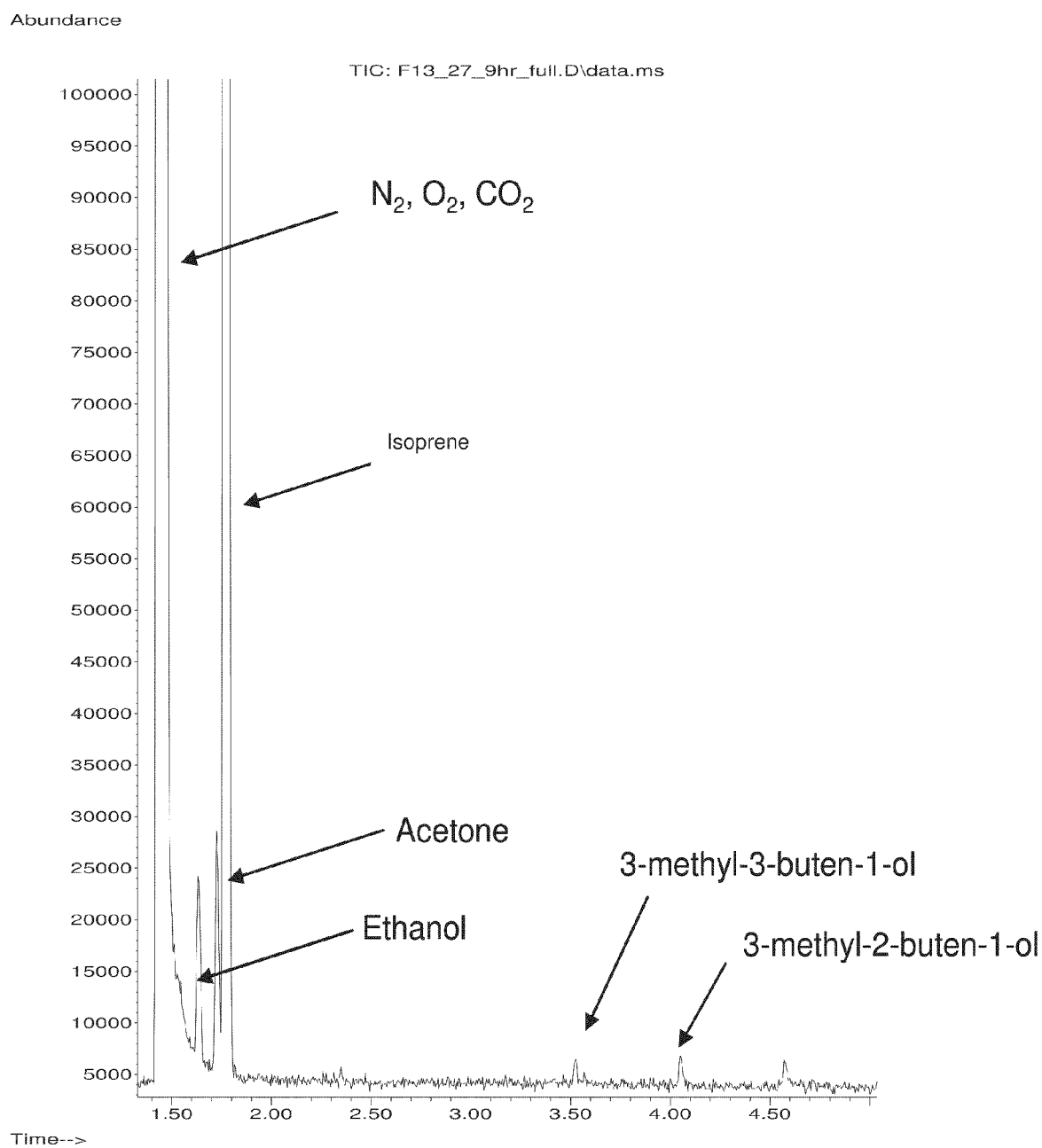
FIG. 86B is an expansion of FIG. 86A to show minor volatiles present in fermentation off-gas.
Figure 87A:
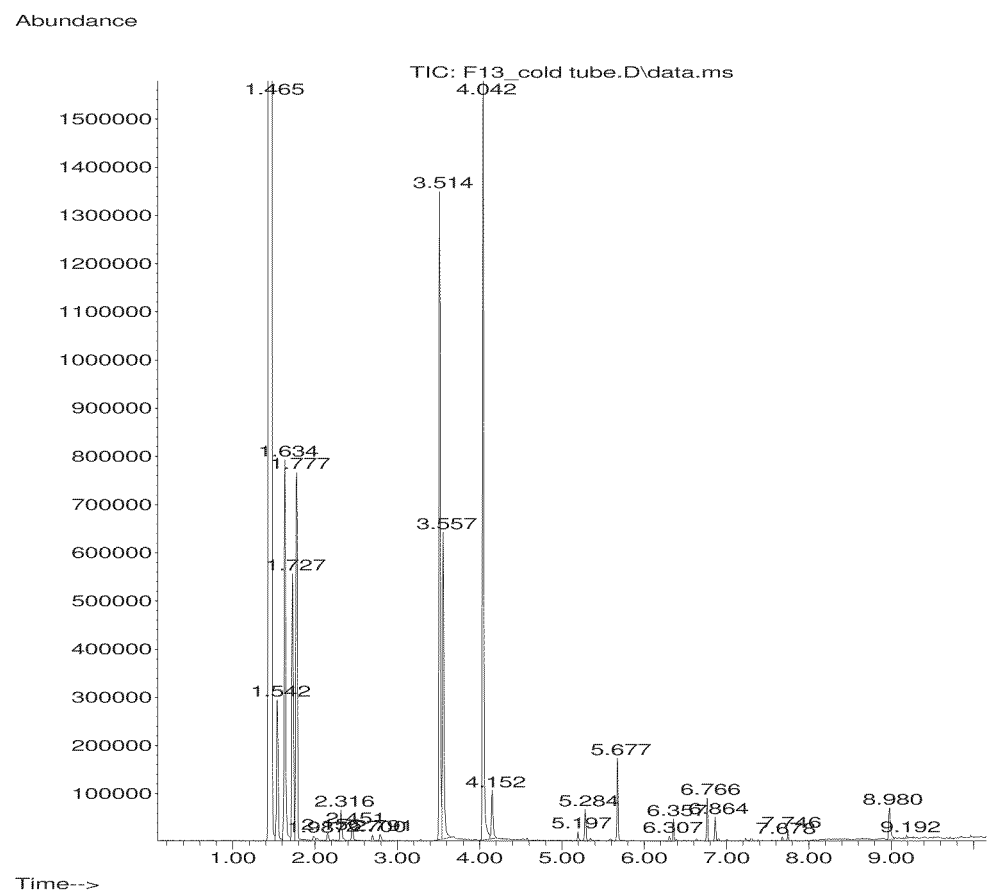
FIG. 87A is a GC/MS chromatogram of trace volatiles present in off-gas following cryo-trapping at −78° C.
Figure 87B:
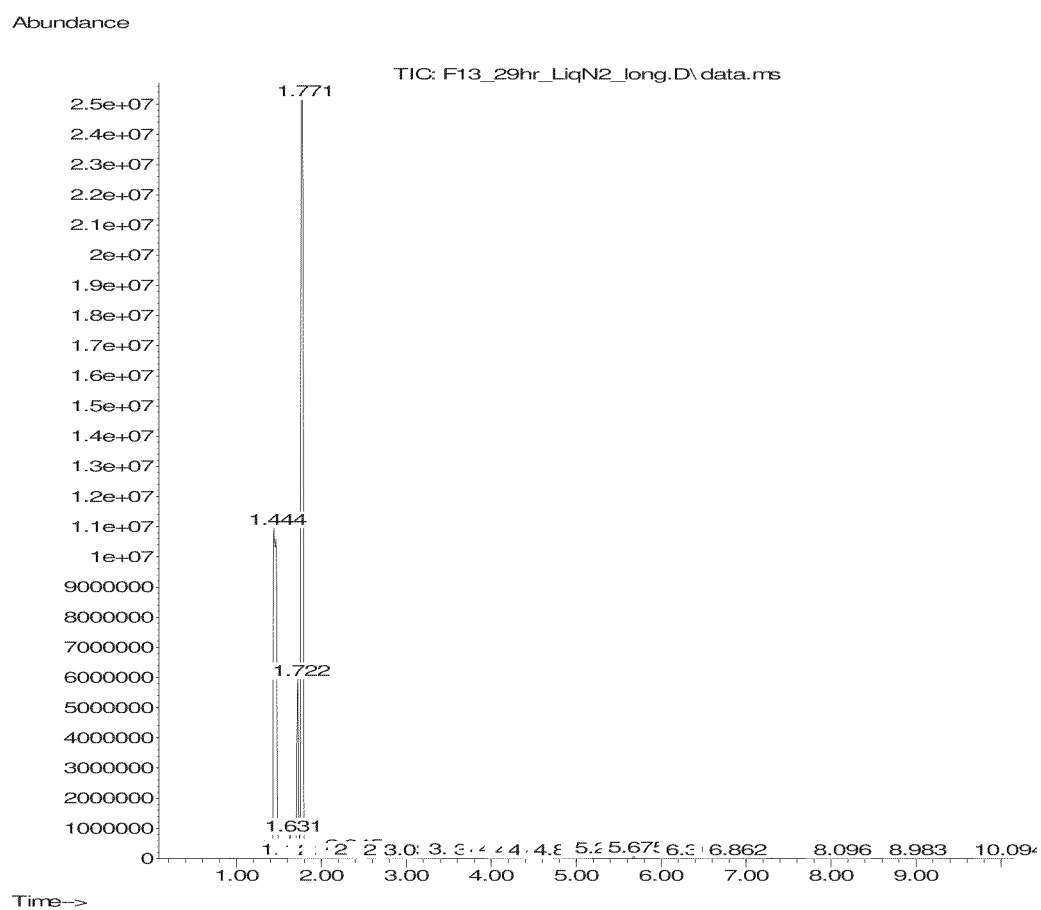
FIG. 87B is a GC/MS chromatogram of trace volatiles present in off-gas following cryo-trapping at −196° C.
Figure 87C:
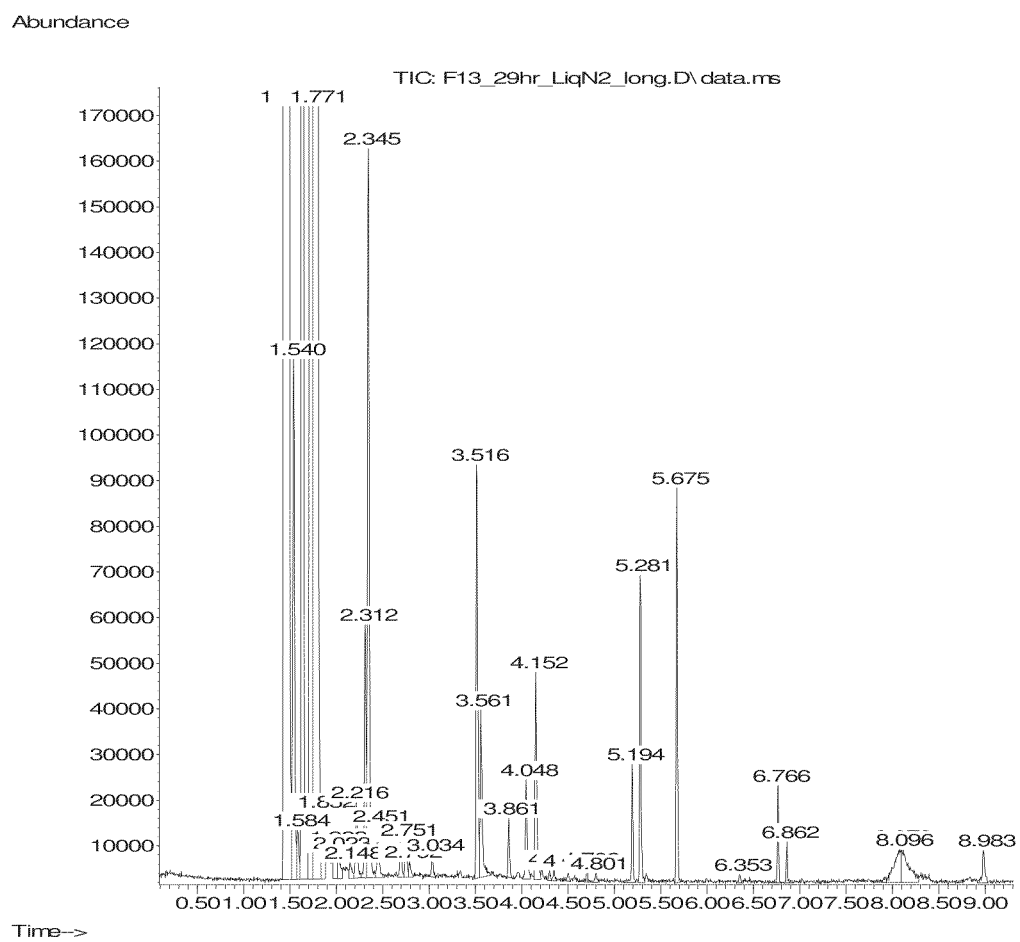
FIG. 87C is an expansion of FIG. 87B.
Figure 87D:
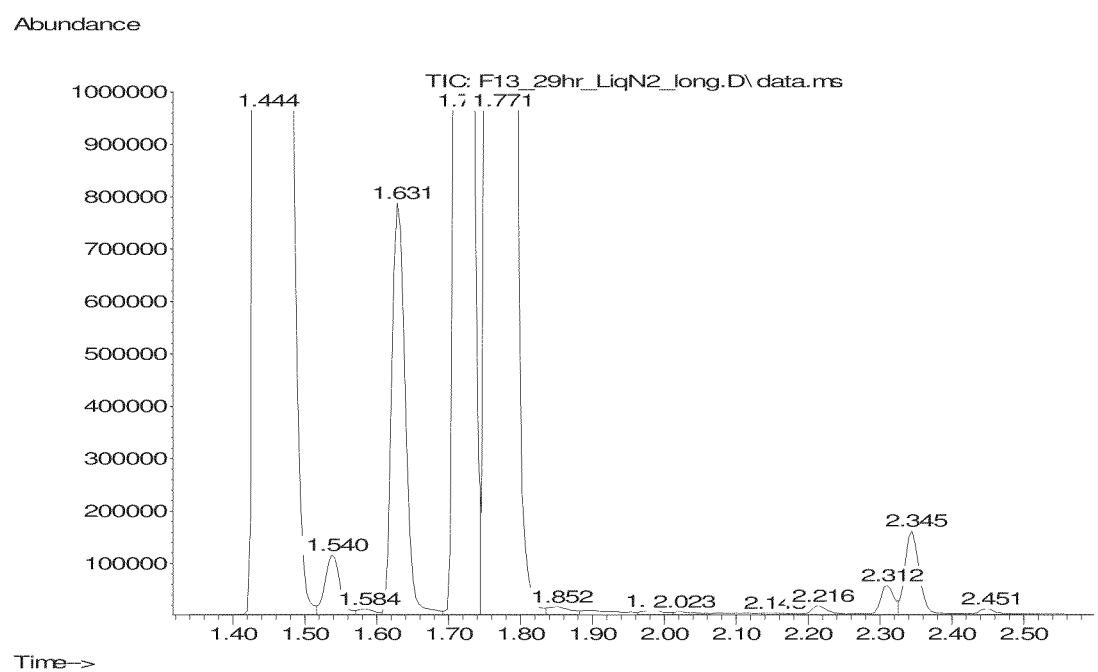

The off-gas consists of 99.925% (v/v) permanent gases (N$_2$, CO$_2$ and O$_2$), approximately 0.075% isoprene (2-methyl-1,3-butadiene) (~750 ppmv, 2100 μg/L) and minor amounts (<50 ppmv) of ethanol, acetone, and two C5 prenyl alcohols. The amount of water vapor is not determined but is estimated to be equal to the equilibrium vapor pressure at 0° C. The composition of the volatile organic fraction is determined by integration of the area under the peaks in the GC/MS chromatogram (FIGS. 86A and 86B) and is listed in Table 10-1. Calibration curves for ethanol and acetone standards enable the conversion of GC area to gas phase concentration in units of ug/L using standard methods.

TABLE 10-1

Composition of volatile organic components in fermentation off-gas. The off-gas is analyzed at the 27.9 hour time point of a fermentation using an *E. coli* BL21(DE3) strain expressing a heterologous mevalonate pathway, an isoprenyl pyrophosphate isomerase from yeast, and an isoprene synthase from Kudzu.

| Compound | RT (min) | GC area | Area % | Conc. (ug/L) |
|---|---|---|---|---|
| Ethanol | 1.669 | 239005 | 0.84 | 62 +/− 6 |
| Acetone | 1.703 | 288352 | 1.02 | 42 +/− 4 |
| Isoprene (2-methyl-1,3-butadiene) | 1.829 | 27764544 | 97.81 | 2000 +/− 200 |
| 3-methyl-3-buten-1-ol | 3.493 | 35060 | 0.12 | <10 |
| 3-methyl-2-buten-1-ol | 4.116 | 58153 | 0.20 | <10 |

II. Measurement of Trace Volatile Organic Compounds (VOCs) Co-Produced with Isoprene During Fermentation of a Recombinant *E. coli* Strain A 14 L scale fermentation is performed with a recombinant *E. coli* BL21(DE3) strain containing two plasmids (pCL upperMev; pTrcKKDyIkIS) encoding the full mevalonate pathway for isoprenoid precursor biosynthesis, an isoprenyl pyrophosphate isomerase from yeast, and an isoprene synthase from Kudzu.

Fermentation off-gas is passed through cooled headspace vials in order to concentrate and identify trace volatile organic components. The off-gas from this fermentation is sampled at a rate of 1 L/min for 10 minutes through a 20 mL headspace vial packed with quartz wool (2 g) and cooled to −78° C. with dry ice. The vial is recapped with a fresh vial cap and analyzed by headspace GC/MS for trapped VOCs using the conditions described in Example 10, part I. The ratios of compounds observed in FIGS. 87A-87D are a combination of overall level in the fermentation off-gas, the relative vapor pressure at −78° C., and the detector response of the mass spectrometer. For example, the low level of isoprene relative to oxygenated volatiles (e.g., acetone and ethanol) is a function of the high volatility of this material such that it does not accumulate in the headspace vial at −78° C.

The presence of many of these compounds is unique to isoprene compositions derived from biological sources. The results are depicted in FIGS. 87A-87D and summarized in Tables 10-2 and 10-3.

TABLE 10-2

Trace volatiles present in off-gas produced by *E. coli* BL21(DE3) (pCL upperMev; pTrcKKDyIkIS) following cryo-trapping at −78° C.

| Compound | RT (min) | GC Area[1] | Area %[2] | Ratio %[3] |
|---|---|---|---|---|
| Acetaldehyde | 1.542 | 4019861 | 4.841 | 40.14 |
| Ethanol | 1.634 | 10553620 | 12.708 | 105.39 |
| Acetone | 1.727 | 7236323 | 8.714 | 72.26 |
| 2-methyl-1,3-butadiene | 1.777 | 10013714 | 12.058 | 100.00 |

TABLE 10-2-continued

Trace volatiles present in off-gas produced by *E. coli* BL21(DE3) (pCL upperMev; pTrcKKDyIkIS) following cryo-trapping at −78° C.

| Compound | RT (min) | GC Area[1] | Area %[2] | Ratio %[3] |
|---|---|---|---|---|
| 1-propanol | 1.987 | 163574 | 0.197 | 1.63 |
| Diacetyl | 2.156 | 221078 | 0.266 | 2.21 |
| 2-methyl-3-buten-2-ol | 2.316 | 902735 | 1.087 | 9.01 |
| 2-methyl-1-propanol | 2.451 | 446387 | 0.538 | 4.46 |
| 3-methyl-1-butanal | 2.7 | 165162 | 0.199 | 1.65 |
| 1-butanol | 2.791 | 231738 | 0.279 | 2.31 |
| 3-methyl-3-buten-1-ol | 3.514 | 14851860 | 17.884 | 148.32 |
| 3-methyl-1-butanol | 3.557 | 8458483 | 10.185 | 84.47 |
| 3-methyl-2-buten-1-ol | 4.042 | 18201341 | 21.917 | 181.76 |
| 3-methyl-2-butenal | 4.153 | 1837273 | 2.212 | 18.35 |
| 3-methylbutyl acetate | 5.197 | 196136 | 0.236 | 1.96 |
| 3-methyl-3-buten-1-yl acetate | 5.284 | 652132 | 0.785 | 6.51 |
| 2-heptanone | 5.348 | 67224 | 0.081 | 0.67 |
| 2,5-dimethylpyrazine | 5.591 | 58029 | 0.070 | 0.58 |
| 3-methyl-2-buten-1-yl acetate | 5.676 | 1686507 | 2.031 | 16.84 |
| 6-methyl-5-hepten-2-one | 6.307 | 101797 | 0.123 | 1.02 |
| 2,4,5-trimethylpyridine | 6.39 | 68477 | 0.082 | 0.68 |
| 2,3,5-trimethylpyrazine | 6.485 | 30420 | 0.037 | 0.30 |
| (E)-3,7-dimethyl-1,3,6-octatriene | 6.766 | 848928 | 1.022 | 8.48 |
| (Z)-3,7-dimethyl-1,3,6-octatriene | 6.864 | 448810 | 0.540 | 4.48 |
| 3-methyl-2-buten-1-yl_butyrate | 7.294 | 105356 | 0.127 | 1.05 |
| Citronellal | 7.756 | 208092 | 0.251 | 2.08 |
| 2,3-cycloheptenolpyridine | 8.98 | 1119947 | 1.349 | 11.18 |

[1]GC area is the uncorrected area under the peak corresponding to the listed compound.
[2]Area % is the peak area expressed as a % relative to the total peak area of all compounds.
[3]Ratio % is the peak area expressed as a % relative to the peak area of 2-methyl-1,3-butadiene.

TABLE 10-3

Trace volatiles present in off-gas produced by *E. coli* BL21(DE3) (pCL upperMev; pTrcKKDyIkIS) following cryo-trapping at −196° C.

| Compound | RT (min) | GC Area[1] | Area %[2] | Ratio %[3] |
|---|---|---|---|---|
| Acetaldehyde | 1.54 | 1655710 | 0.276 | 0.33 |
| Methanethiol | 1.584 | 173620 | 0.029 | 0.03 |
| Ethanol | 1.631 | 10259680 | 1.707 | 2.03 |
| Acetone | 1.722 | 73089100 | 12.164 | 14.43 |
| 2-methyl-1,3-butadiene | 1.771 | 506349429 | 84.269 | 100.00 |
| methyl acetate | 1.852 | 320112 | 0.053 | 0.06 |
| 1-propanol | 1.983 | 156752 | 0.026 | 0.03 |
| Diacetyl | 2.148 | 67635 | 0.011 | 0.01 |
| 2-butanone | 2.216 | 254364 | 0.042 | 0.05 |
| 2-methyl-3-buten-2-ol | 2.312 | 684708 | 0.114 | 0.14 |
| ethyl acetate | 2.345 | 2226391 | 0.371 | 0.44 |
| 2-methyl-1-propanol | 2.451 | 187719 | 0.031 | 0.04 |
| 3-methyl-1-butanal | 2.696 | 115723 | 0.019 | 0.02 |
| 3-methyl-2-butanone | 2.751 | 116861 | 0.019 | 0.02 |
| 1-butanol | 2.792 | 54555 | 0.009 | 0.01 |
| 2-pentanone | 3.034 | 66520 | 0.011 | 0.01 |
| 3-methyl-3-buten-1-ol | 3.516 | 1123520 | 0.187 | 0.22 |
| 3-methyl-1-butanol | 3.561 | 572836 | 0.095 | 0.11 |
| ethyl isobutyrate | 3.861 | 142056 | 0.024 | 0.03 |
| 3-methyl-2-buten-1-ol | 4.048 | 302558 | 0.050 | 0.06 |
| 3-methyl-2-butenal | 4.152 | 585690 | 0.097 | 0.12 |
| butyl acetate | 4.502 | 29665 | 0.005 | 0.01 |
| 3-methylbutyl acetate | 5.194 | 271797 | 0.045 | 0.05 |
| 3-methyl-3-buten-1-yl acetate | 5.281 | 705366 | 0.117 | 0.14 |
| 3-methyl-2-buten-1-yl acetate | 5.675 | 815186 | 0.136 | 0.16 |
| (E)-3,7-dimethyl-1,3,6-octatriene | 6.766 | 207061 | 0.034 | 0.04 |

TABLE 10-3-continued

Trace volatiles present in off-gas produced by E. coli BL21(DE3) (pCL upperMev; pTrcKKDyIkIS) following cryo-trapping at −196° C.

| Compound | RT (min) | GC Area[1] | Area %[2] | Ratio %[3] |
|---|---|---|---|---|
| (Z)-3,7-dimethyl-1,3,6-octatriene | 6.863 | 94294 | 0.016 | 0.02 |
| 2,3-cycloheptenolpyridine | 8.983 | 135104 | 0.022 | 0.03 |

[1]GC area is the uncorrected area under the peak corresponding to the listed compound.
[2]Area % is the peak area expressed as a % relative to the total peak area of all compounds.
[3]Ratio % is the peak area expressed as a % relative to the peak area of 2-methyl-1,3-butadiene.

III. Absence of C5 Hydrocarbon Isomers in Isoprene Derived from Fermentation.

Cryo-trapping of isoprene present in fermentation off-gas is performed using a 2 mL headspace vial cooled in liquid nitrogen. The off-gas (1 L/min) is first passed through a 20 mL vial containing sodium hydroxide pellets in order to minimize the accumulation of ice and solid $CO_2$ in the 2 mL vial (−196° C.). Approximately 10 L of off-gas is passed through the vial, after which it is allowed to warm to −78° C. with venting, followed by resealing with a fresh vial cap and analysis by GC/MS.

GC/MS headspace analysis is performed with an Agilent 6890 GC/MS system using a 100 uL gas tight syringe in headspace mode. A Zebron ZB-624 GC/MS column (30 m×250 μm; 1.40 μm film thickness) is used for separation of analytes. The GC autoinjector is fitted with a gas-tight 100 uL syringe, and the needle height is adjusted to allow the injection of a 50 uL headspace sample from a 2 mL GC vial. The GC/MS method utilizes helium as the carrier gas at a flow of 1 mL/min. The injection port is held at 200° C. with a split ratio of 20:1. The oven temperature is held at 37° C. for the 5 minute duration of the analysis. The Agilent 5793N mass selective detector is run in single ion monitoring (SIM) mode on m/z 55, 66, 67 and 70. Under these conditions, isoprene is observed to elute at 2.966 minutes (FIG. 88B). A standard of petroleum derived isoprene (Sigma-Aldrich) is also analyzed using this method and is found to contain additional C5 hydrocarbon isomers, which elute shortly before or after the main peak and are quantified based on corrected GC area (FIG. 88A).

TABLE 10-4

GC/MS analysis of petroleum-derived isoprene

| Compound | RT (min) | GC area | Area % of total C5 hydrocarbons |
|---|---|---|---|
| 2-methyl-1-butene | 2.689 | $18.2 \times 10^3$ | 0.017% |
| (Z)-2-pentene | 2.835 | $10.6 \times 10^4$ | 0.101% |
| Isoprene | 2.966 | $10.4 \times 10^7$ | 99.869% |
| 1,3-cyclopentadiene (CPD) | 3.297 | $12.8 \times 10^3$ | 0.012% |

TABLE 10-5

GC/MS analysis of fermentation-derived isoprene (% total C5 hydrocarbons)

| Compound | RT (min) | Corrected GC Area | % of total C5 hydrocarbons |
|---|---|---|---|
| Isoprene | 2.966 | $8.1 \times 10^7$ | 100% |

In a separate experiment, a standard mixture of C5 hydocarbons is analyzed to determine if the detector response is the same for each of the compounds. The compounds are 2-methyl-1-butene, 2-methyl-1,3-butadiene, (E)-2-pentene, (Z)-2-pentene and (E)-1,3-pentadiene. In this case, the analysis is performed on an Agilent DB-Petro column (100 m×0.25 mm, 0.50 um film thickness) held at 50° C. for 15 minutes. The GC/MS method utilizes helium as the carrier gas at a flow of 1 mL/min. The injection port is held at 200° C. with a split ratio of 50:1. The Agilent 5793N mass selective detector is run in full scan mode from m/z 19 to m/z 250. Under these conditions, a 100 ug/L concentration of each standard produces the same detector response within experimental error.

IV. Compositions Comprising Isoprene Adsorbed to a Solid Phase.

Biologically-produced isoprene is adsorbed to activated carbon resulting in a solid phase containing 50 to 99.9% carbon, 0.1% to 50% isoprene, 0.01% to 5% water, and minor amounts (<0.1%) of other volatile organic components.

Fermentation off-gas is run through a copper condensation coil held at 0° C., followed by a granulated silica desiccant filter in order to remove water vapor. The dehumidified off-gas is then run through carbon containing filters (Koby Jr, Koby Filters, Mass.) to the point at which breakthrough of isoprene is detected in the filter exhaust by GC/MS. The amount of isoprene adsorbed to the cartridge can be determined indirectly by calculating the concentration in the off-gas, the overall flow rate and the percent breakthrough over the collection period. Alternately the adsorbed isoprene can be recovered from the filters by thermal, vacuum, or solvent-mediated desorption.

V. Collection and Analysis of Condensed Isoprene.

Fermentation off-gas is dehumidified, and the $CO_2$ removed by filtration through a suitable adsorbant (e.g., ascarite). The resulting off-gas stream is then run through a liquid nitrogen-cooled condenser in order to condense the VOCs in the stream. The collection vessel contains t-butyl catechol to inhibit the resulting isoprene condensate. The condensate is analyzed by GC/MS and NMR in order to determine purity using standard methods, such as those described herein.

VI. Production of Prenyl Alcohols by Fermentation

Analysis of off-gas from an *E. coli* BL21(DE3) strain expressing a kudzu isoprene synthase reveals the presence of both isoprene and 3-methyl-3-buten-1-ol (isoprenol). The levels of the two compounds in the fermentation off-gas over the fermentation are shown in FIG. 89 as determined by headspace GC/MS. Levels of isoprenol (3-methyl-3-buten-1-ol, 3-MBA) attained are nearly 10 ug/$L_{offgas}$ in this experiment. Additional experiments produce levels of approximately 20 ug/$L_{offgas}$ in the fermentation off-gas.

Example 11

De-Coupling of Growth and Production of Isoprene in *E. coli* Expressing Genes of the Mevalonic Acid Pathway and Fermented in a Fed-Batch Culture This example illustrates the de-coupling of cell growth from mevalonic acid and isoprene production.

I. Fermentation Conditions

Medium Recipe (per liter fermentation medium): The medium is generated using the following components per liter fermentation medium: $K_2HPO_4$ 7.5 g, $MgSO_4 \cdot 7H_2O$ 2 g, citric acid monohydrate 2 g, ferric ammonium citrate 0.3 g, yeast extract 0.5 g, and 1000× modified trace metal solution 1 ml. All of the components are added together and dissolved in diH2O. This solution is autoclaved. The pH is adjusted to 7.0 with ammonium hydroxide (30%) and q.s. to volume. Glucose 10 g, thiamine.HCl 0.1 g, and antibiotics are added after sterilization and pH adjustment.

1000× Modified Trace Metal Solution: The 1000× modified trace metal solution is generated using the following components: citric acid.$H_2O$ 40 g, $MnSO_4.H_2$ 30 g, NaCl 10 g, $FeSO_4.7H_2O$ 1 g, $CoCl2.6H_2O$ 1 g, $ZnSO_4.7H_2$ 1 g, $CuSO_4.5H_2O$ 100 mg, $H_3BO_3$ 100 mg, and $NaMoO_4.2H_2O$ 100 mg. Each component is dissolved one at a time in Di $H_2O$, pH to 3.0 with HCl/NaOH, then q.s. to volume, and filter sterilized with a 0.22 micron filter.

Fermentation is performed with *E. coli* cells containing the pTrcHis2AUpperPathway (also called pTrcUpperMVA, FIGS. 91 and 92A-92C) (50 μg/ml carbenicillin) or the pCL PtrcUpperMVA (also called pCL PtrcUpperPathway (FIG. 26)) (50 μg/ml spectinomycin) plasmids. For experiments in which isoprene is produced, the *E. coli* cells also contain the pTrc KKDyIkIS (50 μg/ml kanamycin) plasmid. These experiments are carried out to monitor mevalonic acid or isoprene formation from glucose at the desired fermentation pH 7.0 and temperature 30° C. An inoculum of an *E. coli* strain taken from a frozen vial is streaked onto an LA broth agar plate (with antibiotics) and incubated at 37° C. A single colony is inoculated into tryptone-yeast extract medium. After the inoculum grows to optical density 1.0 when measured at 550 nm, it is used to inoculate the bioreactor.

Glucose is fed at an exponential rate until cells reach the stationary phase. After this time the glucose feed is decreased to meet metabolic demands. Induction is achieved by adding IPTG. The mevalonic acid concentration in fermentation broth is determined by applying perchloric acid (Sigma-Aldrich #244252) treated samples (0.3 M incubated at 4° C. for 5 minutes) to an organic acids HPLC column (BioRad #125-0140). The concentration is determined by comparing the broth mevalonic acid peak size to a calibration curve generated from mevalonolactone (Sigma-Aldrich #M4667) treated with perchloric acid to form D,L-mevalonate. The isoprene level in the off gas from the bioreactor is determined as described herein. The isoprene titer is defined as the amount of isoprene produced per liter of fermentation broth.

Figure 60A:
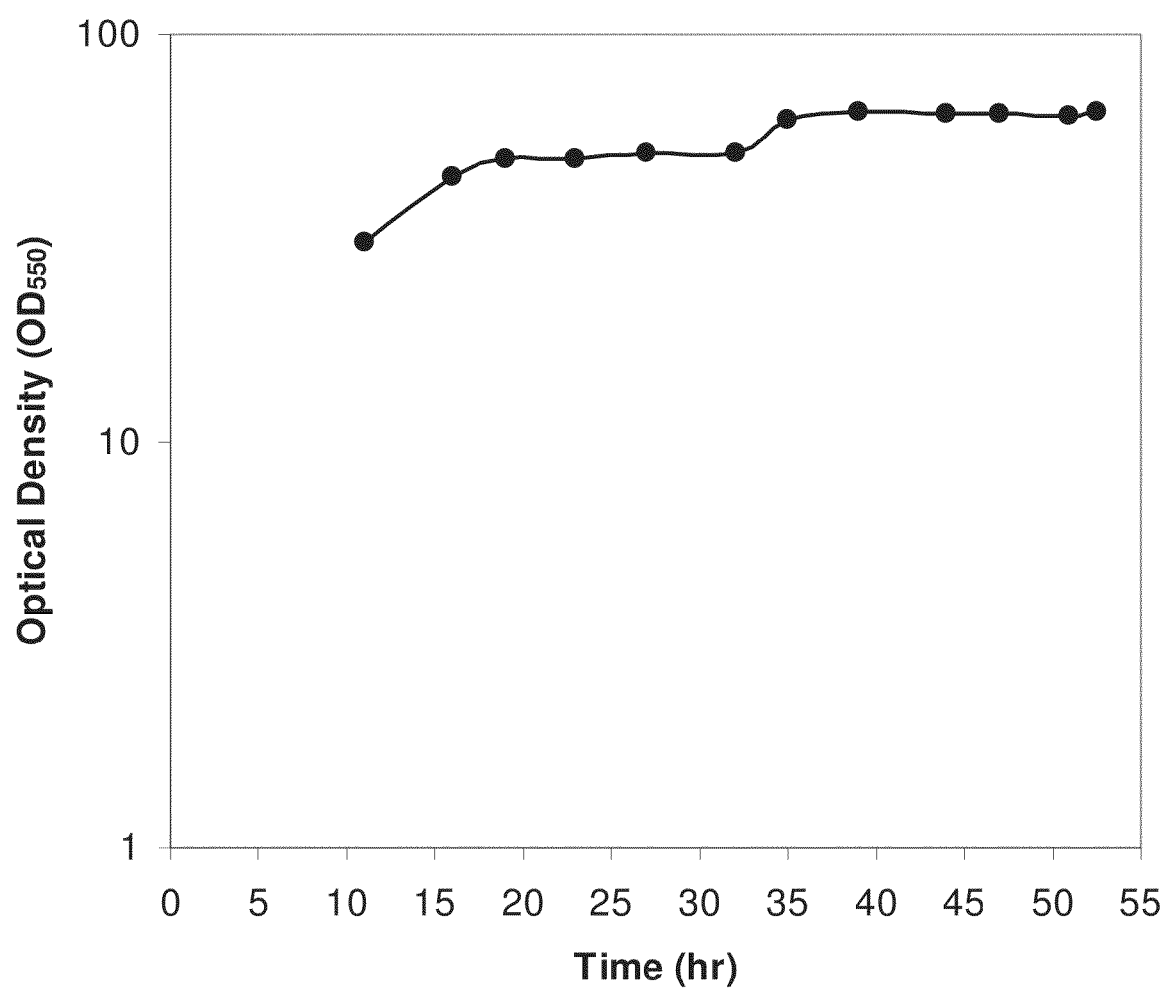
FIGS. 60A-60C are the time courses of optical density, mevalonic acid titer, and specific productivity within the 150-L bioreactor fed with glucose.
Figure 60B:
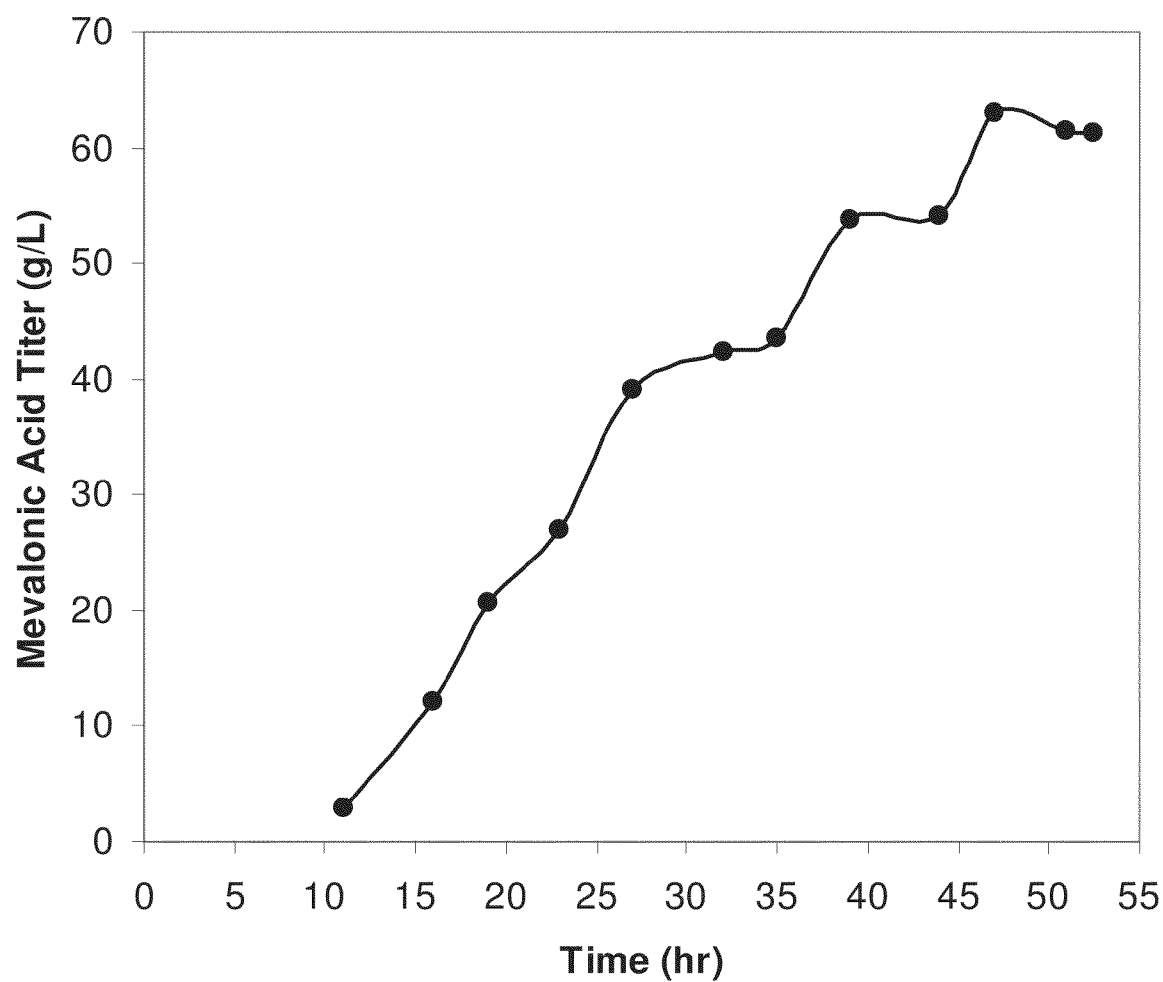
Figure 60C:
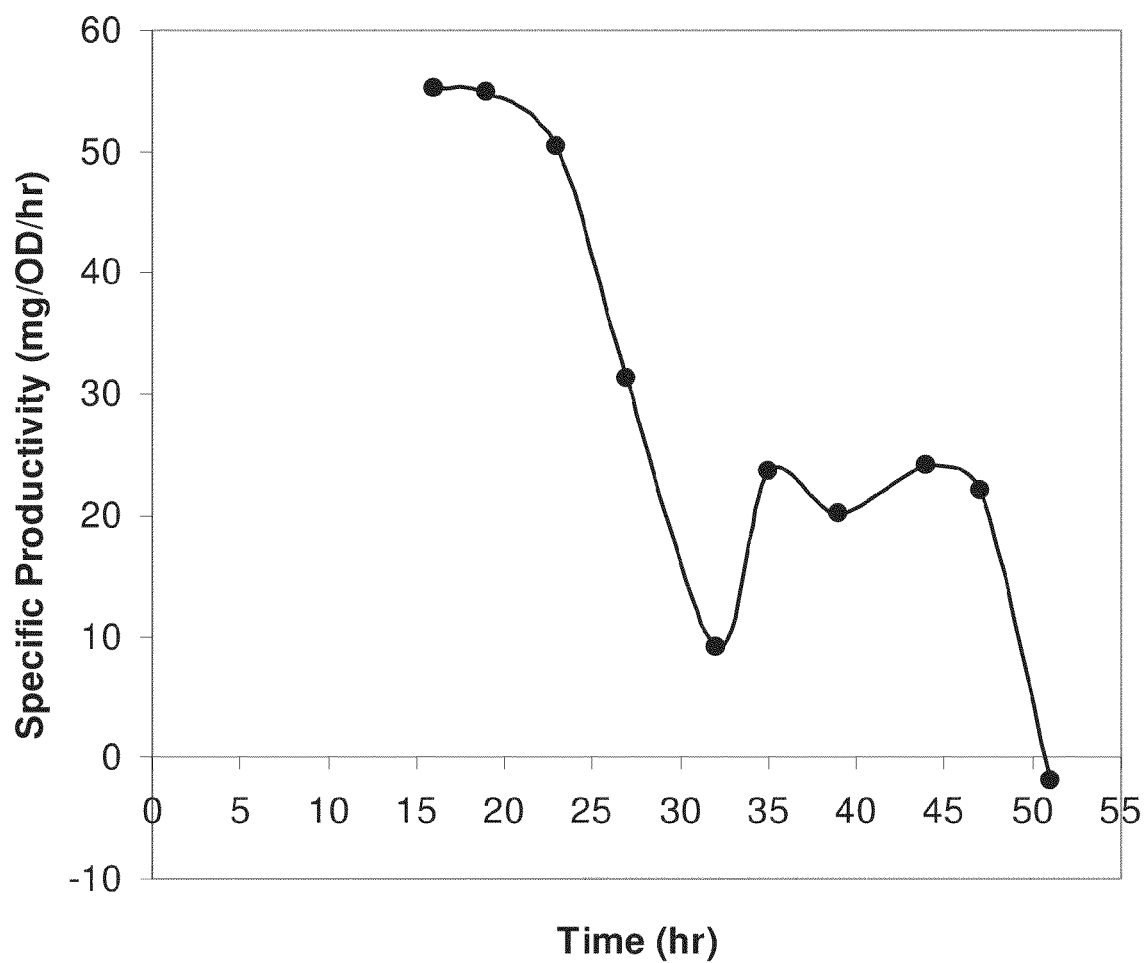

II. Mevalonic Acid Production from *E. coli* BL21(DE3) cells expressing the pTrcUpperMVA Plasmid at a 150-L Scale BL21(DE3) cells that are grown on a plate as explained above in part I are inoculated into a flask containing 45 mL of tryptone-yeast extract medium and incubated at 30° C. with shaking at 170 rpm for 5 hours. This solution is transferred to a 5-L bioreactor of tryptone-yeast extract medium, and the cells are grown at 30° C. and 27.5 rpm until the culture reaches an $OD_{550}$ of 1.0. The 5 L of inoculum is seeded into a 150-L bioreactor containing 45-kg of medium. The IPTG concentration is brought to 1.1 mM when the $OD_{550}$ reaches a value of 10. The $OD_{550}$ profile within the bioreactor over time is shown in FIG. 60A. The mevalonic acid titer increases over the course of the fermentation to a final value of 61.3 g/L (FIG. 60B). The specific productivity profile throughout the fermentation is shown in FIG. 60C and a comparison to FIG. 60A illustrates the de-coupling of growth and mevalonic acid production. The total amount of mevalonic acid produced during the 52.5 hour fermentation is 4.0 kg from 14.1 kg of utilized glucose. The molar yield of utilized carbon that goes into producing mevalonic acid during fermentation is 34.2%.

Figure 61A:
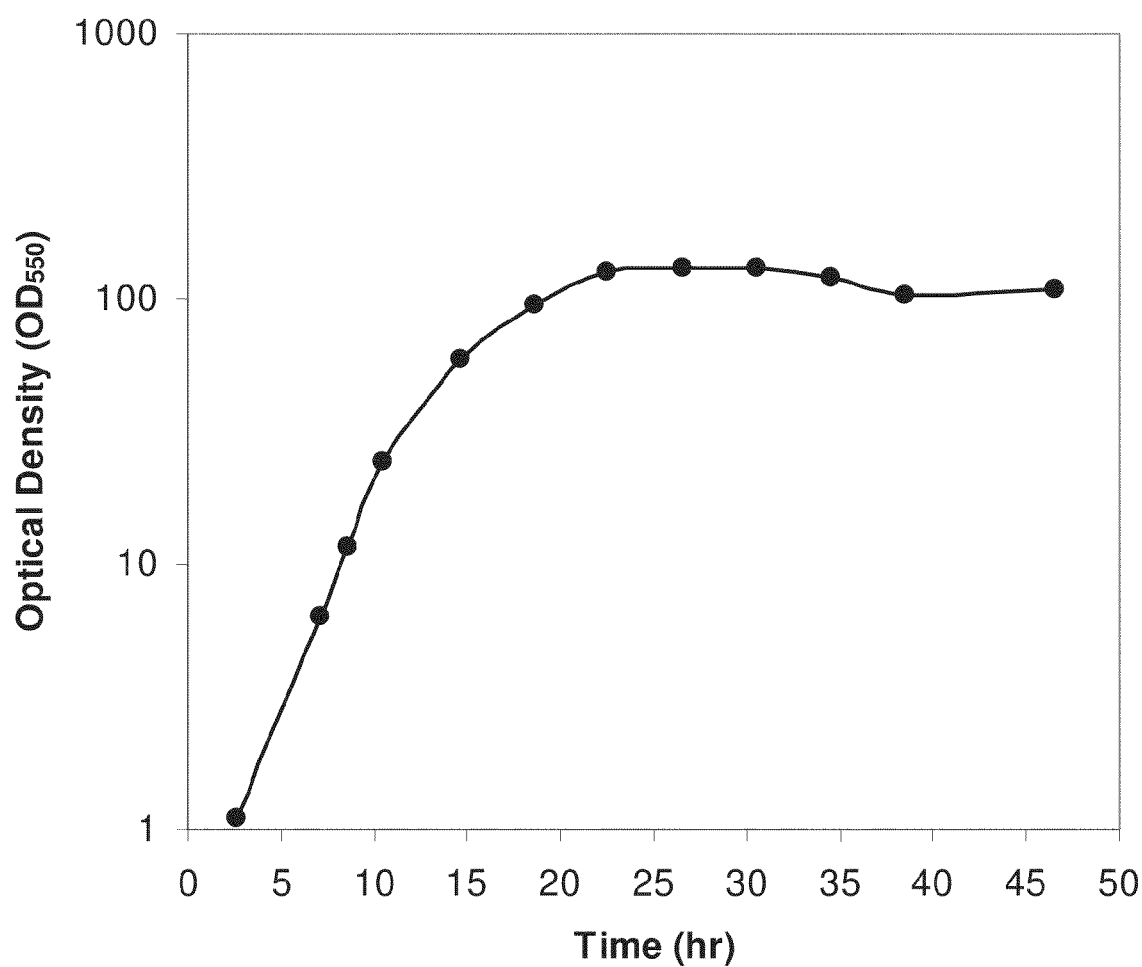
FIGS. 61A-61C are the time courses of optical density, mevalonic acid titer, and specific productivity within the 15-L bioreactor fed with glucose.
Figure 61B:
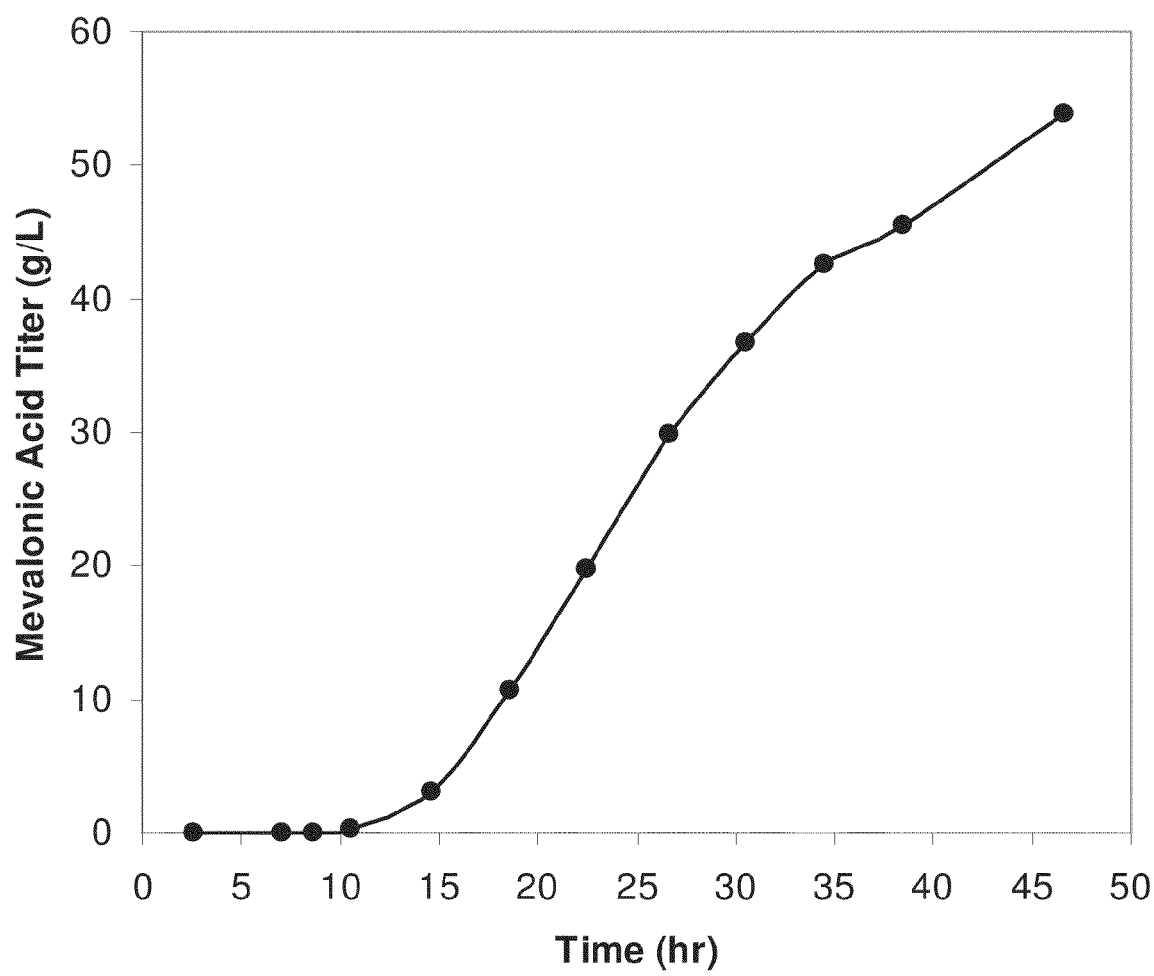
Figure 61C:
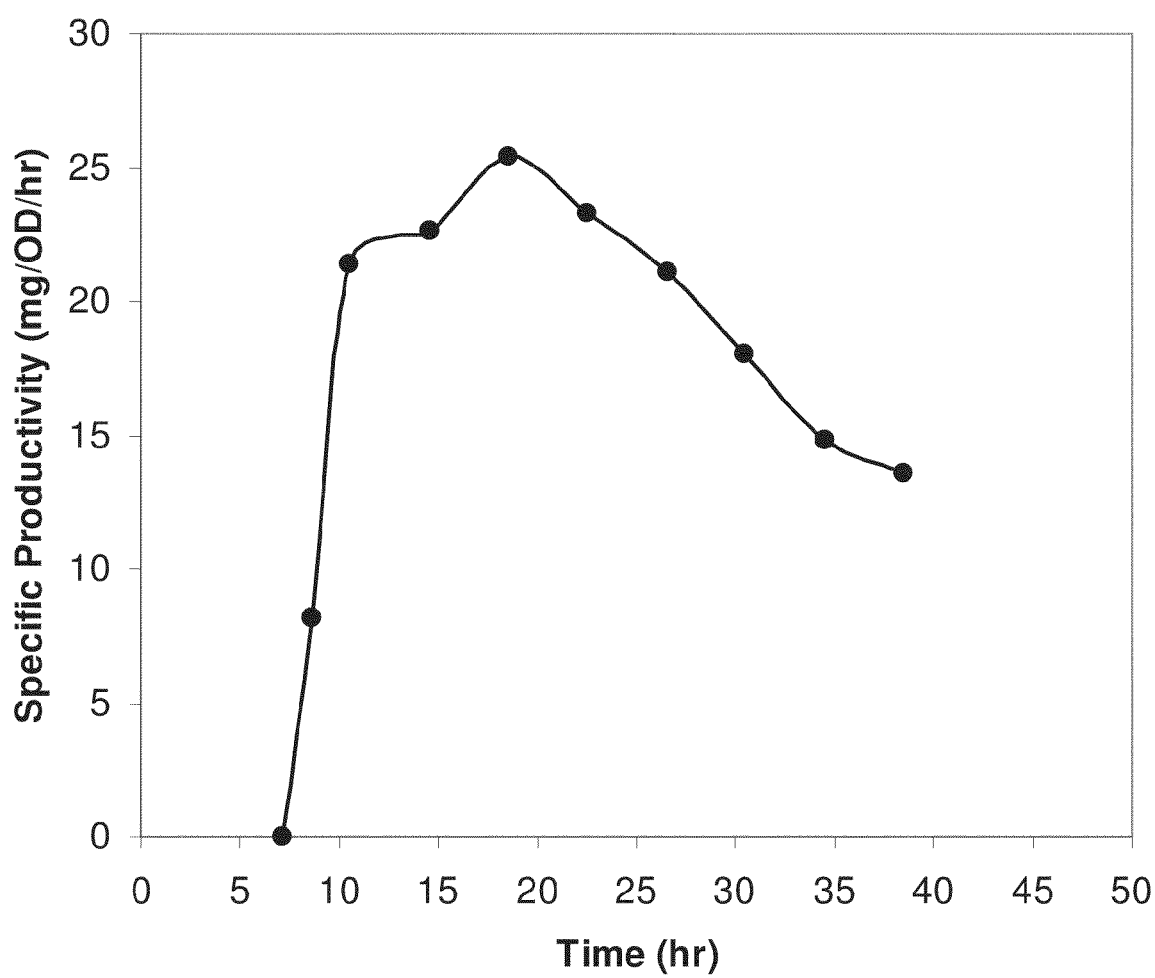

III. Mevalonic Acid Production from *E. coli* BL21(DE3) Cells Expressing the pTrcUpperMVA Plasmid at a 15-L Scale BL21(DE3) cells that are grown on a plate as explained above in part I are inoculated into a flask containing 500 mL of tryptone-yeast extract medium and grown at 30° C. at 160 rpm to $OD_{550}$ 1.0. This material is seeded into a 15-L bioreactor containing 4.5-kg of medium. The IPTG concentration is brought to 1.0 mM when the $OD_{550}$ reaches a value of 10. The $OD_{550}$ profile within the bioreactor over time is shown in FIG. 61A. The mevalonic acid titer increases over the course of the fermentation to a final value of 53.9 g/L (FIG. 61B). The specific productivity profile throughout the fermentation is shown in FIG. 61C and a comparison to FIG. 61A illustrates the de-coupling of growth and mevalonic acid production. The total amount of mevalonic acid produced during the 46.6 hour fermentation is 491 g from 2.1 kg of utilized glucose. The molar yield of utilized carbon that goes into producing mevalonic acid during fermentation is 28.8%.

Figure 62A:
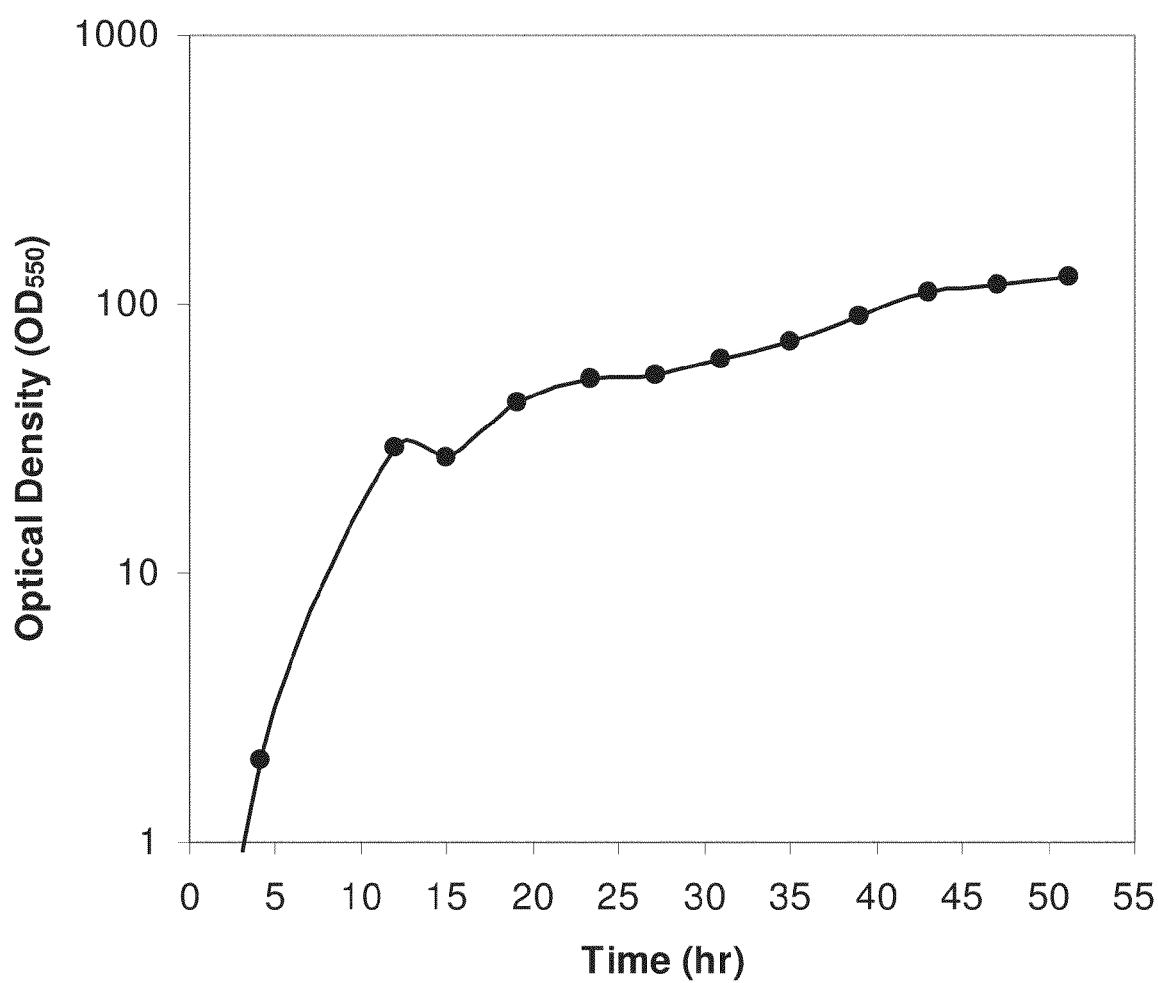
FIGS. 62A-62C are the time courses of optical density, mevalonic acid titer, and specific productivity within the 15-L bioreactor fed with glucose.
Figure 62B:
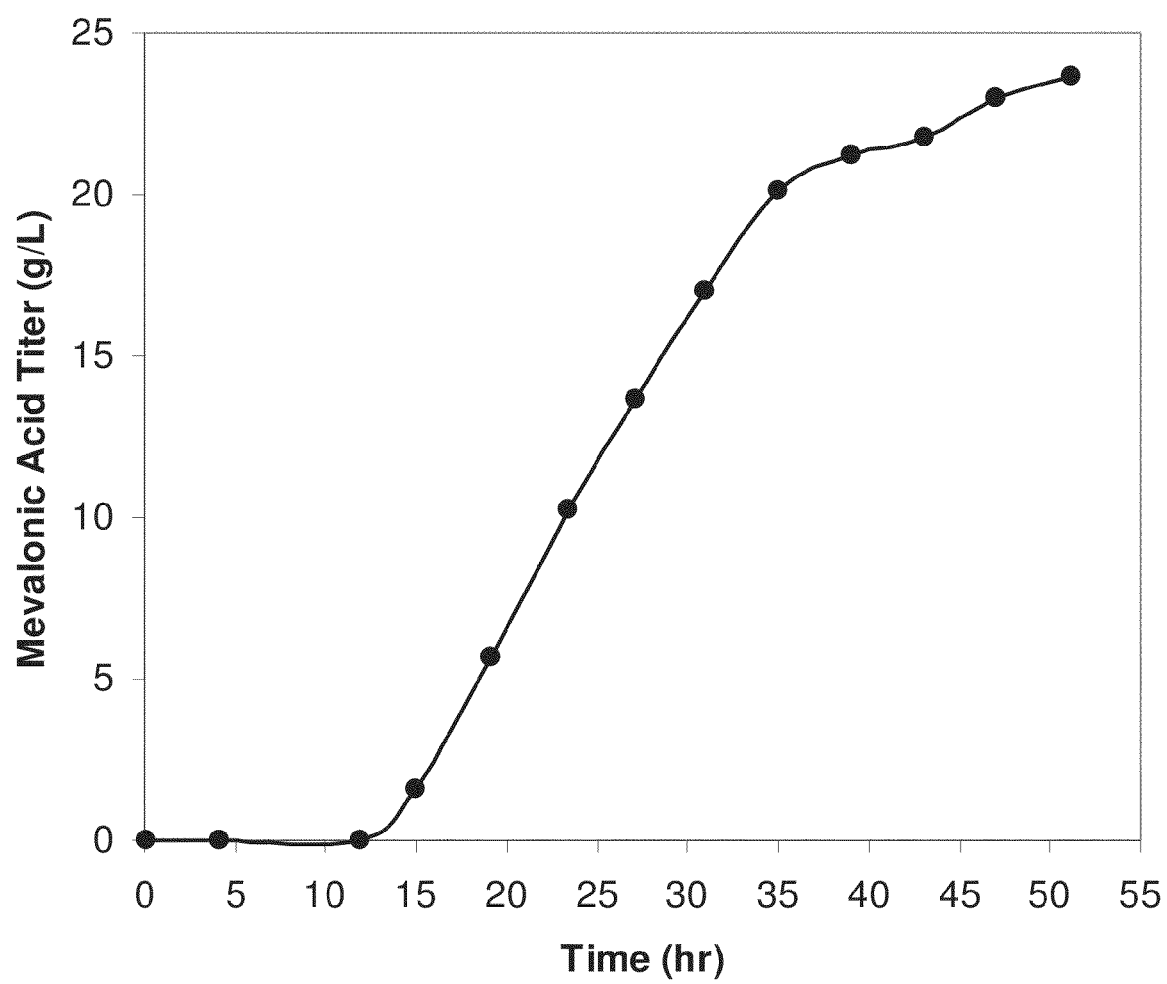
Figure 62C:
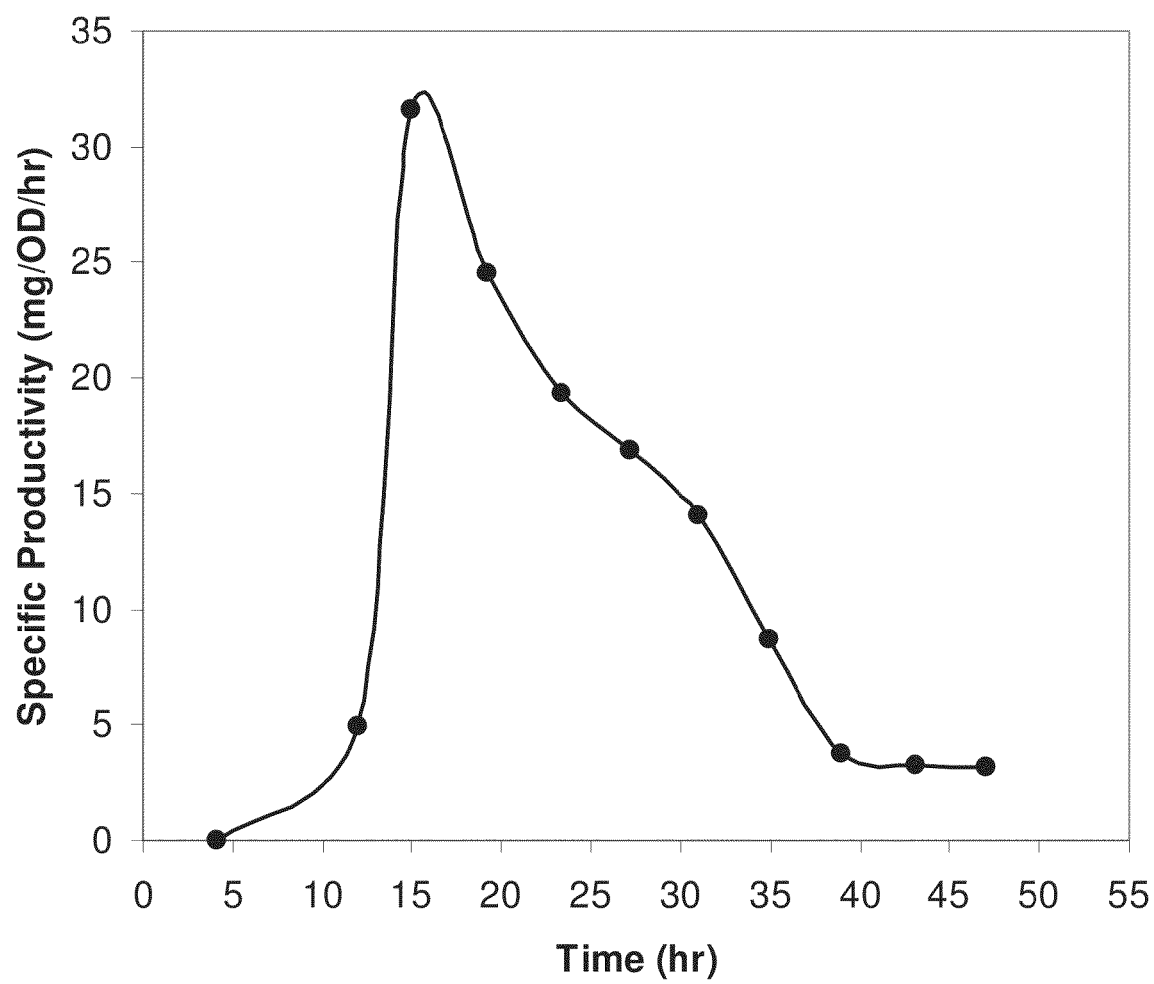

IV. Mevalonic Acid Production from *E. coli* FM5 Cells Expressing the pTrcUpperMVA Plasmid at a 15-L Scale FM5 cells that are grown on a plate as explained above in part I are inoculated into a flask containing 500 mL of tryptone-yeast extract medium and grown at 30° C. at 160 rpm to $OD_{550}$ 1.0. This material is seeded into a 15-L bioreactor containing 4.5-kg of medium. The IPTG concentration is brought to 1.0 mM when the $OD_{550}$ reached a value of 30. The $OD_{550}$ profile within the bioreactor over time is shown in FIG. 62A. The mevalonic acid titer increases over the course of the fermentation to a final value of 23.7 g/L (FIG. 62B). The specific productivity profile throughout the fermentation is shown in FIG. 62C and a comparison to FIG. 62A illustrates the de-coupling of growth and mevalonic acid production. The total amount of mevalonic acid produced during the 51.2 hour fermentation is 140 g from 1.1 kg of utilized glucose. The molar yield of utilized carbon that went into producing mevalonic acid during fermentation is 15.2%.

Figure 63A:
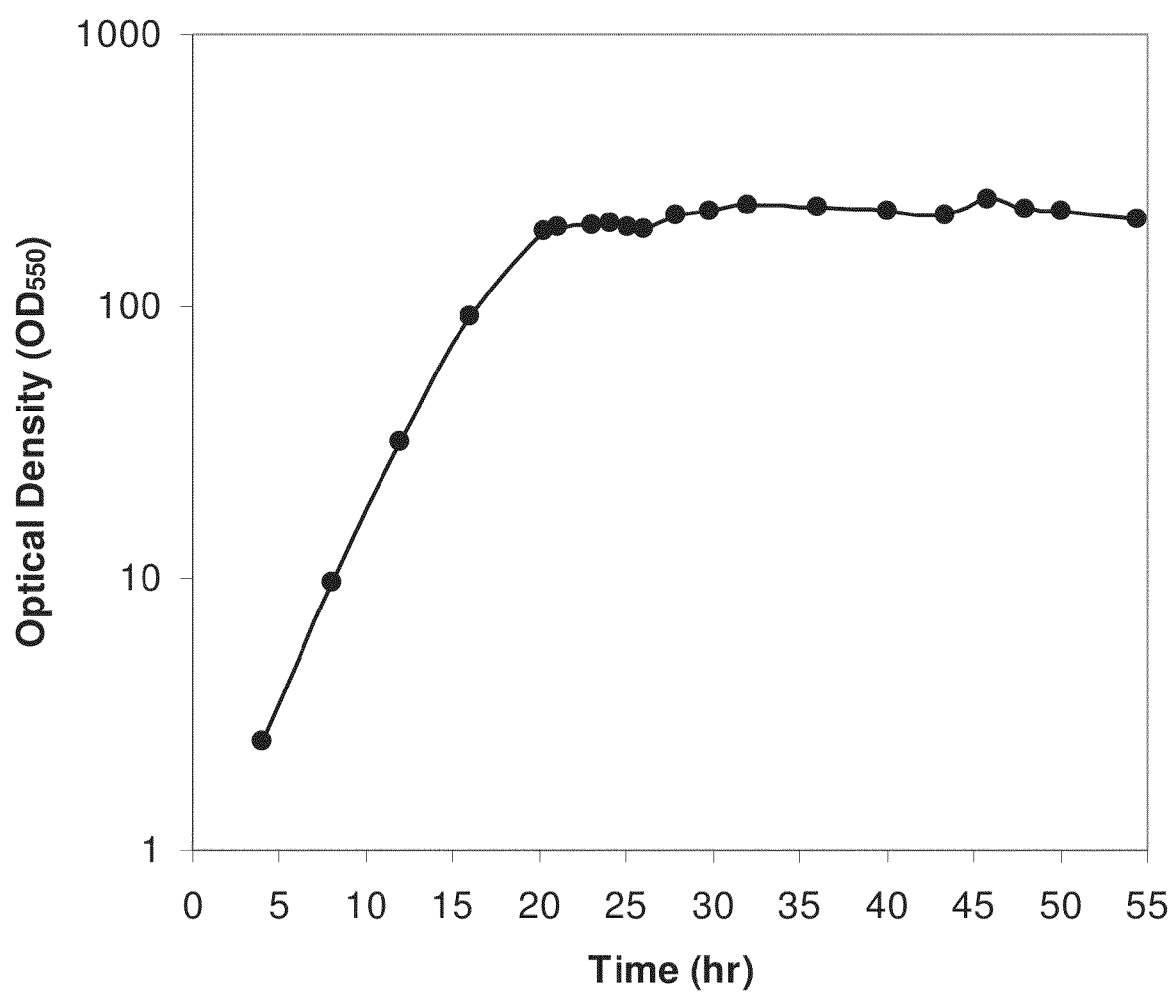
FIG. 63A-63C are the time courses of optical density, isoprene titer, and specific productivity within the 15-L bioreactor fed with glucose.
Figure 63B:
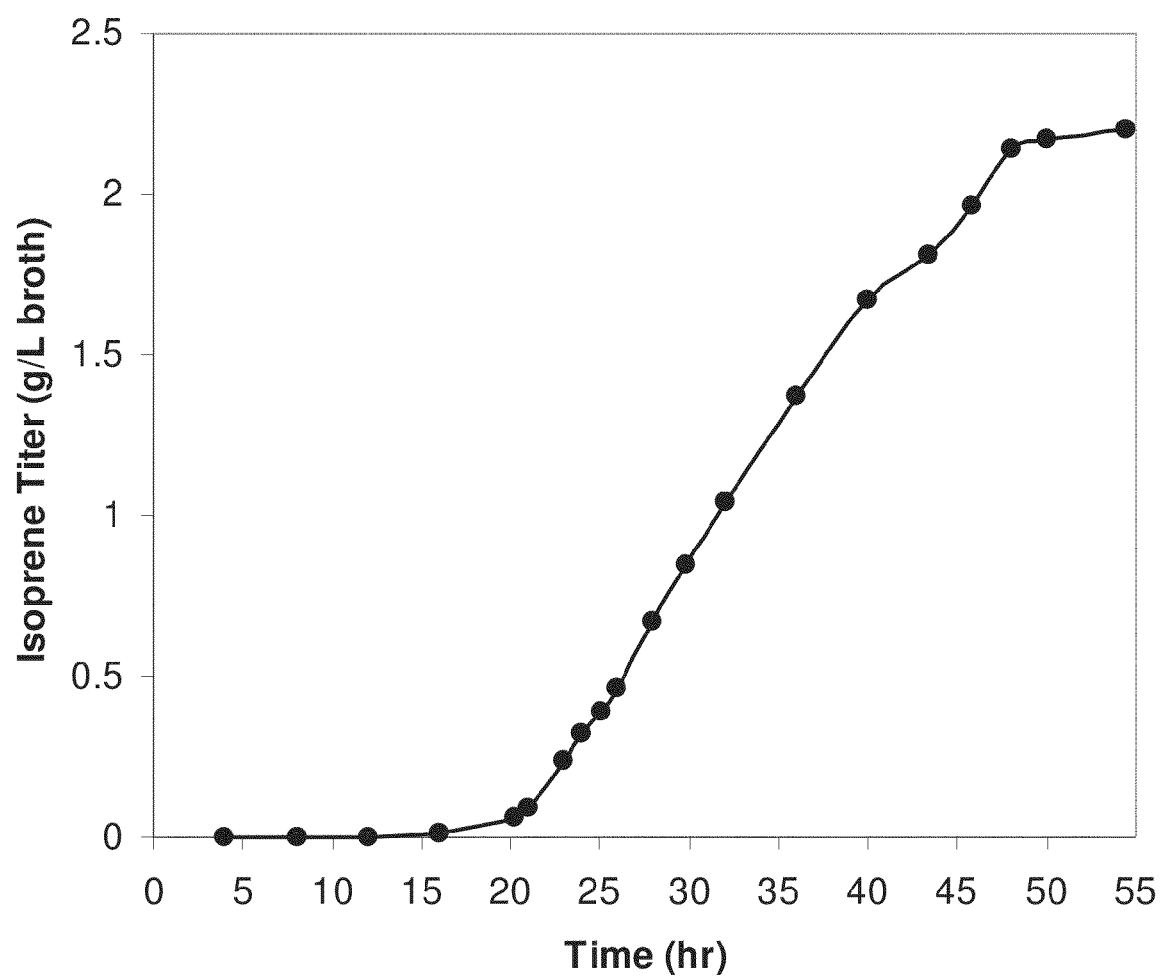
Figure 63C:
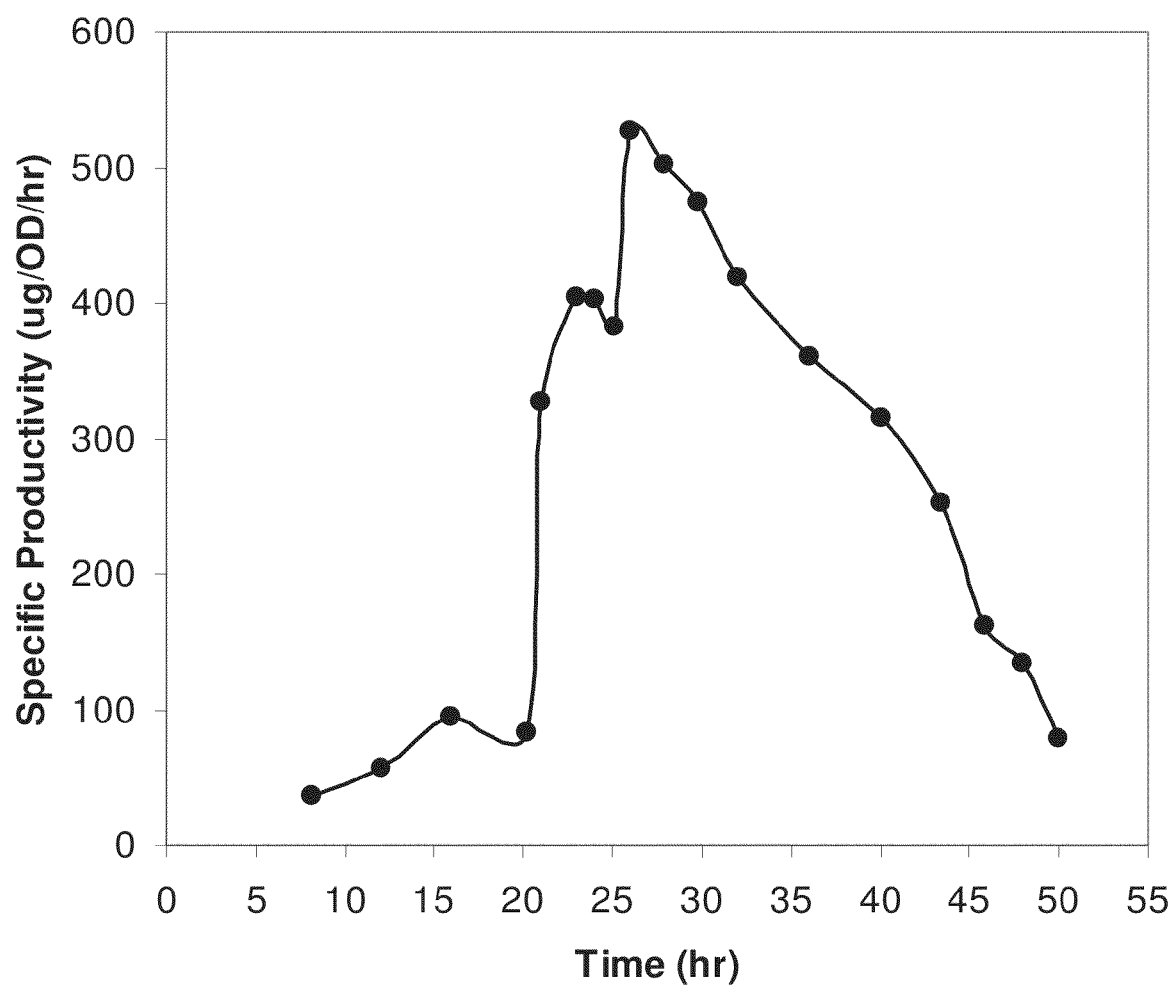

V. Isoprene Production from *E. coli* BL21(DE3) Cells Expressing the pCL PtrcUpperMVA and pTrc KKDyIkIS Plasmids at a 15-L scale BL21(DE3) cells expressing the pCL PtrcUpperMVA and pTrc KKDyIkIS plasmids that are grown on a plate as explained above in part I are inoculated into a flask containing 500 mL of tryptone-yeast extract medium and grown at 30° C. at 160 rpm to $OD_{550}$ 1.0. This material is seeded into a 15-L bioreactor containing 4.5-kg of medium. The IPTG concentration is brought to 25 μM when the $OD_{550}$ reaches a value of 10. The IPTG concentration is raised to 50 uM when $OD_{550}$ reaches 190. The IPTG concentration is raised to 100 uM at 38 hours of fermentation. The $OD_{550}$ profile within the bioreactor over time is shown in FIG. 63A. The isoprene titer increases over the course of the fermentation to a final value of 2.2 g/L broth (FIG. 63B). The specific productivity profile throughout the fermentation is shown in FIG. 63C and a comparison to FIG. 63A illustrates the de-coupling of growth and isoprene production. The total amount of isoprene produced during the 54.4 hour fermentation is 15.9 g from 2.3 kg of utilized glucose. The molar yield of utilized carbon that goes into producing isoprene during fermentation is 1.53%.

Figure 64A:
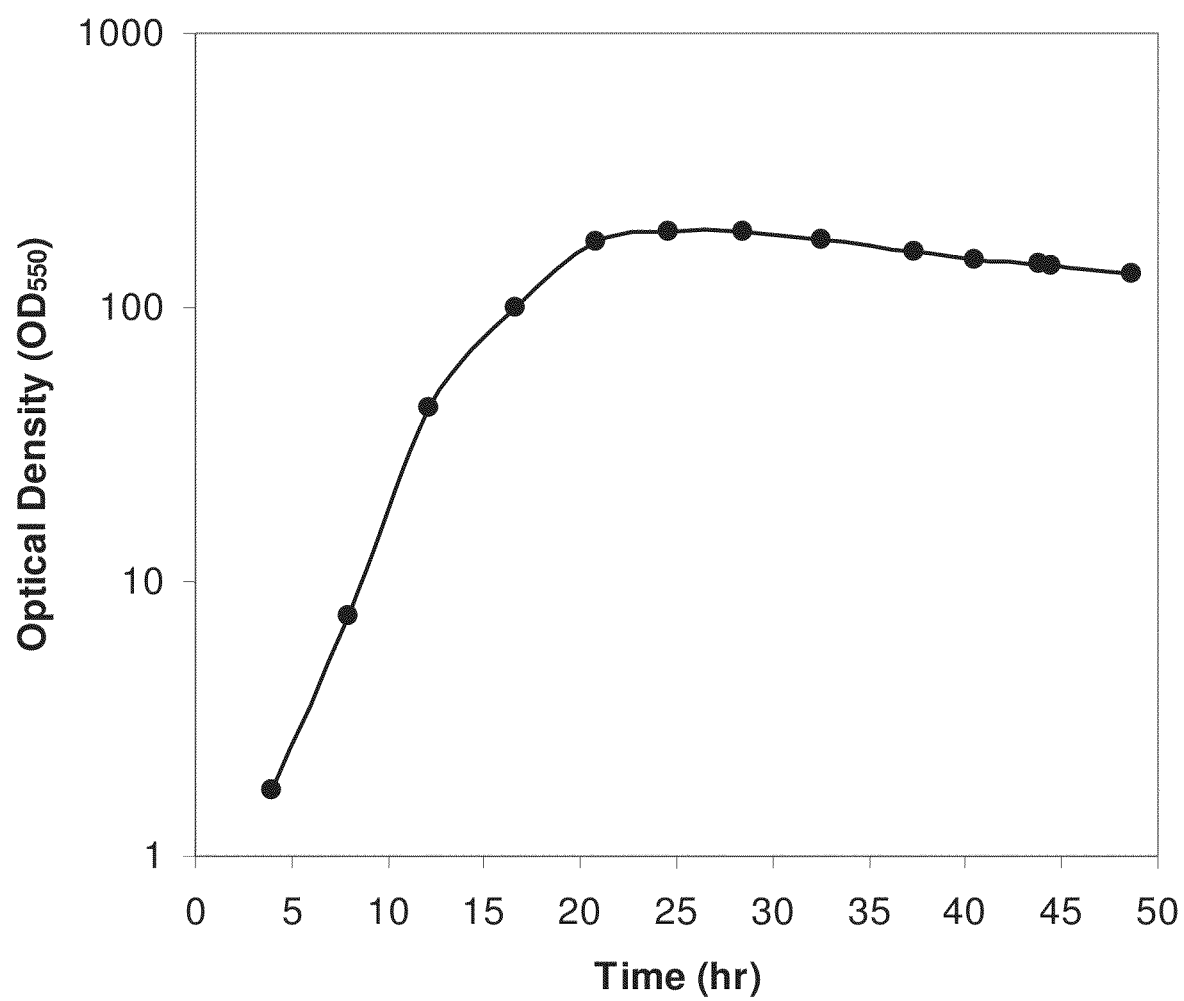
FIGS. 64A-64C are the time courses of optical density, isoprene titer, and specific productivity within the 15-L bioreactor fed with glucose.
Figure 64B:
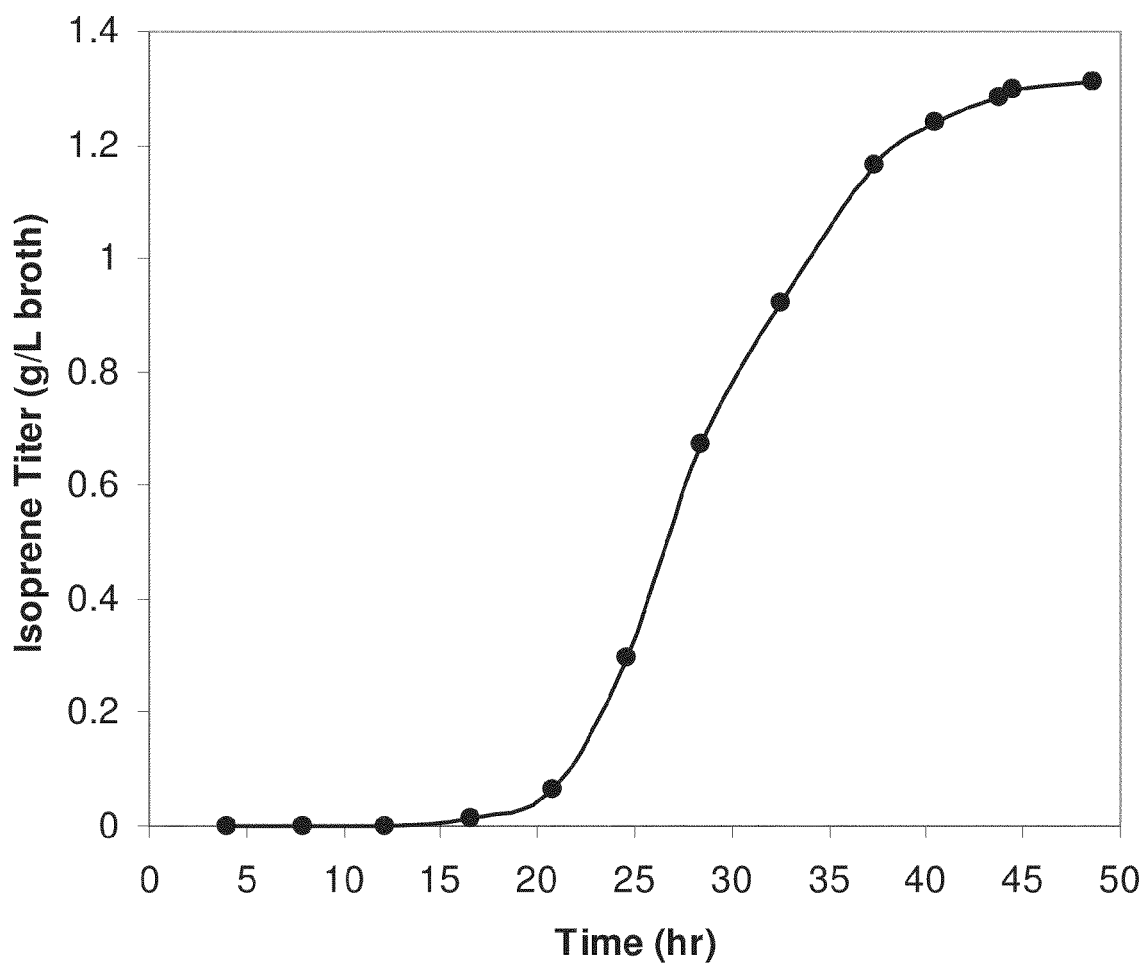
Figure 64C:
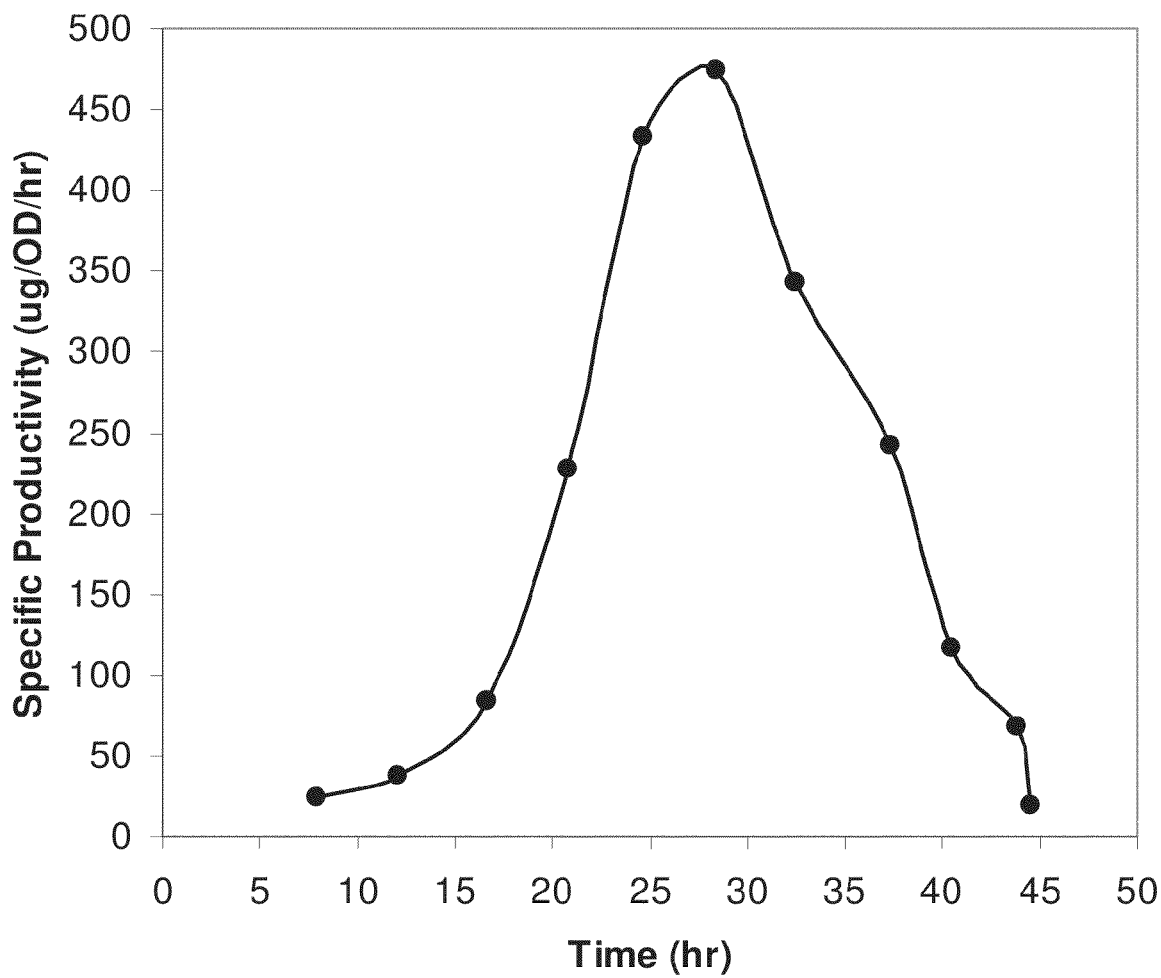

VI. Isoprene production from *E. coli* BL21(DE3) Tuner Cells Expressing the pCL PtrcUpperMVA and pTrc KKDyIkIS Plasmids at a 15-L Scale BL21(DE3) tuner cells expressing the pCL PtrcUpperMVA and pTrc KKDyIkIS plasmids that are grown on a plate as explained above in part I are inoculated into a flask containing 500 mL of tryptone-yeast extract medium and grown at 30° C. at 160 rpm to $OD_{550}$ 1.0. This material is seeded into a 15-L bioreactor containing 4.5-kg of medium. The IPTG concentration is brought to 26 μM when the $OD_{550}$ reaches a value of 10. The IPTG concentration is raised to 50 uM when $OD_{550}$ reaches 175. The $OD_{550}$ profile within the bioreactor over time is shown in FIG. 64A. The isoprene titer increases over the course of the fermentation to a final value of 1.3 g/L broth (FIG. 64B). The specific productivity profile throughout the fermentation is shown in FIG. 64C and a comparison to FIG. 64A illustrates the de-coupling of growth and isoprene production. The total amount of isoprene produced during the 48.6 hour fermentation is 9.9 g from 1.6 kg of utilized glucose. The molar yield of utilized carbon that goes into producing isoprene during fermentation is 1.34%.

Figure 65A:
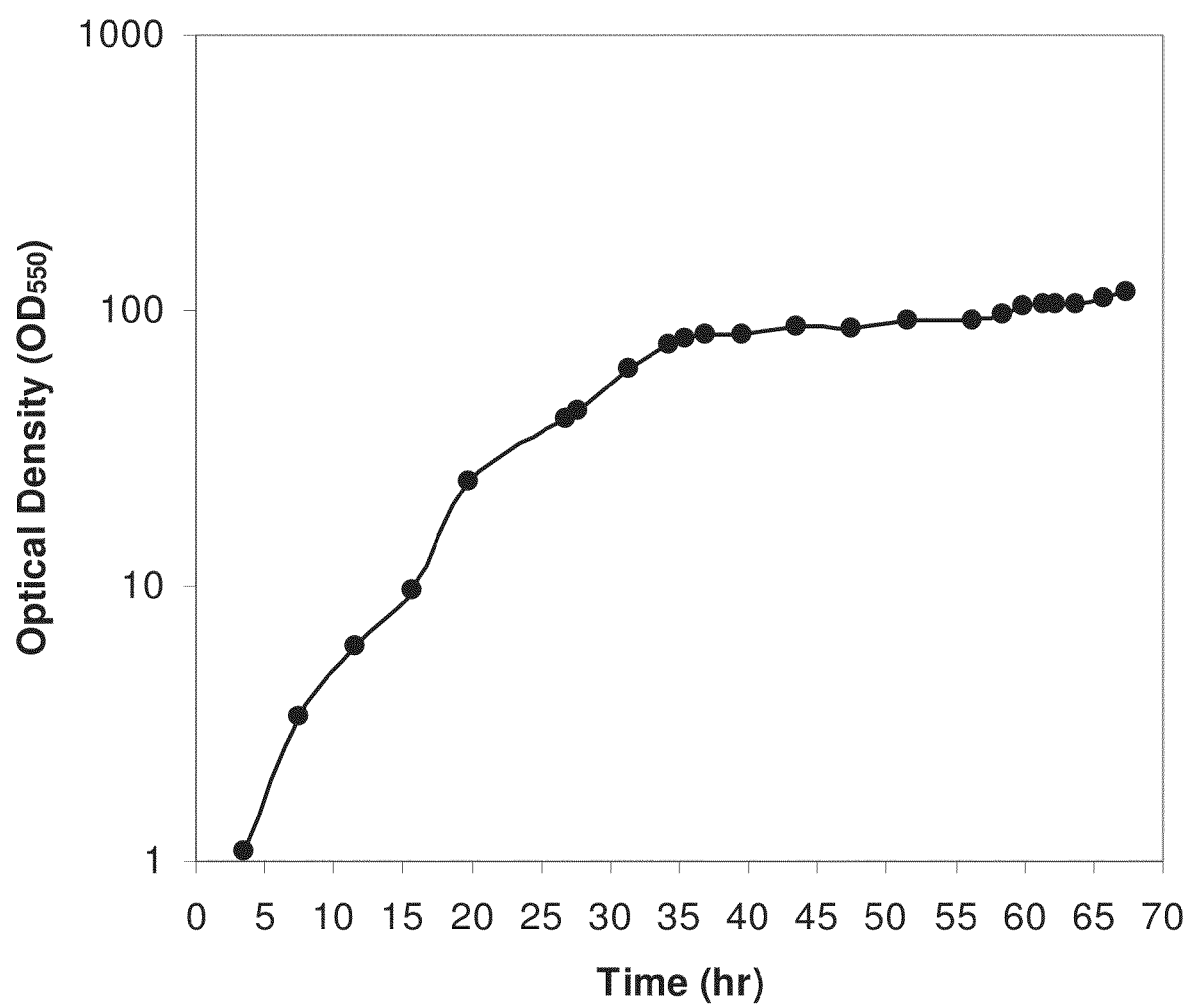
FIGS. 65A-65C are the time courses of optical density, isoprene titer, and specific productivity within the 15-L bioreactor fed with glucose.
Figure 65B:
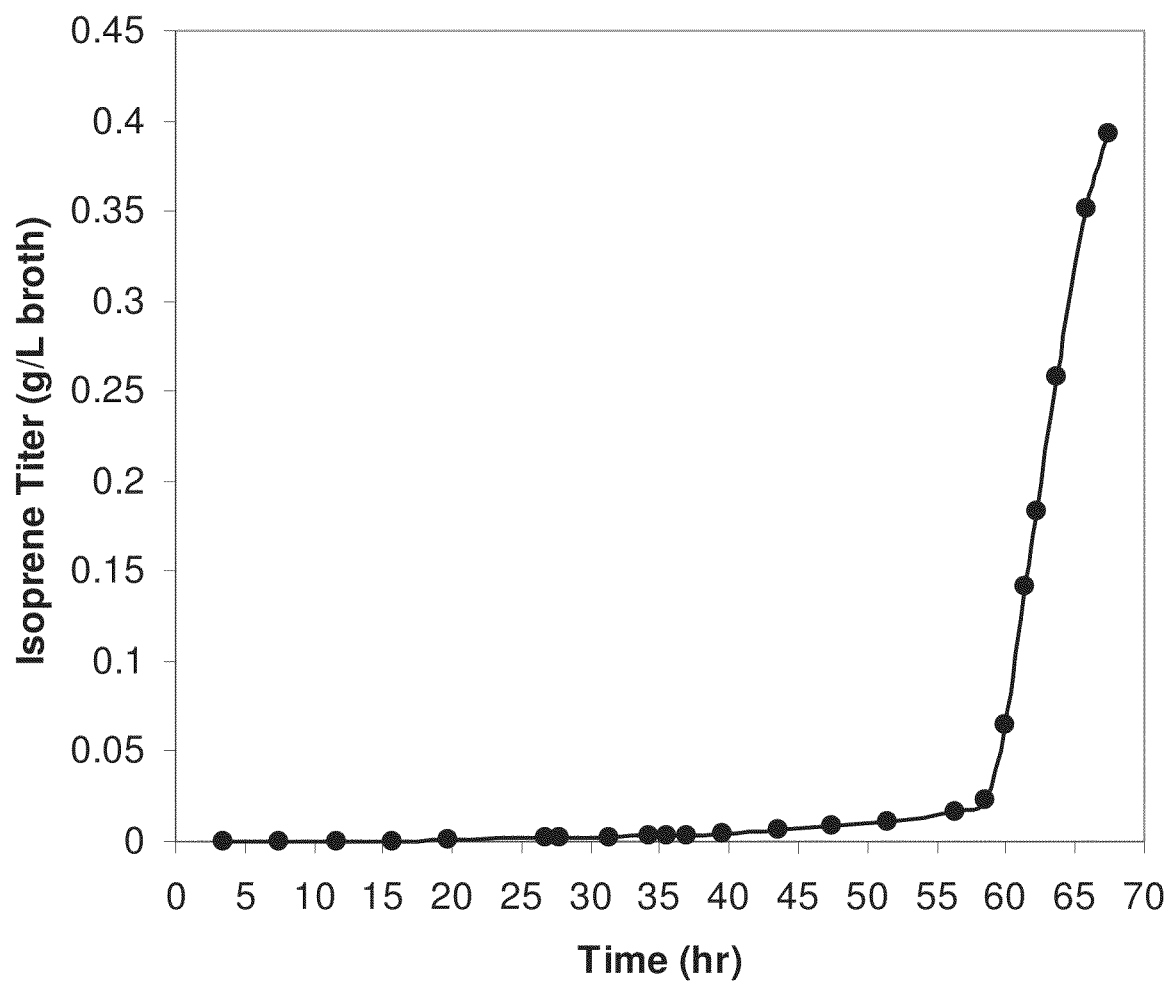
Figure 65C:
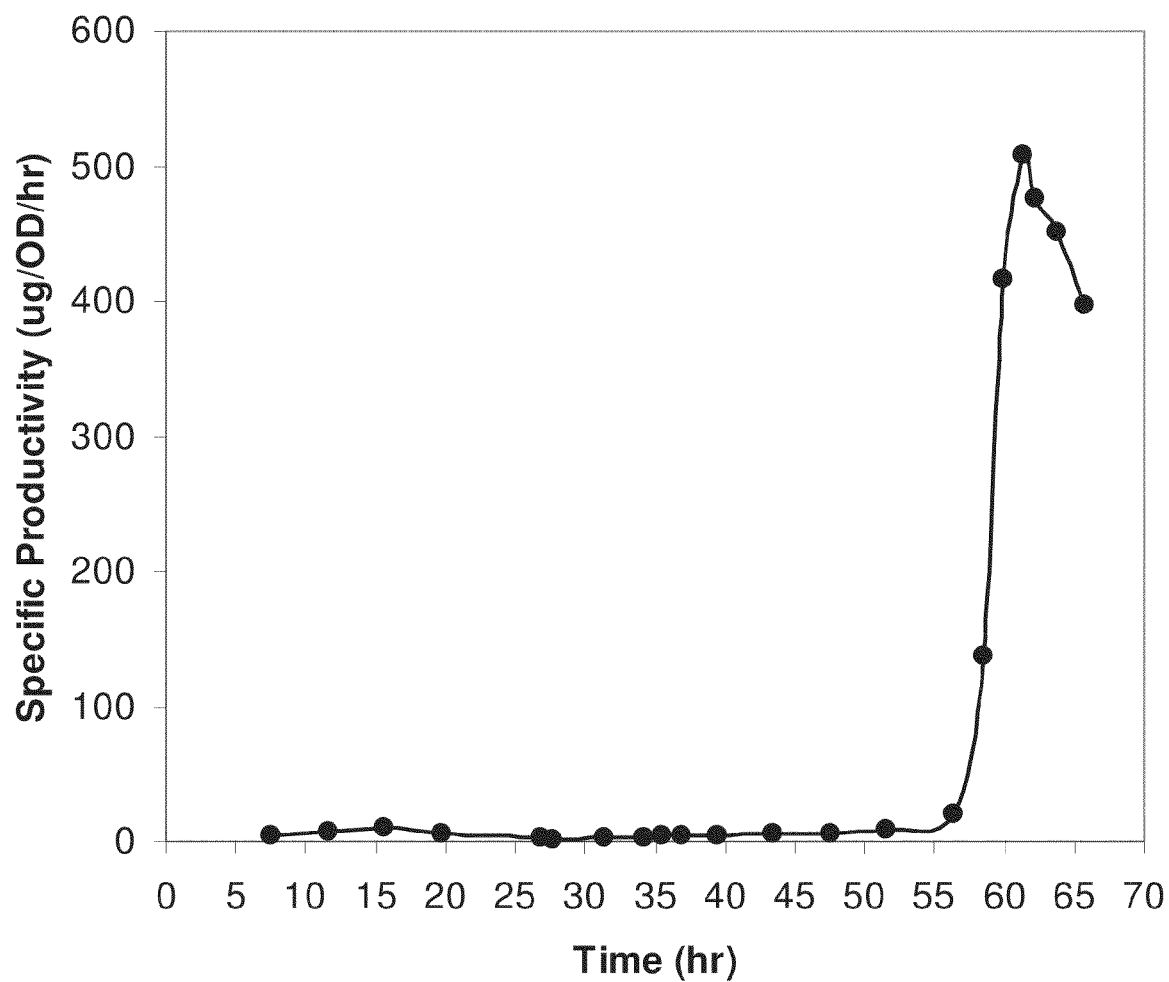

VII. Isoprene Production from *E. coli* MG1655 Cells Expressing the pCL PtrcUpperMVA and pTrc KKDyIkIS Plasmids at a 15-L Scale MG1655 cells expressing the pCL PtrcUpperMVA and pTrc KKDyIkIS plasmids that are grown on a plate as explained above in part I are inoculated into a flask containing 500 mL of tryptone-yeast extract medium and grown at 30° C. at 160 rpm to $OD_{550}$ 1.0. This material is seeded into a 15-L bioreactor containing 4.5-kg of medium. The IPTG concentration is brought to 24 µM when the $OD_{550}$ reaches a value of 45. The $OD_{550}$ profile within the bioreactor over time is shown in FIG. 65A. The isoprene titer increases over the course of the fermentation to a final value of 393 mg/L broth (FIG. 65B). The specific productivity profile throughout the fermentation is shown in FIG. 65C and a comparison to FIG. 65A illustrates the de-coupling of growth and isoprene production. The total amount of isoprene produced during the 67.4 hour fermentation is 2.2 g from 520 g of utilized glucose. The molar yield of utilized carbon that goes into producing isoprene during fermentation is 0.92%.

Figure 66A:
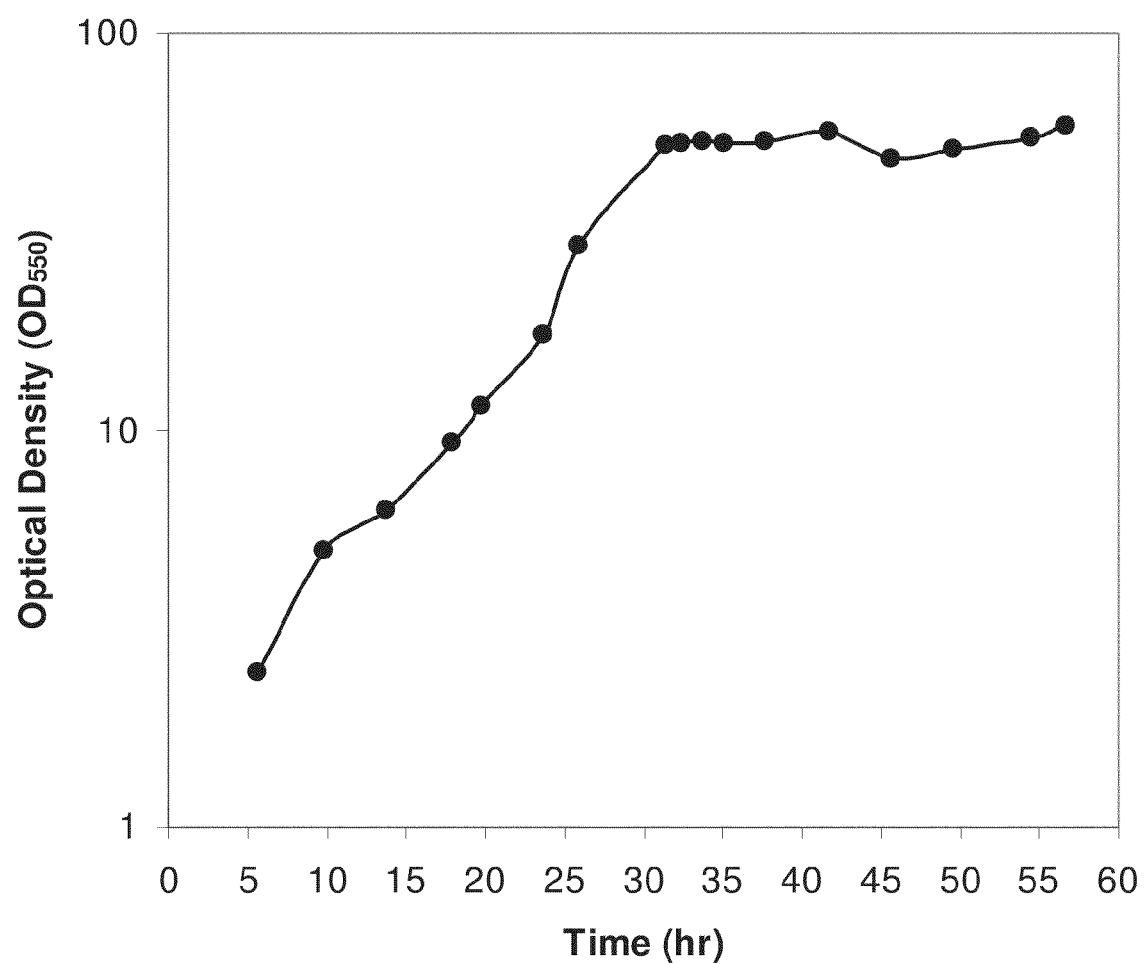
FIGS. 66A-66C are the time courses of optical density, isoprene titer, and specific productivity within the 15-L bioreactor fed with glucose.
Figure 66B:
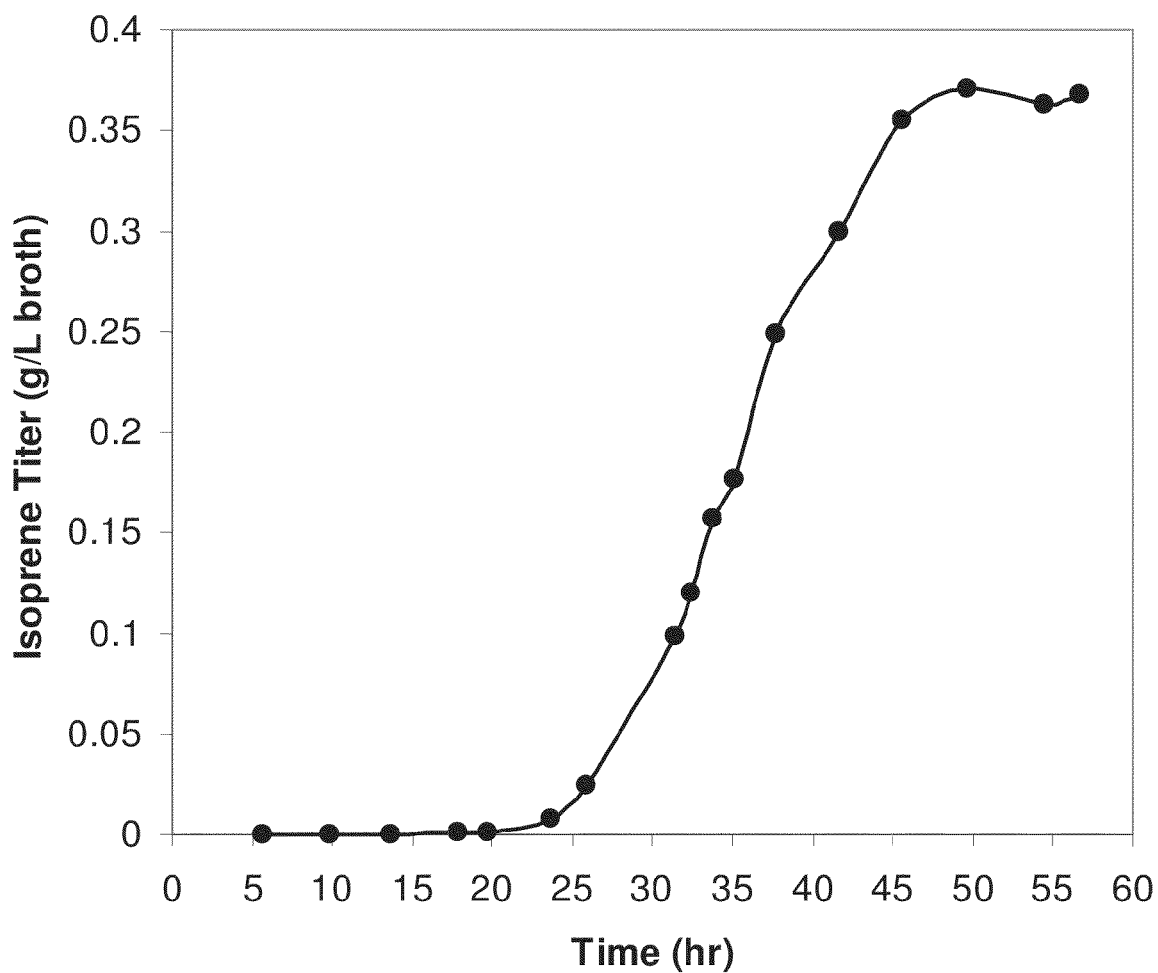
Figure 66C:
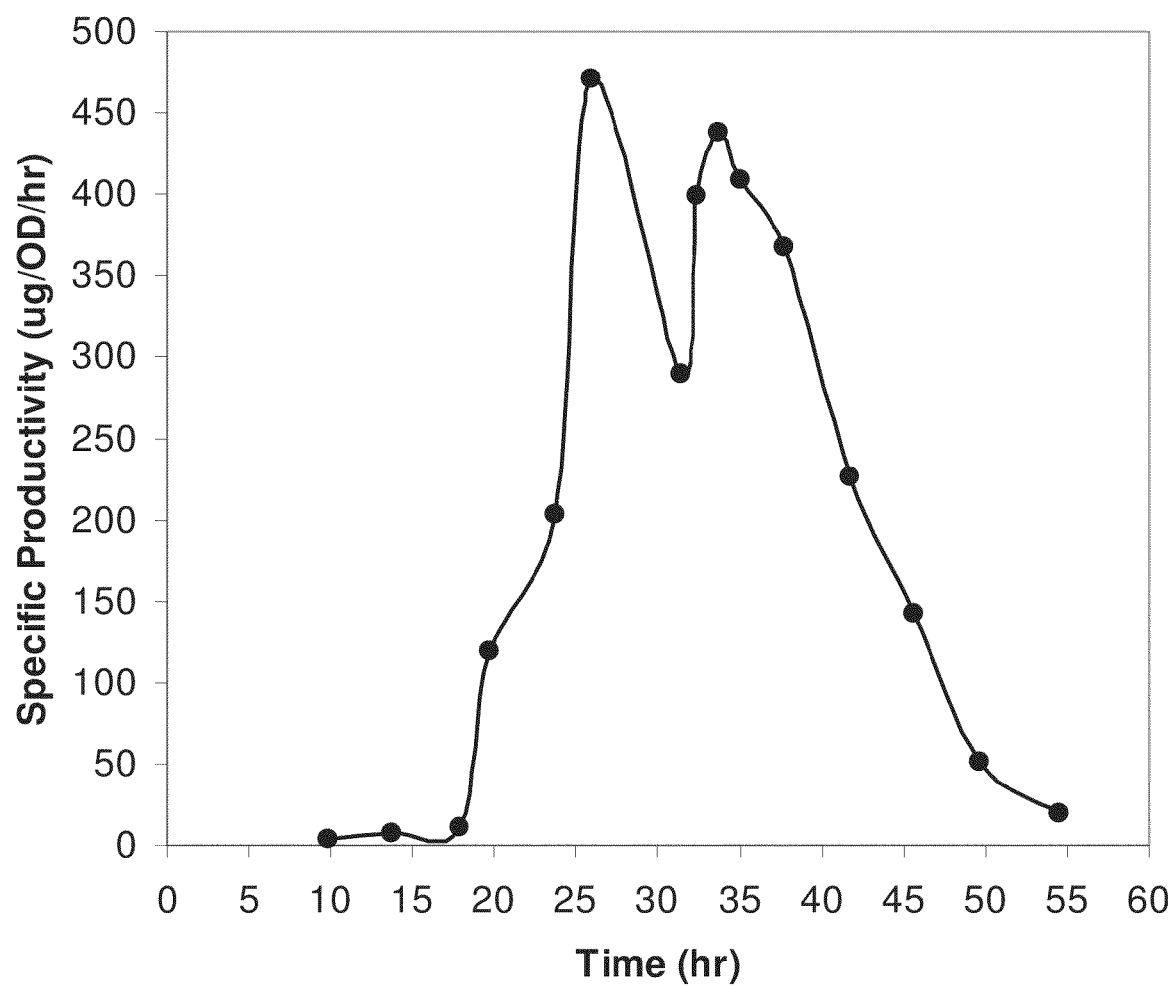

VIII. Isoprene Production from *E. coli* MG1655ack-pta Cells Expressing the pCL PtrcUpperMVA and pTrc KKDyIkIS plasmids at a 15-L Scale MG1655ack-pta cells expressing the pCL PtrcUpperMVA and pTrc KKDyIkIS plasmids that are grown on a plate as explained above in part I are inoculated into a flask containing 500 mL of tryptone-yeast extract medium and grown at 30° C. at 160 rpm to $OD_{550}$ 1.0. This material is seeded into a 15-L bioreactor containing 4.5-kg of medium. The IPTG concentration is brought to 30 µM when the $OD_{550}$ reaches a value of 10. The $OD_{550}$ profile within the bioreactor over time is shown in FIG. 66A. The isoprene titer increases over the course of the fermentation to a final value of 368 mg/L broth (FIG. 66B). The specific productivity profile throughout the fermentation is shown in FIG. 66C and a comparison to FIG. 66A illustrates the de-coupling of growth and isoprene production. The total amount of isoprene produced during the 56.7 hour fermentation is 1.8 g from 531 g of utilized glucose. The molar yield of utilized carbon that goes into producing isoprene during fermentation is 0.73%.

Figure 67A:
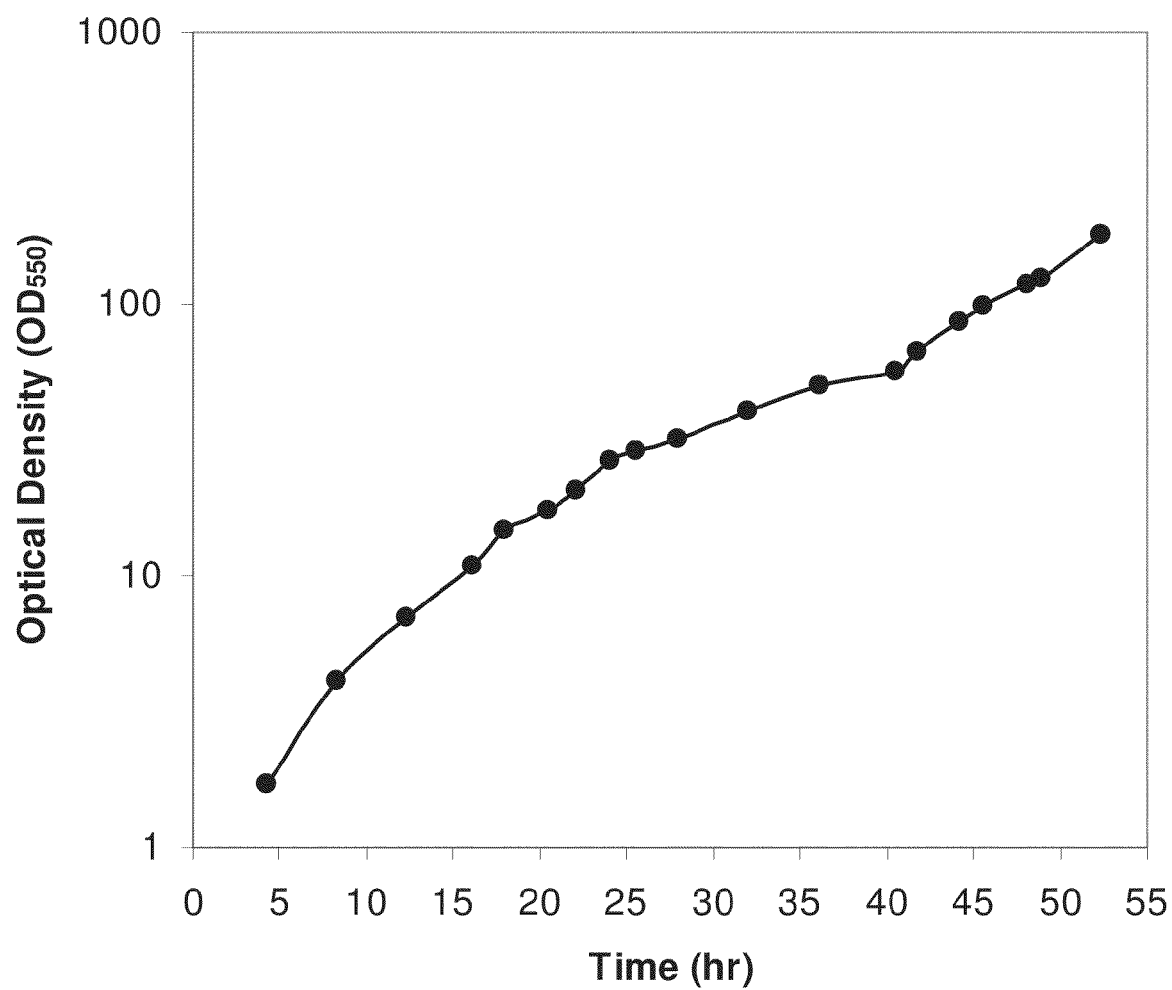
FIG. 67A-67C are the time courses of optical density, isoprene titer, and specific productivity within the 15-L bioreactor fed with glucose.
Figure 67B:
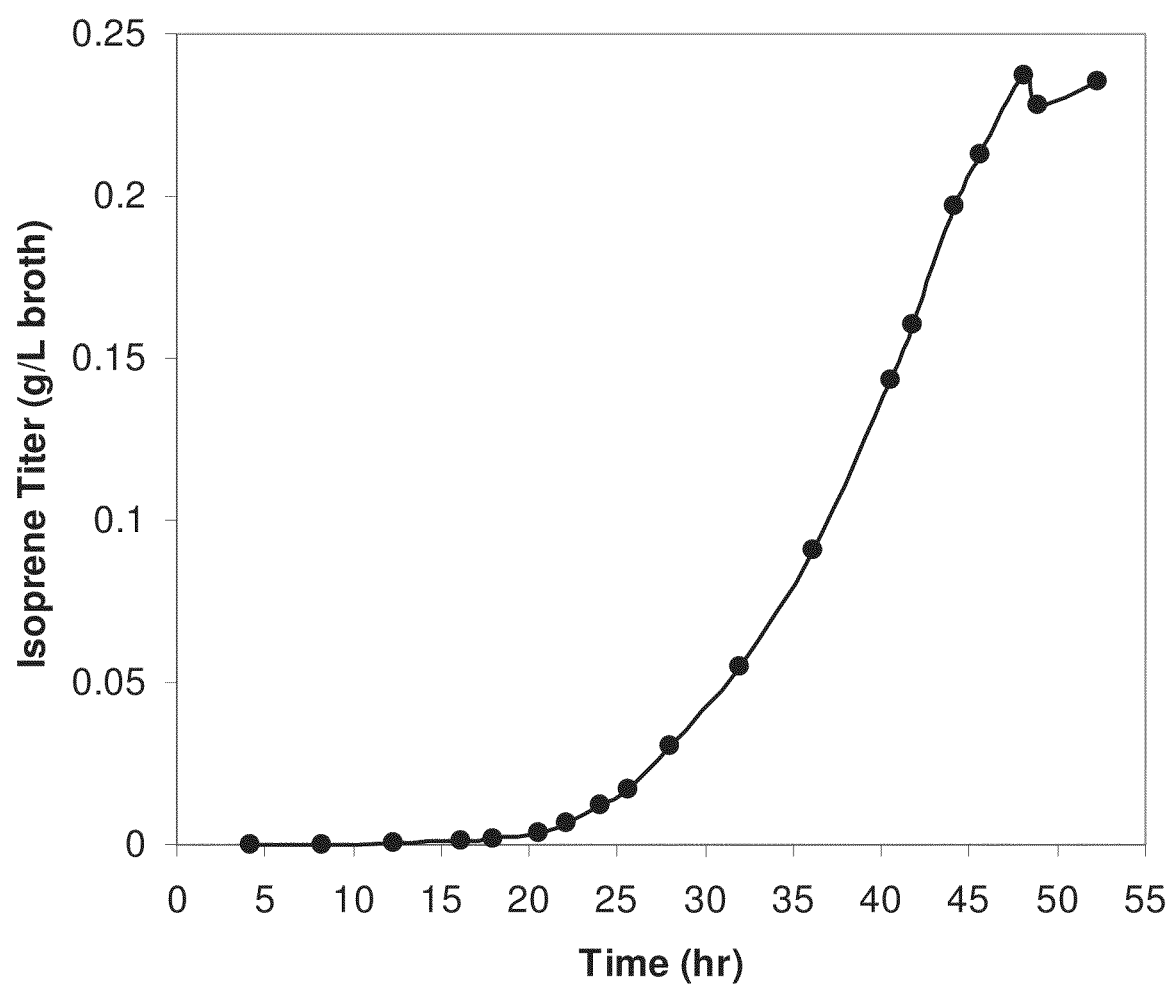
Figure 67C:
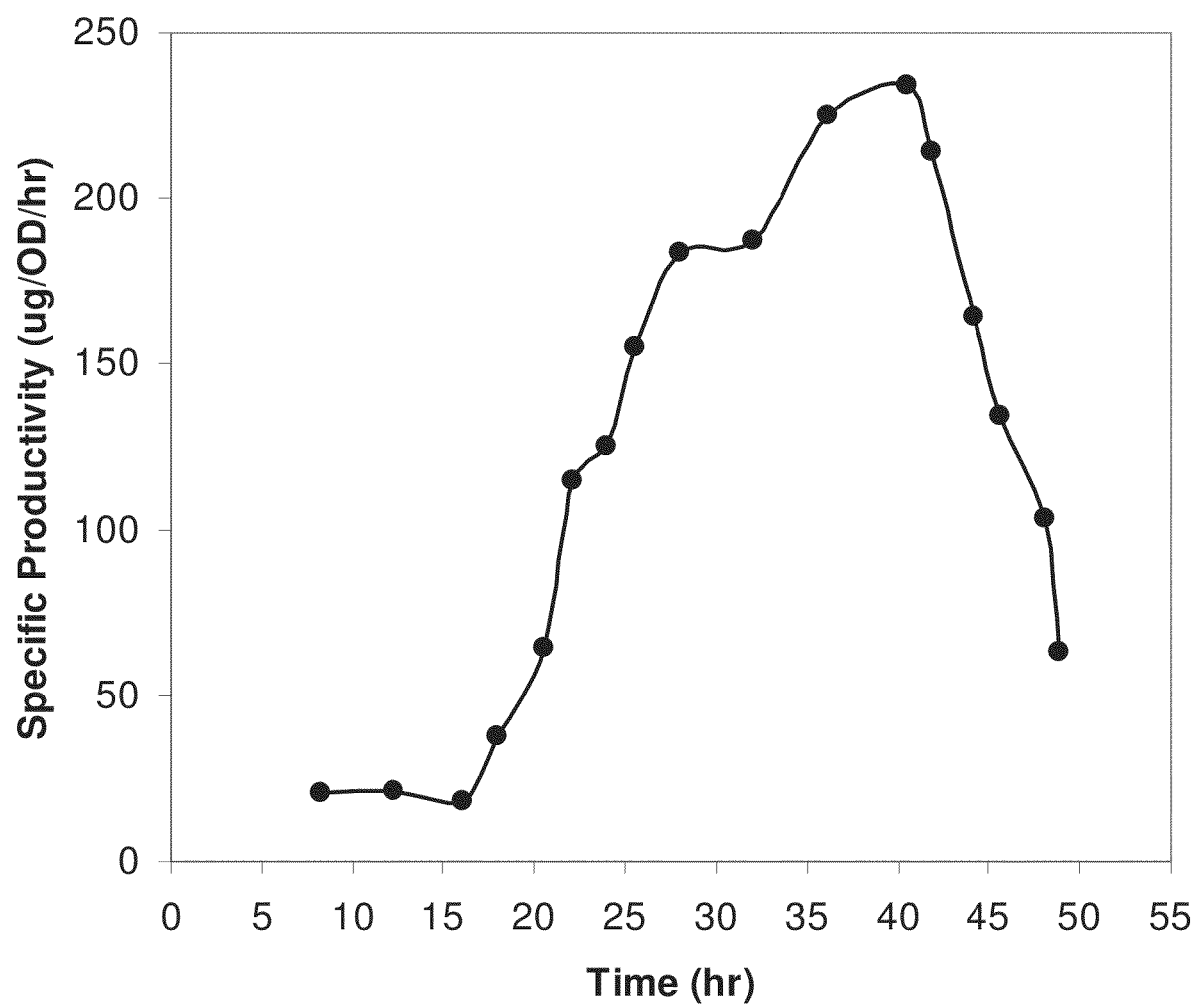

IX. Isoprene Production from *E. coli* FM5 Cells Expressing the pCL PtrcUpperMVA and pTrc KKDyIkIS Plasmids at a 15-L Scale FM5 cells expressing the pCL PtrcUpperMVA and pTrc KKDyIkIS plasmids that are grown on a plate as explained above in part I are inoculated into a flask containing 500 mL of tryptone-yeast extract medium and grown at 30° C. at 160 rpm to $OD_{550}$ 1.0. This material is seeded into a 15-L bioreactor containing 4.5-kg of medium. The IPTG concentration is brought to 27 µM when the $OD_{550}$ reaches a value of 15. The $OD_{550}$ profile within the bioreactor over time is shown in FIG. 67A. The isoprene titer increases over the course of the fermentation to a final value of 235 mg/L broth (FIG. 67B). The specific productivity profile throughout the fermentation is shown in FIG. 67C and a comparison to FIG. 67A illustrates the de-coupling of growth and isoprene production. The total amount of isoprene produced during the 52.3 hour fermentation is 1.4 g from 948 g of utilized glucose. The molar yield of utilized carbon that goes into producing isoprene during fermentation is 0.32%.

Example 12

Production of Isoprene During the Exponential Growth Phase of *E. coli* Expressing Genes of the Mevalonic Acid Pathway and Fermented in a Fed-Batch Culture This example illustrates the production of isoprene during the exponential growth phase of cells.

Medium Recipe (per liter fermentation medium): The medium is generated using the following components per liter fermentation medium: $K_2HPO_4$ 7.5 g, $MgSO_4.7H_2O$ 2 g, citric acid monohydrate 2 g, ferric ammonium citrate 0.3 g, yeast extract 0.5 g, and 1000× modified trace metal solution 1 ml. All of the components are added together and dissolved in $diH_2O$. This solution is autoclaved. The pH is adjusted to 7.0 with ammonium hydroxide (30%) and q.s. to volume. Glucose 10 g, thiamine.HCl 0.1 g, and antibiotics are added after sterilization and pH adjustment.

1000× Modified Trace Metal Solution: The 1000× modified trace metal solution is generated using the following components: citric acid.$H_2O$ 40 g, $MnSO_4.H_2O$ 30 g, NaCl 10 g, $FeSO_4.7H_2O$ 1 g, $CoCl2.6H_2O$ 1 g, $ZnSO_4.7H_2O$ 1 g, $CuSO_4.5H_2O$ 100 mg, $H_3BO_3$ 100 mg, and $NaMoO_4.2H_2O$ 100 mg. Each component is dissolved one at a time in Di H2O, pH to 3.0 with HCl/NaOH, then q.s. to volume and filter sterilized with 0.22 micron filter.

Fermentation is performed in a 15-L bioreactor with ATCC11303 *E. coli* cells containing the pCL PtrcUpperMVA and pTrc KKDyIkIS plasmids. This experiment is carried out to monitor isoprene formation from glucose at the desired fermentation pH 7.0 and temperature 30° C. An inoculum of *E. coli* strain taken from a frozen vial is streaked onto an LB broth agar plate (with antibiotics) and incubated at 37° C. A single colony is inoculated into tryptone-yeast extract medium. After the inoculum grows to OD 1.0, measured at 550 nm, 500 mL is used to inoculate a 15-L bioreactor containing an initial working volume of 5 L.

Glucose is fed at an exponential rate until cells reach the stationary phase. After this time the glucose feed is decreased to meet metabolic demands. The total amount of glucose delivered to the bioreactor during the 50 hour fermentation is 2.0 kg. Induction is achieved by adding IPTG. The IPTG concentration is brought to 25 uM when the optical density at 550 nm ($OD_{550}$) reaches a value of 10. The IPTG concentration is raised to 50 uM when $OD_{550}$ reaches 190. The $OD_{550}$ profile within the bioreactor over time is shown in FIG. 99. The isoprene level in the off gas from the bioreactor is determined as described herein. The isoprene titer increases over the course of the fermentation to a final value of 1.4 g/L (FIG. 100). The total amount of isoprene produced during the 50 hour fermentation is 10.0 g. The profile of the isoprene specific productivity over time within the bioreactor is shown in FIG. 101. The molar yield of utilized carbon that contributes to producing isoprene during fermentation is 1.1%. The weight percent yield of isoprene from glucose is 0.5%.

Example 13

Flammability Modeling and Testing of Isoprene

I. Summary of Flammability Modeling and Testing of Isoprene

Flammability modeling and experiments are performed for various hydrocarbon/oxygen/nitrogen/water/carbon dioxide mixtures. This modeling and experimental tested is aimed at defining isoprene and oxygen/nitrogen flammability curves under specified steam and carbon monoxide concentrations at a fixed pressure and temperature. A matrix of the model conditions is shown in Table 13-1, and a matrix of the experiments performed is shown in Table 13-2.

TABLE 13-1

Summary of Modeled Isoprene Flammability

| Series | Temperature (° C.) | Pressure (psig) | Steam Concentration (wt %) | $CO_2$ Concentration (wt. %) | Isoprene Concentration (vol. %) | Oxygen Concentration (vol. %) |
|---|---|---|---|---|---|---|
| A | 40 | 0 | 0 | 0 | Varying | Varying |
| B | 40 | 0 | 4 | 0 | Varying | Varying |
| C | 40 | 0 | 0 | 5 | Varying | Varying |
| D | 40 | 0 | 0 | 10 | Varying | Varying |
| E | 40 | 0 | 0 | 15 | Varying | Varying |
| F | 40 | 0 | 0 | 20 | Varying | Varying |
| G | 40 | 0 | 0 | 30 | Varying | Varying |

TABLE 13-2

Summary of Isoprene Flammability Tests

| Series Number | Temperature (° C.) | Pressure (psig) | Steam Concentration (vol. %) | Isoprene Concentration (vol. %) | Oxygen Concentration (vol. %) |
|---|---|---|---|---|---|
| 1 | 40 | 0 | 0 | Varying | Varying |
| 2 | 40 | 0 | 4 | Varying | Varying |

II. Description of Calculated Adiabatic Flame Temperature (CAFT) Model

Calculated adiabatic flame temperatures (CAFT) along with a selected limit flame temperature for combustion propagation are used to determine the flammability envelope for isoprene. The computer program used in this study to calculate the flame temperatures is the NASA Glenn Research Center CEA (Chemical Equilibrium with Applications) software.

There are five steps involved in determining the flammability envelope using an adiabatic flame temperature model for a homogeneous combustion mechanism (where both the fuel and oxidant are in the gaseous state): selection of the desired reactants, selection of the test condition, selection of the limit flame temperature, modification of the reactants, and construction of a flammability envelope from calculations.

In this first step, selection of desired reactants, a decision must be made as to the reactant species that will be present in the system and the quantities of each. In many cases the computer programs used for the calculations have a list of reactant and product species. If any of the data for the species to be studied are not found in the program, they may be obtained from other sources such as the JANAF tables or from the internet. In this current model data for water, nitrogen, oxygen and carbon dioxide are present in the program database. The program database does not have isoprene as a species; therefore the thermodynamic properties are incorporated manually.

The next step is to decide whether the initial pressure and temperature conditions that the combustion process is taking place in. In this model the pressure is 1 atmosphere (absolute) and the temperature is 40° C., the boiling point of isoprene.

The limit flame temperature for combustion can be either selected based on theoretical principles or determined experimentally. Each method has its own limitations.

Based on prior studies, the limit flame temperatures of hydrocarbons fall in the range of 1000 K to 1500 K. For this model, the value of 1500 K is selected. This is the temperature at which the reaction of carbon monoxide to carbon dioxide (a highly exothermic reaction and constitutes a significant proportion of the flame energy) becomes self sustaining.

Once the limit flame temperature has been decided upon, model calculations are performed on the given reactant mixture (species concentrations) and the adiabatic flame temperature is determined. Flame propagation is considered to have occurred only if the temperature is greater than the limit flame temperature. The reactant mixture composition is then modified to create data sets for propagation and non-propagation mixtures.

This type of model shows good agreement with the experimentally determined flammability limits. Regions outside the derived envelope are nonflammable and regions within it are flammable. The shape of the envelope forms a nose. The nose of the envelope is related to the limiting oxygen concentration (LOC) for gaseous fuels.

III. Results from Calculated Adiabatic Flame Temperature (CAFT) Model

Plotted in FIGS. 68 through 74 are the CAFT model results for Series A to G, respectively. The figures plot the calculated adiabatic flame temperature (using the NASA CEA program) as a function of fuel concentration (by weight) for several oxygen/nitrogen ratios (by weight). The parts of the curve that are above 1500 K, the selected limit flame temperature, contain fuel levels sufficient for flame propagation. The results may be difficult to interpret in the form presented in FIGS. 68 through 74. Additionally, the current form is not conducive to comparison with experimental data which is generally presented in terms of volume percent.

Figure 68:
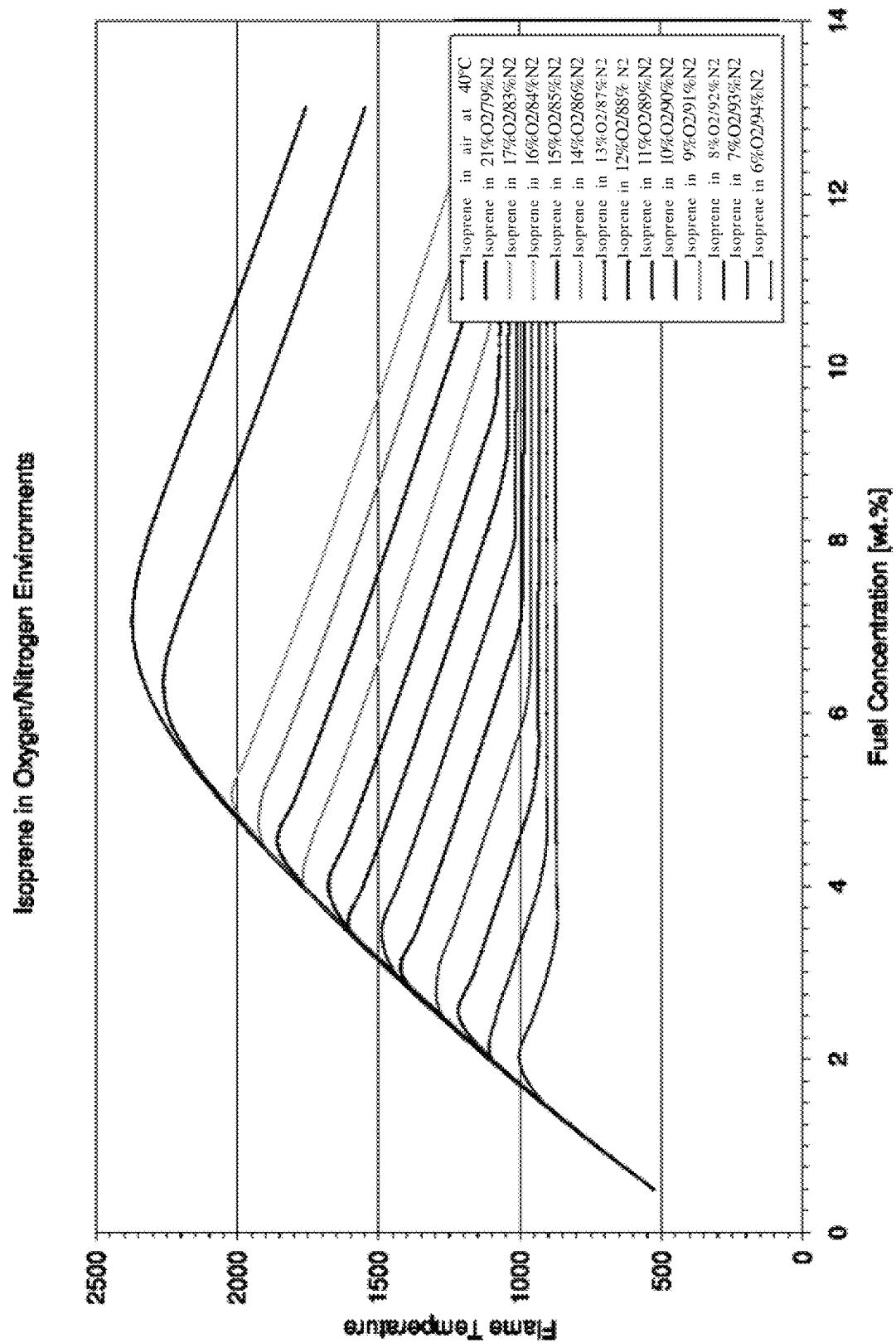
FIG. 68 is a graph of the calculated adiabatic flame temperatures for Series A as a function of fuel concentration for various oxygen levels. The figure legend lists the curves in the order in which they appear in the graph. For example, the first entry in the figure legend (isoprene in air at 40° C.) corresponds to the highest curve in the graph.
Figure 69:
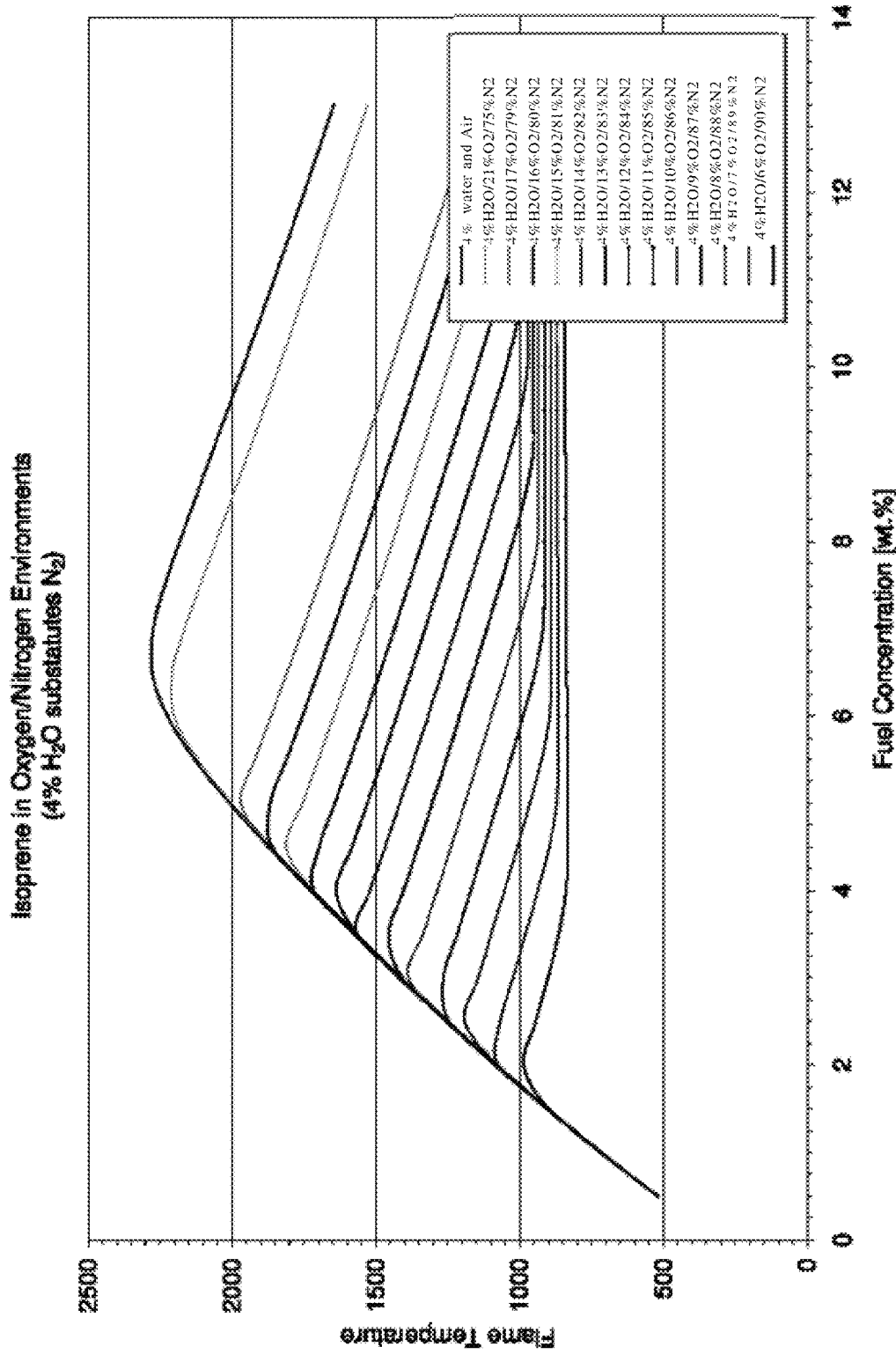
FIG. 69 is a graph of the calculated adiabatic flame temperatures for Series B as a function of fuel concentration for various oxygen levels with 4% water. The figure legend lists the curves in the order in which they appear in the graph.
Figure 70:
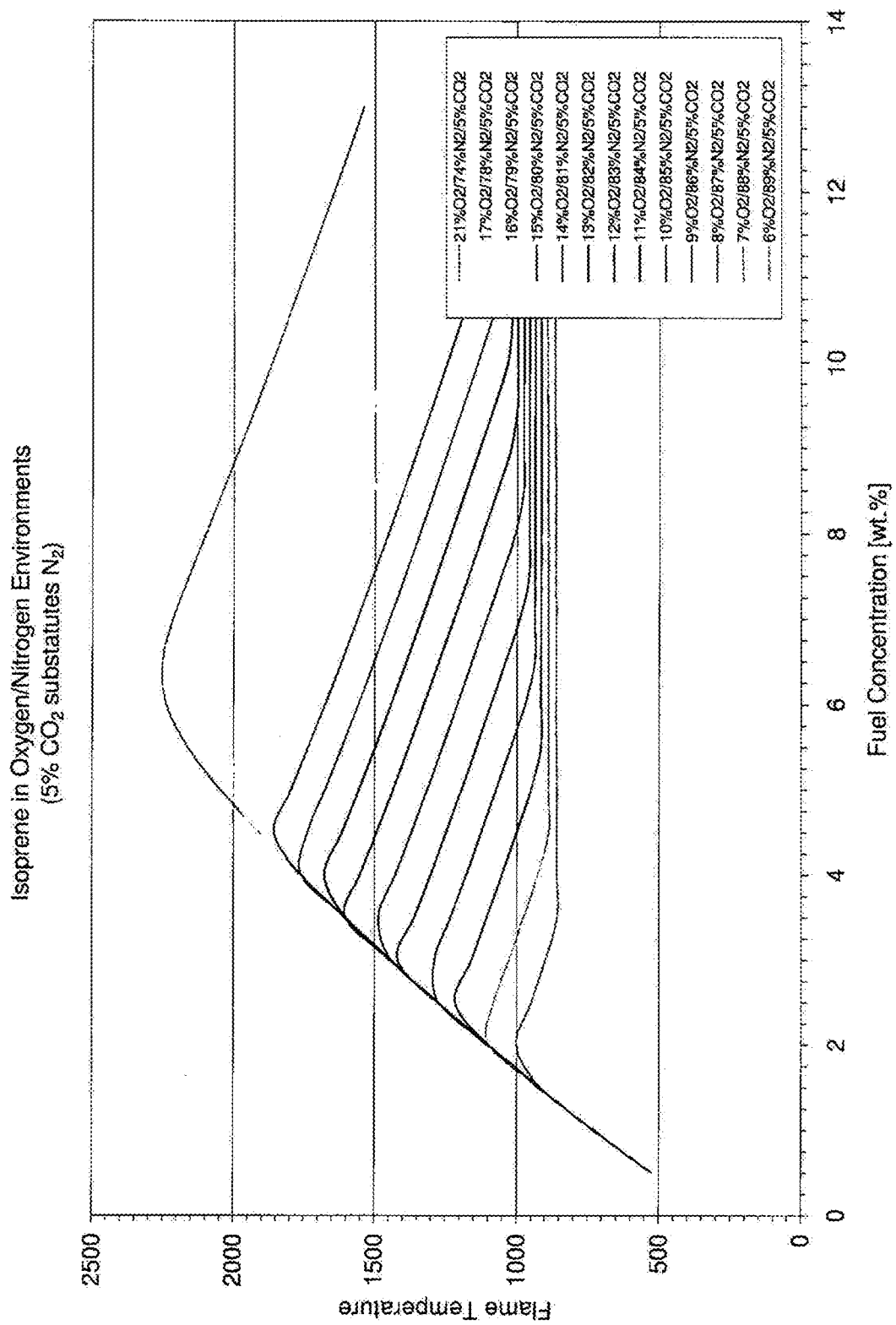
FIG. 70 is a graph of the calculated adiabatic flame temperatures for Series C as a function of fuel concentration for various oxygen levels with 5% $CO_2$. The figure legend lists the curves in the order in which they appear in the graph.
Figure 71:
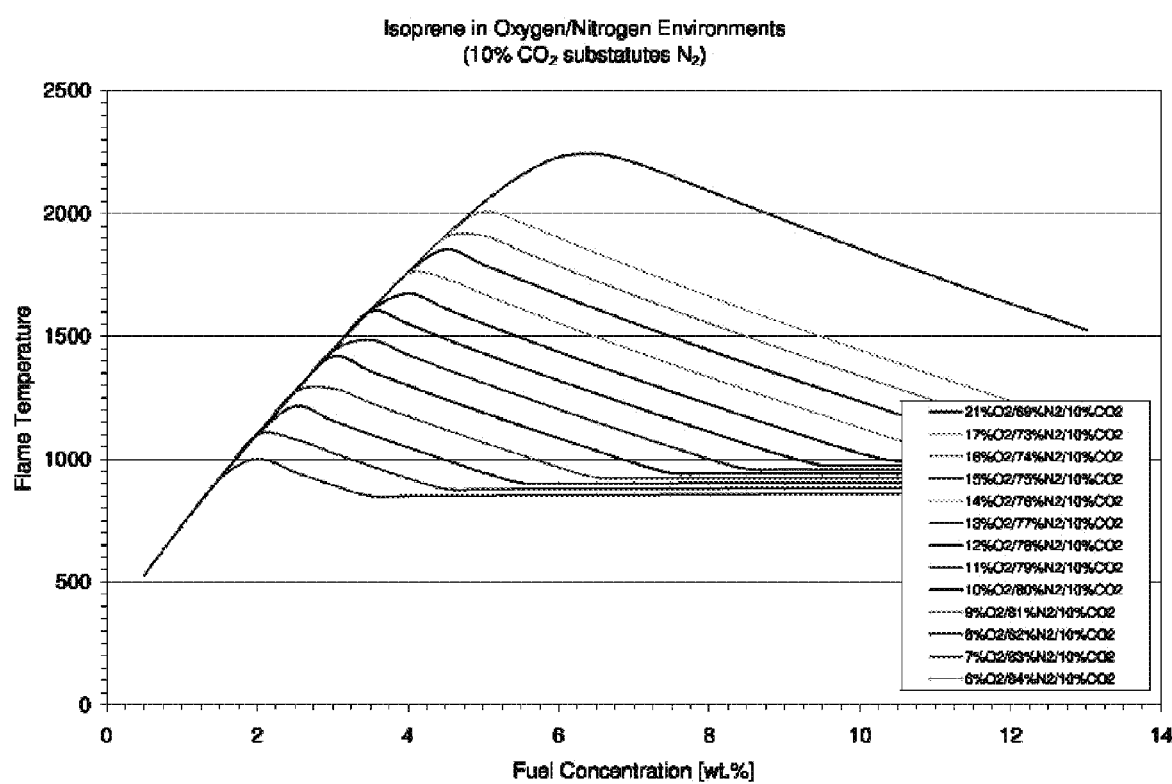
FIG. 71 is a graph of the calculated adiabatic flame temperatures for Series D as a function of fuel concentration for various oxygen levels with 10% $CO_2$. The figure legend lists the curves in the order in which they appear in the graph.
Figure 72:
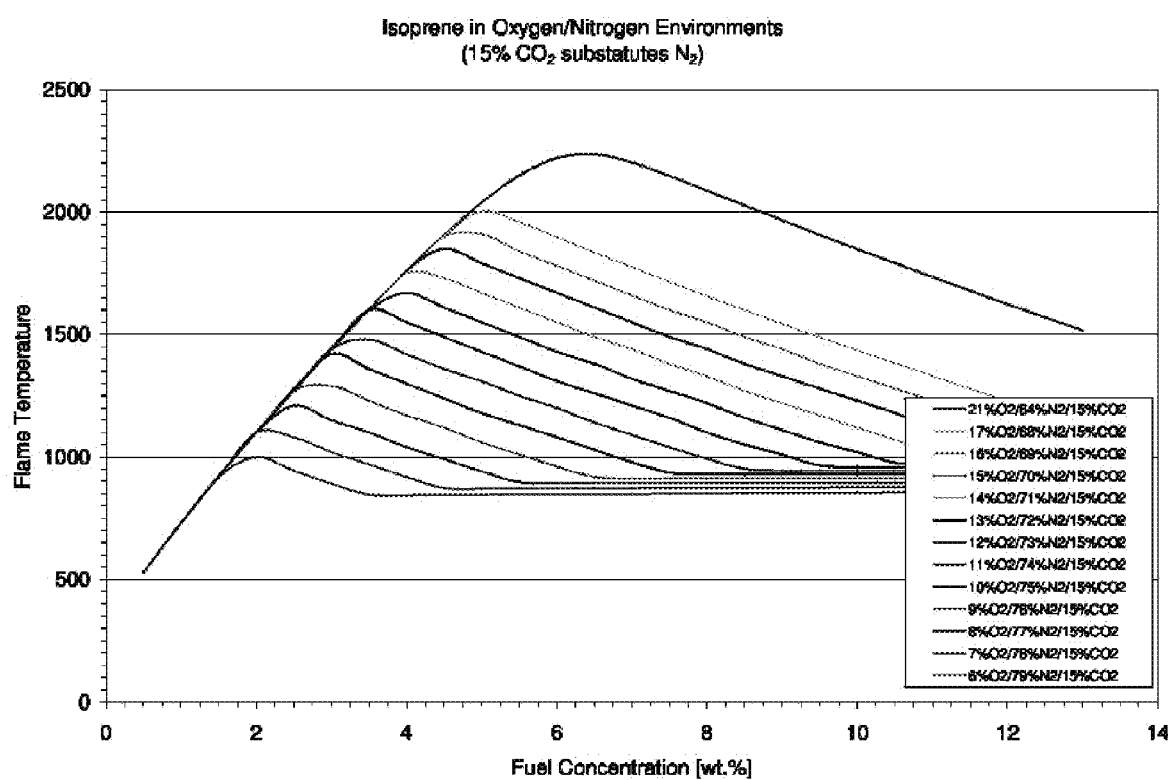
FIG. 72 is a graph of the calculated adiabatic flame temperatures for Series E as a function of fuel concentration for various oxygen levels with 15% $CO_2$. The figure legend lists the curves in the order in which they appear in the graph.
Figure 73:
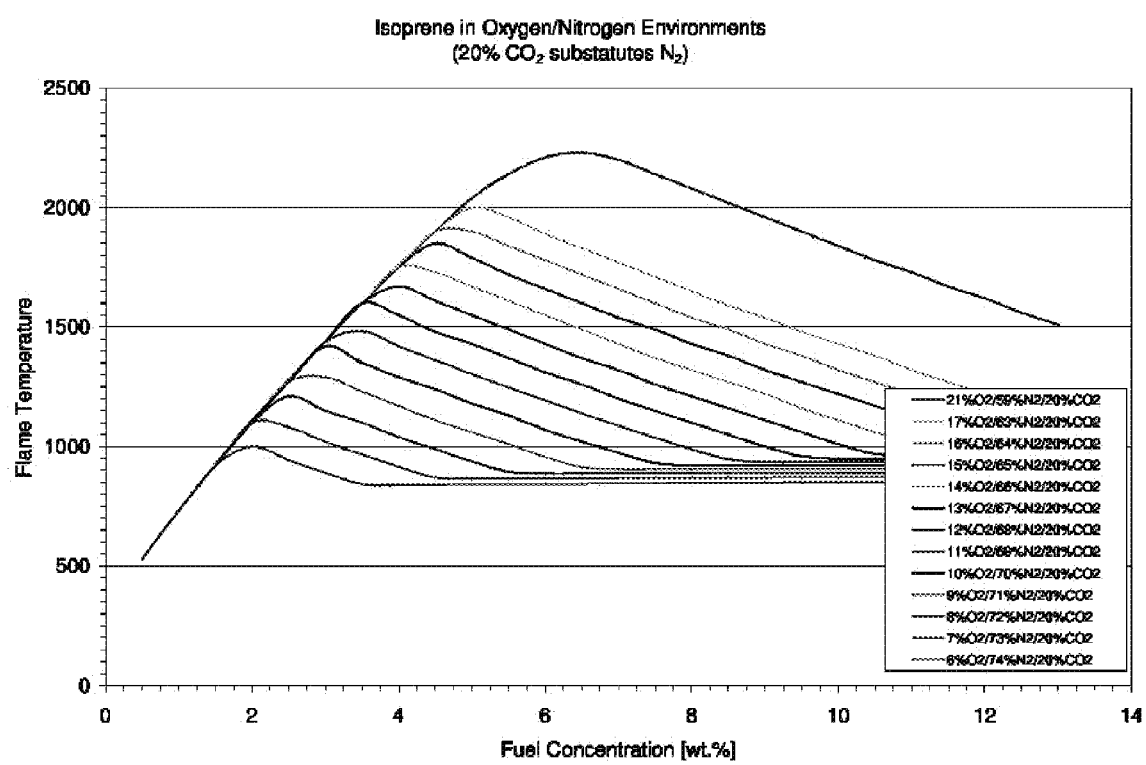
FIG. 73 is a graph of the calculated adiabatic flame temperatures for Series F as a function of fuel concentration for various oxygen levels with 20% $CO_2$. The figure legend lists the curves in the order in which they appear in the graph.
Figure 74:
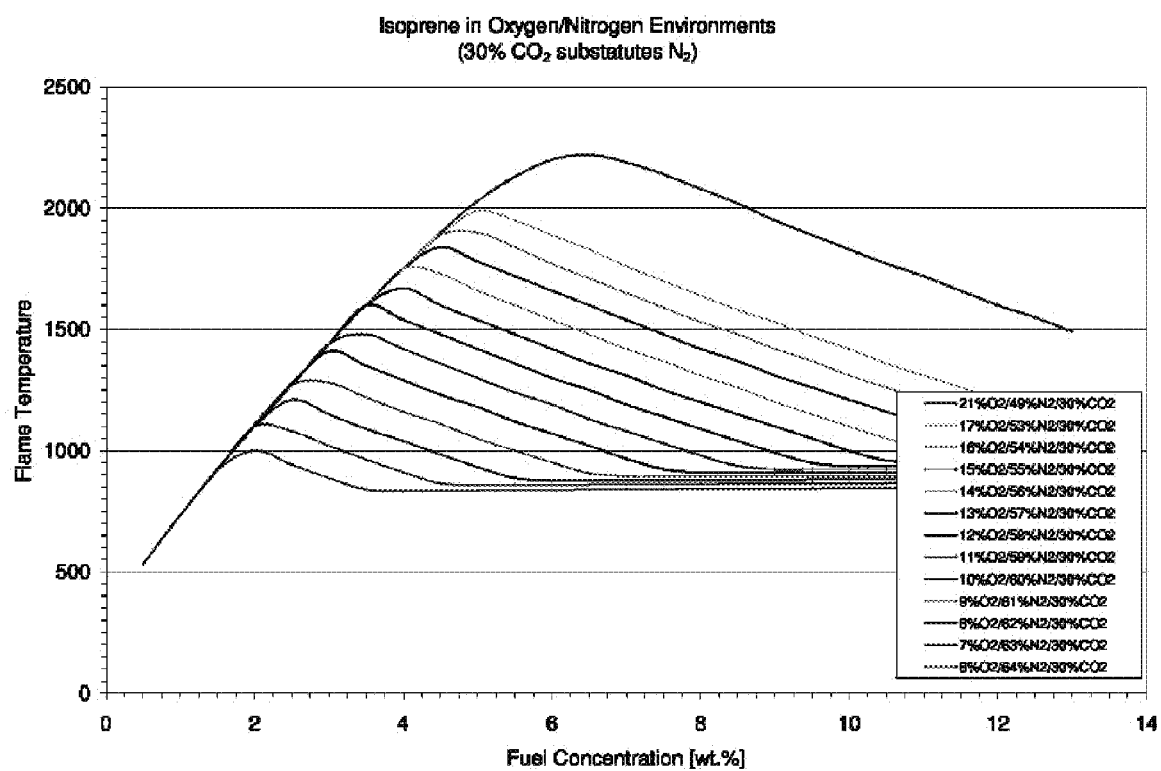
FIG. 74 is a graph of the calculated adiabatic flame temperatures for Series G as a function of fuel concentration for various oxygen levels with 30% $CO_2$. The figure legend lists the curves in the order in which they appear in the graph.

Using Series A as an example the data in FIG. 68 can be plotted in the form of a traditional flammability envelope. Using FIG. 68 and reading across the 1500 K temperature line on the ordinate one can determine the fuel concentration for this limit flame temperature by dropping a tangent to the abscissa for each curve (oxygen to nitrogen ratio) that it intersects. These values can then be tabulated as weight percent of fuel for a given weight percent of oxidizer (FIG. 75A). Then knowing the composition of the fuel (100 wt. % isoprene) and the composition of the oxidizer (relative content of water, oxygen and nitrogen) molar quantities can be established.

Figure 75B:
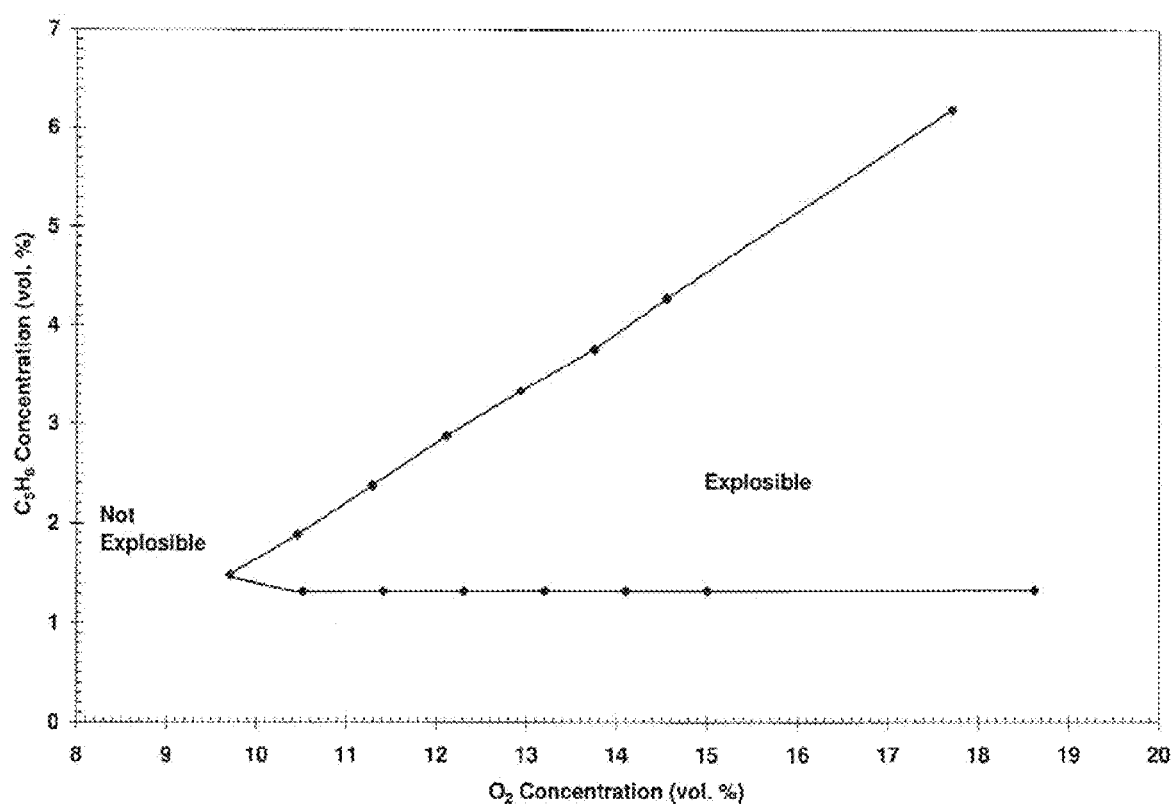
FIG. 75B is a graph of the flammability results from the CAFT model for Series A in FIG. 68 plotted as volume percent.
Figure 76B:
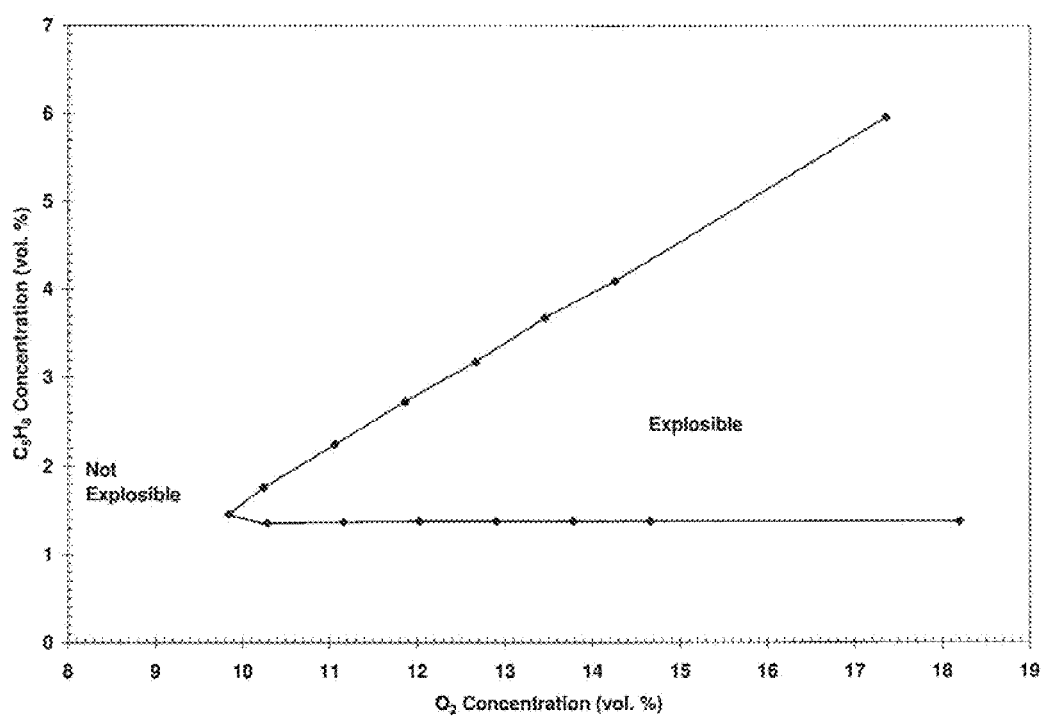
FIG. 76B is a graph of the flammability results from the CAFT model for Series B in FIG. 69 plotted as volume percent.

From these molar quantities percentage volume concentrations can be calculated. The concentrations in terms of volume percent can then be plotted to generate a flammability envelope (FIG. 75B). The area bounded by the envelope is the explosible range and the area excluded is the non-explosible range. The "nose" of the envelope is the limiting oxygen concentration. FIGS. 76A and 76B contain the calculated volume concentrations for the flammability envelope for Series B generated from data presented in FIG. 69. A similar approach can be used on data presented in FIGS. 70-74.

IV. Flammability Testing Experimental Equipment and Procedure

Figure 77:
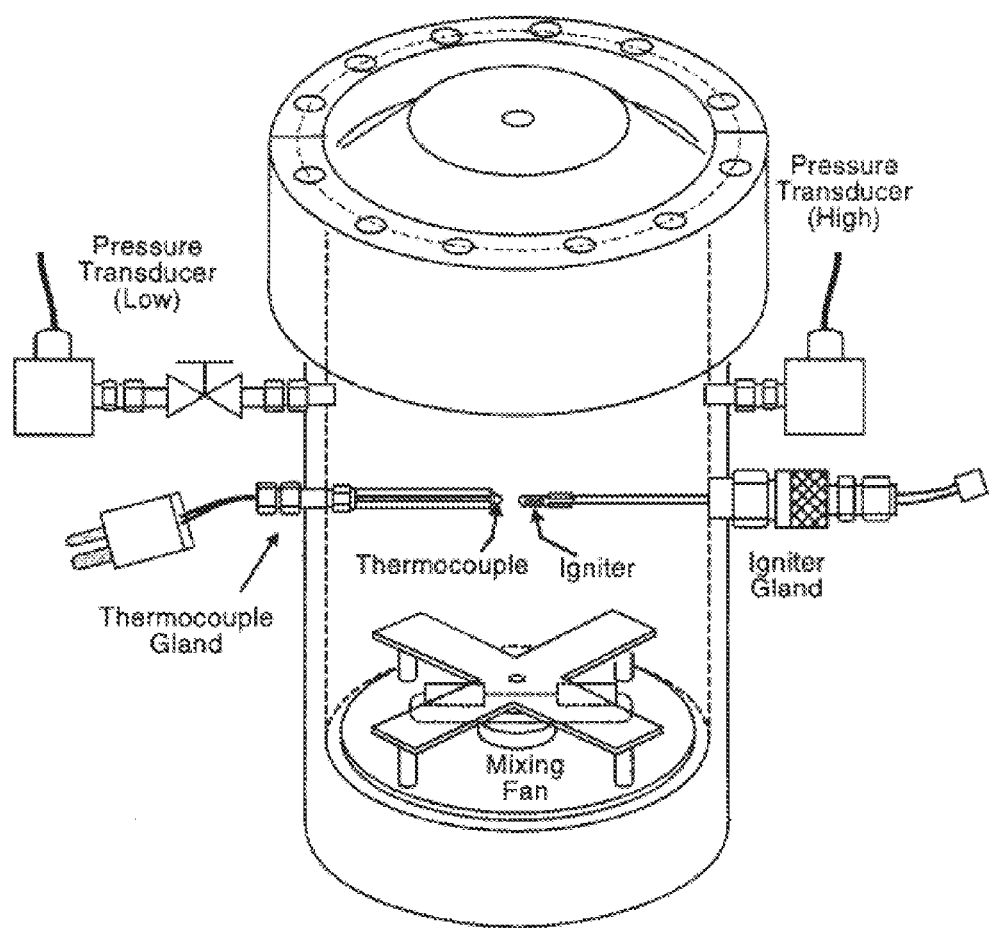
FIG. 77 is a figure of the flammability test vessel.

Flammability testing is conducted in a 4 liter high pressure vessel. The vessel is cylindrical in shape with an inner diameter of 6" and an internal height of 8.625". The temperature of the vessel (and the gases inside) is maintained using external heaters that are controlled by a PID controller. To prevent heat losses, ceramic wool and reflective insulation are wrapped around the pressure vessel. Type K thermocouples are used the measure the temperature of the gas space as well as the temperature of the vessel itself. FIG. 77 illustrates the test vessel.

Before a test is ran, the vessel is evacuated and purged with nitrogen to ensure that any gases from previous tests are removed. A vacuum is then pulled on the vessel. The pressure after this had been done is typically around 0.06 bar(a). Due to the nitrogen purging, the gas responsible for this initial pressure is assumed to be nitrogen. Using partial pressures, water, isoprene, nitrogen, and oxygen are then added in the appropriate amounts to achieve the test conditions in question. A magnetically driven mixing fan within the vessel ensures mixing of the gaseous contents. The gases are allowed to mix for about 2 minutes with the fan being turned off approximately 1 minute prior to ignition.

The igniter is comprised of a 1.5 ohm nicrome coil and an AC voltage source on a timer circuit. Using an oscilloscope, it is determined that 34.4 VAC are delivered to the igniter for 3.2 seconds. A maximum current of 3.8 amps occurs approximately halfway into the ignition cycle. Thus, the maximum power is 131 W and the total energy provided over the ignition cycle is approximately 210 J.

Deflagration data is acquired using a variable reluctance Validyne DP215 pressure transducer connected to a data acquisition system. A gas mixture is considered to have deflagrated if the pressure rise was greater than or equal to 5%.

V. Results of Flammability Testing

The first experimental series (Series 1) is run at 40° C. and 0 psig with no steam. Running tests at varying concentrations of isoprene and oxygen produces the flammability curve shown in FIG. 78A. The data points shown in this curve are only those that border the curve. A detailed list of all the data points taken for this series is shown in FIGS. 80A and 80B.

FIG. 78B summarizes the explosibility data points shown in FIG. 78A. FIG. 78C is a comparison of the experimental data with the CAFT model predicted flammability envelope. The model agrees very well with the experimental data. Discrepancies may be due to the non-adiabatic nature of the test chamber and limitations of the model. The model looks at an infinite time horizon for the oxidation reaction and does not take into consideration any reaction kinetic limitation.

Additionally, the model is limited by the number of equilibrium chemical species that are in its database and thus may not properly predict pyrolytic species. Also, the flammability envelope developed by the model uses one value for a limit flame temperature (1500K). The limit flame temperature can be a range of values from 1,000K to 1,500K depending on the reacting chemical species. The complex nature of pyrolytic chemical species formed at fuel concentrations above the stoichiometric fuel/oxidizer level is one reason why the model may not accurately predict the upper flammable limit for this system.

The second experimental series (Series 2) is run at 40° C. and 0 psig with a fixed steam concentration of 4%. Running tests at varying concentrations of isoprene and oxygen produces the flammability curve shown in FIG. 79A. The data points shown in this curve are only those that border the curve. A detailed list of all the data points taken for this series is shown in FIG. 81. Due to the similarity between the data in Series 1 only the key points of lower flammable limit, limiting oxygen concentration, and upper flammable limits are tested. The addition of 4% steam to the test mixture does not significantly change the key limits of the flammability envelope. It should be noted that higher concentrations of steam/water and or other inertants may influence the flammability envelope.

Figure 79C:
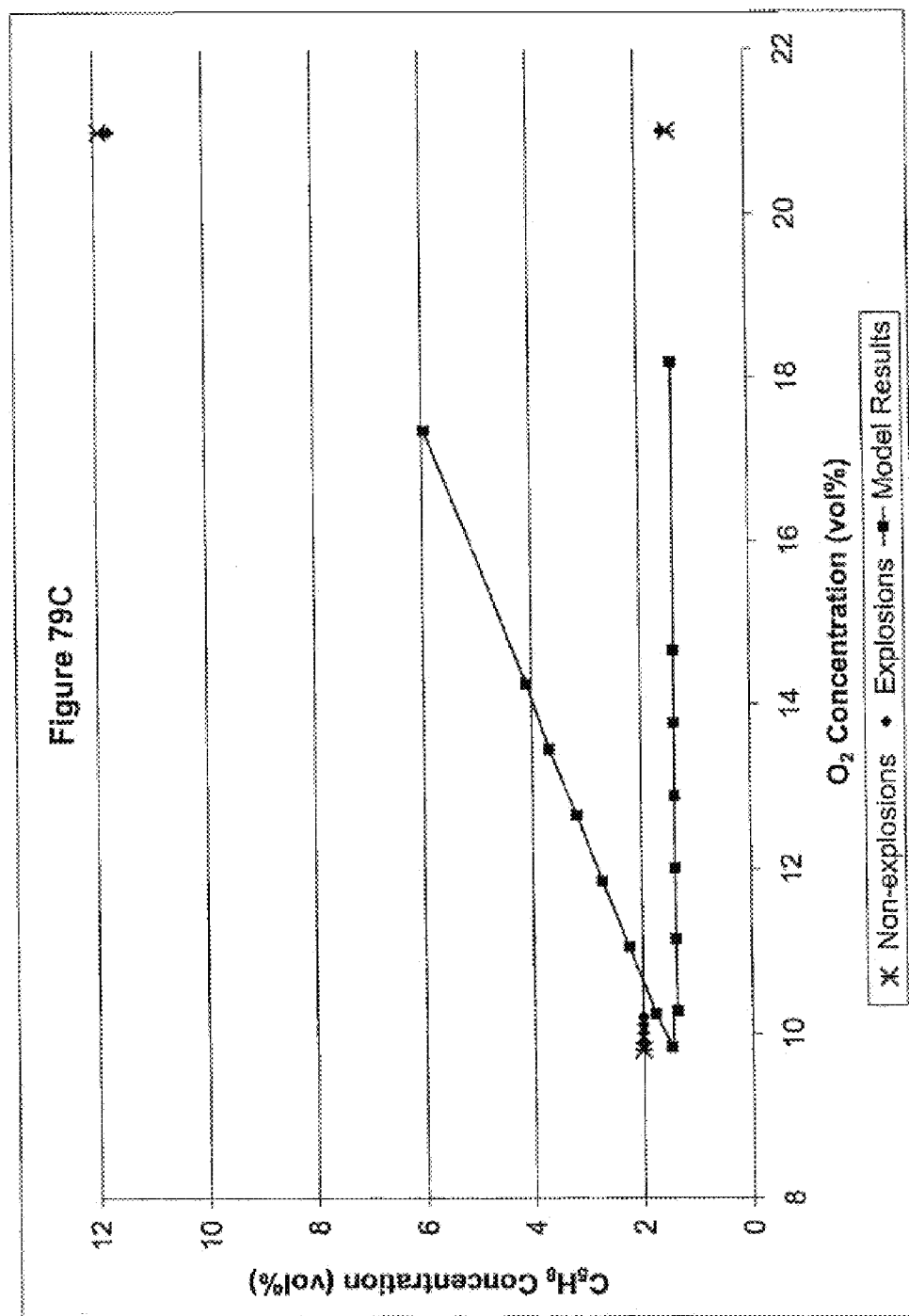
FIG. 79C is a graph of the flammability curve for Test Series 2 compared with the CAFT Model.

FIG. 79B summarizes the explosibility data points shown in FIG. 79A. FIG. 79C is a comparison of the experimental data with the CAFT model predicted flammability envelope. The model agrees very well with the experimental data. Discrepancies may be due to the same factors described in Series 1

V. Calculation of Flammability Limits of Isoprene in Air at 3 Atmospheres of Pressure The methods described in Example 12, parts I to IV are also used to calculate the flammability limits of isoprene at an absolute system pressure of 3 atmospheres and 40° C. These results are compared to those of Example 12, parts I to IV at an absolute system pressure of 1 atmosphere and 40° C. This higher pressure is tested because the flammability envelope expands or grows larger as the initial system pressure is increased. The upper flammability limit is affected the most, followed by the limiting oxygen composition. The lower flammability limit is the least affected (see, for example, "Bulletin 627—Flammability Characteristics of Combustible Gases and Vapors" written by Michael G. Zabetakis and published by the former US Bureau of Mines (1965), which is hereby incorporated by reference in its entirety, in particular with respect to the calculation of flammability limits).

Figure 82:
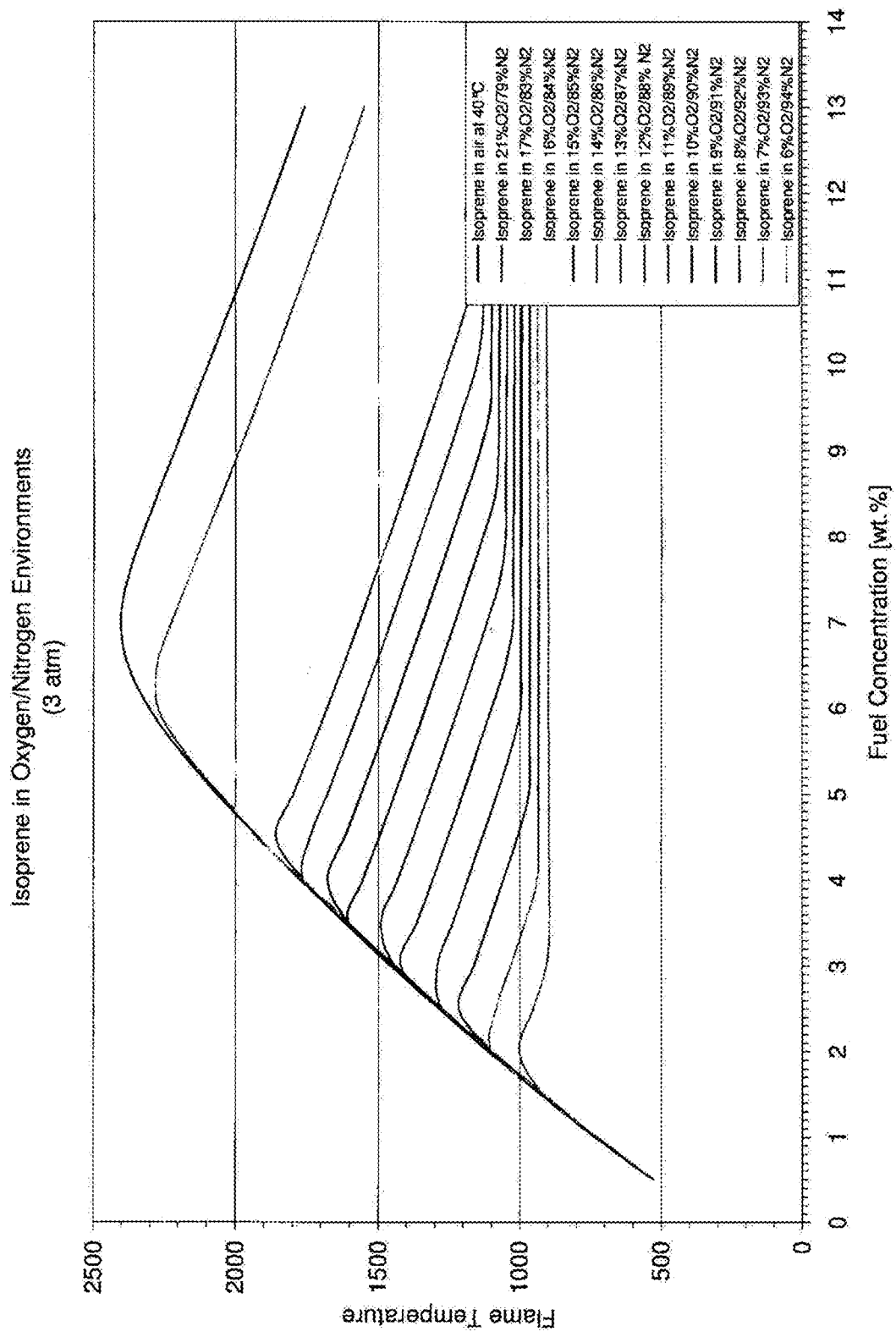
FIG. 82 is a graph of the calculated adiabatic flame temperature plotted as a function of fuel concentration for various nitrogen/oxygen ratios at 3 atmospheres of pressure.
Figure 83:
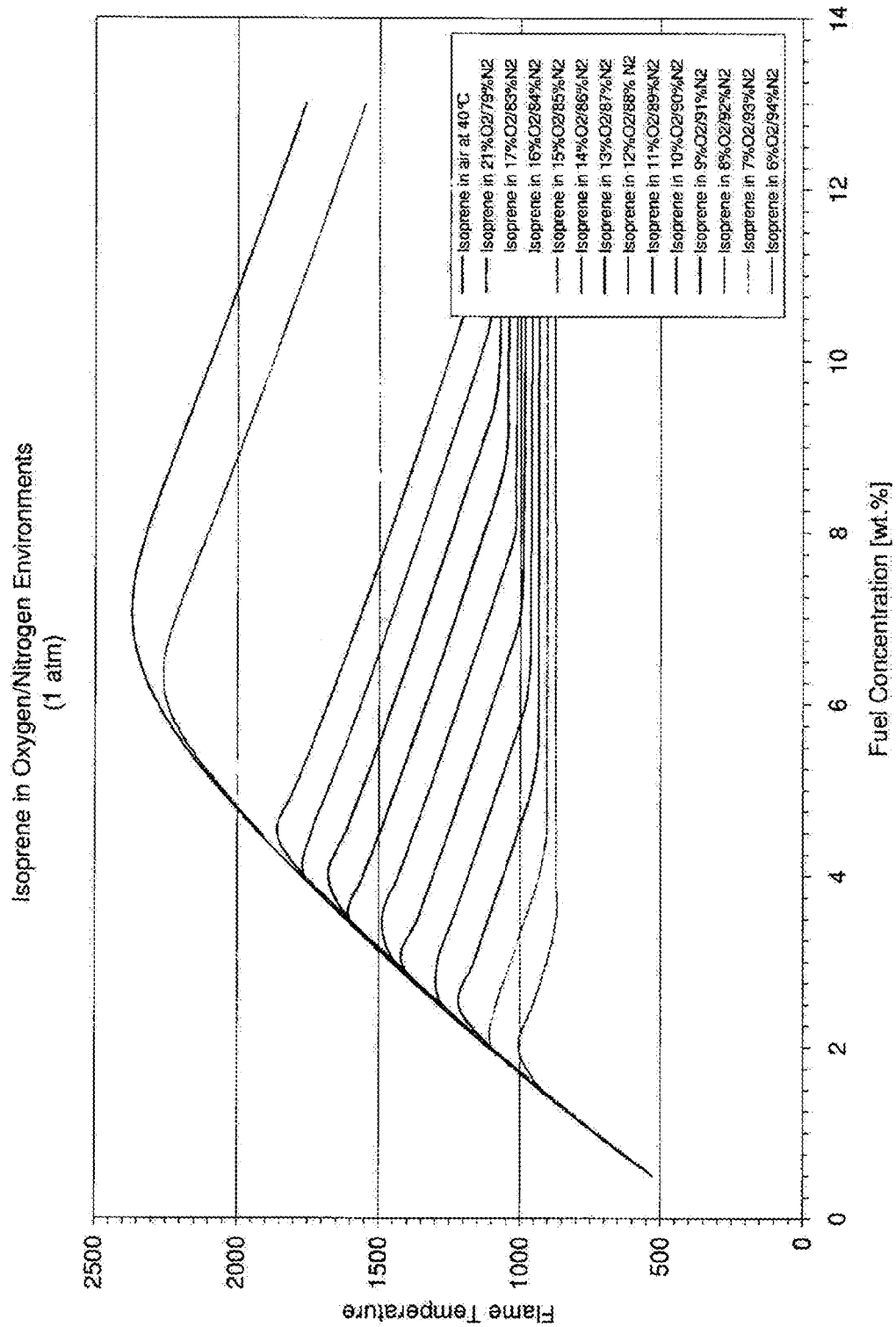
FIG. 83 is a graph of the calculated adiabatic flame temperature plotted as a function of fuel concentration for various nitrogen/oxygen ratios at 1 atmosphere of pressure.
Figure 84:
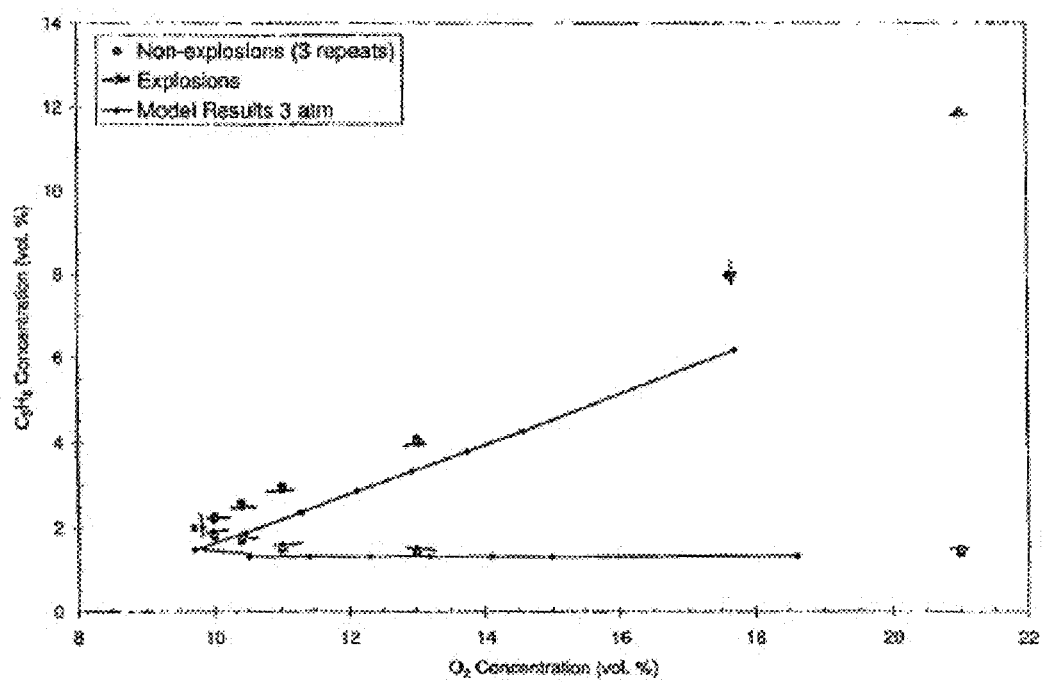
FIG. 84 is a graph of the flammability envelope constructed using data from FIG. 82 and following the methodology described in Example 12. The experimental data points (circles) are from tests described herein that were conducted at 1 atmosphere initial system pressure.
Figure 85:
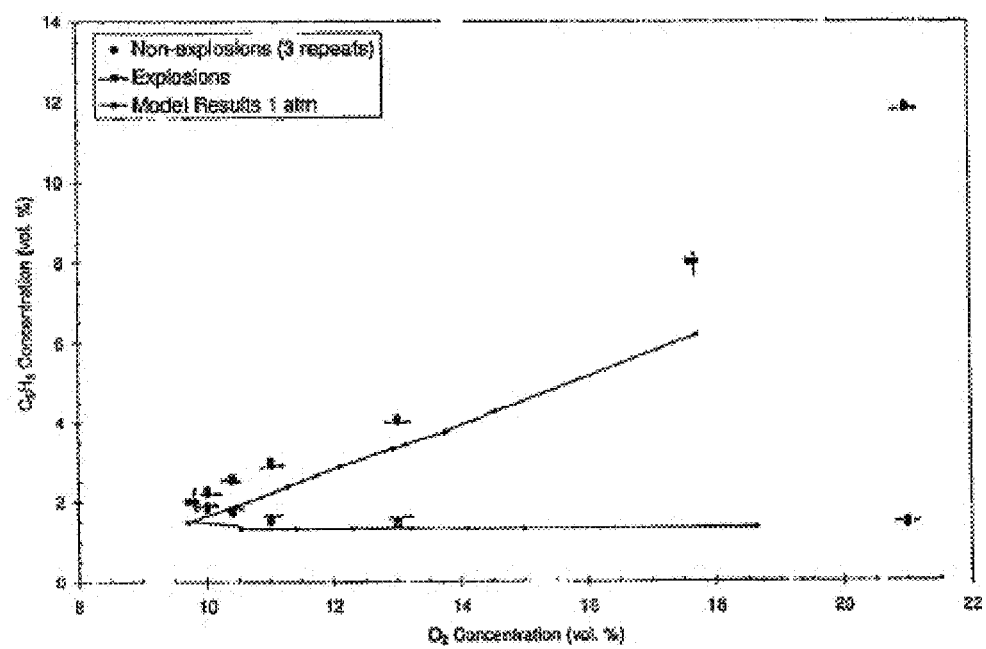
FIG. 85 is a graph of the flammability envelope constructed using data from FIG. 83 and following the methodology described in Example 12. The experimental data points (circles) are from tests described herein that were conducted at 1 atmosphere initial system pressure.

In FIG. 82, the calculated adiabatic flame temperature is plotted as a function of isoprene (fuel) concentration, expressed in weight percent of the total fuel/nitrogen/oxygen, where the system pressure was initially 3 atmospheres. The calculated flame temperatures are very similar to those determined initially in the 1 atmosphere system (FIG. 83). As a result, when flammability envelopes are generated using the calculated adiabatic flammability data, the curves are very similar (see FIGS. 84 and 85). Therefore, based on these theoretical calculations, a system pressure increase from 1 atmosphere to 3 atmosphere does not result in a significant increase/broadening of the flammability envelope. If desired, these model results may be validated using experimental testing (such as the experimental testing described herein at a pressure of 1 atmosphere).

VII. Summary of Flammability Studies

A calculated adiabatic temperature model is developed for the flammability envelope of the isoprene/oxygen/nitrogen/water/carbon dioxide system at 40° C. and 0 psig. The CAFT model that is developed agrees well with the experimental data generated by the tests conducted in this work. The experimental results from Series 1 and 2 validate the model results from Series A and B.

Example 14

Archaeal Mevalonate Kinase Expression Constructs and Recombinant Bacterial Host Strains I. Construction of Plasmids Encoding Mevalonate Kinase.

A construct encoding the *Methanosarcina mazei* lower MVA pathway (Accession numbers NC_003901.1, NC_003901.1, NC_003901.1, and NC_003901.1, which are each hereby incorporated by reference in their entireties)

is synthesized with codon optimization for expression in *E. coli*. This construct is named *M. mazei* archaeal Lower Pathway operon (FIGS. 112A-112C) and encodes *M. mazei* MVK, decarboxylase, IPK, and IDI enzymes. The gene encoding MVK (Accession number NC_003901.1) is PCR amplified using primers MCM165 and MCM177 (Table 14-1) using the Strategene Herculase II Fusion kit according to the manufacturer's protocol using 30 cycles with an annealing temperature of 55° C. and extension time of 60 seconds. This amplicon is purified using a Qiagen PCR column and then digested at 37° C. in a 10 µL reaction with PmeI (in the presence of NEB buffer 4 and BSA). After one hour, NsiI and Roche buffer H are added for an additional hour at 37° C. The digested DNA is purified over a Qiagen PCR column and ligated to a similarly digested and purified plasmid MCM29 (MCM29 is also called pTrcKudzuKan) in an 11 uL reaction 5 uL Roche Quick Ligase buffer 1, 1 uL buffer 2, 1 uL plasmid, 3 uL amplicon, and 1 uL ligase (1 hour at room temperature). The ligation reaction is introduced into Invitrogen TOP10 cells and transformants selected on LA/kan50 plates incubated at 37° C. overnight. The MVK insert in the resulting plasmid MCM382 is sequenced (FIGS. 113A-113C).

TABLE 14-1

Oligonucleotides

| Primer (Description) | Sequence |
|---|---|
| MCM161 (*M. mazei* MVK for) | CACCATGGTATCCTGTTCTGCG (SEQ ID NO: 105) |
| MCM162 (*M. mazei* MVK rev) | TTAATCTACTTTCAGACCTTGC (SEQ ID NO: 106) |
| MCM 165 (*M. mazei* MVK for w/ RBS) | gcgaacgATGCATAaaggaggtaaaaaaacATGGTATCCTG TTCTGCGCCGGGTAAGATTTACCTG (SEQ ID NO: 107) |
| MCM177 (*M. mazei* MVK rev Pst) | gggcccgtttaaactttaactagactTTAATCTACTTTCAGAC CTTGC (SEQ ID NO: 108) |

II. Creation of Strains Overexpressing Mevalonate Kinase and Isoprene Synthase.

Plasmid MCM382 is transformed into MCM331 cells (which contain chromosomal construct gi1.2KKDyI encoding *S. cerevisiae* mevalonate kinase, mevalonate phosphate kinase, mevalonate pyrophosphate decarboxylase, and IPP isomerase) that had been grown to midlog in LB medium and washed three times in iced, sterile water. 1 µL of DNA is added to 50 µL of cell suspension, and this mixture is electroporated in a 2 mm cuvette at 2.5 volts, 25 uFd followed immediately by recovery in 500 µL LB medium for one hour at 37° C. Transformant was selected on LA/kan50 and named MCM391. Plasmid MCM82 is introduced into this strain by the same electroporation protocol followed by selection on LA/kan50/spec50. The resulting strain MCM401 contains a cmp-marked chromosomal construct gi1.2KKDyI, kan-marked plasmid MCM382, and spec-marked plasmid MCM82 (which is pCL PtrcUpperPathway encoding *E. faecalis* mvaE and mvaS).

TABLE 14-2

Strains Overexpressing Mevalonate Kinase and Isoprene Synthase

| Strain | Genotype |
|---|---|
| MCM382 | *E. coli* BL21 (lambdaDE3) pTrcKudzuMVK(*M. mazei*)GI1.2KKDyI |
| MCM391 | MCM331 pTrcKudzuMVK(*M. mazei*) |
| MCM401 | MCM331pTrcKudzuMVK(*M. mazei*)pCLPtrcUpperpathway |
| MCM396 | MCM333pTrcKudzuMVK(*M. mazei*) |
| MCM406 | MCM333pTrcKudzuMVK(*M. mazei*)pCLPtrcUpperpathway |

III. Construction of Plasmid MCM376—MVK from *M. mazei* Archeal Lower in pET200D.

The MVK ORF from the *M. mazei* archeal Lower Pathway operon (FIGS. 112A-112C) is PCR amplified using primers MCM161 and MCM162 (Table 14-1) using the Invitrogen Platinum HiFi PCR mix. 45 uL of PCR mix is combined with 1 uL template, 1 uL of each primer at 10 uM, and 2 uL water. The reaction was cycled as follows: 94° C. for 2:00; 30 cycles of 94° C. for 0:30, 55° C. for 0:30; and 68° C. for 1:15; and then 72° C. for 7:00, and 4° C. until cool. 3 uL of this PCR reaction is ligated to Invitrogen pET200D plasmid according to the manufacturer's protocol. 3 uL of this ligation is introduced into Invitrogen TOP10 cells, and transformants are selected on LA/kan50. A plasmid from a transformant is isolated and the insert sequenced, resulting in MCM376 (FIGS. 114A-114C).

V. Creation of Expression Strain MCM378.

Plasmid MCM376 is transformed into Invitrogen BL21 (DE3) pLysS cells according to the manufacturer's protocol. Transformant MCM378 is selected on LA/kan50.

Example 15

Production of Isoprene by *E. coli* expressing the Upper and Integrated Lower MVA Pathway, Mevalonate Kinase from *M. mazei*, and Isoprene Synthase from Kudzu Medium Recipe (per liter fermentation medium): Each liter of fermentation medium contains $K_2HPO_4$ 7.5 g, $MgSO_4 \cdot 7H_2O$ 2 g, citric acid monohydrate 2 g, ferric ammonium citrate 0.3 g, yeast extract 0.5 g, and 1000× Modified Trace Metal Solution 1 ml. All of the components are added together and dissolved in $diH_2O$. This solution is autoclaved. The pH is adjusted to 7.0 with ammonium hydroxide (30%) and q.s. to volume. Glucose 10 g, thiamine.HCl 0.1 g, and antibiotics were added after sterilization and pH adjustment.

1000× Modified Trace Metal Solution: 1000× Modified Trace Metal Solution contains citric acid.$H_2O$ 40 g, $MnSO_4 \cdot H_2O$ 30 g, NaCl 10 g, $FeSO_4 \cdot 7H_2O$ 1 g, $CoCl_2 \cdot 6H_2O$ 1 g, ZnSO$_4$.7H$_2$O 1 g, CuSO$_4$.5H$_2$O 100 mg, H$_3$BO$_3$ 100 mg, and NaMoO$_4$.2H$_2$O 100 mg. Each component is dissolved one at a time in DI H$_2$O, pH to 3.0 with HCl/NaOH, then q.s. to volume and filter sterilized with a 0.22 micron filter.

Fermentation is performed in a 15-L bioreactor with BL21 (DE3) *E. coli* cells containing the upper mevalonic acid (MVA) pathway (pCL PtrcUpperPathway encoding *E. faecalis* mvaE and mvaS), the integrated lower MVA pathway (gi1.2KKDyI encoding *S. cerevisiae* mevalonate kinase, mevalonate phosphate kinase, mevalonate pyrophosphate decarboxylase, and IPP isomerase), and high expression of mevalonate kinase from *M. mazei* and isoprene synthase from Kudzu (pTrcKudzuMVK(*M. mazei*)). This experiment is carried out to monitor isoprene formation from glucose at the desired fermentation pH 7.0 and temperature 30° C. An inoculum of *E. coli* strain taken from a frozen vial is streaked onto an LB broth agar plate (with antibiotics) and incubated at 37° C. A single colony is inoculated into tryptone-yeast extract medium. After the inoculum grows to OD 1.0, measured at 550 nm, 500 mL is used to innoculate 5-L of cell medium in the 15-L bioreactor. The liquid volume increases throughout the fermentation (such as to approximately 10 liters).

Glucose is fed at an exponential rate until cells reach the stationary phase. After this time the glucose feed is decreased to meet metabolic demands. The total amount of glucose delivered to the bioreactor during the 55 hour fermentation is 2.2 kg. Induction is achieved by adding IPTG. The IPTG concentration is brought to 51 uM when the optical density at 550 nm (OD$_{550}$) reaches a value of 10. In addition to the IPTG spike, at OD$_{550}$=10 a constant feed begins and delivers 164 mg of IPTG over 18 hours. The OD$_{550}$ profile within the bioreactor over time is shown in FIG. 115A. The isoprene level in the off gas from the bioreactor is determined using a Hiden mass spectrometer. The isoprene titer increases over the course of the fermentation to a final value of 22.0 g/L as shown in FIG. 115B. The total amount of isoprene produced during the 55 hour fermentation is 170.5 g and the time course of production is shown in FIG. 115C. The molar yield of utilized carbon that goes into producing isoprene during fermentation is 16.6%. The weight percent yield of isoprene from glucose over the entire fermentation is 7.7%.

Example 16

Recovery of Prenyl Alcohols from Fermentation Off-Gas

This example provides several suitable methods for recovery of prenyl alcohols for subsequent conversion to isoprene by chemical or biological catalysis. In addition to the gas-stripping, two-phase, and pervaporation recovery methods described below, the prenyl alcohols can be recovered by distillation as known in the art for commercial recovery of ethanol and butanol.

I. Prenyl Alcohol Recovery via Gas Stripping

A fermentation reaction is carried out in a reactor. When the prenyl alcohol concentration reaches the desired level, gas stripping is applied by introducing a stripping gas into the reactor. After passing through the reaction medium, the stripping gas enriched in prenyl alcohols is passed through a condenser where prenyl alcohol vapors are collected. The stripping gases are recycled through the system using a pump. Distilled water is added into the reactor at intervals to compensate for water loss due to gas-stripping and to maintain a constant liquid level inside the reactor. Continuous operation is maintained at optimum flow rates to give the desired level of prenyl alcohol removal.

Alternatively, the prenyl alcohols are recovered as the carboxylic acid ester derivatives, for example as prenyl acetate and isoprenyl acetate. Such ester derivatives are formed biologically, as detailed above in Example 10 (See, e.g., Table 10-2), by the action of an acyltransferase and an acyl donor on the prenyl alcohols). Both prenyl acetate and isoprenyl acetate are collected from the fermentation off-gas by gas stripping.

II. Prenyl Alcohol Recovery via Two-Phase Recovery

A fermentation reaction is carried out in a two-phase partitioning bioreactor. An organic solvent is added to 20% (v/v) of the media volume. Suitable organic solvents are high boiling solvents with low water solubility and low toxicity including but not limited to dodecane, paraffin oil, silicone oils and fluorocarbons. Alternatively, a triglyceride is used to serve a dual purpose as a both a carbon source and a second organic phase. After the prenyl alcohol concentration reaches the desired level in the organic phase, the organic and aqueous layers are separated, and the prenyl alcohols are isolated by evaporation of the organic solvent.

III. Prenyl Alcohol Recovery via Pervaporation

A fermentation reaction is carried out in a reactor. The liquid stream from the fermentation reactor is first passed through a heating module. The heated liquid is then passed into the pervaporation module equipped with a commercial polydimethylsiloxane membrane. A vacuum is applied to the other side of the membrane. The prenyl alcohols permeate through the membrane and evaporate into the vapor phase on the other side of the membrane. The prenyl alcohol enriched vapor phase is passed through a condenser to collect the liquid prenyl alcohols.

Example 17

Chemical Conversion of Biologically-Produced Isoprenol to Isoprene

This example describes the production of isoprene from prenyl alcohols recovered from recombinant host cells. Briefly as described above in Example 10, 3-methyl-3-buten-1-ol (CAS Registry No. 763-32-6, isoprenol) and 3-methyl-2-buten-1-ol (CAS Registry No. 556-82-1, prenol) are produced by recombinant *E. coli* engineered to express enzymes of the full mevalonate pathway (MVAE and MVAS from *E. faecalis*; and MVK, PMK, and MVD from *S. cerevisia*), an isoprenyl pyrophosphate isomerase (IDI from *S. cerevisia*) and an isoprene synthase (IS from *P. montana*). In particular, a significant amount of isoprenol is found in the trace volatile fraction of the bacterial fermentation off-gas following cryo-trapping at −78° C. (See, Table 10-2). However, the compositions and methods of the present invention for chemical conversion of prenyl alcohol to isoprene are not limited to the use of this particular cell line. Other suitable compositions and methods for producing isoprene and for producing prenyl alcohols are provided by U.S. Application No. 61/134,094, filed Jul. 2, 2008 herein incorporated by reference in its entirety.

In alternative embodiments, isoprenol and/or prenol are produced by recombinant *E. coli* containing plasmids encoding the lower mevalonate pathway (MK, PMK, and MVD from *S. cerevisiae*), in the presence or absence of an isoprenyl pyrophosphate isomerase (IDI from *S. cerevisia*), and in the presence of either an ADP-ribose pyrophosphatase (nudF from *B. subtilis*) or another enzyme that utilizes IPP as a substrate (yhfR from *B. subtilis* having homology to a phosphoglycerase mutase). In particular, 3-methyl butenol is found in the organic phase of the liquid culture after extraction with ethyl acetate. However, the compositions and methods of the present invention for chemical conversion of prenyl alcohol to isoprene are not limited to the use of this particular cell line. Other suitable compositions and methods for producing isoprene and for producing prenyl alcohols are provided by U.S. Publication No. 2008/0092829 of Renninger et al., herein incorporated by reference in its entirety.

The C5 prenyl alcohols, are produced by recombinant bacterial cells engineered to express at least the lower portion of the mevalonate pathway, is recovered from the fermentation off-gas or from the liquid culture of a shake flask. In preferred embodiments the recombinant bacterials cells are further engineered to express a phosphatase for removal of the pyrophosphate group from IPP or DMAPP for subsequent conversion into isoprenol to prenol respectively. Suitable enzymes for catalyzing conversion of IPP or DMAPP into a C5 prenyl alcohol include but are not limited to an allyl diphosphatase, an ADP-sugar pyrophosphatase, an ADP-sugar phophorylase, a nucleoside triphosphate pyrophosphatase, a FAD pyrophosphatase, a monoterpenyl pyrophosphastase, an alkaline phosphatase, an acid phosphatase, and other phosphatases classified under enzyme commission classes 3.6.1, 3.1.7 or 3.1.3.

Production of isoprene from isoprenol is accomplished by dehydration of isoprenol in an acidic salt (e.g., HCl/NaCl) solution as known in the art (Weitz and Loser, "Isoprene," in *Ullmann's Encyclopedia of Industrial Chemistry*, 7$^{th}$ edition, electronic release, Wiley-VCH Verlag GMBH, Weinheim, pp. 1-20, 2005; and U.S. Pat. No. 3,792,104 to Mueller). Briefly, a 400 parts sodium chloride, 600 parts water and 40 parts of a 35% hydrochloric acid solution is placed in a reaction (e.g., dehydration) vessel equipped with a reflux condenser (operated at 45° C.), which is connected to a descending condenser (operated at -10° C.). The descending condenser causes condensation of the isoprene product and the isopentenols.

About 0.45 part/hr (dehydration rate of the system) of 3-methyl-3-buten-1-ol is metered to the stirred dehydration vessel, which is heated at 95° C. The hourly output is about 0.350 part of condensate, which consists of 0.33 part isoprene, 0.01 part dimethyvinyl carbinol and 0.01 part water. The aqueous phase is continuously recycled to the dehydration vessel, while the organic phase is neutralized with a concentrated aqueous sodium carbonate solution and the separated to pure isoprene and isopentenols in a continuous fractionating column. The aqueous phase is removed from the dehydrator at intervals of one hour to keep the liquid at its original level. Common salt and hydrochloric acid are replenished. At one hour intervals, the higher-boiling oligomers are removed from the dehydrator. Alternatively, prenol in the off-gas is continuously converted to isoprene by passing the off-gas over a suitable heterogenous catalyst.

Example 18

Biological Conversion of Dimethyl Allyl Alcohol to Isoprene by Recombinant Bacteria This example describes the conversion of dimethyl allyl alcohol to isoprene by recombinant *E. coli*.

The bacterial host cells used in this example are of the MCM343 strain, which is a production strain having a BL21 (DE3) background that expresses heterologous integrated lower and upper MVA pathway enzymes as well as kudzu isoprene synthase. The MCM343 strain is grown in TM3 containing spectinomycin (50 µg/ml) and kanamycin (50 µg/ml) at 37° C. with shaking at 200 rpm to an $OD_{600}$ of 0.6 and then induced with 400 µM IPTG. The cultures are allowed to grow for a further 5 hours at 30° C. An 800 µL aliquot is placed in a GC headspace vial and dimethyl allyl alcohol (DMAPP-OL) is added (12 mM). The vial is sealed and incubated at 30° C. for a further 14 hours. The isoprene is then measured using the Headspace assay.

Results are shown as compared to no alcohol (control) added and to DMAPP added to the culture (FIG. 116). Interestingly addition of DMAPP and DMAPP-OL increase the amount of isoprene obtained from the culture. The control cells produce 142 µg/L of isoprene compared to 202 µg/L produced by the cells to which DMAPP-OL was added. This demonstrates a 25% increase in isoprene in cultures supplemented with dimethyl allyl alcohol.

Example 19

Biological Conversion of Dimethyl Allyl Alcohol to Isoprene by Recombinant Yeast This example describes the conversion of dimethyl allyl alcohol to isoprene by recombinant *S. cerevisiae*.

I. Expression of isoprene synthase and production of isoprene in *S. cerevisiae*

The kudzu isoprene synthase enzyme is optimized for expression according to a hybrid *Saccharomyces cerevisia/Pichia pastoris* codon usage table, synthesized, and cloned into pDONR221:19430 bp DNA 2.0. A GATEWAY® Cloning (Invitrogen) reaction is performed according to the manufacturer's protocol. Since pDONR221:19430 is an "entry" vector, the LR Clonase II enzyme (the LR Reaction) is used to introduce the codon-optimized isoprene synthase into the "destination" vector pYES-DEST52 (Invitrogen). The LR Reaction is then transformed into Top10 chemically competent cells (Invitrogen) according to the manufacturer's protocol, and bacteria harboring pYES-DEST52 plasmids with the isoprene synthase ORF are selected for on LA plates containing 50 µg/ml carbenicillin. Individual positive transformants are tested by colony PCR using illustra PuReTaq READY-TO-GOT™ PCR Beads (GE Healthcare) with the T7 forward primer and the YeastHGS-Rev2 primer at a concentration of 0.4 µM each in 25 µl total volume/reaction. For analysis of plasmids resulting from the LR Clonase reaction (Invitrogen), a small amount of bacteria from individual colonies on a selective plate is added to each tube containing the PCR mix. PCR cycling parameters were as follows: 1) 95° C.-4 min; 2) 95° C.-20 sec; 3) 52° C.-20 sec; 4) 72° C.-30 sec; 5 cycles of steps 2 through 4; 5) 95° C.-20 sec; 6) 55° C.-20 sec; 7) 72° C.-30 sec; 25 cycles of steps 5 through 7; 72° C.-10 min; and 4° C.—end. Plasmids that yield a PCR fragment of the correct size (1354 bp) are purified by miniprep (Qiagen) and sent for sequencing (Quintara Biosciences, Berkeley, Calif.) with the T7 Forward and YeastHGS-For2 primers. The primers used are as follows: YeastHGS-For2: 5'-CACCAAA-GAC TTCATAGACT-3' (SEQ ID NO:109); YeastHGSRev2: 5'-AGAGATATCT TCCTGCTGCT-3' (SEQ ID NO:110); and T7 forward, 5'-TAATACGACT CACTATAGGG-3' (SEQ ID NO:111). Results from sequencing runs are compared to the known sequence of pDONR221:19430 (using Vector NTI software, Invitrogen), and a single plasmid designated as pDW14 (FIG. 117A) is selected for further study. The kudzu isoprene synthase sequence of pDW14 diverges from that of pDONR221:19430 bp a single nucleotide, which is marked in bold in the sequences of FIG. 117B (SEQ ID NO:112), and FIG. 117C-D (SEQ ID NO:113), respectively. The single nucleotide change (G to A) does not result in a change in the ORF, since it is in the third position of a lysine-encoding codon.

Purified pDW14 is transformed into *S. cerevisiae* strain INVSc-1 using the protocol described in the S. c. EasyComp Transformation kit (Invitrogen). INVSc-1 strains harboring pDW14 or pYES-DEST52 (which contains an intact URA3 gene) are selected for and maintained on SC Minimal Medium with 2% glucose without uracil, as described in the pYES-DEST52 Gateway Vector manual (Invitrogen). Two independent isolates of INVSc-1 containing pDW14 and a single control strain with pYES-DEST52 are chosen for further analysis. To induce isoprene synthase expression, cultures are grown overnight in liquid SC minimal medium (as described above). The cultures are then diluted to an $OD_{600}$ of approximately 0.2 and grown for 2-3 hours. Cultures are spun by centrifugation, washed once, resuspended in an equal volume (10 ml) of SC minimal medium with 1% raffinose, 2% galactose without uracil, and grown overnight to induce the expression of isoprene synthase. The $OD_{600}$ of the strains is determined and strains are harvested by centrifugation and resuspended in 2 ml of lysis buffer (1:1 mix of 50% glycerol and PEB pH 7.4: tris base 2.423 g/L, MgCl2 (Anhydrous) 1.904 g/L, KCl 14.910 g/L, DTT 0.154 g/L, glycerol 50 mL/L).

The lysis mixtures are passed through a French press three times, and lysates are analyzed by SDS-PAGE. For Coomassie gel analysis (FIG. 118A), samples are diluted 1:1 with 2× SDS loading buffer with reducing agent, loaded (20 μl total volume) onto a 4-12% bis-tris gel, run in MES buffer, and stained using SimplyBlue SafeStain according to the manufacturer's protocol (Invitrogen Novex system). The WesternBreeze kit (Invitrogen) is used for transfer and chromogenic detection of isoprene synthase on a nitrocellulose membrane. The primary antibody is 1799A 10 week diluted 1:1000 in Invitrogen antibody diluent. All subsequent steps for Western detection are performed according to the manufacturer's protocol. Isoprene synthase is found to be present in the induced INVSc-1 strains harboring pDW14 (FIG. 118B, lanes 2 and 3) in comparison to the control harboring pYES-DEST52 (FIG. 118B, lane 1). The DMAPP assay for HG headspace is performed on 25 μl of the lysate from each strain. DMAPP Assay Reagents (total volume of 100 μL) included: 25 μL lysate mixture; 5 μL $MgCl_2$ (1 M); 5 DMAPP (100 mM); and 65 μL 50 mM Tris pH 8. The reaction was performed at 30° C. for 15 minutes in a gas tight 1.8 mL GC tube. Reactions are terminated by the addition of 100 μL 250 mM EDTA (pH 8). The $OD_{600}$ and the specific activity values (in μg isoprene/L/OD) of the induced strains harboring pDW14 are shown in comparison to the control (FIGS. 119A and 119B). Induced strains harboring pDW14 display approximately 20× higher activity than the control lacking isoprene synthase.

II. Growth Conditions

INVSc-1 strains harboring pDW14 or the parent plasmid pYES-DEST52 (which contains an intact URA3 gene) are streaked from frozen glycerol stocks and grown for two days at 30° C. on SC minimal medium plates with 2% glucose without uracil, as described in the pYES-DEST52 Gateway Vector manual (Invitrogen). To induce isoprene synthase expression, cultures are inoculated from single colonies and grown overnight in liquid SC minimal medium with 2% glucose without uracil at 30° C. The cultures are then diluted to an $OD_{600}$ of approximately 0.2 and grown for 4 hours. Cultures are spun by centrifugation, washed once, resuspended in an equal volume (10 ml) of SC minimal medium with 1% raffinose, 2% galactose without uracil (induction medium), and grown overnight to induce the expression of isoprene synthase. The following day, the culture of INVSc-1 harboring pYES-DEST52 is back-diluted in induction medium to the same $OD_{600}$ as INVSc-1 harboring pDW14 (since induction of isoprene synthase at low initial $OD_{600}$ prohibits growth compared to the control). Thus the $OD_{600}$ of both strains prior to addition of isoprenol or dimethyl allyl alcohol in sealed 2 ml GC vials is approximately 2.0.

III. Assay

In the appropriate media, 200 μL of 5 mg/mL dimethyl allyl alcohol or isoprenol is prepared. Then, 800 μl of culture is added to a headspace vial along with 200 μL of media, media supplemented with prenol, or media supplemented with isoprenol. This is then incubated for 17 hours at 37° C. and the isoprene (ug/L) is measured on the GC/MS as described for the Headspace Assay. Results are shown as compared to no alcohol (no alc) added (FIG. 120).

Example 20

Production of Isoprene using Cell Culture System for Overflow

This example describes the use of cells as an overflow system for producing isoprene. Isoprene is made by using a cell culture system which includes one or more substrates, such as isoprenyl derivatives. The cells used are any one of the cells described supra. The cells process the substrates to produce isoprene biologically using the MVA pathway and/or the DXP pathway. In some cases, such as when the isoprene production through the biological pathways is maxed out, the cells also produce other derivatives, including the isoprenyl derivatives as described herein. These isoprenyl derivatives are then chemically converted to isoprene using the chemical reactions known to one of skill in the art and/or as described herein. The isoprenyl derivatives produced by the cells are also recycled as substrates for the cells.

Unless defined otherwise, the meanings of all technical and scientific terms used herein are those commonly understood by one of skill in the art to which this invention belongs. Singleton, et al., Dictionary of Microbiology and Molecular Biology, 2nd ed., John Wiley and Sons, New York (1994), and Hale & Marham, The Harper Collins Dictionary of Biology, Harper Perennial, N.Y. (1991) provide one of skill with a general dictionary of many of the terms used in this invention. It is to be understood that this invention is not limited to the particular methodology, protocols, and reagents described, as these may vary. One of skill in the art will also appreciate that any methods and materials similar or equivalent to those described herein can also be used to practice or test the invention.

The headings provided herein are not limitations of the various aspects or embodiments of the invention which can be had by reference to the specification as a whole.

For use herein, unless clearly indicated otherwise, use of the terms "a", "an," and the like refers to one or more.

Reference to "about" a value or parameter herein includes (and describes) embodiments that are directed to that value or parameter per se. For example, description referring to "about X" includes description of "X." Numeric ranges are inclusive of the numbers defining the range.

It is understood that aspects and embodiments of the invention described herein include "comprising," "consisting," and "consisting essentially of" aspects and embodiments.

APPENDIX 1

Exemplary 1-deoxy-D-xylulose-5-phosphate Synthase Nucleic Acids and Polypeptides ATH: AT3G21500(DXPS1)
AT4G15560(CLA1)
AT5G11380(DXPS3)
OSA: 4338768 4340090 4342614
CME: CMF089C
PFA: MAL13P1.186
TAN: TA20470
TPV: TP01_0516
ECO: b0420(dxs)
ECJ: JW0410(dxs)
ECE: Z0523(dxs)
ECS: ECs0474
ECC: c0531(dxs)
ECI: UTI89_C0443(dxs)
ECP: ECP_0479
ECV: APECO1_1590(dxs)
ECW: EcE24377A_0451(dxs)
ECX: EcHS_A0491
STY: STY0461(dxs)
STT: t2441(dxs)
SPT: SPA2301(dxs)
SEC: SC0463(dxs)
STM: STM0422(dxs)
YPE: YPO3177(dxs)
YPK: y1008(dxs)
YPM: YP_0754(dxs)
YPA: YPA_2671
YPN: YPN_0911
YPP: YPDSF_2812
XCC: XCC2434(dxs)
XCB: XC_1678
XCV: XCV2764(dxs)
XAC: XAC2565(dxs)
XOO: XOO2017(dxs)
XOM: XOO_1900(XOO1900)
VCH: VC0889
VVU: VV1_0315
VVY: VV0868
VPA: VP0686
VFI: VF0711
PPR: PBPRA0805
PAE: PA4044(dxs)
PAU: PA14_11550(dxs)
PAP: PSPA7_1057(dxs)
PPU: PP_0527(dxs)
PST: PSPTO_0698(dxs)
PSB: Psyr_0604
PSP: PSPPH_0599(dxs)
PFL: PFL_5510(dxs)
PFO: Pfl_5007
PEN: PSEEN0600(dxs)
PMY: Pmen_3844
PAR: Psyc_0221(dxs)
PCR: Pcryo_0245
ACI: ACIAD3247(dxs)
SON: SO_1525(dxs)
SDN: Sden_2571
SFR: Sfri_2790
SAZ: Sama_2436
SBL: Sbal_1357
NMC: NMC0352(dxs)
NGO: NGO0036
CVI: CV_2692(dxs)
RSO: RSc2221(dxs)
REU: Reut_A0882
REH: H16_A2732(dxs)
YPS: YPTB0939(dxs)
YPI: YpsIP31758_3112(dxs)
SFL: SF0357(dxs)
SFX: S0365(dxs)
SFV: SFV_0385(dxs)
SSN: SSON_0397(dxs)
SBO: SBO_0314(dxs)
SDY: SDY_0310(dxs)
ECA: ECA1131(dxs)
PLU: plu3887(dxs)
BUC: BU464(dxs)
BAS: BUsg448(dxs)
WBR: WGLp144(dxs)
SGL: SG0656
KPN: KPN_00372(dxs)
BFL: Bfl238(dxs)
BPN: BPEN_244(dxs)
HIN: HI1439(dxs)
HIT: NTHI1691(dxs)
HIP: CGSHiEE_04795
HIQ: CGSHiGG_01080
HDU: HD0441(dxs)
HSO: HS_0905(dxs)
PMU: PM0532(dxs)
MSU: MS1059(dxs)
APL: APL_0207(dxs)
XFA: XF2249
XFT: PD1293(dxs)
SLO: Shew_2771
SHE: Shewmr4_2731
SHM: Shewmr7_2804
SHN: Shewana3_2901
SHW: Sputw3181_2831
ILO: IL2138(dxs)
CPS: CPS_1088(dxs)
PHA: PSHAa2366(dxs)
PAT: Patl_1319
SDE: Sde_3381
PIN: Ping_2240
MAQ: Maqu_2438
MCA: MCA0817(dxs)
FTU: FTT1018c(dxs)
FTF: FTF1018c(dxs)
FTW: FTW_0925(dxs)
FTL: FTL_1072
FTH: FTH_1047(dxs)
FTA: FTA_1131(dxs)
FTN: FTN_0896(dxs)
NOC: Noc_1743
AEH: Mlg_1381
HCH: HCH_05866(dxs)
CSA: Csal_0099
ABO: ABO_2166(dxs)
AHA: AHA_3321(dxs)
BCI: BCI_0275(dxs)
RMA: Rmag_0386
VOK: COSY_0360(dxs)
NME: NMB1867
NMA: NMA0589(dxs)
NEU: NE1161(dxs)
NET: Neut_1501
NMU: Nmul_A0236
EBA: ebA4439(dxs)
AZO: azo1198(dxs)
DAR: Daro_3061
TBD: Tbd_0879
MFA: Mfla_2133
RME: Rmet_2615
BMA: BMAA0330(dxs)
BMV: BMASAVP1_1512(dxs)
BML: BMA10299_1706(dxs)
BMN: BMA10247_A0364(dxs)
BXE: Bxe_B2827
BUR: Bcep18194_B2211
BCN: Bcen_4486
BCH: Bcen2424_3879
BAM: Bamb_3250
BPS: BPSS1762(dxs)
BPM: BURPS1710b_A0842(dxs)
BPL: BURPS1106A_A2392(dxs)
BPD: BURPS668_A2534(dxs)
BTE: BTH_II0614(dxs)
BPE: BP2798(dxs)
BPA: BPP2464(dxs)
BBR: BB1912(dxs)
RFR: Rfer_2875
POL: Bpro_1747
PNA: Pnap_1501
AJS: Ajs_1038
MPT: Mpe_A2631
HAR: HEAR0279(dxs)
MMS: mma_0331
PPD: Ppro_1191 Ppro_2403
DVU: DVU1350(dxs)
DVL: Dvul_1718
DDE: Dde_2200
LIP: LI0408(dsx)
DPS: DP2700
ADE: Adeh_1097
MXA: MXAN_4643(dxs)
SAT: SYN_02456
SFU: Sfum_1418
PUB: SAR11_0611(dxs)
MLO: mlr7474
MES: Meso_0735
SME: SMc00972(dxs)
ATU: Atu0745(dxs)
ATC: AGR_C_1351
RET: RHE_CH00913(dxs)
RLE: RL0973(dxs)
BME: BMEI1498
BMF: BAB1_0462(dxs)
BMS: BR0436(dxs)
BMB: BruAb1_0458(dxs)
BOV: BOV_0443(dxs)
BJA: bll2651(dxs)
BRA: BRADO2161(dxs)
BBT: BBta_2479(dxs)
RPA: RPA0952(dxs)
RPB: RPB_4460
RPC: RPC_1149
RPD: RPD_4305
RPE: RPE_1067
BCA: BCE_4249(dxs)
BCZ: BCZK3930(dxs)
BTK: BT9727_3919(dxs)
BTL: BALH_3785(dxs)
BLI: BL01523(dxs)
BLD: BLi02598(dxs)
BCL: ABC2462(dxs)
BAY: RBAM_022600
BPU: BPUM_2159
GKA: GK2392
GTN: GTNG_2322
LMO: lmo1365(tktB)
LMF: LMOf2365_1382(dxs)
LIN: lin1402(tktB)
LWE: lwe1380(tktB)
LLA: L108911(dxsA) L123365(dxsB)
LLC: LACR_1572 LACR_1843
LLM: llmg_0749(dxsB)
SAK: SAK_0263
LPL: lp_2610(dxs)
LJO: LJ0406
LAC: LBA0356
LSL: LSL_0209(dxs)
HPY: HP0354(dxs)
HPJ: jhp0328(dxs)
HPA: HPAG1_0349
HHE: HH0608(dxs)
HAC: Hac_0968(dxs)
WSU: WS1996
TDN: Tmden_0475
CJE: Cj0321(dxs)
CJR: CJE0366(dxs)
CJJ: CJJ81176_0343(dxs)
CJU: C8J_0298(dxs)
CJD: JJD26997_1642(dxs)
CFF: CFF8240_0264(dxs)
CCV: CCV52592_1671(dxs)
CCV52592_1722
CHA: CHAB381_1297(dxs)
CCO: CCC13826_1594(dxs)
ABU: Abu_2139(dxs)
NIS: NIS_0391(dxs)
SUN: SUN_2055(dxs)
GSU: GSU0686(dxs-1) GSU1764(dxs-2)
GME: Gmet_1934 Gmet_2822
PCA: Pcar_1667
NWI: Nwi_0633
NHA: Nham_0778
BHE: BH04350(dxs)
BQU: BQ03540(dxs)
BBK: BARBAKC583_0400(dxs)
CCR: CC_2068
SIL: SPO0247(dxs)
SIT: TM1040_2920
RSP: RSP_0254(dxsA) RSP_1134(dxs)
JAN: Jann_0088 Jann_0170
RDE: RD1_0101(dxs) RD1_0548(dxs)
MMR: Mmar10_0849
HNE: HNE_1838(dxs)
ZMO: ZMO1234(dxs) ZMO1598(dxs)
NAR: Saro_0161
SAL: Sala_2354
ELI: ELI_12520
GOX: GOX0252
GBE: GbCGDNIH1_0221 GbCGDNIH1_2404
RRU: Rru_A0054 Rru_A2619
MAG: amb2904
MGM: Mmc1_1048
SUS: Acid_1783
BSU: BG11715(dxs)
BHA: BH2779
BAN: BA4400(dxs)
BAR: GBAA4400(dxs)
BAA: BA_4853
BAT: BAS4081
BCE: BC4176(dxs)
CTH: Cthe_0828
CDF: CD1207(dxs)
CBO: CBO1881(dxs)
CBA: CLB_1818(dxs)
CBH: CLC_1825(dxs)
CBF: CLI_1945(dxs)
CKL: CKL_1231(dxs)
CHY: CHY_1985(dxs)
DSY: DSY2348
DRM: Dred_1078
PTH: PTH_1196(dxs)
SWO: Swol_0582
CSC: Csac_1853
TTE: TTE1298(dxs)
MTA: Moth_1511
MPE: MYPE730
MGA: MGA_1268(dxs)
MTU: Rv2682c(dxsl)
Rv3379c(dxs2)
MTC: MT2756(dxs)
MBO: Mb2701c(dxs1)
Mb3413c(dxs2)

LGA: LGAS_0350
STH: STH1842
CAC: CAC2077
CA_P0106(dxs)
CPE: CPE1819
CPF: CPF_2073(dxs)
CPR: CPR_1787(dxs)
CTC: CTC01575
CNO: NT01CX_1983
RHA: RHA1_ro06843
SCO: SCO6013(SC1C3.01)
SCO6768(SC6A5.17)
SMA: SAV1646(dxs1)
SAV2244(dxs2)
TWH: TWT484
TWS: TW280(Dxs)
LXX: Lxx10450(dxs)
CMI: CMM_1660(dxsA)
AAU: AAur_1790(dxs)
PAC: PPA1062
TFU: Tfu_1917
FRA: Francci3_1326
FAL: FRAAL2088(dxs)
ACE: Acel_1393
SEN: SACE_1815(dxs)
SACE_4351
BLO: BL1132(dxs)
BAD: BAD_0513(dxs)
FNU: FN1208 FN1464
RBA: RB2143(dxs)
CTR: CT331(dxs)
CTA: CTA_0359(dxs)
CMU: TC0608
CPN: CPn1060(tktB_2)
CPA: CP0790
CPJ: CPj1060(tktB_2)
CPT: CpB1102
CCA: CCA00304(dxs)
CAB: CAB301(dxs)
CFE: CF0699(dxs)
PCU: pc0619(dxs)
TPA: TP0824
PME: NATL1_09721(dxs)
TER: Tery_3042
BTH: BT_1403 BT_4099
BFR: BF0873 BF4306
BFS: BF0796(dxs) BF4114
PGI: PG2217(dxs)
CHU: CHU_3643(dxs)
GFO: GFO_3470(dxs)
FPS: FP0279(dxs)
CTE: CT0337(dxs)
CPH: Cpha266_0671
MLE: ML1038(dxs)
MPA: MAP2803c(dxs)
MAV: MAV_3577(dxs)
MSM: MSMEG_2776(dxs)
MMC: Mmcs_2208
CGL: NCgl1827(cgl1902)
CGB: cg2083(dxs)
CEF: CE1796
CDI: DIP1397(dxs)
CJK: jk1078(dxs)
NFA: nfa37410(dxs)
TDE: TDE1910(dxs)
LIL: LA3285(dxs)
LIC: LIC10863(dxs)
LBJ: LBJ_0917(dxs)
LBL: LBL_0932(dxs)
SYN: sll1945(dxs)
SYW: SYNW1292(Dxs)
SYC: syc1087_c(dxs)
SYF: Synpcc7942_0430
SYD: Syncc9605_1430
SYE: Syncc9902_1069
SYG: sync_1410(dxs)
SYR: SynRCC307_1390(dxs)
SYX: SynWH7803_1223(dxs)
CYA: CYA_1701(dxs)
CYB: CYB_1983(dxs)
TEL: tll0623
GVI: gll0194
ANA: alr0599
AVA: Ava_4532
PMA: Pro0928(dxs)
PMM: PMM0907(Dxs)
PMT: PMT0685(dxs)
PMN: PMN2A_0300
PMI: PMT9312_0893
PMB: A9601_09541(dxs)
PMC: P9515_09901(dxs)
PMF: P9303_15371(dxs)
PMG: P9301_09521(dxs)
PMH: P9215_09851
PMJ: P9211_08521
PVI: Cvib_0498
PLT: Plut_0450
DET: DET0745(dxs)
DEH: cbdb_A720(dxs)
DRA: DR_1475
DGE: Dgeo_0994
TTH: TTC1614
TTJ: TTHA0006
AAE: aq_881
TMA: TM1770
PMO: Pmob_1001

Exemplary acetyl-CoA-acetyltransferase Nucleic Acids and Polypeptides
HSA: 38(ACAT1) 39(ACAT2)
PTR: 451528(ACAT1)
MCC: 707653(ACAT1) 708750(ACAT2)
MMU: 110446(Acat1) 110460(Acat2)
RNO: 25014(Acat1)
CFA: 484063(ACAT2) 489421(ACAT1)
GGA: 418968(ACAT1) 421587(RCJMB04_34i5)
XLA: 379569(MGC69098) 414622(MGC81403) 414639(MGC81256) 444457(MGC83664)
XTR: 394562(acat2)
DRE: 30643(acat2)
SPU: 759502(LOC759502)
DME: Dmel_CG10932 Dmel_CG9149
CEL: T02G5.4 T02G5.7 T02G5.8(kat-1)
ATH: AT5G48230(ACAT2/EMB1276)
OSA: 4326136 4346520
CME: CMA042C CME087C
SCE: YPL028W(ERG10)
AGO: AGOS_ADR165C
PIC: PICST_31707(ERG10)
CAL: CaO19.1591(erg10)
CGR: CAGL0L12364g
SPO: SPBC215.09c
MGR: MGG_01755 MGG_13499
ANI: AN1409.2
AFM: AFUA_6G14200 AFUA_8G04000
AOR: AO090103000012 AO090103000406
CNE: CNC05280
UMA: UM03571.1
DDI: DDB_0231621
PFA: PF14_0484
TET: TTHERM_00091590 TTHERM_00277470 TTHERM_00926980
TCR: 511003.60
ECO: b2224(atoB)
ECJ: JW2218(atoB) JW5453(yqeF)
ECE: Z4164(yqeF)
ECS: ECs3701
ECC: c2767(atoB) c3441(yqeF)
ECI: UTI89_C2506(atoB) UTI89_C3247(yqeF)
ECP: ECP_2268 ECP_2857
ECV: APECO1_3662(yqeF) APECO1_4335(atoB) APECO1_43352(atoB)
ECX: EcHS_A2365
STY: STY3164(yqeF)
STT: t2929(yqeF)
SPT: SPA2886(yqeF)
SEC: SC2958(yqeF)
STM: STM3019(yqeF)
SFL: SF2854(yqeF)
SFX: S3052(yqeF)
SFV: SFV_2922(yqeF)
SSN: SSON_2283(atoB) SSON_3004(yqeF)
SBO: SBO_2736(yqeF)
ECA: ECA1282(atoB)
ENT: Ent638_3299
SPE: Spro_0592
HIT: NTHI0932(atoB)
XCC: XCC1297(atoB)
XCB: XC_2943
XCV: XCV1401(thlA)
XAC: XAC1348(atoB)
XOO: XOO1881(atoB)
XOM: XOM_1778(XOO1778)
VCH: VCA0690
VCO: VCO395_0630
VVU: VV2_0494 VV2_0741
VVY: VVA1043 VVA1210
VPA: VPA0620 VPA1123 VPA1204
PPR: PBPRB1112 PBPRB1840
PAE: PA2001(atoB) PA2553 PA3454 PA3589 PA3925
PAU: PA14_38630(atoB)
PPU: PP_2051(atoB) PP_2215(fadAx) PP_3754 PP_4636
PPF: Pput_2009 Pput_2403 Pput_3523 Pput_4498
PST: PSPTO_0957(phbA-1) PSPTO_3164(phbA-2)
PSB: Psyr_0824 Psyr_3031
PSP: PSPPH_0850(phbA1) PSPPH_2209(phbA2)
PFL: PFL_1478(atoB-2) PFL_2321 PFL_3066 PFL_4330(atoB-2) PFL_5283
PFO: Pfl_1269 Pfl_1739 Pfl_2074 Pfl_2868
PEN: PSEEN3197 PSEEN3547(fadAx) PSEEN4635(phbA)
PMY: Pmen_1138 Pmen_2036 Pmen_3597 Pmen_3662 Pmen_3820
PAR: Psyc_0252 Psyc_1169
PCR: Pcryo_0278 Pcryo_1236 Pcryo_1260
PRW: PsycPRwf_2011

ACI: ACIAD0694 ACIAD1612 ACIAD2516(atoB)
SON: SO_1677(atoB)
SDN: Sden_1943
SFR: Sfri_1338 Sfri_2063
SAZ: Sama_1375
SBL: Sbal_1495
SBM: Shew185_1489
SBN: Sba1195_1525
SLO: Shew_1667 Shew_2858
SPC: Sputcn32_1397
SSE: Ssed_1473 Ssed_3533
SPL: Spea_2783
SHE: Shewmr4_2597
SHM: Shewmr7_2664
SHN: Shewana3_2771
SHW: Sputw3181_2704
ILO: IL0872
CPS: CPS_1605 CPS_2626
PHA: PSHAa0908 PSHAa1454(atoB) PSHAa1586(atoB)
PAT: Patl_2923
SDE: Sde_3149
PIN: Ping_0659 Ping_2401
MAQ: Maqu_2117 Maqu_2489 Maqu_2696 Maqu_3162
CBU: CBU_0974
LPN: lpg1825(atoB)
LPF: lpl1789
LPP: lpp1788
NOC: Noc_1891
AEH: Mlg_0688 Mlg_2706
HHA: Hhal_1685
HCH: HCH_05299
CSA: Csal_0301 Csal_3068
ABO: ABO_0648(fadAx)
MMW: Mmwyl1_0073 Mmwyl1_3021 Mmwyl1_3053 Mmwyl1_3097 Mmwyl1_4182
AHA: AHA_2143(atoB)
CVI: CV_2088(atoB) CV_2790(phaA)
RSO: RSc0276(atoB) RSc1632(phbA) RSc1637(bktB) RSc1761(RS02948)
REU: Reut_A0138 Reut_A1348 Reut_A1353 Reut_B4561 Reut_B4738 Reut_B5587 Reut_C5943 Reut_C6062
REH: H16_A0170 H16_A0867 H16_A0868 H16_A0872 H16_A1297 H16_A1438(phaA) H16_A1445(bktB) H16_A1528 H16_A1713 H16_A1720 H16_A1887 H16_A2148 H16_B0380 H16_B0381 H16_B0406 H16_B0662 H16_B0668 H16_B0759 H16_B1369 H16_B1771
RME: Rmet_0106 Rmet_1357 Rmet_1362 Rmet_5156
BMA: BMA1316 BMA1321(phbA) BMA1436
BMV: BMASAVP1_A1805(bktB) BMASAVP1_A1810(phbA)
BML: BMA10299_A0086(phbA) BMA10299_A0091
BMN: BMA10247_1076(bktB) BMA10247_1081(phbA)
BXE: Bxe_A2273 Bxe_A2335 Bxe_A2342 Bxe_A4255 Bxe_B0377 Bxe_B0739 Bxe_C0332 Bxe_C0574 Bxe_C0915
BVI: Bcep1808_0519 Bcep1808_1717 Bcep1808_2877 Bcep1808_3594 Bcep1808_4015 Bcep1808_5507 Bcep1808_5644
BUR: Bcep18194_A3629 Bcep18194_A5080 Bcep18194_A5091 Bcep18194_A6102 Bcep18194_B0263 Bcep18194_B1439 Bcep18194_C6652 Bcep18194_C6802 Bcep18194_C6874 Bcep18194_C7118 Bcep18194_C7151 Bcep18194_C7332
BCN: Bcen_1553 Bcen_1599 Bcen_2158 Bcen_2563 Bcen_2998 Bcen_6289
BCH: Bcen2424_0542 Bcen2424_1790 Bcen2424_2772 Bcen2424_5368 Bcen2424_6232 Bcen2424_6276
BAM: Bamb_0447 Bamb_1728 Bamb_2824 Bamb_4717 Bamb_5771 Bamb_5969
BPS: BPSL1426 BPSL1535(phbA) BPSL1540
BPM: BURPS1710b_2325(bktB) BURPS1710b_2330(phbA) BURPS1710b_2453(atoB-2)
BPL: BURPS1106A_2197(bktB) BURPS1106A_2202(phbA)
BPD: BURPS668_2160(bktB) BURPS668_2165(phbA)
BTE: BTH_I2144 BTH_I2256 BTH_I2261
PNU: Pnuc_0927
BPE: BP0447 BP0668 BP2059
BPA: BPP0608 BPP1744 BPP3805 BPP4216 BPP4361
BBR: BB0614 BB3364 BB4250 BB4804 BB4947
RFR: Rfer_0272 Rfer_1000 Rfer_1871 Rfer_2273 Rfer_2561 Rfer_2594 Rfer_3839
POL: Bpro_1577 Bpro_2140 Bpro_3113 Bpro_4187
PNA: Pnap_0060 Pnap_0458 Pnap_0867 Pnap_1159 Pnap_2136 Pnap_2804
AAV: Aave_0031 Aave_2478 Aave_3944 Aave_4368
AJS: Ajs_0014 Ajs_0124 Ajs_1931 Ajs_2073 Ajs_2317 Ajs_3548 Ajs_3738 Ajs_3776
VEI: Veis_1331 Veis_3818 Veis_4193
DAC: Daci_0025 Daci_0192 Daci_3601 Daci_5988
MPT: Mpe_A1536 Mpe_A1776 Mpe_A1869 Mpe_A3367
HAR: HEAR0577(phbA)
MMS: mma_0555
NEU: NE2262(bktB)
NET: Neut_0610
EBA: ebA5202 p2A409(tioL)
AZO: azo0464(fadA1) azo0469(fadA2) azo2172(thlA)
DAR: Daro_0098 Daro_3022
HPA: HPAG1_0675
HAC: Hac_0958(atoB)
GME: Gmet_1719 Gmet_2074 Gmet_2213 Gmet_2268 Gmet_3302
GUR: Gura_3043
BBA: Bd0404(atoB) Bd2095
DOL: Dole_0671 Dole_1778 Dole_2160 Dole_2187
ADE: Adeh_0062 Adeh_2365
AFW: Anae109_0064 Anae109_1504
MXA: MXAN_3791
SAT: SYN_02642
SFU: Sfum_2280 Sfum_3582
RPR: RP737
RCO: RC1134 RC1135
RFE: RF_0163(paaJ)
RBE: RBE_0139(paaJ)
RAK: A1C_05820
RBO: A11_07215
RCM: A1E_04760
PUB: SAR11_0428(thlA)
MLO: mlr3847
MES: Meso_3374
PLA: Plav_1573 Plav_2783
SME: SMa1450 SMc03879(phbA)
SMD: Smed_0499 Smed_3117 Smed_5094 Smed_5096
ATU: Atu2769(atoB) Atu3475
ATC: AGR_C_5022(phbA) AGR_L_2713
RET: RHE_CH04018(phbAch) RHE_PC00068(ypc00040) RHE_PF00014(phbAf)
RLE: RL4621(phaA) pRL100301 pRL120369
BME: BMEI0274 BMEII0817
BMF: BAB1_1783(phbA-1) BAB2_0790(phbA-2)
BMS: BR1772(phbA-1) BRA0448(phbA-2)
BMB: BruAb1_1756(phbA-1) BruAb2_0774(phbA-2)

BOV: BOV_1707(phbA-1)
OAN: Oant_1130 Oant_3107 Oant_3718 Oant_4020
BJA: b110226(atoB) b113949 b117400 b117819 b1r3724 (phbA)
BRA: BRADO0562(phbA) BRADO0983(pimB) BRADO3110 BRADO3134(atoB)
BBT: BBta_3558 BBta_3575(atoB) BBta_5147(pimB) BBta_7072(pimB) BBta_7614(phbA)
RPA: RPA0513(pcaF) RPA0531 RPA3715(pimB)
RPB: RPB_0509 RPB_0525 RPB_1748
RPC: RPC_0504 RPC_0636 RPC_0641 RPC_0832 RPC_1050 RPC_2005 RPC_2194 RPC_2228
RPD: RPD_0306 RPD_0320 RPD 3105 RPD_3306
RPE: RPE 0168 RPE_0248 RPE 3827
NWI: Nwi_3060
XAU: Xaut_3108 Xaut_4665
CCR: CC_0510 CC_0894 CC_3462
SIL: SPO0142(bktB) SPO0326(phbA) SPO0773 SPO3408
SIT: TM1040_0067 TM1040_2790 TM1040_3026 TM1040_3735
RSP: RSP_0745 RSP_1354 RSP_3184
RSH: Rsph17029_0022 Rsph17029_2401 Rsph17029_3179 Rsph17029_3921
RSQ: Rsph17025_0012 Rsph17025_2466 Rsph17025_2833
JAN: Jann_0262 Jann_0493 Jann_4050
RDE: RD1_0025 RD1_0201(bktB) RD1_3394(phbA)
PDE: Pden_2026 Pden_2663 Pden_2870 Pden_2907 Pden_4811 Pden_5022
DSH: Dshi_0074 Dshi_3066 Dshi_3331
MMR: Mmar10_0697
HNE: HNE_2706 HNE_3065 HNE_3133
NAR: Saro_0809 Saro_1069 Saro_1222 Saro_2306 Saro_2349
SAL: Sala_0781 Sala_1244 Sala_2896 Sala 3158
SWI: Swit_0632 Swit_0752 Swit_2893 Swit_3602 Swit_4887 Swit_5019 Swit_5309
ELI: ELI_01475 ELI_06705 ELI_12035
GBE: GbCGDNIH1_0447
ACR: Acry_1847 Acry_2256
RRU: Rru_A0274 Rru_A1380 Rru_A1469 Rru_A1946 Rru_A3387
MAG: amb0842
MGM: Mmc1_1165
ABA: Acid345_3239
BSU: BG11319(mmgA) BG13063(yhfS)
BHA: BH1997 BH2029 BH3801(mmgA)
BAN: BA3687 BA4240 BA5589
BAR: GBAA3687 GBAA4240 GBAA5589
BAA: BA_0445 BA_4172 BA_4700
BAT: BAS3418 BAS3932 BAS5193
BCE: BC3627 BC4023 BC5344
BCA: BCE_3646 BCE_4076 BCE_5475
BCZ: BCZK3329(mmgA) BCZK3780(thl) BCZK5044(atoB)
BCY: Bcer98_2722 Bcer98_3865
BTK: BT9727_3379(mmgA) BT9727_3765(thl) BT9727_5028(atoB)
BTL: BALH_3262(mmgA) BALH_3642(fadA) BALH_4843(atoB)
BLI: BL03925(mmgA)
BLD: BLi03968(mmgA)
BCL: ABC0345 ABC2989 ABC3617 ABC3891(mmgA)
BAY: RBAM_022450
BPU: BPUM_2374(yhfS) BPUM_2941 BPUM_3373
OIH: OB0676 OB0689 OB2632 OB3013
GKA: GK1658 GK3397
SAU: SA0342 SA0534(vraB)
SAV: SAV0354 SAV0576(vraB)
SAM: MW0330 MW0531(vraB)
SAR: SAR0351(th1) SAR0581
SAS: SAS0330 SAS0534
SAC: SACOL0426 SACOL0622(atoB)
SAB: SAB0304(th1) SAB0526
SAA: SAUSA300_0355 SAUSA300_0560(vraB)
SAO: SAOUHSC_00336 SAOUHSC_00558
SAJ: SaurJH9_0402
SAH: SaudH1_0412
SEP: SE0346 SE2384
SER: SERP0032 SERP0220
SHA: SH0510(mvaC) SH2417
SSP: SSP0325 SSP2145
LMO: lmo1414
LMF: LMOf2365_1433
LIN: lin1453
LWE: lwe1431
LLA: L11745(thiL) L25946(fadA)
LLC: LACR_1665 LACR_1956
LLM: llmg_0930(thiL)
SPY: SPy_0140 SPy_1637(atoB)
SPZ: M5005_Spy_0119 M5005_Spy_0432 M5005_Spy_1344(atoB)
SPM: spyM18_0136 spyM18_1645(atoB)
SPG: SpyM3_0108 SpyM3_1378(atoB)
SPS: SPs0110 SPs0484
SPH: MGAS10270_Spy0121 MGAS10270_Spy0433 MGAS10270_Spy1461(atoB)
SPI: MGAS10750_Spy0124 MGAS10750_Spy0452 MGAS10750_Spy1453(atoB)
SPJ: MGAS2096_Spy0123 MGAS2096_Spy0451 MGAS2096_Spy1365(atoB)
SPK: MGAS9429_Spy0121 MGAS9429_Spy0431 MGAS9429_Spy1339(atoB)
SPF: SpyM50447(atoB2)
SPA: M6_Spy0166 M6_Spy0466 M6_Spy1390
SPB: M28_Spy0117 M28_Spy0420 M28_Spy1385(atoB)
SAK: SAK_0568
LJO: LJ1609
LAC: LBA0626(thiL)
LSA: LSA1486
LDB: Ldb0879
LBU: LBUL_0804
LBR: LVIS_2218
LCA: LSEI_1787
LGA: LGAS_1374
LRE: Lreu_0052
EFA: EF1364
OOE: OEOE_0529
STH: STH2913 STH725 STH804
CAC: CAC2873 CA_P0078(thiL)
CPE: CPE2195(atoB)
CPF: CPF_2460
CPR: CPR_2170
CTC: CTC00312
CNO: NT01CX_0538 NT01CX_0603
CDF: CD1059(th1A1) CD2676(th1A2)
CBO: CBO3200(th1)
CBE: Cbei_0411 Cbei_3630
CKL: CKL_3696(th1A1) CKL_3697(th1A2) CKL_3698(th1A3)
AMT: Amet_4630
AOE: Clos_0084 Clos_0258
CHY: CHY_1288 CHY_1355(atoB) CHY_1604 CHY_1738

DSY: DSY0632 DSY0639 DSY1567 DSY1710 DSY2402 DSY3302
DRM: Dred_0400 Dred_1491 Dred_1784 Dred 1892
SWO: Swol_0308 Swol_0675 Swol_0789 Swol_1486 Swol_1934 Swol_2051
TTE: TTE0549(paaJ)
MTA: Moth_1260
MTU: Rv1135A Rv1323(fadA4) Rv3546(fadA5)
MTC: MT1365(phbA)
MBO: Mb1167 Mb1358(fadA4) Mb3576(fadA5) Mb3586c(fadA6)
MBB: BCG_1197 BCG_1385(fadA4) BCG_3610(fadA5) BCG_3620c(fadA6)
MLE: ML1158(fadA4)
MPA: MAP2407c(fadA3) MAP2436c(fadA4)
MAV: MAV_1544 MAV_1573 MAV_1863 MAV_5081
MSM: MSMEG_2224 MSMEG_4920
MUL: MUL_0357
MVA: Mvan_1976 Mvan_1988 Mvan_4305 Mvan_4677 Mvan_4891
MGI: Mflv_1347 Mflv_1484 Mflv_2040 Mflv_2340 Mflv_4356 Mflv_4368
MMC: Mmcs_1758 Mmcs_1769 Mmcs_3796 Mmcs_3864
MKM: Mkms_0251 Mkms_1540 Mkms_1805 Mkms_1816 Mkms_2836 Mkms_3159 Mkms_3286 Mkms_3869 Mkms_3938 Mkms_4227 Mkms_4411 Mkms_4580 Mkms_4724 Mkms_4764 Mkms_4776
MJL: Mjls_0231 Mjls_1739 Mjls_1750 Mjls_2819 Mjls_3119 Mjls_3235 Mjls_3800 Mjls_3850 Mjls_4110 Mjls_4383 Mjls_4705 Mjls_4876 Mjls_5018 Mjls_5063 Mjls_5075
CGL: NCgl2309(cgl2392)
CGB: cg2625(pcaF)
CEF: CE0731 CE2295
CJK: jk1543(fadA3)
NFA: nfa10750(fadA4)
RHA: RHA1_ro01455 RHA1_ro01623 RHA1_ro01876 RHA1_ro02517(catF) RHA1_ro03022 RHA1_ro03024 RHA1_ro03391 RHA1_ro03892 RHA1_ro04599 RHA1_ro05257 RHA1_ro08871
SCO: SCO5399(SC8F4.03)
SMA: SAV1384(fadA5) SAV2856(fadA1)
ART: Arth_1160 Arth_2986 Arth_3268 Arth_4073
NCA: Noca_1371 Noca_1797 Noca_1828 Noca_2764 Noca_4142
TFU: Tfu_1520 Tfu_2394
FRA: Francci3_3687
FRE: Franean1_1044 Franean1_2711 Franean1_2726 Franean1_3929 Franean1_4037 Franean1_4577
FAL: FRAAL2514 FRAAL2618 FRAAL5910(atoB)
ACE: Acel_0626 Acel_0672
SEN: SACE_1192(mmgA) SACE_2736(fadA6) SACE_4011(catF) SACE_6236(fadA4)
STP: Strop_3610
SAQ: Sare_1316 Sare_3991
RXY: Rxyl_1582 Rxyl_1842 Rxyl_2389 Rxyl_2530
FNU: FN0495
BGA: BG0110(fadA)
BAF: BAPKO_0110(fadA)
LIL: LA0457(thiL1) LA0828(thiL2) LA4139(fadA)
LIC: LIC10396(phbA)
LBJ: LBJ_2862(paaJ-4)
LBL: LBL_0209(paaJ-4)
SYN: slr1993(phaA)
SRU: SRU_1211(atoB) SRU_1547
CHU: CHU_1910(atoB)
GFO: GFO_1507(atoB)
FJO: Fjoh_4612
FPS: FP0770 FP1586 FP1725
RRS: RoseRS_3911 RoseRS_4348
RCA: Rcas_0702 Rcas_3206
HAU: Haur_0522
DRA: DR_1072 DR_1428 DR_1960 DR_2480 DR_A0053
DGE: Dgeo_0755 Dgeo_1305 Dgeo_1441 Dgeo_1883
TTH: TTC0191 TTCO330
TTJ: TTHA0559
TME: Tmel_1134
FNO: Fnod_0314
PMO: Pmob_0515
HMA: rrnAC0896(acaB3) rrnAC2815(aca2) rrnAC3497(yqeF) rrnB0240(aca1) rrnB0242(acaB2) rrnB0309(acaB1)
TAC: Ta0582
TVO: TVN0649
PTO: PTO1505
APE: APE_2108
SSO: SSO2377(acaB-4)
STO: ST0514
SAI: Saci_0963 Saci_1361(acaB1)
MSE: Msed_0656
PAI: PAE1220
PIS: Pisl_0029 Pisl_1301
PCL: Pcal_0781
PAS: Pars_0309 Pars_1071
CMA: Cmaq_1941

Exemplary HMG-CoA Synthase Nucleic Acids and Polypeptides

HSA: 3157(HMGCS1) 3158(HMGCS2)
PTR: 457169(HMGCS2) 461892(HMGCS1)
MCC: 702553(HMGCS1) 713541(HMGCS2)
MMU: 15360(Hmgcs2) 208715(Hmgcs1)
RNO: 24450(Hmgcs2) 29637(Hmgcs1)
CFA: 479344(HMGCS1) 607923(HMGCS2)
BTA: 407767(HMGCS1)
SSC: 397673(CH242-38B5.1)
GGA: 396379(HMGCS1)
XLA: 380091(hmgcs1) 447204(MGC80816)
DRE: 394060(hmgcs1)
SPU: 578259(L00578259)
DME: Dmel_CG4311(Hmgs)
CEL: F25B4.6
ATH: AT4G11820(BAP1)
OSA: 4331418 4347614
CME: CMM189C
SCE: YML126C(ERG13)
AGO: AGOS_ADL356C
PIC: PICST_83020
CAL: CaO19_7312(CaO19.7312)
CGR: CAGLOH04081g
SPO: SPAC4F8.14c(hcs)
MGR: MGG_01026
ANI: AN4923.2
AFM: AFUA_3G10660 AFUA_8G07210
AOR: AO090003000611 AO090010000487
CNE: CNC05080 CNG02670
SAR: SAR2626(mvaS)
SAS: SAS2432
SAC: SACOL2561
SAB: SAB2420(mvaS)
SAA: SAUSA300_2484
SAO: SAOUHSC_02860
SAJ: Saur.M9_2569
SAH: SaurJH1_2622
SEP: SE2110
SER: SERP2122
UMA: UM05362.1
ECU: ECU10_0510
DDI: DDBDRAFT_0217522
DDB: DDB_0219924(hgsA)
TET: TTHERM_00691190
TBR: Tb927.8.6110
YPE: YPO1457
YPK: y2712(pksG)
YPM: YP_1349(pksG)
YPA: YPA_0750
YPN: YPN_2521
YPP: YPDSF_1517
YPS: YPTB1475
CBD: COXBU7E912_1931
TCX: Tcr_1719
DNO: DNO_0799
BMA: BMAA1212
BPS: BPSS1002
BPM: BURPS1710b_A2613
BPL: BURPS1106A_A1384
BPD: BURPS668_A1470
BTE: BTH_II1670
MXA: MXAN_3948(tac) MXAN_4267(mvaS)
BSU: BG10926(pksG)
OIH: OB2248
SAU: SA2334(mvaS)
SAV: SAV2546(mvaS)
SAM: MW2467(mvaS)
SPN: SP_1727
SPR: spr1571(mvaS)
SPD: SPD_1537(mvaS)
SAG: SAG1316
SAN: gbs1386
SAK: SAK 1347
SMU: SMU.943c
STC: str0577(mvaS)
STL: stu0577(mvaS)
STE: STER_0621

-continued

SHA: SH0508(mvaS)
SSP: SSP0324
LMO: lmo1415
LMF: LMOf2365_1434(mvaS)
LIN: lin1454
LWE: lwe1432(mvaS)
LLA: L13187(hmcM)
LLC: LACR_1666
LLM: llmg_0929(hmcM)
SPY: SPy_0881(mvaS.2)
SPZ: M5005_Spy_0687(mvaS.1)
SPM: spyM18_0942(mvaS2)
SPG: SpyM3_0600(mvaS.2)
SPS: SPs1253
SPH: MGAS 10270_Spy0745(mvaS1)
SPI: MGAS 10750_Spy0779(mvaS1)
SPJ: MGAS2096_Spy0759(mvaS1)
SPK: MGAS9429_Spy0743(mvaS1)
SPF: SpyM51121(mvaS)
SPA: M6_Spy0704
SPB: M28_Spy0667(mvaS.1)
BBU: BB0683
BGA: BG0706
BAF: BAPKO_0727
FJO: Fjoh_0678
HAL: VNG1615G(mvaB)
SSA: SSA_0338(mvaS)
SSU: SSU05_1641
SSV: SSU98_1652
SGO: SGO_0244
LPL: lp_2067(mvaS)
LJO: LJ1607
LAC: LBA0628(hmcS)
LSA: LSA1484(mvaS)
LSL: LSL_0526
LDB: Ldb0881(mvaS)
LBU: LBUL_0806
LBR: LVIS_1363
LCA: LSEI_1785
LGA: LGAS_1372
LRE: Lreu_0676
PPE: PEPE_0868
EFA: EF1363
OOE: OEOE_0968
LME: LEUM_1184
NFA: nfa22120
SEN: SACE_4570(pksG)
HMA: rrnAC1740(mvaS)
HWA: HQ2868A(mvaB)
NPH: NP2608A(mvaB_1)
NP4836A(mvaB_2)

Exemplary hydroxymethylglutaryl-CoA Reductase Nucleic Acids and Polypeptides

HSA: 3156(HMGCR)
PTR: 471516(HMGCR)
MCC: 705479(HMGCR)
MMU: 15357(Hmgcr)
RNO: 25675(Hmgcr)
CFA: 479182(HMGCR)
BTA: 407159(HMGCR)
GGA: 395145(RCJMB04_14m24)
SPU: 373355(LOC373355)
DME: Dmel_CG10367(Hmgcr)
CEL: F08F8.2
OSA: 4347443
SCE: YLR450W(HMG2)
YML075C(HMG1)
AGO: AGOS_AER152W
CGR: CAGL0L11506g
SPO: SPCC162.09c(hmg1)
ANI: AN3817.2
AFM: AFUA_1G11230 AFUA_2G03700
AOR: AO090103000311 AO090120000217
CNE: CNF04830
UMA: UM03014.1
ECU: ECU10_1720
DDI: DDB_0191125(hmgA)
DDB_0215357(hmgB)
TBR: Tb927.6.4540
TCR: 506831.40 509167.20
LMA: LmjF30.3190
VCH: VCA0723
SPK: MGAS9429_Spy0742
SPA: M6_Spy0703
SPN: SP_1726
SAG: SAG1317
SAN: gbs1387
STC: str0576(mvaA)
STL: stu0576(mvaA)
STE: STER_0620
SSA: SSA_0337(mvaA)
LPL: lp_0447(mvaA)
LJO: 111608
LSL: LSL_0224
LBR: LVIS_0450
LGA: LGAS_1373

EFA: EF1364
NFA: nfa22110
VCO: VC0395_0662
VVU: VV2_0117
VVY: VVA0625
VPA: VPA0968
VFI: VFA0841
PAT: Pat1_0427
CBU: CBU_0030 CBU_0610
CBD: COXBU7E912_0151
COXBU7E912_0622(hmgA)
TCX: Tcr_1717
DNO: DNO_0797
CVI: CV_1806
SUS: Acid_5728 Acid_6132
SAU: SA2333(mvaA)
SAV: SAV2545(mvaA)
SAM: MW2466(mvaA)
SAB: SAB2419c(mvaA)
SEP: SE2109
LWE: lwe0819(mvaA)
LLA: L10433(mvaA)
LLC: LACR_1664
LLM: llmg_0931(mvaA)
SPY: SPy_0880(mvaS.1)
SPM: spyM18_0941(mvaS1)
SPG: SpyM3_0599(mvaS.1)
SPS: SPs1254
SPH: MGAS10270_Spy0744
SPI: MGAS10750_Spy0778
SPJ: MGAS2096_Spy0758
MKA: MK0355(HMG1)
AFU: AF1736(mvaA)
HAL: VNG1875G(mvaA)
HMA: rrnAC3412(mvaA)
HWA: HQ3215A(hmgR)
NPH: NP0368A(mvaA_2)
NP2422A(mvaA_1)
TAC: Ta0406m
TVO: TVN1168
PTO: PTO1143
PAB: PAB2106(mvaA)
PFU: PF1848
TKO: TK0914
RCI: RC1X1027(hmgA)
RCIX376(hmgA)
APE: APE_1869
IHO: Igni_0476

BGA: BG0708(mvaA)
SRU: SRU_2422
FPS: FP2341
MMP: MMP0087(hmgA)
MMQ: MmarC5_1589
MAC: MA3073(hmgA)
MBA: Mbar_A1972
MMA: MM_0335
MBU: Mbur_1098
MHU: Mhun_3004
MEM: Memar_2365
MBN: Mboo_0137
MTH: MTH562
MST: Msp_0584(hmgA)
MSI: Msm_0227
HBU: Hbut_1531
SSO: SSO0531
STO: ST1352
SAI: Saci_1359
PAI: PAE2182
PIS: Pisl_0814
PCL: Pcal_1085
PAS: Pars_0796

Exemplary Mevalonate Kinase Nucleic Acids and Polypeptides

HSA: 4598(MVK)
MCC: 707645(MVK)
MMU: 17855(Mvk)
RNO: 81727(Mvk)
CFA: 486309(MVK)
BTA: 505792(MVK)
GGA: 768555(MVK)
DRE: 492477(zgc:103473)
SPU: 585785(LOC585785)
DME: Dmel_CG33671
OSA: 4348331
SCE: YMR208W(ERG12)
AGO: AGOS_AER335W
PIC: PICST_40742(ERG12)
CGR: CAGL0F01861g
SPO: SPAC13G6.11c
MGR: MGG_06946
ANI: AN3869.2
AFM: AFUA_4G07780
AOR: AO090023000793
CNE: CNK01740
ECU: ECU09_1780
DDI: DDBDRAFT_0168621
TET: TTHERM_00637680
TBR: Tb927.4.4070
TCR: 436521.9 509237.10
LMA: LmjF31.0560
CBU: CBU_0608 CBU_0609
CBD: COXBU7E912_0620(mvk)
SPG: SpyM3_0595(mvaK1)
SPS: SPs1258
SPH: MGAS10270_Spy0740(mvaK1)
SPI: MGAS10750_Spy0774(mvaK1)
SPJ: MGAS2096_Spy0753(mvaK1)
SPK: MGAS9429_Spy0737(mvaK1)
SPF: SpyM51126(mvaK1)
SPA: M6_Spy0699
SPB: M28_Spy0662(mvaK1)
SPN: SP_0381
SPR: spr0338(mvk)
SPD: SPD_0346(mvk)
SAG: SAG1326
SAN: gbs1396
SAK: SAK_1357(mvk)
SMU: SMU.181
STC: str0559(mvaK1)
STL: stu0559(mvaK1)
STE: STER_0598
SSA: SSA_0333(mvaK1)
SSU: SSU05_0289
SSV: SSU98_0285
SGO: SGO_0239(mvk)
LPL: lp_1735(mvaK1)
LJO: LJ1205
LAC: LBA1167(mvaK)
LSA: LSA0908(mvaK1)
LSL: LSL_0685(eRG)

LPN: lpg2039
LPF: lp12017
LPP: lpp2022
BBA: Bd1027(1mbP) Bd1630(mvk)
MXA: MXAN_5019(mvk)
OIH: OB0225
SAU: SA0547(mvaK1)
SAV: SAV0590(mvaK1)
SAM: MW0545(mvaK1)
SAR: SAR0596(mvaK1)
SAS: SAS0549
SAC: SACOL0636(mvk)
SAB: SAB0540(mvaK1)
SAA: SAUSA300_0572(mvk)
SAO: SAOUHSC_00577
SEP: SE0361
SER: SERP0238(mvk)
SHA: SH2402(mvaK1)
SSP: SSP2122
LMO: lmo0010
LMF: LM0f2365_0011
LIN: lin0010
LWE: lwe0011(mvk)
LLA: L7866(yeaG)
LLC: LACR_0454
LLM: llmg_0425(mvk)
SPY: SPy_0876(mvaK1)
SPZ: M5005_Spy_0682(mvaK1)
SPM: spyM18_0937(mvaK1)
LCA: LSEI_1491
LGA: LGAS_1033
LRE: Lreu_0915
PPE: PEPE_0927
EFA: EF0904(mvk)
OOE: 0E0E_1100
LME: LEUM_1385
NFA: nfa22070
BGA: BG0711
BAF: BAPKO_0732
FPS: FP0313
MMP: MMP1335
MAE: Maeo_0775
MAC: MA0602(mvk)
MBA: Mbar_A1421
MMA: MM_1762
MBU: Mbur_2395
MHU: Mhun_2890
MEM: Memar_1812
MBN: Mboo_2213
MST: Msp_0858(mvk)
MSI: Msm_1439
MKA: MK0993(ERG12)
HAL: VNG1145G(mvk)
HMA: rrnAC0077(mvk)
HWA: HQ2925A(mvk)
NPH: NP2850A(mvk)
PTO: PTO1352

-continued

| | |
|---|---|
| LDB: Ldb0999(mvk) | PHO: PH1625 |
| LBU: LBUL_0906 | PAB: PAB0372(mvk) |
| LBR: LVIS_0858 | PFU: PF1637(mvk) |
| TKO: TK1474 | SAI: Saci_2365(mvk) |
| RCI: LRC399(mvk) | MSE: Msed_1602 |
| APE: APE_2439 | PAI: PAE3108 |
| HBU: Hbut_0877 | PIS: Pisl_0467 |
| SSO: SSO0383 | PCL: Pcal_1835 |
| STO: ST2185 | |

Exemplary Phosphomevalonate Kinase Nucleic Acids and Polypeptides

| | |
|---|---|
| HSA: 10654(PMVK) | SAR: SAR0598(mvaK2) |
| PTR: 457350(PMVK) | SAS: SAS0551 |
| MCC: 717014(PMVK) | SAC: SACOL0638 |
| MMU: 68603(Pmvk) | SAB: SAB0542(mvaK2) |
| CFA: 612251(PMVK) | SAA: SAUSA300_0574 |
| BTA: 513533(PMVK) | SAO: SAOUHSC_00579 |
| DME: Dmel_CG10268 | SAJ: SaurJH9_0615 |
| ATH: AT1G31910 | SEP: SE0363 |
| OSA: 4332275 | SER: SERP0240 |
| SCE: YMR220W(ERG8) | SHA: SH2400(mvaK2) |
| AGO: AGOS_AER354W | SSP: SSP2120 |
| PIC: PICST_52257(ERG8) | LMO: lmo0012 |
| CGR: CAGL0F03993g | LMF: LMOf2365_0013 |
| SPO: SPAC343.01c | LIN: lin0012 |
| MGR: MGG_05812 | LWE: lwe0013 |
| ANI: AN2311.2 | LLA: L10014(yebA) |
| AFM: AFUA_5G10680 | LLC: LACR_0456 |
| AOR: AO090010000471 | LLM: llmg_0427 |
| CNE: CNM00100 | SPY: SPy_0878(mvaK2) |
| UMA: UM00760.1 | SPZ: M5005_Spy_0684(mvaK2) |
| DDI: DDBDRAFT_0184512 | SPM: spyM18_0939 |
| TBR: Tb09.160.3690 | SPG: SpyM3_0597(mvaK2) |
| TCR: 507913.20 508277.140 | SPS: SPs1256 |
| LMA: LmjF15.1460 | SPH: MGAS10270_Spy0742(mvaK2) |
| MXA: MXAN_5017 | SPI: MGAS10750_Spy0776(mvaK2) |
| OIH: OB0227 | SPJ: MGAS2096_Spy0755(mvaK2) |
| SAU: SA0549(mvaK2) | SPK: MGAS9429_Spy0739(mvaK2) |
| SAV: SAV0592(mvaK2) | SPF: SpyM51124(mvaK2) |
| SAM: MW0547(mvaK2) | SPA: M6_Spy0701 |
| SPB: M28_Spy0664(mvaK2) | NPH: NP2852A |
| SPN: SP_0383 | SSO: SSO2988 |
| SPR: spr0340(mvaK2) | STO: ST0978 |
| SPD: SPD_0348(mvaK2) | SAI: Saci_1244 |
| SAG: SAG1324 | |
| SAN: gbs1394 | |
| SAK: SAK_1355 | |
| SMU: SMU.938 | |
| STC: str0561(mvaK2) | |
| STL: stu0561(mvaK2) | |
| STE: STER_0600 | |
| SSA: SSA_0335(mvaK2) | |
| SSU: SSU05_0291 | |
| SSV: SSU98_0287 | |
| SGO: SGO_0241 | |
| LPL: lp_1733(mvaK2) | |
| LJO: LJ1207 | |
| LAC: LBA1169 | |
| LSA: LSA0906(mvaK2) | |
| LSL: LSL_0683 | |
| LDB: Ldb0997(mvaK) | |
| LBU: LBUL_0904 | |
| LBR: LVIS_0860 | |
| LCA: LSEI_1092 | |
| LGA: LGAS_1035 | |
| LRE: Lreu_0913 | |
| PPE: PEPE_0925 | |
| EFA: EF0902 | |
| NFA: nfa22090 | |
| BGA: BG0710 | |
| BAF: BAPKO_0731 | |

Exemplary diphosphomevalonate Decarboxylase Nucleic Acids and Polypeptides

| | |
|---|---|
| HSA: 4597(MVD) | TCX: Tcr_1734 |
| PTR: 468069(MVD) | DNO: DNO_0504(mvaD) |
| MCC: 696865(MVD) | BBA: Bd1629 |
| MMU: 192156(Mvd) | MXA: MXAN_5018(mvaD) |
| RNO: 81726(Mvd) | OIH: OB0226 |
| CFA: 489663(MVD) | SAU: SA0548(mvaD) |
| GGA: 425359(MVD) | SAV: SAV0591(mvaD) |
| DME: Dmel_CG8239 | SAM: MW0546(mvaD) |
| SCE: YNR043W(MVD1) | SAR: SAR0597(mvaD) |
| AGO: AGOS_AGL232C | SAS: SAS0550 |
| PIC: PICST_90752 | SAC: SACOL0637(mvaD) |
| CGR: CAGL0C03630g | SAB: SAB0541(mvaD) |
| SPO: SPAC24C9.03 | SAA: SAUSA300_0573(mvaD) |
| MGR: MGG_09750 | SAO: SAOUHSC_00578 |
| ANI: AN4414.2 | SAJ: SaurJH9_0614 |
| AFM: AFUA_4G07130 | SAH: SaurJH1_0629 |
| AOR: AO090023000862 | SEP: SE0362 |
| CNE: CNL04950 | SER: SERP0239(mvaD) |
| UMA: UM05179.1 | SHA: SH2401(mvaD) |
| DDI: DDBDRAFT_0218058 | SSP: SSP2121 |
| TET: TTHERM_00849200 | LMO: lmo0011 |
| TBR: Tb10.05.0010 Tb10.61.2745 | LMF: LMOf2365_0012(mvaD) |
| TCR: 507993.330 511281.40 | LIN: lin0011 |
| LMA: LmjF18.0020 | LWE: lwe0012(mvaD) |
| CBU: CBU_0607(mvaD) | LLA: L9089(yeaH) |
| CBD: COXBU7E912_0619(mvaD) | LLC: LACR_0455 |
| LPN: lpg2040 | LLM: llmg_0426(mvaD) |
| LPF: lpl2018 | SPY: SPy_0877(mvaD) |
| LPP: lpp2023 | SPZ: M5005_Spy_0683(mvaD) |
| SPM: spyM18_0938(mvd) | LBR: LVIS_0859 |
| SPG: SpyM3_0596(mvaD) | LCA: LSEI_1492 |
| SPS: SPs1257 | LGA: LGAS_1034 |
| SPH: MGAS10270_Spy0741(mvaD) | LRE: Lreu_0914 |
| SPI: MGAS10750_Spy0775(mvaD) | PPE: PEPE_0926 |
| SPJ: MGAS2096_Spy0754(mvaD) | EFA: EF0903(mvaD) |
| SPK: MGAS9429_Spy0738(mvaD) | LME: LEUM_1386 |
| SPF: SpyM51125(mvaD) | NFA: nfa22080 |
| SPA: M6_Spy0700 | BBU: BB0686 |
| SPB: M28_Spy0663(mvaD) | BGA: BG0709 |
| SPN: SP_0382 | BAF: BAPKO_0730 |
| SPR: spr0339(mvd1) | GFO: GFO_3632 |
| SPD: SPD_0347(mvaD) | FPS: FP0310(mvaD) |
| SAG: SAG1325(mvaD) | HAU: Haur_1612 |
| SAN: gbs1395 | HAL: VNG0593G(dmd) |
| SAK: SAK_1356(mvaD) | HMA: rrnAC1489(dmd) |
| SMU: SMU.937 | HWA: HQ1525A(mvaD) |
| STC: str0560(mvaD) | NPH: NP1580A(mvaD) |
| STL: stu0560(mvaD) | PTO: PTO0478 PTO1356 |
| STE: STER_0599 | SSO: SSO2989 |
| SSA: SSA_0334(mvaD) | STO: ST0977 |
| SSU: SSU05_0290 | SAI: Saci_1245(mvd) |
| SSV: SSU98_0286 | MSE: Msed_1576 |
| SGO: SGO_0240(mvaD) | |
| LPL: lp_1734(mvaD) | |
| LJO: LJ1206 | |
| LAC: LBA1168(mvaD) | |
| LSA: LSA0907(mvaD) | |
| LSL: LSL_0684 | |
| LDB: Ldb0998(mvaD) | |
| LBU: LBUL_0905 | |

Exemplary Isopentenyl Phosphate Kinases (IPK) Nucleic Acids and Polypeptides
*Methanobacterium thermoautotrophicum* gi|2621082
*Methanococcus jannaschii* DSM 2661 gi|1590842;
*Methanocaldococcus jannaschii* gi|1590842
*Methanothermobacter thermautotrophicus* gi|2621082
*Picrophilus torridus* DSM9790 (IG-57) gi|48477569
*Pyrococcus abyssi* gi|14520758
*Pyrococcus horikoshii* OT3 gi|3258052
*Archaeoglobus fulgidus* DSM4304 gi|2648231
Exemplary isopentenyl-diphosphate Delta-isomerase (IDI) Nucleic Acids and Polypeptides HSA: 3422(IDI1) 91734(IDI2)
PTR: 450262(IDI2) 450263(IDI1)
MCC: 710052(LOC710052) 721730(LOC721730)
MMU: 319554(Idi1)
RNO: 89784(Idi1)
GGA: 420459(IDI1)
XLA: 494671(LOC494671)
XTR: 496783(idi2)
SPU: 586184(LOC586184)
CEL: K06H7.9(idi-1)
ATH: AT3G02780(IPP2)
OSA: 4338791 4343523
CME: CMB062C
SCE: YPL117C(IDI1)
AGO: AGOS_ADL268C
PIC: PICST_68990(IDI1)
CGR: CAGL0J06952g
SPO: SPBC106.15(idi1)
ANI: AN0579.2
AFM: AFUA_6G11160
AOR: AO090023000500
CNE: CNA02550
UMA: UM04838.1
ECU: ECU02_0230
DDI: DDB_0191342(ipi)
TET: TTHERM_00237280 TTHERM_00438860
TBR: Tb09.211.0700
VFI: VF0403
PPR: PBPRA0469(mvaD)
PEN: PSEEN4850
CBU: CBU_0607(mvaD)
CBD: COXBU7E912_0619(mvaD)
LPN: lpg2051
LPF: lpl2029
LPP: lpp2034
TCX: Tcr_1718
HHA: Hhal_1623
DNO: DNO_0798
EBA: ebA5678 p2A143
DVU: DVU1679(idi)
DDE: Dde_1991
LIP: LI1134
BBA: Bd1626
AFW: Anae109_4082
MXA: MXAN_5021(fni)
RPR: RP452
RTY: RT0439(idi)
RCO: RC0744
RFE: RF_0785(fni)
RBE: RBE_0731(fni)
RAK: A1C_04190
RBO: A1I_04755
RCM: A1E_02555
RRI: A1G_04195
MLO: mlr6371
RET: RHE_PD00245(ypd00046)
XAU: Xaut_4134
SIL: SPO0131
SAO: SAOUHSC_02623
SEP: SE1925
SER: SERP1937(fni-2)
SHA: SH0712(fni)
SSP: SSP0556
LMO: lmo1383
LMF: LMOf2365_1402(fni)
LIN: lin1420
LWE: lwe1399(fni)
LLA: L11083(yebB)
LLC: LACR_0457
LLM: llmg_0428(fni)
SPY: SPy_0879
SPZ: M5005_Spy_0685
SPM: spyM18_0940
SPG: SpyM3_0598
SPS: SPs1255
SPH: MGAS10270_Spy0743
SPI: MGAS10750_Spy0777
SPJ: MGAS2096_Spy0756
TCR: 408799.19 510431.10
LMA: LmjF35.5330
EHI: 46.t00025
ECO: b2889(idi)
ECJ: JW2857(idi)
ECE: Z4227
ECS: ECs3761
ECC: c3467
ECI: UTI89_C3274
ECP: ECP_2882
ECV: APECO1_3638
ECW: EcE24377A_3215(idi)
ECX: EcHS_A3048
STY: STY3195
STT: t2957
SPT: SPA2907(idi)
SEC: SC2979(idi)
STM: STM3039(idi)
SFL: SF2875(idi)
SFX: S3074
SFV: SFV_2937
SSN: SSON_3042
SSON_3489(yhfK)
SBO: SBO_3103
SDY: SDY_3193
ECA: ECA2789
PLU: plu3987
ENT: Ent638_3307
SPE: Spro_2201
VPA: VPA0278
SIT: TM1040_3442
RSP: RSP_0276
RSH: Rsph17029_1919
RSQ: Rsph17025_1019
JAN: Jann_0168
RDE: RD1_0147(idi)
DSH: Dshi_3527
BSU: BG11440(ypgA)
BAN: BA1520
BAR: GBAA1520
BAA: BA_2041
BAT: BAS1409
BCE: BC1499
BCA: BCE_1626
BCZ: BCZK1380(fni)
BCY: Bcer98_1222
BTK: BT9727_1381(fni)
BTL: BALH_1354
BLI: BL02217(fni)
BLD: BLi02426
BAY: RBAM_021020(fni)
BPU: BPUM_2020(fni)
OIH: OB0537
SAU: SA2136(fni)
SAV: SAV2346(fni)
SAM: MW2267(fni)
SAR: SAR2431(fni)
SAS: SAS2237
SAC: SACOL2341(fni)
SAB: SAB2225c(fni)
SAA: SAUSA300_2292(fni)
STC: str0562(idi)
STL: stu0562(idi)
STE: STER_0601
SSA: SSA_0336
SGO: SGO_0242
LPL: lp_1732(idi1)
LJO: LJ1208
LAC: LBA1171
LSA: LSA0905(idi)
LSL: LSL_0682
LDB: Ldb0996(fni)
LBU: LBUL_0903
LBR: LVIS_0861
LCA: LSEI_1493
LGA: LGAS_1036
LRE: Lreu_0912
EFA: EF0901
OOE: OEOE_1103
STH: STH1674
SPK: MGAS9429_Spy0740
SPF: SpyM51123(fni)
SPA: M6_Spy0702
SPB: M28_Spy0665
SPN: SP_0384
SPR: spr0341(fni)
SPD: SPD_0349(fni)
SAG: SAG1323
SAN: gbs1393
SAK: SAK_1354(fni)
SMU: SMU.939
MUL: MUL_0380(idi2)
MVA: Mvan_1582 Mvan_2176
MGI: Mflv_1842 Mflv_4187
MMC: Mmcs_1954
MKM: Mkms_2000
MJL: Mjls_1934
CGL: NCgl2223(cgl2305)
CGB: cg2531(idi)
CEF: CE2207
CDI: D1P1730(idi)
NFA: nfa19790 nfa22100
RHA: RHA1_ro00239
SCO: SCO6750(SC5F2A.33c)
SMA: SAV1663(idi)
LXX: Lxx23810(idi)
CMI: CMM_2889(idiA)
AAU: AAur_0321(idi)
PAC: PPA2115
FRA: Francci3_4188
FRE: Franean1_5570
FAL: FRAAL6504(idi)
KRA: Krad_3991
SEN: SACE_2627(idiB_2)
SACE_5210(idi)
STP: Strop_4438
SAQ: Sare_4564 Sare_4928
RXY: Rxyl_0400
BBU: BB0684
BGA: BG0707
SYN: sll1556
SYC: syc2161_c
SYF: Synpcc7942_1933
MBA: Mbar_A1419
MMA: MM_1764
MBU: Mbur_2397
MTP: Mthe_0474
MHU: Mhun_2888
MLA: Mlab_1665
MEM: Memar_1814
MBN: Mboo_2211
MTH: MTH48
MST: Msp_0856(fni)
MSI: Msm_1441
MKA: MK0776(lldD)
AFU: AF2287
HAL: VNG1818G(idi)
VNG6081G(crt_1)
VNG6445G(crt_2)
VNG7060 VNG7149
HMA: rrnAC3484(idi)
HWA: HQ2772A(idiA)
HQ2847A(idiB)
NPH: NP0360A(idiB_1)
NP4826A(idiA)
NP5124A(idiB_2)
TAC: Ta0102
TVO: TVN0179
PTO: PTO0496
PHO: PH1202
PAB: PAB1662
PFU: PF0856
TKO: TK1470
CBE: Cbei_3081
DRM: Dred_0474
SWO: Swol_1341
MTA: Moth_1328
MTU: Rv1745c(idi)
MTC: MT1787(idi)
MBO: Mb1774c(idi)
MBB: BCG_1784c(idi)
MPA: MAP3079c
MAV: MAV_3894(fni)
MSM: MSMEG_1057(fni)
MSMEG_2337(fni)
CYA: CYA_2395(fni)
CYB: CYB_2691(fni)
TEL: tll1403
ANA: all4591
AVA: Ava_2461 Ava_B0346
TER: Tery_1589
SRU: SRU_1900(idi)
CHU: CHU_0674(idi)
GFO: GFO_2363(idi)
FJO: Fjoh_0269
FPS: FP1792(idi)
CTE: CT0257
CCH: Cag_1445
CPH: Cpha266_0385
PVI: Cvib_1545
PLT: Plut_1764
RRS: RoseRS_2437
RCA: Rcas_2215
HAU: Haur_4687
DRA: DR_1087
DGE: Dgeo_1381
TTH: TT_P0067
TTJ: TTHB110
MJA: MJ0862
MMP: MMP0043
MMQ: MmarC5_1637
MMX: MmarC6_0906
MMZ: MmarC7_1040
MAE: Maeo_1184
MVN: Mevan_1058
MAC: MA0604(idi)
SSO: SSO0063
STO: ST2059
SAI: Saci_0091
MSE: Msed_2136
PAI: PAE0801
PIS: Pisl_1093
PCL: Pcal_0017
PAS: Pars_0051
TPE: Tpen_0272

| | | |
|---|---|---|
| RCI: LRC397(fni) | | |
| APE: APE_1765.1 | | |
| SMR: Smar_0822 | | |
| IHO: Igni_0804 | | |
| HBU: Hbut_0539 | | |

Exemplary Isoprene Synthase Nucleic Acids and Polypeptides
Genbank Accession Nos.
AY341431
AY316691
AY279379
AJ457070
AY182241

We claim:

1. A method of producing isoprene, the method comprising
(a) culturing recombinant cells in culture medium for the production of isoprene, wherein said culture medium comprises a prenyl derivative of Formula (I):

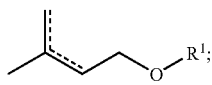

wherein $R^1$ is hydrogen or —C(O)$R^2$; and $R^2$ is a C1-C5 linear or branched alkyl; and wherein said recombinant cells comprise:
(i) a heterologous nucleic acid that encodes an isoprene synthase polypeptide in operable combination with a promoter,
(ii) nucleic acids encoding all of the polypeptides of the mevalonate (MVA) pathway, and
(iii) a heterologous gene encoding a polypeptide having prenol kinase activity; and
(b) recovering said isoprene.

2. The method of claim 1, wherein the cells are bacterial cells or yeast cells.

3. The method of claim 1, wherein the cells are selected from the group consisting of *Escherichia coli, Pantoea citrea, Bacillus subtilis, Trichoderma reesei, Yarrowia lipolytica*, and *Saccharomyces cerevisiae*.

4. The method of claim 1, wherein the prenyl derivative comprises one or more of prenol (3-methyl-2-buten-1-ol), isoprenol (3-methyl-3-buten-1-ol), 3-methyl-3-buten-1-yl acetate, and 3-methyl-2-buten-1-yl acetate.

5. The method of claim 1, wherein the cells further comprise one or more of an isopentenyl-diphosphate delta-isomerase (IDI) polypeptide and a non-mevalonate (DXP) pathway enzyme.

6. The method of claim 1, wherein the cells further comprise an isopentenyl-diphosphate delta-isomerase (IDI) polypeptide.

7. The method of claim 1 wherein the cells further comprise an endogenous gene encoding a polypeptide having prenol kinase activity.

8. The method of claim 1, wherein said nucleic acids encoding the polypeptides of the mevalonate (MVA) pathway are encoded by heterologous nucleic acids.

9. The method of claim 1, wherein said nucleic acids encoding the polypeptides of the mevalonate (MVA) pathway are encoded by endogenous nucleic acids.

10. The method of claim 1, wherein $R^1$ is hydrogen.

11. The method of claim 1, wherein the cells are selected from the group consisting of *Escherichia coli, Trichoderma reesei, Yarrowia lipolytica*, and *Saccharomyces cerevisiae*.

12. The method of claim 1, wherein the polypeptides of the MVA pathway comprise acetyl-CoA acetyltransferase (AACT), HMG-CoA synthase (HMGS), HMG-CoA reductase (HMGR), mevalonate kinase (MVK), phosphomevalonate kinase (PMK), and diphosphomevalonate decarboxylase (MVD).

13. The method of claim 1, wherein the polypeptides of the mevalonate (MVA) pathway comprise acetyl-CoA acetyltransferase (AACT), HMG-CoA synthase (HMGS), HMG-CoA reductase (HMGR), mevalonate kinase (MVK), phosphomevalonate decarboxylase (PMDC), and isopentenyl phosphate kinase (IPK).

14. The method of claim 8, wherein one or more vectors comprise the heterologous nucleic acids of the MVA pathway.

\* \* \* \* \*

SEQUENCE LISTING

<160> NUMBER OF SEQ ID NOS: 114

<210> SEQ ID NO 1
<211> LENGTH: 1701
<212> TYPE: DNA
<213> ORGANISM: Artificial Sequence
<220> FEATURE:
<223> OTHER INFORMATION: Synthetic Construct

<400> SEQUENCE: 1

```
atgtgtgcga cctcttctca atttactcag attaccgagc ataattcccg tcgttccgca      60
aactatcagc caaacctgtg gaatttcgaa ttcctgcaat ccctggagaa cgacctgaaa     120
gtggaaaagc tggaggagaa agcgaccaaa ctggaggaag aagttcgctg catgatcaac     180
cgtgtagaca cccagccgct gtccctgctg gagctgatcg acgatgtgca gcgcctgggt     240
ctgacctaca atttgaaaa agacatcatt aaagccctgg aaaacatcgt actgctggac     300
gaaaacaaaa agaacaaatc tgacctgcac gcaaccgctc tgtctttccg tctgctgcgt     360
cagcacggtt tcgaggtttc tcaggatgtt tttgagcgtt tcaaggataa agaaggtggt     420
ttcagcggtg aactgaaagg tgacgtccaa ggcctgctga gcctgtatga agcgtcttac     480
ctgggtttcg agggtgagaa cctgctggag gaggcgcgta ccttttccat cacccacctg     540
aagaacaacc tgaaagaagg cattaatacc aaggttgcag aacaagtgag ccacgccctg     600
gaactgccat atcaccagcg tctgcaccgt ctggaggcac gttggttcct ggataaatac     660
gaaccgaaag aaccgcatca ccagctgctg ctggagctgg cgaagctgga ttttaacatg     720
gtacagaccc tgcaccagaa agagctgcaa gatctgtccc gctggtggac cgagatgggc     780
ctggctagca aactggattt tgtacgcgac cgcctgatgg aagtttattt ctgggcactg     840
ggtatggcgc cagacccgca gtttggtgaa tgtcgcaaag ctgttactaa aatgtttggt     900
ctggtgacga tcatcgatga cgtgtatgac gtttatggca ctctggacga actgcaactg     960
ttcaccgatg ctgtagagcg ctgggacgtt aacgctatta cacccctgcc ggactatatg    1020
aaactgtgtt tcctggcact gtacaacacc gttaacgaca cgtcctattc tattctgaaa    1080
gagaaaggtc ataacaacct gtcctatctg acgaaaagct ggcgtgaact gtgcaaagcc    1140
tttctgcaag aggcgaaatg gtccaacaac aaaattatcc cggcttttct caagtacctg    1200
gaaaacgcca gcgtttcctc ctccggtgta gcgctgctgg cgccgtctta cttttccgta    1260
tgccagcagc aggaagacat ctccgaccac gcgctgcgtt ccctgaccga cttccatggt    1320
ctggtgcgtt ctagctgcgt tatcttccgc ctgtgcaacg atctggccac ctctgcggcg    1380
gagctggaac gtggcgagac taccaattct atcattagct acatgcacga aaacgatggt    1440
accagcgagg aacaggcccg cgaagaactg cgtaaactga tcgacgccga atggaaaaag    1500
atgaatcgtg aacgcgttag cgactccacc ctgctgccta aagcgttcat ggaaatcgca    1560
gttaacatgg cacgtgtttc ccactgcacc taccagtatg cgatggctct gggtcgccca    1620
gactacgcga ctgaaaaccg catcaaactg ctgctgattg accctttccc gattaaccag    1680
```
ctgatgtatg tctaactgca g                                             1701

<210> SEQ ID NO 2
<211> LENGTH: 6080
<212> TYPE: DNA
<213> ORGANISM: Artificial Sequence
<220> FEATURE:
<223> OTHER INFORMATION: Synthetic Construct

<400> SEQUENCE: 2

```
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatgtgtgc     420
gacctcttct caatttactc agattaccga gcataattcc cgtcgttccg caaactatca     480
gccaaacctg tggaatttcg aattcctgca atccctggag aacgacctga agtggaaaa     540
gctggaggag aaagcgacca aactggagga agaagttcgc tgcatgatca accgtgtaga     600
cacccagccg ctgtccctgc tggagctgat cgacgatgtg cagcgcctgg gtctgaccta     660
caaatttgaa aaagacatca ttaaagccct ggaaaacatc gtactgctgg acgaaaacaa     720
aaagaacaaa tctgacctgc acgcaaccgc tctgtctttc cgtctgctgc gtcagcacgg     780
tttcgaggtt tctcaggatg ttttttgagcg tttcaaggat aaagaaggtg gtttcagcgg     840
tgaactgaaa ggtgacgtcc aaggcctgct gagcctgtat gaagcgtctt acctgggttt     900
cgagggtgag aacctgctgg aggaggcgcg tacctttttcc atcacccacc tgaagaacaa     960
cctgaaagaa ggcattaata ccaaggttgc agaacaagtg agccacgccc tggaactgcc    1020
atatcaccag cgtctgcacc gtctggaggc acgttggttc ctggataaat acgaaccgaa    1080
agaaccgcat caccagctgc tgctggagct ggcgaagctg gattttaaca tggtacagac    1140
cctgcaccag aaaagagctgc aagatctgtc ccgctggtgg accgagatgg gcctggctag    1200
caaactggat tttgtacgcg accgcctgat ggaagtttat ttctgggcac tgggtatggc    1260
gccagacccg cagtttggtg aatgtcgcaa agctgttact aaaatgtttg gtctggtgac    1320
gatcatcgat gacgtgtatg acgtttatgg cactctggac gaactgcaac tgttcaccga    1380
tgctgtagag cgctgggacg ttaacgctat taacaccctg ccggactata tgaaactgtg    1440
tttcctggca ctgtacaaca ccgttaacga cacgtcctat tctattctga agagaaagg    1500
tcataacaac ctgtcctatc tgacgaaaag ctggcgtgaa ctgtgcaaag cctttctgca    1560
agaggcgaaa tggtccaaca caaaattat cccggctttc tccaagtacc tggaaaacgc    1620
cagcgttttcc tcctcggtg tagcgctgct ggcgccgtct tacttttccg tatgccagca    1680
gcaggaagac atctccgacc acgcgctgcg ttccctgacc gacttccatg gtctggtgcg    1740
ttctagctgc gttatcttcc gcctgtgcaa cgatctggcc acctctgcgg cggagctgga    1800
acgtggcgag actaccaatt ctatcattag ctacatgcac gaaaacgatg gtaccagcga    1860
ggaacaggcc cgcgaagaac tgcgtaaact gatcgacgcc gaatggaaa agatgaatcg    1920
tgaacgcgtt agcgactcca ccctgctgcc taaagcgttc atggaaatcg cagttaacat    1980
ggcacgtgtt tcccactgca cctaccagta tggcgatggt ctgggtcgcc cagactacgc    2040
```

```
gactgaaaac cgcatcaaac tgctgctgat tgacccttc  ccgattaacc agctgatgta    2100
tgtctaactg cagctggtac catatgggaa ttcgaagctt tctagaacaa aaactcatct   2160
cagaagagga tctgaatagc gccgtcgacc atcatcatca tcatcattga gtttaaacgg   2220
tctccagctt ggctgttttg gcggatgaga aagattttc  agcctgatac agattaaatc   2280
agaacgcaga agcggtctga taaaacagaa tttgcctggc ggcagtagcg cggtggtccc   2340
acctgacccc atgccgaact cagaagtgaa acgccgtagc gccgatggta gtgtggggtc   2400
tccccatgcg agagtaggga actgccaggc atcaaataaa acgaaaggct cagtcgaaag   2460
actgggcctt tcgttttatc tgttgtttgt cggtgaacgc tctcctgagt aggacaaatc   2520
cgccgggagc ggatttgaac gttgcgaagc aacggcccgg agggtggcgg caggacgcc   2580 cgccataaac tgccaggcat caaattaagc agaaggccat cctgacggat ggcctttttg   2640
cgtttctaca aactcttttt gtttattttt ctaaatacat tcaaatatgt atccgctcat   2700
gagacaataa ccctgataaa tgcttcaata atattgaaaa aggaagagta tgagtattca   2760
acatttccgt gtcgccctta ttcccttttt tgcggcattt tgccttcctg tttttgctca   2820
cccagaaacg ctggtgaaag taaaagatgc tgaagatcag ttgggtgcac gagtgggtta   2880
catcgaactg gatctcaaca gcggtaagat ccttgagagt tttcgccccg aagaacgttt   2940
tccaatgatg agcactttta aagttctgct atgtggcgcg gtattatccc gtgttgacgc   3000
cgggcaagag caactcggtc gccgcataca ctattctcag aatgacttgg ttgagtactc   3060
accagtcaca gaaaagcatc ttacggatgg catgacagta agagaattat gcagtgctgc   3120
cataaccatg agtgataaca ctgcggccaa cttacttctg acaacgatcg gaggaccgaa   3180
ggagctaacc gcttttttgc acaacatggg ggatcatgta actcgccttg atcgttggga   3240
accggagctg aatgaagcca taccaaacga cgagcgtgac accacgatgc ctgtagcaat   3300
ggcaacaacg ttgcgcaaac tattaactgg cgaactactt actctagctt cccggcaaca   3360
attaatagac tggatggagg cggataaagt tgcaggacca cttctgcgct cggcccttcc   3420
ggctggctgg tttattgctg ataaatctgg agccggtgag cgtgggtctc gcggtatcat   3480
tgcagcactg gggccagatg gtaagccctc ccgtatcgta gttatctaca cgacggggag   3540
tcaggcaact atggatgaac gaaatagaca gatcgctgag ataggtgcct cactgattaa   3600
gcattggtaa ctgtcagacc aagtttactc atatatactt tagattgatt taaaacttca   3660
tttttaattt aaaaggatct aggtgaagat cctttttgat aatctcatga ccaaaatccc   3720
ttaacgtgag ttttcgttcc actgagcgtc agaccccgta gaaaagatca aaggatcttc   3780
ttgagatcct ttttttctgc gcgtaatctg ctgcttgcaa acaaaaaaac caccgctacc   3840
agcggtggtt tgtttgccgg atcaagagct accaactctt tttccgaagg taactggctt   3900
cagcagagcg cagataccaa atactgtcct tctagtgtag ccgtagttag gccaccactt   3960
caagaactct gtagcaccgc ctacatacct cgctctgcta atcctgttac cagtggctgc   4020
tgccagtggc gataagtcgt gtcttaccgg gttggactca agacgatagt taccggataa   4080
ggcgcagcgg tcgggctgaa cggggggttc gtgcacacag cccagcttgg agcgaacgac   4140
ctacaccgaa ctgagatacc tacagcgtga gctatgagaa agcgccacgc ttcccgaagg   4200
gagaaaggcg gacaggtatc cggtaagcgg cagggtcgga acaggagagc gcacgaggga   4260
gcttccaggg ggaaacgcct ggtatcttta tagtcctgtc gggtttcgcc acctctgact   4320
tgagcgtcga ttttgtgat  gctcgtcagg ggggcggagc ctatggaaaa acgccagcaa   4380
cgcggccttt ttacggttcc tggccttttg ctggcctttt gctcacatgt tctttcctgc   4440
```

```
gttatcccct gattctgtgg ataaccgtat taccgccttt gagtgagctg ataccgctcg   4500
ccgcagccga acgaccgagc gcagcgagtc agtgagcgag gaagcggaag agcgcctgat   4560
gcggtatttt ctccttacgc atctgtgcgg tatttcacac cgcatatggt gcactctcag   4620
tacaatctgc tctgatgccg catagttaag ccagtataca ctccgctatc gctacgtgac   4680
tgggtcatgg ctgcgccccg acacccgcca cacccgctg acgcgccctg acgggcttgt    4740
ctgctcccgg catccgctta cagacaagct gtgaccgtct ccgggagctg catgtgtcag   4800
aggttttcac cgtcatcacc gaaacgcgcg aggcagcaga tcaattcgcg cgcgaaggcg   4860
aagcggcatg catttacgtt gacaccatcg aatggtgcaa aacctttcgc ggtatggcat   4920
gatagcgccc ggaagagagt caattcaggg tggtgaatgt gaaaccagta acgttatacg   4980
atgtcgcaga gtatgccggt gtctcttatc agaccgtttc ccgcgtggtg aaccaggcca   5040
gccacgtttc tgcgaaaacg cgggaaaaag tggaagcggc gatggcggag ctgaattaca   5100
ttcccaaccg cgtggcacaa caactggcgg gcaaacagtc gttgctgatt ggcgttgcca   5160
cctccagtct ggccctgcac gcgccgtcgc aaattgtcgc ggcgattaaa tctcgcgccg   5220
atcaactggg tgccagcgtg gtggtgtcga tggtagaacg aagcggcgtc gaagcctgta   5280
aagcggcggt gcacaatctt ctcgcgcaac gcgtcagtgg gctgatcatt aactatccgc   5340
tggatgacca ggatgccatt gctgtggaag ctgcctgcac taatgttccg gcgttatttc   5400
ttgatgtctc tgaccagaca cccatcaaca gtattatttt ctcccatgaa gacggtacgc   5460
gactgggcgt ggagcatctg gtcgcattgg gtcaccagca aatcgcgctg ttagcgggcc   5520
cattaagttc tgtctcggcg cgtctgcgtc tggctggctg gcataaatat ctcactcgca   5580
atcaaattca gccgatagcg gaacgggaag gcgactggag tgccatgtcc ggttttcaac   5640
aaaccatgca aatgctgaat gagggcatcg ttcccactgc gatgctggtt gccaacgatc   5700
agatggcgct gggcgcaatg cgcgccatta ccgagtccgg gctgcgcgtt ggtgcggata   5760
tctcggtagt gggatacgac gataccgaag acagctcatg ttatatcccg ccgtcaacca   5820
ccatcaaaca ggattttcgc ctgctggggc aaaccagcgt ggaccgcttg ctgcaactct   5880
ctcagggcca ggcggtgaag ggcaatcagc tgttgcccgt ctcactggtg aaaagaaaaa   5940
ccaccctggc gcccaatacg caaaccgcct ctccccgcgc gttggccgat tcattaatgc   6000
agctggcacg acaggtttcc cgactggaaa gcgggcagtg agcgcaacgc aattaatgtg   6060
agttagcgcg aattgatctg                                              6080
```

<210> SEQ ID NO 3
<211> LENGTH: 37
<212> TYPE: DNA
<213> ORGANISM: Artificial Sequence
<220> FEATURE:
<223> OTHER INFORMATION: Synthetic Construct

<400> SEQUENCE: 3
cgtgagatca tatgtgtgcg acctcttctc aatttac                             37

<210> SEQ ID NO 4
<211> LENGTH: 38
<212> TYPE: DNA
<213> ORGANISM: Artificial Sequence
<220> FEATURE:
<223> OTHER INFORMATION: Synthetic Construct

<400> SEQUENCE: 4
cggtcgacgg atccctgcag ttagacatac atcagctg                            38

<210> SEQ ID NO 5
<211> LENGTH: 7404
<212> TYPE: DNA
<213> ORGANISM: Artificial Sequence
<220> FEATURE:
<223> OTHER INFORMATION: Synthetic Construct

<400> SEQUENCE: 5

| | | | | | |
|---|---|---|---|---|---|
| ttctcatgtt | tgacagctta | tcatcgataa | gctttaatgc | ggtagtttat | cacagttaaa | 60 |
| ttgctaacgc | agtcaggcac | cgtgtatgaa | atctaacaat | gcgctcatcg | tcatcctcgg | 120 |
| caccgtcacc | ctggatgctg | taggcatagg | cttggttatg | ccggtactgc | cgggcctctt | 180 |
| gcgggatatc | cggatatagt | tcctcctttc | agcaaaaaac | ccctcaagac | ccgtttagag | 240 |
| gccccaaggg | gttatgctag | ttattgctca | gcggtggcag | cagccaactc | agcttccttt | 300 |
| cgggctttgt | tagcagccgg | atccctgcag | ttagacatac | atcagctggt | taatcgggaa | 360 |
| agggtcaatc | agcagcagtt | tgatgcggtt | ttcagtcgcg | tagtctgggc | gacccagacc | 420 |
| atcgccatac | tggtaggtgc | agtgggaaac | acgtgccatg | ttaactgcga | tttccatgaa | 480 |
| cgctttaggc | agcagggtgg | agtcgctaac | gcgttcacga | ttcatctttt | tccattcggc | 540 |
| gtcgatcagt | ttacgcagtt | cttcgcgggc | ctgttcctcg | ctggtaccat | cgttttcgtg | 600 |
| catgtagcta | atgatagaat | tggtagtctc | gccacgttcc | agctccgccg | cagaggtggc | 660 |
| cagatcgttg | cacaggcgga | agataacgca | gctagaacgc | accagaccat | ggaagtcggt | 720 |
| cagggaacgc | agcgcgtggt | cggagatgtc | ttcctgctgc | tggcatacgg | aaaagtaaga | 780 |
| cggcgccagc | agcgctacac | cggaggagga | aacgctggcg | ttttccaggt | acttggagaa | 840 |
| agccgggata | attttgttgt | tggaccattt | cgcctcttgc | agaaaggctt | tgcacagttc | 900 |
| acgccagctt | ttcgtcagat | aggacaggtt | gttatgacct | ttctctttca | gaatagaata | 960 |
| ggacgtgtcg | ttaacggtgt | tgtacagtgc | caggaaacac | agtttcatat | agtccggcag | 1020 |
| ggtgttaata | gcgttaacgt | cccagcgctc | tacagcatcg | gtgaacagtt | gcagttcgtc | 1080 |
| cagagtgcca | taaacgtcat | acacgtcatc | gatgatcgtc | accagaccaa | acattttagt | 1140 |
| aacagctttg | cgacattcac | caaactgcgg | gtctggcgcc | atacccagtg | cccagaaata | 1200 |
| aacttccatc | aggcggtcgc | gtacaaaatc | cagtttgcta | gccaggccca | tctcggtcca | 1260 |
| ccagcgggac | agatcttgca | gctctttctg | gtgcagggtc | tgtaccatgt | taaaatccag | 1320 |
| cttcgccagc | tccagcagca | gctggtgatg | cggttctttc | ggttcgtatt | tatccaggaa | 1380 |
| ccaacgtgcc | tccagacggt | gcagacgctg | gtgatatggc | agttccaggg | cgtggctcac | 1440 |
| ttgttctgca | accttggtat | taatgccttc | tttcaggttg | ttcttcaggt | gggtgatgga | 1500 |
| aaaggtacgc | gcctcctcca | gcaggttctc | accctcgaaa | cccaggtaag | acgcttcata | 1560 |
| caggctcagc | aggccttgga | cgtcaccttt | cagttcaccg | ctgaaaccac | cttctttatc | 1620 |
| cttgaaacgc | tcaaaaacat | cctgagaaac | ctcgaaaccg | tgctgacgca | gcagacggaa | 1680 |
| agacagagcg | gttgcgtgca | ggtcagattt | gttcttttg | ttttcgtcca | gcagtacgat | 1740 |
| gttttccagg | gctttaatga | tgtcttttc | aaatttgtag | gtcagaccca | ggcgctgcac | 1800 |
| atcgtcgatc | agctccagca | gggacagcgg | ctgggtgtct | acacggttga | tcatgcagcg | 1860 |
| aacttcttcc | tccagtttgg | tcgctttctc | ctccagcttt | tccactttca | ggtcgttctc | 1920 |
| cagggattgc | aggaattcga | aattccacag | gtttggctga | tagtttgcgg | aacgacggga | 1980 |
| attatgctcg | gtaatctgag | taaattgaga | agaggtcgca | cacatatgac | gaccttcgat | 2040 |
| atggccgctg | ctgtgatgat | gatgatgatg | atgatgatga | tggcccatgg | tatatctcct | 2100 |

```
tcttaaagtt aaacaaaatt atttctagag gggaattgtt atccgctcac aattcccta    2160
tagtgagtcg tattaatttc gcgggatcga gatctcgatc ctctacgccg gacgcatcgt   2220
ggccggcatc accggcgcca caggtgcggt tgctggcgcc tatatcgccg acatcaccga   2280
tggggaagat cgggctcgcc acttcgggct catgagcgct tgtttcggcg tgggtatggt   2340
ggcaggcccc gtggccgggg gactgttggg cgccatctcc ttgcatgcac cattccttgc   2400
ggcggcggtg ctcaacggcc tcaacctact actgggctgc ttcctaatgc aggagtcgca   2460
taagggagag cgtcgagatc ccggacacca tcgaatggcg caaaaccttt cgcggtatgg   2520
catgatagcg cccggaagag agtcaattca gggtggtgaa tgtgaaacca gtaacgttat   2580
acgatgtcgc agagtatgcc ggtgtctctt atcagaccgt ttcccgcgtg gtgaaccagg   2640
ccagccacgt ttctgcgaaa acgcgggaaa aagtggaagc ggcgatggcg gagctgaatt   2700
acattcccaa ccgcgtggca caacaactgg cgggcaaaca gtcgttgctg attggcgttg   2760
ccacctccag tctggccctg cacgcgccgt cgcaaattgt cgcggcgatt aaatctcgcg   2820
ccgatcaact gggtgccagc gtggtggtgt cgatggtaga acgaagcggc gtcgaagcct   2880
gtaaagcggc ggtgcacaat cttctcgcgc aacgcgtcag tgggctgatc attaactatc   2940
cgctggatga ccaggatgcc attgctgtgg aagctgcctg cactaatgtt ccggcgttat   3000
ttcttgatgt ctctgaccag acacccatca acagtattat tttctcccat gaagacggta   3060
cgcgactggg cgtggagcat ctggtcgcat tgggtcacca gcaaatcgcg ctgttagcgg   3120
gcccattaag ttctgtctcg gcgcgtctgc gtctggctgg ctggcataaa tatctcactc   3180
gcaatcaaat tcagccgata gcggaacggg aaggcgactg gagtgccatg tccggttttc   3240
aacaaaccat gcaaatgctg aatgagggca tcgttcccac tgcgatgctg gttgccaacg   3300
atcagatggc gctgggcgca atgcgcgcca ttaccgagtc cgggctgcgc gttggtgcgg   3360
atatctcggt agtgggatac gacgataccg aagacagctc atgttatatc ccgccgttaa   3420
ccaccatcaa acaggatttt cgcctgctgg ggcaaaccag cgtggaccgc ttgctgcaac   3480
tctctcaggg ccaggcggtg aagggcaatc agctgttgcc cgtctcactg gtgaaaagaa   3540
aaaccaccct ggcgcccaat acgcaaaccg cctctccccg cgcgttggcc gattcattaa   3600
tgcagctggc acgacaggtt tcccgactgg aaagcgggca gtgagcgcaa cgcaattaat   3660
gtaagttagc tcactcatta ggcaccggga tctcgaccga tgcccttgag agccttcaac   3720
ccagtcagct ccttccggtg ggcgcggggc atgactatcg tcgccgcact tatgactgtc   3780
ttctttatca tgcaactcgt aggacaggtg ccggcagcgc tctgggtcat tttcggcgag   3840
gaccgctttc gctggagcgc gacgatgatc ggcctgtcgc ttgcggtatt cggaatcttg   3900
cacgccctcg ctcaagcctt cgtcactggt cccgccacca aacgtttcgg cgagaagcag   3960
gccattatcg ccggcatggc ggccgacgcg ctgggctacg tcttgctggc gttcgcgacg   4020
cgaggctgga tggccttccc cattatgatt cttctcgctt ccggcggcat cgggatgccc   4080
gcgttgcagg ccatgctgtc caggcaggta gatgacgacc atcagggaca gcttcaagga   4140
tcgctcgcgg ctcttaccag cctaacttcg atcactggac cgctgatcgt cacggcgatt   4200
tatgccgcct cggcgagcac atggaacggg ttggcatgga ttgtaggcgc cgccctatac   4260
cttgtctgcc tccccgcgtt gcgtcgcggt gcatggagcc gggccacctc gacctgaatg   4320
gaagccggcg gcacctcgct aacggattca ccactccaag aattggagcc aatcaattct   4380
tgcggagaac tgtgaatgcg caaaccaacc cttggcagaa catatccatc gcgtccgcca   4440
tctccagcag ccgcacgcgg cgcatctcgg gcagcgttgg gtcctggcca cgggtgcgca   4500
```

```
tgatcgtgct cctgtcgttg aggacccggc taggctggcg gggttgcctt actggttagc    4560
agaatgaatc accgatacgc gagcgaacgt gaagcgactg ctgctgcaaa acgtctgcga    4620
cctgagcaac aacatgaatg gtcttcggtt tccgtgtttc gtaaagtctg gaaacgcgga    4680
agtcagcgcc ctgcaccatt atgttccgga tctgcatcgc aggatgctgc tggctaccct    4740
gtggaacacc tacatctgta ttaacgaagc gctggcattg accctgagtg attttctct    4800
ggtcccgccg catccatacc gccagttgtt taccctcaca acgttccagt aaccgggcat    4860
gttcatcatc agtaacccgt atcgtgagca tcctctctcg tttcatcggt atcattaccc    4920
ccatgaacag aaatccccct tacacggagg catcagtgac caaacaggaa aaaaccgccc    4980
ttaacatggc ccgctttatc agaagccaga cattaacgct tctggagaaa ctcaacgagc    5040
tggacgcgga tgaacaggca gacatctgtg aatcgcttca cgaccacgct gatgagcttt    5100
accgcagctg cctcgcgcgt ttcggtgatg acggtgaaaa cctctgacac atgcagctcc    5160
cggagacggt cacagcttgt ctgtaagcgg atgccgggag cagacaagcc cgtcagggcg    5220
cgtcagcggg tgttggcggg tgtcggggcg cagccatgac ccagtcacgt agcgatagcg    5280
gagtgtatac tggcttaact atgcggcatc agagcagatt gtactgagag tgcaccatat    5340
atgcggtgtg aaataccgca cagatgcgta aggagaaaat accgcatcag gcgctcttcc    5400
gcttcctcgc tcactgactc gctgcgctcg gtcgttcggc tgcggcgagc ggtatcagct    5460
cactcaaagg cggtaatacg gttatccaca gaatcagggg ataacgcagg aaagaacatg    5520
tgagcaaaag gccagcaaaa ggccaggaac cgtaaaaagg ccgcgttgct ggcgtttttc    5580
cataggctcc gcccccctga cgagcatcac aaaaatcgac gctcaagtca gaggtggcga    5640
aacccgacag gactataaag ataccaggcg tttccccctg gaagctccct cgtgcgctct    5700
cctgttccga ccctgccgct taccggatac ctgtccgcct ttctcccttc gggaagcgtg    5760
gcgctttctc atagctcacg ctgtaggtat ctcagttcgg tgtaggtcgt tcgctccaag    5820
ctgggctgtg tgcacgaacc ccccgttcag cccgaccgct gcgccttatc cggtaactat    5880
cgtcttgagt ccaacccggt aagacacgac ttatcgccac tggcagcagc cactggtaac    5940
aggattagca gagcgaggta tgtaggcggt gctacagagt tcttgaagtg gtggcctaac    6000
tacggctaca ctagaaggac agtatttggt atctgcgctc tgctgaagcc agttaccttc    6060
ggaaaaagag ttggtagctc ttgatccggc aaacaaacca ccgctggtag cggtggtttt    6120
tttgtttgca agcagcagat tacgcgcaga aaaaaaggat ctcaagaaga tcctttgatc    6180
ttttctacgg ggtctgacgc tcagtggaac gaaaactcac gttaagggat tttggtcatg    6240
agattatcaa aaaggatctt cacctagatc cttttaaatt aaaaatgaag ttttaaatca    6300
atctaaagta tatatgagta aacttggtct gacagttacc aatgcttaat cagtgaggca    6360
cctatctcag cgatctgtct atttcgttca tccatagttg cctgactccc cgtcgtgtag    6420
ataactacga tacgggaggg cttaccatct ggccccagtg ctgcaatgat accgcgagac    6480
ccacgctcac cggctccaga tttatcagca ataaaccagc cagccggaag ggccgagcgc    6540
agaagtggtc ctgcaacttt atccgcctcc atccagtcta ttaattgttg ccgggaagct    6600
agagtaagta gttcgccagt taatagtttg cgcaacgttg ttgccattgc tgcaggcatc    6660
gtggtgtcac gctcgtcgtt tggtatggct tcattcagct ccggttccca acgatcaagg    6720
cgagttacat gatcccccat gttgtgcaaa aaagcggtta gctccttcgg tcctccgatc    6780
gttgtcagaa gtaagttggc cgcagtgtta tcactcatgg ttatggcagc actgcataat    6840
tctcttactg tcatgccatc cgtaagatgc ttttctgtga ctggtgagta ctcaaccaag    6900
```

```
tcattctgag aatagtgtat gcggcgaccg agttgctctt gcccggcgtc aacacgggat    6960
aataccgcgc cacatagcag aactttaaaa gtgctcatca ttggaaaacg ttcttcgggg    7020
cgaaaactct caaggatctt accgctgttg agatccagtt cgatgtaacc cactcgtgca    7080
cccaactgat cttcagcatc ttttactttc accagcgttt ctgggtgagc aaaaacagga    7140
aggcaaaatg ccgcaaaaaa gggaataagg gcgacacgga aatgttgaat actcatactc    7200 ttccttttc aatattattg aagcatttat cagggttatt gtctcatgag cggatacata    7260
tttgaatgta tttagaaaaa taaacaaata ggggttccgc gcacatttcc ccgaaaagtg    7320
ccacctgacg tctaagaaac cattattatc atgacattaa cctataaaaa taggcgtatc    7380
acgaggccct ttcgtcttca agaa    7404
```

<210> SEQ ID NO 6
<211> LENGTH: 41
<212> TYPE: DNA
<213> ORGANISM: Artificial Sequence
<220> FEATURE:
<223> OTHER INFORMATION: Synthetic Construct

<400> SEQUENCE: 6

```
catatgaaag cttgtatcga ttaaataagg aggaataaac c    41
```

<210> SEQ ID NO 7
<211> LENGTH: 6266
<212> TYPE: DNA
<213> ORGANISM: Artificial Sequence
<220> FEATURE:
<223> OTHER INFORMATION: Synthetic Construct

<400> SEQUENCE: 7

```
cccgtcttac tgtcgggaat tcgcgttggc cgattcatta atgcagctgg cacgacaggt    60
ttcccgactg gaaagcgggc agtgagcgca acgcaattaa tgtgagttag ctcactcatt    120
aggcacccca ggctttacac tttatgcttc cggctcgtat gttgtgtgga attgtgagcg    180
gataacaatt tcacacagga aacagctatg accatgatta cgccaagctt gtatcgatta    240
aataaggagg aataaaccat gtgtgcgacc tcttctcaat ttactcagat taccgagcat    300
aattcccgtc gttccgcaaa ctatcagcca aacctgtgga atttcgaatt cctgcaatcc    360
ctggagaacg acctgaaagt ggaaaagctg gaggagaaag cgaccaaact ggaggaagaa    420
gttcgctgca tgatcaaccg tgtagacacc cagccgctgt ccctgctgga gctgatcgac    480
gatgtgcagc gcctgggtct gacctacaaa tttgaaaaag acatcattaa agcctggaa    540 aacatcgtac tgctggacga aaacaaaaag aacaaatctg acctgcacgc aaccgctctg    600
tctttccgtc tgctgcgtca gcacggtttc gaggtttctc aggatgtttt tgagcgtttc    660
aaggataaag aaggtggttt cagcggtgaa ctgaaaggtg acgtccaagg cctgctgagc    720
ctgtatgaag cgtcttacct gggtttcgag ggtgagaacc tgctggagga ggcgcgtacc    780
ttttccatca cccacctgaa gaacaacctg aaagaaggca ttaataccaa ggttgcagaa    840
caagtgagcc acgccctgga actgccatat caccagcgtc tgcaccgtct ggaggcacgt    900
tggttcctgg ataaatacga accgaaagaa ccgcatcacc agctgctgct ggagctggcg    960
aagctggatt ttaacatggt acagaccctg caccagaaag ctgcaagatc tgtcccgc    1020 tggtggaccg agatgggcct ggctagcaaa ctggattttg tacgcgaccg cctgatggaa    1080
gtttatttct gggcactggg tatggcgcca gaccgcagtt tggtgaatg tcgcaaagct    1140 gttactaaaa tgtttggtct ggtgacgatc atcgatgacg tgtatgacgt ttatggcact    1200
```

```
ctggacgaac tgcaactgtt caccgatgct gtagagcgct gggacgttaa cgctattaac    1260
accctgccgg actatatgaa actgtgtttc ctggcactgt acaacaccgt taacgacacg    1320
tcctattcta ttctgaaaga gaaaggtcat aacaacctgt cctatctgac gaaaagctgg    1380
cgtgaactgt gcaaagcctt tctgcaagag gcgaaatggt ccaacaacaa aattatcccg    1440
gctttctcca agtacctgga aaacgccagc gtttcctcct ccggtgtagc gctgctggcg    1500
ccgtcttact tttccgtatg ccagcagcag gaagacatct ccgaccacgc gctgcgttcc    1560
ctgaccgact ccatggtctc ggtgcgttct agctgcgtta tcttccgcct gtgcaacgat    1620
ctggccacct ctgcggcgga gctggaacgt ggcgagacta ccaattctat cattagctac    1680
atgcacgaaa acgatggtac cagcgaggaa caggcccgcg aagaactgcg taaactgatc    1740
gacgccgaat ggaaaaagat gaatcgtgaa cgcgttagcg actccaccct gctgcctaaa    1800
gcgttcatgg aaatcgcagt taacatggca cgtgtttccc actgcaccta ccagtatggc    1860
gatggtctgg gtcgcccaga ctacgcgact gaaaaccgca tcaaactgct gctgattgac    1920 ccttcccga ttaaccagct gatgtatgtc taactgcagg tcgactctag aggatccccg    1980
ggtaccgagc tcgaattcac tggccgtcgt tttacaacgt cgtgactggg aaaaccctgg    2040
cgttacccaa cttaatcgcc ttgcagcaca tcccccttc gccagctggc gtaatagcga    2100
agaggcccgc accgatcgcc cttcccaaca gttgcgcagc ctgaatggcg aatggcgcct    2160
gatgcggtat tttctcctta cgcatctgtg cggtatttca caccgcatat ggtgcactct    2220
cagtacaatc tgctctgatg ccgcatagtt aagccagccc cgacacccgc caacacccgc    2280
tgacgagctt agtaaagccc tcgctagatt ttaatgcgga tgttgcgatt acttcgccaa    2340
ctattgcgat aacaagaaaa agccagcctt tcatgatata tctcccaatt tgtgtagggc    2400
ttattatgca cgcttaaaaa taataaaagc agacttgacc tgatagtttg gctgtgagca    2460
attatgtgct tagtgcatct aacgcttgag ttaagccgcg ccgcgaagcg gcgtcggctt    2520
gaacgaattg ttagacatta tttgccgact accttggtga tctcgccttt cacgtagtgg    2580
acaaattctt ccaactgatc tgcgcgcgag gccaagcgat cttcttcttg tccaagataa    2640
gcctgtctag cttcaagtat gacgggctga tactgggccg gcaggcgctc cattgcccag    2700
tcggcagcga catccttcgg cgcgattttg ccggttactg cgctgtacca aatgcgggac    2760
aacgtaagca ctacatttcg ctcatcgcca gcccagtcgg gcggcgagtt ccatagcgtt    2820
aaggtttcat ttagcgcctc aaatagatcc tgttcaggaa ccggatcaaa gagttcctcc    2880
gccgctggac ctaccaaggc aacgctatgt tctcttgctt ttgtcagcaa gatagccaga    2940
tcaatgtcga tcgtggctgg ctcgaagata cctgcaagaa tgtcattgcg ctgccattct    3000
ccaaattgca gttcgcgctt agctggataa cgccacggaa tgatgtcgtc gtgcacaaca    3060
atggtgactt ctacagcgcg gagaatctcg ctctctccag gggaagccga agtttccaaa    3120
aggtcgttga tcaaagctcg ccgcgttgtt tcatcaagcc ttacggtcac cgtaaccagc    3180
aaatcaatat cactgtgtgg cttcaggccg ccatccactg cggagccgta caaatgtacg    3240
gccagcaacg tcggttcgag atggcgctcg atgacgccaa ctacctctga tagttgagtc    3300
gatacttcgg cgatcaccgc ttccctcatg atgtttaact tgtttttagg gcgactgccc    3360
tgctgcgtaa catcgttgct gctccataac atcaaacatc gacccacggc gtaacgcgct    3420
tgctgcttgg atgcccgagg catagactgt accccaaaaa aacagtcata acaagccatg    3480
aaaaccgcca ctgcgccgtt accacgctg cgttcggtca aggttctgga ccagttgcgt    3540
gagcgcatac gctacttgca ttacagctta cgaaccgaac aggcttatgt ccactgggtt    3600
```

```
cgtgccttca tccgtttcca cggtgtgcgt cacccggcaa ccttgggcag cagcgaagtc    3660
gaggcatttc tgtcctggct ggcgaacgag cgcaaggttt cggtctccac gcatcgtcag    3720
gcattggcgg ccttgctgtt cttctacggc aaggtgctgt gcacggatct gccctggctt    3780
caggagatcg aagacctcg gccgtcgcgg cgcttgccgg tggtgctgac cccggatgaa    3840
gtggttcgca tcctcggttt tctggaaggc gagcatcgtt tgttcgccca gcttctgtat    3900
ggaacgggca tgcggatcag tgagggtttg caactgcggg tcaaggatct ggatttcgat    3960
cacggcacga tcatcgtgcg ggagggcaag ggctccaagg atcgggcctt gatgttaccc    4020
gagagcttgg cacccagcct gcgcgagcag gggaattaat tcccacgggt tttgctgccc    4080
gcaaacgggc tgttctggtg ttgctagttt gttatcagaa tcgcagatcc ggcttcagcc    4140
ggtttgccgg ctgaaagcgc tatttcttcc agaattgcca tgatttttc cccacgggag    4200 gcgtcactgg ctcccgtgtt gtcggcagct ttgattcgat aagcagcatc gcctgtttca    4260
ggctgtctat gtgtgactgt tgagctgtaa caagttgtct caggtgttca atttcatgtt    4320
ctagttgctt tgttttactg gtttcacctg ttctattagg tgttacatgc tgttcatctg    4380
ttacattgtc gatctgttca tggtgaacag ctttgaatgc accaaaaact cgtaaaagct    4440
ctgatgtatc tatcttttttt acaccgtttt catctgtgca tatggacagt tttcccttg    4500 atatgtaacg gtgaacagtt gttctacttt tgtttgttag tcttgatgct tcactgatag    4560
atacaagagc cataagaacc tcagatcctt ccgtatttag ccagtatgtt ctctagtgtg    4620
gttcgttgtt tttgcgtgag ccatgagaac gaaccattga gatcatactt actttgcatg    4680
tcactcaaaa attttgcctc aaaactggtg agctgaattt ttgcagttaa agcatcgtgt    4740 agtgttttc ttagtccgtt atgtaggtag gaatctgatg taatggttgt ggtattttg    4800 tcaccattca ttttatctg gttgttctca agttcggtta cgagatccat ttgtctatct    4860
agttcaactt ggaaaatcaa cgtatcagtc gggcggcctc gcttatcaac caccaatttc    4920
atattgctgt aagtgtttaa atctttactt attggtttca aaacccattg gttaagcctt    4980
ttaaactcat ggtagttatt ttcaagcatt aacatgaact taaattcatc aaggctaatc    5040
tctatatttg ccttgtgagt tttctttttgt gttagttctt ttaataacca ctcataaatc    5100
ctcatagagt atttgtttc aaaagactta acatgttcca gattatattt tatgaatttt    5160
tttaactgga aaagataagg caatatctct tcactaaaaa ctaattctaa ttttttcgctt    5220 gagaacttgg catagtttgt ccactggaaa atctcaaagc ctttaaccaa aggattcctg    5280
atttccacag ttctcgtcat cagctctctg gttgctttag ctaatacacc ataagcatt    5340 tccctactga tgttcatcat ctgagcgtat tggttataag tgaacgatac cgtccgttct    5400
ttccttgtag ggttttcaat cgtggggttg agtagtgcca cacagcataa aattagcttg    5460
gtttcatgct ccgttaagtc atagcgacta atcgctagtt catttgcttt gaaaacaact    5520
aattcagaca tacatctcaa ttggtctagg tgattttaat cactatacca attgagatgg    5580
gctagtcaat gataattact agtccttttc ctttgagttg tgggtatctg taaattctgc    5640
tagacctttg ctggaaaact tgtaaattct gctagaccct ctgtaaattc cgctagacct    5700
ttgtgtgttt ttttgttta tattcaagtg gttataattt atagaataaa gaaagaataa    5760 aaaagataa aaagaataga tcccagcccct gtgtataact cactactta gtcagttccg    5820 cagtattaca aaaggatgtc gcaaacgctg tttgctcctc tacaaaacag accttaaaac    5880
cctaaaggct taagtagcac cctcgcaagc tcgggcaaat cgctgaatat tccttttgtc    5940
tccgaccatc aggcacctga gtcgctgtct ttttcgtgac attcagttcg ctgcgctcac    6000
```

```
ggctctggca gtgaatgggg gtaaatggca ctacaggcgc cttttatgga ttcatgcaag    6060
gaaactaccc ataatacaag aaaagcccgt cacgggcttc tcagggcgtt ttatggcggg    6120
tctgctatgt ggtgctatct gacttttgc tgttcagcag ttcctgccct ctgattttcc     6180
agtctgacca cttcggatta tcccgtgaca ggtcattcag actggctaat gcacccagta    6240
aggcagcggt atcatcaaca ggctta                                         6266

<210> SEQ ID NO 8
<211> LENGTH: 1695
<212> TYPE: DNA
<213> ORGANISM: Artificial Sequence
<220> FEATURE:
<223> OTHER INFORMATION: Synthetic Construct

<400> SEQUENCE: 8
atgtgtgcaa cctcctccca gtttactcag attaccgagc ataattctcg acgatctgct      60
aactaccagc cgaacctttg gaactttgag tttctccagt ctctcgaaaa tgacctgaag     120
gtggaaaagc tcgaggagaa ggcgaccaaa ctcgaggagg aggtgcgatg tatgatcaac     180
agagttgaca cccaaccct gtctttgctg gagctgatcg acgatgtgca gcggttgggt      240
ttgacttata aattcgagaa ggacattatc aaggcactgg agaacattgt gctcctcgac     300
gagaacaaga gaacaagtc tgatcttcac gctaccgctc tctcttttccg acttcttcga    360 caacacggct tcgaggtgtc gcaggacgtc ttcgagagat ttaaggacaa ggagggagga    420
tttagcggcg agctgaaggg agacgttcag ggtcttctct ccttgtacga ggcgtcctac    480
ctgggattcg agggagagaa cctcctggag gaagctcgta cattttccat cactcacctt    540
aagaataacc ttaaggaggg aattaacacc aaggtggccg agcaggtttc tcacgccctg    600
gagctcccct accaccaacg gctccataga ctggaggctc gttggttcct ggacaaatat    660
gagccaaagg agcctcatca tcagttgctg ttggagttgg ccaagctgga cttcaatatg    720
gttcagacgc tgcaccaaaa ggagttgcag gacctgtctc gatggtggac cgagatggga    780
ttggcctcga gctggatttt gtccgtgac cgacttatgg aggtctatt ttgggccctt      840 ggaatggcgc ctgacccca gttcggagag tgccggaagg cggtgacgaa gatgttcggt     900
cttgtgacta tcatcgacga cgtctacgat gtctacggca cactcgacga gttgcagctg    960
ttcactgacg ccgtcgagcg atgggatgtg aacgccatta atactctccc tgactatatg    1020
aagctgtgct cctggctct gtacaacact gtcaacgata cctcgtactc tatcctcaag    1080
gagaagggac acaacaatct ctcctacttg accaaatcct ggcgagaact gtgcaaggct    1140
tttctgcagg aggctaaatg gtccaataac aagatcattc ctgctttttc taaataccctg   1200 gaaaatgcct cggtgtcgag ctctggcgtc gcccttctgg cccttccta cttctccgtc    1260 tgccagcagc aggaggatat ttccgatcat gctcttagat cgctgaccga ttttcacggc    1320
ctcgtgcgat cttcctgcgt gattttcgg ttgtgtaatg accttgcgac ctctgctgct    1380
gagctggaac gaggcgagac tacaaattcc attatttctt acatgcacga aaacgatgga    1440
acatctgaag aacaggctag agaggaactg cgaaagttga tcgacgccga gtggaagaag    1500
atgaacagag agcgggtgtc cgactctacc ctgcttccca aggccttcat ggagatcgcc    1560
gtgaacatgg ctcgagtttc ccattgtact taccagtacg tgacggcct gggtcgtccg     1620 gactacgcta cagagaaccg aatcaagctg ctgctcatcg accccttccc tatcaaccaa    1680
ttgatgtacg tgtaa                                                    1695
```

<210> SEQ ID NO 9
<211> LENGTH: 40
<212> TYPE: DNA
<213> ORGANISM: Artificial Sequence
<220> FEATURE:
<223> OTHER INFORMATION: Synthetic Construct

<400> SEQUENCE: 9
gcttatggat cctctagact attacacgta catcaattgg         40

<210> SEQ ID NO 10
<211> LENGTH: 30
<212> TYPE: DNA
<213> ORGANISM: Artificial Sequence
<220> FEATURE:
<223> OTHER INFORMATION: Synthetic Construct

<400> SEQUENCE: 10
caccatgtgt gcaacctcct cccagtttac         30

<210> SEQ ID NO 11
<211> LENGTH: 8191
<212> TYPE: DNA
<213> ORGANISM: Artificial Sequence
<220> FEATURE:
<223> OTHER INFORMATION: Synthetic Construct

<400> SEQUENCE: 11
tcgaccggtg agaagaacag catcgggaca agggaaggaa gaacaaagac aaagaaaaca         60
aaagaaagca attgaaaaca aaacaaaaca attttcattc cttctcttat cattcctttt        120
cttttctttt ctctcattca acgcactcca tcgtatccgt attcctctta tttttctct         180 ttctctatat ccatttcttt ctctctaggt gtgtcctctc tctctcttca atttctctac        240
tccgcattcc aacgcatcct tcccccaacc tcccatttcc tccttacggc ccgatagcga        300
tcgtctttcc ctcgctatca ctcgctaccg gcccctcctc tgcaccgtaa cctcctacgt        360
atttaccata tcataaagtt ttttccgacg cttatcgctg accccctgtc gccctcctat        420
tggcttccgg attatcttct tgtccataag gtgatccatg cttcctgaag attcccgaaa        480
tgtgtccact ttggcgggga atcattccat ccacttcttt ctctctcgct ttcctcattc        540
ggcgctcccc ttccgcgtct cattggtctt ccgctccgtt tttgctttgc cgatgttact        600
tggggagagg tgcgataatc ctttcgcaaa aactcggttt gacgcctccc atggtataaa        660
tagtgggtgg tggacaggtg ccttcgcttt tctttaagca agagaatccc attgtcttga        720
ctatcacgaa ttcacataca ttatgaagat caccgctgtc attgcccttt tattctcact        780
tgctgctgcc tcacctattc cagttgccga tcctggtgtg gtttcagtta gcaagtcata        840
tgctgatttc cttcgtgttt accaaagttg gaacactttt gctaatcctg atagacccaa        900
ccttaagaag agaaatgata cacctgcaag tggatatcaa gttgaaaaag tcgtaattt         960 gtcacgtcac ggtgttaggg cccctacaaa aatgactcaa accatgcgtg atgtcactcc       1020
taatacatgg ccagaatggc ccgttaaatt aggatatatt acaccaagag gtgaacactt       1080
gatatcactt atgggcggtt tttaccgtca aaaattccag caacaaggaa tcctttctca       1140
gggctcctgt cctactccta actccatata tgtctgggct gacgtcgatc agcgtacttt       1200
aaaaactggt gaagcattcc ttgctggttt ggcaccacac tgtggcttga caattcatca       1260
ccaacaaaat cttgagaaag ctgatcctct ttttcatccc gttaaagctg gaacctgctc       1320
tatggataaa actcaagttc aacagctgtt gagaaggag gcacaaactc ctatagataa       1380
tttgaatcaa cattacatcc ccttttttagc tttaatgaat acaacattaa attttagtac       1440

```
ttctgcctgg tgccaaaaac actctgctga taaatcctgt gacctaggtt tatccatgcc   1500
ttctaaattg tccataaaag ataatggtaa caaggtcgca ttggatggag ctattggtct   1560
atcctctact ttggccgaga ttttcttct tgaatatgct caaggcatgc ctcaagctgc    1620
ttggggtaac atccactcag agcaagagtg ggcttccttg ctaaagttgc ataatgttca   1680
attcgatttg atggcccgaa caccttatat tgctcgacat aacggtactc ctttattgca   1740
agctatatca aatgcccta atcccaacgc cactgaatca aaacttccag atatttcacc    1800
tgataacaaa atattgttca ttgcaggtca tgacacaaat attgctaata tagccggcat   1860
gttaaatatg cgttggacat taccaggtca accagataat actcctccag gtggtgccct   1920
agtatttgaa cgtcttgctg ataaaagtgg aaaacaatat gtttctgtat ctatggttta   1980
tcaaacacta gaacaacttc gatcacagac tccccttct ctaaatcagc ctgccggatc    2040
tgttcaactt aaaattccag gttgcaatga tcaaacagcc gagggttact gtcctctttc   2100 cactttaca agagttgttt cccaatctgt tgaacctgga tgccaacttc aataatgagg    2160
atccaagtaa gggaatgaga atgtgatcca cttttaattc ctaatgaata catgcctata   2220 gttctttct tttgttcttt atgtcgtttt tcgatggtac ggccgttgtc aatctcagtt    2280
tgtgtgcttg gttgcagctt ggtttcaaat ctgttcatct catgaatctt ttaccattc    2340 accacacgtt tataccattc tctcatagaa tcttcatcaa accatctcgg ggttagagtg   2400
gaaagaaagt cttgttcttt tatttccttt tttccatctt caaggctttt cttttcttcc   2460
tcctcctcgt tcatcttgag gtttgacgtg tctgtttaga attttgagct gttgcagcat   2520 cttatttt gttttgcgaa acgaagcgc tttactctct tcatcagttg gacgattgta      2580
cctttgaaaa ccaactactt ttgcatgttt tgtatagaaa tcaatgatat tagaatccca   2640
tcctttaatt tctttcaaag tagttgagct atagttaagt gtaagggccc tactgcgaaa   2700
gcatttgcca aggatgtttt cattaatcaa gaacgaaagt tagggatcg aagacgatca     2760 gataccgtcg tagtcttaac cataaactat gccgactagg gatcgggcaa tgtttcattt   2820
atcgacttgc tcggcacctt acgagaaatc aaagtctttg ggttccgggg ggagtatggt   2880
cgcaaggctg aaacttaaag gaattgacgg aagggcacca caatggagtg gagcctgcgg   2940
cttaatttga ctcaacacgg ggaaactcac caggtccaga catagtaagg attgacagat   3000
tgagagctct ttcttgattc tatgggtggt ggtgcatggc cgttcttagt tggtggagtg   3060
atttgtctgc ttaattgcga taacgaacga gaccttaacc tgctaaatag ctggatcagc   3120
cattttggct gatcattagc ttcttagagg gactattggc ataaagccaa tggaagtttg   3180
aggcaataac aggtctgtga tgcccttaga tgttctgggc cgcacgcgcg ctacactgac   3240
ggagccaacg agttgaaaaa atctttga ttttttatcc ttggccggaa ggtctgggta    3300
atcttgttaa actccgtcgt gctggggata gagcattgca attattgcgg ccgctcctca   3360
attcgatgtt gcagatttta caagtttta aaatgtattt cattattact ttttatatgc    3420
ctaataaaaa agccatagtt taatctatag ataactttt ttccagtgca ctaacggacg    3480
ttacattccc atacaaaact gcgtagttaa agctaaggaa aagttaatat catgttaatt   3540
aaatacgcta tttacaataa gacattgaac tcatttatat cgttgaatat gaataaccaa   3600
tttcagcgaa ttttaacaa acatcgttca cctcgtttaa ggatatcttg tgtatggggt    3660
gttgacttgc tttatcgaat aattaccgta cctgtaattg gcttgctgga tatagcggta   3720
gtctaatatc tagcaaaaat cttttgggtg aaaaggcttg caatttcacg acaccgaact   3780
atttgtcatt tttaataag gaagttttcc ataaattcct gtaattctcg gttgatctaa    3840
```

```
ttgaaaagag tagttttgca tcacgatgag gagggctttt gtagaaagaa atacgaacga   3900
aacgaaaatc agcgttgcca tcgctttgga caaagctccc ttacctgaag agtcgaattt   3960
tattgatgaa cttataactt ccaagcatgc aaaccaaaag ggagaacaag taatccaagt   4020
agacacggga attggattct tggatcacat gtatcatgca ctggctaaac atgcaggctg   4080
gagcttacga ctttactcaa gaggtgattt aatcatcgat gatcatcaca ctgcagaaga   4140
tactgctatt gcacttggta ttgcattcaa gcaggctatg ggtaactttg ccggcgttaa   4200
aagatttgga catgcttatt gtccacttga cgaagctctt tctagaagcg tagttgactt   4260
gtcgggacgg ccctatgctg ttatcgattt gggattaaag cgtgaaaagg ttggggaatt   4320
gtcctgtgaa atgatccctc acttactata ttccttttcg gtagcagctg gaattacttt   4380
gcatgttacc tgcttatatg gtagtaatga ccatcatcgt gctgaaagcg cttttaaatc   4440
tctggctgtt gccatgcgcg cggctactag tcttactgga agttctgaag tcccaagcac   4500
gaagggagtg ttgtaaagat gaattggatt atgtcaggaa aagaacgaca attttgcatc   4560
caaattgtct aaattttaga gttgcttgaa acaatagaa ccttacttgc tttataatta   4620
cgttaattag aagcgttatc tcgtgaagga atatagtacg tagccgtata aattgaattg   4680
aatgttcagc ttatagaata gagacacttt gctgttcaat gcgtcgtcac ttaccatact   4740
cactttatta tacgacttta agtataaact ccgcggttat ggtaaaatta atgatgcaca   4800
aacgtccgat tccatatggg tacactacaa ttaaatactt ttaagctgat cccccacaca   4860
ccatagcttc aaaatgtttc tactcctttt ttactcttcc agattttctc ggactccgcg   4920
catcgccgta ccacttcaaa acacccaagc acagcatact aaattttccc tctttcttcc   4980
tctagggtgt cgttaattac ccgtactaaa ggtttggaaa agaaaaaga accgcctcg   5040
tttcttttc ttcgtcgaaa aaggcaataa aaattttat cacgtttctt tttcttgaaa   5100
tttttttttt tagttttttt ctcttcagt gacctccatt gatatttaag ttaataaacg   5160
gtcttcaatt tctcaagttt cagtttcatt tttcttgttc tattacaact tttttactt   5220
cttgttcatt agaaagaaag catagcaatc taatctaagg gcggtgttga caattaatca   5280
tcggcatagt atatcggcat agtataatac gacaaggtga ggaactaaac catggccaag   5340
ttgaccagtg ccgttccggt gctcaccgcg cgcgacgtcg ccggagcggt cgagttctgg   5400
accgaccggc tcgggttctc ccgggacttc gtggaggacg acttcgccgg tgtggtccgg   5460
gacgacgtga ccctgttcat cagcgcggtc caggaccagg tggtgccgga caacaccctg   5520
gcctgggtgt gggtgcgcgg cctggacgag ctgtacgccg agtggtcgga ggtcgtgtcc   5580
acgaacttcc gggacgcctc cgggccggcc atgaccgaga tcggcgagca gccgtggggg   5640
cgggagttcg ccctgcgcga cccggccggc aactgcgtgc acttcgtggc cgaggagcag   5700
gactgacacg tccgacggcg gcccacgggt cccaggcctc ggagatccgt ccccttttc   5760
ctttgtcgat atcatgtaat tagttatgtc acgcttacat tcacgccctc cccccacatc   5820
cgctctaacc gaaaggaag gagttagaca acctgaagtc taggtcccta tttattttt   5880
tatagttatg ttagtattaa gaacgttatt tatatttcaa atttttcttt tttttctgta   5940
cagacgcgag cttcccagta aatgtgccat ctcgtaggca gaaacggtt ccccgtagg   6000
gtctctctct tggcctcctt tctaggtcgg gctgattgct cttgaagctc tctagggggg   6060
ctcacaccat aggcagataa cgttcccac cggctcgcct cgtaagcgca caaggactgc   6120
tcccaaagat cctaggcggg attttgccga tttcggccta aaggaaccgg aacacgtaga   6180
aagccagtcc gcagaaacgg tgctgacccc ggatgaatgt cagctactgg gctatctgga   6240
```

```
caagggaaaa cgcaagcgca aagagaaagc aggtagcttg cagtgggctt acatggcgat    6300
agctagactg ggcggtttta tggacagcaa gcgaaccgga attgccagct ggggcgccct    6360
ctggtaaggt tgggaagccc tgcaaagtaa actggatggc tttcttgccg ccaaggatct    6420
gatggcgcag gggatcaaga tctgatcaag agacaggatg aggatcgttt cgcatgattg    6480
aacaagatgg attgcacgca ggttctccgg ccgcttgggt ggagaggcta ttcggctatg    6540
actgggcaca acagacaatc ggctgctctg atgccgccgt gttccggctg tcagcgcagg    6600
ggcgcccggt tctttttgtc aagaccgacc tgtccggtgc cctgaatgaa ctgcaggacg    6660
aggcagcgcg gctatcgtgg ctggccacga cgggcgttcc ttgcgcagct gtgctcgacg    6720
ttgtcactga agcgggaagg gactggctgc tattgggcga agtgccgggg caggatctcc    6780
tgtcatctcg ccttgctcct gccgagaaag tatccatcat ggctgatgca atgcggcggc    6840
tgcatacgct tgatccggct acctgcccat tcgaccacca agcgaaacat cgcatcgagc    6900
gagcacgtac tcggatggaa gccggtcttg tcgatcagga tgatctggac gaagagcatc    6960
aggggctcgc gccagccgaa ctgttcgcca ggctcaaggc gcgcatgccc gacggcgagg    7020
atctcgtcgt gatccatggc gatgcctgct tgccgaatat catggtggaa aatggccgct    7080
tttctggatt caacgactgt ggccggctgg gtgtggcgga ccgctatcag gacatagcgt    7140
tggatacccg tgatattgct gaagagcttg gcggcgaatg ggctgaccgc ttcctcgtgc    7200
tttacggtat cgccgctccc gattcgcagc gcatcgcctt ctatcgcctt cttgacgagt    7260
tcttctgaat tgaaaaggt accaagttta ctcatatata ctttagattg atttaaaact    7320 tcattttta tttaaaagga tctaggtgaa gatcctttt gataatctca tgaccaaaat    7380
cccttaacgt gagttttcgt tccactgagc gtcagacccc gtagaaaaga tcaaaggatc    7440
ttcttgagat cctttttttc tgcgcgtaat ctgctgcttg caaacaaaaa aaccaccgct    7500
accagcggtg gtttgtttgc cggatcaaga gctaccaact cttttccga aggtaactgg    7560 cttcagcaga gcgcagatac caaatactgt ccttctagtg tagccgtagt taggccacca    7620
cttcaagaac tctgtagcac cgcctacata cctcgctctg ctaatcctgt taccagtggc    7680
tgctgccagt ggcgataagt cgtgtcttac cgggttggac tcaagacgat agttaccgga    7740
taaggcgcag cggtcgggct gaacggggggg ttcgtgcaca cagcccagct tggagcgaac    7800
gacctacacc gaactgagat acctacagcg tgagcattga gaaagcgcca cgcttcccga    7860
agggagaaag gcggacaggt atccggtaag cggcagggtc ggaacaggag agcgcacgag    7920
ggagcttcca gggggaaacg cctggtatct ttatagtcct gtcgggtttc gccacctctg    7980
acttgagcgt cgatttttgt gatgctcgtc agggggggcgg agcctatgga aaaacgccag    8040
caacgcggcc ttttacggt tcctggcctt ttgctggcct tttgctcaca tgttctttcc    8100
tgcgttatcc cctgattctg tggataaccg tattaccgcc tttgagtgag ctgataccgc    8160
tcgccgcagc cgaacgaccg agcgcagcga g                                  8191
```

<210> SEQ ID NO 12
<211> LENGTH: 1724
<212> TYPE: DNA
<213> ORGANISM: Artificial Sequence
<220> FEATURE:
<223> OTHER INFORMATION: Synthetic Construct

<400> SEQUENCE: 12

```
gaattcaaaa caaatgtgt gcaacctcct cccagtttac tcagattacc gagcataatt       60
ctcgacgatc tgctaactac cagccgaacc tttggaactt tgagtttctc cagtctctcg     120
```

```
aaaatgacct gaaggtggaa aagctcgagg agaaggcgac caaactcgag gaggaggtgc      180
gatgtatgat caacagagtt gacacccaac ccctgtcttt gctggagctg atcgacgatg      240
tgcagcggtt gggttttgact tataaattcg agaaggacat tatcaaggca ctggagaaca     300
ttgtgctcct cgacgagaac aagaagaaca agtctgatct tcacgctacc gctctctctt      360
tccgacttct tcgacaacac ggcttcgagg tgtcgcagga cgtcttcgag agatttaagg      420
acaaggaggg aggatttagc ggcgagctga agggagacgt tcagggtctt ctctccttgt      480
acgaggcgtc ctacctggga ttcgagggag agaacctcct ggaggaagct cgtacatttt      540
ccatcactca ccttaagaat aaccttaagg agggaattaa caccaaggtg gccgagcagg      600
tttctcacgc cctggagctc ccctaccacc aacggctcca tagactggag gctcgttggt      660
tcctggacaa atatgagcca aaggagcctc atcatcagtt gctgttggag ttggccaagc      720
tggacttcaa tatggttcag acgctgcacc aaaaggagtt gcaggacctg tctcgatggt      780
ggaccgagat gggattggcc tcgaagctgg attttgtccg tgaccgactt atggaggtct      840 attttttgggc ccttggaatg gcgcctgacc cccagttcgg agagtgccgg aaggcggtga    900
cgaagatgtt cggtcttgtg actatcatcg acgacgtcta cgatgtctac ggcacactcg      960
acgagttgca gctgttcact gacgccgtcg agcgatggga tgtgaacgcc attaatactc     1020
tccctgacta tatgaagctg tgcttcctgg ctctgtacaa cactgtcaac gatacctcgt     1080
actctatcct caaggagaag ggacacaaca atctctccta cttgaccaaa tcctggcgag     1140
aactgtgcaa ggcttttctg caggaggcta aatggtccaa taacaagatc attcctgctt     1200
tttctaaata cctggaaaat gcctcggtgt cgagctctgg cgtcgcccctt ctggcccctt     1260 cctacttctc cgtctgccag cagcaggagg atatttccga tcatgctctt agatcgctga     1320
ccgattttca cggcctcgtg cgatcttcct gcgtgatttt tcggttgtgt aatgaccttg     1380
cgacctctgc tgctgagctg gaacgaggcg agactacaaa ttccattatt tcttacatgc     1440
acgaaaacga tggaacatct gaagaacagg ctagagagga actgcgaaag ttgatcgacg     1500
ccgagtggaa gaagatgaac agagagcggg tgtccgactc taccctgctt cccaaggcct     1560
tcatggagat cgccgtgaac atggctcgag tttcccattg tacttaccag tacggtgacg     1620
gcctgggtcg tccggactac gctacagaga accgaatcaa gctgctgctc atcgaccct     1680 tccctatcaa ccaattgatg tacgtgtaat agtctagagg atcc                      1724
```

<210> SEQ ID NO 13
<211> LENGTH: 1701
<212> TYPE: DNA
<213> ORGANISM: Artificial Sequence
<220> FEATURE:
<223> OTHER INFORMATION: Synthetic Construct

<400> SEQUENCE: 13

```
gaattcaaca aaaatgtgct ctgtttccac tgagaacgtg tcctttactg agactgagac       60
tgaagcacgt agaagcgcca actacgaacc caactcctgg gattatgact ttctgctgtc      120
ttctgacacc gacgagtcga tcgaggttta aaggataag gccaagaaac ttgaggccga       180
ggtcagacga gagattaaca acgagaaggc cgagttcctg acccttcttg agctgatcga      240
caacgttcaa cgacttggtc ttggttaccg tttcgaatcc gatatccgac gtgcattgga      300
tcgatttgtc tcgtccggag gtttcgatgg tgtgactaag acgtcgctgc acgccacagc      360
tctttccttc agactgttgc ggcagcatgg atttgaggtt tcccaggaag cctttttctgg     420 tttcaaggat cagaacggaa actttttgga gaatctcaag gaggacacca aggccatcct     480
```

-continued

```
gtcgttgtat gaggcctcgt tcctggctct tgagggcgag aatattctgg atgaggctcg      540
ggttttcgct atttcgcacc tgaaggagtt gtcggaggaa aagatcggaa aggaactggc      600
cgagcaggtc aaccatgcac ttgaacttcc cctgcatcga cgtacccagc gactggaggc      660
cgtgtggagc atcgaggcgt acagaaaaaa ggaggatgct aatcaggttc tgctcgaact      720
cgctatcctc gactataaca tgattcagag cgtgtaccag cgtgacttgc gagagacaag      780
ccggtggtgg cgacgggtgg gactggccac gaagctccac tttgctaaag atcgattgat      840
tgagtcgttc tactgggcag tgggtgtggc ctttgagcct cagtactccg actgccgaaa      900
ctccgttgca aagatgtttt cttttgtcac tatcatcgac gacatctacg atgtttacgg      960
cactctcgat gaactcgaac tcttcacgga cgctgtcgag cgatgggatg tgaatgccat     1020
taatgatctg ccagattata tgaagttgtg tttcttggcg ctctacaaca caattaatga     1080
aattgcctac gacaacctca aggacaaggg agagaacatt ctgccctacc ttactaaagc     1140
ctgggccgac ctgtgtaacg cctttttgca ggaagccaag tggctctata caaatctac      1200 tcctacattt gatgactact cggcaacgc ttggaagtct ccagcggcc ctctccagtt       1260 gatcttcgct tactttgcag tggtccagaa catcaagaaa gaggagattg agaacctcca     1320
gaagtatcac gacatcatct cccgaccttc gcacatcttt cgactgtgca atgaccttgc     1380
ctccgcatcc gctgagattg cccgaggaga acagcaat tctgtgtcgt gttacatgcg       1440
tacaaagggc atctccgagg agctggctac cgagtctgtg atgaacctga tcgatgaaac     1500
ctgtaagaag atgaacaaag agaaactggg cggttctctg ttcgccaaac catttgttga    1560
aaccgcgatc aatctggctc gtcagtctca ttgtacttac cataacggtg acgcgcacac     1620
ttcgccggac gaattgaccc gtaagcgtgt gctttcggtg attaccgagc cgatcctgcc     1680
gttcgaaaga taataggatc c                                                1701
```

<210> SEQ ID NO 14
<211> LENGTH: 28
<212> TYPE: DNA
<213> ORGANISM: Artificial Sequence
<220> FEATURE:
<223> OTHER INFORMATION: Synthetic Construct

<400> SEQUENCE: 14
gatcaagctt aaccggaatt gccagctg                                          28

<210> SEQ ID NO 15
<211> LENGTH: 33
<212> TYPE: DNA
<213> ORGANISM: Artificial Sequence
<220> FEATURE:
<223> OTHER INFORMATION: Synthetic Construct

<400> SEQUENCE: 15
gatccgatcg tcagaagaac tcgtcaagaa ggc                                    33

<210> SEQ ID NO 16
<211> LENGTH: 38
<212> TYPE: DNA
<213> ORGANISM: Artificial Sequence
<220> FEATURE:
<223> OTHER INFORMATION: Synthetic Construct

<400> SEQUENCE: 16
catcaatgca tcgcccttag gaggtaaaaa aaaatgac                               38

```
<210> SEQ ID NO 17
<211> LENGTH: 26
<212> TYPE: DNA
<213> ORGANISM: Artificial Sequence
<220> FEATURE:
<223> OTHER INFORMATION: Synthetic Construct

<400> SEQUENCE: 17
ccttctgcag gacgcgttgt tatagc                                            26

<210> SEQ ID NO 18
<211> LENGTH: 60
<212> TYPE: DNA
<213> ORGANISM: Artificial Sequence
<220> FEATURE:
<223> OTHER INFORMATION: Synthetic Construct

<400> SEQUENCE: 18
gatcatgcat tcgcccttag gaggtaaaaa aacatgagtt ttgatattgc caaatacccg       60

<210> SEQ ID NO 19
<211> LENGTH: 31
<212> TYPE: DNA
<213> ORGANISM: Artificial Sequence
<220> FEATURE:
<223> OTHER INFORMATION: Synthetic Construct

<400> SEQUENCE: 19
catgctgcag ttatgccagc caggccttga t                                      31

<210> SEQ ID NO 20
<211> LENGTH: 8804
<212> TYPE: DNA
<213> ORGANISM: Artificial Sequence
<220> FEATURE:
<223> OTHER INFORMATION: Synthetic Construct

<400> SEQUENCE: 20
gctggtacca tatgggaatt cgaagctttc tagaacaaaa actcatctca gaagaggatc       60
tgaatagcgc cgtcgaccat catcatcatc atcattgagt ttaaacggtc tccagcttgg      120
ctgttttggc ggatgagaga agattttcag cctgatacag attaaatcag aacgcagaag      180
cggtctgata aaacagaatt tgcctggcgg cagtagcgcg gtggtcccac ctgaccccat      240
gccgaactca gaagtgaaac gccgtagcgc cgatggtagt gtggggtctc cccatgcgag      300
agtagggaac tgccaggcat caaataaaac gaaaggctca gtcgaaagac tgggcctttc      360
gttttatctg ttgtttgtcg gtgaacgctc tcctgagtag acaaatccg ccgggagcgg      420 atttgaacgt tgcgaagcaa cggcccggag ggtggcgggc aggacgcccg ccataaactg      480
ccaggcatca aattaagcag aaggccatcc tgacggatgg cctttttgcg tttctacaaa      540 ctcttttgt ttatttttct aaatacattc aaatatgtat ccgcttaacc ggaattgcca      600 gctgggcgc cctctggtaa ggttgggaag ccctgcaaag taaactggat ggctttctcg      660
ccgccaagga tctgatggcg caggggatca agctctgatc aagagacagg atgaggatcg      720
tttcgcatga ttgaacaaga tggattgcac gcaggttctc cggccgcttg ggtggagagg      780
ctattcggct atgactgggc acaacagaca atcggctgct ctgatgccgc cgtgttccgg      840
ctgtcagcgc aggggcgccc ggttcttttt gtcaagaccg acctgtccgg tgccctgaat      900
gaactgcaag acgaggcagc gcggctatcg tggctggcca cgacgggcgt tccttgcgca      960
gctgtgctcg acgttgtcac tgaagcggga agggactggc tgctattggg cgaagtgccg     1020
gggcaggatc tcctgtcatc tcaccttgct cctgccgaga agtatccat catggctgat     1080
```

```
gcaatgcggc ggctgcatac gcttgatccg gctacctgcc cattcgacca ccaagcgaaa    1140
catcgcatcg agcgagcacg tactcggatg aagccggtc ttgtcgatca ggatgatctg     1200
gacgaagagc atcaggggct cgcgccagcc gaactgttcg ccaggctcaa ggcgagcatg    1260
cccgacggcg aggatctcgt cgtgacccat ggcgatgcct gcttgccgaa tatcatggtg    1320
gaaaatggcc gcttttctgg attcatcgac tgtggccggc tgggtgtggc ggaccgctat    1380
caggacatag cgttggctac ccgtgatatt gctgaagagc ttggcggcga atgggctgac    1440
cgcttcctcg tgctttacgg tatcgccgct cccgattcgc agcgcatcgc cttctatcgc    1500
cttcttgacg agttcttctg acatgaccaa aatcccttaa cgtgagtttt cgttccactg    1560
agcgtcagac cccgtagaaa agatcaaagg atcttcttga tccttttttt ttctgcgcgt    1620
aatctgctgc ttgcaaacaa aaaaaccacc gctaccagcg gtggtttgtt tgccggatca    1680
agagctacca actctttttc cgaaggtaac tggcttcagc agagcgcaga taccaaatac    1740
tgtccttcta gtgtagccgt agttaggcca ccacttcaag aactctgtag caccgcctac    1800
atacctcgct ctgctaatcc tgttaccagt ggctgctgcc agtggcgata agtcgtgtct    1860
taccgggttg gactcaagac gatagttacc ggataaggcg cagcggtcgg gctgaacggg    1920
gggttcgtgc acacagccca gcttggagcg aacgacctac accgaactga gatacctaca    1980
gcgtgagcta tgagaaagcg ccacgcttcc cgaaggggaga aaggcggaca ggtatccggt    2040
aagcggcagg gtcggaacag gagagcgcac gagggagctt ccaggggggaa acgcctggta    2100 tctttatagt cctgtcgggt ttcgccacct ctgacttgag cgtcgatttt tgtgatgctc    2160 gtcaggggg cggagcctat ggaaaaacgc cagcaacgcg gcctttttac ggttcctggc     2220
cttttgctgg ccttttgctc acatgttctt cctgcgtta ccccctgatt ctgtggataa     2280
ccgtattacc gcctttgagt gagctgatac cgctcgccgc agccgaacga ccgagcgcag    2340
cgagtcagtg agcgaggaag cggaagagcg cctgatgcgg tattttctcc ttacgcatct    2400
gtgcggtatt tcacaccgca tatggtgcac tctcagtaca atctgctctg atgccgcata    2460
gttaagccag tatacactcc gctatcgcta cgtgactggg tcatggctgc gccccgacac    2520
ccgccaacac ccgctgacgc gccctgacgg gcttgtctgc tcccggcatc cgcttacaga    2580
caagctgtga ccgtctccgg gagctgcatg tgtcagaggt tttcaccgtc atcaccgaaa    2640
cgcgcgaggc agcagatcaa ttcgcgcgcg aaggcgaagc ggcatgcatt tacgttgaca    2700
ccatcgaatg gtgcaaaacc tttcgcggta tggcatgata gcgcccggaa gagagtcaat    2760
tcagggtggt gaatgtgaaa ccagtaacgt tatacgatgt cgcagagtat gccggtgtct    2820
cttatcagac cgtttcccgc gtggtgaacc aggccagcca cgtttctgcg aaaacgcggg    2880
aaaaagtgga agcggcgatg gcggagctga attacattcc caaccgcgtg gcacaacaac    2940
tggcgggcaa acagtcgttg ctgattggcg ttgccacctc cagtctggcc ctgcacgcgc    3000
cgtcgcaaat tgtcgcggcg attaaatctc gcgccgatca actgggtgcc agcgtggtgg    3060
tgtcgatggt agaacgaagc ggcgtcgaag cctgtaaagc ggcggtgcac aatcttctcg    3120
cgcaacgcgt cagtgggctg atcattaact atccgctgga tgaccaggat gccattgctg    3180
tggaagctgc ctgcactaat gttccggcgt tatttcttga tgtctctgac cagacaccca    3240
tcaacagtat tattttctcc catgaagacg gtacgcgact gggcgtggag catctggtcg    3300
cattgggtca ccagcaaatc gcgctgttag cgggcccatt aagttctgtc tcggcgcgtc    3360
tgcgtctggc tggctggcat aaatatctca ctcgcaatca aattcagccg atagcggaac    3420
gggaaggcga ctggagtgcc atgtccggtt ttcaacaaac catgcaaatg ctgaatgagg    3480
```

```
gcatcgttcc cactgcgatg ctggttgcca acgatcagat ggcgctgggc caatgcgcg    3540 ccattaccga gtccgggctg cgcgttggtg cggatatctc ggtagtggga tacgacgata    3600
ccgaagacag ctcatgttat atcccgccgt caaccaccat caaacaggat tttcgcctgc    3660
tggggcaaac cagcgtggac cgcttgctgc aactctctca gggccaggcg gtgaagggca    3720
atcagctgtt gcccgtctca ctggtgaaaa gaaaaaccac cctggcgccc aatacgcaaa    3780
ccgcctctcc ccgcgcgttg gccgattcat taatgcagct ggcacgacag gtttcccgac    3840
tggaaagcgg gcagtgagcg caacgcaatt aatgtgagtt agcgcgaatt gatctggttt    3900
gacagcttat catcgactgc acggtgcacc aatgcttctg cgtcaggca gccatcggaa    3960 gctgtggtat ggctgtgcag gtcgtaaatc actgcataat tcgtgtcgct caaggcgcac    4020
tcccgttctg gataatgttt tttgcgccga catcataacg gttctggcaa atattctgaa    4080
atgagctgtt gacaattaat catccggctc gtataatgtg tggaattgtg agcggataac    4140
aatttcacac aggaaacagc gccgctgaga aaaagcgaag cggcactgct ctttaacaat    4200
ttatcagaca atctgtgtgg gcactcgacc ggaattatcg attaacttta ttattaaaaa    4260
ttaaagaggt atatattaat gtatcgatta ataaggagg aataaaccat gtgtgcgacc    4320
tcttctcaat ttactcagat taccgagcat aattcccgtc gttccgcaaa ctatcagcca    4380
aacctgtgga atttcgaatt cctgcaatcc ctggagaacg acctgaaagt ggaaaagctg    4440
gaggagaaag cgaccaaact ggaggaagaa gttcgctgca tgatcaaccg tgtagacacc    4500
cagccgctgt ccctgctgga gctgatcgac gatgtgcagc gcctgggtct gacctacaaa    4560
tttgaaaaag acatcattaa agccctggaa acatcgtac tgctggacga aaacaaaaag    4620
aacaaatctg acctgcacgc aaccgctctg tctttccgtc tgctgcgtca gcacggtttc    4680
gaggtttctc aggatgtttt tgagcgtttc aaggataaag aaggtggttt cagcggtgaa    4740
ctgaaaggtg acgtccaagg cctgctgagc ctgtatgaag cgtcttacct gggtttcgag    4800
ggtgagaacc tgctggagga ggcgcgtacc ttttccatca cccacctgaa gaacaacctg    4860
aaagaaggca ttaataccaa ggttgcagaa caagtgagcc acgccctgga actgccatat    4920
caccagcgtc tgcaccgtct ggaggcacgt tggttcctgg ataaatacga accgaaagaa    4980
ccgcatcacc agctgctgct ggagctggcg aagctggatt ttaacatggt acagaccctg    5040
caccagaaag agctgcaaga tctgtcccgc tggtggaccg agatgggcct ggctagcaaa    5100
ctggattttg tacgcgaccg cctgatggaa gtttatttct gggcactggg tatggcgcca    5160
gacccgcagt ttggtgaatg tcgcaaagct gttactaaaa tgtttggtct ggtgacgatc    5220
atcgatgacg tgtatgacgt ttatggcact ctggacgaac tgcaactgtt caccgatgct    5280
gtagagcgct gggacgttaa cgctattaac accctgccgg actatatgaa actgtgtttc    5340
ctggcactgt acaacaccgt taacgacacg tcctattcta ttctgaaaga gaaaggtcat    5400
aacaacctgt cctatctgac gaaaagctgg cgtgaactgt gcaaagcctt tctgcaagag    5460
gcgaaatggt ccaacaacaa aattatcccg ctttctcca agtacctgga aaacgccagc    5520
gtttcctcct ccggtgtagc gctgctggcg ccgtcttact tttccgtatg ccagcagcag    5580
gaagacatct ccgaccacgc gctgcgttcc ctgaccgact ccatggtct ggtgcgttct    5640 agctgcgtta tcttccgcct gtgcaacgat ctggccacct ctgcggcgga gctggaacgt    5700
ggcgagacta ccaattctat cattagctac atgcacgaaa acgatggtac cagcgaggaa    5760
caggcccgcg aagaactgcg taaactgatc gacgccgaat ggaaaagat gaatcgtgaa    5820 cgcgttagcg actccaccct gctgcctaaa gcgttcatgg aaatcgcagt taacatggca    5880
```

```
cgtgtttccc actgcaccta ccagtatggc gatggtctgg gtcgcccaga ctacgcgact    5940
gaaaaccgca tcaaactgct gctgattgac ccttttcccga ttaaccagct gatgtatgtc   6000
taactgcatc gcccttagga ggtaaaaaaa aatgactgcc gacaacaata gtatgcccca   6060
tggtgcagta tctagttacg ccaaattagt gcaaaaccaa acacctgaag acattttgga   6120
agagtttcct gaaattattc cattacaaca aagacctaat acccgatcta gtgagacgtc   6180
aaatgacgaa agcggagaaa catgtttttc tggtcatgat gaggagcaaa ttaagttaat   6240
gaatgaaaat tgtattgttt tggattggga cgataatgct attggtgccg gtaccaagaa   6300
agtttgtcat ttaatggaaa atattgaaaa gggtttacta catcgtgcat tctccgtctt   6360
tattttcaat gaacaaggtg aattactttt acaacaaaga gccactgaaa aataactttt   6420
ccctgatctt tggactaaca catgctgctc tcatccacta tgtattgatg acgaattagg   6480
tttgaagggt aagctagacg ataagattaa gggcgctatt actgcggcgg tgagaaaact   6540
agatcatgaa ttaggtattc cagaagatga aactaagaca aggggtaagt ttcactttt   6600 aaacagaatc cattacatgg caccaagcaa tgaaccatgg ggtgaacatg aaattgatta   6660 catcctatt tataagatca acgctaaaga aaacttgact gtcaacccaa acgtcaatga   6720
agttagagac ttcaaatggg tttcaccaaa tgatttgaaa actatgtttg ctgacccaag   6780
ttacaagttt acgccttggt ttaagattat ttgcgagaat tacttattca actggtggga   6840
gcaattagat gacctttctg aagtggaaaa tgacaggcaa attcatagaa tgctataaca   6900
acgcgtcctg cattcgccct taggaggtaa aaaaacatga gttttgatat tgccaaatac   6960
ccgaccctgg cactggtcga ctccacccag gagttacgac tgttgccgaa agagagttta   7020
ccgaaactct gcgacgaact gcgccgctat ttactgaca gcgtgagccg ttccagcggg   7080
cacttcgcct ccgggctggg cacggtcgaa ctgaccgtgg cgctgcacta tgtctacaac   7140
accccgtttg accaattgat ttgggatgtg gggcatcagg cttatccgca taaaattttg   7200
accggacgcc gcgacaaaat cggcaccatc cgtcagaaag gcggtctgca cccgttcccg   7260
tggcgcggcg aaagcgaata tgacgtatta agcgtcgggc attcatcaac ctccatcagt   7320
gccggaattg gtattgcggt tgctgccgaa aaagaaggca aaaatcgccg caccgtctgt   7380
gtcattggcg atggcgcgat taccgcaggc atggcgtttg aagcgatgaa tcacgcgggc   7440
gatatccgtc ctgatatgct ggtgattctc aacgacaatg aaatgtcgat ttccgaaaat   7500
gtcggcgcgc tcaacaacca tctggcacag ctgcttttccg gtaagcttta ctcttcactg   7560
cgcgaaggcg ggaaaaaagt tttctctggc gtgccgccaa ttaaagagct gctcaaacgc   7620
accgaagaac atattaaagg catggtagtg cctggcacgt tgtttgaaga gctgggcttt   7680
aactacatcg gcccggtgga cggtcacgat gtgctggggc ttatcaccac gctaaagaac   7740
atgcgcgacc tgaaaggccc gcagttcctg catatcatga ccaaaaaagg tcgtggttat   7800
gaaccggcag aaaaagaccc gatcactttc cacgccgtgc ctaaatttga tccctccagc   7860
ggttgtttgc cgaaaagtag cggcggtttg ccgagctatt caaaaatctt tggcgactgg   7920
ttgtgcgaaa cggcagcgaa agacaacaag ctgatggcga ttactccggc gatgcgtgaa   7980
ggttccggca tggtcgagtt ttcacgtaaa ttcccggatc gctacttcga cgtggcaatt   8040
gccgagcaac acgcggtgac ctttgctgcg ggtctggcga ttggtgggta caaacccatt   8100
gtcgcgattt actccacttt cctgcaacgc gcctatgatc aggtgctgca tgacgtggcg   8160
attcaaaagc ttccggtcct gttcgccatc gaccgcgcgg gcattgttgg tgctgacggt   8220
caaacccatc agggtgcttt tgatctctct tacctgcgct gcataccgga aatggtcatt   8280
```

```
atgaccccga gcgatgaaaa cgaatgtcgc cagatgctct ataccggcta tcactataac    8340
gatggcccgt cagcggtgcg ctacccgcgt ggcaacgcgg tcggcgtgga actgacgccg    8400
ctggaaaaac taccaattgg caaaggcatt gtgaagcgtc gtggcgagaa actggcgatc    8460
cttaactttg gtacgctgat gccagaagcg gcgaaagtcg ccgaatcgct gaacgccacg    8520
ctggtcgata tgcgttttgt gaaaccgctt gatgaagcgt taattctgga atgccgcc      8580 agccatgaag cgctggtcac cgtagaagaa acgccatta tgggcggcgc aggcagcggc    8640
gtgaacgaag tgctgatggc ccatcgtaaa ccagtacccg tgctgaacat tggcctgccg    8700
gacttcttta ttccgcaagg aactcaggaa gaaatgcgcg ccgaactcgg cctcgatgcc    8760
gctggtatgg aagccaaaat caaggcctgg ctggcataac tgca                      8804
```

<210> SEQ ID NO 21
<211> LENGTH: 41
<212> TYPE: DNA
<213> ORGANISM: Artificial Sequence
<220> FEATURE:
<223> OTHER INFORMATION: Synthetic Construct

<400> SEQUENCE: 21
aggaggtaaa aaaacatgtc attaccgttc ttaacttctg c    41

<210> SEQ ID NO 22
<211> LENGTH: 52
<212> TYPE: DNA
<213> ORGANISM: Artificial Sequence
<220> FEATURE:
<223> OTHER INFORMATION: Synthetic Construct

<400> SEQUENCE: 22
atggctgcag gcctatcgca aattagctta tgaagtccat ggtaaattcg tg    52

<210> SEQ ID NO 23
<211> LENGTH: 23
<212> TYPE: DNA
<213> ORGANISM: Artificial Sequence
<220> FEATURE:
<223> OTHER INFORMATION: Synthetic Construct

<400> SEQUENCE: 23
gaattcgccc ttctgcagct acc    23

<210> SEQ ID NO 24
<211> LENGTH: 38
<212> TYPE: DNA
<213> ORGANISM: Artificial Sequence
<220> FEATURE:
<223> OTHER INFORMATION: Synthetic Construct

<400> SEQUENCE: 24
cgactggtgc acccttaagg aggaaaaaaa catgtcag    38

<210> SEQ ID NO 25
<211> LENGTH: 25
<212> TYPE: DNA
<213> ORGANISM: Artificial Sequence
<220> FEATURE:
<223> OTHER INFORMATION: Synthetic Construct

<400> SEQUENCE: 25
gtgctggaat tcgcccttct gcagc    25

```
<210> SEQ ID NO 26
<211> LENGTH: 32
<212> TYPE: DNA
<213> ORGANISM: Artificial Sequence
<220> FEATURE:
<223> OTHER INFORMATION: Synthetic Construct

<400> SEQUENCE: 26
gtagatgcat gcagaattcg cccttaagga gg                                    32

<210> SEQ ID NO 27
<211> LENGTH: 26
<212> TYPE: DNA
<213> ORGANISM: Artificial Sequence
<220> FEATURE:
<223> OTHER INFORMATION: Synthetic Construct

<400> SEQUENCE: 27
ccttctgcag gacgcgttgt tatagc                                           26

<210> SEQ ID NO 28
<211> LENGTH: 38
<212> TYPE: DNA
<213> ORGANISM: Artificial Sequence
<220> FEATURE:
<223> OTHER INFORMATION: Synthetic Construct

<400> SEQUENCE: 28
catcaatgca tcgcccttag gaggtaaaaa aaaatgac                              38

<210> SEQ ID NO 29
<211> LENGTH: 25
<212> TYPE: DNA
<213> ORGANISM: Artificial Sequence
<220> FEATURE:
<223> OTHER INFORMATION: Synthetic Construct

<400> SEQUENCE: 29
gtgtgatgga tatctgcaga attcg                                            25

<210> SEQ ID NO 30
<211> LENGTH: 36
<212> TYPE: DNA
<213> ORGANISM: Artificial Sequence
<220> FEATURE:
<223> OTHER INFORMATION: Synthetic Construct

<400> SEQUENCE: 30
catcaatgca tcgcccttag gaggtaaaaa aacatg                                36

<210> SEQ ID NO 31
<211> LENGTH: 60
<212> TYPE: DNA
<213> ORGANISM: Artificial Sequence
<220> FEATURE:
<223> OTHER INFORMATION: Synthetic Construct

<400> SEQUENCE: 31
gatcatgcat tcgcccttag gaggtaaaaa aacatgtgtg cgacctcttc tcaatttact      60

<210> SEQ ID NO 32
<211> LENGTH: 38
<212> TYPE: DNA
<213> ORGANISM: Artificial Sequence
<220> FEATURE:
<223> OTHER INFORMATION: Synthetic Construct

<400> SEQUENCE: 32
```

-continued cggtcgacgg atccctgcag ttagacatac atcagctg 38

<210> SEQ ID NO 33
<211> LENGTH: 10992
<212> TYPE: DNA
<213> ORGANISM: Artificial Sequence
<220> FEATURE:
<223> OTHER INFORMATION: Synthetic Construct

<400> SEQUENCE: 33

| | |
|---|---|
| gtttgacagc ttatcatcga ctgcacggtg caccaatgct tctggcgtca ggcagccatc | 60 |
| ggaagctgtg gtatggctgt gcaggtcgta atcactgca taattcgtgt cgctcaaggc | 120 |
| gcactcccgt tctggataat gttttttgcg ccgacatcat aacggttctg gcaaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatggatcc | 420 |
| gagctcggat ccactagtaa cggccgccag tgtgctggaa ttcgcccta ggaggtaaaa | 480 |
| aaacatgtca ttaccgttct taacttctgc accgggaaag gttattattt tggtgaaca | 540 |
| ctctgctgtg tacaacaagc ctgccgtcgc tgctagtgtg tctgcgttga aacctacct | 600 |
| gctaataagc gagtcatctg caccagatac tattgaattg gacttcccgg acattagctt | 660 |
| taatcataag tggtccatca atgatttcaa tgccatcacc gaggatcaag taaactccca | 720 |
| aaaattggcc aaggctcaac aagccaccga tggcttgtct caggaactcg ttagtctttt | 780 |
| ggatccgttg ttagctcaac tatccgaatc cttccactac catgcagcgt tttgtttcct | 840 |
| gtatatgttt gtttgcctat gcccccatgc caagaatatt aagttttctt taaagtctac | 900 |
| tttacccatc ggtgctgggt tgggctcaag cgcctctatt tctgtatcac tggccttagc | 960 |
| tatggcctac ttgggggggt taataggatc taatgacttg gaaaagctgt cagaaaacga | 1020 |
| taagcatata gtgaatcaat gggccttcat aggtgaaaag tgtattcacg gtacccttc | 1080 |
| aggaatagat aacgctgtgg ccacttatgg taatgccctg ctatttgaaa aagactcaca | 1140 |
| taatggaaca ataaacacaa acaattttaa gttcttagat gatttcccag ccattccaat | 1200 |
| gatcctaacc tatactagaa ttccaaggtc tacaaaagat cttgttgctc gcgttcgtgt | 1260 |
| gttggtcacc gagaaatttc ctgaagttat gaagccaatt ctagatgcca tgggtgaatg | 1320 |
| tgccctacaa ggcttagaga tcatgactaa gttaagtaaa tgtaaaggca ccgatgacga | 1380 |
| ggctgtagaa actaataatg aactgtatga caactattg gaattgataa gaataaatca | 1440 |
| tggactgctt gtctcaatcg gtgtttctca tcctggatta gaacttatta aaaatctgag | 1500 |
| cgatgatttg agaattggct ccacaaaact taccggtgct ggtggcggcg gttgctcttt | 1560 |
| gactttgtta cgaagagaca ttactcaaga gcaaattgac agcttcaaaa agaaattgca | 1620 |
| agatgatttt agttacgaga catttgaaac agacttgggt gggactggct gctgtttgtt | 1680 |
| aagcgcaaaa aatttgaata agatcttaa aatcaaatcc ctagtattcc aattatttga | 1740 |
| aaataaaact accacaaagc aacaattga cgatctatta ttgccaggaa acacgaattt | 1800 |
| accatggact tcataagcta atttgcgata ggcctgcacc cttaaggagg aaaaaaacat | 1860 |
| gtcagagttg agagccttca gtgccccagg gaaagcgtta ctagctggtg gatatttagt | 1920 |
| tttagataca aaatatgaag catttgtagt cggattatcg gcaagaatgc atgctgtagc | 1980 |
| ccatccttac ggttcattgc aagggtctga taagtttgaa gtgcgtgtga aaagtaaaca | 2040 |

```
atttaaagat ggggagtggc tgtaccatat aagtcctaaa agtggcttca ttcctgtttc   2100
gataggcgga tctaagaacc cttttcattga aaaagttatc gctaacgtat ttagctactt   2160
taaacctaac atggacgact actgcaatag aaacttgttc gttattgata ttttctctga   2220
tgatgcctac cattctcagg aggatagcgt taccgaacat cgtggcaaca gaagattgag   2280
ttttcattcg cacagaattg aagaagttcc caaaacaggg ctgggctcct cggcaggttt   2340
agtcacagtt ttaactacag ctttggcctc cttttttgta tcggacctgg aaaataatgt   2400
agacaaatat agagaagtta ttcataattt agcacaagtt gctcattgtc aagctcaggg   2460
taaaattgga agcgggtttg atgtagcggc ggcagcatat ggatctatca gatatagaag   2520
attcccaccc gcattaatct ctaatttgcc agatattgga agtgctactt acggcagtaa   2580
actggcgcat ttggttgatg aagaagactg gaatattacg attaaaagta accatttacc   2640
ttcgggatta actttatgga tgggcgatat taagaatggt tcagaaacag taaaactggt   2700
ccagaaggta aaaaattggt atgattcgca tatgccagaa agcttgaaaa tatatacaga   2760
actcgatcat gcaaattcta gatttatgga tggactatct aaactagatc gcttacacga   2820
gactcatgac gattacagcg atcagatatt tgagtctctt gagaggaatg actgtacctg   2880
tcaaaagtat cctgaaatca cagaagttag agatgcagtt gccacaatta gacgttcctt   2940
tagaaaaata actaaagaat ctggtgccga tatcgaccct cccgtacaaa ctagcttatt   3000
ggatgattgc cagaccttaa aaggagttct tacttgctta atacctggtg ctggtggtta   3060
tgacgccatt gcagtgatta ctaagcaaga tgttgatctt agggctcaaa ccgctaatga   3120
caaaagattt tctaaggttc aatggctgga tgtaactcag gctgactggg gtgttaggaa   3180
agaaaaagat ccggaaactt atcttgataa ataacttaag gtagctgcat gcagaattcg   3240
cccttaagga ggaaaaaaaa atgaccgttt acacagcatc cgttaccgca cccgtcaaca   3300
tcgcaaccct taagtattgg gggaaaaggg acacgaagtt gaatctgccc accaattcgt   3360
ccatatcagt gactttatcg caagatgacc tcagaacgtt gacctctgcg gctactgcac   3420
ctgagtttga acgcgacact ttgtggttaa atggagaacc acacagcatc gacaatgaaa   3480
gaactcaaaa ttgtctgcgc gacctacgcc aattaagaaa ggaaatggaa tcgaaggacg   3540
cctcattgcc cacattatct caatggaaac tccacattgt ctccgaaaat aacttttcta   3600
cagcagctgg tttagcttcc tccgctgctg gctttgctgc attggtctct gcaattgcta   3660
agttatacca attaccacag tcaacttcag aaatatctag aatagcaaga aaggggtctg   3720
gttcagcttg tagatcgttg tttggcggat acgtggcctg ggaaatggga aaagctgaag   3780
atggtcatga ttccatggca gtacaaatcg cagacagctc tgactggcct cagatgaaag   3840
cttgtgtcct agttgtcagc gatattaaaa aggatgtgag ttccactcag ggtatgcaat   3900
tgaccgtggc aacctccgaa ctatttaaag aaagaattga acatgtcgta ccaaagagat   3960
ttgaagtcat gcgtaaagcc attgttgaaa agatttcgc cacctttgca aaggaaacaa   4020
tgatggattc caactctttc catgccacat gtttggactc tttccctcca atattctaca   4080
tgaatgacac ttccaagcgt atcatcagtt ggtgccacac cattaatcag ttttacggag   4140
aaacaatcgt tgcatacacg tttgatgcag gtccaaatgc tgtgttgtac tacttagctg   4200
aaaatgagtc gaaactcttt gcatttatct ataaattgtt tggctctgtt cctggatggg   4260
acaagaaatt tactactgag cagcttgagg ctttcaacca tcaatttgaa tcatctaact   4320
ttactgcacg tgaattggat cttgagttgc aaaaggatgt tgccagagtg attttaactc   4380
aagtcggttc aggcccacaa gaaacaaacg aatctttgat tgacgcaaag actggtctac   4440
```

```
caaaggaata agatcaattc gctgcatcgc ccttaggagg taaaaaaaaa tgactgccga    4500
caacaatagt atgccccatg gtgcagtatc tagttacgcc aaattagtgc aaaaccaaac    4560
acctgaagac attttggaag agtttcctga aattattcca ttacaacaaa gacctaatac    4620
ccgatctagt gagacgtcaa atgacgaaag cggagaaaca tgttttctg  gtcatgatga    4680 ggagcaaatt aagttaatga atgaaaattg tattgttttg gattgggacg ataatgctat    4740
tggtgccggt accaagaaag tttgtcattt aatggaaaat attgaaaagg gtttactaca    4800
tcgtgcattc tccgtcttta ttttcaatga acaaggtgaa ttacttttac aacaaagagc    4860
cactgaaaaa ataactttcc ctgatctttg gactaacaca tgctgctctc atccactatg    4920
tattgatgac gaattaggtt tgaagggtaa gctagacgat aagattaagg gcgctattac    4980
tgcggcggtg agaaaactag atcatgaatt aggtattcca gaagatgaaa ctaagacaag    5040
gggtaagttt cacttttttaa acagaatcca ttacatggca ccaagcaatg aaccatgggg    5100
tgaacatgaa attgattaca tcctatttta taagatcaac gctaaagaaa acttgactgt    5160
caacccaaac gtcaatgaag ttagagactt caaatgggtt tcaccaaatg atttgaaaac    5220
tatgtttgct gacccaagtt acaagtttac gccttggttt aagattattt gcgagaatta    5280
cttattcaac tggtgggagc aattagatga cctttctgaa gtggaaaatg acaggcaaat    5340
tcatagaatg ctataacaac gcgtcctgca ttcgcccctta ggaggtaaaa aaacatgtgt    5400
gcgacctctt ctcaatttac tcagattacc gagcataatt cccgtcgttc cgcaaactat    5460
cagccaaacc tgtggaattt cgaattcctg caatccctgg agaacgacct gaaagtggaa    5520
aagctggagg agaaagcgac caaactggag gaagaagttc gctgcatgat caaccgtgta    5580
gacacccagc cgctgtccct gctggagctg atcgacgatg tgcagcgcct gggtctgacc    5640
tacaaatttg aaaaagacat cattaaagcc ctggaaaaca tcgtactgct ggacgaaaac    5700
aaaaagaaca aatctgacct gcacgcaacc gctctgtctt ccgtctgct  gcgtcagcac    5760 ggtttcgagg tttctcagga tgtttttgag cgtttcaagg ataaagaagg tggtttcagc    5820
ggtgaactga aggtgacgt  ccaaggcctg ctgagcctgt atgaagcgtc ttacctgggt    5880
ttcgagggtg agaacctgct ggaggaggcg cgtaccttt  ccatcaccca cctgaagaac    5940
aacctgaaag aaggcattaa taccaaggtt gcagaacaag tgagccacgc cctggaactg    6000
ccatatcacc agcgtctgca ccgtctggag gcacgttggt tcctggataa atacgaaccg    6060
aaagaaccgc atcaccagct gctgctggag ctggcgaagc tggatttaa  catggtacag    6120 accctgcacc agaaagagct gcaagatctg tcccgctggt ggaccgagat gggcctggct    6180
agcaaactgg attttgtacg cgaccgcctg atggaagttt atttctgggc actgggtatg    6240
gcgccagacc cgcagtttgg tgaatgtcgc aaagctgtta ctaaaatgtt tggtctggtg    6300
acgatcatcg atgacgtgta tgacgtttat ggcactctgg acgaactgca actgttcacc    6360
gatgctgtag agcgctggga cgttaacgct attaacaccc tgccggacta tatgaaactg    6420
tgtttcctgg cactgtacaa caccgttaac gacacgtcct attctattct gaaagagaaa    6480
ggtcataaca acctgtccta tctgacgaaa agctggcgtg aactgtgcaa agcctttctg    6540
caagaggcga atggtccaa  caacaaaatt atcccggctt tctccaagta cctggaaaac    6600
gccagcgttt cctcctccgg tgtagcgctg ctggcgccgt cttactttc  cgtatgccag    6660 cagcaggaag acatctccga ccacgcgctg cgttccctga ccgacttcca tggtctggtg    6720
cgttctagct gcgttatctt ccgcctgtgc aacgatctgg ccacctctgc ggcggagctg    6780
gaacgtggcg agactaccaa ttctatcatt agctacatgc acgaaaacga tggtaccagc    6840
```

```
gaggaacagg cccgcgaaga actgcgtaaa ctgatcgacg ccgaatggaa aaagatgaat    6900
cgtgaacgcg ttagcgactc caccctgctg cctaaagcgt tcatggaaat cgcagttaac    6960
atggcacgtg tttcccactg cacctaccag tatggcgatg gtctgggtcg cccagactac    7020
gcgactgaaa accgcatcaa actgctgctg attgacccct tcccgattaa ccagctgatg    7080
tatgtctaac tgcagctggt accatatggg aattcgaagc tttctagaac aaaaactcat    7140
ctcagaagag gatctgaata gcgccgtcga ccatcatcat catcatcatt gagtttaaac    7200
ggtctccagc ttggctgttt tggcggatga gagaagattt tcagcctgat acagattaaa    7260
tcagaacgca gaagcggtct gataaaacag aatttgcctg gcggcagtag cgcggtggtc    7320
ccacctgacc ccatgccgaa ctcagaagtg aaacgccgta gcgccgatgg tagtgtgggg    7380
tctccccatg cgagagtagg gaactgccag gcatcaaata aaacgaaagg ctcagtcgaa    7440
agactgggcc tttcgtttta tctgttgttt gtcggtgaac gctctcctga gtaggacaaa    7500
tccgccggga gcggatttga acgttgcgaa gcaacgcccc ggagggtggc gggcaggacg    7560
cccgccataa actgccaggc atcaaattaa gcagaaggcc atcctgacgg atggcctttt    7620
tgcgtttcta caaactcttt ttgtttattt ttctaaatac attcaaatat gtatccgctt    7680
aaccggaatt gccagctggg gcgccctctg gtaaggttgg gaagccctgc aaagtaaact    7740
ggatggcttt ctcgccgcca aggatctgat ggcgcagggg atcaagctct gatcaagaga    7800
caggatgagg atcgtttcgc atgattgaac aagatggatt gcacgcaggt tctccggccg    7860
cttgggtgga gaggctattc ggctatgact gggcacaaca gacaatcggc tgctctgatg    7920
ccgccgtgtt ccggctgtca gcgcaggggc gcccggttct ttttgtcaag accgacctgt    7980
ccggtgccct gaatgaactg caagacgagg cagcgcggct atcgtggctg gccacgacgg    8040
gcgttccttg cgcagctgtg ctcgacgttg tcactgaagc gggaagggac tggctgctat    8100
tgggcgaagt gccggggcag gatctcctgt catctcacct tgctcctgcc gagaaagtat    8160
ccatcatggc tgatgcaatg cggcggctgc atacgcttga tccggctacc tgcccattcg    8220
accaccaagc gaaacatcgc atcgagcgag cacgtactcg gatggaagcc ggtcttgtcg    8280
atcaggatga tctggacgaa gagcatcagg ggctcgcgcc agccgaactg ttcgccaggc    8340
tcaaggcgag catgcccgac ggcgaggatc tcgtcgtgac ccatggcgat gcctgcttgc    8400
cgaatatcat ggtggaaaat ggccgctttt ctggattcat cgactgtggc cggctgggtg    8460
tggcggaccg ctatcaggac atagcgttgg ctacccgtga tattgctgaa gagcttggcg    8520
gcgaatgggc tgaccgcttc ctcgtgcttt acggtatcgc cgctcccgat tcgcagcgca    8580
tcgccttcta tcgccttctt gacgagttct tctgacgcat gaccaaaatc ccttaacgtg    8640
agttttcgtt ccactgagcg tcagaccccg tagaaaagat caaaggatct tcttgagatc    8700
cttttttttct gcgcgtaatc tgctgcttgc aaacaaaaaa accaccgcta ccagcggtgg    8760
tttgtttgcc ggatcaagag ctaccaactc tttttccgaa ggtaactggc ttcagcagag    8820
cgcagatacc aaatactgtc cttctagtgt agccgtagtt aggccaccac ttcaagaact    8880
ctgtagcacc gcctacatac ctcgctctgc taatcctgtt accagtggct gctgccagtg    8940
gcgataagtc gtgtcttacc gggttggact caagacgata gttaccggat aaggcgcagc    9000
ggtcgggctg aacggggggt tcgtgcacac agcccagctt ggagcgaacg acctacaccg    9060
aactgagata cctacagcgt gagctatgag aaagcgccac gcttcccgaa gggagaaagg    9120
cggacaggta tccggtaagc ggcagggtcg gaacaggaga gcgcacgagg gagcttccag    9180
ggggaaacgc ctggtatctt tatagtcctg tcgggtttcg ccacctctga cttgagcgtc    9240
```

```
gattttttgtg atgctcgtca gggggggcgga gcctatggaa aaacgccagc aacgcggcct    9300
ttttacggtt cctggccttt tgctggcctt ttgctcacat gttctttcct gcgttatccc    9360
ctgattctgt ggataaccgt attaccgcct ttgagtgagc tgataccgct cgccgcagcc    9420
gaacgaccga gcgcagcgag tcagtgagcg aggaagcgga agagcgcctg atgcggtatt    9480
ttctccttac gcatctgtgc ggtatttcac accgcatatg gtgcactctc agtacaatct    9540
gctctgatgc cgcatagtta agccagtata cactccgcta tcgctacgtg actgggtcat    9600
ggctgcgccc cgacacccgc caacacccgc tgacgcgccc tgacgggctt gtctgctccc    9660
ggcatccgct tacagacaag ctgtgaccgt ctccgggagc tgcatgtgtc agaggttttc    9720
accgtcatca ccgaaacgcg cgaggcagca gatcaattcg cgcgcgaagg cgaagcggca    9780
tgcatttacg ttgacaccat cgaatggtgc aaaacctttc gcggtatggc atgatagcgc    9840
ccggaagaga gtcaattcag ggtggtgaat gtgaaaccag taacgttata cgatgtcgca    9900
gagtatgccg gtgtctctta tcagaccgtt tcccgcgtgg tgaaccaggc cagccacgtt    9960
tctgcgaaaa cgcgggaaaa agtggaagcg gcgatggcgg agctgaatta cattcccaac   10020
cgcgtggcac aacaactggc gggcaaacag tcgttgctga ttggcgttgc cacctccagt   10080
ctggccctgc acgcgccgtc gcaaattgtc gcggcgatta atctcgcgc cgatcaactg   10140
ggtgccagcg tggtggtgtc gatggtagaa cgaagcggcg tcgaagcctg taaagcggcg   10200
gtgcacaatc ttctcgcgca acgcgtcagt gggctgatca ttaactatcc gctggatgac   10260
caggatgcca ttgctgtgga agctgcctgc actaatgttc cggcgttatt tcttgatgtc   10320
tctgaccaga cacccatcaa cagtattatt ttctcccatg aagacggtac gcgactgggc   10380
gtggagcatc tggtcgcatt gggtcaccag caaatcgcgc tgttagcggg cccattaagt   10440
tctgtctcgg cgcgtctgcg tctggctggc tggcataaat atctcactcg caatcaaatt   10500
cagccgatag cggaacggga aggcgactgg agtgccatgt ccggttttca acaaaccatg   10560
caaatgctga atgagggcat cgttcccact gcgatgctgg ttgccaacga tcagatggcg   10620
ctgggcgcaa tgcgcgccat taccgagtcc gggctgcgcg ttggtgcgga tatctcggta   10680
gtgggatacg acgataccga agacagctca tgttatatcc cgccgtcaac caccatcaaa   10740
caggattttc gcctgctggg gcaaaccagc gtggaccgct tgctgcaact ctctcagggc   10800
caggcggtga agggcaatca gctgttgccc gtctcactgg tgaaaagaaa aaccaccctg   10860
gcgcccaata cgcaaaccgc ctctccccgc gcgttggccg attcattaat gcagctggca   10920
cgacaggttt cccgactgga aagcgggcag tgagcgcaac gcaattaatg tgagttagcg   10980
cgaattgatc tg                                                       10992
```

<210> SEQ ID NO 34
<211> LENGTH: 50
<212> TYPE: DNA
<213> ORGANISM: Artificial Sequence
<220> FEATURE:
<223> OTHER INFORMATION: Synthetic Construct

<400> SEQUENCE: 34
gagacatgag ctcaggaggt aaaaaaacat gaaaacagta gttattattg                50

<210> SEQ ID NO 35
<211> LENGTH: 54
<212> TYPE: DNA
<213> ORGANISM: Artificial Sequence
<220> FEATURE:
<223> OTHER INFORMATION: Synthetic Construct

```
<400> SEQUENCE: 35
tttatcaatc ccaattgtca tgttttttta cctcctttat tgttttctta aatc    54

<210> SEQ ID NO 36
<211> LENGTH: 54
<212> TYPE: DNA
<213> ORGANISM: Artificial Sequence
<220> FEATURE:
<223> OTHER INFORMATION: Synthetic Construct

<400> SEQUENCE: 36
gatttaagaa aacaataaag gaggtaaaaa aacatgacaa ttgggattga taaa    54

<210> SEQ ID NO 37
<211> LENGTH: 40
<212> TYPE: DNA
<213> ORGANISM: Artificial Sequence
<220> FEATURE:
<223> OTHER INFORMATION: Synthetic Construct

<400> SEQUENCE: 37
gacatgacat agatctttag tttcgataag aacgaacggt                    40

<210> SEQ ID NO 38
<211> LENGTH: 26
<212> TYPE: DNA
<213> ORGANISM: Artificial Sequence
<220> FEATURE:
<223> OTHER INFORMATION: Synthetic Construct

<400> SEQUENCE: 38
atgaaaacag tagttattat tgatgc                                   26

<210> SEQ ID NO 39
<211> LENGTH: 33
<212> TYPE: DNA
<213> ORGANISM: Artificial Sequence
<220> FEATURE:
<223> OTHER INFORMATION: Synthetic Construct

<400> SEQUENCE: 39
atgttattgt tttcttaaat catttaaaat agc                           33

<210> SEQ ID NO 40
<211> LENGTH: 26
<212> TYPE: DNA
<213> ORGANISM: Artificial Sequence
<220> FEATURE:
<223> OTHER INFORMATION: Synthetic Construct

<400> SEQUENCE: 40
atgacaattg ggattgataa aattag                                   26

<210> SEQ ID NO 41
<211> LENGTH: 24
<212> TYPE: DNA
<213> ORGANISM: Artificial Sequence
<220> FEATURE:
<223> OTHER INFORMATION: Synthetic Construct

<400> SEQUENCE: 41
ttagtttcga taagaacgaa cggt                                     24

<210> SEQ ID NO 42
<211> LENGTH: 23
```

```
<212> TYPE: DNA
<213> ORGANISM: Artificial Sequence
<220> FEATURE:
<223> OTHER INFORMATION: Synthetic Construct

<400> SEQUENCE: 42
gaaatagccc cattagaagt atc                                              23

<210> SEQ ID NO 43
<211> LENGTH: 24
<212> TYPE: DNA
<213> ORGANISM: Artificial Sequence
<220> FEATURE:
<223> OTHER INFORMATION: Synthetic Construct

<400> SEQUENCE: 43
ttgccaatca tatgattgaa aatc                                             24

<210> SEQ ID NO 44
<211> LENGTH: 25
<212> TYPE: DNA
<213> ORGANISM: Artificial Sequence
<220> FEATURE:
<223> OTHER INFORMATION: Synthetic Construct

<400> SEQUENCE: 44
gctatgcttc attagatcct tatcg                                            25

<210> SEQ ID NO 45
<211> LENGTH: 25
<212> TYPE: DNA
<213> ORGANISM: Artificial Sequence
<220> FEATURE:
<223> OTHER INFORMATION: Synthetic Construct

<400> SEQUENCE: 45
gaaacctaca tccaatcttt tgccc                                            25

<210> SEQ ID NO 46
<211> LENGTH: 8703
<212> TYPE: DNA
<213> ORGANISM: Artificial Sequence
<220> FEATURE:
<223> OTHER INFORMATION: Synthetic Construct

<400> SEQUENCE: 46
cccgtcttac tgtcgggaat tcgcgttggc cgattcatta atgcagattc tgaaatgagc        60
tgttgacaat taatcatccg gctcgtataa tgtgtggaat tgtgagcgga taacaatttc       120
acacaggaaa cagcgccgct gagaaaaagc gaagcggcac tgctctttaa caatttatca       180
gacaatctgt gtgggcactc gaccggaatt atcgattaac tttattatta aaaattaaag       240
aggtatatat taatgtatcg attaaataag gaggaataaa ccatggatcc gagctcagga       300
ggtaaaaaaa catgaaaaca gtagttatta ttgatgcatt acgaacacca attggaaaat       360
ataaaggcag cttaagtcaa gtaagtgccg tagacttagg aacacatgtt acaacacaac       420
ttttaaaaag acattccact atttctgaag aaattgatca agtaatcttt ggaaatgttt       480
tacaagctgg aaatggccaa atcccgcac gacaaatagc aataaacagc ggtttgtctc       540
atgaaattcc cgcaatgacg gttaatgagg tctgcggatc aggaatgaag gccgttattt       600
tggcgaaaca attgattcaa ttaggagaag cggaagtttt aattgctggc gggattgaga       660
atatgtccca agcacctaaa ttacaacgtt ttaattacga aacagaaagc tacgatgcgc       720 cttttttctag tatgatgtat gatggattaa cggatgcctt tagtggtcag gcaatgggct       780
```

```
taactgctga aaatgtggcc gaaaagtatc atgtaactag agaagagcaa gatcaatttt    840
ctgtacattc acaattaaaa gcagctcaag cacaagcaga agggatattc gctgacgaaa    900
tagccccatt agaagtatca ggaacgcttg tggagaaaga tgaagggatt cgccctaatt    960
cgagcgttga gaagctagga acgcttaaaa cagttttta agaagacggt actgtaacag   1020
cagggaatgc atcaaccatt aatgatgggg cttctgcttt gattattgct tcacaagaat   1080
atgccgaagc acacggtctt ccttatttag ctattattcg agacagtgtg gaagtcggta   1140
ttgatccagc ctatatggga atttcgccga ttaaagccat tcaaaaactg ttagcgcgca   1200
atcaacttac tacggaagaa attgatctgt atgaaatcaa cgaagcattt gcagcaactt   1260
caatcgtggt ccaaagagaa ctggctttac cagaggaaaa ggtcaacatt tatggtggcg   1320
gtatttcatt aggtcatgcg attggtgcca caggtgctcg tttattaacg agtttaagtt   1380
atcaattaaa tcaaaaagaa aagaaatatg gagtggcttc tttatgtatc ggcggtggct   1440
taggactcgc tatgctacta gagagacctc agcaaaaaaa aaacagccga ttttatcaaa   1500
tgagtcctga ggaacgcctg gcttctcttc ttaatgaagg ccagatttct gctgatacaa   1560
aaaaagaatt tgaaaatacg gctttatctt cgcagattgc caatcatatg attgaaaatc   1620
aaatcagtga aacagaagtg ccgatgggcg ttggcttaca tttaacagtg gacgaaactg   1680
attatttggt accaatggcg acagaagagc cctcagttat tgcggctttg agtaatggtg   1740
caaaaatagc acaaggattt aaaacagtga atcaacaacg cttaatgcgt ggacaaatcg   1800
ttttttacga tgttgcagat cccgagtcat tgattgataa actacaagta agagaagcgg   1860
aagtttttca acaagcagag ttaagttatc catctatcgt taaacggggc ggcggcttaa   1920
gagatttgca atatcgtact tttgatgaat catttgtatc tgtcgacttt ttagtagatg   1980
ttaaggatgc aatgggggca aatatcgtta acgctatgtt ggaaggtgtg gccgagttgt   2040
tccgtgaatg gtttgcggag caaaagattt tattcagtat tttaagtaat tatgccacgg   2100
agtcggttgt tacgatgaaa acggctattc cagtttcacg tttaagtaag gggagcaatg   2160
gccgggaaat tgctgaaaaa attgttttag cttcacgcta tgcttcatta gatccttatc   2220
gggcagtcac gcataacaaa ggaatcatga atggcattga agctgtagtt ttagctacag   2280
gaaatgatac acgcgctgtt agcgcttctt gtcatgcttt tgcggtgaag gaaggtcgct   2340
accaaggctt gactagttgg acgctggatg gcgaacaact aattggtgaa atttcagttc   2400
cgcttgcttt agccacggtt ggcggtgcca caaaagtctt acctaaatct caagcagctg   2460
ctgatttgtt agcagtgacg gatgcaaaag aactaagtcg agtagtagcg gctgttggtt   2520
tggcacaaaa tttagcggcg ttacgggcct tagtctctga aggaattcaa aaaggacaca   2580
tggctctaca agcacgttct ttagcgatga cggtcggagc tactggtaaa gaagttgagg   2640
cagtcgctca acaattaaaa cgtcaaaaaa cgatgaacca agaccgagcc atggctattt   2700
taaatgattt aagaaaacaa taaggaggt aaaaaaacat gacaattggg attgataaaa   2760
ttagttttt tgtgcccct tattatattg atatgacggc actggctgaa gccagaaatg   2820
tagaccctgg aaaatttcat attggtattg ggcaagacca aatggcggtg aacccaatca   2880
gccaagatat tgtgacattt gcagccaatg ccgcagaagc gatcttgacc aagaagata   2940
aagaggccat tgatatggtg attgtcggga ctgagtccag tatcgatgag tcaaaagcgg   3000
ccgcagttgt cttacatcgt ttaatgggga ttcaaccttt cgctcgctct ttcgaaatca   3060
aggaagcttt tacggagca acagcaggct tacagttagc taagaatcac gtagccttac   3120
atccagataa aaaagtcttg gtcgtagcgg cagatattgc aaaatatggc ttaaattctg   3180
```

```
gcggtgagcc tacacaagga gctggggcgg ttgcaatgtt agttgctagt gaaccgcgca   3240
ttttggcttt aaaagaggat aatgtgatgc tgacgcaaga tatctatgac ttttggcgtc   3300
caacaggcca cccgtatcct atggtcgatg gtcctttgtc aaacgaaacc tacatccaat   3360
cttttgccca agtctgggat gaacataaaa acgaaccgg tcttgatttt gcagattatg    3420
atgctttagc gttccatatt ccttacacaa aaatgggcaa aaaagcctta ttagcaaaaa    3480
tctccgacca aactgaagca gaacaggaac gaattttagc ccgttatgaa gaaagtatcg    3540
tctatagtcg tcgcgtagga aacttgtata cgggttcact ttatctggga ctcatttccc    3600
ttttagaaaa tgcaacgact ttaaccgcag gcaatcaaat tggtttattc agttatggtt    3660
ctggtgctgt cgctgaattt ttcactggtg aattagtagc tggttatcaa atcatttac    3720 aaaaagaaac tcatttagca ctgctggata tcggacaga actttctatc gctgaatatg    3780
aagccatgtt tgcagaaact ttagacacag acattgatca aacgttagaa gatgaattaa    3840
aatatagtat ttctgctatt aataataccg ttcgttctta tcgaaactaa gagatctgca    3900
gctggtacca tatgggaatt cgaagcttgg gcccgaacaa aaactcatct cagaagagga    3960
tctgaatagc gccgtcgacc atcatcatca tcatcattga gtttaaacgg tctccagctt    4020
ggctgttttg gcggatgaga gaagattttc agcctgatac agattaaatc agaacgcaga    4080
agcggtctga taaaacagaa tttgcctggc ggcagtagcg cggtggtccc acctgacccc    4140
atgccgaact cagaagtgaa acgccgtagc gccgatggta gtgtggggtc tccccatgcg    4200
agagtaggga actgccaggc atcaaataaa acgaaaggct cagtcgaaag actgggcctt    4260
tcgttttatc tgttgtttgt cggtgaacgc tctcctgagt aggacaaatc cgccgggagc    4320
ggatttgaac gttgcgaagc aacggcccgg agggtggcgg gcaggacgcc cgccataaac    4380
tgccaggcat caaattaagc agaaggccat cctgacggat ggcctttttg cgtttctaca    4440
aactcttttt gttatttttt ctaaatacat tcaaatatgt atccgctcat gagacaataa    4500
ccctgataaa tgcttcaata atctggcgta atagcgaaga ggcccgcacc gatcgccctt    4560
cccaacagtt gcgcagcctg aatggcgaat ggcgcctgat gcggtatttt ctccttacgc    4620
atctgtgcgg tatttcacac cgcatatggt gcactctcag tacaatctgc tctgatgccg    4680
catagttaag ccagcccga cacccgccaa cacccgctga cgagcttagt aaagccctcg    4740
ctagatttta atgcggatgt tgcgattact tcgccaacta ttgcgataac aagaaaaagc    4800
cagcctttca tgatatatct cccaatttgt gtagggctta ttatgcacgc ttaaaaataa    4860
taaaagcaga cttgacctga tagtttggct gtgagcaatt atgtgcttag tgcatctaac    4920
gcttgagtta agccgcgccg cgaagcggcg tcggcttgaa cgaattgtta gacattattt    4980
gccgactacc ttggtgatct cgcctttcac gtagtggaca aattcttcca actgatctgc    5040
gcgcgaggcc aagcgatctt cttcttgtcc aagataagcc tgtctagctt caagtatgac    5100
gggctgatac tgggccggca ggcgctccat gcccagtcg gcagcgacat ccttcggcgc    5160
gattttgccg gttactgcgc tgtaccaaat gcgggacaac gtaagcacta catttcgctc    5220
atcgccagcc cagtcgggcg cgagttcca tagcgttaag gtttcattta gcgcctcaaa    5280
tagatcctgt tcaggaaccg gatcaaagag ttcctccgcc gctggaccta ccaaggcaac    5340
gctatgttct cttgctttg tcagcaagat agccagatca atgtcgatcg tggctggctc    5400
gaagatacct gcaagaatgt cattgcgctg ccattctcca aattgcagtt cgcgcttagc    5460
tggataacgc cacggaatga tgtcgtcgtg cacaacaatg gtgacttcta cagcgcggag    5520
aatctcgctc tctccagggg aagccgaagt ttccaaaagg tcgttgatca aagctcgccg    5580
```

```
cgttgtttca tcaagcctta cggtcaccgt aaccagcaaa tcaatatcac tgtgtggctt      5640
caggccgcca tccactgcgg agccgtacaa atgtacggcc agcaacgtcg gttcgagatg      5700
gcgctcgatg acgccaacta cctctgatag ttgagtcgat acttcggcga tcaccgcttc      5760
cctcatgatg tttaactttg ttttagggcg actgccctgc tgcgtaacat cgttgctgct      5820
ccataacatc aaacatcgac ccacggcgta acgcgcttgc tgcttggatg cccgaggcat      5880
agactgtacc ccaaaaaaac agtcataaca agccatgaaa accgccactg cgccgttacc      5940
accgctgcgt tcggtcaagg ttctggacca gttgcgtgag cgcatacgct acttgcatta      6000
cagcttacga accgaacagg cttatgtcca ctgggttcgt gccttcatcc gtttccacgg      6060
tgtgcgtcac ccggcaacct tgggcagcag cgaagtcgag gcatttctgt cctggctggc      6120
gaacgagcgc aaggtttcgg tctccacgca tcgtcaggca ttggcggcct tgctgttctt      6180
ctacggcaag gtgctgtgca cggatctgcc ctggcttcag gagatcggaa gacctcggcc      6240
gtcgcggcgc ttgccggtgg tgctgacccc ggatgaagtg gttcgcatcc tcggttttct      6300
ggaaggcgag catcgtttgt tcgcccagct tctgtatgga acgggcatgc ggatcagtga      6360
gggtttgcaa ctgcgggtca aggatctgga tttcgatcac ggcacgatca tcgtgcggga      6420
gggcaagggc tccaaggatc gggccttgat gttacccgag agcttggcac ccagcctgcg      6480
cgagcagggg aattaattcc cacgggtttt gctgcccgca aacgggctgt tctggtgttg      6540
ctagtttgtt atcagaatcg cagatccggc ttcagccggt ttgccggctg aaagcgctat      6600
ttcttccaga attgccatga ttttttcccc acgggaggcg tcactggctc ccgtgttgtc      6660
ggcagctttg attcgataag cagcatcgcc tgtttcaggc tgtctatgtg tgactgttga      6720
gctgtaacaa gttgtctcag gtgttcaatt tcatgttcta gttgctttgt tttactggtt      6780
tcacctgttc tattaggtgt tacatgctgt tcatctgtta cattgtcgat ctgttcatgg      6840
tgaacagctt tgaatgcacc aaaaactcgt aaaagctctg atgtatctat cttttttaca      6900 ccgtttcat ctgtgcatat ggacagtttt ccctttgata tgtaacggtg aacagttgtt      6960 ctactttgt ttgttagtct tgatgcttca ctgatagata caagagccat aagaacctca      7020
gatccttccg tatttagcca gtatgttctc tagtgtggtt cgttgttttt gcgtgagcca      7080
tgagaacgaa ccattgagat catacttact ttgcatgtca ctcaaaaatt ttgcctcaaa      7140
actggtgagc tgaattttg cagttaaagc atcgtgtagt gttttttctta gtccgttatg      7200 taggtaggaa tctgatgtaa tggttgttgg tattttgtca ccattcattt ttatctggtt      7260
gttctcaagt tcggttacga gatccatttg tctatctagt tcaacttgga aaatcaacgt      7320
atcagtcggg cggcctcgct tatcaaccac caatttcata ttgctgtaag tgtttaaatc      7380
tttacttatt ggtttcaaaa cccattggtt aagccttta aactcatggt agttatttc      7440 aagcattaac atgaacttaa attcatcaag gctaatctct atatttgcct tgtgagtttt      7500
cttttgtgtt agttctttta ataccactc ataaatcctc atagagtatt tgttttcaaa      7560
agacttaaca tgttccagat tatatttat gaattttttt aactggaaaa gataaggcaa      7620
tatctcttca ctaaaaacta attctaattt ttcgcttgag aacttggcat agtttgtcca      7680
ctggaaaatc tcaaagcctt taaccaaagg attcctgatt tccacagttc tcgtcatcag      7740
ctctctggtt gctttagcta atacaccata agcattttcc ctactgatgt tcatcatctg      7800
agcgtattgg ttataagtga acgataccgt ccgttctttc cttgtagggt tttcaatcgt      7860
ggggttgagt agtgccacac agcataaaat tagcttggtt tcatgctccg ttaagtcata      7920
gcgactaatc gctagttcat ttgctttgaa aacaactaat tcagacatac atctcaattg      7980
```

```
gtctaggtga ttttaatcac tataccaatt gagatgggct agtcaatgat aattactagt    8040
ccttttcctt tgagttgtgg gtatctgtaa attctgctag acctttgctg gaaaacttgt    8100
aaattctgct agaccctctg taaattccgc tagacctttg tgtgtttttt ttgtttatat    8160
tcaagtggtt ataatttata gaataaagaa agaataaaaa aagataaaaa gaatagatcc    8220
cagccctgtg tataactcac tactttagtc agttccgcag tattacaaaa ggatgtcgca    8280
aacgctgttt gctcctctac aaaacagacc ttaaaaccct aaaggcttaa gtagcaccct    8340
cgcaagctcg ggcaaatcgc tgaatattcc ttttgtctcc gaccatcagg cacctgagtc    8400
gctgtctttt tcgtgacatt cagttcgctg cgctcacggc tctggcagtg aatgggggta    8460
aatggcacta caggcgcctt ttatggattc atgcaaggaa actacccata atacaagaaa    8520
agcccgtcac gggcttctca gggcgtttta tggcgggtct gctatgtggt gctatctgac    8580
tttttgctgt tcagcagttc ctgccctctg attttccagt ctgaccactt cggattatcc    8640
cgtgacaggt cattcagact ggctaatgca cccagtaagg cagcggtatc atcaacaggc    8700
tta                                                                 8703

<210> SEQ ID NO 47
<211> LENGTH: 9371
<212> TYPE: DNA
<213> ORGANISM: Artificial Sequence
<220> FEATURE:
<223> OTHER INFORMATION: Synthetic Construct

<400> SEQUENCE: 47
tgtaaccttt gctttcaaat gagtagaaat aatgcacatc catgtttgta tcgtgcaaat      60
aaagtgtttc atccgtagga aaaatgact ttagtatctg ttccgctttt tctgatgaaa     120
tgtgctcccc gacaaaattg aatgaatcat ggacatttgc tggctttgat acagcgaaag     180
cagccgttcc tatgttatat atcggattta acagcaggac aaaaaacacc atgacagcca     240
tcgtcaccca cttattcaca cgcacataaa cctttcctga cttttggaac agatgatagc     300
tcatcaaaaa tcccgccatt gccaaataaa tcgtatatgg cattactgca ccataatctt     360
ttgagatttg attgggatat ggcgcaagca gcaagacaag cagtccgata atcagcgtat     420
aaaataagcc tagtaagatc ttatccgttc tccaatacag cttgaaaaac actacattca     480
acgcaatggg aagagtgatg atgaaaaaca gaaacacgaa tgcaatcggc tccatcccat     540
ccgggtattc cttccaatac gaaaagaaac taaaaatcat tgtacgatc ggcaaactga     600 caacagcaag gtcgaacgta taaaacttac cctttccgcc atgatcacgc ggcatcagca     660
tatagtgaaa agccgtcagc agcacatatc cgtataacaa aaaatgcagc agcggcagca     720
gttcttttcc gtcctctctt aagtaagcgc tggtgaagtt tgttgattgc acctggtgaa     780
taagttcaac agacactccc gccagcagca caatccgcaa tataacaccc gccaagaaca     840
ttgtgcgctg ccggtttatt tgggatgat gcaccaaaag atataagccc gccagaacaa     900
caattgacca ttgaatcagc agggtgcttt gtctgcttaa tataaaataa cgttcgaaat     960
gcaatacata atgactgaat aactccaaca cgaacaacaa ctccattttc ttctgctatc    1020
aaaataacag actcgtgatt ttccaaacga gctttcaaaa aagcctctgc cccttgcaaa    1080
tcggatgcct gtctataaaa ttcccgatat tggttaaaca gcggcgcaat ggcggccgca    1140
tctgatgtct ttgcttggcg aatgttcatc ttatttcttc ctccctctca ataattttt    1200 cattctatcc cttttctgta aagtttattt ttcagaatac tttatcatc atgctttgaa    1260 aaaatatcac gataatatcc attgttctca cggaagcaca cgcaggtcat ttgaacgaat    1320
```

```
tttttcgaca ggaatttgcc gggactcagg agcatttaac ctaaaaaagc atgacatttc   1380
agcataatga acatttactc atgtctattt tcgttctttt ctgtatgaaa atagttattt   1440
cgagtctcta cggaaatagc gagagatgat atacctaaat agagataaaa tcatctcaaa   1500
aaaatgggtc tactaaaata ttattccatc tattacaata aattcacaga atagtctttt   1560
aagtaagtct actctgaatt tttttaaaag gagagggtaa agagtgtcat taccgttctt   1620
aacttctgca ccgggaaagg ttattatttt tggtgaacac tctgctgtgt acaacaagcc   1680
tgccgtcgct gctagtgtgt ctgcgttgag aacctacctg ctaataagcg agtcatctgc   1740
accagatact attgaattgg acttcccgga cattagcttt aatcataagt ggtccatcaa   1800
tgatttcaat gccatcaccg aggatcaagt aaactcccaa aaattggcca aggctcaaca   1860
agccaccgat ggcttgtctc aggaactcgt tagtcttttg gatccgttgt tagctcaact   1920
atccgaatcc ttccactacc atgcagcgtt ttgtttcctg tatatgtttg tttgcctatg   1980
cccccatgcc aagaatatta agttttcttt aaagtctact ttacccatcg gtgctgggtt   2040
gggctcaagc gcctctattt ctgtatcact ggccttagct atggcctact tggggggtt    2100 aataggatct aatgacttgg aaaagctgtc agaaaacgat aagcatatag tgaatcaatg   2160
ggccttcata ggtgaaaagt gtattcacgg taccccttca ggaatagata acgctgtggc   2220
cacttatggt aatgccctgc tatttgaaaa agactcacat aatggaacaa taacacaaa    2280 caattttaag ttcttagatg atttcccagc cattccaatg atcctaacct atactagaat   2340
tccaaggtct acaaaagatc ttgttgctcg cgttcgtgtg ttggtcaccg agaaatttcc   2400
tgaagttatg aagccaattc tagatgccat gggtgaatgt gccctacaag cttagagat   2460 catgactaag ttaagtaaat gtaaaggcac cgatgacgag gctgtagaaa ctaataatga   2520
actgtatgaa caactattgg aattgataag aataaatcat ggactgcttg tctcaatcgg   2580
tgtttctcat cctggattag aacttattaa aaatctgagc gatgatttga gaattggctc   2640
cacaaaactt accggtgctg gtggcggcgg ttgctctttg actttgttac gaagagacat   2700
tactcaagag caaattgaca gcttcaaaaa gaaattgcaa gatgattta gttacgagac    2760 atttgaaaca gacttgggtg ggactggctg ctgtttgtta agcgcaaaaa atttgaataa   2820
agatcttaaa atcaaatccc tagtattcca attatttgaa aataaaacta ccacaaagca   2880
acaaattgac gatctattat tgccaggaaa cacgaattta ccatggactt cataaaagga   2940
gagggtgtca gagttgagag ccttcagtgc cccagggaaa gcgttactag ctggtggata   3000
tttagtttta gatacaaaat atgaagcatt tgtagtcgga ttatcggcaa gaatgcatgc   3060
tgtagcccat ccttacggtt cattgcaagg gtctgataag tttgaagtgc gtgtgaaaag   3120
taaacaattt aaagatgggg agtggctgta ccatataagt cctaaaagtg gcttcattcc   3180
tgtttcgata ggcggatcta agaacccttt cattgaaaaa gttatcgcta acgtatttag   3240
ctactttaaa cctaacatgg acgactactg caatagaaac ttgttcgtta ttgatatttt   3300
ctctgatgat gcctaccatt ctcaggagga tagcgttacc gaacatcgtg gcaacagaag   3360
attgagtttt cattcgcaca gaattgaaga agttcccaaa acagggctgg gctcctcggc   3420
aggtttagtc acagttttaa ctacagcttt ggcctccttt tttgtatcgg acctggaaaa   3480
taatgtagac aaatatagag aagttattca aatttagca caagttgctc attgtcaagc    3540
tcagggtaaa attggaagcg ggtttgatgt agcggcggca gcatatggat ctatcagata   3600
tagaagattc ccacccgcat taatctctaa tttgccagat attggaagtg ctacttacgg   3660
cagtaaactg gcgcatttgg ttgatgaaga agactggaat attacgatta aaagtaaccca  3720
```

```
tttaccttcg ggattaactt tatggatggg cgatattaag aatggttcag aaacagtaaa   3780
actggtccag aagtaaaaaa attggtatga ttcgcatatg ccagaaagct tgaaaatata   3840
tacagaactc gatcatgcaa attctagatt tatggatgga ctatctaaac tagatcgctt   3900
acacgagact catgacgatt acagcgatca gatatttgag tctcttgaga ggaatgactg   3960
tacctgtcaa aagtatcctg aaatcacaga agttagagat gcagttgcca caattagacg   4020
ttcctttaga aaaataacta aagaatctgg tgccgatatc gaacctcccg tacaaactag   4080
cttattggat gattgccaga ccttaaaagg agttcttact tgcttaatac ctggtgctgg   4140
tggttatgac gccattgcag tgattactaa gcaagatgtt gatcttaggg ctcaaaccgc   4200
taatgacaaa agattttcta aggttcaatg gctggatgta actcaggctg actggggtgt   4260
taggaaagaa aaagatccgg aaacttatct tgataaataa aaggagaggg tgaccgttta   4320
cacagcatcc gttaccgcac ccgtcaacat cgcaacccct aagtattggg ggaaaaggga   4380
cacgaagttg aatctgccca ccaattcgtc catatcagtg actttatcgc aagatgacct   4440
cagaacgttg acctctgcgg ctactgcacc tgagtttgaa cgcgacactt tgtggttaaa   4500
tggagaacca cacagcatcg acaatgaaag aactcaaaat tgtctgcgcg acctacgcca   4560
attaagaaag gaaatggaat cgaaggacgc ctcattgccc acattatctc aatggaaact   4620
ccacattgtc tccgaaaata actttcctac agcagctggt ttagcttcct ccgctgctgg   4680
ctttgctgca ttggtctctg caattgctaa gttataccaa ttaccacagt caacttcaga   4740
aatatctaga atagcaagaa aggggtctgg ttcagcttgt agatcgttgt ttggcggata   4800
cgtggcctgg gaaatgggaa aagctgaaga tggtcatgat tccatggcag tacaaatcgc   4860
agacagctct gactggcctc agatgaaagc ttgtgtccta gttgtcagcg atattaaaaa   4920
ggatgtgagt tccactcagg gtatgcaatt gaccgtggca acctccgaac tatttaaaga   4980
aagaattgaa catgtcgtac caaagagatt tgaagtcatg cgtaaagcca ttgttgaaaa   5040
agatttcgcc acctttgcaa aggaaacaat gatggattcc aactctttcc atgccacatg   5100
tttggactct ttccctccaa tattctacat gaatgacact tccaagcgta tcatcagttg   5160
gtgccacacc attaatcagt tttacggaga acaatcgtt gcatacacgt ttgatgcagg   5220
tccaaatgct gtgttgtact acttagctga aaatgagtcg aaactctttg catttatcta   5280
taaattgttt ggctctgttc ctggatggga caagaaattt actactgagc agcttgaggc   5340
tttcaaccat caatttgaat catctaactt tactgcacgt gaattggatc ttgagttgca   5400
aaaggatgtt gccagagtga ttttaactca agtcggttca ggcccacaag aaacaaacga   5460
atctttgatt gacgcaaaga ctggtctacc aaaggaataa aaggagaggg tgactgccga   5520
caacaatagt atgccccatg gtgcagtatc tagttacgcc aaattagtgc aaaaccaaac   5580
acctgaagac atttttggaag agtttcctga aattattcca ttacaacaaa gacctaatac   5640
ccgatctagt gagacgtcaa atgacgaaag cggagaaaca tgtttttctg gtcatgatga   5700
ggagcaaatt aagttaatga atgaaaattg tattgttttg gattgggacg ataatgctat   5760
tggtgccggt accaagaaag tttgtcattt aatggaaaat attgaaaagg gtttactaca   5820
tcgtgcattc tccgtcttta ttttcaatga acaaggtgaa ttactttttac aacaaagagc   5880 cactgaaaaa ataactttcc ctgatctttg gactaacaca tgctgctctc atccactatg   5940
tattgatgac gaattaggtt tgaagggtaa gctagacgat aagattaagg gcgctattac   6000
tgcggcggtg agaaaactag atcatgaatt aggtattcca gaagatgaaa ctaagacaag   6060
gggtaagttt cactttttaa acagaatcca ttacatggca ccaagcaatg aaccatgggg   6120
```

```
tgaacatgaa attgattaca tcctatttta taagatcaac gctaaagaaa acttgactgt   6180
caacccaaac gtcaatgaag ttagagactt caaatgggtt tcaccaaatg atttgaaaac   6240
tatgtttgct gacccaagtt acaagtttac gccttggttt aagattattt gcgagaatta   6300
cttattcaac tggtgggagc aattagatga cctttctgaa gtggaaaatg acaggcaaat   6360
tcatagaatg ctataaaaaa aaccggcctt ggccccgccg gttttttatt attttcttc    6420 ctccgcatgt tcaatccgct ccataatcga cggatggctc cctctgaaaa ttttaacgag   6480
aaacggcggg ttgacccggc tcagtcccgt aacggccaag tcctgaaacg tctcaatcgc   6540
cgcttcccgg tttccggtca gctcaatgcc gtaacggtcg gcggcgtttt cctgataccg   6600
ggagacggca ttcgtaattt gaatacatac gaacaaatta ataaagtgaa aaaaatactt   6660
cggaaacatt taaaaaataa ccttattggt acttacatgt ttggatcagg agttgagagt   6720
ggactaaaac caaatagtga tcttgacttt ttagtcgtcg tatctgaacc attgacagat   6780
caaagtaaag aaatacttat acaaaaaatt agacctattt caaaaaaaat aggagataaa   6840
agcaacttac gatatattga attaacaatt attattcagc aagaaatggt accgtggaat   6900
catcctccca aacaagaatt tatttatgga gaatggttac aagagcttta tgaacaagga   6960
tacattcctc agaaggaatt aaattcagat ttaaccataa tgctttacca agcaaaacga   7020
aaaaataaaa gaatatacgg aaattatgac ttagaggaat tactacctga tattccattt   7080
tctgatgtga gaagagccat tatggattcg tcagaggaat aatagataa ttatcaggat   7140 gatgaaacca actctatatt aactttatgc cgtatgattt taactatgga cacgggtaaa   7200
atcataccaa aagatattgc gggaaatgca gtggctgaat cttctccatt agaacatagg   7260
gagagaattt tgttagcagt tcgtagttat cttggagaga atattgaatg gactaatgaa   7320
aatgtaaatt taactataaa ctatttaaat aacagattaa aaaaattata atgtaacctt   7380
tgctttcaaa tgagtagaaa taatgcacat ccatgtttgt atcgtgcaaa taaagtgttt   7440
catccgtagg aaaaaatgac tttagtatct gttccgcttt ttctgatgaa atgtgctccc   7500
cgacaaaatt gaatgaatca tggacatttg ctggctttga tacagcgaaa gcagccgttc   7560
ctatgttata tatcggattt aacagcagga caaaaaacac catgacagcc atcgtcaccc   7620
acttattcac acgcacataa acctttcctg actttggaa cagatgatag ctcatcaaaa    7680
atcccgccat tgccaaataa atcgtatatg gcattactgc accataatct tttgagattt   7740
gattgggata tggcgcaagc agcaagacaa gcagtccgat aatcagcgta taaaataagc   7800
ctagtaagat cttatccgtt ctccaataca gcttgaaaaa cactacattc aacgcaatgg   7860
gaagagtgat gatgaaaaac agaaacacga atgcaatcgg ctccatccca tccgggtatt   7920
ccttccaata cgaaaagaaa ctaaaaatca tttgtacgat cggcaaactg acaacagcaa   7980
ggtcgaacgt ataaaactta cccttttccgc catgatcacg cggcatcagc atatagtgaa   8040
aagccgtcag cagcacatat ccgtataaca aaaaatgcag cagcggcagc agttcttttc   8100
cgtcctctct taagtaagcg ctggtgaagt ttgttgattg cacctggtga ataagttcaa   8160
cagacactcc cgccagcagc acaatccgca atataacacc cgccaagaac attgtgcgct   8220
gccggtttat tttgggatga tgcaccaaaa gatataagcc cgccagaaca acaattgacc   8280
attgaatcag cagggtgctt tgtctgctta atataaaata cgttcgaaa tgcaatacat    8340 aatgactgaa taactccaac acgaacaaca aaagtgcgca ttttataaaa gctaatgatt   8400
cagtccacat aattgataga cgaattctgc tacaggtcac gtggctatgt gaaggatcgc   8460
gcgtccagtt aagagcaaaa acattgacaa aaaaattat ttatgctaaa atttactatt    8520
```

```
aatatatttg tatgtataat aagattctcc tggccagggg aatcttattt tttgtggagg    8580
atcatttcat gaggaaaaat gagtccagct taacgtctct aatttcagct tttgcccgtg    8640
catatcacag ccgatatgac acacctctta tttttgatga ttttatcgca aaagatctca    8700
ttaacgaaaa agagtttatc gacatcagta aaaatatgat tcaagaaata tcgttttca    8760 acaaagagat cgccgaacgt cttcaaaatg atcctgaaaa aatattaaaa tgggttgcac    8820
aaatccagct gtctccaacg cccctagcac gtgcttctta ttgtgaaaaa gtcttgcaca    8880
acgaattaat cctgggggca aaacagtatg tcattcttgg agcgggactg gatactttct    8940
gctttcggca tccagaatta gaaaacagct tacaggtttt cgaggttgat catccggcca    9000
cacagcaatt gaaaaaaaat aagctgaagg atgcaaatct gacaattccg ggtcatcttc    9060
attttgttcc tatggatttc accaaaacgt tttcgtatga tcctctctta gatgaaggat    9120
ttaaaaacac aaaaacattc ttcagccttc tcggagtgtc ttattatgta acacgggaag    9180
aaaatgcaag cttgatcagc aatttatttt ctcatgtccc gcctggaagc tctattgttt    9240
ttgattatgc ggacgaaaca cttttacag caaaagggac gtcgaatcga gttaacata    9300 tggtgaagat ggctgccgca agcggggaac cgatgaaatc atgtttcact tatcaagaga    9360
ttgaacatct g                                                        9371
```

<210> SEQ ID NO 48
<211> LENGTH: 4339
<212> TYPE: DNA
<213> ORGANISM: Artificial Sequence
<220> FEATURE:
<223> OTHER INFORMATION: Synthetic Construct

<400> SEQUENCE: 48

```
tagaaaaact catcgagcat caaatgaaac tgcaatttat tcatatcagg attatcaata      60
ccatattttt gaaaaagccg tttctgtaat gaaggagaaa actcaccgag gcagttccat     120
aggatggcaa gatcctggta tcggtctgcg attccgactc gtccaacatc aatacaacct     180
attaatttcc cctcgtcaaa ataaggttca tcaagtgaga atcaccatg agtgacgact     240 gaatccggtg agaatggcaa agtttatgc atttcttccc agacttgttc aacaggccag     300
ccattacgct cgtcatcaaa atcactcgca tcaaccaaac cgttattcat tcgtgattgc     360
gcctgagcga ggcgaaatac gcgatcgctg ttaaaaggac aattacaaac aggaatcgag     420
tgcaaccggc gcaggaacac tgccagcgca tcaacaatat tttcacctga atcaggatat     480
tcttctaata cctggaacgc tgtttttccg gggatcgcag tggtgagtaa ccatgcatca     540
tcaggagtac ggataaaatg cttgatggtc ggaagtggca taaattccgt cagccagttt     600
agtctgacca tctcatctgt aacatcattg gcaacgctac ctttgccatg tttcagaaac     660
aactctggcg catcgggctt cccatacaag cgatagattg tcgcacctga ttgcccgaca     720
ttatcgcgag cccatttata cccatataaa tcagcatcca tgttggaatt taatcgcggc     780
ctcgacgttt cccgttgaat atggctcata ttcttccttt ttcaatatta ttgaagcatt     840
tatcagggtt attgtctcat gagcggatac atatttgaat gtatttagaa aaataaacaa     900
ataggggtca gtgttacaac caattaacca attctgaaca ttatcgcgag cccatttata     960
cctgaatatg gctcataaca cccttgttt gcctggcggc agtagcgcgg tggtcccacc    1020
tgaccccatg ccgaactcag aagtgaaacg ccgtagcgcc gatggtagtg tggggactcc    1080
ccatgcgaga gtagggaact gccaggcatc aaataaaacg aaaggctcag tcgaaagact    1140
gggcctttcg cccgggctaa ttaggggtg tcgcccttta gtcgctgaac atgtgctctg    1200
```

```
tttctaccga gaacgtttcc ttcactgaga cggaaaccga ggcacgtcgt agcgcgaact    1260
acgagccgaa tagctgggac tacgatttcc tgctgtcttc cgatactgac gaatctattg    1320
aggtgtacaa agacaaagca aagaaactgg aggctgaagt gcgccgcgaa attaacaacg    1380
agaaagctga attcctgact ctgctggagc tgatcgataa cgtacagcgc ctgggtctgg    1440
gttaccgctt cgaatctgat atccgtcgcg cactggatcg tttcgtaagc agcggcggtt    1500
tcgatggcgt gaccaaaacg agcctgcacg ctaccgcgct gtccttccgt ctgctgcgtc    1560
agcacggctt cgaagtttct caggaagcat tctccggttt caaagatcaa acggtaact     1620 tcctggaaaa cctgaaagaa gacactaagg cgatcctgag cctgtatgag gcaagctttc    1680
tggccctgga gggtgagaac atcctggatg aggcgcgcgt attcgccatc tcccatctga    1740
aagagctgtc tgaagagaaa atcggtaagg aactggcaga gcaggttaat cacgcactgg    1800
aactgccgct gcatcgtcgt acccagcgtc tggaggcggt ttggtccatc gaagcgtacc    1860 gcaaaagga ggatgctaac caggttctgc tggaactggc catcctggac tacaacatga    1920
tccagtccgt ttaccagcgt gatctgcgtg aaacctcccg ttggtggcgc cgtgtgggcc    1980
tggcgaccaa actgcacttc gctaaggacc gcctgattga gtcttttttac tgggcagtcg    2040 gcgttgcgtt cgaacctcag tattctgact gccgtaacag cgttgcgaaa atgttcagct    2100
tcgttactat tatcgacgac atcacgacg tttacggtac tctggacgag ctggaactgt    2160
ttaccgacgc tgtcgaacgt tgggatgtta acgccatcaa cgatctgcct gactacatga    2220
aactgtgctt cctggcactg tataacacga tcaacgaaat tgcatacgac aacctgaaag    2280
acaaaggtga aaacatcctg ccgtacctga ctaaagcgtg ggcggatctg tgtaacgctt    2340
ttctgcaaga agcgaaatgg ctgtataaca atccactcc gaccctttgac gattatttcg    2400 gcaatgcctg gaaatccagc tctggcccgc tgcaactgat cttcgcttat tttgcggttg    2460
tccaaaacat caaaaaggag gaaattgaaa acctgcaaaa ataccacgat atcattagcc    2520
gtccttctca tatctttcgc ctgtgcaacg acctggcaag cgcgtccgca gagatcgcac    2580
gtggcgaaac cgctaactct gtttcctgct acatgcgcac caagggcatt tccgaagagc    2640
tggcaaccga gagcgtaatg aatctgatcg acgaaacctg taagaaaatg aacaaagaaa    2700
aactgggtgg ctccctgttc gctaaaccgt tcgtagagac tgctattaac ctggcacgtc    2760
agagccactg cacctaccac aatggtgacg cacatactag cccggatgaa ctgactcgta    2820
aacgtgtact gtctgttatc accgaaccga ttctgccgtt cgaacgttaa ctgcagcgtc    2880
aatcgaaagg gcgacacaaa atttattcta aatgcataat aaatactgat aacatcttat    2940
agtttgtatt atattttgta ttatcgttga catgtataat tttgatatca aaaactgatt    3000
ttccctttat tattttcgag atttattttc ttaattctct ttaacaaact agaaatattg    3060
tatatacaaa aaatcataaa taatagatga atagtttaat tataggtgtt catcaatcga    3120
aaaagcaacg tatcttattt aaagtgcgtt gcttttttct catttataag gttaaataat    3180
tctcatatat caagcaaagt gacaggcgcc cttaaatatt ctgacaaatg ctctttccct    3240
aaactccccc cataaaaaaa cccgccgaag cgggttttta cgttatttgc ggattaacga    3300
ttactcgtta tcagaaccgc ccaggggggcc cgagcttaag actggccgtc gttttacaac    3360
acagaaagag tttgtagaaa cgcaaaaagg ccatccgtca ggggcttct gcttagtttg    3420 atgcctggca gttccctact ctcgccttcc gcttcctcgc tcactgactc gctgcgctcg    3480
gtcgttcggt gcggcgagc ggtatcagct cactcaaagg cggtaatacg gttatccaca    3540
gaatcagggg ataacgcagg aaagaacatg tgagcaaaag gccagcaaaa ggccaggaac    3600
```

| | |
|---|---|
| cgtaaaaagg ccgcgttgct ggcgtttttc cataggctcc gccccctga cgagcatcac | 3660 |
| aaaaatcgac gctcaagtca gaggtggcga acccgacag gactataaag ataccaggcg | 3720 |
| tttccccctg gaagctccct cgtgcgctct cctgttccga ccctgccgct taccggatac | 3780 |
| ctgtccgcct ttctcccttc gggaagcgtg gcgctttctc atagctcacg ctgtaggtat | 3840 |
| ctcagttcgg tgtaggtcgt tcgctccaag ctgggctgtg tgcacgaacc ccccgttcag | 3900 |
| cccgaccgct gcgccttatc cggtaactat cgtcttgagt ccaacccggt aagacacgac | 3960 |
| ttatcgccac tggcagcagc cactggtaac aggattagca gagcgaggta tgtaggcggt | 4020 |
| gctacagagt tcttgaagtg gtgggctaac tacggctaca ctagaagaac agtatttggt | 4080 |
| atctgcgctc tgctgaagcc agttaccttc ggaaaaagag ttggtagctc ttgatccggc | 4140 |
| aaacaaacca ccgctggtag cggtggtttt tttgtttgca agcagcagat tacgcgcaga | 4200 |
| aaaaaaggat ctcaagaaga tcctttgatc ttttctacgg ggtctgacgc tcagtggaac | 4260 |
| gacgcgcgcg taactcacgt taagggattt tggtcatgag cttgcgccgt cccgtcaagt | 4320 |
| cagcgtaatg ctctgctttt | 4339 |

<210> SEQ ID NO 49
<211> LENGTH: 6065
<212> TYPE: DNA
<213> ORGANISM: Artificial Sequence
<220> FEATURE:
<223> OTHER INFORMATION: Synthetic Construct

<400> SEQUENCE: 49

| | |
|---|---|
| gtttgacagc ttatcatcga ctgcacggtg caccaatgct tctggcgtca ggcagccatc | 60 |
| ggaagctgtg gtatggctgt gcaggtcgta aatcactgca taattcgtgt cgctcaaggc | 120 |
| gcactcccgt tctggataat gttttttgcg ccgacatcat aacggttctg gcaaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatgtgctc | 420 |
| tgtttctacc gagaacgttt ccttcactga gacggaaacc gaggcacgtc gtagcgcgaa | 480 |
| ctacgagccg aatagctggg actacgattt cctgctgtct tccgatactg acgaatctat | 540 |
| tgaggtgtac aaagacaaag caaagaaact ggaggctgaa gtgcgccgcg aaattaacaa | 600 |
| cgagaaagct gaattcctga ctctgctgga gctgatcgat aacgtacagc gcctgggtct | 660 |
| gggttaccgc ttcgaatctg atatccgtcg cgcactggat cgtttcgtaa gcagcggcgg | 720 |
| tttcgatggc gtgaccaaaa cgagcctgca cgctaccgcg ctgtccttcc gtctgctgcg | 780 |
| tcagcacggc ttcgaagttt ctcaggaagc attctccggt ttcaaagatc aaaacgtaa | 840 |
| cttcctggaa aacctgaaag aagacactaa ggcgatcctg agcctgtatg aggcaagctt | 900 |
| tctggcctg gagggtgaga acatcctgga tgaggcgcgc gtattcgcca tctcccatct | 960 |
| gaaagagctg tctgaagaga aaatcggtaa ggaactggca gagcaggtta atcacgcact | 1020 |
| ggaactgccg ctgcatcgtc gtacccagtc tctggaggcg gtttggtcca tcgaagcgta | 1080 |
| ccgcaaaaag gaggatgcta accaggttct gctgaactg gccatcctgg actacaacat | 1140 |
| gatccagtcc gtttaccagc gtgatctgcg tgaaacctcc gttggtggc gccgtgtggg | 1200 |
| cctggcgacc aaactgcact cgctaaggga ccgcctgatt gagtcttttt actgggcagt | 1260 |
| cggcgttgcg ttcgaacctc agtattctga ctgccgtaac agcgttgcga aaatgttcag | 1320 |

```
cttcgttact attatcgacg acatctacga cgtttacggt actctggacg agctggaact    1380
gtttaccgac gctgtcgaac gttgggatgt taacgccatc aacgatctgc ctgactacat    1440
gaaactgtgc ttcctggcac tgtataacac gatcaacgaa attgcatacg acaacctgaa    1500
agacaaaggt gaaaacatcc tgccgtacct gactaaagcg tgggcggatc tgtgtaacgc    1560
ttttctgcaa gaagcgaaat ggctgtataa caaatccact ccgacctttg acgattattt    1620
cggcaatgcc tggaaatcca gctctggccc gctgcaactg atcttcgctt attttgcggt    1680
tgtccaaaac atcaaaaagg aggaaattga aacctgcaa aaataccacg atatcattag    1740
ccgtccttct catatctttc gcctgtgcaa cgacctggca agcgcgtccg cagagatcgc    1800
acgtggcgaa accgctaact ctgtttcctg ctacatgcgc accaagggca tttccgaaga    1860
gctggcaacc gagagcgtaa tgaatctgat cgacgaaacc tgtaagaaaa tgaacaaaga    1920
aaaactgggt ggctccctgt tcgctaaacc gttcgtagag actgctatta acctggcacg    1980
tcagagccac tgcacctacc acaatggtga cgcacatact agcccggatg aactgactcg    2040
taaacgtgta ctgtctgtta tcaccgaacc gattctgccg ttcgaacgtt aactgcagct    2100
ggtaccatat gggaattcga agcttttctag aacaaaaact catctcagaa gaggatctga    2160
atagcgccgt cgaccatcat catcatcatc attgagttta aacggtctcc agcttggctg    2220
ttttggcgga tgagagaaga ttttcagcct gatacagatt aaatcagaac gcagaagcgg    2280
tctgataaaa cagaatttgc ctggcggcag tagcgcggtg gtcccacctg accccatgcc    2340
gaactcagaa gtgaaacgcc gtagcgccga tggtagtgtg gggtctcccc atgcgagagt    2400
agggaactgc caggcatcaa ataaaacgaa aggctcagtc gaaagactgg gcctttcgtt    2460
ttatctgttg tttgtcggtg aacgctctcc tgagtaggac aaatccgccg ggagcggatt    2520
tgaacgttgc gaagcaacgg cccggagggt ggcgggcagg acgcccgcca taaactgcca    2580
ggcatcaaat taagcagaag gccatcctga cggatggcct ttttgcgttt ctacaaactc    2640
tttttgttta ttttttctaaa tacattcaaa tatgtatccg ctcatgagac aataaccctg    2700
ataaatgctt caataatatt gaaaaggaa gagtatgagt attcaacatt tccgtgtcgc    2760
ccttattccc ttttttgcgg cattttgcct tcctgttttt gctcacccag aaacgctggt    2820
gaaagtaaaa gatgctgaag atcagttggg tgcacgagtg ggttacatcg aactggatct    2880
caacagcggt aagatccttg agagttttcg ccccgaagaa cgttttccaa tgatgagcac    2940
ttttaaagtt ctgctatgtg gcgcggtatt atcccgtgtt gacgccgggc aagagcaact    3000
cggtcgccgc atacactatt ctcagaatga cttggttgag tactcaccag tcacagaaaa    3060
gcatcttacg gatggcatga cagtaagaga attatgcagt gctgccataa ccatgagtga    3120
taacactgcg gccaacttac ttctgacaac gatcggagga ccgaaggagc taaccgcttt    3180
tttgcacaac atgggggatc atgtaactcg ccttgatcgt tgggaaccgg agctgaatga    3240
agccatacca aacgacgagc gtgacaccac gatgcctgta gcaatggcaa caacgttgcg    3300
caaactatta actggcgaac tacttactct agcttcccgg caacaattaa tagactggat    3360
ggaggcggat aaagttgcag gaccacttct gcgctcggcc cttccggctg gctggtttat    3420
tgctgataaa tctggagccg gtgagcgtgg gtctcgcggt atcattgcag cactggggcc    3480
agatggtaag ccctcccgta tcgtagttat ctacacgacg gggagtcagg caactatgga    3540
tgaacgaaat agacagatcg ctgagatagg tgcctcactg attaagcatt ggtaactgtc    3600
agaccaagtt tactcatata cttttagat tgatttaaaa cttcattttt aatttaaaag    3660
gatctaggtg aagatccttt ttgataatct catgaccaaa atcccttaac gtgagttttc    3720
```

```
gttccactga gcgtcagacc ccgtagaaaa gatcaaagga tcttcttgag atccttttt    3780
tctgcgcgta atctgctgct tgcaaacaaa aaaaccaccg ctaccagcgg tggtttgttt    3840
gccggatcaa gagctaccaa ctcttttcc gaaggtaact ggcttcagca gagcgcagat    3900
accaaatact gtccttctag tgtagccgta gttaggccac cacttcaaga actctgtagc    3960
accgcctaca tacctcgctc tgctaatcct gttaccagtg ctgctgcca gtggcgataa    4020
gtcgtgtctt accgggttgg actcaagacg atagttaccg gataaggcgc agcggtcggg    4080
ctgaacgggg ggttcgtgca cacagcccag cttggagcga acgacctaca ccgaactgag    4140
atacctacag cgtgagctat gagaaagcgc cacgcttccc gaagggagaa aggcggacag    4200
gtatccggta agcggcaggg tcggaacagg agagcgcacg agggagcttc caggggggaaa    4260
cgcctggtat ctttatagtc ctgtcgggtt cgccacctc tgacttgagc gtcgatttt    4320
gtgatgctcg tcagggggc ggagcctatg aaaaacgcc agcaacgcgg cctttttacg    4380
gttcctggcc ttttgctggc cttttgctca catgttcttt cctgcgttat cccctgattc    4440
tgtggataac cgtattaccg cctttgagtg agctgatacc gctcgccgca gccgaacgac    4500
cgagcgcagc gagtcagtga gcgaggaagc ggaagagcgc ctgatgcggt attttctcct    4560
tacgcatctg tgcggtattt cacaccgcat atggtgcact ctcagtacaa tctgctctga    4620
tgccgcatag ttaagccagt atacactccg ctatcgctac gtgactgggt catggctgcg    4680
ccccgacacc cgccaacacc cgctgacgcg ccctgacggg cttgtctgct cccggcatcc    4740
gcttacagac aagctgtgac cgtctccggg agctgcatgt gtcagaggtt ttcaccgtca    4800
tcaccgaaac gcgcgaggca gcagatcaat tcgcgcgcga aggcgaagcg gcatgcattt    4860
acgttgacac catcgaatgg tgcaaaacct ttcgcggtat ggcatgatag cgcccggaag    4920
agagtcaatt cagggtggtg aatgtgaaac cagtaacgtt atacgatgtc gcagagtatg    4980
ccggtgtctc ttatcagacc gtttcccgcg tggtgaacca ggccagccac gtttctgcga    5040
aaacgcggga aaaagtggaa gcggcgatgg cggagctgaa ttacattccc aaccgcgtgg    5100
cacaacaact ggcgggcaaa cagtcgttgc tgattggcgt tgccacctcc agtctggccc    5160
tgcacgcgcc gtcgcaaatt gtcgcggcga ttaaatctcg cgccgatcaa ctgggtgcca    5220
gcgtggtggt gtcgatggta gaacgaagcg gcgtcgaagc ctgtaaagcg gcggtgcaca    5280
atcttctcgc gcaacgcgtc agtgggctga tcattaacta tccgctggat gaccaggatg    5340
ccattgctgt ggaagctgcc tgcactaatg ttccggcgtt atttcttgat gtctctgacc    5400
agacacccat caacagtatt attttctccc atgaagacgg tacgcgactg ggcgtggagc    5460
atctggtcgc attgggtcac cagcaaatcg cgctgttagc gggcccatta agttctgtct    5520
cggcgcgtct gcgtctggct ggctggcata aatatctcac tcgcaatcaa attcagccga    5580
tagcggaacg ggaaggcgac tggagtgcca tgtccggttt tcaacaaacc atgcaaatgc    5640
tgaatgaggg catcgttccc actgcgatgc tggttgccaa cgatcagatg gcgctgggcg    5700
caatgcgcgc cattaccgag tccgggctgc gcgttggtgc ggatatctcg gtagtgggat    5760
acgacgatac cgaagacagc tcatgttata tcccgccgtc aaccaccatc aaacaggatt    5820
ttcgcctgct ggggcaaacc agcgtggacc gcttgctgca actctctcag gccaggcgg    5880
tgaagggcaa tcagctgttg cccgtctcac tggtgaaaag aaaaaccacc ctggcgccca    5940
atacgcaaac cgcctctccc cgcgcgttgg ccgattcatt aatgcagctg gcacgacagg    6000
tttcccgact ggaaagcggg cagtgagcgc aacgcaatta atgtgagtta gcgcgaattg    6060
atctg                                                               6065
```

<210> SEQ ID NO 50
<211> LENGTH: 6912
<212> TYPE: DNA
<213> ORGANISM: Artificial Sequence
<220> FEATURE:
<223> OTHER INFORMATION: Synthetic Construct

<400> SEQUENCE: 50

| | | | | | |
|---|---|---|---|---|---|
| ttgtctgctc | ccggcatccg | cttacagaca | agctgtgacc | gtctccggga | gctgcatgtg | 60 |
| tcagaggttt | tcaccgtcat | caccgaaacg | cgcgaggcag | cagatcaatt | cgcgcgcgaa | 120 |
| ggcgaagcgg | catgcattta | cgttgacacc | atcgaatggt | gcaaaacctt | tcgcggtatg | 180 |
| gcatgatagc | gcccggaaga | gagtcaattc | agggtggtga | atgtgaaacc | agtaacgtta | 240 |
| tacgatgtcg | cagagtatgc | cggtgtctct | tatcagaccg | tttcccgcgt | ggtgaaccag | 300 |
| gccagccacg | tttctgcgaa | aacgcgggaa | aaagtggaag | cggcgatggc | ggagctgaat | 360 |
| tacattccca | accgcgtggc | acaacaactg | gcgggcaaac | agtcgttgct | gattggcgtt | 420 |
| gccacctcca | gtctggccct | gcacgcgccg | tcgcaaattg | tcgcggcgat | taaatctcgc | 480 |
| gccgatcaac | tgggtgccag | cgtggtggtg | tcgatgctag | aacgaagcgg | cgtcgaagcc | 540 |
| tgtaaagcgg | cggtgcacaa | tcttctcgcg | caacgcgtca | gtgggctgat | cattaactat | 600 |
| ccgctggatg | accaggatgc | cattgctgtg | gaagctgcct | gcactaatgt | tccggcgtta | 660 |
| tttcttgatg | tctctgacca | gacacccatc | aacagtatta | ttttctccca | tgaagacggt | 720 |
| acgcgactgg | gcgtggagca | tctggtcgca | ttgggtcacc | agcaaatcgc | gctgttagcg | 780 |
| ggcccattaa | gttctgtctc | ggcgcgtctg | cgtctggctg | ctggcataa | atatctcact | 840 |
| cgcaatcaaa | ttcagccgat | agcggaacgg | gaaggcgact | ggagtgccat | gtccggtttt | 900 |
| caacaaacca | tgcaaatgct | gaatgagggc | atcgttccca | ctgcgatgct | ggttgccaac | 960 |
| gatcagatgg | cgctgggcgc | aatgcgcgcc | attaccgagt | ccgggctgcg | cgttggtgcg | 1020 |
| gatatctcgg | tagtgggata | cgacgatacc | gaagacagct | catgttatat | cccgccgtca | 1080 |
| accaccatca | acaggatttt | cgcctgctg | gggcaaacca | gcgtggaccg | cttgctgcaa | 1140 |
| ctctctcagg | gccaggcggt | gaagggcaat | cagctgttgc | ccgtctcact | ggtgaaaaga | 1200 |
| aaaaccaccc | tggcgcccaa | tacgcaaacc | gcctctcccc | gcgcgttggc | cgattcatta | 1260 |
| atgcagctgg | cacgacaggt | ttcccgactg | gaaagcgggc | agtgagcgca | acgcaattaa | 1320 |
| tgtgagttag | cgcgaattga | tctggtttga | cagcttatca | tcgactgcac | ggtgcaccaa | 1380 |
| tgcttctggc | gtcaggcagc | catcggaagc | tgtggtatgg | ctgtgcaggt | cgtaaatcac | 1440 |
| tgcataattc | gtgtcgctca | aggcgcactc | ccgttctgga | taatgttttt | tgcgccgaca | 1500 |
| tcataacggt | tctggcaaat | attctgaaat | gagctgttga | caattaatca | tccggctcgt | 1560 |
| ataatgtgtg | gaattgtgag | cggataacaa | tttcacacag | gaaacagcgc | cgctgagaaa | 1620 |
| aagcgaagcg | gcactgctct | ttaacaattt | atcagacaat | ctgtgtgggc | actcgaccgg | 1680 |
| aattatcgat | taactttatt | attaaaaatt | aaagaggtat | atattaatgt | atcgattaaa | 1740 |
| taaggaggaa | taaccatgt | gtgcgacctc | ttctcaattt | actcagatta | ccgagcataa | 1800 |
| ttcccgtcgt | tccgcaaact | atcagccaaa | cctgtggaat | ttcgaattcc | tgcaatccct | 1860 |
| ggagaacgac | ctgaaagtgg | aaaagctgga | ggagaaagcg | accaaactgg | aggaagaagt | 1920 |
| tcgctgcatg | atcaaccgtg | tagacaccca | gccgctgtcc | ctgctggagc | tgatcgacga | 1980 |
| tgtgcagcgc | ctgggtctga | cctacaaatt | tgaaaaagac | atcattaaag | ccctggaaaa | 2040 |
| catcgtactg | ctggacgaaa | acaaaaagaa | caaatctgac | ctgcacgcaa | ccgctctgtc | 2100 |

```
tttccgtctg ctgcgtcagc acggtttcga ggtttctcag gatgttttg agcgtttcaa      2160 ggataaagaa ggtggtttca gcggtgaact gaaaggtgac gtccaaggcc tgctgagcct      2220
gtatgaagcg tcttacctgg gtttcgaggg tgagaacctg ctggaggagg cgcgtacctt      2280
ttccatcacc cacctgaaga acaacctgaa agaaggcatt aataccaagg ttgcagaaca      2340
agtgagccac gccctggaac tgccatatca ccagcgtctg caccgtctgg aggcacgttg      2400
gttcctggat aaatacgaac cgaaagaacc gcatcaccag ctgctgctgg agctggcgaa      2460
gctggatttt aacatggtac agaccctgca ccagaaagag ctgcaagatc tgtcccgctg      2520
gtggaccgag atgggcctgg ctagcaaact ggattttgta cgcgaccgcc tgatggaagt      2580
ttatttctgg gcactgggta tggcgccaga cccgcagttt ggtgaatgtc gcaaagctgt      2640
tactaaaatg tttggtctgg tgacgatcat cgatgacgtg tatgacgttt atggcactct      2700
ggacgaactg caactgttca ccgatgctgt agagcgctgg gacgttaacg ctattaacac      2760
cctgccggac tatatgaaac tgtgtttcct ggcactgtac aacaccgtta acgacacgtc      2820
ctattctatt ctgaaagaga aaggtcataa caacctgtcc tatctgacga aaagctggcg      2880
tgaactgtgc aaagcctttc tgcaagaggc gaaatggtcc aacaacaaaa ttatcccggc      2940
tttctccaag tacctggaaa acgccagcgt ttcctcctcc ggtgtagcgc tgctggcgcc      3000
gtcttacttt tccgtatgcc agcagcagga agacatctcc gaccacgcgc tgcgttccct      3060
gaccgacttc catggtctgg tgcgttctag ctgcgttatc ttccgcctgt gcaacgatct      3120
ggccacctct gcggcggagc tggaacgtgg cgagactacc aattctatca ttagctacat      3180
gcacgaaaac gatggtacca gcgaggaaca ggcccgcgaa gaactgcgta aactgatcga      3240
cgccgaatgg aaaaagatga atcgtgaacg cgttagcgac tccaccctgc tgcctaaagc      3300
gttcatggaa atcgcagtta acatggcacg tgtttcccac tgcacctacc agtatggcga      3360
tggtctgggt cgcccagact acgcgactga aaaccgcatc aaactgctgc tgattgaccc      3420
tttcccgatt aaccagctga tgtatgtcta actgcatcgc ccttaggagg taaaaaaaaa      3480
tgactgccga caacaatagt atgccccatg gtgcagtatc tagttacgcc aaattagtgc      3540
aaaaccaaac acctgaagac atttggaag agttcctga aattattcca ttacaacaaa       3600
gacctaatac ccgatctagt gagacgtcaa atgacgaaag cggagaaaca tgttttctg       3660 gtcatgatga ggagcaaatt aagttaatga atgaaaattg tattgttttg gattgggacg      3720
ataatgctat tggtgccggt accaagaaag tttgtcattt aatggaaaat attgaaaagg      3780
gtttactaca tcgtgcattc tccgtctta tttttcaatga acaaggtgaa ttacttttac      3840
aacaaagagc cactgaaaaa ataactttcc ctgatctttg gactaacaca tgctgctctc      3900
atccactatg tattgatgac gaattaggtt tgaagggtaa gctagacgat aagattaagg      3960
gcgctattac tgcggcggtg agaaaactag atcatgaatt aggtattcca gaagatgaaa      4020
ctaagacaag gggtaagttt cacttttttaa acagaatcca ttacatggca ccaagcaatg      4080
aaccatgggg tgaacatgaa attgattaca tcctatttta taagatcaac gctaaagaaa      4140
acttgactgt caacccaaac gtcaatgaag ttagagactt caaatgggtt tcaccaaatg      4200
atttgaaaac tatgtttgct gacccaagtt acaagtttac gccttggttt aagattattt      4260
gcgagaatta cttattcaac tggtgggagc aattagtgaa cctttctgaa gtggaaaatg      4320
acaggcaaat tcatagaatg ctataacaac gcgtcctgca gctggtacca tatgggaatt      4380
cgaagctttc tagaacaaaa actcatctca gaagaggatc tgaatagcgc cgtcgaccat      4440
catcatcatc atcattgagt ttaaacggtc tccagcttgg ctgttttggc ggatgagaga      4500
```

```
agattttcag cctgatacag attaaatcag aacgcagaag cggtctgata aaacagaatt    4560
tgcctggcgg cagtagcgcg gtggtcccac ctgaccccat gccgaactca gaagtgaaac    4620
gccgtagcgc cgatggtagt gtggggtctc cccatgcgag agtagggaac tgccaggcat    4680
caaataaaac gaaaggctca gtcgaaagac tgggcctttc gttttatctg ttgtttgtcg    4740
gtgaacgctc tcctgagtag gacaaatccg ccgggagcgg atttgaacgt tgcgaagcaa    4800
cggcccggag ggtggcgggc aggacgcccg ccataaactg ccaggcatca aattaagcag    4860
aaggccatcc tgacggatgg cctttttgcg tttctacaaa ctcttttttgt ttatttttct    4920
aaatacattc aaatatgtat ccgcttaacc ggaattgcca gctggggcgc cctctggtaa    4980
ggttgggaag ccctgcaaag taaactggat ggctttctcg ccgccaagga tctgatggcg    5040
caggggatca agctctgatc aagagacagg atgaggatct tttcgcatga ttgaacaaga    5100
tggattgcac gcaggttctc cggccgcttg ggtggagagg ctattcggct atgactgggc    5160
acaacagaca atcggctgct ctgatgccgc cgtgttccgg ctgtcagcgc aggggcgccc    5220
ggttcttttt gtcaagaccg acctgtccgg tgccctgaat gaactgcaag acgaggcagc    5280
gcggctatcg tggctggcca cgacgggcgt tccttgcgca gctgtgctcg acgttgtcac    5340
tgaagcggga agggactggc tgctattggg cgaagtgccg gggcaggatc tcctgtcatc    5400
tcaccttgct cctgccgaga aagtatccat catggctgat gcaatgcggc ggctgcatac    5460
gcttgatccg gctacctgcc cattcgacca ccaagcgaaa catcgcatcg agcgagcacg    5520
tactcggatg gaagccggtc ttgtcgatca ggatgatctg gacgaagagc atcaggggct    5580
cgcgccagcc gaactgttcg ccaggctcaa ggcgagcatg cccgacggcg aggatctcgt    5640
cgtgacccat ggcgatgcct gcttgccgaa tatcatggtg gaaaatggcc gcttttctgg    5700
attcatcgac tgtggccggc tgggtgtggc ggaccgctat caggacatag cgttggctac    5760
ccgtgatatt gctgaagagc ttggcggcga atgggctgac cgcttcctcg tgctttacgg    5820
tatcgccgct cccgattcgc agcgcatcgc cttctatcgc cttcttgacg agttcttctg    5880
acatgaccaa aatcccttaa cgtgagtttt cgttccactg agcgtcagac cccgtagaaa    5940
agatcaaagg atcttcttga gatccttttt ttctgcgcgt aatctgctgc ttgcaaacaa    6000
aaaaaccacc gctaccagcg gtggtttgtt tgccggatca agagctacca actctttttc    6060
cgaaggtaac tggcttcagc agagcgcaga taccaaatac tgtccttcta gtgtagccgt    6120
agttaggcca ccacttcaag aactctgtag caccgcctac atacctcgct ctgctaatcc    6180
tgttaccagt ggctgctgcc agtggcgata agtcgtgtct taccgggttg gactcaagac    6240
gatagttacc ggataaggcg cagcggtcgg gctgaacggg gggttcgtgc acacagccca    6300
gcttggagcg aacgacctac accgaactga gatacctaca gcgtgagcta tgagaaagcg    6360
ccacgcttcc cgaagggaga aaggcggaca ggtatccggt aagcggcagg gtcggaacag    6420
gagagcgcac gagggagctt ccagggggaa acgcctggta tctttatagt cctgtcgggt    6480
ttcgccacct ctgacttgag cgtcgatttt tgtgatgctc gtcaggggggg cggagcctat    6540
ggaaaaacgc cagcaacgcg gcctttttac ggttcctggc cttttgctgg ccttttgctc    6600
acatgttctt tcctgcgtta tcccctgatt ctgtggataa ccgtattacc gcctttgagt    6660
gagctgatac cgctcgccgc agccgaacga ccgagcgcag cgagtcagtg agcgaggaag    6720
cggaagagcg cctgatgcgg tattttctcc ttacgcatct gtgcggtatt tcacaccgca    6780
tatggtgcac tctcagtaca atctgctctg atgccgcata gttaagccag tatacactcc    6840
gctatcgcta cgtgactggg tcatggctgc gccccgacac ccgccaacac ccgctgacgc    6900
```

```
gccctgacgg gc                                                         6912

<210> SEQ ID NO 51
<211> LENGTH: 7902
<212> TYPE: DNA
<213> ORGANISM: Artificial Sequence
<220> FEATURE:
<223> OTHER INFORMATION: Synthetic Construct

<400> SEQUENCE: 51
ttgtctgctc ccggcatccg cttacagaca agctgtgacc gtctccggga gctgcatgtg     60
tcagaggttt tcaccgtcat caccgaaacg cgcgaggcag cagatcaatt cgcgcgcgaa    120
ggcgaagcgg catgcattta cgttgacacc atcgaatggt gcaaaacctt cgcggtatg     180
gcatgatagc gcccggaaga gagtcaattc agggtggtga atgtgaaacc agtaacgtta    240
tacgatgtcg cagagtatgc cggtgtctct tatcagaccg tttccgcgt ggtgaaccag     300
gccagccacg tttctgcgaa aacgcgggaa aaagtggaag cggcgatggc ggagctgaat    360
tacattccca accgcgtggc acaacaactg gcgggcaaac agtcgttgct gattggcgtt    420
gccacctcca gtctggccct gcacgcgccg tcgcaaattg tcgcggcgat taaatctcgc    480
gccgatcaac tgggtgccag cgtggtggtg tcgatggtag aacgaagcgg cgtcgaagcc    540
tgtaaagcgg cggtgcacaa tcttctcgcg caacgcgtca gtgggctgat cattaactat    600
ccgctggatg accaggatgc cattgctgtg aagctgcct gcactaatgt tccggcgtta     660
tttcttgatg tctctgacca gacacccatc aacagtatta ttttctccca tgaagacggt    720
acgcgactgg gcgtggagca tctggtcgca ttgggtcacc agcaaatcgc gctgttagcg    780
ggcccattaa gttctgtctc ggcgcgtctg cgtctggctg gctggcataa atatctcact    840
cgcaatcaaa ttcagccgat agcggaacgg gaaggcgact ggagtgccat gtccggtttt    900
caacaaacca tgcaaatgct gaatgagggc atcgttccca ctgcgatgct ggttgccaac    960
gatcagatgg cgctgggcgc aatgcgcgcc attaccgagt ccgggctgcg cgttggtgcg   1020
gatatctcgg tagtgggata cgacgatacc gaagacagct catgttatat cccgccgtca   1080
accaccatca acaggattt tcgcctgctg gggcaaacca gcgtggaccg cttgctgcaa   1140
ctctctcagg gccaggcggt gaagggcaat cagctgttgc ccgtctcact ggtgaaaaga   1200
aaaaccaccc tggcgcccaa tacgcaaacc gcctctcccc gcgcgttggc cgattcatta   1260
atgcagctgg cacgacaggt ttcccgactg gaaagcgggc agtgagcgca acgcaattaa   1320
tgtgagttag cgcgaattga tctggtttga cagcttatca tcgactgcac ggtgcaccaa   1380
tgcttctggc gtcaggcagc catcggaagc tgtggtatgg ctgtgcaggt cgtaaatcac   1440
tgcataattc gtgtcgctca aggcgcactc ccgttctgga taatgttttt tgcgccgaca   1500
tcataacggt tctggcaaat attctgaaat gagctgttga caattaatca tccggctcgt   1560
ataatgtgtg gaattgtgag cggataacaa tttcacacag aaacagcgc cgctgagaaa    1620
aagcgaagcg gcactgctct ttaacaattt atcagacaat ctgtgtgggc actcgaccgg   1680
aattatcgat taactttatt attaaaaatt aaagaggtat atattaatgt atcgattaaa   1740
taaggaggaa taaccatgt gtgcgacctc ttctcaattt actcagatta ccgagcataa    1800
ttcccgtcgt tccgcaaact atcagccaaa cctgtgaat ttcgaattcc tgcaatccct    1860
ggagaacgac ctgaaagtgg aaaagctgga ggagaaagcg accaaactgg aggaagaagt   1920
tcgctgcatg atcaaccgtg tagacaccca gccgctgtcc ctgctggagc tgatcgacga   1980
tgtgcagcgc ctgggtctga cctacaaatt tgaaaaagac atcattaaag ccctggaaaa   2040
```

```
catcgtactg ctggacgaaa acaaaaagaa caaatctgac ctgcacgcaa ccgctctgtc   2100
tttccgtctg ctgcgtcagc acggtttcga ggtttctcag gatgttttg agcgtttcaa    2160 ggataaagaa ggtggtttca gcggtgaact gaaaggtgac gtccaaggcc tgctgagcct   2220
gtatgaagcg tcttacctgg gtttcgaggg tgagaacctg ctggaggagg cgcgtacctt   2280
ttccatcacc cacctgaaga acaacctgaa agaaggcatt aataccaagg ttgcagaaca   2340
agtgagccac gccctggaac tgccatatca ccagcgtctg caccgtctgg aggcacgttg   2400
gttcctggat aaatacgaac cgaaagaacc gcatcaccag ctgctgctgg agctggcgaa   2460
gctggatttt aacatggtac agaccctgca ccagaaagag ctgcaagatc tgtcccgctg   2520
gtggaccgag atgggcctgg ctagcaaact ggattttgta cgcgaccgcc tgatggaagt   2580
ttatttctgg gcactgggta tggcgccaga cccgcagttt ggtgaatgtc gcaaagctgt   2640
tactaaaatg tttggtctgg tgacgatcat cgatgacgtg tatgacgttt atggcactct   2700
ggacgaactg caactgttca ccgatgctgt agagcgctgg gacgttaacg ctattaacac   2760
cctgccggac tatatgaaac tgtgtttcct ggcactgtac aacaccgtta acgacacgtc   2820
ctattctatt ctgaaagaga aaggtcataa caacctgtcc tatctgacga aaagctggcg   2880
tgaactgtgc aaagcctttc tgcaagaggc gaaatggtcc aacaacaaaa ttatcccggc   2940
tttctccaag tacctggaaa acgccagcgt ttcctcctcc ggtgtagcgc tgctggcgcc   3000
gtcttacttt tccgtatgcc agcagcagga agacatctcc gaccacgcgc tgcgttccct   3060
gaccgacttc catggtctgg tgcgttctag ctgcgttatc ttccgcctgt gcaacgatct   3120
ggccacctct gcggcggagc tggaacgtgg cgagactacc aattctatca ttagctacat   3180
gcacgaaaac gatggtacca gcgaggaaca ggcccgcgaa gaactgcgta aactgatcga   3240
cgccgaatgg aaaaagatga atcgtgaacg cgttagcgac tccaccctgc tgcctaaagc   3300
gttcatggaa atcgcagtta acatggcacg tgtttcccac tgcacctacc agtatgcgga   3360
tggtctgggt cgcccagact acgcgactga aaaccgcatc aaactgctgc tgattgaccc   3420
tttcccgatt aaccagctga tgtatgtcta actgcattcg cccttaggag gtaaaaaaac   3480
atgagttttg atattgccaa atacccgacc ctggcactgg tcgactccac ccaggagtta   3540
cgactgttgc cgaaagagag tttaccgaaa ctctgcgacg aactgcgccg ctatttactc   3600
gacagcgtga gccgttccag cgggcacttc gcctccgggc tgggcacggt cgaactgacc   3660
gtggcgctgc actatgtcta caacaccccg tttgaccaat tgatttggga tgtggggcat   3720
caggcttatc cgcataaaat tttgaccgga cgccgcgaca aaatcggcac catccgtcag   3780
aaaggcggtc tgcacccgtt cccgtggcgc ggcgaaagcg aatatgacgt attaagcgtc   3840
gggcattcat caacctccat cagtgccgga attggtattg cggttgctgc cgaaaaagaa   3900
ggcaaaaatc gccgcaccgt ctgtgtcatt ggcgatggcg cgattaccgc aggcatggcg   3960
tttgaagcga tgaatcacgc gggcgatatc cgtcctgata tgctggtgat tctcaacgac   4020
aatgaaatgt cgatttccga aaatgtcggc gcgctcaaca accatctggc acagctgctt   4080
tccggtaagc tttactcttc actgcgcgaa ggcgggaaaa aagttttctc tggcgtgccg   4140
ccaattaaag agctgctcaa acgcaccgaa gaacatatta aaggcatggt agtgcctggc   4200
acgttgtttg aagagctggg ctttaactac atcggcccgg tggacggtca cgatgtgctg   4260
gggcttatca ccacgctaaa gaacatgcgc gacctgaaag gcccgcagtt cctgcatatc   4320
atgaccaaaa aaggtcgtgg ttatgaaccg gcagaaaaag acccgatcac tttccacgcc   4380
gtgcctaaat ttgatcctc cagcggttgt ttgccgaaaa gtagcggcgg tttgccgagc   4440
```

```
tattcaaaaa tctttggcga ctggttgtgc gaaacggcag cgaaagacaa caagctgatg    4500
gcgattactc cggcgatgcg tgaaggttcc ggcatggtcg agttttcacg taaattcccg    4560
gatcgctact tcgacgtggc aattgccgag caacacgcgg tgacctttgc tgcgggtctg    4620
gcgattggtg ggtacaaacc cattgtcgcg atttactcca ctttcctgca acgcgcctat    4680
gatcaggtgc tgcatgacgt ggcgattcaa aagcttccgg tcctgttcgc catcgaccgc    4740
gcgggcattg ttggtgctga cggtcaaacc catcagggtg cttttgatct ctcttacctg    4800
cgctgcatac cggaaatggt cattatgacc ccgagcgatg aaaacgaatg tcgccagatg    4860
ctctataccg gctatcacta taacgatggc ccgtcagcgg tgcgctaccc gcgtggcaac    4920
gcggtcggcg tggaactgac gccgctggaa aaactaccaa ttggcaaagg cattgtgaag    4980
cgtcgtggcg agaaactggc gatccttaac tttggtacgc tgatgccaga agcggcgaaa    5040
gtcgccgaat cgctgaacgc cacgctggtc gatatgcgtt ttgtgaaacc gcttgatgaa    5100
gcgttaattc tggaaatggc cgccagccat gaagcgctgg tcaccgtaga agaaaacgcc    5160
attatgggcg gcgcaggcag cggcgtgaac gaagtgctga tggcccatcg taaaccagta    5220
cccgtgctga acattggcct gccggacttc tttattccgc aaggaactca ggaagaaatg    5280
cgcgccgaac tcggcctcga tgccgctggt atggaagcca aaatcaaggc ctggctggca    5340
taactgcagc tggtaccata tgggaattcg aagctttcta gaacaaaaac tcatctcaga    5400
agaggatctg aatagcgccg tcgaccatca tcatcatcat cattgagttt aaacggtctc    5460
cagcttggct gttttggcgg atgagagaag attttcagcc tgatacagat taaatcagaa    5520
cgcagaagcg gtctgataaa acagaatttg cctggcggca gtagcgcggt ggtcccacct    5580
gaccccatgc cgaactcaga agtgaaacgc cgtagcgccg atggtagtgt ggggtctccc    5640
catgcgagag tagggaactg ccaggcatca aataaaacga aaggctcagt cgaaagactg    5700
ggcctttcgt tttatctgtt gtttgtcggt gaacgctctc ctgagtagga caaatccgcc    5760
gggagcggat ttgaacgttg cgaagcaacg gcccggaggg tggcgggcag gacgcccgcc    5820
ataaactgcc aggcatcaaa ttaagcagaa ggccatcctg acggatggcc ttttttgcgtt    5880 tctacaaact ctttttgttt attttttctaa atacattcaa atatgtatcc gcttaaccgg    5940
aattgccagc tggggcgccc tctggtaagg ttgggaagcc ctgcaaagta aactggatgg    6000
ctttctcgcc gccaaggatc tgatggcgca ggggatcaag ctctgatcaa gagacaggat    6060
gaggatcgtt tcgcatgatt gaacaagatg gattgcacgc aggttctccg gccgcttggg    6120
tggagaggct attcggctat gactgggcac aacagacaat cggctgctct gatgccgccg    6180
tgttccggct gtcagcgcag gggcgcccgg ttcttttgt caagaccgac ctgtccggtg    6240
ccctgaatga actgcaagac gaggcagcgc ggctatcgtg gctggccacg acgggcgttc    6300
cttgcgcagc tgtgctcgac gttgtcactg aagcgggaag ggactggctg ctattgggcg    6360
aagtgccggg gcaggatctc ctgtcatctc accttgctcc tgccgagaaa gtatccatca    6420
tggctgatgc aatgcggcgg ctgcatacgc ttgatccggc tacctgccca ttcgaccacc    6480
aagcgaaaca tcgcatcgag cgagcacgta ctcggatgga gccggtcttt gtcgatcagg    6540
atgatctgga cgaagagcat caggggctcg cgccagccga actgttcgcc aggctcaagg    6600
cgagcatgcc cgacggcgag gatctcgtcg tgacccatgg cgatgcctgc ttgccgaata    6660
tcatggtgga aaatgccgc tttctggat tcatcgactg tggccggctg ggtgtggcgg    6720
accgctatca ggacatagcg ttggctaccc gtgatattgc tgaagagctt ggcggcgaat    6780
gggctgaccg cttcctcgtg ctttacggta tcgccgctcc cgattcgcag cgcatcgcct    6840
```

```
tctatcgcct tcttgacgag ttcttctgac gcatgaccaa aatcccttaa cgtgagtttt    6900
cgttccactg agcgtcagac cccgtagaaa agatcaaagg atcttcttga gatcctttt     6960 ttctgcgcgt aatctgctgc ttgcaaacaa aaaaaccacc gctaccagcg gtggtttgtt    7020
tgccggatca agagctacca actcttttc  cgaaggtaac tggcttcagc agagcgcaga    7080
taccaaatac tgtccttcta gtgtagccgt agttaggcca ccacttcaag aactctgtag    7140
caccgcctac atacctcgct ctgctaatcc tgttaccagt ggctgctgcc agtggcgata    7200
agtcgtgtct taccgggttg gactcaagac gatagttacc ggataaggcg cagcggtcgg    7260
gctgaacggg gggttcgtgc acacagccca gcttggagcg aacgacctac accgaactga    7320
gatacctaca gcgtgagcta tgagaaagcg ccacgcttcc cgaagggaga aaggcggaca    7380
ggtatccggt aagcggcagg gtcggaacag gagagcgcac gagggagctt ccaggggaa     7440 acgcctggta tctttatagt cctgtcgggt ttcgccacct ctgacttgag cgtcgatttt    7500
tgtgatgctc gtcaggggg  cggagcctat ggaaaaacgc cagcaacgcg gccttttac    7560 ggttcctggc cttttgctgg cctttttgctc acatgttctt tcctgcgtta tcccctgatt   7620
ctgtggataa ccgtattacc gcctttgagt gagctgatac cgctcgccgc agccgaacga    7680
ccgagcgcag cgagtcagtg agcgaggaag cggaagagcg cctgatgcgg tattttctcc    7740
ttacgcatct gtgcggtatt tcacaccgca tatggtgcac tctcagtaca atctgctctg    7800
atgccgcata gttaagccag tatacactcc gctatcgcta cgtgactggg tcatggctgc    7860
gccccgacac ccgccaacac ccgctgacgc gccctgacgg gc                       7902

<210> SEQ ID NO 52
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 52
ctggcgtaat agcgaagagg cccgcaccga tcgcccttcc caacagttgc gcagcctgaa      60
tggcgaatgg cgcctgatgc ggtatttct  ccttacgcat ctgtgcggta tttcacaccg     120
catatggtgc actctcagta caatctgctc tgatgccgca tagttaagcc agccccgaca     180
cccgccaaca cccgctgacg agcttagtaa agccctcgct agattttaat gcggatgttg     240
cgattacttc gccaactatt gcgataacaa gaaaaagcca gcctttcatg atatatctcc     300
caatttgtgt agggcttatt atgcacgctt aaaaataata aaagcagact tgacctgata     360
gtttggctgt gagcaattat gtgcttagtg catctaacgc ttgagttaag ccgcgccgcg     420
aagcggcgtc ggcttgaacg aattgttaga cattatttgc cgactacctt ggtgatctcg     480
cctttcacgt agtggacaaa ttcttccaac tgatctgcgc gcgaggccaa gcgatcttct     540
tcttgtccaa gataagcctg tctagcttca agtatgacgg gctgatactg ggccggcagg     600
cgctccattg cccagtcggc agcgacatcc ttcggcgcga ttttgccggt tactgcgctg     660
taccaaatgc gggacaacgt aagcactaca tttcgctcat cgccagccca gtcgggcggc     720
gagttccata gcgttaaggt ttcatttagc gcctcaaata gatcctgttc aggaaccgga    780
tcaaagagtt cctccgccgc tggacctacc aaggcaacgc tatgttctct tgcttttgtc    840
agcaagatag ccagatcaat gtcgatcgtg gctggctcga agatacctgc aagaatgtca    900
ttgcgctgcc attctccaaa ttgcagttcg cgcttagctg ataacgcca cggaatgatg    960 tcgtcgtgca caacaatggt gacttctaca gcgcggagaa tctcgctctc tccaggggaa   1020
```

```
gccgaagttt ccaaaaggtc gttgatcaaa gctcgccgcg ttgtttcatc aagccttacg   1080
gtcaccgtaa ccagcaaatc aatatcactg tgtggcttca ggccgccatc cactgcggag   1140
ccgtacaaat gtacggccag caacgtcggt tcgagatggc gctcgatgac gccaactacc   1200
tctgatagtt gagtcgatac ttcggcgatc accgcttccc tcatgatgtt taactttgtt   1260
ttagggcgac tgccctgctg cgtaacatcg ttgctgctcc ataacatcaa acatcgaccc   1320
acggcgtaac gcgcttgctg cttggatgcc cgaggcatag actgtacccc aaaaaaacag   1380
tcataacaag ccatgaaaac cgccactgcg ccgttaccac cgctgcgttc ggtcaaggtt   1440
ctggaccagt tgcgtgagcg catacgctac ttgcattaca gcttacgaac cgaacaggct   1500
tatgtccact gggttcgtgc cttcatccgt ttccacggtg tgcgtcaccc ggcaaccttg   1560
ggcagcagcg aagtcgaggc atttctgtcc tggctggcga acgagcgcaa ggtttcggtc   1620
tccacgcatc gtcaggcatt ggcggccttg ctgttcttct acggcaaggt gctgtgcacg   1680
gatctgccct ggcttcagga gatcggaaga cctcggccgt cgcggcgctt gccggtggtg   1740
ctgaccccgg atgaagtggt tcgcatcctc ggttttctgg aaggcgagca tcgtttgttc   1800
gcccagcttc tgtatggaac gggcatgcgg atcagtgagg gtttgcaact gcgggtcaag   1860
gatctggatt tcgatcacgg cacgatcatc gtgcgggagg gcaagggctc caaggatcgg   1920
gccttgatgt tacccgagag cttggcaccc agcctgcgcg agcaggggaa ttaattccca   1980
cgggttttgc tgcccgcaaa cgggctgttc tggtgttgct agtttgttat cagaatcgca   2040
gatccggctt cagccggttt gccggctgaa agcgctattt cttccagaat tgccatgatt   2100
ttttccccac gggaggcgtc actggctccc gtgttgtcgg cagctttgat tcgataagca   2160
gcatcgcctt tttcaggctg tctatgtgtg actgttgagc tgtaacaagt tgtctcaggt   2220
gttcaatttc atgttctagt tgctttgttt tactggtttc acctgttcta ttaggtgtta   2280
catgctgttc atctgttaca ttgtcgatct gttcatggtg aacagctttg aatgcaccaa   2340
aaactcgtaa aagctctgat gtatctatct tttttacacc gttttcatct gtgcatatgg   2400
acagttttcc ctttgatatg taacggtgaa cagttgttct acttttgttt gttagtcttg   2460
atgcttcact gatagataca agagccataa gaacctcaga tccttccgta tttagccagt   2520
atgttctcta gtgtggttcg ttgttttgc gtgagccatg agaacgaacc attgagatca   2580
tacttacttt gcatgtcact caaaaatttt gcctcaaaac tggtgagctg aattttgca   2640 gttaaagcat cgtgtagtgt ttttcttagt ccgttatgta ggtaggaatc tgatgtaatg   2700
gttgttggta ttttgtcacc attcattttt atctggttgt tctcaagttc ggttacgaga   2760
tccatttgtc tatctagttc aacttggaaa atcaacgtat cagtcgggcg gcctcgctta   2820
tcaaccacca atttcatatt gctgtaagtg tttaaatctt tacttattgg tttcaaaacc   2880
cattggttaa gccttttaaa ctcatggtag ttattttcaa gcattaacat gaacttaaat   2940
tcatcaaggc taatctctat atttgccttg tgagttttct tttgtgttag ttcttttaat   3000
aaccactcat aaatcctcat agagtatttg ttttcaaaag acttaacatg ttccagatta   3060
tattttatga attttttaa ctggaaaaga taaggcaata tctcttcact aaaaactaat   3120
tctaattttt cgcttgagaa cttggcatag tttgtccact ggaaaatctc aaagccttta   3180
accaaaggat tcctgattc cacagttctc gtcatcagct ctctggttgc tttagctaat   3240
acaccataag cattttccct actgatgttc atcatctgag cgtattggtt ataagtgaac   3300
gataccgtcc gttcttttcct tgtagggttt tcaatcgtgg ggttgagtag tgccacacag   3360
cataaaatta gcttggtttc atgctccgtt aagtcatagc gactaatcgc tagttcattt   3420
```

```
gctttgaaaa caactaattc agacatacat ctcaattggt ctaggtgatt ttaatcacta     3480
taccaattga gatgggctag tcaatgataa ttactagtcc ttttcctttg agttgtgggt     3540
atctgtaaat tctgctagac ctttgctgga aaacttgtaa attctgctag accctctgta     3600
aattccgcta gacctttgtg tgttttttttt gtttatattc aagtggttat aatttataga    3660
ataaagaaag aataaaaaaa gataaaaaga atagatccca gccctgtgta taactcacta     3720
ctttagtcag ttccgcagta ttacaaaagg atgtcgcaaa cgctgtttgc tcctctacaa     3780
aacagacctt aaaaccctaa aggcttaagt agcaccctcg caagctcggg caaatcgctg     3840
aatattcctt ttgtctccga ccatcaggca cctgagtcgc tgtctttttc gtgacattca     3900
gttcgctgcg ctcacggctc tggcagtgaa tggggtaaa tggcactaca ggcgcctttt      3960
atggattcat gcaaggaaac tacccataat acaagaaaag cccgtcacgg gcttctcagg     4020
gcgttttatg gcgggtctgc tatgtggtgc tatctgactt tttgctgttc agcagttcct     4080
gccctctgat tttccagtct gaccacttcg gattatcccg tgacaggtca ttcagactgg     4140
ctaatgcacc cagtaaggca gcggtatcat caacaggctt accgtcttta ctgtcgggaa     4200
ttcgcgttgg ccgattcatt aatgcagatt ctgaaatgag ctgttgacaa ttaatcatcc     4260
ggctcgtata atgtgtggaa ttgtgagcgg ataacaattt cacacaggaa acagcgccgc     4320
tgagaaaaag cgaagcggca ctgctcttta caaattatc agacaatctg tgtgggcact     4380
cgaccggaat tatcgattaa ctttattatt aaaaattaaa gaggtatata ttaatgtatc     4440
gattaaataa ggaggaataa accatgtgtg cgacctcttc tcaatttact cagattaccg     4500
agcataattc ccgtcgttcc gcaaactatc agccaaacct gtggaatttc gaattcctgc     4560
aatccctgga gaacgacctg aaagtggaaa agctggagga gaaagcgacc aaactggagg     4620
aagaagttcg ctgcatgatc aaccgtgtag acacccagcc gctgtccctg ctggagctga     4680
tcgacgatgt gcagcgcctg ggtctgacct acaaatttga aaaagacatc attaaagccc     4740
tggaaaacat cgtactgctg gacgaaaaca aaaagaacaa atctgacctg cacgcaaccg     4800
ctctgtcttt ccgtctgctg cgtcagcacg gtttcgaggt ttctcaggat gttttttgagc    4860 gtttcaagga taaagaaggt ggtttcagcg gtgaactgaa aggtgacgtc caaggcctgc     4920
tgagcctgta tgaagcgtct tacctggggtt tcgagggtga aacctgctg gaggaggcgc     4980 gtacctttcc catcacccac ctgaagaaca acctgaaaga aggcattaat accaaggttg     5040
cagaacaagt gagccacgcc ctggaactgc catatcacca gcgtctgcac cgtctggagg     5100
cacgttggtt cctggataaa tacgaaccga agaaccgca tcaccagctg ctgctggagc     5160
tggcgaagct ggatttaac atggtacaga ccctgcacca gaaagagctg caagatctgt     5220
cccgctggtg gaccgagatg ggcctggcta gcaaactgga ttttgtacgc gaccgcctga     5280
tggaagttta tttctgggca ctgggtatgg cgccagaccc gcagtttggt gaatgtcgca     5340
aagctgttac taaaatgttt ggtctggtga cgatcatcga tgacgtgtat gacgtttatg     5400
gcactctgga cgaactgcaa ctgttcaccg atgctgtaga gcgctgggac gttaacgcta     5460
ttaacaccct gccggactat atgaaactgt gtttcctggc actgtacaac accgttaacg     5520
acacgtccta ttctattctg aaagagaaag tcataacaa cctgtcctat ctgacgaaaa      5580
gctggcgtga actgtgcaaa gccttctgc aagaggcgaa atggtccaac aacaaaatta     5640
tcccggcttt ctccaagtac ctggaaaacg ccagcgtttc ctcctccggt gtagcgctgc     5700
tggcgccgtt ttacttttcc gtatgccagc agcaggaaga catctccgac cacgcgctgc     5760
gttccctgac cgacttccat ggtctggtgc gttctagctg cgttatcttc cgcctgtgca     5820
```

| | |
|---|---|
| acgatctggc cacctctgcg gcggagctgg aacgtggcga gactaccaat tctatcatta | 5880 |
| gctacatgca cgaaaacgat ggtaccagcg aggaacaggc ccgcgaagaa ctgcgtaaac | 5940 |
| tgatcgacgc cgaatggaaa aagatgaatc gtgaacgcgt tagcgactcc accctgctgc | 6000 |
| ctaaagcgtt catggaaatc gcagttaaca tggcacgtgt ttcccactgc acctaccagt | 6060 |
| atggcgatgg tctgggtcgc ccagactacg cgactgaaaa ccgcatcaaa ctgctgctga | 6120 |
| ttgaccettt cccgattaac cagctgatgt atgtctaact gcagctggta ccatatggga | 6180 |
| attcgaagct ttctagaaca aaaactcatc tcagaagagg atctgaatag cgccgtcgac | 6240 |
| catcatcatc atcatcattg agtttaaacg gtctccagct tggctgtttt ggcggatgag | 6300 |
| agaagatttt cagcctgata cagattaaat cagaacgcag aagcggtctg ataaaacaga | 6360 |
| atttgcctgg cggcagtagc gcggtggtcc cacctgaccc catgccgaac tcagaagtga | 6420 |
| aacgccgtag cgccgatggt agtgtggggt ctccccatgc gagagtaggg aactgccagg | 6480 |
| catcaaataa aacgaaaggc tcagtcgaaa gactgggcct ttcgttttat ctgttgtttg | 6540 |
| tcggtgaacg ctctcctgag taggacaaat ccgccgggag cggatttgaa cgttgcgaag | 6600 |
| caacggcccg gagggtggcg ggcaggacgc ccgccataaa ctgccaggca tcaaattaag | 6660 |
| cagaaggcca tcctgacgga tggcctttt gcgtttctac aaactctttt tgtttatttt | 6720 |
| tctaaataca ttcaaatatg tatccgctca tgagacaata accctgataa atgcttcaat | 6780 |
| aat | 6783 |

<210> SEQ ID NO 53
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 53

| | |
|---|---|
| cccgtcttac tgtcgggaat tcgcgttggc cgattcatta atgcagatta ttgaagcatt | 60 |
| tatcagggtt attgtctcat gagcggatac atatttgaat gtatttagaa aaataaacaa | 120 |
| aaagagtttg tagaaacgca aaaaggccat ccgtcaggat ggccttctgc ttaatttgat | 180 |
| gcctggcagt ttatggcggg cgtcctgccc gccaccctcc gggccgttgc ttcgcaacgt | 240 |
| tcaaatccgc tcccggcgga tttgtcctac tcaggagagc gttcaccgac aaacaacaga | 300 |
| taaaacgaaa ggcccagtct ttcgactgag cctttcgttt tatttgatgc ctggcagttc | 360 |
| cctactctcg catggggaga ccccacacta ccatcggcgc tacggcgttt cacttctgag | 420 |
| ttcggcatgg ggtcaggtgg gaccaccgcg ctactgccgc caggcaaatt ctgttttatc | 480 |
| agaccgcttc tgcgttctga tttaatctgt atcaggctga aaatcttctc tcatccgcca | 540 |
| aaacagccaa gctggagacc gtttaaactc aatgatgatg atgatgatgg tcgacggcgc | 600 |
| tattcagatc ctcttctgag atgagttttt gttctagaaa gcttcgaatt cccatatggt | 660 |
| accagctgca gttagacata catcagctgg ttaatcggga aagggtcaat cagcagcagt | 720 |
| ttgatgcggt tttcagtcgc gtagtctggg cgacccagac catcgccata ctggtaggtg | 780 |
| cagtgggaaa cacgtgccat gttaactgcg atttccatga acgctttagg cagcagggtg | 840 |
| gagtcgctaa cgcgttcacg attcatcttt ttccattcgg cgtcgatcag tttacgcagt | 900 |
| tcttcgcggg cctgttcctc gctggtacca tcgttttcgt gcatgtagct aatgatagaa | 960 |
| ttggtagtct cgccacgttc cagctccgcc gcagaggtgg ccagatcgtt gcacaggcgg | 1020 |
| aagataacgc agctagaacg caccagacca tggaagtcgg tcagggaacg cagcgcgtgg | 1080 |

```
tcggagatgt cttcctgctg ctggcatacg gaaaagtaag acggcgccag cagcgctaca    1140
ccggaggagg aaacgctggc gttttccagg tacttggaga aagccgggat aattttgttg    1200
ttggaccatt tcgcctcttg cagaaaggct ttgcacagtt cacgccagct tttcgtcaga    1260
taggacaggt tgttatgacc tttctctttc agaatagaat aggacgtgtc gttaacggtg    1320
ttgtacagtg ccaggaaaca cagtttcata tagtccggca gggtgttaat agcgttaacg    1380
tcccagcgct ctacagcatc ggtgaacagt tgcagttcgt ccagagtgcc ataaacgtca    1440
tacacgtcat cgatgatcgt caccagacca aacattttag taacagcttt gcgacattca    1500
ccaaactgcg ggtctggcgc catacccagt gcccagaaat aaacttccat caggcggtcg    1560
cgtacaaaat ccagtttgct agccaggccc atctcggtcc accagcggga cagatcttgc    1620
agctcttcct ggtgcagggt ctgtaccatg ttaaaatcca gcttcgccag ctccagcagc    1680
agctggtgat gcggttcttt cggttcgtat ttatccagga accaacgtgc ctccagacgg    1740
tgcagacgct ggtgatatgg cagttccagg gcgtggctca cttgttctgc aaccttggta    1800
ttaatgcctt ctttcaggtt gttcttcagg tgggtgatgg aaaaggtacg cgcctcctcc    1860
agcaggttct caccctcgaa acccaggtaa gacgcttcat acaggctcag caggccttgg    1920
acgtcacctt tcagttcacc gctgaaacca ccttctttat ccttgaaacg ctcaaaaaca    1980
tcctgagaaa cctcgaaacc gtgctgacgc agcagacgga aagacagagc ggttgcgtgc    2040
aggtcagatt tgttcttttt gttttcgtcc agcagtacga tgttttccag ggctttaatg    2100
atgtcttttt caaatttgta ggtcagaccc aggcgctgca catcgtcgat cagctccagc    2160
agggacagcg gctgggtgtc tacacggttg atcatgcagc gaacttcttc ctccagtttg    2220
gtcgctttct cctccagctt ttccactttc aggtcgttct ccagggattg caggaattcg    2280
aaattccaca ggtttggctg atagtttgcg gaacgacggg aattatgctc ggtaatctga    2340
gtaaattgag aagaggtcgc acacatggtt tattcctcct tatttaatcg atacattaat    2400
atatacctct ttaattttta ataataaagt taatcgataa ttccggtcga gtgcccacac    2460
agattgtctg ataaattgtt aaagagcagt gccgcttcgc ttttctcag cggcgctgtt    2520 tcctgtgtga aattgttatc cgctcacaat tccacacatt atacgagccg gatgattaat    2580
tgtcaacagc tcatttcaga atctggcgta atagcgaaga ggcccgcacc gatcgccctt    2640
cccaacagtt gcgcagcctg aatggcgaat ggcgcctgat gcggtatttt ctccttacgc    2700
atctgtgcgg tatttcacac cgcatatggt gcactctcag tacaatctgc tctgatgccg    2760
catagttaag ccagccccga cacccgccaa cacccgctga cgagcttagt aaagccctcg    2820
ctagatttta atgcggatgt tgcgattact tcgccaacta ttgcgataac aagaaaaagc    2880
cagcctttca tgatatatct cccaatttgt gtagggctta ttatgcacgc ttaaaaataa    2940
taaaagcaga cttgacctga tagttttggct gtgagcaatt atgtgcttag tgcatctaac    3000
gcttgagtta agccgcgccg cgaagcggcg tcggcttgaa cgaattgtta gacattattt    3060
gccgactacc ttggtgatct cgcctttcac gtagtggaca aattcttcca actgatctgc    3120
gcgcgaggcc aagcgatctt cttcttgtcc aagataagcc tgtctagctt caagtatgac    3180
gggctgatac tgggccggca ggcgctccat tgcccagtcg gcagcgacat ccttcggcgc    3240
gattttgccg gttactgcgc tgtaccaaat gcgggacaac gtaagcacta catttcgctc    3300
atcgccagcc cagtcgggcg cgagttcca tagcgttaag gtttcattta gcgcctcaaa    3360
tagatcctgt tcaggaaccg gatcaaagag ttcctccgcc gctggaccta ccaaggcaac    3420
gctatgttct cttgcttttg tcagcaagat agccagatca atgtcgatcg tggctggctc    3480
```

```
gaagatacct gcaagaatgt cattgcgctg ccattctcca aattgcagtt cgcgcttagc    3540
tggataacgc cacggaatga tgtcgtcgtg cacaacaatg gtgacttcta cagcgcggag    3600
aatctcgctc tctccagggg aagccgaagt ttccaaaagg tcgttgatca aagctcgccg    3660
cgttgtttca tcaagcctta cggtcaccgt aaccagcaaa tcaatatcac tgtgtggctt    3720
caggccgcca tccactgcgg agccgtacaa atgtacggcc agcaacgtcg gttcgagatg    3780
gcgctcgatg acgccaacta cctctgatag ttgagtcgat acttcggcga tcaccgcttc    3840
cctcatgatg tttaactttg ttttagggcg actgccctgc tgcgtaacat cgttgctgct    3900
ccataacatc aaacatcgac ccacggcgta acgcgcttgc tgcttggatg cccgaggcat    3960
agactgtacc ccaaaaaaac agtcataaca agccatgaaa accgccactg cgccgttacc    4020
accgctgcgt tcggtcaagg ttctggacca gttgcgtgag cgcatacgct acttgcatta    4080
cagcttacga accgaacagg cttatgtcca ctgggttcgt gccttcatcc gtttccacgg    4140
tgtgcgtcac ccggcaacct tgggcagcag cgaagtcgag gcatttctgt cctggctggc    4200
gaacgagcgc aaggtttcgg tctccacgca tcgtcaggca ttggcggcct tgctgttctt    4260
ctacggcaag gtgctgtgca cggatctgcc ctggcttcag gagatcggaa gacctcggcc    4320
gtcgcggcgc ttgccggtgg tgctgacccc ggatgaagtg gttcgcatcc tcggttttct    4380
ggaaggcgag catcgtttgt tcgcccagct tctgtatgga acgggcatgc ggatcagtga    4440
gggtttgcaa ctgcgggtca aggatctgga tttcgatcac ggcacgatca tcgtgcggga    4500
gggcaagggc tccaaggatc gggccttgat gttacccgag agcttggcac ccagcctgcg    4560
cgagcagggg aattaattcc cacgggtttt gctgcccgca aacgggctgt tctggtgttg    4620
ctagtttgtt atcagaatcg cagatccggc ttcagccggt ttgccggctg aaagcgctat    4680
ttcttccaga attgccatga tttttttcccc acgggaggcg tcactggctc ccgtgttgtc    4740
ggcagctttg attcgataag cagcatcgcc tgtttcaggc tgtctatgtg tgactgttga    4800
gctgtaacaa gttgtctcag gtgttcaatt tcatgttcta gttgctttgt tttactggtt    4860
tcacctgttc tattaggtgt tacatgctgt tcatctgtta cattgtcgat ctgttcatgg    4920
tgaacagctt tgaatgcacc aaaaactcgt aaaagctctg atgtatctat ctttttaca    4980 ccgtttcat ctgtgcatat ggacagtttt ccctttgata tgtaacggtg aacagttgtt    5040
ctacttttgt ttgttagtct tgatgcttca ctgatagata caagagccat aagaacctca    5100
gatccttccg tatttagcca gtatgttctc tagtgtggtt cgttgttttt gcgtgagcca    5160
tgagaacgaa ccattgagat catacttact ttgcatgtca ctcaaaaatt ttgcctcaaa    5220
actggtgagc tgaattttg cagttaaagc atcgtgtagt gtttttctta gtccgttatg    5280
taggtaggaa tctgatgtaa tggttgttgg tattttgtca ccattcattt ttatctggtt    5340
gttctcaagt tcggttacga gatccatttg tctatctagt tcaacttgga aaatcaacgt    5400
atcagtcggg cggcctcgct tatcaaccac caatttcata ttgctgtaag tgtttaaatc    5460
tttacttatt ggtttcaaaa cccattggtt aagccttta aactcatggt agttattttc    5520
aagcattaac atgaacttaa attcatcaag gctaatctct atatttgcct tgtgagtttt    5580
cttttgtgtt agttctttta ataaccactc ataaatcctc atagagtatt tgttttcaaa    5640
agacttaaca tgttccagat tatattttat gaattttttt aactggaaaa gataaggcaa    5700
tatctcttca ctaaaaacta attctaattt ttcgcttgag aacttggcat agtttgtcca    5760
ctggaaaatc tcaaagcctt taaccaaagg attcctgatt tccacagttc tcgtcatcag    5820
ctctctggtt gctttagcta atacaccata agcatttcc ctactgatgt tcatcatctg    5880
```

| | |
|---|---|
| agcgtattgg ttataagtga acgataccgt ccgttctttc cttgtagggt tttcaatcgt | 5940 |
| ggggttgagt agtgccacac agcataaaat tagcttggtt tcatgctccg ttaagtcata | 6000 |
| gcgactaatc gctagttcat ttgctttgaa aacaactaat tcagacatac atctcaattg | 6060 |
| gtctaggtga ttttaatcac tataccaatt gagatgggct agtcaatgat aattactagt | 6120 |
| ccttttcctt tgagttgtgg gtatctgtaa attctgctag acctttgctg gaaaacttgt | 6180 |
| aaattctgct agaccctctg taaattccgc tagacctttg tgtgttttt ttgtttatat | 6240 |
| tcaagtggtt ataatttata gaataaagaa agaataaaaa aagataaaaa gaatagatcc | 6300 |
| cagccctgtg tataactcac tactttagtc agttccgcag tattacaaaa ggatgtcgca | 6360 |
| aacgctgttt gctcctctac aaaacagacc ttaaaaccct aaaggcttaa gtagcaccct | 6420 |
| cgcaagctcg ggcaaatcgc tgaatattcc ttttgtctcc gaccatcagg cacctgagtc | 6480 |
| gctgtctttt tcgtgacatt cagttcgctg cgctcacggc tctggcagtg aatggggta | 6540 |
| aatggcacta caggcgcctt ttatggattc atgcaaggaa actacccata atacaagaaa | 6600 |
| agcccgtcac gggcttctca gggcgtttta tggcgggtct gctatgtggt gctatctgac | 6660 |
| tttttgctgt tcagcagttc ctgccctctg attttccagt ctgaccactt cggattatcc | 6720 |
| cgtgacaggt cattcagact ggctaatgca cccagtaagg cagcggtatc atcaacaggc | 6780 |
| tta | 6783 |

<210> SEQ ID NO 54
<211> LENGTH: 7687
<212> TYPE: DNA
<213> ORGANISM: Artificial Sequence
<220> FEATURE:
<223> OTHER INFORMATION: Synthetic Construct

<400> SEQUENCE: 54

| | |
|---|---|
| ctggcgtaat agcgaagagg cccgcaccga tcgcccttcc caacagttgc gcagcctgaa | 60 |
| tggcgaatgg cgcctgatgc ggtatttctc ccttacgcat ctgtgcggta tttcacaccg | 120 |
| catatggtgc actctcagta caatctgctc tgatgccgca tagttaagcc agccccgaca | 180 |
| cccgccaaca cccgctgacg agcttagtaa agccctcgct agattttaat gcggatgttg | 240 |
| cgattacttc gccaactatt gcgataacaa gaaaaagcca gcctttcatg atatatctcc | 300 |
| caatttgtgt agggcttatt atgcacgctt aaaaataata aaagcagact tgacctgata | 360 |
| gtttggctgt gagcaattat gtgcttagtg catctaacgc ttgagttaag ccgcgccgcg | 420 |
| aagcggcgtc ggcttgaacg aattgttaga cattatttgc cgactacctt ggtgatctcg | 480 |
| cctttcacgt agtggacaaa ttcttccaac tgatctgcgc gcgaggccaa gcgatcttct | 540 |
| tcttgtccaa gataagcctg tctagcttca agtatgacgg gctgatactg ggccggcagg | 600 |
| cgctccattg cccagtcggc agcgacatcc ttcggcgcga ttttgccggt tactgcgctg | 660 |
| taccaaatgc gggacaacgt aagcactaca tttcgctcat cgccagccca gtcgggcggc | 720 |
| gagttccata cgttaaggt tcatttagc gcctcaaata gatcctgttc aggaaccgga | 780 |
| tcaaagagtt cctccgccgc tggacctacc aaggcaacgc tatgttctct tgcttttgtc | 840 |
| agcaagatag ccagatcaat gtcgatcgtg gctggctcga agatacctgc aagaatgtca | 900 |
| ttgcgctgcc attctccaaa ttgcagttcg cgcttagctg gataacgcca cggaatgatg | 960 |
| tcgtcgtgca caacaatggt gacttctaca gcgcggagaa tctcgctctc tccaggggaa | 1020 |
| gccgaagttt ccaaaaggtc gttgatcaaa gctcgccgcg ttgtttcatc aagccttacg | 1080 |
| gtcaccgtaa ccagcaaatc aatatcactg tgtggcttca ggccgccatc cactgcggag | 1140 |

```
ccgtacaaat gtacggccag caacgtcggt tcgagatggc gctcgatgac gccaactacc   1200
tctgatagtt gagtcgatac ttcggcgatc accgcttccc tcatgatgtt aactttgtt   1260 ttagggcgac tgccctgctg cgtaacatcg ttgctgctcc ataacatcaa acatcgaccc   1320
acggcgtaac gcgcttgctg cttggatgcc cgaggcatag actgtacccc aaaaaaacag   1380
tcataacaag ccatgaaaac cgccactgcg ccgttaccac cgctgcgttc ggtcaaggtt   1440
ctggaccagt tgcgtgagcg catacgctac ttgcattaca gcttacgaac cgaacaggct   1500
tatgtccact gggttcgtgc cttcatccgt ttccacggtg tgcgtcaccc ggcaaccttg   1560
ggcagcagcg aagtcgaggc atttctgtcc tggctggcga acgagcgcaa ggtttcggtc   1620
tccacgcatc gtcaggcatt ggcggccttg ctgttcttct acggcaaggt gctgtgcacg   1680
gatctgccct ggcttcagga gatcggaaga cctcggccgt cgcggcgctt gccggtggtg   1740
ctgaccccgg atgaagtggt tcgcatcctc ggttttctgg aaggcgagca tcgtttgttc   1800
gcccagcttc tgtatggaac gggcatgcgg atcagtgagg gtttgcaact gcgggtcaag   1860
gatctggatt tcgatcacgg cacgatcatc gtgcgggagg gcaagggctc caaggatcgg   1920
gccttgatgt tacccgagag cttggcaccc agcctgcgcg agcaggggaa ttaattccca   1980
cgggttttgc tgcccgcaaa cgggctgttc tggtgttgct agtttgttat cagaatcgca   2040
gatccggctt cagccggttt gccggctgaa agcgctattt cttccagaat tgccatgatt   2100
ttttccccac gggaggcgtc actggctccc gtgttgtcgg cagctttgat tcgataagca   2160
gcatcgcctt tttcaggctg tctatgtgtg actgttgagc tgtaacaagt tgtctcaggt   2220
gttcaatttc atgttctagt tgctttgttt tactggtttc acctgttcta ttaggtgtta   2280
catgctgttc atctgttaca ttgtcgatct gttcatggtg aacagctttg aatgcaccaa   2340
aaactcgtaa aagctctgat gtatctatct ttttacacc gttttcatct gtgcatatgg   2400
acagttttcc ctttgatatg taacggtgaa cagttgttct acttttgttt gttagtcttg   2460
atgcttcact gatagataca agagccataa gaacctcaga tccttccgta tttagccagt   2520
atgttctcta gtgtggttcg ttgttttgc gtgagccatg agaacgaacc attgagatca   2580
tacttacttt gcatgtcact caaaaatttt gcctcaaaac tggtgagctg aattttgca   2640 gttaaagcat cgtgtagtgt ttttcttagt ccgttatgta ggtaggaatc tgatgtaatg   2700
gttgttggta ttttgtcacc attcattttt atctggttgt tctcaagttc ggttacgaga   2760
tccatttgtc tatctagttc aacttggaaa atcaacgtat cagtcgggcg gcctcgctta   2820
tcaaccacca atttcatatt gctgtaagtg tttaaatctt tacttattgg tttcaaaacc   2880
cattggttaa gccttttaaa ctcatggtag ttattttcaa gcattaacat gaacttaaat   2940
tcatcaaggc taatctctat atttgccttg tgagttttct tttgtgttag ttcttttaat   3000
aaccactcat aaatcctcat agagtatttg ttttcaaaag acttaacatg ttccagatta   3060
tattttatga attttttaa ctggaaaaga taaggcaata tctcttcact aaaaactaat   3120
tctaattttt cgcttgagaa cttggcatag tttgtccact ggaaaatctc aaagccttta   3180
accaaaggat tcctgatttc cacagttctc gtcatcagct ctctggttgc tttagctaat   3240
acaccataag cattttccct actgatgttc atcatctgag cgtattggtt ataagtgaac   3300
gataccgtcc gttctttcct tgtagggttt tcaatcgtgg ggttgagtag tgccacacag   3360
cataaaatta gcttggtttc atgctccgtt aagtcatagc gactaatcgc tagttcattt   3420
gctttgaaaa caactaattc agacatacat ctcaattggt ctaggtgatt ttaatcacta   3480
taccaattga gatgggctag tcaatgataa ttactagtcc ttttcctttg agttgtgggt   3540
```

```
atctgtaaat tctgctagac ctttgctgga aaacttgtaa attctgctag accctctgta    3600
aattccgcta gacctttgtg tgttttttt gtttatattc aagtggttat aatttataga    3660
ataaagaaag aataaaaaaa gataaaaaga atagatccca gccctgtgta taactcacta    3720
ctttagtcag ttccgcagta ttacaaaagg atgtcgcaaa cgctgtttgc tcctctacaa    3780
aacagacctt aaaaccctaa aggcttaagt agcaccctcg caagctcggg caaatcgctg    3840
aatattcctt ttgtctccga ccatcaggca cctgagtcgc tgtctttttc gtgacattca    3900
gttcgctgcg ctcacggctc tggcagtgaa tgggggtaaa tggcactaca ggcgcctttt    3960
atggattcat gcaaggaaac tacccataat acaagaaaag cccgtcacgg gcttctcagg    4020
gcgttttatg gcgggtctgc tatgtggtgc tatctgactt tttgctgttc agcagttcct    4080
gccctctgat tttccagtct gaccacttcg gattatcccg tgacaggtca ttcagactgg    4140
ctaatgcacc cagtaaggca gcggtatcat caacaggctt accgtctta ctgtcgggaa    4200 ttcgcgttgg ccgattcatt aatgcagatt ctgaaatgag ctgttgacaa ttaatcatcc    4260
ggctcgtata atgtgtggaa ttgtgagcgg ataacaattt cacacaggaa acagcgccgc    4320
tgagaaaaag cgaagcggca ctgctcttta acaatttatc agacaatctg tgtgggcact    4380
cgaccggaat tatcgattaa ctttattatt aaaaattaaa gaggtatata ttaatgtatc    4440
gattaaataa ggaggaataa accatgtgtg cgacctcttc tcaatttact cagattaccg    4500
agcataattc ccgtcgttcc gcaaactatc agccaaacct gtggaatttc gaattcctgc    4560
aatccctgga gaacgacctg aaagtggaaa agctggagga gaaagcgacc aaactggagg    4620
aagaagttcg ctgcatgatc aaccgtgtag acacccagcc gctgtccctg ctggagctga    4680
tcgacgatgt gcagcgcctg ggtctgacct acaaatttga aaagacatc attaaagccc    4740 tggaaaacat cgtactgctg gacgaaaaca aaaagaacaa atctgacctg cacgcaaccg    4800
ctctgtcttt ccgtctgctg cgtcagcacg gtttcgaggt ttctcaggat gtttttgagc    4860
gtttcaagga taagaaggt ggtttcagcg gtgaactgaa aggtgacgtc caaggcctgc    4920
tgagcctgta tgaagcgtct tacctgggtt cgagggtga aacctgctg gaggaggcgc    4980 gtacctttc catcacccac ctgaagaaca acctgaaaga aggcattaat accaaggttg    5040
cagaacaagt gagccacgcc ctggaactgc atatccacca gcgtctgcac cgtctggagg    5100
cacgttggtt cctggataaa tacgaaccga agaaccgca tcaccagctg ctgctggagc    5160
tggcgaagct ggattttaac atggtacaga ccctgcacca gaaagagctg caagatctgt    5220
cccgctggtg gaccgagatg ggcctggcta gcaaactgga ttttgtacgc gaccgcctga    5280
tggaagttta tttctgggca ctgggtatgg cgccagaccc gcagtttggt gaatgtcgca    5340
aagctgttac taaaatgttt ggtctggtga cgatcatcga tgacgtgtat gacgtttatg    5400
gcactctgga cgaactgcaa ctgttcaccg atgctgtaga gcgctgggac gttaacgcta    5460
ttaacaccct gccggactat atgaaactgt gtttcctggc actgtacaac accgttaacg    5520
acacgtccta ttctattctg aaagagaaag gtcataacaa cctgtcctat ctgacgaaaa    5580
gctggcgtga actgtgcaaa gccttctctc aagaggcgaa atggtccaac aacaaaatta    5640
tcccggcttt ctccaagtac ctggaaaacg ccagcgtttc ctcctccggt gtagcgctgc    5700
tggcgccgtc ttactttttcc gtatgccagc agcaggaaga catctccgac cacgcgctgc    5760
gttccctgac cgacttccat ggtctggtgc gttctagctg cgttatcttc cgcctgtgca    5820
acgatctggc cacctctgcg gcggagctgg aacgtggcga gactaccaat tctatcatta    5880
gctacatgca cgaaaacgat ggtaccagcg aggaacaggc ccgcgaagaa ctgcgtaaac    5940
```

```
tgatcgacgc cgaatggaaa aagatgaatc gtgaacgcgt tagcgactcc accctgctgc   6000
ctaaagcgtt catggaaatc gcagttaaca tggcacgtgt ttcccactgc acctaccagt   6060
atggcgatgg tctgggtcgc ccagactacg cgactgaaaa ccgcatcaaa ctgctgctga   6120
ttgacccttt cccgattaac cagctgatgt atgtctaact gcatcgccct taggaggtaa   6180
aaaaaaatga ctgccgacaa caatagtatg ccccatggtg cagtatctag ttacgccaaa   6240
ttagtgcaaa accaaacacc tgaagacatt ttggaagagt ttcctgaaat tattccatta   6300
caacaaagac ctaatacccg atctagtgag acgtcaaatg acgaaagcgg agaaacatgt   6360
ttttctggtc atgatgagga gcaaattaag ttaatgaatg aaaattgtat tgttttggat   6420
tgggacgata atgctattgg tgccggtacc aagaaagttt gtcatttaat ggaaaatatt   6480
gaaaagggtt tactacatcg tgcattctcc gtctttattt tcaatgaaca aggtgaatta   6540
cttttacaac aaagagccac tgaaaaaata actttccctg atctttggac taacacatgc   6600
tgctctcatc cactatgtat tgatgacgaa ttaggtttga agggtaagct agacgataag   6660
attaagggcg ctattactgc ggcggtgaga aaactagatc atgaattagg tattccagaa   6720
gatgaaacta agacaagggg taagtttcac ttttttaaaca gaatccatta catggcacca   6780
agcaatgaac catggggtga acatgaaatt gattacatcc tattttataa gatcaacgct   6840
aaagaaaact tgactgtcaa cccaaacgtc aatgaagtta gagacttcaa atgggtttca   6900
ccaaatgatt tgaaaactat gtttgctgac ccaagttaca agtttacgcc ttggtttaag   6960
attatttgcg agaattactt attcaactgg tgggagcaat tagatgacct ttctgaagtg   7020
gaaaatgaca ggcaaattca tagaatgcta taacgacgcg tcctgcagct ggtaccatat   7080
gggaattcga agctttctag aacgaaaact catctcagaa gaggatctga atagcgccgt   7140
cgaccatcat catcatcatc attgagttta acggtctcca gcttggctg ttttggcgga   7200 tgagagaaga ttttcagcct gatacagatt aaatcagaac gcagaagcgg tctgataaaa   7260
cagaatttgc ctggcggcag tagcgcggtg gtcccacctg accccatgcc gaactcagaa   7320
gtgaaacgcc gtagcgccga tggtagtgtg gggtctcccc atgcgagagt agggaactgc   7380
caggcatcaa ataaaacgaa aggctcagtc gaaagactgg gcctttcgtt ttatctgttg   7440
tttgtcggtg aacgctctcc tgagtaggac aaatccgccg ggagcggatt tgaacgttgc   7500
gaagcaacgg cccggagggt ggcgggcagg acgcccgcca taaactgcca ggcatcaaat   7560
taagcagaag gccatcctga cggatggcct ttttgcgttt ctacaaactc ttttttgttta   7620 tttttctaaa tacattcaaa tatgtatccg ctcatgagac aataaccctg ataaatgctt   7680
caataat                                                             7687
```

<210> SEQ ID NO 55
<211> LENGTH: 8675
<212> TYPE: DNA
<213> ORGANISM: Artificial Sequence
<220> FEATURE:
<223> OTHER INFORMATION: Synthetic Construct

<400> SEQUENCE: 55

```
cccgtcttac tgtcgggaat tcgcgttggc cgattcatta atgcagatta ttgaagcatt     60
tatcagggtt attgtctcat gagcggatac atatttgaat gtatttagaa aaataaacaa    120
aaagagtttg tagaaacgca aaaaggccat ccgtcaggat ggccttctgc ttaatttgat    180
gcctggcagt ttatgcgggc gtcctgcccg ccaccctccc gggccgttgc ttcgcaacgt    240
tcaaatccgc tcccggcgga tttgtcctac tcaggagagc gttcaccgac aaacaacaga    300
```

```
taaaacgaaa ggcccagtct ttcgactgag cctttcgttt tatttgatgc ctggcagttc    360
cctactctcg catggggaga ccccacacta ccatcggcgc tacggcgttt cacttctgag    420
ttcggcatgg ggtcaggtgg gaccaccgcg ctactgccgc caggcaaatt ctgttttatc    480
agaccgcttc tgcgttctga tttaatctgt atcaggctga aaatcttctc tcatccgcca    540
aaacagccaa gctggagacc gtttaaactc aatgatgatg atgatgatgg tcgacggcgc    600
tattcagatc ctcttctgag atgagttttt gttctagaaa gcttcgaatt cccatatggt    660
accagctgca gttatgccag ccaggccttg attttggctt ccataccagc ggcatcgagg    720
ccgagttcgg cgcgcatttc ttcctgagtt ccttgcggaa taagaagtc cggcaggcca    780 atgttcagca cgggtactgg tttacgatgg ccatcagca cttcgttcac gccgctgcct    840
gcgccgccca taatggcgtt ttcttctacg gtgaccagcg cttcatggct ggcggccatt    900
tccagaatta acgcttcatc aagcggtttc acaaaacgca tatcgaccag cgtggcgttc    960
agcgattcgg cgactttcgc cgcttctggc atcagcgtac caaagttaag gatcgccagt    1020
ttctcgccac gacgcttcac aatgcctttg ccaattggta gttttccag cggcgtcagt    1080 tccacgccga ccgcgttgcc acgcgggtag cgcaccgctg acgggccatc gttatagtga    1140
tagccggtat agagcatctg gcgacattcg ttttcatcgc tcgggtcat aatgaccatt    1200 tccggtatgc agcgcaggta agagagatca aaagcaccct gatgggtttg accgtcagca    1260
ccaacaatgc ccgcgcggtc gatggcgaac aggaccggaa gcttttgaat cgccacgtca    1320
tgcagcacct gatcataggc gcgttgcagg aaagtggagt aaatcgcgac aatgggtttg    1380
tacccaccaa tcgccagacc cgcagcaaag gtcaccgcgt gttgctcggc aattgccacg    1440
tcgaagtagc gatccgggaa tttacgtgaa aactcgacca tgccggaacc ttcacgcatc    1500
gccggagtaa tcgccatcag cttgttgtct ttcgctgccg tttcgcacaa ccagtcgcca    1560 aagattttg aatagctcgg caaaccgccg ctacttttcg gcaaacaacc gctggaggga    1620
tcaaatttag gcacggcgtg gaaagtgatc gggtcttttt ctgccggttc ataaccacga    1680
ccttttttgg tcatgatatg caggaactgc gggccttca ggtcgcgcat gttcttagc    1740 gtggtgataa gccccagcac atcgtgaccg tccaccgggc cgatgtagtt aaagcccagc    1800
tcttcaaaca acgtgccagg cactaccatg ccttttaatat gttcttcggt gcgtttgagc    1860 agctcttaa ttggcggcac gccagagaaa actttttcc cgccttcgcg cagtgaagag    1920
taaagcttac cggaaagcag ctgtgccaga tggttgttga gcgcgccgac attttcggaa    1980
atcgacattt cattgtcgtt gagaatcacc agcatatcag gacggatatc gcccgcgtga    2040
ttcatcgctt caaacgccat gcctgcggta atcgcgccat cgccaatgac acagacggtg    2100
cggcgatttt tgccttcttt ttcggcagca accgcaatac caattccggc actgatggag    2160
gttgatgaat gcccgacgct taatacgtca tattcgcttt cgccgcgcca cgggaacggg    2220
tgcagaccgc ctttctgacg gatggtgccg attttgtcgc ggcgtccggt caaaattta    2280 tgcggataag cctgatgccc cacatcccaa atcaattggt caaacggggt gttgtagaca    2340
tagtgcagcg ccacggtcag ttcgaccgtg cccagcccgg aggcgaagtg cccgctggaa    2400
cggctcacgc tgtcgagtaa atagcggcgc agttcgtcgc agagtttcgg taaactctct    2460
ttcggcaaca gtcgtaactc ctgggtggag tcgaccagtg ccaggtcgg gtatttggca    2520 atatcaaaac tcatgttttt ttacctccta agggcgaatg cagttagaca tacatcagct    2580
ggttaatcgg gaaagggtca atcagcagca gtttgatgcg gttttcagtc gcgtagtctg    2640
ggcgacccag accatcgcca tactggtagg tgcagtggga aacacgtgcc atgttaactg    2700
```

| | |
|---|---|
| cgatttccat gaacgcttta ggcagcaggg tggagtcgct aacgcgttca cgattcatct | 2760 |
| ttttccattc ggcgtcgatc agtttacgca gttcttcgcg ggcctgttcc tcgctggtac | 2820 |
| catcgttttc gtgcatgtag ctaatgatag aattggtagt ctcgccacgt tccagctccg | 2880 |
| ccgcagaggt ggccagatcg ttgcacaggc ggaagataac gcagctagaa cgcaccagac | 2940 |
| catggaagtc ggtcagggaa cgcagcgcgt ggtcggagat gtcttcctgc tgctggcata | 3000 |
| cggaaaagta agacggcgcc agcagcgcta caccggagga ggaaacgctg gcgttttcca | 3060 |
| ggtacttgga gaaagccggg ataatttttgt tgttggacca tttcgcctct tgcagaaagg | 3120 |
| ctttgcacag ttcacgccag cttttcgtca gataggacag gttgttatga cctttctctt | 3180 |
| tcagaataga ataggacgtg tcgttaacgg tgttgtacag tgccaggaaa cacagtttca | 3240 |
| tatagtccgg cagggtgtta atagcgttaa cgtcccagcg ctctacagca tcggtgaaca | 3300 |
| gttgcagttc gtccagagtg ccataaacgt catacacgtc atcgatgatc gtcaccagac | 3360 |
| caaacatttt agtaacagct tgcgacatt caccaaactg cgggtctggc gccataccca | 3420 |
| gtgcccagaa ataaacttcc atcaggcggt cgcgtacaaa atccagtttg ctagccaggc | 3480 |
| ccatctcggt ccaccagcgg gacagatctt gcagctcttt ctggtgcagg gtctgtacca | 3540 |
| tgttaaaatc cagcttcgcc agctccagca gcagctggtg atgcggttct ttcggttcgt | 3600 |
| atttatccag gaaccaacgt gcctccagac ggtgcagacg ctggtgatat ggcagttcca | 3660 |
| gggcgtggct cacttgttct gcaaccttgg tattaatgcc ttctttcagg ttgttcttca | 3720 |
| ggtgggtgat ggaaaggta cgcgcctcct ccagcaggtt ctcaccctcg aaacccaggt | 3780 |
| aagacgcttc atacaggctc agcaggcctt ggacgtcacc tttcagttca ccgctgaaac | 3840 |
| caccttcttt atccttgaaa cgctcaaaaa catcctgaga aacctcgaaa ccgtgctgac | 3900 |
| gcagcagacg gaaagacaga gcggttgcgt gcaggtcaga tttgttcttt ttgttttcgt | 3960 |
| ccagcagtac gatgttttcc agggctttaa tgatgtcttt ttcaaatttg taggtcagac | 4020 |
| ccaggcgctg cacatcgtcg atcagctcca gcagggacag cggctgggtg tctacacggt | 4080 |
| tgatcatgca gcgaacttct tcctccagtt ggtcgctttt ctcctccagc ttttccactt | 4140 |
| tcaggtcgtt ctccagggat gcaggaattt cgaaattcca caggtttggc tgatagtttg | 4200 |
| cggaacgacg ggaattatgc tcggtaatct gagtaaattg agaagaggtc gcacacatgg | 4260 |
| tttattcctc cttatttaat cgatacatta atatatacct ctttaatttt taataataaa | 4320 |
| gttaatcgat aattccggtc gagtgcccac acagattgtc tgataaattg ttaaagagca | 4380 |
| gtgccgcttc gcttttttctc agcggcgctg tttcctgtgt gaaattgtta ccgctcaca | 4440 |
| attccacaca ttatacgagc cggatgatta attgtcaaca gctcatttca gaatctggcg | 4500 |
| taatagcgaa gaggcccgca ccgatcgccc ttcccaacag ttgcgcagcc tgaatggcga | 4560 |
| atggcgcctg atgcggtatt ttctccttac gcatctgtgc ggtatttcac accgcatatg | 4620 |
| gtgcactctc agtacaatct gctctgatgc cgcatagtta agccagcccc gacacccgcc | 4680 |
| aacacccgct gacgagctta gtaaagccct cgctagattt taatgcggat gttgcgatta | 4740 |
| cttcgccaac tattgcgata caagaaaaa gccagccttt catgatatat ctcccaattt | 4800 |
| gtgtagggct tattatgcac gcttaaaaat aataaaagca gacttgacct gatagtttgg | 4860 |
| ctgtgagcaa ttatgtgctt agtgcatcta acgcttgagt taagccgcgc cgcgaagcgg | 4920 |
| cgtcggcttg aacgaattgt tagacattat ttgccgacta ccttggtgat ctcgcctttc | 4980 |
| acgtagtgga caaattcttc caactgatct gcgcgcgagg ccaagcgatc ttcttcttgt | 5040 |
| ccaagataag cctgtctagc ttcaagtatg acgggctgat actgggccgg caggcgctcc | 5100 |

```
attgcccagt cggcagcgac atccttcggc gcgattttgc cggttactgc gctgtaccaa    5160
atgcgggaca acgtaagcac tacatttcgc tcatcgccag cccagtcggg cggcgagttc    5220
catagcgtta aggtttcatt tagcgcctca aatagatcct gttcaggaac cggatcaaag    5280
agttcctccg ccgctggacc taccaaggca acgctatgtt ctcttgcttt tgtcagcaag    5340
atagccagat caatgtcgat cgtggctggc tcgaagatac ctgcaagaat gtcattgcgc    5400
tgccattctc caaattgcag ttcgcgctta gctggataac gccacggaat gatgtcgtcg    5460
tgcacaacaa tggtgacttc tacagcgcgg agaatctcgc tctctccagg ggaagccgaa    5520
gtttccaaaa ggtcgttgat caaagctcgc cgcgttgttt catcaagcct tacggtcacc    5580
gtaaccagca aatcaatatc actgtgtggc ttcaggccgc catccactgc ggagccgtac    5640
aaatgtacgg ccagcaacgt cggttcgaga tggcgctcga tgacgccaac tacctctgat    5700
agttgagtcg atacttcggc gatcaccgct tccctcatga tgtttaactt tgttttaggg    5760
cgactgccct gctgcgtaac atcgttgctg ctccataaca tcaaacatcg acccacggcg    5820
taacgcgctt gctgcttgga tgcccgaggc atagactgta ccccaaaaaa acagtcataa    5880
caagccatga aaaccgccac tgcgccgtta ccaccgctgc gttcggtcaa ggttctggac    5940
cagttgcgtg agcgcatacg ctacttgcat tacagcttac gaaccgaaca ggcttatgtc    6000
cactgggttc gtgccttcat ccgtttccac ggtgtgcgtc acccggcaac cttgggcagc    6060
agcgaagtcg aggcatttct gtcctggctg gcgaacgagc gcaaggtttc ggtctccacg    6120
catcgtcagg cattggcggc cttgctgttc ttctacggca aggtgctgtg cacggatctg    6180
ccctggcttc aggagatcgg aagacctcgg ccgtcgcggc gcttgccggt ggtgctgacc    6240
ccggatgaag tggttcgcat cctcggtttt ctggaaggcg agcatcgttt gttcgcccag    6300
cttctgtatg aacgggcat gcggatcagt gagggtttgc aactgcgggt caaggatctg    6360
gatttcgatc acggcacgat catcgtgcgg gagggcaagg gctccaagga tcgggccttg    6420
atgttacccg agagcttggc acccagcctg cgcgagcagg ggaattaatt cccacgggtt    6480
ttgctgcccg caaacgggct gttctggtgt tgctagtttg ttatcagaat cgcagatccg    6540
gcttcagccg gtttgccggc tgaaagcgct atttcttcca gaattgccat gattttttcc    6600
ccacgggagg cgtcactggc tcccgtgttg tcggcagctt tgattcgata agcagcatcg    6660
cctgtttcag gctgtctatg tgtgactgtt gagctgtaac aagttgtctc aggtgttcaa    6720
tttcatgttc tagttgcttt gttttactgg tttcacctgt tctattaggt gttacatgct    6780
gttcatctgt tacattgtcg atctgttcat ggtgaacagc tttgaatgca ccaaaaactc    6840
gtaaaagctc tgatgtatct atcttttta caccgttttc atctgtgcat atggacagtt    6900 ttcccttga tatgtaacgg tgaacagttg ttctactttt gtttgttagt cttgatgctt    6960
cactgataga tacaagagcc ataagaacct cagatccttc cgtatttagc cagtatgttc    7020
tctagtgtgg ttcgttgttt ttgcgtgagc catgagaacg aaccattgag atcatactta    7080
ctttgcatgt cactcaaaaa ttttgcctca aaactggtga gctgaatttt tgcagttaaa    7140
gcatcgtgta gtgttttct tagtccgtta tgtaggtagg aatctgatgt aatggttgtt    7200
ggtattttgt caccattcat ttttatctgg ttgttctcaa gttcggttac gagatccatt    7260
tgtctatcta gttcaacttg gaaaatcaac gtatcagtcg gcggcctcg cttatcaacc    7320 accaatttca tattgctgta agtgtttaaa tctttactta ttggtttcaa aacccattgg    7380
ttaagccttt taaactcatg gtagttattt tcaagcatta acatgaactt aaattcatca    7440
aggctaatct ctatatttgc cttgtgagtt ttctttgtg ttagttcttt taataaccac    7500
```

```
tcataaatcc tcatagagta tttgttttca aaagacttaa catgttccag attatatttt    7560
atgaattttt ttaactggaa aagataaggc aatatctctt cactaaaaac taattctaat    7620
ttttcgcttg agaacttggc atagtttgtc cactggaaaa tctcaaagcc tttaaccaaa    7680
ggattcctga tttccacagt tctcgtcatc agctctctgg ttgctttagc taatacacca    7740
taagcatttt ccctactgat gttcatcatc tgagcgtatt ggttataagt gaacgatacc    7800
gtccgttctt tccttgtagg gttttcaatc gtggggttga gtagtgccac acagcataaa    7860
attagcttgg tttcatgctc cgttaagtca tagcgactaa tcgctagttc atttgctttg    7920
aaaacaacta attcagacat acatctcaat tggtctaggt gattttaatc actataccaa    7980
ttgagatggg ctagtcaatg ataattacta gtccttttcc tttgagttgt gggtatctgt    8040
aaattctgct agacctttgc tggaaaactt gtaaattctg ctagaccctc tgtaaattcc    8100
gctagacctt tgtgtgtttt ttttgtttat attcaagtgg ttataattta tagaataaag    8160
aaagaataaa aaagataaa aagaatagat cccagccctg tgtataactc actactttag     8220
tcagttccgc agtattacaa aaggatgtcg caaacgctgt ttgctcctct acaaaacaga    8280
ccttaaaacc ctaaaggctt aagtagcacc ctcgcaagct cgggcaaatc gctgaatatt    8340 cctttttgtct ccgaccatca ggcacctgag tcgctgtctt tttcgtgaca ttcagttcgc   8400
tgcgctcacg gctctggcag tgaatggggg taaatggcac tacaggcgcc ttttatggat    8460
tcatgcaagg aaactaccca taatacaaga aaagcccgtc acgggcttct cagggcgttt    8520
tatggcgggt ctgctatgtg gtgctatctg acttttttgct gttcagcagt tcctgccctc   8580 tgatttttcca gtctgaccac ttcggattat cccgtgacag gtcattcaga ctggctaatg   8640
cacccagtaa ggcagcggta tcatcaacag gctta                               8675

<210> SEQ ID NO 56
<211> LENGTH: 8032
<212> TYPE: DNA
<213> ORGANISM: Artificial Sequence
<220> FEATURE:
<223> OTHER INFORMATION: Synthetic Construct

<400> SEQUENCE: 56
tcgctgcgct cggtcgttcg gctgcggcga gcggtatcag ctcactcaaa ggcggtaata      60
cggttatcca cagaatcagg ggataacgca ggaaagaaca tgtgagcaaa aggccagcaa     120
aaggccagga accgtaaaaa ggccgcgttg ctggcgtttt tccataggct ccgcccccct    180
gacgagcatc acaaaaatcg acgctcaagt cagaggtggc gaaacccgac aggactataa    240
agataccagg cgtttccccc tggaagctcc ctcgtgcgct ctcctgttcc gaccctgccg    300
cttaccggat acctgtccgc ctttctccct tcgggaagcg tggcgctttc tcatagctca    360
cgctgtaggt atctcagttc ggtgtaggtc gttcgctcca agctgggctg tgtgcacgaa    420
ccccccgttc agcccgaccg ctgcgcctta tccggtaact atcgtcttga gtccaacccg    480
gtaagacacg acttatcgcc actggcagca gccactggta acaggattag cagagcgagg    540
tatgtaggcg gtgctacaga gttcttgaag tggtggccta actacggcta cactagaaga    600
acagtatttg gtatctgcgc tctgctgaag ccagttacct tcggaaaaag agttggtagc    660
tcttgatccg gcaaacaaac caccgctggt agcggtggtt tttttgtttg caagcagcag    720
attacgcgca gaaaaaaagg atctcaagaa gatcctttga tcttttctac ggggtctgac    780
gctcagtgga acgaaaactc acgttaaggg attttggtca tgagattatc aaaaaggatc    840
ttcacctaga tccttttaaa ttaaaaatga agttttaaat caatctaaag tatatatgag    900
```

-continued

```
taaacttggt ctgacagtta ccaatgctta atcagtgagg cacctatctc agcgatctgt    960
ctatttcgtt catccatagt tgcctgactc cccgtcgtgt agataactac gatacgggag   1020
ggcttaccat ctggcccag tgctgcaatg ataccgcgag acccacgctc accggctcca   1080
gatttatcag caataaacca gccagccgga agggccgagc gcagaagtgg tcctgcaact   1140
ttatccgcct ccatccagtc tattaattgt tgccggaag ctagagtaag tagttcgcca   1200
gttaatagtt tgcgcaacgt tgttgccatt gctacaggca tcgtggtgtc acgctcgtcg   1260
tttggtatgg cttcattcag ctccggttcc caacgatcaa ggcgagttac atgatccccc   1320
atgttgtgca aaaaagcggt tagctccttc ggtcctccga tcgttgtcag aagtaagttg   1380
gccgcagtgt tatcactcat ggttatggca gcactgcata attctcttac tgtcatgcca   1440
tccgtaagat gcttttctgt gactggtgag tactcaacca agtcattctg agaatagtgt   1500
atgcggcgac cgagttgctc ttgcccggcg tcaatacggg ataataccgc gccacatagc   1560
agaactttaa aagtgctcat cattggaaaa cgttcttcgg ggcgaaaact ctcaaggatc   1620
ttaccgctgt tgagatccag ttcgatgtaa cccactcgtg cacccaactg atcttcagca   1680
tcttttactt tcaccagcgt ttctgggtga gcaaaaacag gaaggcaaaa tgccgcaaaa   1740
aagggaataa gggcgacacg gaaatgttga atactcatac tcttcctttt tcaatattat   1800
tgaagcattt atcagggtta ttgtctcatg agcggataca tatttgaatg tatttagaaa   1860
aataaacaaa taggggttcc gcgcacattt ccccgaaaag tgccacctga cgtctaagaa   1920
accattatta tcatgacatt aacctataaa aataggcgta tcacgaggcc ctttcgtctc   1980
gcgcgtttcg gtgatgacgg tgaaaacctc tgacacatgc agctcccgga gacggtcaca   2040
gcttgtctgt aagcggatgc cgggagcaga caagcccgtc agggcgcgtc agcgggtgtt   2100
ggcgggtgtc ggggctggct taactatgcg gcatcagagc agattgtact gagagtgcac   2160
catagatctg gagctgtaat ataaaaacct tcttcaacta acggggcagg ttagtgacat   2220
tagaaaaccg actgtaaaaa gtacagtcgg cattatctca tattataaaa gccagtcatt   2280
aggcctatct gacaattcct gaatagagtt cataaacaat cctgcatgat aaccatcaca   2340
aacagaatga tgtacctgta agatagcgg taaatatatt gaattacctt tattaatgaa   2400
ttttcctgct gtaataatgg gtagaaggta attactatta ttattgatat ttaagttaaa   2460
cccagtaaat gaagtccatg gaataataga aagagaaaaa gcattttcag gtataggtgt   2520
tttgggaaac aatttccccg aaccattata tttctctaca tcagaaaggt ataaatcata   2580
aaactctttg aagtcattct ttacaggagt ccaaatacca gagaatgttt tagatacacc   2640
atcaaaaatt gtataaagtg ctctaactt atcccaataa cctaactctc cgtcgctatt   2700
gtaaccagtt ctaaaagctg tatttgagtt tatcacccct gtcactaaga aaataaatgc   2760
agggtaaaat ttatatcctt cttgttttat gtttcggtat aaaacactaa tatcaatttc   2820
tgtggttata ctaaaagtcg tttgttggtt caaataatga ttaaatatct cttttctctt   2880
ccaattgtct aaatcaattt tattaaagtt catttgatat gcctcctaaa ttttttatcta   2940
aagtgaattt aggaggctta cttgtctgct ttcttcatta gaatcaatcc ttttttaaaa   3000
gtcaatatta ctgtaacata aatatatatt ttaaaaatat cccactttat ccaattttcg   3060
tttgttgaac taatgggtgc tttagttgaa gaataaaaga cctatgcggt gtgaaatacc   3120
gcacagatgc gtaaggagaa aataccgcat caggcgccat cgccattca ggctgcgcaa   3180
ctgttgggaa gggcgatcgg tgcgggcctc ttcgctatta cgccagctgg cgaaaggggg   3240
atgtgctgca aggcgattaa gttgggtaac gccagggttt tcccagtcac gacgttgtaa   3300
```

```
aacgacggcc agtgccaagc ttgcatgcct gcactccatt ttcttctgct atcaaaataa   3360
cagactcgtg attttccaaa cgagctttca aaaaagcctc tgccccttgc aaatcggatg   3420
cctgtctata aaattcccga tattggttaa acagcggcgc aatggcggcc gcatctgatg   3480
tctttgcttg gcgaatgttc atcttatttc ttcctccctc tcaataattt tttcattcta   3540
tcccttttct gtaaagttta tttttcagaa tacttttatc atcatgcttt gaaaaaatat   3600
cacgataata tccattgttc tcacggaagc acacgcaggt catttgaacg aattttttcg   3660
acaggaattt gccgggactc aggagcattt aacctaaaaa agcatgacat ttcagcataa   3720
tgaacattta ctcatgtcta ttttcgttct tttctgtatg aaaatagtta tttcgagtct   3780
ctacggaaat agcgagagat gatataccta aatagagata aaatcatctc aaaaaaatgg   3840
gtctactaaa atattattcc atctattaca ataaattcac agaatagtct tttaagtaag   3900
tctactctga attttttaa aaggagaggg taaagagtga aaacagtagt tattattgat   3960
gcattacgaa caccaattgg aaaatataaa ggcagcttaa gtcaagtaag tgccgtagac   4020
ttaggaacac atgttacaac acaacttta aaaagacatt ccactatttc tgaagaaatt   4080
gatcaagtaa tctttggaaa tgttttacaa gctggaaatg gccaaaatcc cgcacgacaa   4140
atagcaataa acagcggttt gtctcatgaa attcccgcaa tgacggttaa tgaggtctgc   4200
ggatcaggaa tgaaggccgt tattttggcg aaacaattga ttcaattagg agaagcggaa   4260
gttttaattg ctggcgggat tgagaatatg tcccaagcac ctaaattaca acgttttaat   4320
tacgaaacag aaagctacga tgcgcctttt tctagtatga tgtatgatgg attaacggat   4380
gcctttagtg gtcaggcaat gggcttaact gctgaaaatg tggccgaaaa gtatcatgta   4440
actagagaag agcaagatca atttctgta cattcacaat aaaagcagc tcaagcacaa   4500 gcagaaggga tattcgctga cgaaatagcc ccattagaag tatcaggaac gcttgtggag   4560
aaagatgaag ggattcgccc taattcgagc gttgagaagc taggaacgct taaaacagtt   4620
tttaaagaag acggtactgt aacagcaggg aatgcatcaa ccattaatga tggggcttct   4680
gctttgatta ttgcttcaca agaatatgcc gaagcacacg tcttccctta tttagctatt   4740
attcgagaca gtgtggaagt cggtattgat ccagcctata tgggaatttc gccgattaaa   4800
gccattcaaa aactgttagc gcgcaatcaa cttactacgg aagaaattga tctgtatgaa   4860
atcaacgaag catttgcagc aacttcaatc gtggtccaaa gagaactggc tttaccagag   4920
gaaaaggtca acatttatgg tggcggtatt tcattaggtc atgcgattgg tgccacaggt   4980
gctcgtttat taacgagttt aagttatcaa ttaaatcaaa agaaaagaa atatggagtg   5040 gcttctttat gtatcggcgg tggcttagga ctcgctatgc tactagagag acctcagcaa   5100
aaaaaaaaca gccgatttta tcaaatgagt cctgaggaac gcctggcttc tcttcttaat   5160
gaaggccaga tttctgctga tacaaaaaaa gaatttgaaa atacggcttt atcttcgcag   5220
attgccaatc atatgattga aaatcaaatc agtgaaacag aagtgccgat gggcgttggc   5280
ttacatttaa cagtggacga aactgattat ttggtaccaa tggcgacaga agagccctca   5340
gttattgcgg ctttgagtaa tggtgcaaaa atagcacaag gatttaaaac agtgaatcaa   5400
caacgcttaa tgcgtggaca aatcgttttt tacgatgttg cagatcccga gtcattgatt   5460
gataaactac aagtaagaga agcggaagtt tttcaacaag cagagttaag ttatccatct   5520
atcgttaaac ggggcggcgg cttaagagat ttgcaatatc gtactttga tgaatcattt   5580 gtatctgtcg acttttagt agatgttaag gatgcaatgg gggcaaatat cgttaacgct   5640
atgttggaag gtgtggccga gttgttccgt gaatggtttg cggagcaaaa gatttattc   5700
```

```
agtattttaa gtaattatgc cacggagtcg gttgttacga tgaaaacggc tattccagtt   5760
tcacgtttaa gtaaggggag caatggccgg gaaattgctg aaaaaattgt tttagcttca   5820
cgctatgctt cattagatcc ttatcgggca gtcacgcata acaaaggaat catgaatggc   5880
attgaagctg tagttttagc tacaggaaat gatacacgcg ctgttagcgc ttcttgtcat   5940
gcttttgcgg tgaaggaagg tcgctaccaa ggcttgacta gttggacgct ggatggcgaa   6000
caactaattg gtgaaatttc agttccgctt gctttagcca cggttggcgg tgccacaaaa   6060
gtcttaccta aatctcaagc agctgctgat ttgttagcag tgacggatgc aaaagaacta   6120
agtcgagtag tagcggctgt tggtttggca caaaatttag cggcgttacg ggccttagtc   6180
tctgaaggaa ttcaaaaagg acacatggct ctacaagcac gttctttagc gatgacggtc   6240
ggagctactg gtaaagaagt tgaggcagtc gctcaacaat taaaacgtca aaaaacgatg   6300
aaccaagacc gagccatggc tattttaaat gatttaagaa acaataaaaa ggagagggtg   6360
acaattggga ttgataaaat tagttttttt gtgcccccct attatattga tatgacggca   6420
ctggctgaag ccagaaatgt agaccctgga aaatttcata ttggtattgg gcaagaccaa   6480
atggcggtga acccaatcag ccaagatatt gtgacatttg cagccaatgc cgcagaagcg   6540
atcttgacca agaagataa agaggccatt gatatggtga ttgtcgggac tgagtccagt   6600
atcgatgagt caaaagcggc cgcagttgtc ttacatcgtt taatgggat caacctttc   6660
gctcgctctt tcgaaatcaa ggaagcttgt tacggagcaa cagcaggctt acagttagct   6720
aagaatcacg tagccttaca tccagataaa aaagtcttgg tcgtagcggc agatattgca   6780
aaatatggct taaattctgg cggtgagcct acacaaggag ctgggcggt tgcaatgtta   6840
gttgctagtg aaccgcgcat tttggcttta aagaggata atgtgatgct gacgcaagat   6900
atctatgact tttggcgtcc aacaggccac ccgtatccta tggtcgatgg tccttttgtca   6960
aacgaaacct acatccaatc ttttgcccaa gtctgggatg aacataaaaa acgaaccggt   7020
cttgattttg cagattatga tgcttagcg ttccatattc cttacacaaa aatgggcaaa   7080
aaagccttat tagcaaaaat ctccgaccaa actgaagcag aacaggaacg aattttagcc   7140
cgttatgaag aaagtatcgt ctatagtcgt cgcgtaggaa acttgtatac gggttcactt   7200
tatctgggac tcatttccct tttagaaaat gcaacgactt taaccgcagg caatcaaatt   7260
ggtttattca gttatggttc tggtgctgtc gctgaatttt tcactggtga attagtagct   7320
ggttatcaaa atcatttaca aaagaaact catttagcac tgctggataa tcggacagaa   7380
cttttctatcg ctgaatatga agccatgttt gcagaaactt tagacacaga cattgatcaa   7440
acgttagaag atgaattaaa atatagtatt tctgctatta ataataccgt tcgttcttat   7500
cgaaactaaa aaaaccggc cttggccccg ccggttttt attattttc ttcctccgca   7560
tgttcaatcc gctccataat cgacggatgg ctccctctga aaattttaac gagaaacggc   7620
gggttgaccc ggctcagtcc cgtaacggcc aagtcctgaa acgtctcaat cgccgcttcc   7680
cggtttccgg tcagctcaat gccgtaacgg tcggcggcgt tttcctgata ccggagacg   7740
gcattcgtaa tcgggatccc cgggtaccga gctcgaattc gtaatcatgt catagctgtt   7800
tcctgtgtga aattgttatc cgctcacaat tccacacaac atacgagccg gaagcataaa   7860
gtgtaaagcc tggggtgcct aatgagtgag ctaactcaca ttaattgcgt tgcgctcact   7920
gcccgctttc cagtcgggaa acctgtcgtg ccagctgcat taatgaatcg gccaacgcgc   7980
ggggagaggc ggtttgcgta ttgggcgctc ttccgcttcc tcgctcactg ac           8032
```

```
<210> SEQ ID NO 57
<211> LENGTH: 6592
<212> TYPE: DNA
<213> ORGANISM: Artificial Sequence
<220> FEATURE:
<223> OTHER INFORMATION: Synthetic Construct

<400> SEQUENCE: 57
gaattgctcc attttcttct gctatcaaaa taacagactc gtgattttcc aaacgagctt      60
tcaaaaaagc ctctgcccct tgcaaatcgg atgcctgtct ataaaattcc cgatattggt     120
taaacagcgg cgcaatggcg gccgcatctg atgtctttgc ttggcgaatg ttcatcttat     180
ttcttcctcc ctctcaataa ttttttcatt ctatcccttt tctgtaaagt ttattttca     240 gaatactttt atcatcatgc tttgaaaaaa tatcacgata atatccattg ttctcacgga     300
agcacacgca ggtcatttga acgaattttt tcgacaggaa tttgccggga ctcaggagca     360
tttaacctaa aaaagcatga catttcagca taatgaacat ttactcatgt ctattttcgt     420
tcttttctgt atgaaaatag ttatttcgag tctctacgga aatagcgaga gatgatatac     480
ctaaatagag ataaaatcat ctcaaaaaaa tgggtctact aaaatattat tccatctatt     540
acaataaatt cacagaatag tcttttaagt aagtctactc tgaattttt taaaaggaga     600 gggtaaagag tgtgtgcgac ctcttctcaa tttactcaga ttaccgagca taattcccgt     660
cgttccgcaa actatcagcc aaacctgtgg aatttcgaat tcctgcaatc cctggagaac     720
gacctgaaag tggaaaagct ggaggagaaa gcgaccaaac tggaggaaga agttcgctgc     780
atgatcaacc gtagacacc ccagccgctg tccctgctgg agctgatcga cgatgtgcag     840
cgcctgggtc tgacctacaa atttgaaaaa gacatcatta aagccctgga aacatcgta     900 ctgctggacg aaaacaaaaa gaacaaatct gacctgcacg caaccgctct gtctttccgt     960
ctgctgcgtc agcacggttt cgaggtttct caggatgttt ttgagcgttt caaggataaa    1020
gaaggtggtt tcagcggtga actgaaaggt gacgtccaag gcctgctgag cctgtatgaa    1080
gcgtcttacc tgggtttcga gggtgagaac ctgctggagg aggcgcgtac cttttccatc    1140
acccacctga gaacaaacct gaagaaggc attaatacca aggttgcaga acaagtgagc    1200
cacgccctgg aactgccata tcaccagcgt ctgcaccgtc tggaggcacg ttggttcctg    1260
gataaatacg aaccgaaaga accgcatcac cagctgctgc tggagctggc gaagctggat    1320
tttaacatgg tacagaccct gcaccagaaa gagctgcaag atctgtcccg ctggtggacc    1380
gagatgggcc tggctagcaa actggatttt gtacgcgacc gcctgatgga agtttatttc    1440
tgggcactgg gtatggcgcc agacccgcag tttggtgaat gtcgcaaagc tgttactaaa    1500
atgtttggtc tggtgacgat catcgatgac gtgtatgacg tttatggcac tctggacgaa    1560
ctgcaactgt tcaccgatgc tgtagagcgc tgggacgtta acgctattaa caccctgccg    1620
gactatatga actgtgtttt cctggcactg tacaacaccg ttaacgacac gtcctattct    1680
attctgaaag agaaaggtca taacaacctg tcctatctga cgaaaagctg gcgtgaactg    1740
tgcaaagcct ttctgcaaga ggcgaaatgg tccaacaaca aaattatccc ggctttctcc    1800
aagtacctgg aaaacgccag cgtttcctcc tccggtgtag cgctgctggc gccgtcttac    1860
ttttccgtat gccagcagca ggaagacatc tccgaccacg cgctgcgttc cctgaccgac    1920
ttccatggtc tggtgcgttc tagctgcgtt atcttccgcc tgtgcaacga tctggccacc    1980 tctgcgcgg agctggaacg tggcgagact accaattcta tcattagcta catgcacgaa    2040
aacgatggta ccagcgagga acaggcccgc gaagaactgc gtaaactgat cgacgccgaa    2100
tggaaaaaga tgaatcgtga acgcgttagc gactccaccc tgctgcctaa agcgttcatg    2160
```

```
gaaatcgcag ttaacatggc acgtgtttcc cactgcacct accagtatgg cgatggtctg    2220
ggtcgcccag actacgcgac tgaaaaccgc atcaaactgc tgctgattga ccctttcccg    2280
attaaccagc tgatgtatgt ctaaaaaaaa ccggccttgg ccccgccggt ttttattat     2340 ttttcttcct ccgcatgttc aatccgctcc ataatcgacg gatggctccc tctgaaaatt    2400
ttaacgagaa acggcgggtt gacccggctc agtcccgtaa cggccaagtc ctgaaacgtc    2460
tcaatcgccg cttcccggtt tccggtcagc tcaatgccgt aacggtcggc ggcgttttcc    2520
tgataccggg agacggcatt cgtaatcgga tcctctagag tcgacctgca ggcatgcaag    2580 cttttgcctcg cgcgtttcgg tgatgacggt gaaaacctct gacacatgca gctcccggag   2640
acggtcacag cttgtctgta agcggatgcc gggagcagac aagcccgtca gggcgcgtca    2700
gcgggtgttg gcgggtgtcg gggcgcagcc atgacccagt cacgtagcga tagcggagtg    2760
tatactggct taactatgcg gcatcagagc agattgtact gagagtgcac catatgcggt    2820
gtgaaatacc gcacagatgc gtaaggagaa ataccgcat caggcgctct tccgcttcct     2880
cgctcactga ctcgctgcgc tcggtcgttc ggctgcggcg agcggtatca gctcactcaa    2940
aggcggtaat acgttatcc acagaatcag ggataacgc aggaaagaac atgtgagcaa      3000
aaggccagca aaaggccagg aaccgtaaaa aggccgcgtt gctggcgttt tccataggc     3060 tccgcccccc tgacgagcat cacaaaaatc gacgctcaag tcagaggtgg cgaaacccga    3120
caggactata aagataccag gcgtttcccc ctggaagctc cctcgtgcgc tctcctgttc    3180
cgaccctgcc gcttaccgga tacctgtccg ccttctctcc ttcgggaagc gtggcgcttt    3240
ctcaatgctc acgctgtagg tatctcagtt cggtgtaggt cgttcgctcc aagctgggct    3300
gtgtgcacga accccccgtt cagcccgacc gctgcgcctt atccggtaac tatcgtcttg    3360
agtccaaccc ggtaagacac gacttatcgc cactggcagc agccactggt aacaggatta    3420
gcagagcgag gtatgtaggc ggtgctacag agttcttgaa gtggtggcct aactacggct    3480
acactagaag gacagtattt ggtatctgcg ctctgctgaa gccagttacc ttcggaaaaa    3540
gagttggtag ctcttgatcc ggcaaacaaa ccaccgctgg tagcggtggt ttttttgttt    3600
gcaagcagca gattacgcgc agaaaaaaag gatctcaaga agatcctttg atcttttcta    3660
cggggtctga cgctcagtgg aacgaaaact cacgttaagg gattttggtc atgagattat    3720
caaaaaggat cgaagtcggt tcagaaaaag aaggatatgg atctggagct gtaatataaa    3780
aaccttcttc aactaacggg gcaggttagt gacattagaa aaccgactgt aaaaagtaca    3840
gtcggcatta tctcatatta taaaagccag tcattaggcc tatctgacaa ttcctgaata    3900
gagttcataa acaatcctgc atgataacca tcacaaacag aatgatgtac ctgtaaagat    3960
agcggtaaat atattgaatt acctttatta atgaattttc ctgctgtaat aatgggtaga    4020
aggtaattac tattattatt gatatttaag ttaaacccag taatgaagt ccatggaata     4080 atagaaagag aaaaagcatt ttcaggtata ggtgttttgg gaaacaattt aaaagaacca    4140
ttatatttct ctacatcaga aaggtataaa tcataaaact ctttgaagtc attctttaca    4200
ggagtccaaa taccagagaa tgttttagat acaccatcaa aaattgtata aagtggctct    4260
aacttatccc aataacctaa ctctccgtcg ctattgtaac cagttctaaa agctgtatt     4320 gagtttatca cccttgtcac taagaaaata aatgcagggt aaaatttata tccttcttgt    4380
tttatgtttc ggtataaaac actaatatca atttctgtgg ttatactaaa agtcgtttgt    4440
tggttcaaat aatgattaaa tatctctttt ctcttccaat tgtctaaatc aattttatta    4500
aagttcattt gatatgcctc ctaaattttt atctaaagtg aatttaggag gcttacttgt    4560
```

```
ctgctttctt cattagaatc aatccttttt taaagtcaat attactgtaa cataaatata    4620
tattttaaaa atatcccact ttatccaatt ttcgtttgtt gaactaatgg gtgctttagt    4680
tgaagaataa agaccacatt aaaaaatgtg gtcttttgtg ttttttttaaa ggatttgagc   4740
gtacgcgaaa atccttttc tttctttctt atcttgataa taagggtaac tattgccggt    4800
tgtccattca tggctgaact ctgcttcctc tgttgacatg acacacatca tctcaatatc    4860
cgaatagggc ccatcagtct gacgaccaag agagccataa acaccaatag ccttaacatc    4920
atccccatat ttatccaata ttcgttcctt aatttcatga acaatcttca ttctttcttc    4980
tctagtcatt attattggtc cattcactat tctcattccc ttttcagata attttagatt    5040
tgcttttcta ataagaata tttggagagc accgttctta ttcagctatt aataactcgt    5100
cttcctaagc atccttcaat cctttaata acaattatag catctaatct tcaacaaact    5160
ggcccgtttg ttgaactact ctttaataaa ataattttc cgttcccaat tccacattgc    5220
aataatagaa atccatctt catcggcttt ttcgtcatca tctgtatgaa tcaaatcgcc    5280
ttcttctgtg tcatcaaggt ttaattttt atgtatttct tttaacaaac caccatagga    5340
gattaacctt ttacggtgta aaccttcctc caaatcagaa aaacgtttca aattcttttc    5400
ttcatcatcg gtcataaaat ccgtatcctt tacaggatat tttgcagttt cgtcaattgc    5460
cgattgtata tccgatttat atttatttt cggtcgaatc atttgaactt ttacatttgg    5520
atcatagtct aatttcattg cctttttcca aaattgaatc cattgttttt gattcacgta    5580
gttttctgtt attctaaaat aagttggttc cacacatacc attacatgca tgtgctgatt    5640
ataagaatta tctttattat ttattgtcac atccgttgca cgcataaaac caacaagatt    5700
tttattaatt tttttatatt gcatcattcg gcgaaatcct tgagccatat ctgtcaaact    5760
cttatttaat tcttcgccat cataaacatt tttaactgtt aatgtgagaa acaaccaacg    5820
aactgttggc ttttgtttaa taacttcagc aacaacctttt tgtgactgaa tgccatgttt    5880
cattgctctc ctccagttgc acattggaca aagcctggat ttgcaaaacc acactcgata    5940
ccactttctt tcgcctgttt cacgattttg tttatactct aatatttcag cacaatcttt    6000
tactctttca gccttttaa attcaagaat atgcagaagt tcaaagtaat caacattagc     6060
gattttcttt tctctccatg gtctcacttt tccactttttt gtcttgtcca ctaaaaccct    6120
tgattttca tctgaataaa tgctactatt aggacacata atattaaaag aaacccccat     6180
ctatttagtt atttgtttag tcacttataa ctttaacaga tggggttttt ctgtgcaacc    6240
aatttaagg gttttcaata ctttaaaaca catacatacc aacacttcaa cgcaccttc     6300
agcaactaaa ataaaatga cgttattct atatgtatca agataagaaa gaacaagttc     6360
aaaaccatca aaaaagaca ccttttcagg tgcttttttt attttataaa ctcattccct     6420
gatctcgact tcgttctttt tttacctctc ggttatgagt tagttcaaat tcgttctttt    6480
taggttctaa atcgtgtttt tcttggaatt gtgctgtttt atcctttacc ttgtctacaa    6540
acccctaaaa aacgtttta aaggctttta agccgtctgt acgttcctta ag             6592
```

```
<210> SEQ ID NO 58
<211> LENGTH: 31
<212> TYPE: DNA
<213> ORGANISM: Artificial Sequence
<220> FEATURE:
<223> OTHER INFORMATION: Synthetic Construct

<400> SEQUENCE: 58
gacatcaatt gctccatttt cttctgctat c                                    31
```

<210> SEQ ID NO 59
<211> LENGTH: 41
<212> TYPE: DNA
<213> ORGANISM: Artificial Sequence
<220> FEATURE:
<223> OTHER INFORMATION: Synthetic Construct

<400> SEQUENCE: 59
attgagaaga ggtcgcacac actctttacc ctctcctttt a     41

<210> SEQ ID NO 60
<211> LENGTH: 41
<212> TYPE: DNA
<213> ORGANISM: Artificial Sequence
<220> FEATURE:
<223> OTHER INFORMATION: Synthetic Construct

<400> SEQUENCE: 60
taaaaggaga gggtaaagag tgtgtgcgac ctcttctcaa t     41

<210> SEQ ID NO 61
<211> LENGTH: 41
<212> TYPE: DNA
<213> ORGANISM: Artificial Sequence
<220> FEATURE:
<223> OTHER INFORMATION: Synthetic Construct

<400> SEQUENCE: 61
ccaaggccgg ttttttttag acatacatca gctggttaat c     41

<210> SEQ ID NO 62
<211> LENGTH: 41
<212> TYPE: DNA
<213> ORGANISM: Artificial Sequence
<220> FEATURE:
<223> OTHER INFORMATION: Synthetic Construct

<400> SEQUENCE: 62
gattaaccag ctgatgtatg tctaaaaaaa accggccttg g     41

<210> SEQ ID NO 63
<211> LENGTH: 32
<212> TYPE: DNA
<213> ORGANISM: Artificial Sequence
<220> FEATURE:
<223> OTHER INFORMATION: Synthetic Construct

<400> SEQUENCE: 63
gacatgacgg atccgattac gaatgccgtc tc     32

<210> SEQ ID NO 64
<211> LENGTH: 31
<212> TYPE: DNA
<213> ORGANISM: Artificial Sequence
<220> FEATURE:
<223> OTHER INFORMATION: Synthetic Construct

<400> SEQUENCE: 64
gacatcaatt gctccatttt cttctgctat c     31

<210> SEQ ID NO 65
<211> LENGTH: 27
<212> TYPE: DNA
<213> ORGANISM: Artificial Sequence
<220> FEATURE:
<223> OTHER INFORMATION: Synthetic Construct

<400> SEQUENCE: 65
gacatgaatt cctccatttt cttctgc                                    27

<210> SEQ ID NO 66
<211> LENGTH: 20
<212> TYPE: DNA
<213> ORGANISM: Artificial Sequence
<220> FEATURE:
<223> OTHER INFORMATION: Synthetic Construct

<400> SEQUENCE: 66
aggagagggt aaagagtgag                                            20

<210> SEQ ID NO 67
<211> LENGTH: 22
<212> TYPE: DNA
<213> ORGANISM: Artificial Sequence
<220> FEATURE:
<223> OTHER INFORMATION: Synthetic Construct

<400> SEQUENCE: 67
cttttccatc acccacctga ag                                         22

<210> SEQ ID NO 68
<211> LENGTH: 28
<212> TYPE: DNA
<213> ORGANISM: Artificial Sequence
<220> FEATURE:
<223> OTHER INFORMATION: Synthetic Construct

<400> SEQUENCE: 68
ggcgaaatgg tccaacaaca aaattatc                                   28

<210> SEQ ID NO 69
<211> LENGTH: 51
<212> TYPE: DNA
<213> ORGANISM: Artificial Sequence
<220> FEATURE:
<223> OTHER INFORMATION: Synthetic Construct

<400> SEQUENCE: 69
ggtgaattca gtctactggg gattcccaaa tctatatata ctgcaggtga c          51

<210> SEQ ID NO 70
<211> LENGTH: 23
<212> TYPE: DNA
<213> ORGANISM: Artificial Sequence
<220> FEATURE:
<223> OTHER INFORMATION: Synthetic Construct

<400> SEQUENCE: 70
gcaggtggga aactatgcac tcc                                        23

<210> SEQ ID NO 71
<211> LENGTH: 36
<212> TYPE: DNA
<213> ORGANISM: Artificial Sequence
<220> FEATURE:
<223> OTHER INFORMATION: Synthetic Construct

<400> SEQUENCE: 71
cctgaattct gttggattgg aggattggat agtggg                          36

<210> SEQ ID NO 72
<211> LENGTH: 30

```
<212> TYPE: DNA
<213> ORGANISM: Artificial Sequence
<220> FEATURE:
<223> OTHER INFORMATION: Synthetic Construct

<400> SEQUENCE: 72
ggtgtcgacg tacggtcgag cttattgacc                                      30

<210> SEQ ID NO 73
<211> LENGTH: 32
<212> TYPE: DNA
<213> ORGANISM: Artificial Sequence
<220> FEATURE:
<223> OTHER INFORMATION: Synthetic Construct

<400> SEQUENCE: 73
ggtgggcccg cattttgcca cctacaagcc ag                                   32

<210> SEQ ID NO 74
<211> LENGTH: 40
<212> TYPE: DNA
<213> ORGANISM: Artificial Sequence
<220> FEATURE:
<223> OTHER INFORMATION: Synthetic Construct

<400> SEQUENCE: 74
ggtgaattct agaggatccc aacgctgttg cctacaacgg                           40

<210> SEQ ID NO 75
<211> LENGTH: 36
<212> TYPE: DNA
<213> ORGANISM: Artificial Sequence
<220> FEATURE:
<223> OTHER INFORMATION: Synthetic Construct

<400> SEQUENCE: 75
ggtgcggccg ctgtctggac ctggtgagtt tccccg                               36

<210> SEQ ID NO 76
<211> LENGTH: 37
<212> TYPE: DNA
<213> ORGANISM: Artificial Sequence
<220> FEATURE:
<223> OTHER INFORMATION: Synthetic Construct

<400> SEQUENCE: 76
ggtgggccca ttaaatcagt tatcgtttat ttgatag                              37

<210> SEQ ID NO 77
<211> LENGTH: 35
<212> TYPE: DNA
<213> ORGANISM: Artificial Sequence
<220> FEATURE:
<223> OTHER INFORMATION: Synthetic Construct

<400> SEQUENCE: 77
ggtgaccagc aagtccatgg gtggtttgat catgg                                35

<210> SEQ ID NO 78
<211> LENGTH: 35
<212> TYPE: DNA
<213> ORGANISM: Artificial Sequence
<220> FEATURE:
<223> OTHER INFORMATION: Synthetic Construct

<400> SEQUENCE: 78
ggtgcggccg cctttggagt acgactccaa ctatg                                35
```

<210> SEQ ID NO 79
<211> LENGTH: 31
<212> TYPE: DNA
<213> ORGANISM: Artificial Sequence
<220> FEATURE:
<223> OTHER INFORMATION: Synthetic Construct

<400> SEQUENCE: 79
gcggccgcag actaaattta tttcagtctc c                            31

<210> SEQ ID NO 80
<211> LENGTH: 7
<212> TYPE: DNA
<213> ORGANISM: Artificial Sequence
<220> FEATURE:
<223> OTHER INFORMATION: Synthetic Construct

<400> SEQUENCE: 80 aggaggt                                                        7

<210> SEQ ID NO 81
<211> LENGTH: 7
<212> TYPE: DNA
<213> ORGANISM: Artificial Sequence
<220> FEATURE:
<223> OTHER INFORMATION: Synthetic Construct

<400> SEQUENCE: 81 aaggagg                                                        7

<210> SEQ ID NO 82
<211> LENGTH: 27
<212> TYPE: DNA
<213> ORGANISM: Artificial Sequence
<220> FEATURE:
<223> OTHER INFORMATION: Synthetic Construct

<400> SEQUENCE: 82
gacatctgca gctccatttt cttctgc                                 27

<210> SEQ ID NO 83
<211> LENGTH: 42
<212> TYPE: DNA
<213> ORGANISM: Artificial Sequence
<220> FEATURE:
<223> OTHER INFORMATION: Synthetic Construct

<400> SEQUENCE: 83
caataataac tactgttttc actctttacc ctctcctttt aa                42

<210> SEQ ID NO 84
<211> LENGTH: 42
<212> TYPE: DNA
<213> ORGANISM: Artificial Sequence
<220> FEATURE:
<223> OTHER INFORMATION: Synthetic Construct

<400> SEQUENCE: 84
ttaaaaggag agggtaaaga gtgaaaacag tagttattat tg                42

<210> SEQ ID NO 85
<211> LENGTH: 45
<212> TYPE: DNA
<213> ORGANISM: Artificial Sequence
<220> FEATURE:
<223> OTHER INFORMATION: Synthetic Construct

<400> SEQUENCE: 85

```
cggggccaag gccggttttt tttagtttcg ataagaacga acggt                45
```

<210> SEQ ID NO 86
<211> LENGTH: 8000
<212> TYPE: DNA
<213> ORGANISM: Artificial Sequence
<220> FEATURE:
<223> OTHER INFORMATION: Synthetic Construct

<400> SEQUENCE: 86

```
gtttgacagc ttatcatcga ctgcacggtg caccaatgct tctggcgtca ggcagccatc      60
ggaagctgtg gtatggctgt gcaggtcgta atcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatggatcc     420
gagctcagga ggtaaaaaaa catgaaaaca gtagttatta ttgatgcatt acgaacacca     480
attggaaaat ataaaggcag cttaagtcaa gtaagtgccg tagacttagg aacacatgtt     540
acaacacaac ttttaaaaag acattccact atttctgaag aaattgatca agtaatcttt     600
ggaaatgttt tacaagctgg aaatggccaa atcccgcac gacaaatagc aataaacagc     660
ggtttgtctc atgaaattcc cgcaatgacg gttaatgagg tctgcggatc aggaatgaag     720
gccgttattt tggcgaaaca attgattcaa ttaggagaag cggaagtttt aattgctggc     780
gggattgaga atatgtccca agcacctaaa ttacaacgtt ttaattacga aacagaaagc     840
tacgatgcgc cttttttctag tatgatgtat gatggattaa cggatgcctt tagtggtcag     900
gcaatgggct taactgctga aaatgtggcc gaaaagtatc atgtaactag agaagagcaa     960
gatcaatttt ctgtacattc acaattaaaa gcagctcaag cacaagcaga agggatattc    1020
gctgacgaaa tagccccatt agaagtatca ggaacgcttg tggagaaaga tgaagggatt    1080
cgccctaatt cgagcgttga gaagctagga acgcttaaaa cagttttttaa agaagacggt    1140
actgtaacag cagggaatgc atcaaccatt aatgatgggg cttctgcttt gattattgct    1200
tcacaagaat atgccgaagc acacggtctt ccttatttag ctattattcg agacagtgtg    1260
gaagtcggta ttgatccagc ctatatggga atttcgccga ttaaagccat tcaaaaactg    1320
ttagcgcgca atcaacttac tacggaagaa attgatctgt atgaaatcaa cgaagcattt    1380
gcagcaactt caatcgtggt ccaaagagaa ctggctttac agaggaaaaa ggtcaacatt    1440
tatggtggcg gtatttcatt aggtcatgcg attggtgcca caggtgctcg tttattaacg    1500
agtttaagtt atcaattaaa tcaaaaagaa aagaaatatg gagtggcttc tttatgtatc    1560
ggcggtggct taggactcgc tatgctacta gagagacctc agcaaaaaaa aaacagccga    1620
ttttatcaaa tgagtcctga ggaacgcctg gcttctcttc ttaatgaagg ccagatttct    1680
gctgatacaa aaaagaatt tgaaaatacg gctttatctt cgcagattgc caatcatatg    1740
attgaaaatc aaatcagtga aacagaagtg ccgatgggcg ttggcttaca tttaacagtg    1800
gacgaaactg attatttggt accaatggcg acagaagagc cctcagttat tgcggctttg    1860
agtaatggtg caaaaatagc acaaggattt aaaacagtga atcaacaacg cttaatgcgt    1920
ggacaaatcg ttttttacga tgttgcagat cccgagtcat tgattgataa actacaagta    1980
```

```
agagaagcgg aagtttttca acaagcagag ttaagttatc catctatcgt taaacggggc   2040
ggcggcttaa gagatttgca atatcgtact tttgatgaat catttgtatc tgtcgacttt   2100
ttagtagatg ttaaggatgc aatgggggca aatatcgtta acgctatgtt ggaaggtgtg   2160
gccgagttgt tccgtgaatg gtttgcggag caaaagattt tattcagtat tttaagtaat   2220
tatgccacgg agtcggttgt tacgatgaaa acggctattc cagtttcacg tttaagtaag   2280
gggagcaatg gccgggaaat tgctgaaaaa attgttttag cttcacgcta tgcttcatta   2340
gatccttatc gggcagtcac gcataacaaa ggaatcatga atggcattga agctgtagtt   2400
ttagctacag gaaatgatac acgcgctgtt agcgcttctt gtcatgcttt tgcggtgaag   2460
gaaggtcgct accaaggctt gactagttgg acgctggatg gcgaacaact aattggtgaa   2520
atttcagttc cgcttgcttt agccacggtt ggcggtgcca caaaagtctt acctaaatct   2580
caagcagctg ctgatttgtt agcagtgacg gatgcaaaag aactaagtcg agtagtagcg   2640
gctgttggtt tggcacaaaa tttagcggcg ttacgggcct tagtctctga aggaattcaa   2700
aaaggacaca tggctctaca agcacgttct ttagcgatga cggtcggagc tactggtaaa   2760
gaagttgagg cagtcgctca acaattaaaa cgtcaaaaaa cgatgaacca agaccgagcc   2820
atggctattt taaatgattt aagaaaacaa taaggaggt aaaaaaacat gacaattggg   2880
attgataaaa ttagtttttt tgtgcccccct tattatattg atatgacggc actggctgaa   2940
gccagaaatg tagaccctgg aaaatttcat attggtattg ggcaagacca aatggcggtg   3000
aacccaatca gccaagatat tgtgacattt gcagccaatg ccgcagaagc gatcttgacc   3060
aaagaagata agaggccat tgatatggtg attgtcggga ctgagtccag tatcgatgag   3120
tcaaaagcgg ccgcagttgt cttacatcgt ttaatgggaa ttcaacccttt cgctcgctct   3180 ttcgaaatca aggaagcttg ttacggagca acagcaggct tacagttagc taagaatcac   3240
gtagccttac atccagataa aaaagtcttg gtcgtagcgg cagatattgc aaaatatggc   3300
ttaaattctg gcggtgagcc tacacaagga gctggggcgg ttgcaatgtt agttgctagt   3360
gaaccgcgca ttttggcttt aaaagaggat aatgtgatgc tgacgcaaga tatctatgac   3420
ttttggcgtc aacaggcca cccgtatcct atggtcgatg gtccttttgtc aaacgaaacc   3480 tacatccaat cttttgccca agtctgggat gaacataaaa aacgaaccgg tcttgatttt   3540
gcagattatg atgctttagc gttccatatt ccttacacaa aaatgggcaa aaaagcctta   3600
ttagcaaaaa tctccgacca aactgaagca gaacaggaac gaattttagc ccgttatgaa   3660
gaaagtatcg tctatagtcg tcgcgtagga aacttgtata cgggttcact ttatctggga   3720
ctcatttccc ttttagaaaa tgcaacgact ttaaccgcag gcaatcaaat tggtttattc   3780
agttatggtt ctggtgctgt cgctgaattt ttcactggtg aattagtagc tggttatcaa   3840
aatcatttac aaaagaaac tcatttagca ctgctggata tcggacaga actttctatc   3900 gctgaatatg aagccatgtt tgcagaaact ttagacacag acattgatca aacgttagaa   3960
gatgaattaa aatatagtat ttctgctatt aataataccg ttcgttctta tcgaaactaa   4020
gagatctgca gctggtacca tatgggaatt cgaagcttgg gcccgaacaa aaactcatct   4080
cagaagagga tctgaatagc gccgtcgacc atcatcatca tcatcattga gtttaaacgg   4140
tctccagctt ggctgttttg gcggatgaga agattttc agcctgatac agattaaatc   4200
agaacgcaga gcggtctga taaaacagaa tttgcctggc ggcagtagcg cggtggtccc   4260
acctgacccc atgccgaact cagaagtgaa acgccgtagc gccgatggta gtgtggggtc   4320
tccccatgcg agagtaggga actgccaggc atcaaataaa acgaaaggct cagtcgaaag   4380
```

```
actgggcctt tcgttttatc tgttgtttgt cggtgaacgc tctcctgagt aggacaaatc    4440
cgccgggagc ggatttgaac gttgcgaagc aacggcccgg agggtggcgg gcaggacgcc    4500
cgccataaac tgccaggcat caaattaagc agaaggccat cctgacggat ggcctttttg    4560
cgtttctaca aactcttttt gtttatttt ctaaatacat tcaaatatgt atccgctcat     4620
gagacaataa ccctgataaa tgcttcaata atattgaaaa aggaagagta tgagtattca    4680
acatttccgt gtcgccctta ttccctttt tgcggcattt tgccttcctg tttttgctca    4740
cccagaaacg ctggtgaaag taaaagatgc tgaagatcag ttgggtgcac gagtgggtta    4800
catcgaactg gatctcaaca gcggtaagat ccttgagagt tttcgccccg aagaacgttt    4860
tccaatgatg agcactttta aagttctgct atgtggcgcg gtattatccc gtgttgacgc    4920
cgggcaagag caactcggtc gccgcataca ctattctcag aatgacttgg ttgagtactc    4980
accagtcaca gaaaagcatc ttacggatgg catgacagta agagaattat gcagtgctgc    5040
cataaccatg agtgataaca ctgcggccaa cttacttctg acaacgatcg gaggaccgaa    5100
ggagctaacc gcttttttgc acaacatggg ggatcatgta actcgccttg atcgttggga    5160
accggagctg aatgaagcca taccaaacga cgagcgtgac accacgatgc ctgtagcaat    5220
ggcaacaacg ttgcgcaaac tattaactgg cgaactactt actctagctt cccggcaaca    5280
attaatagac tggatggagg cggataaagt tgcaggacca cttctgcgct cggcccttcc    5340
ggctggctgg tttattgctg ataaatctgg agccggtgag cgtgggtctc gcggtatcat    5400
tgcagcactg gggccagatg gtaagccctc ccgtatcgta gttatctaca cgacggggag    5460
tcaggcaact atgatgaac gaaatagaca gatcgctgag ataggtgcct cactgattaa    5520
gcattggtaa ctgtcagacc aagtttactc atatatactt tagattgatt taaaacttca    5580
tttttaattt aaaaggatct aggtgaagat cctttttgat aatctcatga ccaaaatccc    5640
ttaacgtgag ttttcgttcc actgagcgtc agaccccgta gaaaagatca aaggatcttc    5700
ttgagatcct ttttttctgc gcgtaatctg ctgcttgcaa acaaaaaaac caccgctacc    5760
agcggtggtt tgtttgccgg atcaagagct accaactctt tttccgaagg taactggctt    5820
cagcagagcg cagataccaa atactgtcct tctagtgtag ccgtagttag gccaccactt    5880
caagaactct gtagcaccgc ctacatacct cgctctgcta atcctgttac cagtggctgc    5940
tgccagtggc gataagtcgt gtcttaccgg gttggactca agacgatagt taccggataa    6000
ggcgcagcgg tcgggctgaa cggggggttc gtgcacacag cccagcttgg agcgaacgac    6060
ctacaccgaa ctgagatacc tacagcgtga gctatgagaa agcgccacgc ttcccgaagg    6120
gagaaaggcg gacaggtatc cggtaagcgg cagggtcgga acaggagagc gcacgaggga    6180
gcttccaggg ggaaacgcct ggtatcttta tagtcctgtc gggtttcgcc acctctgact    6240
tgagcgtcga tttttgtgat gctcgtcagg gggcggagc ctatggaaaa acgccagcaa    6300
cgcggccttt ttacggttcc tggccttttg ctggccttt gctcacatgt tctttcctgc    6360
gttatcccct gattctgtgg ataaccgtat taccgccttt gagtgagctg ataccgctcg    6420
ccgcagccga acgaccgagc gcagcgagtc agtgagcgag gaagcggaag agcgcctgat    6480
gcggtatttt ctccttacgc atctgtgcgg tatttcacac cgcatatggt gcactctcag    6540
tacaatctgc tctgatgccg catagttaag ccagtataca ctccgctatc gctacgtgac    6600
tgggtcatgg ctgcgccccg acacccgcca acacccgctg acgcgccctg acgggcttgt    6660
ctgctcccgg catccgctta cagacaagct gtgaccgtct ccgggagctg catgtgtcag    6720
aggttttcac cgtcatcacc gaaacgcgcg aggcagcaga tcaattcgcg cgcgaaggcg    6780
```

```
aagcggcatg catttacgtt gacaccatcg aatggtgcaa aacctttcgc ggtatggcat    6840
gatagcgccc ggaagagagt caattcaggg tggtgaatgt gaaaccagta acgttatacg    6900
atgtcgcaga gtatgccggt gtctcttatc agaccgtttc ccgcgtggtg aaccaggcca    6960
gccacgtttc tgcgaaaacg cgggaaaaag tggaagcggc gatggcggag ctgaattaca    7020
ttcccaaccg cgtggcacaa caactggcgg gcaaacagtc gttgctgatt ggcgttgcca    7080
cctccagtct ggccctgcac gcgccgtcgc aaattgtcgc ggcgattaaa tctcgcgccg    7140
atcaactggg tgccagcgtg gtggtgtcga tggtagaacg aagcggcgtc gaagcctgta    7200
aagcggcggt gcacaatctt ctcgcgcaac gcgtcagtgg gctgatcatt aactatccgc    7260
tggatgacca ggatgccatt gctgtggaag ctgcctgcac taatgttccg gcgttatttc    7320
ttgatgtctc tgaccagaca cccatcaaca gtattatttt ctcccatgaa gacggtacgc    7380
gactgggcgt ggagcatctg gtcgcattgg gtcaccagca aatcgcgctg ttagcgggcc    7440
cattaagttc tgtctcggcg cgtctgcgtc tggctggctg gcataaatat ctcactcgca    7500
atcaaattca gccgatagcg gaacgggaag gcgactggag tgccatgtcc ggttttcaac    7560
aaaccatgca aatgctgaat gagggcatcg ttcccactgc gatgctggtt gccaacgatc    7620
agatggcgct gggcgcaatg cgcgccatta ccagtccgg gctgcgcgtt ggtgcggata    7680
tctcggtagt gggatacgac gataccgaag acagctcatg ttatatcccg ccgtcaacca    7740
ccatcaaaca ggattttcgc ctgctggggc aaaccagcgt ggaccgcttg ctgcaactct    7800
ctcagggcca ggcggtgaag ggcaatcagc tgttgcccgt ctcactggtg aaaagaaaaa    7860
ccaccctggc gcccaatacg caaaccgcct ctccccgcgc gttggccgat tcattaatgc    7920
agctggcacg acaggtttcc cgactggaaa gcgggcagtg agcgcaacgc aattaatgtg    7980
agttagcgcg aattgatctg                                                8000

<210> SEQ ID NO 87
<211> LENGTH: 10433
<212> TYPE: DNA
<213> ORGANISM: Artificial Sequence
<220> FEATURE:
<223> OTHER INFORMATION: Synthetic Construct

<400> SEQUENCE: 87
cccgtcttac tgtcgggaat tcgcgttggc cgattcatta atgcagattc tgaaatgagc      60
tgttgacaat taatcatccg gctcgtataa tgtgtggaat tgtgagcgga taacaatttc     120
acacaggaaa cagcgccgct gagaaaaagc gaagcggcac tgctctttaa caatttatca     180
gacaatctgt gtgggcactc gaccggaatt atcgattaac tttattatta aaaattaaag     240
aggtatatat taatgtatcg attaaataag gaggaataaa ccatggatcc gagctcagga     300
ggtaaaaaaa catgaaaaca gtagttatta ttgatgcatt acgaacacca attggaaaat     360
ataaaggcag cttaagtcaa gtaagtgccg tagacttagg aacacatgtt acaacacaac     420
ttttaaaaag acattccact atttctgaag aaattgatca gtaatctttt ggaaatgttt     480
tacaagctgg aaatggccaa aatcccgcac gacaaatagc aataaacagc ggtttgtctc     540
atgaaattcc cgcaatgacg gttaatgagg tctgcggatc aggaatgaag gccgttatt     600 tggcgaaaca attgattcaa ttaggagaag cggaagtttt aattgctggc gggattgaga     660
atatgtccca agcacctaaa ttacaacgtt ttaattacga aacagaaagc tacgatgcgc     720
cttttttcta gtatgatgta tgatggattaa cggatgcctt tagtggtcag gcaatgggct     780
taactgctga aaatgtggcc gaaaagtatc atgtaactag agaagagcaa gatcaatttt     840
```

```
ctgtacattc acaattaaaa gcagctcaag cacaagcaga agggatattc gctgacgaaa   900
tagcccccatt agaagtatca ggaacgcttg tggagaaaga tgaagggatt cgccctaatt   960
cgagcgttga gaagctagga acgcttaaaa cagtttttaa agaagacggt actgtaacag  1020
cagggaatgc atcaaccatt aatgatgggg cttctgcttt gattattgct tcacaagaat  1080
atgccgaagc acacggtctt ccttatttag ctattattcg agacagtgtg gaagtcggta  1140
ttgatccagc ctatatggga atttcgccga ttaaagccat tcaaaaactg ttagcgcgca  1200
atcaacttac tacggaagaa attgatctgt atgaaatcaa cgaagcattt gcagcaactt  1260
caatcgtggt ccaaagagaa ctggctttac cagaggaaaa ggtcaacatt tatggtggcg  1320
gtatttcatt aggtcatgcg attggtgcca caggtgctcg tttattaacg agtttaagtt  1380
atcaattaaa tcaaaagaa aagaaatatg gagtggcttc tttatgtatc ggcggtggct  1440
taggactcgc tatgctacta gagagacctc agcaaaaaaa aaacagccga ttttatcaaa  1500
tgagtcctga ggaacgcctg gcttctcttc ttaatgaagg ccagatttct gctgatacaa  1560
aaaaagaatt tgaaaatacg gctttatctt cgcagattgc caatcatatg attgaaaatc  1620
aaaatcagtga aacagaagtg ccgatgggcg ttggcttaca tttaacagtg gacgaaactg  1680
attatttggt accaatggcg acagaagagc cctcagttat tgcggctttg agtaatggtg  1740
caaaaatagc acaaggattt aaaacagtga atcaacaacg cttaatgcgt ggacaaatcg  1800
ttttttacga tgttgcagat cccgagtcat tgattgataa actacaagta agagaagcgg  1860
aagttttttca acaagcagag ttaagttatc catctatcgt taaacggggc ggcggcttaa  1920
gagatttgca atatcgtact tttgatgaat catttgtatc tgtcgacttt ttagtagatg  1980
ttaaggatgc aatgggggca aatatcgtta acgctatgtt ggaaggtgtg gccgagttgt  2040
tccgtgaatg gttttgcggag caaaagattt tattcagtat tttaagtaat tatgccacgg  2100
agtcggttgt tacgatgaaa acggctattc cagtttcacg tttaagtaag gggagcaatg  2160
gccgggaaat tgctgaaaaa attgttttag cttcacgcta tgcttcatta gatccttatc  2220
gggcagtcac gcataacaaa ggaatcatga atggcattga agctgtagtt ttagctacag  2280
gaaatgatac acgcgctgtt agcgcttctt gtcatgcttt tgcggtgaag aaggtcgct   2340
accaaggctt gactagttgg acgctggatg gcgaacaact aattggtgaa atttcagttc  2400
cgcttgcttt agccacggtt ggcggtgcca caaagtctt acctaaatct caagcagctg  2460
ctgatttgtt agcagtgacg gatgcaaaag aactaagtcg agtagtagcg gctgttggtt  2520
tggcacaaaa tttagcggcg ttacgggcct tagtctctga aggaattcaa aaaggacaca  2580
tggctctaca agcacgttct ttagcgatga cggtcggagc tactggtaaa gaagttgagg  2640
cagtcgctca acaattaaaa cgtcaaaaaa cgatgaacca agaccgagcc atggctattt  2700
taaatgattt aagaaaacaa taaggaggt aaaaaaacat gacaattggg attgataaaa  2760
ttagtttttt tgtgcccccct tattatattg atatgacggc actggctgaa gccagaaatg  2820
tagaccctgg aaaatttcat attggtattg ggcaagacca atggcggtg aacccaatca  2880
gccaagatat tgtgacattt gcagccaatg ccgcagaagc gatcttgacc aaagaagata  2940
aagaggccat tgatatggtg attgtcggga ctgagtccag tatcgatgag tcaaaagcgg  3000
ccgcagttgt cttacatcgt ttaatgggga ttcaacctt cgctcgctct ttcgaaatca  3060
aggaagcttg ttacggagca acagcaggct tacagttagc taagaatcac gtagccttac  3120
atccagataa aaaagtcttg gtcgtagcgg cagatattgc aaaatatggc ttaaattctg  3180
gcggtgagcc tacacaagga gctggggcgg ttgcaatgtt agttgctagt gaaccgcgca  3240
```

```
ttttggcttt aaaagaggat aatgtgatgc tgacgcaaga tatctatgac tttttggcgtc   3300
caacaggcca cccgtatcct atggtcgatg gtcctttgtc aaacgaaacc tacatccaat   3360
cttttgccca agtctgggat gaacataaaa aacgaaccgg tcttgatttt gcagattatg   3420
atgctttagc gttccatatt ccttacacaa aaatgggcaa aaaagcctta ttagcaaaaa   3480
tctccgacca aactgaagca gaacaggaac gaattttagc ccgttatgaa gaaagtatcg   3540
tctatagtcg tcgcgtagga aacttgtata cgggttcact ttatctggga ctcatttccc   3600
ttttagaaaa tgcaacgact ttaaccgcag gcaatcaaat tggtttattc agttatggtt   3660
ctggtgctgt cgctgaattt ttcactggtg aattagtagc tggttatcaa atcatttac   3720
aaaaagaaac tcatttagca ctgctggata atcggacaga actttctatc gctgaatatg   3780
aagccatgtt tgcagaaact ttagacacag acattgatca aacgttagaa gatgaattaa   3840
aatatagtat ttctgctatt aataataccg ttcgttctta tcgaaactaa agatctgcat   3900
cctgcattcg cccttaggag gtaaaaaaac atgtgtgcga cctcttctca atttactcag   3960
attaccgagc ataattcccg tcgttccgca aactatcagc caaacctgtg gaatttcgaa   4020
ttcctgcaat ccctggagaa cgacctgaaa gtggaaaagc tggaggagaa agcgaccaaa   4080
ctggaggaag aagttcgctg catgatcaac cgtgtagaca cccagccgct gtccctgctg   4140
gagctgatcg acgatgtgca gcgcctgggt ctgacctaca aatttgaaaa agacatcatt   4200
aaagccctgg aaaacatcgt actgctggac gaaaacaaaa gaacaaatc tgacctgcac   4260
gcaaccgctc tgtctttccg tctgctgcgt cagcacggtt tcgaggtttc tcaggatgtt   4320
tttgagcgtt tcaaggataa agaaggtggt ttcagcggtg aactgaaagg tgacgtccaa   4380
ggcctgctga gcctgtatga agcgtcttac ctgggtttcg agggtgagaa cctgctggag   4440
gaggcgcgta ccttttccat cacccacctg aagaacaacc tgaaagaagg cattaatacc   4500
aaggttgcag aacaagtgag ccacgccctg gaactgccat atcaccagcg tctgcaccgt   4560
ctggaggcac gttggttcct ggataaatac gaaccgaaag aaccgcatca ccagctgctg   4620
ctggagctgg cgaagctgga ttttaacatg gtacagaccc tgcaccagaa agagctgcaa   4680
gatctgtccc gctggtggac cgagatgggc ctggctagca aactggattt tgtacgcgac   4740
cgcctgatgg aagtttattt ctgggcactg ggtatggcgc cagacccgca gtttggtgaa   4800
tgtcgcaaag ctgttactaa aatgtttggt ctggtgacga tcatcgatga cgtgtatgac   4860
gtttatggca ctctggacga actgcaactg ttcaccgatg ctgtagagcg ctgggacgtt   4920
aacgctatta acaccctgcc ggactatatg aaactgtgtt tcctggcact gtacaacacc   4980
gttaacgaca cgtcctattc tattctgaaa gagaaaggtc ataacaacct gtcctatctg   5040
acgaaaagct ggcgtgaact gtgcaaagcc tttctgcaag aggcgaaatg gtccaacaac   5100
aaaattatcc cggcttttct caagtacctg gaaaacgcca gcgtttcctc ctccggtgta   5160
gcgctgctgg cgccgtctta cttttccgta tgccagcagc aggaagacat ctccgaccac   5220
gcgctgcgtt ccctgaccga cttccatggt ctggtgcgtt ctagctgcgt tatcttccgc   5280
ctgtgcaacg atctggccac ctctgcgcg gagctggaac gtggcgagac taccaattct   5340
atcattagct acatgcacga aaacgatggt accagcgagg aacaggcccg cgaagaactg   5400
cgtaaactga tcgacgccga atggaaaaag atgaatcgtg aacgcgttag cgactccacc   5460
ctgctgccta aagcgttcat ggaaatcgca gttaacatgg cacgtgtttc ccactgcacc   5520
taccagtatg cgatggtct gggtcgccca gactacgcga ctgaaaaccg catcaaactg   5580
ctgctgattg acccctttccc gattaaccag ctgatgtatg tctaactgca gctggtacca   5640
```

```
tatgggaatt cgaagcttgg gcccgaacaa aaactcatct cagaagagga tctgaatagc   5700
gccgtcgacc atcatcatca tcatcattga gtttaaacgg tctccagctt ggctgttttg   5760
gcggatgaga gaagattttc agcctgatac agattaaatc agaacgcaga agcggtctga   5820
taaaacagaa tttgcctggc ggcagtagcg cggtggtccc acctgacccc atgccgaact   5880
cagaagtgaa acgccgtagc gccgatggta gtgtggggtc tccccatgcg agagtaggga   5940
actgccaggc atcaaataaa acgaaaggct cagtcgaaag actgggcctt tcgttttatc   6000
tgttgtttgt cggtgaacgc tctcctgagt aggacaaatc cgccgggagc ggatttgaac   6060
gttgcgaagc aacggcccgg agggtggcgg gcaggacgcc cgccataaac tgccaggcat   6120
caaattaagc agaaggccat cctgacggat ggcctttttg cgtttctaca aactctttt   6180 gtttattttt ctaaatacat tcaaatatgt atccgctcat gagacaataa ccctgataaa   6240
tgcttcaata atctggcgta atagcgaaga ggcccgcacc gatcgccctt cccaacagtt   6300
gcgcagcctg aatggcgaat ggcgcctgat gcggtatttt ctccttacgc atctgtgcgg   6360
tatttcacac cgcatatggt gcactctcag tacaatctgc tctgatgccg catagttaag   6420
ccagccccga cacccgccaa cacccgctga cgagcttagt aaagccctcg ctagatttta   6480
atgcggatgt tgcgattact tcgccaacta ttgcgataac aagaaaaagc cagcctttca   6540
tgatatatct cccaatttgt gtagggctta ttatgcacgc ttaaaaataa taaaagcaga   6600
cttgacctga tagtttggct gtgagcaatt atgtgcttag tgcatctaac gcttgagtta   6660
agccgcgccg cgaagcggcg tcggcttgaa cgaattgtta gacattattt gccgactacc   6720
ttggtgatct cgcctttcac gtagtggaca aattcttcca actgatctgc gcgcgaggcc   6780
aagcgatctt cttcttgtcc aagataagcc tgtctagctt caagtatgac gggctgatac   6840
tgggccggca ggcgctccat gcccagtcg gcagcgacat ccttcggcgc gattttgccg   6900
gttactgcgc tgtaccaaat gcgggacaac gtaagcacta catttcgctc atcgccagcc   6960
cagtcgggcg gcgagttcca tagcgttaag gtttcattta gcgcctcaaa tagatcctgt   7020
tcaggaaccg gatcaaagag ttcctccgcc gctggaccta ccaaggcaac gctatgttct   7080
cttgcttttg tcagcaagat agccagatca atgtcgatcg tggctggctc gaagatacct   7140
gcaagaatgt cattgcgctg ccattctcca aattgcagtt cgcgcttagc tggataacgc   7200
cacggaatga tgtcgtcgtg cacaacaatg gtgacttcta cagcgcggag aatctcgctc   7260
tctccagggg aagccgaagt ttccaaaagg tcgttgatca agctcgccg cgttgtttca   7320 tcaagcctta cggtcaccgt aaccagcaaa tcaatatcac tgtgtggctt caggccgcca   7380
tccactgcgg agccgtacaa atgtacggcc agcaacgtcg gttcgagatg gcgctcgatg   7440
acgccaacta cctctgatag ttgagtcgat acttcggcga tcaccgcttc cctcatgatg   7500
tttaactttg ttttagggcg actgccctgc tgcgtaacat cgttgctgct ccataacatc   7560
aaacatcgac ccacggcgta acgcgcttgc tgcttggatg cccgaggcat agactgtacc   7620
ccaaaaaaac agtcataaca agccatgaaa accgccactg cgccgttacc accgctgcgt   7680
tcggtcaagg ttctggacca gttgcgtgag cgcatacgct acttgcatta cagcttacga   7740
accgaacagg cttatgtcca ctgggttcgt gccttcatcc gtttccacgg tgtgcgtcac   7800
ccggcaacct gggcagcag cgaagtcgag gcatttctgt cctggctggc gaacgagcgc   7860
aaggtttcgg tctccacgca tcgtcaggca ttggcggcct tgctgttctt ctacggcaag   7920
gtgctgtgca cggatctgcc ctggcttcag agatcggaa gacctcggcc gtcgcggcgc   7980
ttgccggtgg tgctgacccc ggatgaagtg gttcgcatcc tcggttttct ggaaggcgag   8040
```

```
catcgtttgt tcgcccagct tctgtatgga acgggcatgc ggatcagtga gggtttgcaa    8100
ctgcgggtca aggatctgga tttcgatcac ggcacgatca tcgtgcggga gggcaagggc    8160
tccaaggatc gggccttgat gttacccgag agcttggcac ccagcctgcg cgagcagggg    8220
aattaattcc cacgggtttt gctgcccgca aacgggctgt tctggtgttg ctagtttgtt    8280
atcagaatcg cagatccggc ttcagccggt ttgccggctg aaagcgctat ttcttccaga    8340
attgccatga ttttttcccc acgggaggcg tcactggctc ccgtgttgtc ggcagctttg    8400
attcgataag cagcatcgcc tgtttcaggc tgtctatgtg tgactgttga gctgtaacaa    8460
gttgtctcag gtgttcaatt tcatgttcta gttgctttgt tttactggtt tcacctgttc    8520
tattaggtgt tacatgctgt tcatctgtta cattgtcgat ctgttcatgg tgaacagctt    8580
tgaatgcacc aaaaactcgt aaaagctctg atgtatctat cttttttaca ccgttttcat    8640
ctgtgcatat ggacagtttt ccctttgata tgtaacggtg aacagttgtt ctacttttgt    8700
ttgttagtct tgatgcttca ctgatagata caagagccat aagaacctca gatccttccg    8760
tatttagcca gtatgttctc tagtgtggtt cgttgttttt gcgtgagcca tgagaacgaa    8820
ccattgagat catacttact ttgcatgtca ctcaaaaatt ttgcctcaaa actggtgagc    8880 tgaattttg cagttaaagc atcgtgtagt gttttcttta gtccgttatg taggtaggaa    8940
tctgatgtaa tggttgttgg tattttgtca ccattcattt ttatctggtt gttctcaagt    9000
tcggttacga gatccatttg tctatctagt tcaacttgga aaatcaacgt atcagtcggg    9060
cggcctcgct tatcaaccac caatttcata ttgctgtaag tgtttaaatc tttacttatt    9120
ggtttcaaaa cccattggtt aagccttta aactcatggt agttattttc aagcattaac    9180
atgaacttaa attcatcaag gctaatctct atatttgcct tgtgagtttt cttttgtgtt    9240
agttctttta ataaccactc ataaatcctc atagagtatt tgttttcaaa agacttaaca    9300
tgttccagat tatattttat gaatttttt aactggaaaa gataaggcaa tatctcttca    9360
ctaaaaacta attctaattt ttcgcttgag aacttggcat agtttgtcca ctggaaaatc    9420
tcaaagcctt taaccaaagg attcctgatt tccacagttc tcgtcatcag ctctctggtt    9480
gctttagcta atacaccata agcatttcc ctactgatgt tcatcatctg agcgtattgg    9540
ttataagtga acgataccgt ccgttctttc cttgtagggt tttcaatcgt ggggttgagt    9600
agtgccacac agcataaaat tagcttggtt tcatgctccg ttaagtcata gcgactaatc    9660
gctagttcat ttgctttgaa aacaactaat tcagacatac atctcaattg gtctaggtga    9720
ttttaatcac tataccaatt gagatgggct agtcaatgat aattactagt ccttttcctt    9780
tgagttgtgg gtatctgtaa attctgctag acctttgctg gaaaacttgt aaattctgct    9840
agaccctctg taaattccgc tagaccttg tgtgtttttt ttgtttatat tcaagtggtt    9900
ataatttata gaataaagaa agaataaaaa aagataaaaa gaatagatcc cagccctgtg    9960
tataactcac tactttagtc agttccgcag tattacaaaa ggatgtcgca aacgctgttt   10020
gctcctctac aaaacagacc ttaaaaccct aaaggcttaa gtagcaccct cgcaagctcg   10080
ggcaaatcgc tgaatattcc ttttgtctcc gaccatcagg cacctgagtc gctgtctttt   10140
tcgtgacatt cagttcgctg cgctcacggc tctggcagtg aatgggggta aatggcacta   10200
caggcgcctt ttatggattc atgcaaggaa actacccata atacaagaaa agcccgtcac   10260
gggcttctca gggcgtttta tggcgggtct gctatgtggt gctatctgac ttttgctgt   10320 tcagcagttc ctgccctctg attttccagt ctgaccactt cggattatcc cgtgacaggt   10380
cattcagact ggctaatgca cccagtaagg cagcggtatc atcaacaggc tta          10433
```

<210> SEQ ID NO 88
<211> LENGTH: 31
<212> TYPE: DNA
<213> ORGANISM: Artificial Sequence
<220> FEATURE:
<223> OTHER INFORMATION: Synthetic Construct

<400> SEQUENCE: 88
cttgatgcat cctgcattcg cccttaggag g                           31

<210> SEQ ID NO 89
<211> LENGTH: 23
<212> TYPE: DNA
<213> ORGANISM: Artificial Sequence
<220> FEATURE:
<223> OTHER INFORMATION: Synthetic Construct

<400> SEQUENCE: 89
ccaggcaaat tctgttttat cag                                    23

<210> SEQ ID NO 90
<211> LENGTH: 10356
<212> TYPE: DNA
<213> ORGANISM: Artificial Sequence
<220> FEATURE:
<223> OTHER INFORMATION: Synthetic Construct

<400> SEQUENCE: 90
caagaaaaat gccccgctta cgcagggcat ccatttatta ctcaaccgta accgattttg    60
ccaggttacg cggctggtca acgtcggtgc ctttgatcag cgcgacatgg taagccagca   120
gctgcagcgg aacggtgtag aagatcggtg caatcacctc ttccacatgc ggcatctcga   180
tgatgtgcat gttatcgcta cttacaaaac ccgcatcctg atcggcgaag acatacaact   240
gaccgccacg cgcgcgaact tcttcaatgt tggatttcag ttttttccagc aattcgttgt   300
tcggtgcaac aacaataacc ggcatatcgg catcaattag cgccagcgga ccgtgtttca   360
gttcgccagc agcgtaggct tcagcgtgaa tgtaagagat ctctttcaac ttcaatgcgc   420
cttccagcgc gattgggtac tgatcgccac ggcccaggaa cagcgcgtga tgtttgtcag   480
agaaatcttc tgccagcgct tcaatgcgtt tgtcctgaga cagcatctgc tcaatacggc   540
tcggcagcgc ctgcagacca tgcacgatgt catgttcaat ggaggcatcc agacctttca   600
ggcgagacag cttcgccacc agcatcaaca gcacagttaa ctgagtggtg aatgctttag   660
tggatgccac gccgatttct gtacccgcgt tggtcattag cgccagatcg gattcgcgca   720
ccagagaaga acccggaacg ttacagattg ccagtgaacc aaggtaaccc agctctttcg   780
acagacgcag gccagccagg gtatccgcgg tttcgccaga ctgtgacacg atcgcccttc   840
ccaacagttg cgcagcctat acgtacggca gtttaaggtt tacacctata aaagagagag   900
ccgttatcgt ctgtttgtgg atgtacagag tgatattatt gacacgccgg ggcgacggat   960
ggtgatcccc ctggccagtg cacgtctgct gtcagataaa gtctcccgtg aactttaccc  1020
ggtggtgcat atcggggatg aaagctggcg catgatgacc accgatatgg ccagtgtgcc  1080
ggtctccgtt atcggggaag aagtggctga tctcagccac cgcgaaaatg acatcaaaaa  1140
cgccattaac ctgatgttct ggggaatata aatgtcaggc atgagattat caaaaaggat  1200
cttcacctag atcctttttca cgtagaaagc cagtccgcag aaacggtgct gaccccggat  1260
gaatgtcagc tactgggcta tctgacaagg gaaaacgca agcgcaaaga gaaagcaggt  1320
agcttgcagt gggcttacat ggcgatagct agactgggcg gttttatgga cagcaagcga  1380

```
accggaattg ccagctgggg cgccctctgg taaggttggg aagccctgca aagtaaactg   1440
gatggctttc tcgccgccaa ggatctgatg gcgcagggga tcaagctctg atcaagagac   1500
aggatgagga tcgtttcgca tgattgaaca agatggattg cacgcaggtt ctccggccgc   1560
ttgggtggag aggctattcg gctatgactg ggcacaacag acaatcggct gctctgatgc   1620
cgccgtgttc cggctgtcag cgcaggggcg cccggttctt tttgtcaaga ccgacctgtc   1680
cggtgccctg aatgaactgc aagacgaggc agcgcggcta tcgtggctgg ccacgacggg   1740
cgttccttgc gcagctgtgc tcgacgttgt cactgaagcg ggaagggact ggctgctatt   1800
gggcgaagtg ccggggcagg atctcctgtc atctcacctt gctcctgccg agaaagtatc   1860
catcatggct gatgcaatgc ggcggctgca tacgcttgat ccggctacct gcccattcga   1920
ccaccaagcg aaacatcgca tcgagcgagc acgtactcgg atggaagccg gtcttgtcga   1980
tcaggatgat ctggacgaag agcatcaggg gctcgcgcca gccgaactgt tcgccaggct   2040
caaggcgagc atgcccgacg gcgaggatct cgtcgtgacc catggcgatg cctgcttgcc   2100
gaatatcatg gtggaaaatg gccgcttttc tggattcatc gactgtggcc ggctgggtgt   2160
ggcggaccgc tatcaggaca tagcgttggc tacccgtgat attgctgaag agcttggcgg   2220
cgaatgggct gaccgcttcc tcgtgcttta cggtatcgcc gctcccgatt cgcagcgcat   2280
cgccttctat cgccttcttg acgagttctt ctgaattatt aacgcttaca atttcctgat   2340
gcggtatttt ctccttacgc atctgtgcgg tatttcacac cgcatacagg tggacttttt   2400
cggggaaatg tgcgcggaac ccctatttgt ttatttttct aaatacattc aaatatgtat   2460
ccgctcatga caataaacc ctgataaatg cttcaataat agcacgtgag gagggccacc   2520
atggccaagt tgaccagtgc cgttccggtg ctcaccgcgc gcgacgtcgc cggagcggtc   2580
gagttctgga ccgaccggct cgggttctcc cctagtaacg gccgccagtg tgctggaatt   2640
caggcagttc aacctgttga tagtacgtac taagctctca tgtttcacgt actaagctct   2700
catgtttaac gtactaagct ctcatgttta cgaactaaa ccctcatggc taacgtacta   2760
agctctcatg gctaacgtac taagctctca tgtttcacgt actaagctct catgtttgaa   2820
caataaaatt aatataaatc agcaacttaa atagcctcta aggttttaag ttttataaga   2880
aaaaaagaa tatataaggc ttttaaagct tttaaggttt aacggttgtg acaacaagc    2940
cagggatgta acgcactgag aagcccttag agcctctcaa agcaattttc agtgacacag   3000
gaacacttaa cggctgacag cctgaattct gcagatatct gttttccac tcttcgttca    3060
ctttcgccag gtagctggtg aagacgaagg aagtcccgga gccatctgcg cggcgtacta   3120
cagcaatgtt ttgtgaaggc agtttcagac ccggattcag tttggcgatg gcttcatcat   3180
cccacttctt gattttgccc aggtagatgt cgccgagggt tttaccatcc agcaccagtt   3240
cgccagactt cagccctgga atgttaaccg ccagcaccac gccgcaatc acggtcggga    3300
actgaacag accttcctga gccagttttt cgtcagacag cggcgcgtca gaggcaccaa    3360
aatcaacggt attagcgata atctgtttta cgccaccgga gaaccgata ccctggtagt    3420
taactttatt accggtttct ttctggtaag tgtcagccca tttggcatac accggcgcag   3480
ggaaggttgc acctgcacct gtcaggcttg cttctgcaaa cacagagaaa gcactcatcg   3540
ataaggtcgc ggcgacaaca gttgcgacgg tggtacgcat aactttcata atgtctcctg   3600
ggaggattca taaagcattg tttgttggct acgagaagca aaataggaca aacaggtgac   3660
agttatatgt aaggaatatg acagttttat gacagagaga taaagtcttc agtctgatttt  3720
aaataagcgt tgatattcag tcaattacaa acattaataa cgaagagatg acagaaaaat   3780
```

-continued

```
tttcattctg tgacagagaa aaagtagccg aagatgacgg tttgtcacat ggagttggca   3840
ggatgtttga ttaaaagcaa ttaaccctca ctaaagggcg gccgcgaagt tcctattctc   3900
tagaaagtat aggaacttca ttctaccggg taggggaggc gcttttccca aggcagtctg   3960
gagcatgcgc tttagcagcc ccgctgggca cttggcgcta cacaagtggc ctctggcctc   4020
gcacacattc cacatccacc ggtaggcgcc aaccggctcc gttctttggt ggcccctccg   4080
cgccaccttc cactcctccc ctagtcagga agttcccccc cgccccgcag ctcgcgtcgt   4140
gcaggacgtg acaaatggaa gtagcacgtc tcactagtct cgtgcagatg gacagcaccg   4200
ctgagcaatg gaagcgggta ggcctttggg gcagcggcca atagcagctt tgctccttcg   4260
ctttctgggc tcagaggctg ggaaggggtg ggtccggggg cgggctcagg ggcgggctca   4320
ggggcggggc gggcgcccga aggtcctccg gaggcccggc attctgcacg cttcaaaagc   4380
gcacgtctgc cgcgctgttc tcctcttcct catctccggg cctttcgacc tgcagcagca   4440
cgtgttgaca attaatcatc ggcatagtat atcggcatag tataatacga caaggtgagg   4500
aactaaaccca tggagaaaaa aatcactgga tataccaccg ttgatatatc ccaatggcat   4560
cgtaaagaac attttgaggc atttcagtca gttgctcaat gtacctataa ccagaccgtt   4620
cagctggata ttacggcctt tttaaagacc gtaaagaaaa ataagcacaa gttttatccg   4680
gcctttattc acattcttgc ccgcctgatg aatgctcatc cggaattccg tatggcaatg   4740
aaagacggtg agctggtgat atgggatagt gttcacccct gttacaccgt tttccatgag   4800
caaactgaaa cgttttcatc gctctggagt gaataccacg acgatttccg gcagtttcta   4860
cacatatatt cgcaagatgt ggcgtgttac ggtgaaaacc tggcctattt ccctaaaggg   4920
tttattgaga atatgttttt cgtctcagcc aatccctggg tgagtttcac cagttttgat   4980
ttaaacgtgg ccaatatgga aacttcttc gcccccgttt tcaccatggg caaatattat   5040
acgcaaggcg acaaggtgct gatgccgctg gcgattcagg ttcatcatgc cgtttgtgat   5100
ggcttccatg tcggcagaat gcttaatgaa ttacaacagt actgcgatga gtggcagggc   5160
ggggcgtaag cgggactctg gggttcgaat aaagaccgac caagcgacgt ctgagagctc   5220
cctggcgaat tcggtaccaa taaaagagct ttattttcat gatctgtgtg ttggtttttg   5280
tgtgcggcgc ggaagttcct attctctaga agtataggaa cttcctcga gcccctatagt   5340
gagtcgtatt agcccttgac gatgccacat cctgagcaaa taattcaacc actaattgtg   5400
agcggataac acaaggagga aacagctatg tcattaccgt tcttaacttc tgcaccggga   5460
aaggttatta ttttggtga acactctgct gtgtacaaca gcctgccgt cgctgctagt   5520
gtgtctgcgt tgagaaccta cctgctaata agcgagtcat ctgcaccaga tactattgaa   5580
ttggacttcc cggacattag ctttaatcat aagtggtcca tcaatgattt caatgccatc   5640
accgaggatc aagtaaactc ccaaaaattg gccaaggctc aacaagccac cgatggcttg   5700
tctcaggaac tcgttagtct tttggatccg ttgttagctc aactatccga atccttccac   5760
taccatgcag cgttttgttt cctgtatatg tttgttgcc tatgccccca tgccaagaat   5820
attaagtttt ctttaaagtc tactttaccc atcggtgctg ggttgggctc aagcgcctct   5880
atttctgtat cactggcctt agctatggcc tacttggggg ggttaatagg atctaatgac   5940
ttggaaaagc tgtcagaaaa cgataagcat atagtgaatc aatgggcctt cataggtgaa   6000
aagtgtattc acggtacccc ttcaggaata gataacgctg tggccactta tggtaatgcc   6060
ctgctatttg aaaaagactc acataatgga acaataaaca caaacaattt taagttctta   6120
gatgatttcc cagccattcc aatgatccta acctatacta gaattccaag gtctacaaaa   6180
```

```
gatcttgttg ctcgcgttcg tgtgttggtc accgagaaat ttcctgaagt tatgaagcca    6240
attctagatg ccatgggtga atgtgccta caaggcttag agatcatgac taagttaagt    6300
aaatgtaaag gcaccgatga cgaggctgta gaaactaata atgaactgta tgaacaacta    6360
ttggaattga taagaataaa tcatggactg cttgtctcaa tcggtgtttc tcatcctgga    6420
ttagaactta ttaaaaatct gagcgatgat ttgagaattg gctccacaaa acttaccggt    6480
gctggtggcg gcggttgctc tttgactttg ttacgaagag acattactca agagcaaatt    6540
gacagcttca aaagaaatt gcaagatgat tttagttacg agacatttga aacagacttg    6600
ggtgggactg gctgctgttt gttaagcgca aaaatttga ataaagatct taaaatcaaa    6660
tccctagtat tccaattatt tgaaaataaa actaccacaa agcaacaaat tgacgatcta    6720
ttattgccag aaacacgaa tttaccatgg acttcataag ctaatttgcg ataggcctgc    6780
acccttaagg aggaaaaaaa catgtcagag ttgagagcct tcagtgcccc agggaaagcg    6840
ttactagctg gtggatattt agttttagat acaaaatatg aagcatttgt agtcggatta    6900
tcggcaagaa tgcatgctgt agcccatcct tacggttcat tgcaagggtc tgataagttt    6960
gaagtgcgtg tgaaaagtaa acaatttaaa gatggggagt ggctgtacca tataagtcct    7020
aaaagtggct tcattcctgt ttcgataggc ggatctaaga acccttcat tgaaaaagtt    7080 atcgctaacg tatttagcta cttttaaacct aacatggacg actactgcaa tagaaacttg    7140
ttcgttattg atattttctc tgatgatgcc taccattctc aggaggatag cgttaccgaa    7200
catcgtggca acagaagatt gagttttcat tcgcacagaa ttgaagaagt tcccaaaaca    7260
gggctgggct cctcggcagg tttagtcaca gtttttaacta cagctttggc ctccttttt    7320 gtatcggacc tggaaaataa tgtagacaaa tatagagaag ttattcataa tttagcacaa    7380
gttgctcatt gtcaagctca gggtaaaatt ggaagcgggt ttgatgtagc ggcggcagca    7440
tatggatcta tcagatatag aagattccca cccgcattaa tctctaattt gccagatatt    7500
ggaagtgcta cttacggcag taaactggcg catttggttg atgaagaaga ctggaatatt    7560
acgattaaaa gtaaccattt accttcggga ttaactttat ggatgggcga tattaagaat    7620
ggttcagaaa cagtaaaact ggtccagaag gtaaaaaatt ggtatgattc gcatatgcca    7680
gaaagcttga aaatatatac agaactcgat catgcaaatt ctagatttat ggatggacta    7740
tctaaactag atcgcttaca cgagactcat gacgattaca gcgatcagat atttgagtct    7800
cttgagagga atgactgtac ctgtcaaaag tatcctgaaa tcacagaagt tagagatgca    7860
gttgccacaa ttagacgttc ctttagaaaa ataactaaag aatctggtgc cgatatcgaa    7920
cctcccgtac aaactagctt attggatgat tgccagacct taaaggagt tcttacttgc    7980 ttaatacctg gtgctggtgg ttatgacgcc attgcagtga ttactaagca agatgttgat    8040
cttagggctc aaaccgctaa tgacaaaaga ttttctaagg ttcaatggct ggatgtaact    8100
caggctgact ggggtgttag gaaagaaaaa gatccggaaa cttatcttga taaataactt    8160
aaggtagctg catgcagaat tcgcccttaa ggaggaaaaa aaatgaccg tttacacagc    8220 atccgttacc gcacccgtca acatcgcaac ccttaagtat tgggggaaaa gggacacgaa    8280
gttgaatctg cccaccaatt cgtccatatc agtgacttta tcgcaagatg acctcagaac    8340
gttgacctct gcggctactg cacctgagtt tgaacgcgac actttgtggt taaatggaga    8400
accacacagc atcgacaatg aaagaactca aaattgtctg cgcgacctac gccaattaag    8460
aaaggaaatg gaatcgaagg acgcctcatt gcccacatta tctcaatgga aactccacat    8520
tgtctccgaa aataactttc ctacagcagc tggtttagct tcctccgctg ctggctttgc    8580
```

```
tgcattggtc tctgcaattg ctaagttata ccaattacca cagtcaactt cagaaatatc    8640
tagaatagca agaaaggggt ctggttcagc ttgtagatcg ttgtttggcg gatacgtggc    8700
ctgggaaatg ggaaaagctg aagatggtca tgattccatg gcagtacaaa tcgcagacag    8760
ctctgactgg cctcagatga aagcttgtgt cctagttgtc agcgatatta aaaggatgt     8820 gagttccact cagggtatgc aattgaccgt ggcaacctcc gaactattta agaaagaat     8880 tgaacatgtc gtaccaaaga gatttgaagt catgcgtaaa gccattgttg aaaaagattt    8940
cgccaccttt gcaaaggaaa caatgatgga ttccaactct ttccatgcca catgtttgga    9000
ctctttccct ccaatattct acatgaatga cacttccaag cgtatcatca gttggtgcca    9060
caccattaat cagttttacg gagaaacaat cgttgcatac acgtttgatg caggtccaaa    9120
tgctgtgttg tactacttag ctgaaaatga gtcgaaactc tttgcattta tctataaatt    9180
gtttggctct gttcctggat gggacaagaa atttactact gagcagcttg aggctttcaa    9240
ccatcaattt gaatcatcta actttactgc acgtgaattg gatcttgagt tgcaaaagga    9300
tgttgccaga gtgattttaa ctcaagtcgg ttcaggccca caagaaacaa cgaatctttt   9360
gattgacgca aagactggtc taccaaagga ataagatcaa ttcgctgcat cgcccttagg    9420
aggtaaaaaa aaatgactgc cgacaacaat agtatgcccc atggtgcagt atctagttac    9480
gccaaattag tgcaaaacca aacacctgaa gacattttgg aagagtttcc tgaaattatt    9540
ccattacaac aaagacctaa tacccgatct agtgagacgt caaatgacga agcggagaa     9600 acatgttttt ctggtcatga tgaggagcaa attaagttaa tgaatgaaaa ttgtattgtt    9660
ttggattggg acgataatgc tattggtgcc ggtaccaaga aagtttgtca tttaatggaa    9720
aatattgaaa agggtttact acatcgtgca ttctccgtct ttattttcaa tgaacaaggt    9780
gaattacttt tacaacaaag agccactgaa aaaataactt tccctgatct ttggactaac    9840
acatgctgct ctcatccact atgtattgat gacgaattag gtttgaaggg taagctagac    9900
gataagatta agggcgctat tactgcggcg gtgagaaaac tagatcatga attaggtatt    9960
ccagaagatg aaactaagac aagggggtaag tttcactttt taaacagaat ccattacatg   10020
gcaccaagca atgaaccatg gggtgaacat gaaattgatt acatcctatt ttataagatc    10080
aacgctaaag aaaacttgac tgtcaaccca aacgtcaatg aagttagaga cttcaaatgg    10140
gtttcaccaa atgatttgaa aactatgttt gctgacccaa gttacaagtt tacgccttgg    10200
tttaagatta tttgcgagaa ttacttattc aactggtggg agcaattaga tgacctttct    10260
gaagtggaaa atgacaggca aattcataga atgctataac aacgcgtcta caaataaaaa    10320
aggcacgtca gatgacgtgc ctttttctt ggggcc                              10356
```

<210> SEQ ID NO 91
<211> LENGTH: 43
<212> TYPE: DNA
<213> ORGANISM: Artificial Sequence
<220> FEATURE:
<223> OTHER INFORMATION: Synthetic Construct

<400> SEQUENCE: 91

```
gcatgctcga gcggccgctt ttaatcaaac atcctgccaa ctc                       43
```

<210> SEQ ID NO 92
<211> LENGTH: 37
<212> TYPE: DNA
<213> ORGANISM: Artificial Sequence
<220> FEATURE:
<223> OTHER INFORMATION: Synthetic Construct

<400> SEQUENCE: 92
gatcgaaggg cgatcgtgtc acagtctggc gaaaccg    37

<210> SEQ ID NO 93
<211> LENGTH: 43
<212> TYPE: DNA
<213> ORGANISM: Artificial Sequence
<220> FEATURE:
<223> OTHER INFORMATION: Synthetic Construct

<400> SEQUENCE: 93
ctgaattctg cagatatctg tttttccact cttcgttcac ttt    43

<210> SEQ ID NO 94
<211> LENGTH: 33
<212> TYPE: DNA
<213> ORGANISM: Artificial Sequence
<220> FEATURE:
<223> OTHER INFORMATION: Synthetic Construct

<400> SEQUENCE: 94
tctagagggc ccaagaaaaa tgccccgctt acg    33

<210> SEQ ID NO 95
<211> LENGTH: 111
<212> TYPE: DNA
<213> ORGANISM: Artificial Sequence
<220> FEATURE:
<223> OTHER INFORMATION: Synthetic Construct

<400> SEQUENCE: 95
gatcgcggcc gcgcccttga cgatgccaca tcctgagcaa ataattcaac cactaattgt    60
gagcggataa cacaaggagg aaacagctat gtcattaccg ttcttaactt c    111

<210> SEQ ID NO 96
<211> LENGTH: 75
<212> TYPE: DNA
<213> ORGANISM: Artificial Sequence
<220> FEATURE:
<223> OTHER INFORMATION: Synthetic Construct

<400> SEQUENCE: 96
gatcgggccc caagaaaaaa ggcacgtcat ctgacgtgcc tttttatttt gtagacgcgt    60
tgttatagca ttcta    75

<210> SEQ ID NO 97
<211> LENGTH: 81
<212> TYPE: DNA
<213> ORGANISM: Artificial Sequence
<220> FEATURE:
<223> OTHER INFORMATION: Synthetic Construct

<400> SEQUENCE: 97
aaagtagccg aagatgacgg tttgtcacat ggagttggca ggatgtttga ttaaaagcaa    60
ttaaccctca ctaaagggcg g    81

<210> SEQ ID NO 98
<211> LENGTH: 160
<212> TYPE: DNA
<213> ORGANISM: Artificial Sequence
<220> FEATURE:
<223> OTHER INFORMATION: Synthetic Construct

<400> SEQUENCE: 98

```
agagtgttca ccaaaaataa taacctttcc cggtgcagaa gttaagaacg gtaatgacat    60
agctgtttcc tccttgtgtt atccgctcac aattagtggt tgaattattt gctcaggatg   120
tggcatcgtc aagggctaat acgactcact atagggctcg                         160
```

<210> SEQ ID NO 99
<211> LENGTH: 60
<212> TYPE: DNA
<213> ORGANISM: Artificial Sequence
<220> FEATURE:
<223> OTHER INFORMATION: Synthetic Construct

<400> SEQUENCE: 99

```
gatcatgcat tcgcccttag gaggtaaaaa aacatgtgtg cgacctcttc tcaatttact    60
```

<210> SEQ ID NO 100
<211> LENGTH: 38
<212> TYPE: DNA
<213> ORGANISM: Artificial Sequence
<220> FEATURE:
<223> OTHER INFORMATION: Synthetic Construct

<400> SEQUENCE: 100

```
cggtcgacgg atccctgcag ttagacatac atcagctg                            38
```

<210> SEQ ID NO 101
<211> LENGTH: 6974
<212> TYPE: DNA
<213> ORGANISM: Artificial Sequence
<220> FEATURE:
<223> OTHER INFORMATION: Synthetic Construct

<400> SEQUENCE: 101

```
gtgcggccgc aagcttgtcg acggagctcg aattcggatc cctgcagtta gacatacatc    60
agctggttaa tcgggaaagg gtcaatcagc agcagtttga tgcggttttc agtcgcgtag   120
tctgggcgac ccagaccatc gccatactgg taggtgcagt gggaaacacg tgccatgtta   180
actgcgattt ccatgaacgc tttaggcagc agggtggagt cgctaacgcg ttcacgattc   240 atcttttttcc attcggcgtc gatcagttta cgcagttctt cgcgggcctg ttcctcgctg   300
gtaccatcgt tttcgtgcat gtagctaatg atagaattgg tagtctcgcc acgttccagc   360
tccgccgcag aggtggccag atcgttgcac aggcggaaga taacgcagct agaacgcacc   420
agaccatgga gtcggtcag ggaacgcagc gcgtggtcgg agatgtcttc ctgctgctgg    480
catacggaaa agtaagacgg cgccagcagc gctacaccgg aggaggaaac gctggcgttt   540
tccaggtact tggagaaagc cgggataatt tgttgttgg accatttcgc ctcttgcaga    600
aaggctttgc acagttcacg ccagcttttc gtcagatagg acaggttgtt atgacctttc   660
tctttcagaa tagaatagga cgtgtcgtta acgtgttgt acagtgccag gaaacacagt    720
ttcatatagt ccggcagggt gttaatagcg ttaacgtccc agcgctctac agcatcggtg   780
aacagttgca gttcgtccag agtgccataa acgtcataca cgtcatcgat gatcgtcacc   840
agaccaaaca ttttagtaac agctttgcga cattcaccaa actgcgggtc tggcgccata   900
cccagtgccc agaaataaac ttccatcagg cggtcgcgta caaaatccag tttgctagcc   960
aggcccatct cggtccacca gcgggacaga tcttgcagct cttctggtg cagggtctgt    1020 accatgttaa aatccagctt cgccagctcc agcagcagct ggtgatgcgg ttctttcggt   1080 tcgtattttat ccaggaacca acgtgcctcc agacggtgca gacgctggtg atatggcagt  1140
tccagggcgt ggctcacttg ttctgcaacc ttggtattaa tgccttctttt caggttgttc   1200
```

```
ttcaggtggg tgatggaaaa ggtacgcgcc tcctccagca ggttctcacc ctcgaaaccc   1260
aggtaagacg cttcatacag gctcagcagg ccttggacgt cacctttcag ttcaccgctg   1320
aaaccacctt ctttatcctt gaaacgctca aaaacatcct gagaaacctc gaaaccgtgc   1380
tgacgcagca gacggaaaga cagagcggtt gcgtgcaggt cagatttgtt cttttttgttt  1440
tcgtccagca gtacgatgtt ttccagggct ttaatgatgt cttttttcaaa tttgtaggtc  1500
agacccaggc gctgcacatc gtcgatcagc tccagcaggg acagcggctg ggtgtctaca   1560
cggttgatca tgcagcgaac ttcttcctcc agtttggtcg cttttctcctc cagcttttttcc 1620
actttcaggt cgttctccag ggattgcagg aattcgaaat tccacaggtt tggctgatag   1680
tttgcggaac gacgggaatt atgctcggta atctgagtaa attgagaaga ggtcgcacac   1740
atggtatatc tccttcttaa agttaaacaa aattatttct agaggggaat tgttatccgc   1800
tcacaattcc cctatagtga gtcgtattaa tttcgcggga tcgagatctc gatcctctac   1860
gccggacgca tcgtggccgg catcaccggc gccacaggtg cggttgctgg cgcctatatc   1920
gccgacatca ccgatgggga agatcgggct cgccacttcg ggctcatgag cgcttgtttc   1980
ggcgtgggta tggtggcagg ccccgtggcc gggggactgt tgggcgccat ctccttgcat   2040
gcaccattcc ttgcggcggc ggtgctcaac ggcctcaacc tactactggg ctgcttccta   2100
atgcaggagt cgcataaggg agagcgtcga gatcccggac accatcgaat ggcgcaaaac   2160
ctttcgcggt atggcatgat agcgcccgga agagagtcaa ttcagggtgg tgaatgtgaa   2220
accagtaacg ttatacgatg tcgcagagta tgccggtgtc tcttatcaga ccgtttcccg   2280
cgtggtgaac caggccagcc acgtttctgc gaaaacgcgg gaaaaagtgg aagcggcgat   2340
ggcggagctg aattacattc ccaaccgcgt ggcacaacaa ctggcgggca aacagtcgtt   2400
gctgattggc gttgccacct ccagtctggc cctgcacgcg ccgtcgcaaa ttgtcgcggc   2460
gattaaatct cgcgccgatc aactgggtgc cagcgtggtg gtgtcgatgg tagaacgaag   2520
cggcgtcgaa gcctgtaaag cggcggtgca caatcttctc gcgcaacgcg tcagtgggct   2580
gatcattaac tatccgctgg atgaccagga tgccattgct gtggaagctg cctgcactaa   2640
tgttccggcg ttatttcttg atgtctctga ccagacaccc atcaacagta ttatttttctc  2700
ccatgaagac ggtacgcgac tgggcgtgga gcatctggtc gcattgggtc accagcaaat   2760
cgcgctgtta gcgggcccat taagttctgt ctcggcgcgt ctgcgtctgg ctggctggca   2820
taaatatctc actcgcaatc aaattcagcc gatagcggaa cgggaaggcg actggagtgc   2880
catgtccggt tttcaacaaa ccatgcaaat gctgaatgag ggcatcgttc ccactgcgat   2940
gctggttgcc aacgatcaga tggcgctggg cgcaatgcgc gccattaccg agtccgggct   3000
gcgcgttggt gcggatatct cggtagtggg atacgacgat accgaagaca gctcatgtta   3060
tatcccgccg ttaaccacca tcaaacagga ttttcgcctg ctggggcaaa ccagcgtgga   3120
ccgcttgctg caactctctc agggccaggc ggtgaagggc aatcagctgt tgcccgtctc   3180
actggtgaaa agaaaaacca ccctggcgcc caatacgcaa accgcctctc cccgcgcgtt   3240
ggccgattca ttaatgcagc tggcacgaca ggtttcccga ctggaaagcg ggcagtgagc   3300
gcaacgcaat taatgtaagt tagctcactc attaggcacc gggatctcga ccgatgccct   3360
tgagagcctt caacccagtc agctccttcc ggtgggcgcg gggcatgact atcgtcgccg   3420
cacttatgac tgtcttcttt atcatgcaac tcgtaggaca ggtgccggca gcgctctggg   3480
tcattttcgg cgaggaccgc tttcgctgga gcgcgacgat gatcggcctg tcgcttgcgg   3540
tattcggaat cttgcacgcc ctcgctcaag ccttcgtcac tggtcccgcc accaaacgtt   3600
```

```
tcggcgagaa gcaggccatt atcgccggca tggcggcccc acgggtgcgc atgatcgtgc    3660
tcctgtcgtt gaggacccgg ctaggctggc ggggttgcct tactggttag cagaatgaat    3720
caccgatacg cgagcgaacg tgaagcgact gctgctgcaa aacgtctgcg acctgagcaa    3780
caacatgaat ggtcttcggt ttccgtgttt cgtaaagtct ggaaacgcgg aagtcagcgc    3840
cctgcaccat tatgttccgg atctgcatcg caggatgctg ctggctaccc tgtggaacac    3900
ctacatctgt attaacgaag cgctggcatt gaccctgagt gattttctc tggtcccgcc    3960 gcatccatac cgccagttgt ttaccctcac aacgttccag taaccgggca tgttcatcat    4020
cagtaacccg tatcgtgagc atcctctctc gtttcatcgg tatcattacc cccatgaaca    4080
gaaatccccc ttacacgagg catcagtga ccaaacagga aaaaaccgcc cttaacatgg    4140
cccgctttat cagaagccag acattaacgc ttctggagaa actcaacgag ctggacgcgg    4200
atgaacaggc agacatctgt gaatcgcttc acgaccacgc tgatgagctt taccgcagct    4260
gcctcgcgcg tttcggtgat gacggtgaaa acctctgaca catgcagctc ccggagacgg    4320
tcacagcttg tctgtaagcg gatgccggga gcagacaagc ccgtcagggc gcgtcagcgg    4380
gtgttggcgg gtgtcgggc gcagccatga cccagtcacg tagcgatagc ggagtgtata    4440
ctggcttaac tatgcggcat cagagcagat tgtactgaga gtgcaccata tatgcggtgt    4500
gaaataccgc acagatgcgt aaggagaaaa taccgcatca ggcgctcttc cgcttcctcg    4560
ctcactgact cgctgcgctc ggtcgttcgg ctgcggcgag cggtatcagc tcactcaaag    4620
gcggtaatac ggttatccac agaatcaggg gataacgcag gaaagaacat gtgagcaaaa    4680
ggccagcaaa aggccaggaa ccgtaaaaag gccgcgttgc tggcgttttt ccataggctc    4740
cgcccccctg acgagcatca caaaaatcga cgctcaagtc agaggtggcg aaacccgaca    4800
ggactataaa gataccaggc gtttccccct ggaagctccc tcgtgcgctc tcctgttccg    4860
accctgccgc ttaccggata cctgtccgcc tttctccctt cgggaagcgt ggcgctttct    4920
catagctcac gctgtaggta tctcagttcg gtgtaggtcg ttcgctccaa gctgggctgt    4980
gtgcacgaac cccccgttca gcccgaccgc tgcgccttat ccggtaacta tcgtcttgag    5040
tccaacccgg taagacacga cttatcgcca ctggcagcag ccactggtaa caggattagc    5100
agagcgaggt atgtaggcgg tgctacagag ttcttgaagt ggtggcctaa ctacggctac    5160
actagaagga cagtatttgg tatctgcgct ctgctgaagc cagttacctt cggaaaaaga    5220
gttggtagct cttgatccgg caaacaaacc accgctggta gcggtggttt ttttgtttgc    5280
aagcagcaga ttacgcgcag aaaaaaagga tctcaagaag atcctttgat cttttctacg    5340
gggtctgacg ctcagtggaa cgaaaactca cgttaaggga ttttggtcat gaacaataaa    5400
actgtctgct tacataaaca gtaatacaag gggtgttatg agccatattc aacgggaaac    5460
gtcttgctct aggccgcgat taaattccaa catggatgct gatttatatg ggtataaatg    5520
ggctcgcgat aatgtcgggc aatcaggtgc gacaatctat cgattgtatg ggaagcccga    5580
tgcgccagag ttgtttctga acatggcaa aggtagcgtt gccaatgatg ttacagatga    5640
gatggtcaga ctaaactggc tgacggaatt tatgcctctt ccgaccatca agcattttat    5700
ccgtactcct gatgatgcat ggttactcac cactgcgatc cccgggaaaa cagcattcca    5760
ggtattagaa gaatatcctg attcaggtga aatattgtt gatgcgctgg cagtgttcct    5820
gcgccggttg cattcgattc ctgtttgtaa ttgtccttt aacagcgatc gcgtatttcg    5880
tctcgctcag gcgcaatcac gaatgaataa cggtttggtt gatgcgagtg attttgatga    5940
cgagcgtaat ggctggcctg ttgaacaagt ctggaaagaa atgcataaac ttttgccatt    6000
```

| | |
|---|---|
| ctcaccggat tcagtcgtca ctcatggtga tttctcactt gataaccttat ttttgacga | 6060 |
| ggggaaatta ataggttgta ttgatgttgg acgagtcgga atcgcagacc gataccagga | 6120 |
| tcttgccatc ctatggaact gcctcggtga gttttctcct tcattacaga aacggctttt | 6180 |
| tcaaaaatat ggtattgata atcctgatat gaataaattg cagtttcatt tgatgctcga | 6240 |
| tgagttttc taagaattaa ttcatgagcg gatacatatt tgaatgtatt tagaaaaata | 6300 |
| aacaaatagg ggttccgcgc acatttcccc gaaaagtgcc acctgaaatt gtaaacgtta | 6360 |
| atattttgtt aaaattcgcg ttaaattttt gttaaatcag ctcatttttt aaccaatagg | 6420 |
| ccgaaatcgg caaaatccct tataaatcaa aagaatagac cgagatagggg ttgagtgttg | 6480 |
| ttccagtttg gaacaagagt ccactattaa agaacgtgga ctccaacgtc aaagggcgaa | 6540 |
| aaaccgtcta tcagggcgat ggcccactac gtgaaccatc accctaatca agttttttgg | 6600 |
| ggtcgaggtg ccgtaaagca ctaaatcgga acctaaagg agcccccga tttagagctt | 6660 |
| gacggggaaa gccggcgaac gtggcgagaa aggaagggaa gaaagcgaaa ggagcgggcg | 6720 |
| ctagggcgct ggcaagtgta gcggtcacgc tgcgcgtaac caccacaccc gccgcgctta | 6780 |
| atgcgccgct acagggcgcg tcccattcgc caatccggat atagttcctc ctttcagcaa | 6840 |
| aaaaccctc aagacccgtt tagaggcccc aaggggttat gctagttatt gctcagcggt | 6900 |
| ggcagcagcc aactcagctt cctttcgggc tttgttagca gccggatctc agtggtggtg | 6960 |
| gtggtggtgc tcga | 6974 |

<210> SEQ ID NO 102
<211> LENGTH: 3913
<212> TYPE: DNA
<213> ORGANISM: Artificial Sequence
<220> FEATURE:
<223> OTHER INFORMATION: Synthetic Construct

<400> SEQUENCE: 102

| | |
|---|---|
| gcggccgcgc ccttgacgat gccacatcct gagcaaataa ttcaaccact aattgtgagc | 60 |
| ggataacaca aggaggaaac agccatggta tcctgttctg cgccgggtaa gatttacctg | 120 |
| ttcggtgaac acgccgtagt ttatggcgaa actgcaattg cgtgtgcggt ggaactgcgt | 180 |
| acccgtgttc gcgcggaact caatgactct atcactattc agagccagat cggccgcacc | 240 |
| ggtctggatt tcgaaaagca cccttatgtg tctgcggtaa ttgagaaaat gcgcaaatct | 300 |
| attcctatta acggtgtttt cttgaccgtc gattccgaca tcccggtggg ctccggtctg | 360 |
| ggtagcagcg cagccgttac tatcgcgtct attggtgcgc tgaacgagct gttcggcttt | 420 |
| ggcctcagcc tgcaagaaat cgctaaactg ggccacgaaa tcgaaattaa agtacagggt | 480 |
| gccgcgtccc caaccgatac gtatgtttct accttcggcg gcgtggttac catcccggaa | 540 |
| cgtcgcaaac tgaaaactcc ggactgcggc attgtgattg cgataccgg cgttttctcc | 600 |
| tccaccaaag agttagtagc taacgtacgt cagctgcgcg aaagctaccc ggatttgatc | 660 |
| gaaccgctga tgacctctat tggcaaaatc tctcgtatcg cgaacaact ggttctgtct | 720 |
| ggcgactacg catccatcgg ccgcctgatg aacgtcaacc agggtctcct ggacgccctg | 780 |
| ggcgttaaca tcttagaact gagccagctg atctattccg ctcgtgcggc aggtgcgttt | 840 |
| ggcgctaaaa tcacgggcgc tggcggcggt ggctgtatgg ttgcgctgac cgtccggaa | 900 |
| aaatgcaacc aagtggcaga agcggtagca ggcgctggcg gtaaagtgac tatcactaaa | 960 |
| ccgaccgagc aaggtctgaa agtagattaa gccttgactt aatagctgct tatttcgccc | 1020 |
| ttatggtacc tagtaggagg aaaaaaacat ggaaatgcgt caaccggctg tcgcaggtca | 1080 |

```
attctaccca ctgcgttgcg agaacctgga aaacgaactg aaacgctgct tcgaaggcct    1140
ggagatccgc gaacaagaag tgctgggcgc agtctgtccg cacgccggtt atatgtactc    1200
tggcaaagtt gcggcgcacg tctatgccac tctgccggaa gctgatacct acgtaatctt    1260
cggcccgaac cacaccggct acggtagccc tgtctctgtg agccgtgaaa cttggaagac    1320
cccgttgggc aatatcgatg ttgacctgga actggcggac ggcttcctgg gttccatcgt    1380
agatgcggat gaactcggtc acaaatacga acactctatc gaagttcagc tgccgtttct    1440
gcaataccgt tttgaacgcg atttcaaaat tctgccaatc tgcatgggta tgcaagacga    1500
agaaaccgcg gtcgaagtag gtaacctgct ggcggatctg atcagcgagt ccggtaaacg    1560
tgctgtgatc atcgcaagct ctgatttcac ccactatgag acggctgaac gtgccaaaga    1620
aatcgattcc gaagttattg attctatcct gaactttgac atctctggca tgtacgatcg    1680
cctgtatcgc cgtaacgcct ctgtttgcgg ttacggcccg atcaccgcta tgctgacggc    1740
aagcaaaaag ctgggcggct ctcgtgcgac tttgctgaaa tacgcaaaca gcggtgacgt    1800
gtccggtgat aaagacgctg tggtgggcta cgccgccatc atcgttgagt aagctgatta    1860
aaggttgaac agataggatt tcgtcatgga tcctacaagg aggaaaaaaa catgaatgct    1920
tctaatgaac cggtgattct gaaactgggt ggctctgcta ttaccgacaa aggtgcctac    1980
gaaggcgtag ttaaggaagc tgatttgctg cgcatcgcac aggaagttag cggtttccgt    2040
ggcaagatga tcgtggttca tggtgctggt agcttcggcc atacgtacgc gaagaaatac    2100
ggcctggacc gtaccttcga cccagagggc gcaattgtta tcatgaatc tgttaaaaag    2160
ctcgcctcca agttgtagg tgctctgaat agcttcggcg tgcgtgctat cgcggtgcat    2220
cctatggact gcgcagtatg ccgtaacggt cgtatcgaaa cgatgtatct ggactccatc    2280
aagttaatgc tggaaaaagg tctggtgccg ttctgcacg gcgacgtcgc aatggatatt    2340
gaactgggca cttgtatcct gtccggtgat caaatcgttc cttacctggc caaagaactg    2400
ggtatctccc gcctcggcct gggcagcgca gaggatggtg tgctggatat ggagggcaaa    2460
cctgtaccgg aaatcacccc agaaactttc gaagagttcc gccactgcat cggtggttct    2520
ggttctactg atgtaaccgg tggcatgctg ggcaaagtgc tggaacttct ggaattgagc    2580
aaaaattctt ccattactag ctacattttc aacgctggta agcagacaa catctaccgc    2640
tttctgaatg gtgagtccat cggcactcgc atcagcccgg acaagcgtgt ttaagctagt    2700
tattaaccta aatgctctaa accagttatg agctctacaa ggaggaaaaa aacatgatta    2760
acactaccag ccgccgcaaa attgaacacc tgaaactctg cgcagaatcc ccggttgaag    2820
cgcgtcaggt atctgccggc tttgaagacg ttactctgat ccaccgcgct ttaccggagc    2880
tgaacatgga tgaactggac ctcagcgttg atttcctggg taaacgcatc aaagcgccgt    2940
tcctgattgc gtctatcacg ggtggtcacc cagataccat cccggttaac gctgcgctgg    3000
cagctgctgc tgaggagctg ggtgttggca tcggcgttgg ctctcagcgc gcggccattg    3060
atgatccgag ccaggaagac agcttccgtg tagtgcgtga tgaagcccca gatgcgtttg    3120
tttatggcaa cgtcggcgca gcacagatcc gtcagtatgg tgttgaaggt gttgaaaaac    3180
tgatcgaaat gattgacgca gatgccttgg caatccacct gaactttctg caagaagcgg    3240
tccaaccgga aggtgaccgc gacgcgaccg gttgcctgga catgattacc gaaatttgct    3300
ctcagattaa aactccggta atcgtgaaag aaaccggtgc aggcattagc cgtgaagatg    3360
cgattctgtt ccagaaagct ggcgtgagcg caatcgacgt tggcggcgcg ggcggcacct    3420
cctgggctgg cgtcgaggtc taccgtgcta agaaagccg tgactctgtt agcgagcgtt    3480
```

```
taggtgagct gttttgggat ttcggcattc cgacggtagc ttctctgatt gaatcccgcg    3540
tttccttgcc gctgatcgca accggcggta tccgtaacgg tctggacatt gctaaaagca    3600
ttgctctcgg cgcaagcgct gccagcgccg ctctgccgtt cgttggtccg tccctggagg    3660
gcaaagaatc cgttgtacgt gtgctgagct gcatgctgga agaatttaaa gcagcaatgt    3720
ttttgtgcgg ttgcggcaac atcaaagacc tgcacaactc tccagtagtg gtaactggtt    3780
ggacccgcga atacctggag cagcgcggtt ttaacgttaa ggacctctcc ctgccgggca    3840
acgctctgta agcttcaacg cgtctacaaa taaaaaaggc acgtcagatg acgtgccttt    3900
tttcttgtct aga                                                      3913
```

<210> SEQ ID NO 103
<211> LENGTH: 6848
<212> TYPE: DNA
<213> ORGANISM: Artificial Sequence
<220> FEATURE:
<223> OTHER INFORMATION: Synthetic Construct

<400> SEQUENCE: 103

```
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatgtgtgc     420
gacctcttct caatttactc agattaccga gcataattcc cgtcgttccg caaactatca     480
gccaaacctg tggaatttcg aattcctgca atccctggag aacgacctga agtggaaaa      540 gctggaggag aaagcgacca aactggagga agaagttcgc tgcatgatca accgtgtaga     600
cacccagccg ctgtccctgc tggagctgat cgacgatgtg cagcgcctgg gtctgaccta     660
caaatttgaa aaagacatca ttaaagccct ggaaaacatc gtactgctgg acgaaaacaa     720
aaagaacaaa tctgacctgc acgcaaccgc tctgtctttc cgtctgctgc gtcagcacgg     780
tttcgaggtt tctcaggatg ttttttgagcg tttcaaggat aaagaaggtg gtttcagcgg     840
tgaactgaaa ggtgacgtcc aaggcctgct gagcctgtat gaagcgtctt acctgggttt     900
cgagggtgag aacctgctgg aggaggcgcg taccttttcc atcacccacc tgaagaacaa     960
cctgaaagaa ggcattaata ccaaggttgc agaacaagtg agccacgccc tggaactgcc    1020
atatcaccag cgtctgcacc gtctggaggc acgttggttc ctggataaat acgaaccgaa    1080
agaaccgcat caccagctgc tgctggagct ggcgaagctg gattttaaca tggtacagac    1140
cctgcaccag aaagagctgc aagatctgtc ccgctggtgg accgagatgg gcctggctag    1200
caaactggat tttgtacgcg accgcctgat ggaagtttat ttctgggcac tgggtatggc    1260
gccagacccg cagtttggtg aatgtcgcaa agctgttact aaaatgtttg gtctggtgac    1320
gatcatcgat gacgtgtatg acgtttatgg cactctggac gaactgcaac tgttcaccga    1380
tgctgtagag cgctggacg ttaacgctat taacaccctg ccggactata tgaaactgtg    1440 ttcctggca ctgtacaaca ccgttaacga cacgtcctat tctattctga agagaaagg     1500 tcataacaac ctgtccctatc tgacgaaaag ctggcgtgaa ctgtgcaaag cctttctgca    1560
agaggcgaaa tggtccaaca acaaaattat cccggctttc tccaagtacc tggaaaacgc    1620
```

```
cagcgtttcc tcctccggtg tagcgctgct ggcgccgtct tacttttccg tatgccagca   1680
gcaggaagac atctccgacc acgcgctgcg ttccctgacc gacttccatg gtctggtgcg   1740
ttctagctgc gttatcttcc gcctgtgcaa cgatctggcc acctctgcgg cggagctgga   1800
acgtggcgag actaccaatt ctatcattag ctacatgcac gaaaacgatg gtaccagcga   1860
ggaacaggcc cgcgaagaac tgcgtaaact gatcgacgcc gaatggaaaa agatgaatcg   1920
tgaacgcgtt agcgactcca ccctgctgcc taaagcgttc atggaaatcg cagttaacat   1980
ggcacgtgtt tcccactgca cctaccagta tggcgatggt ctgggtcgcc cagactacgc   2040
gactgaaaac cgcatcaaac tgctgctgat tgacccttc ccgattaacc agctgatgta    2100
tgtctaactg cataaaggag gtaaaaaaac atggtatcct gttctgcgcc gggtaagatt   2160
tacctgttcg gtgaacacgc cgtagtttat ggcgaaactg caattgcgtg tgcggtggaa   2220
ctgcgtaccc gtgttcgcgc ggaactcaat gactctatca ctattcagag ccagatcggc   2280
cgcaccggtc tggatttcga aaagcaccct tatgtgtctg cggtaattga aaaatgcgc    2340 aaatctattc ctattaacgg tgttttcttg accgtcgatt ccgacatccc ggtgggctcc   2400
ggtctgggta gcagcgcagc cgttactatc gcgtctattg gtgcgctgaa cgagctgttc   2460
ggctttggcc tcagcctgca agaaatcgct aaactgggcc acgaaatcga attaaagta    2520 cagggtgccg cgtccccaac cgatacgtat gtttctacct tcggcggcgt ggttaccatc   2580
ccggaacgtc gcaaactgaa aactccggac tgcggcattg tgattggcga taccggcgtt   2640
ttctcctcca ccaaagagtt agtagctaac gtacgtcagc tgcgcgaaag ctacccggat   2700
ttgatcgaac gctgatgac  ctctattggc aaaatctctc gtatcggcga caactggtt    2760 ctgtctggcg actacgcatc catcggccgc ctgatgaacg tcaaccaggg tctcctggac   2820
gccctgggcg ttaacatctt agaactgagc cagctgatct attccgctcg tgcggcaggt   2880
gcgtttggcc ctaaaatcac gggcgctggc ggcgtggct gtatggttgc gctgaccgct   2940
ccggaaaaat gcaaccaagt ggcagaagcg gtagcaggcg ctggcggtaa agtgactatc   3000
actaaaccga ccgagcaagg tctgaaagta gattaaagtc tagttaaagt ttaaacggtc   3060
tccagcttgg ctgttttggc ggatgagaga agattttcag cctgatacag attaaatcag   3120
aacgcagaag cggtctgata aaacagaatt tgcctggcgg cagtagcgcg gtggtcccac   3180
ctgaccccat gccgaactca gaagtgaaac gccgtagcgc cgatggtagt gtgggtctc    3240 cccatgcgag agtagggaac tgccaggcat caaataaaac gaaaggctca gtcgaaagac   3300
tgggcctttc gttttatctg ttgtttgtcg gtgaacgctc tcctgagtag gacaaatccg   3360
ccgggagcgg atttgaacgt tgcgaagcaa cggcccggag ggtggcgggc aggacgcccg   3420
ccataaactg ccaggcatca aattaagcag aaggccatcc tgacggatgg ccttttttgcg   3480 tttctacaaa ctctttttgt ttattttct aaatacattc aaatatgtat ccgcttaacc    3540
ggaattgcca gctggggcgc cctctggtaa ggttgggaag ccctgcaaag taaactggat   3600
ggctttctcg ccgccaagga tctgatggcg caggggatca agctctgatc aagagacagg   3660
atgaggatcg tttcgcatga ttgaacaaga tggattgcac gcaggttctc cggccgcttg   3720
ggtggagagg ctattcggct atgactgggc acaacagaca atcggctgct ctgatgccgc   3780
cgtgttccgc ctgtcagcgc aggggcgccc ggttcttttt gtcaagaccg acctgtccgg   3840
tgccctgaat gaactgcaag acgaggcagc gcggctatcg tggctggcca cgacgggcgt   3900
tccttgcgca gctgtgctcg acgttgtcac tgaagcggga agggactggc tgctattggg   3960
cgaagtgccg gggcaggatc tcctgtcatc tcaccttgct cctgccgaga agtatccat    4020
```

```
catggctgat gcaatgcggc ggctgcatac gcttgatccg gctacctgcc cattcgacca    4080
ccaagcgaaa catcgcatcg agcgagcacg tactcggatg gaagccggtc ttgtcgatca    4140
ggatgatctg gacgaagagc atcaggggct cgcgccagcc gaactgttcg ccaggctcaa    4200
ggcgagcatg cccgacggcg aggatctcgt cgtgacccat ggcgatgcct gcttgccgaa    4260
tatcatggtg gaaaatggcc gcttttctgg attcatcgac tgtggccggc tgggtgtggc    4320
ggaccgctat caggacatag cgttggctac ccgtgatatt gctgaagagc ttggcggcga    4380
atgggctgac cgcttcctcg tgctttacgg tatcgccgct cccgattcgc agcgcatcgc    4440
cttctatcgc cttcttgacg agttcttctg acgcatgacc aaaatccctt aacgtgagtt    4500
ttcgttccac tgagcgtcag accccgtaga aagatcaaa ggatcttctt gagatccttt     4560
ttttctgcgc gtaatctgct gcttgcaaac aaaaaaacca ccgctaccag cggtggtttg    4620
tttgccggat caagagctac caactctttt tccgaaggta actggcttca gcagagcgca    4680
gataccaaat actgtccttc tagtgtagcc gtagttaggc caccacttca agaactctgt    4740
agcaccgcct acatacctcg ctctgctaat cctgttacca gtggctgctg ccagtggcga    4800
taagtcgtgt cttaccgggt tggactcaag acgatagtta ccggataagg cgcagcggtc    4860
gggctgaacg ggggggttcgt gcacacagcc cagcttggag cgaacgacct acaccgaact    4920
gagataccta cagcgtgagc tatgagaaag cgccacgctt cccgaaggga aaaggcgga    4980
caggtatccg gtaagcggca gggtcggaac aggagagcgc acgagggagc ttccaggggg    5040
aaacgcctgg tatctttata gtcctgtcgg gtttcgccac ctctgacttg agcgtcgatt    5100
tttgtgatgc tcgtcagggg ggcggagcct atggaaaaac gccagcaacg cggccttttt   5160
acggttcctg gcctttgct ggcctttgc tcacatgttc tttcctgcgt tatcccctga    5220
ttctgtggat aaccgtatta ccgcctttga gtgagctgat accgctcgcc gcagccgaac    5280
gaccgagcgc agcgagtcag tgagcgagga agcggaagag cgcctgatgc ggtattttct    5340
ccttacgcat ctgtgcggta tttcacaccg catatggtgc actctcagta caatctgctc    5400
tgatgccgca tagttaagcc agtatacact ccgctatcgc tacgtgactg gtcatggct    5460
gcgccccgac acccgccaac acccgctgac gcgccctgac gggcttgtct gctcccggca    5520
tccgcttaca gacaagctgt gaccgtctcc gggagctgca tgtgtcagag gttttcaccg    5580
tcatcaccga aacgcgcgag gcagcagatc aattcgcgcg cgaaggcgaa gcggcatgca    5640
tttacgttga caccatcgaa tggtgcaaaa ccttttcgcgg tatggcatga tagcgcccgg    5700
aagagagtca attcagggtg gtgaatgtga accagtaaac gttatacgat gtcgcagagt    5760
atgccggtgt ctcttatcag accgtttccc gcgtggtgaa ccaggccagc cacgtttctg    5820
cgaaaacgcg ggaaaaagtg gaagcggcga tggcggagct gaattacatt cccaaccgcg    5880
tggcacaaca actggcggc aaacagtcgt tgctgattgg cgttgccacc tccagtctgg    5940
ccctgcacgc gccgtcgcaa attgtcgcgg cgattaaatc tcgcgccgat caactgggtg    6000
ccagcgtggt ggtgtcgatg gtagaacgaa gcggcgtcga agcctgtaaa gcggcggtgc    6060
acaatcttct cgcgcaacgc gtcagtgggc tgatcattaa ctatccgctg gatgaccagg    6120
atgccattgc tgtggaagct gcctgcacta atgttccggc gttatttctt gatgtctctg    6180
accagacacc catcaacagt attattttct cccatgaaga cggtacgcga ctgggcgtgg    6240
agcatctggt cgcattgggt caccagcaaa tcgcgctgtt agcgggccca ttaagttctg    6300
tctcggcgcg tctgcgtctg gctggctggc ataaatatct cactcgcaat caaattcagc    6360
cgatagcgga acgggaaggc gactggagtg ccatgtccgg ttttcaacaa accatgcaaa    6420
```

```
tgctgaatga gggcatcgtt cccactgcga tgctggttgc caacgatcag atggcgctgg   6480
gcgcaatgcg cgccattacc gagtccgggc tgcgcgttgg tgcggatatc tcggtagtgg   6540
gatacgacga taccgaagac agctcatgtt atatcccgcc gtcaaccacc atcaaacagg   6600
attttcgcct gctggggcaa accagcgtgg accgcttgct gcaactctct cagggccagg   6660
cggtgaaggg caatcagctg ttgcccgtct cactggtgaa agaaaaacc accctggcgc    6720 ccaatacgca aaccgcctct ccccgcgcgt tggccgattc attaatgcag ctggcacgac   6780
aggtttcccg actggaaagc gggcagtgag cgcaacgcaa ttaatgtgag ttagcgcgaa   6840
ttgatctg                                                            6848

<210> SEQ ID NO 104
<211> LENGTH: 6647
<212> TYPE: DNA
<213> ORGANISM: Artificial Sequence
<220> FEATURE:
<223> OTHER INFORMATION: Synthetic Construct

<400> SEQUENCE: 104
aagggcgagc tcaacgatcc ggctgctaac aaagcccgaa aggaagctga gttggctgct     60
gccaccgctg agcaataact agcataaccc cttggggcct ctaaacgggt cttgaggagt    120 ttttgctga aggaggaac tatatccgga tatcccgcaa gaggcccggc agtaccggca      180
taaccaagcc tatgcctaca gcatccaggg tgacggtgcc gaggatgacg atgagcgcat    240
tgttagattt catacacggt gcctgactgc gttagcaatt taactgtgat aaactaccgc    300
attaaagctt atcgatgata agctgtcaaa catgagaatt aattcttgaa gacgaaaggg    360
cctcgtgata cgcctatttt tataggttaa tgtcatgata ataatggttt cttagacgtc    420
aggtggcact tttcggggaa atgtgcgcgg aacccctatt tgtttatttt tctaaataca    480
ttcaaatatg tatccgctca tgagacaata accctgataa atgcttcaat aatattgaaa    540
aaggaagagt atgattgaac aagatggatt gcacgcaggt tctccggccg cttgggtgga    600
gaggctattc ggctatgact gggcacaact gacaatcggc tgctctgatg ccgccgtgtt    660
ccggctgtca gcgcaggggc gcccggttct ttttgtcaag accgacctgt ccggtgccct    720
gaatgaactg caggacgagg cagcgcggct atcgtggctg gccacgacgg gcgttccttg    780
cgcagctgtg ctcgacgttg tcactgaagc gggaagggac tggctgctat tgggcgaagt    840
gccggggcag gatctcctgt catctcacct tgctcctgcc gagaaagtat ccatcatggc    900
tgatgcaatg cggcggctgc atacgcttga tccggctacc tgcccattcg accaccaagc    960
gaaacatcgc atcgagcggg cacgtactcg gatggaagcc ggtcttgtcg atcaggatga   1020
tctggacgaa gagcatcagg ggctcgcgcc agccgaactg ttcgccaggc tcaaggcgcg   1080
catgcccgac ggcgaggatc tcgtcgtgac acatggcgat gcctgcttgc cgaatatcat   1140
ggtggaaaat ggccgctttt ctggattcat cgactgtggc cggctgggtg tggcggaccg   1200
ctatcaggac atagcgttgg ctacccgtga tattgctgaa gagcttggcg gcgaatgggc   1260
tgaccgcttc ctcgtgcttt acggtatcgc cgctcccgat tcgcagcgca tcgccttcta   1320
tcgccttctt gacgagttct tctgagcggg actctgggt tcgaaatgac cgaccaagcg   1380
acgcctaact gtcagaccaa gtttactcat atatacttta gattgattta aaacttcatt   1440
tttaatttaa aaggatctag gtgaagatcc ttttttgataa tctcatgacc aaaatccctt   1500
aacgtgagtt ttcgttccac tgagcgtcag acccgtaga aagatcaaa ggatcttctt    1560 gagatccttt ttttctgcgc gtaatctgct gcttgcaaac aaaaaaacca ccgctaccag   1620
```

```
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagatacccta cagcgtgagc tatgagaaag cgccacgctt cccgaaggga   1980
gaaaggcgga caggtatccg gtaagcggca gggtcggaac aggagagcgc acagggagc    2040 ttccaggggg aaacgcctgg tatctttata gtcctgtcgg gtttcgccac ctctgacttg   2100
agcgtcgatt tttgtgatgc tcgtcagggg ggcggagcct atggaaaaac gccagcaacg   2160 cggcctttt  acggttcctg gccttttgct ggccttttgc tcacatgttc tttcctgcgt   2220 tatccctga  ttctgtggat aaccgtatta ccgcctttga gtgagctgat accgctcgcc   2280
gcagccgaac gaccgagcgc agcgagtcag tgagcgagga gcggaagag  cgcctgatgc   2340 ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg ggcttgtctg   2520
ctcccggcat ccgcttacag acaagctgtg accgtctccg ggagctgcat gtgtcagagg   2580
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg ccatgttaa  gggcggtttt tcctgtttg    2760 gtcactgatg cctccgtgta agggggattt ctgttcatgg ggtaatgat  accgatgaaa   2820 cgagagagga tgctcacgat acgggttact gatgatgaac atgcccggtt actggaacgt   2880
tgtgagggta acaactggcg gtatggatg  cggcgggacc agagaaaaat cactcagggt   2940
caatgccagc gcttcgttaa tacagatgta ggtgttccac agggtagcca gcagcatcct   3000
gcgatgcaga tccggaacat aatggtgcag ggcgctgact ccgcgtttc  cagactttac   3060 gaaacacgga aaccgaagac cattcatgtt gttgctcagg tcgcagacgt tttgcagcag   3120
cagtcgcttc acgttcgctc gcgtatcggt gattcattct gctaaccagt aaggcaaccc   3180
cgccagccta gccgggtcct caacgacagg agcacgatca tgcgcacccg tggccaggac   3240
ccaacgctgc ccgagatgcg ccgcgtgcgg ctgctggaga tggcggacgc gatggatatg   3300
ttctgccaag ggttggtttg cgcattcaca gttctccgca agaattgatt ggctccaatt   3360
cttggagtgg tgaatccgtt agcgaggtgc cgccggcttc cattcaggtc gaggtggccc   3420
ggctccatgc accgcgacgc aacgcgggga ggcagacaag gtatagggcg cgcctacaa   3480 tccatgccaa cccgttccat gtgctcgccg aggcggcata atcgccgtg  acgatcagcg   3540 gtccaatgat cgaagttagg ctggtaagag ccgcgagcga tccttgaagc tgtccctgat   3600
ggtcgtcatc tacctgcctg gacagcatgg cctgcaacgc gggcatcccg atgccgccgg   3660
aagcgagaag aatcataatg gggaaggcca tccagcctcg cgtcgcgaac gccagcaaga   3720
cgtagcccag cgcgtcggcc gccatgccgg cgataatggc ctgcttctcg ccgaaacgtt   3780
tggtggcggg accagtgacg aaggcttgag cgagggcgtg caagattccg aataccgcaa   3840
gcgacaggcc gatcatcgtc gcgctccagc gaaagcggtc ctcgccgaaa atgacccaga   3900
gcgctgccgg cacctgtcct acgagttgca tgataaagaa gacagtcata agtgcggcga   3960
cgatagtcat gccccgcgcc caccggaagg agctgactgg gttgaaggct ctcaagggca   4020
```

-continued

```
tcggtcgaga tcccggtgcc taatgagtga gctaacttac attaattgcg ttgcgctcac    4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
gagctgtctt cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg gatagttaat gatcagccca    4800
ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acgcgcgtg cagggccaga ctggaggtgg caacgccaat cagcaacgac    4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctccctta tgcgactcct gcattaggaa    5280
gcagcccagt agtaggttga ggccgttgag caccgccgcc gcaaggaatg gtgcatgcaa    5340
ggagatggcg cccaacagtc ccccggccac ggggcctgcc accataccca cgccgaaaca    5400
agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta tagggaattg tgagcggat    5580 aacaattccc ctctagaaat aattttgttt aactttaaga aggagatata catatgcggg    5640
gttctcatca tcatcatcat catggtatgg ctagcatgac tggtggacag caaatgggtc    5700
gggatctgta cgacgatgac gataaggatc atcccttcac catggtatcc tgttctgcgc    5760
cgggtaagat ttacctgttc ggtgaacacg ccgtagttta tggcgaaact gcaattgcgt    5820
gtgcggtgga actgcgtacc cgtgttcgcg cggaactcaa tgactctatc actattcaga    5880
gccagatcgg ccgcaccggt ctggatttcg aaaagcaccc ttatgtgtct gcggtaattg    5940
agaaaatgcg caaatctatt cctattaacg gtgttttctt gaccgtcgat ccgacatcc    6000 cggtgggctc cggtctgggt agcagcgcag ccgttactat cgcgtctatt ggtgcgctga    6060
acgagctgtt cggctttggc ctcagcctgc aagaaatcgc taaactgggc cacgaaatcg    6120
aaattaaagt acagggtgcc gcgtccccaa ccgatacgta tgtttctacc ttcggcggcg    6180
tggttaccat cccggaacgt cgcaaactga aaactccgga ctgcggcatt gtgattggcg    6240
ataccggcgt tttctcctcc accaaagagt tagtagctaa cgtacgtcag ctgcgcgaaa    6300
gctacccgga tttgatcgaa ccgctgatga cctctattgg caaaatctct cgtatcggcg    6360
aacaactggt tctgtctggc gactacgcat ccatcggccg cctgatgaac gtcaaccagg    6420
```

```
gtctcctgga cgccctgggc gttaacatct tagaactgag ccagctgatc tattccgctc    6480
gtgcggcagg tgcgtttggc gctaaaatca cgggcgctgg cggcggtggc tgtatggttg    6540
cgctgaccgc tccggaaaaa tgcaaccaag tggcagaagc ggtagcaggc gctggcggta    6600
aagtgactat cactaaaccg accgagcaag gtctgaaagt agattaa                  6647
```

<210> SEQ ID NO 105
<211> LENGTH: 22
<212> TYPE: DNA
<213> ORGANISM: Artificial Sequence
<220> FEATURE:
<223> OTHER INFORMATION: Synthetic Construct
<400> SEQUENCE: 105

```
caccatggta tcctgttctg cg                                              22
```

<210> SEQ ID NO 106
<211> LENGTH: 22
<212> TYPE: DNA
<213> ORGANISM: Artificial Sequence
<220> FEATURE:
<223> OTHER INFORMATION: Synthetic Construct
<400> SEQUENCE: 106

```
ttaatctact ttcagacctt gc                                              22
```

<210> SEQ ID NO 107
<211> LENGTH: 66
<212> TYPE: DNA
<213> ORGANISM: Artificial Sequence
<220> FEATURE:
<223> OTHER INFORMATION: Synthetic Construct
<400> SEQUENCE: 107

```
gcgaacgatg cataaaggag gtaaaaaaac atggtatcct gttctgcgcc gggtaagatt    60
tacctg                                                                66
```

<210> SEQ ID NO 108
<211> LENGTH: 48
<212> TYPE: DNA
<213> ORGANISM: Artificial Sequence
<220> FEATURE:
<223> OTHER INFORMATION: Synthetic Construct
<400> SEQUENCE: 108

```
gggcccgttt aaactttaac tagactttaa tctactttca gaccttgc                  48
```

<210> SEQ ID NO 109
<211> LENGTH: 20
<212> TYPE: DNA
<213> ORGANISM: Artificial Sequence
<220> FEATURE:
<223> OTHER INFORMATION: Synthetic Construct
<400> SEQUENCE: 109

```
caccaaagac ttcatagact                                                 20
```

<210> SEQ ID NO 110
<211> LENGTH: 20
<212> TYPE: DNA
<213> ORGANISM: Artificial Sequence
<220> FEATURE:
<223> OTHER INFORMATION: Synthetic Construct
<400> SEQUENCE: 110

```
agagatatct tcctgctgct                                                  20
```

<210> SEQ ID NO 111
<211> LENGTH: 20
<212> TYPE: DNA
<213> ORGANISM: Artificial Sequence
<220> FEATURE:
<223> OTHER INFORMATION: Synthetic Construct

<400> SEQUENCE: 111

```
taatacgact cactataggg                                                  20
```

<210> SEQ ID NO 112
<211> LENGTH: 1719
<212> TYPE: DNA
<213> ORGANISM: Artificial Sequence
<220> FEATURE:
<223> OTHER INFORMATION: Synthetic Construct

<400> SEQUENCE: 112

```
gaattcaaaa tgtgtgcaac ttcatcccaa ttcactcaaa tcacagagca taattctaga      60
cgttcagcta actaccaacc aaatctgtgg aattttgaat tcttcaatc ccttgaaaat      120
gatttgaaag tggaaaagtt ggaggaaaaa gccacaaaac tagaggaaga agttagatgt     180
atgataaaca gagtagatac acaacctctg tcactactag aattgattga cgatgtccag    240
aggctgggtt taacatataa gttcgaaaag gatataatca aagccttaga aaacatagtc    300
cttctagatg aaaacaagaa gaataagtct gacttgcacg caaccgctct gagttttaga    360
ttgctgagac aacatggttt tgaagtaagt caagatgtgt ttgaaaggtt caaagacaaa    420
gagggaggat tctcaggaga attaaaggga gatgtgcagg gtctgttgtc attgtacgag    480
gccagttatt tggggtttga aggggaaaat ctactagagg aggccagaac cttctctata    540
acccatctga agaataactt gaagaaggca atcaatacaa aagtggctga acaagtttca    600
catgcattgg aattgcccta ccaccaaaga cttcatagac ttgaagccag atggttttg    660
gacaagtatg aaccaaagga gcctcaccat caacttttat tggaattagc aaaactggat    720
tttaacatgg ttcagacatt acaccagaaa gaattgcagg acctatcaag atggtggacg    780
gagatgggtt tagccagcaa gttagatttc gttagagata gattgatgga agtttacttt    840
tgggcactgg gaatggcacc agatcctcaa tttggtgaat gtagaaaggc agttacaaag    900
atgtttggtc tagtaacaat cattgatgat gtttatgatg tgtacggaac tttggatgaa    960
ttacaactat tcaccgacgc agttgaacgt tgggatgtaa acgcaataaa cacgttgcct   1020
gattatatga gctgtgtttt tctggcattg tacaacacag tcaatgacac ttcttactcc   1080
attttaaagg agaaagggca taacaatcta tcctatttga caaaatcatg gagggagtta   1140
tgcaaagcat tccttcaaga agctaagtgg tctaacaata agataatccc agcattctcc   1200
aagtatcttg aaaacgcttc cgtatcctcc tccggtgtgg ccctactagc accatcatat   1260
tttccgtct gccagcagca ggaagatatc tctgatcatg ctttgagatc cttaacagat   1320
tttcatggtc tagtcagatc ctcttgcgtg atttttcagat tgtgcaatga tttggctact   1380
tcagccgcag agttagagag gggtgaaacc acgaactcaa ttattagtta tatgcacgag   1440
aatgatggaa catccgaaga acaagcccgt gaagaattaa gaaaactgat cgatgctgaa   1500
tggaagaaga tgaatagaga aagagtttcc gacagcactt tgctgcctaa ggcattcatg   1560
gagatagctg ttaacatggc tagggtttca cactgtacat accaatacgg ggacggtctt   1620
ggaaggcccg actacgccac tgaaaataga attaaactgc tactgattga tccttttccc   1680
```

-continued

```
attaaccagt taatgtacgt gtaataggga tccgaattc                        1719
```

<210> SEQ ID NO 113
<211> LENGTH: 7658
<212> TYPE: DNA
<213> ORGANISM: Artificial Sequence
<220> FEATURE:
<223> OTHER INFORMATION: Synthetic Construct

<400> SEQUENCE: 113

```
acggattaga agccgccgag cgggtgacag ccctccgaag gaagactctc ctccgtgcgt     60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagctatcaa acaagtttgt acaaaaaagc aggctgaatt    540
caaaatgtgt gcaacttcat cccaattcac tcaaatcaca gagcataatt ctagacgttc    600
agctaactac caaccaaatc tgtggaattt tgaatttctt caatcccttg aaaatgattt    660
gaaagtggaa aagttggagg aaaaagccac aaaactagag gaagaagtta gatgtatgat    720
aaacagagta gatacacaac ctctgtcact actagaattg attgacgatg tccagaggct    780
gggtttaaca tataagttcg aaaaggtata aatcaaagcc ttagaaaaca tagtccttct    840
agatgaaaac aagaagaata gtctgactt gcacgcaacc gctctgagtt ttagattgct    900
gagacaacat ggttttgaag taagtcaaga tgtgtttgaa aggttcaaag acaaagaggg    960
aggattctca ggagaattaa agggagatgt gcagggtctg ttgtcattgt acgaggccag   1020
ttatttgggg tttgaagggg aaaatctact agaggaggcc agaaccttct ctataaccca   1080
tctgaagaat aacttgaaag aaggcatcaa tacaaaagtg gctgaacaag tttcacatgc   1140
attggaattg ccctaccacc aaagacttca tagacttgaa gccagatggt ttttggacaa   1200
gtatgaacca aaggagcctc accatcaact tttattggaa ttagcaaaac tggattttaa   1260
catggttcag acattacacc agaaagaatt gcaggaccta tcaagatggt ggacggagat   1320
gggtttagcc agcaagttag atttcgttag agatagattg atggaagttt acttttgggc   1380
actgggaatg gcaccagatc ctcaatttgg tgaatgtaga aaggcagtta caaagatgtt   1440
tggtctagta acaatcattg atgatgttta tgatgtgtac ggaactttgg atgaattaca   1500
actattcacc gacgcagttg aacgttggga tgtaaacgca ataaacacgt tgcctgatta   1560
tatgaagctg tgttttctgg cattgtacaa cacagtcaat gacacttctt actccatttt   1620
aaaggagaaa gggcataaca atctatccta tttgacaaaa tcatggaggg agttatgcaa   1680
agcattcctt caagaagcta agtggtctaa caataagata atcccagcat tctccaagta   1740
tcttgaaaac gcttccgtat cctcctccgg tgtggcccta ctagcaccat catattttc    1800
cgtctgccag cagcaggaag atatctctga tcatgctttg agatccttaa cagattttca   1860
tggtctagtc agatcctctt gcgtgatttt cagattgtgc aatgatttgg ctacttcagc   1920
cgcagagtta gagaggggtg aaaccacgaa ctcaattatt agttatatgc acgagaatga   1980
tggaacatcc gaagaacaag cccgtgaaga attaagaaaa ctgatcgatg ctgaatggaa   2040
```

```
gaagatgaat agagaaagag tttccgacag cactttgctg cctaaagcat tcatggagat    2100
agctgttaac atggctaggg tttcacactg tacataccaa tacggggacg gtcttggaag    2160
gcccgactac gccactgaaa atagaattaa actgctactg attgatcctt tccccattaa    2220
ccagttaatg tacgtgtaat agggatccga attcacccag ctttcttgta caaagtggtt    2280
cgatctagag ggcccttcga aggtaagcct atccctaacc ctctcctcgg tctcgattct    2340
acgcgtaccg gtcatcatca ccatcaccat tgagtttaaa cccgctgatc ctagagggcc    2400
gcatcatgta attagttatg tcacgcttac attcacgccc tccccccaca tccgctctaa    2460
ccgaaaagga aggagttaga aacctgaag tctaggtccc tatttatttt tttatagtta    2520
tgttagtatt aagaacgtta tttatatttc aaatttttct tttttttctg tacagacgcg    2580
tgtacgcatg taacattata ctgaaaacct tgcttgagaa ggttttggga cgctcgaagg    2640
ctttaatttg caagctgcgg ccctgcatta atgaatcggc caacgcgcgg ggagaggcgg    2700
tttgcgtatt gggcgctctt ccgcttcctc gctcactgac tcgctgcgct cggtcgttcg    2760
gctgcggcga gcggtatcag ctcactcaaa ggcggtaata cggttatcca cagaatcagg    2820
ggataacgca ggaaagaaca tgtgagcaaa aggccagcaa aagcccagga accgtaaaaa    2880
ggccgcgttg ctggcgtttt tccataggct ccgcccccct gacgagcatc acaaaaatcg    2940
acgctcaagt cagaggtggc gaaacccgac aggactataa agataccagg cgtttccccc    3000
tggaagctcc ctcgtgcgct ctcctgttcc gaccctgccg cttaccggat acctgtccgc    3060
ctttctccct tcgggaagcg tggcgctttc tcatagctca cgctgtaggt atctcagttc    3120
ggtgtaggtc gttcgctcca agctgggctg tgtgcacgaa ccccccgttc agcccgaccg    3180
ctgcgcctta tccggtaact atcgtcttga gtccaacccg gtaagacacg acttatcgcc    3240
actggcagca gccactggta acaggattag cagagcgagg tatgtaggcg gtgctacaga    3300
gttcttgaag tggtggccta actacggcta cactagaagg acagtatttg gtatctgcgc    3360
tctgctgaag ccagttacct tcggaaaaag agttggtagc tcttgatccg gcaaacaaac    3420
caccgctggt agcggtggtt tttttgtttg caagcagcag attacgcgca gaaaaaaagg    3480
atctcaagaa gatcctttga tcttttctac ggggtctgac gctcagtgga acgaaaactc    3540
acgttaaggg attttggtca tgagattatc aaaaaggatc ttcacctaga tccttttaaa    3600
ttaaaaatga agttttaaat caatctaaag tatatatgag taaacttggt ctgacagtta    3660
ccaatgctta atcagtgagg cacctatctc agcgatctgt ctatttcgtt catccatagt    3720
tgcctgactc cccgtcgtgt agataactac gatacgggag cgcttaccat ctggccccag    3780
tgctgcaatg ataccgcgag acccacgctc accggctcca gatttatcag caataaacca    3840
gccagccgga agggccgagc gcagaagtgg tcctgcaact ttatccgcct ccatccagtc    3900
tattaattgt tgccgggaag ctagagtaag tagttcgcca gttaatagtt tgcgcaacgt    3960
tgttggcatt gctacaggca tcgtggtgtc actctcgtcg tttggtatgg cttcattcag    4020
ctccggttcc caacgatcaa ggcgagttac atgatccccc atgttgtgca aaaaagcggt    4080
tagctccttc ggtcctccga tcgttgtcag aagtaagttg gccgcagtgt tatcactcat    4140
ggttatggca gcactgcata attctcttac tgtcatgcca tccgtaagat gcttttctgt    4200
gactggtgag tactcaacca agtcattctg agaatagtgt atgcggcgac cgagttgctc    4260
ttgcccggcg tcaatacggg ataatagtgt atcacatagc agaactttaa aagtgctcat    4320
cattggaaaa cgttcttcgg ggcgaaaact ctcaaggatc ttaccgctgt tgagatccag    4380
ttcgatgtaa cccactcgtg cacccaactg atcttcagca tcttttactt tcaccagcgt    4440
```

```
ttctgggtga gcaaaaacag gaaggcaaaa tgccgcaaaa aagggaataa gggcgacacg    4500
gaaatgttga atactcatac tcttcctttt tcaatgggta ataactgata taattaaatt    4560
gaagctctaa tttgtgagtt tagtatacat gcatttactt ataatacagt tttttagttt    4620
tgctggccgc atcttctcaa atatgcttcc cagcctgctt ttctgtaacg ttcaccctct    4680
accttagcat cccttccctt tgcaaatagt cctcttccaa caataataat gtcagatcct    4740
gtagagacca catcatccac ggttctatac tgttgaccca atgcgtctcc cttgtcatct    4800
aaacccacac cgggtgtcat aatcaaccaa tcgtaacctt catctcttcc acccatgtct    4860
ctttgagcaa taaagccgat aacaaaatct ttgtcgctct tcgcaatgtc aacagtaccc    4920
ttagtatatt ctccagtaga tagggagccc ttgcatgaca attctgctaa catcaaaagg    4980
cctctaggtt cctttgttac ttcttctgcc gcctgcttca aaccgctaac aatacctggg    5040
cccaccacac cgtgtgcatt cgtaatgtct gcccattctg ctattctgta tacacccgca    5100
gagtactgca atttgactgt attaccaatg tcagcaaatt ttctgtcttc gaagagtaaa    5160
aaattgtact tggcggataa tgcctttagc ggcttaactg tgccctccat ggaaaaatca    5220
gtcaagatat ccacatgtgt ttttagtaaa caaattttgg gacctaatgc ttcaactaac    5280
tccagtaatt ccttggtggt acgaacatcc aatgaagcac acaagtttgt ttgcttttcg    5340
tgcatgatat taaatagctt ggcagcaaca ggactaggat gagtagcagc acgttcctta    5400
tatgtagctt tcgacatgat ttatcttcgt ttcctgcagg ttttttgttct gtgcagttgg    5460 gttaagaata ctgggcaatt tcatgtttct tcaacactac atatgcgtat atataccaat    5520
ctaagtctgt gctccttcct tcgttcttcc ttctgttcgg agattaccga atcaaaaaaa    5580
tttcaaagaa accgaaatca aaaaaaagaa taaaaaaaaa atgatgaatt gaattgaaaa    5640
gctagcttat cgatgataag ctgtcaaaga tgagaattaa ttccacggac tatagactat    5700
actagatact ccgtcactg tacgatacac ttccgctcag gtccttgtcc tttaacgagg    5760
ccttaccact cttttgttac tctattgatc cagctcagca aaggcagtgt gatctaagat    5820
tctatcttcg cgatgtagta aaactagcta gaccgagaaa gagactagaa atgcaaaagg    5880
cacttctaca atggctgcca tcattattat ccgatgtgac gctgcagctt ctcaatgata    5940
ttcgaatacg ctttgaggag atacagccta atatccgaca aactgttta cagatttacg    6000 atcgtacttg ttacccatca ttgaattttg aacatccgaa cctgggagtt ttccctgaaa    6060
cagatagtat atttgaacct gtataataat atatagtcta gcgctttacg gaagacaatg    6120
tatgtatttc ggttcctgga gaaactattg catctattgc ataggtaatc ttgcacgtcg    6180
catccccggt tcattttctg cgtttccatc ttgcacttca atagcatatc tttgttaacg    6240
aagcatctgt gcttcatttt gtagaacaaa aatgcaacgc gagagcgcta atttttcaaa    6300
caaagaatct gagctgcatt tttacagaac agaaatgcaa cgcgaaagcg ctattttacc    6360
aacgaagaat ctgtgcttca tttttgtaaa acaaaaatgc aacgcgacga gagcgctaat    6420
ttttcaaaca agaatctga gctgcatttt tacagaacag aaatgcaacg cgagagcgct    6480
attttaccaa caaagaatct atacttcttt tttgttctac aaaaatgcat cccgagagcg    6540
ctatttttct aacaaagcat cttagattac ttttttttctc ctttgtgcgc tctataatgc    6600
agtctcttga taacttttg cactgtaggt ccgttaaggt tagaagaagg ctactttggt    6660
gtctattttc tcttccataa aaaaagcctg actccacttc ccgcgtttac tgattactag    6720
cgaagctgcg ggtgcatttt ttcaagataa aggcatcccc gattatattc tataccgatg    6780
tggattgcgc atactttgtg aacagaaagt gatagcgttg atgattcttc attggtcaga    6840
```

```
aaattatgaa cggtttcttc tattttgtct ctatatacta cgtataggaa atgtttacat    6900
tttcgtattg ttttcgattc actctatgaa tagttcttac tacaattttt ttgtctaaag    6960
agtaatacta gagataaaca taaaaaatgt agaggtcgag tttagatgca agttcaagga    7020
gcgaaaggtg gatgggtagg ttatataggg atatagcaca gagatatata gcaaagagat    7080
acttttgagc aatgtttgtg gaagcggtat tcgcaatggg aagctccacc ccggttgata    7140
atcagaaaag ccccaaaaac aggaagattg tataagcaaa tatttaaatt gtaaacgtta    7200
atattttgtt aaaattcgcg ttaaattttt gttaaatcag ctcattttt aacgaatagc     7260 ccgaaatcgg caaaatccct tataaatcaa aagaatagac cgagatagggg ttgagtgttg    7320 ttccagtttc caacaagagt ccactattaa agaacgtgga ctccaacgtc aaagggcgaa    7380
aaagggtcta tcagggcgat ggcccactac gtgaaccatc accctaatca agttttttgg    7440
ggtcgaggtg ccgtaaagca gtaaatcgga agggtaaacg gatgccccca tttagagctt    7500
gacggggaaa gccggcgaac gtggcgagaa aggaagggaa gaaagcgaaa ggagcggggg    7560
ctagggcggt gggaagtgta ggggtcacgc tgggcgtaac caccacaccc gccgcgctta    7620
atggggcgct acagggcgcg tggggatgat ccactagt                            7658

<210> SEQ ID NO 114
<211> LENGTH: 45
<212> TYPE: DNA
<213> ORGANISM: Artificial Sequence
<220> FEATURE:
<223> OTHER INFORMATION: Synthetic Construct

<400> SEQUENCE: 114
accgttcgtt cttatcgaaa ctaaaaaaaa ccggccttgg ccccg                      45
```